US011584765B2

(12) United States Patent
Wang et al.

(10) Patent No.: US 11,584,765 B2
(45) Date of Patent: *Feb. 21, 2023

(54) POLYCYCLIC AMINES AS SIGMA RECEPTOR MODULATORS

(71) Applicant: Ecstasy LLC, Chapel Hill, NC (US)

(72) Inventors: Xiaodong Wang, Chapel Hill, NC (US); Hua Zhong, Acton, MA (US)

(73) Assignee: ECSTASY LLC, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/885,604

(22) Filed: May 28, 2020

(65) Prior Publication Data

US 2022/0411442 A1 Dec. 29, 2022

Related U.S. Application Data

(63) Continuation-in-part of application No. 15/917,866, filed on Mar. 12, 2018, now Pat. No. 10,676,456.

(60) Provisional application No. 62/470,281, filed on Mar. 12, 2017.

(51) Int. Cl.

| | |
|---|---|
| *C07D 205/04* | (2006.01) |
| *C07D 409/04* | (2006.01) |
| *C07D 211/12* | (2006.01) |
| *C07D 211/34* | (2006.01) |
| *C07D 223/04* | (2006.01) |
| *C07D 223/06* | (2006.01) |
| *C07D 401/04* | (2006.01) |
| *C07D 401/12* | (2006.01) |
| *C07D 401/14* | (2006.01) |
| *C07D 405/04* | (2006.01) |
| *C07D 405/14* | (2006.01) |
| *C07D 409/14* | (2006.01) |
| *C07D 413/04* | (2006.01) |
| *C07D 417/04* | (2006.01) |
| *C07D 417/14* | (2006.01) |
| *C07F 5/02* | (2006.01) |
| *C07D 475/00* | (2006.01) |
| *C07D 211/14* | (2006.01) |
| *C07D 207/09* | (2006.01) |
| *C07D 417/06* | (2006.01) |
| *C07D 417/10* | (2006.01) |
| *C07D 409/06* | (2006.01) |
| *C07D 451/02* | (2006.01) |
| *C07D 473/00* | (2006.01) |
| *C07D 471/08* | (2006.01) |
| *C07D 513/04* | (2006.01) |

(52) U.S. Cl.
CPC ............ *C07F 5/025* (2013.01); *C07D 205/04* (2013.01); *C07D 207/09* (2013.01); *C07D 211/14* (2013.01); *C07D 211/34* (2013.01); *C07D 223/04* (2013.01); *C07D 223/06* (2013.01); *C07D 401/04* (2013.01); *C07D 401/12* (2013.01); *C07D 401/14* (2013.01); *C07D 405/04* (2013.01); *C07D 405/14* (2013.01); *C07D 409/04* (2013.01); *C07D 409/06* (2013.01); *C07D 409/14* (2013.01); *C07D 413/04* (2013.01); *C07D 417/04* (2013.01); *C07D 417/06* (2013.01); *C07D 417/10* (2013.01); *C07D 417/14* (2013.01); *C07D 451/02* (2013.01); *C07D 471/08* (2013.01); *C07D 473/00* (2013.01); *C07D 475/00* (2013.01); *C07D 513/04* (2013.01)

(58) Field of Classification Search
CPC .. C07D 205/04; C07D 207/09; C07D 211/14; C07D 211/34; C07D 223/04; C07D 223/06; C07D 401/04; C07D 401/12; C07D 401/14; C07D 405/04; C07D 405/14; C07D 409/04; C07D 409/06; C07D 409/14; C07D 413/04; C07D 417/04; C07D 417/06; C07D 417/10; C07D 451/02; C07D 471/08; C07D 473/00; C07D 475/00; C07D 513/04; C07F 5/025
See application file for complete search history.

(56) References Cited

U.S. PATENT DOCUMENTS

| | | |
|---|---|---|
| 7,915,274 B2 | 3/2011 | Ozaki et al. |
| 2004/0138220 A1 | 7/2004 | Liras |
| 2004/0204453 A1 | 10/2004 | McHardy |
| 2010/0234427 A1 | 9/2010 | Peters et al. |
| 2011/0021556 A1 | 1/2011 | Lucas et al. |

OTHER PUBLICATIONS

Wills, M. T. et al., Azetidines. 5. Reaction of 1,1,3,3—Tetramethyl-andl-Benzyl-l,3,3-trimethylazetidiniulmons with Butyllithium . . . J. Org. Chem. 1968, vol. 33, 2489-98.
H. Aoyama et al., Photocyclization of 4-(Dialkylamin0)-2-aryl-l-butenes J. Org. Chem. 1992, vol. 57, 3037-3041.
JB Lambert et al., Heterocyclic Deformations from Molecular Enlargement J. Org. Chem. 1982, vol. 47, 3890-3893.
J. Paden, The Synthesis of Pyrrolidines, Piperidines and Hexahydroazepines 1936, vol. 58, 2487-99.

(Continued)

*Primary Examiner* — Jared Barsky
(74) *Attorney, Agent, or Firm* — Eric P. Mirabel, JD, LLM

(57) ABSTRACT

The present invention provides a genus of polycyclic amines that are useful as opioid receptor modulators. The compounds of the invention are useful in both therapeutic and diagnostic methods, including for treating pain, neurological disorders, cardiac disorders, bowel disorders, drug and alcohol addiction, drug overdose, urinary disorders, respiratory disorders, sexual dysfunction, psoriasis, graft rejection or cancer.

5 Claims, 2 Drawing Sheets

(56) References Cited

OTHER PUBLICATIONS

PJ Gilligan et al., Piperidinyltetralin sigma Ligands J. Med. Chem. 1994, vol. 37, 364-370.
VB Journigan et al., Nonpeptide Small Molecule Agonist and Antagonist Original Leads for Neuropeptide FF1 and FF2 Receptors J. Med. Chem. 2014, vol. 57, 8903-8927.
P. Maguire, Pharmacological profiles of fentanyl analogs and K opiate receptors, European Journal of Pharmacology, vol. 213 (1992) 219-225.
Written Opinion of the International Searching Authority In PCT/US2018/021906.
"RN 1522695-22-2" Database Registry Chemical Abstracts Service, Columbus, Ohio, Accession No. RN 1522695-22-2, Entered STN: Apr. 23, 2007.
Ito et al., Cancer Science 94(1), 3-8 (2003) (Year: 2003).
Bastin et al., Organic Process Research & Development 2000, 4, 427-435 (Year: 2000).
Ito et al., Cancer Science 94(1), 3-8, 2003 (§).
Bastin et al.. Salt Selection and Optimisation Procedures for Pharmaceutical New Chemical Entities, Organic Process Research & Development 2000, 4, 427-435.

POLYCYCLIC AMINES AS SIGMA RECEPTOR MODULATORS

RELATED APPLICATIONS

This application is a continuation-in-part of U.S. application Ser. No. 15/917,866, filed Mar. 12, 2018 (U.S. Pat. No. 10,676,456), which claims priority to U.S. Provisional No. 62/470,281, filed Mar. 12, 2017.

BACKGROUND OF THE INVENTION

The opioid system is composed of three families of endogenous peptides, the enkephalins, dynorphins and β-endorphin, and three homologous GPCRs, the μ opioid receptor (MOR), δ opioid receptor (DOR) and κ opioid receptor (KOR) (Filizola and Devi, 2013; Cox et al.) and nociception recptors (NOP) (Lord and Waterfield, 1977; Martin and Thompson, 1976). The opioid system plays a key role in reward and motivation, regulates emotional responses and cognition, and modulates nociception, neuroendocrine physiology and autonomic functions (see Walwyn et al., 2010; Feng et al., 2012). These opioid receptors can also form homo- and heterodimeric complexes. These opioid receptors (OR) including monomer, homo- and heterodimeric complexes signal to kinase cascades and scaffold of a variety of proteins.

Opiates have been the subject of intense research since the isolation of morphine in the early 1800s. Opiates such as morphine and fentanyl, a major class of analgesics used in the clinical management of pain exerting their effects through the activation of opioid receptors, are among the most commonly prescribed drugs in the world. Despite their efficacy and utility, side-effects greatly limit the usefulness. These side-effects include respiratory depression, constipation, drug tolerance, physical dependence, reward, and addiction.

There is a continuing need for new OR modulators for the management of pain with reduced or fewer side effects. There is also a continuing need for new OR modulators for cardioprotection and for treating cardiac disorders, analgesia, functional pain, inflammatory pain, peripherally mediated and neuropathic pain, non-somatic pain, arthritis, mental illness, cognitive disorders, depression, Parkinson's disease, locomotor disfunction, urogenital tract disorders, bladder dysfunction, overactive bladder, urinary incontinence, neurogenic bladder, psoriasis, pruritus, non-ulcerogenic dyspepisa, gastro-intestinal disorders, functional bowel disease, diarrhea, inflammatory bowel disease, irritable bowel syndrome, interstitial cystitis, sexual dysfunctions, drug addiction, alcohol addiction, drug overdose, premature ejaculation, asthma, cough, lung edema, disorders of respiratory function, respiratory depression, functional distension, disorders of motility or secretion, and for immunomodulation, inhibiting or preventing organ or skin graft rejection, or treating tumors or cancer,

SUMMARY

The present invention provides polycyclic amines, prodrugs and pharmaceutically acceptable salts thereof ("compounds of the invention"), which are useful in the treatment of diseases through the modulation of opioid receptors.

The compounds of the invention have a structure according to Formula I, and include pharmaceutically acceptable salts of this structure, e.g., HCl salts:

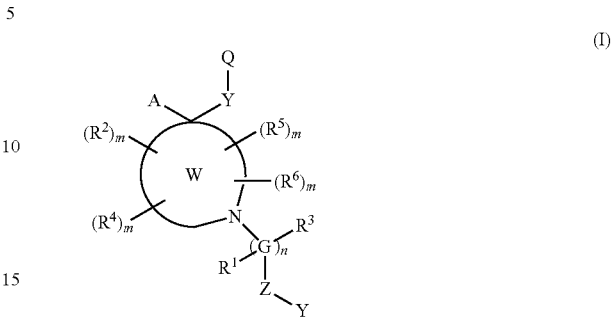

(I)

wherein:

A includes substituted or unsubstituted: alkyl, heteroalkyl, cycloalkyl, heterocycloalkyl, aryl, heteroaryl, and arylalkyl;

Y includes substituted or unsubstituted: alkyl, heteroalkyl, cycloalkyl, and heterocycloalkyl;

Q includes: substituted or unsubstituted: aryl, heteroaryl, and null;

W includes substituted or unsubstituted, saturated or unsaturated: (i) 4- to 8-membered heterocyclic rings including an N-substituent as an atom of the ring; and (ii) bicyclic or heterobicyclic fused rings wherein each ring has 4- to 10-members, and wherein at least one of the rings includes an N-substituent as an atom of the ring;

G includes substituted or unsubstituted alkyl or an N atom;

Z includes substituted or unsubstituted aryl, substituted or unsubstituted heteroaryl, and null;

If Z is null then T is null, but if Z is not null, T is selected from: (i) the moieties H, OH, $NH_2$, $NO_2$, $—SO_2NH_2$, halogen, (ii) substituted or unsubstituted: alkyl, heteroalkyl, cycloalkyl, heterocycloalkyl, aryl, and heteroaryl;

n is an integer from 1-4 when G is alkyl and is 1 when G is an N atom;

$R^1$ and $R^3$ are members independently selected from H and substituted or unsubstituted: alkyl, heteroalkyl, 3- to 7-membered cycloalkyl, 3- to 7-membered heterocycloalkyl, aryl, and heteroaryl;

m is an integer from 0-8 and can be same or different for each of $R^2$, $R^4$, $R^5$ and $R^6$, and wherein $R^2$, $R^4$, $R^5$ and $R^6$ are each independently selected from H and substituted or unsubstituted: alkyl, heteroalkyl, 3- to 7-membered cycloalkyl, 3- to 7-membered heterocycloalkyl, and where m is greater than 1 for any of $R^2$, $R^4$, $R^5$ and $R^6$, each member in such a multi-member $R^2$, $R^4$, $R^5$ and $R^6$ chain can be the same or different; and further provided that the total number of $R^2$, $R^4$, $R^5$ and $R^6$ having an m value greater than 0 is always less than or equal to the number of W ring positions available for covalent bonding; and $R^1$ and $R^3$, or $R^1$ or $R^3$ and Z, or $R^2$ and A, or $R^2$ and Y together with groups to which they may be joined, optionally form a substituted or unsubstituted 3- to 7-membered ring.

In a second aspect, the present invention provides processes for preparing these compounds. In a third aspect, the present invention provides a method for treating a disease through the modulation of opioid receptors. The compounds are useful for preventing or treating a disease or condition selected from the group consisting of cardioprotection, cardiac disorders, analgesia, functional pain, inflammatory pain, peripherally mediated and neuropathic pain, non-somatic pain, arthritis, mental illness, cognitive disorders, depression, Parkinson's disease, locomotor disfunction, urogenital tract disorders, bladder dysfunction, overactive bladder, urinary incontinence, neurogenic bladder, psoriasis, pruritus, emesis, acne, skin lesions, non-ulcerogenic dyspepisa, gastro-intestinal disorders, functional bowel disease, diarrhea, inflammatory bowel disease, irritable bowel syndrome, interstitial cystitis, sexual dysfunctions, drug addiction, alcohol addiction, drug overdose, premature ejaculation, asthma, cough, lung edema, disorders of respiratory function, respiratory depression, functional distension, and disorders of motility or secretion. These compounds are also useful for immunomodulation, inhibiting or preventing organ or skin graft rejection, or treating tumors or cancer. All such treatment involves administering, to a patient, an effective amount of a compound having Formula I.

In a fourth aspect, the present invention provides a pharmaceutical composition comprising a pharmaceutically acceptable carrier and a compound according to Formula I.

These and other aspects and embodiments of the invention will be apparent from the detailed description that follows.

DETAILED DESCRIPTION

I. Abbreviations and Definitions

Figure 1:
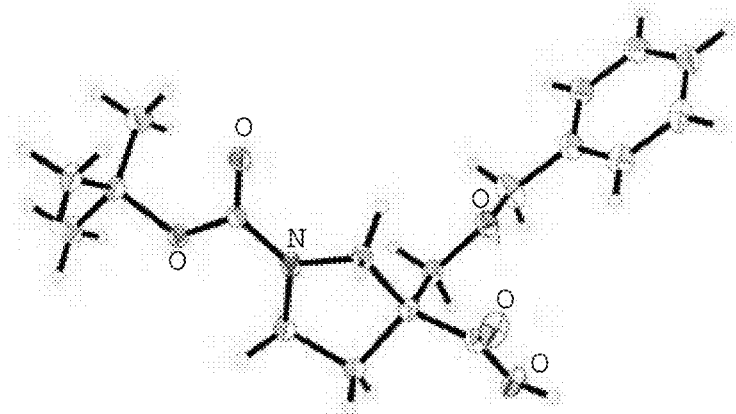
FIG. 1 is an X-ray crystallography depiction of (S)-3-((benzyloxy)methyl)-1-(tert-butoxycarbonyl)pyrrolidine-3-carboxylic acid.

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl" further includes unsubstituted as well as substituted alkyl groups, wherein the substituents of substituted alkyl groups may include any sterically acceptable substituents which are compatible with such alkyl groups compound for its intended utility. Examples of substituents for substituted alkyl groups include halogen (e.g., fluoro, chloro, bromo, and iodo), amino, amido, C1-C10 alkyl, C1-C10 alkoxy, nitro, compound, etc.; saturated alkyl groups as well as unsaturated alkyl groups, the latter including groups such as alkenyl-substituted alkyl groups (e.g., allyl, methallyl, propallyl, butenylmethyl, etc.), alkynyl-substituted alkyl groups, and any other alkyl groups containing sterically acceptable unsaturation which is compatible with such alkyl groups and which does not preclude the efficacy of the compound for its intended utility; and alkyl groups including linking or bridge moieties, e.g., heteroatoms such as nitrogen, oxygen, sulfur, etc.

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quatem/zed. The heteroatom(s) O, N and S and Si may be placed at any interior position of the heteroalkyl group or at the position at which the alkyl group is attached to the remainder of the molecule, or at both termini. Examples include, but are not limited to, —CH$_2$—CH$_2$—O—CH$_3$, —CH$_2$—C(═O)—CH$_3$, —CH$_2$—CH$_2$—CH$_2$—C(═O)—O—C(CH$_3$)—CH$_3$, —CH$_2$—CH$_2$—CH$_2$—C(═O)—N—CH(CH$_3$), —CH$_2$—CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, and —CH═CH—N(CH$_3$)—CH$_3$. Up to two heteroatoms may be consecutive, such as, for example, acetamide, —CH$_2$—NH—OCH$_3$ and —CH$_2$—O—Si(CH$_3$)$_3$. Similarly, the term "heteroalkylene" by itself or as part of another substituent means a divalent radical of a heteroalkyl above, e.g., —CH$_2$—CH$_2$—S—CH$_2$—CH$_2$— and —CH$_2$—S—CH$_2$—CH$_2$—NH—CH$_2$—; and including heteroatoms at either or both of the chain termini (e.g., alkyleneoxy, alkylenedioxy, alkyleneamino, alkylenediamino, and the like).

The terms "cycloalkyl" and "heterocycloalkyl", by themselves or in combination with other terms, represent, unless otherwise stated, cyclic versions of "alkyl" and "heteroalkyl", respectively. Thus, a cycloalkyl or heterocycloalkyl can include saturated and unsaturated ring linkages. Additionally, for heterocycloalkyl, one or more heteroatoms can occupy any position. Examples of cycloalkyl include, but are not limited to, cyclopentyl, cyclohexyl, 1-cyclohexenyl, 3-cyclohexenyl, and cycloheptyl. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, and 1-piperazinyl, 2-piperazinyl.

The terms "halo" or "halogen," by themselves or as part of another substituent, mean, unless otherwise stated, a fluorine, chlorine, bromine, or iodine atom. Additionally, "haloalkyl," includes monohaloalkyl and polyhaloalkyl. For example, the term "halo($C_1$-$C_4$)alkyl" includes, but not be limited to, trifluoromethyl, 2,2,2-trifluoroethyl, 4-chlorobutyl, and 3-bromopropyl.

The term "aryl" includes aromatic substituents, including single rings and multiple rings; and further including both fused rings and covalently linked rings where at least one of the rings is aromatic, and is further intended to refer to carbocyclic (e.g., phenyl, naphthyl) as well as heterocyclic aromatic groups (e.g., pyridyl, thienyl, furanyl, etc.) and to encompass unsubstituted as well as substituted aryl groups, wherein the substituents of substituted aryl groups may include any sterically acceptable substituents which are compatible with such aryl groups and which do not preclude the efficacy of the compound for its intended utility. Examples of substituents for substituted aryl groups include one or more of halogen (e.g., fluoro, chloro, bromo, and iodo), amino, amido, C1-C4 alkyl, C1-C4 alkoxy, nitro, trifluoromethyl, hydroxyalkyl containing a C1-C4 alkyl moiety, etc.

The term "heteroaryl" includes all the same single and multiple rings, fused rings and covalently linked ring structures as "aryl," wherein at least one aromatic ring contains one or more heteroatoms e.g., N, O, and S, wherein the nitrogen and sulfur atoms may be oxidized, and the nitrogen atom(s) may be quatern/zed. A heteroaryl group can be attached as a fused ring or attached to the remainder of the molecule through a heteroatom. Non-limiting examples of aryl and heteroaryl groups include phenyl, 1-naphthyl, 2-naphthyl, 4-biphenyl, 2-thiazolyl, 3-thiazolyl, 4-thiazolyl, 5-thiazolyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Where the term "aryl" is used in combination with other terms (e.g., aryloxy, arylthioxy, arylalkyl) the "aryl" term includes both aryl and heteroaryl groups defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, or 3-(1-naphthyloxy)propyl,).

The term "oxo" as used herein means an oxygen that is double bonded to a carbon atom.

Preferred substituents for alkyl and heteroalkyl groups or radicals (including those groups referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: aryl, heteroaryl, alkyl, fluoro or other halogen, —OR', =O, =NR', =N—OR', —NR'R", —SR', —SiR'R"R"', —C(O)R', —$CO_2$R', —OC(O)NR'R", —OC(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$R', —N$_3$, —CH(Ph)$_2$, fluoro($C_1$-$C_4$)alkoxy, and fluoro($C_1$-$C_4$)alkyl, in a number ranging from zero to (2m'+1), where m' is the total number of carbon atoms in such radical. R', R", R"' and R"" each preferably independently refer to hydrogen, and substituted or unsubstituted: alkyl, heteroalkyl, aryl, alkoxy, thioalkoxy, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. The term "substituted" is meant to include groups where carbon or N atoms are bound to groups other than hydrogen groups, e.g., any of the preferred substituents listed herein and further including: haloalkyl (e.g., —$CF_3$ and —$CH_2CF_3$) and acyl (e.g., —C(O)$CH_3$, —C(O)$CF_3$, —C(O)$CH_2$O$CH_3$).

Preferred substituents for substituents for the aryl and heteroaryl groups can be one or more of a variety of groups selected from, but not limited to: aryl or heteroaryl including forming a fused ring or covalently linked structure, alkyl, fluoro or other halogen, —OR', =O, =NR', =N—OR', —NR'R", —SR', —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R"' and R"" each preferably independently refer to hydrogen, and substituted or unsubstituted: alkyl, heteroalkyl, aryl, alkoxy, thioalkoxy, or arylalkyl groups. When a compound of the invention includes more than one R group, for example, each of the R groups is independently selected as are each R', R", R"' and R"" groups when more than one of these groups is present. The term "substituted" is meant to include groups having carbon or N atoms bound to groups other than hydrogen groups, e.g., any of the preferred substituents listed herein and further including: haloalkyl (e.g., —$CF_3$ and —$CH_2CF_3$) and acyl (e.g., —C(O)$CH_3$, —C(O)$CF_3$, —C(O)$CH_2$O$CH_3$).

An example of substituents for aryl or heteroaryl rings include -T-C(O)—(CRR')$_q$—U—, wherein T and U are independently —NR—, —O—, —CRR'— or a single bond, and q is an integer of from 0 to 3; -A-($CH_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R"')$_d$—, where s and d are independently integers of from 0 to 3, and X is —O—, —NR'—, —S—, —S(O)—, —S(O)$_2$—, or —S(O)$_2$NR'—. The substituents R, R', R" and R"' are independently selected from hydrogen or substituted or unsubstituted ($C_1$-$C_6$)alkyl.

As used herein, the term "heterocyclic" includes heterocycloalkyl and heteroaryl rings.

As used herein the term "heterobicyclic" includes two heterocycloalkyl or two heteroaryl rings, as well as bicyclic rings wherein one of the rings is heterocycloalkyl and the other is a heteroaryl ring, as well as bicyclic rings wherein one ring is heterocycloalkyl or heteroaryl and the other ring is cycloalkyl or aryl.

As used herein, the term "heteroatom" includes oxygen (O), nitrogen (N), sulfur (S) and silicon (Si). [0001] The term "poly" as used herein means at least 2. For example, a polyvalent metal ion is a metal ion having a valency of at least 2.

The term "null" means that no group or moiety is present at the position indicated (though a hydrogen may be present where the adjacent group is a radical).

"Moiety" refers to the radical of a molecule that is attached to another moiety.

The symbol $\sim\!\!\sim\!\!\sim$, whether utilized as a bond or displayed perpendicular to a bond indicates the point at which the displayed moiety is attached to the remainder of the molecule.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The compounds of the invention, or their pharmaceutically acceptable salts, may have asymmetric carbon atoms or double bonds in their structure. The compounds of the invention and their pharmaceutical acceptable salts may therefore exit as single stereoisomers, racemates, and as mixtures of enantiomers, diastereomers and geometric isomers. All such single stereoisomers, racemates and mixtures thereof are intended to be within the scope of the invention. Absolute configuration of certain carbon atoms within the compounds, if known, are indicated by the appropriate absolute descriptors R or S.

The tautomeric forms of the compounds of Formula (I) are meant to comprise those compounds of Formula (I) wherein e.g. an enol group is converted into a keto group (keto-enol tautomerism).

The compounds of Formula (I) as prepared in the processes described below may be synthesized in the form of racemic mixtures of enantiomers which can be separated from one another following art-known resolution procedure. The racemic compounds of Formula (I) may be converted into the corresponding diasteromeric salt forms by reaction with a suitable chiral acid. Said diasteromeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

"Therapeutic" as used herein, includes prevention, treatment and/or prophylaxis for humans as well as other animals.

"Pharmaceutically or therapeutically effective dose or amount" refers to a dosage level sufficient to induce a desired biological result. That result may be the alleviation of the signs, symptoms or causes of a disease or any other alteration of a biological system that is desired. The precise dosage will vary according to a variety of factors, including but not limited to the age and size of the subject, the disease and the treatment being effected.

A "host" or "patient" or "subject" is a living mammal, human or animal, for whom therapy is desired. The "host," "patient" or "subject" generally refers to the recipient of the therapy to be practiced according to the method of the invention. It should be noted that the invention described herein may be used for veterinary as well as human applications and that the term "host" should not be construed in a limiting manner. In the case of veterinary applications, the dosage ranges can be determined as described below, taking into account the body weight of the animal.

As used herein, the term "pharmaceutically acceptable" means approved by a regulatory agency of a federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science* 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention. Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

A "pharmaceutical composition" is a formulation comprising the disclosed compounds in a form suitable for administration to a subject. A pharmaceutical composition of the invention is preferably formulated to be compatible with its intended route of administration. Examples of routes of administration include, but are not limited to, oral and parenteral, e.g., intravenous, intradermal, subcutaneous, inhalation, topical, transdermal, transmucosal, and rectal administration.

II. Opioid Receptor Modulators

The compounds of the invention have a structure as in Formula I above.

One broad aspect of the present invention relates to compounds, including inter alia comprising the same and methods for making and using the same.

This invention relates to compounds of Formula I, and pharmaceutical compositions including them, useful as opioid receptor modulators-agonists or antagonists, and having specific bioactivity and characteristics rendering them useful as therapeutic agents for treatment or prophylaxis of a wide variety of physiological and pathological conditions, including a variety of centrally mediated or peripheral indications, e.g., cardioprotection, cardiac disorders, analgesia, functional pain, inflammatory pain, peripherally mediated and neuropathic pain, non-somatic pain, arthritis, mental illness, cognitive disorders, depression, Parkinson's disease, locomotor disfunction, urogenital tract disorders, bladder dysfunction, overactive bladder, urinary incontinence, neurogenic bladder, psoriasis, pruritus, emesis, acne, skin lesions, non-ulcerogenic dyspepsia, gastro-intestinal disorders, functional bowel disease, diarrhea, inflammatory bowel disease, irritable bowel syndrome, interstitial cystitis, sexual dysfunctions, drug addiction, alcohol addiction, drug overdose, premature ejaculation, asthma, cough, lung edema, disorders of respiratory function, respiratory depression, functional distension, and disorders of motility or secretion, as well as immunomodulation, inhibiting or preventing organ or skin graft rejection, or treating tumors or cancer.

In a particularly preferred method of the invention, treatment or prophylaxis of central and peripheral pain, migraine, depression and Parkinson's disease, overactive bladder or urinary incontinence, diarrhea, irritable bowel syndrome and gastro-intestinal disorders, is effected by administering to a subject in need of such treatment or prophylaxis an effective amount of a compound of Formula (1) or a pharmaceutically acceptable ester or salt thereof.

Examples of pharmaceutically acceptable salts of the compound of Formula (1) include salts derived from an appropriate base, such as an alkali metal (for example, sodium, potassium), an alkaline earth metal (for example, calcium, magnesium), ammonium and $NR'_4{}^+$ (wherein R' is $C_1$-$C_4$ alkyl). Pharmaceutically acceptable salts of the compounds of Formula (1) having an amino group include salts of: organic carboxylic acids such as acetic, lactic, tartaric, malic, lactobionic, fumaric, and succinic acids; organic sulfonic acids such as methanesulfonic, ethanesulfonic, isethionic, benzenesulfonic and p-toluenesulfonic acids; and inorganic acids such as hydrochloric, hydrobromic, sulfuric, phosphoric and sulfamic acids. Pharmaceutically acceptable salts of the compounds of Formula (1) having a hydroxyl group consist of the anion of such compounds in combination with a suitable cation such as $Na^+$, $NH_4{}^+$, or $NR'_4{}^+$ (wherein R' is for example a $C_{1-4}$ alkyl group).

The compounds of Formula (1) have utility as exogenous receptor combining or complexing compounds, and may be used for binding with an opioid receptor. Further, the compounds may be used as a conjugate in an agonist/antagonist pair that is employed for transductional assay of neurotransmitter function in appertaining cellular or differentiated tissue systems, as well as for receptor assay, differential binding, and specificity applications for cellular, histological, and corporeal monitoring and assessment purposes.

The compounds of Formula (1) can be administered for therapeutic intervention in a pharmaceutical composition containing the compound and a pharmaceutically acceptable carrier. The invention contemplates the use of any means and/or of modality of administration of the compositions of the invention.

Compounds of the above general Formula (1) exhibit binding selectivity for receptor(s). Depending on the structure and stereo-specificity of the particular Formula (1) compounds, such compounds may exhibit binding ability to receptor(s) selected from the group consisting of delta receptors, mu receptors, kappa receptors, nociception receptors, and combinations of such receptors.

The compounds contemplated by the invention include those of Formula (1) per se, as well as physiologically functional derivatives thereof. "Physiologically functional derivative" includes a pharmaceutically acceptable salt, ether, ester or salt of an ether or ester of the compound of Formula (1) or any other compound which, upon administration to the recipient, is capable of providing (directly or indirectly) the said compound of Formula (1) or an active metabolite or residue thereof. Phenolic $C_1$-$C_6$ alkyl ethers are a sub-class of physiologically functional derivatives of the compounds of Formula (1).

The compounds of the present invention may be readily synthesized within the skill of the art and in view of the illustrative synthesis examples hereinafter set forth.

The compounds of the invention when used in pharmaceutical or diagnostic applications preferably are prepared in a racemic mixture or an essentially pure enantiomer form, with an enantiopurity of at least 90% enantiomeric excess (EE), preferably at least 95% EE, more preferably at least 98% EE, and most preferably at least 99% EE. Enantiomeric excess values provide a quantitative measure of the excess of the percentage amount of a major isomer over the percentage amount of a minor isomer which is present therewith, and may be readily determined by suitable methods well-known and established in the art, as for example chiral high pressure liquid chromatography (HPLC), chiral gas chromatography (GC), nuclear magnetic resonance (NMR) using chiral shift reagents, etc.

Subjects to be treated by the methods of the present invention are preferably human subjects, but also include non-human mammals and other animals (e.g., bird, dog, cat, cow, horse). Depending on the specific condition to be treated, subjects may be administered compounds of Formula (1) at any suitable therapeutically effective and safe dosage, as may readily be determined within the skill of the art, and without undue experimentation, with extrapolation from the animal dosages set forth herein in the examples. In in vitro tests for agonist/antagonist activity, such as receptor binding affinity tests, and inhibition of electrically stimulated muscle twitch tests, compounds of the present invention exhibit potency over a range of from nanomolar to micromolar concentrations, depending on the specific compound employed.

In general, while the effective dosage of compounds of the invention for therapeutic use may be widely varied in the broad practice of the invention, depending on the specific application, condition, or disease state involved, as readily determinable within the skill of the art, suitable therapeutic doses of the compounds of the invention, for each of the appertaining compositions described herein, and for achievement of therapeutic benefit in treatment of each of the conditions described herein, will be in the range of 10 micrograms ($\mu$g) to 100 milligrams (mg) per kilogram body weight of the recipient per day, preferably in the range of 50 $\mu$g to 75 mg per kilogram body weight per day, and most preferably in the range of 100 $\mu$g to 50 mg per kilogram body weight per day. The desired dose is preferably presented as one, two, three, four, five, six, or more sub-doses administered at appropriate intervals throughout the day. These sub-doses may be administered in unit dosage forms, for example, containing from 10 $\mu$g to 1000 mg, preferably from 50 $\mu$g to 500 mg, more preferably from 50 $\mu$g to 250 mg, and most preferably from 50 $\mu$g to 10 mg of active ingredient per unit dosage form. Alternatively, if the condition of the recipient so requires, the doses may be administered as a continuous infusion.

The mode of administration and dosage forms will affect the therapeutic amounts of the compounds which are desirable and efficacious for the given treatment application.

For example, orally administered dosages typically are at least twice, e.g., 2-10 times, the dosage levels used in parenteral administration methods, for the same active ingredient. In oral administration, dosage levels for delta receptor binding compounds of the invention may be on the order of 5-200 mg/70 kg body weight/day. In tablet dosage forms, typical active agent dose levels are on the order of 10-100 mg per tablet.

The compounds of Formula (1) may be administered per se as well as in the form of pharmaceutically acceptable esters, salts, and ethers, as well as other physiologically functional derivatives of such compounds.

The present invention also contemplates pharmaceutical compositions, both for veterinary and for human medical use, which comprise as the active agent one or more compound(s) of the invention.

In such pharmaceutical compositions, the active agent preferably is utilized together with one or more pharmaceutically acceptable carrier(s) therefor and optionally any other therapeutic ingredients. The carrier(s) preferably are compatible with the other ingredients of the formulation and not unduly deleterious to the recipient thereof. The active agent is preferably in a pharmaceutically acceptable amount effective to achieve the desired pharmacological effect.

The formulations include those suitable for parenteral as well as non-parenteral administration, and specific administration modalities include oral, rectal, topical, sub-lingual, mucosal, transdermal, nasal, ophthalmic, subcutaneous, intramuscular, intravenous, transdermal, spinal, intrathecal, intra-articular, intra-arterial, sub-arachnoid, bronchial, lymphatic, and intra-uterine administration. Formulations suitable for oral administration are preferred.

When the active agent is utilized in a formulation comprising a liquid solution, the formulation advantageously may be administered parenterally. When the active agent is employed in a liquid suspension formulation or as a powder in a biocompatible carrier formulation, the formulation may be advantageously administered orally, rectally, or bronchially.

When the active agent is utilized directly in the form of a powdered solid, the active agent may be advantageously administered orally. Alternatively, it may be administered bronchially, via nebulization of the powder in a carrier gas, to form a gaseous dispersion of the powder which is inspired by the patient from a breathing circuit comprising a suitable nebulizer device. In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

The formulations comprising the active agent of the present invention may conveniently be presented in unit dosage forms and may be prepared by any of the methods well known in the art of pharmacy. Such methods generally include the step of bringing the active compound(s) into association with a carrier that constitutes one or more accessory ingredients. Typically, the formulations are prepared by uniformly and intimately bringing the active compound(s) into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each containing a predetermined amount of the active ingredient as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert compound, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Nasal spray formulations comprise purified aqueous solutions of the active compounds with preservative agents and isotonic agents. Such formulations are preferably adjusted to a pH and isotonic state compatible with the nasal mucous membranes.

Formulations for rectal administration may be presented as a suppository with a suitable carrier such as cocoa butter, hydrogenated fats, or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media, such as mineral oil, petroleum, polyhydroxy alcohols, or other bases used for topical pharmaceutical formulations.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like.

The disease state or physiological condition involved in such therapeutic intervention may be of any type or kind noted above, e.g., centrally mediated disorders; pain, depression, drug addiction, and drug dependence, alcohol addiction; and peripherally mediated neuropathic pain, cough, lung edema, gastro-intestinal disorders, arthritis, psoriasis, asthma, inflammatory bowel disease, disorders of respiratory function, functional bowel disease, irritable bowel syndrome, diarrhea, functional distension, pain (e.g., functional pain, trauma pain, etc.), non-ulcerogenic dyspepsia, urogenital tract disorders, premature ejaculation, overactive bladder, urinary incontinence, organ transplant rejection, skin graft rejection, cardiac disorders, cardioprotection, emesis, acne and skin lesions.

The invention is further illustrated by the following non-limiting preparation schemes and other examples.

III. Preparation of Opioid Receptor Modulators

The following exemplary schemes illustrate methods of preparing the compounds of the invention. These methods are not limited to producing the compounds listed, but can be used to prepare other substrates as well. The compounds of the invention can also be produced by methods not explicitly illustrated in the schemes. The compounds can be prepared using readily available starting materials or known intermediates.

Scheme 1
Compounds where "A" of Formula I is an alkyl or heteroalkyl moiety are synthesized as illustrated in Scheme 1. The synthesis of compounds 1-6 is exemplified.

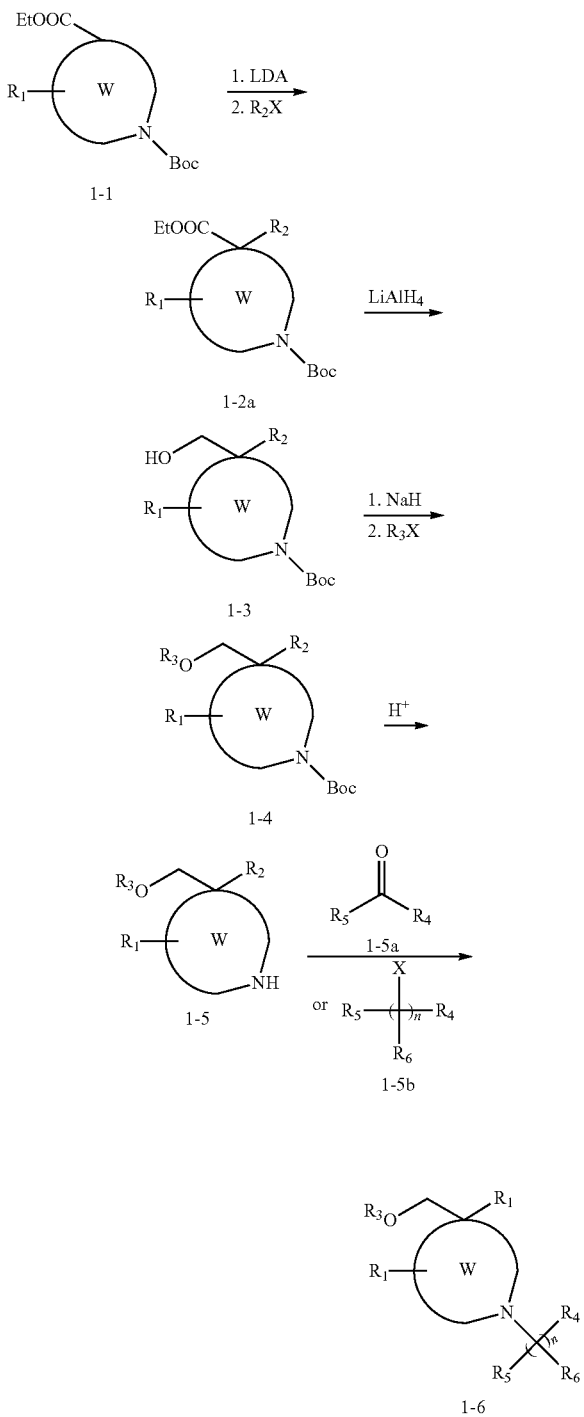

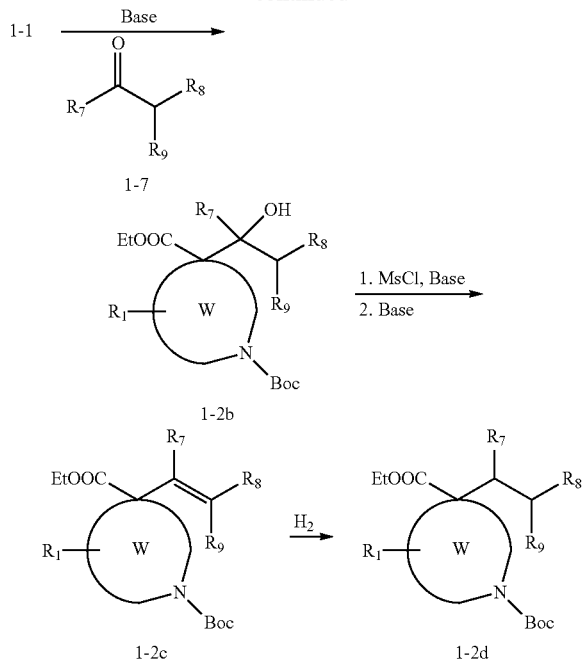

wherein for Scheme I above. X is selected from: Cl, Br, I, p-toluenesulfonyl (Tos), methanesulfonyl (Ms) and trifluoromethanesulfonyl (Tf).

In Scheme I, a substituted cyclic ester 1-1 is deprotonated in the presence of a strong base, such as LDA, LHMDS, or the like, followed by alkylation to produce 1-2a. Reduction of 1-2a followed by alkylation gives the ether 1-4. Deprotection of the Boc group of 1-4 is carried out in the presence of an acid, such as TFA, HCl or the like. Reductive amination of 1-5 with a suitable aldehyde or ketone 1-5a or alkylation of 1-5 with 1-5b under basic conditions gives 1-6. The compounds with different moieties from $R^1$ are exemplified by the synthesis of intermediates such as 1-2b, 1-2c, or 1-2d. Reaction of 1-1 with a suitable ketone or aldehyde 1-7 gives the intermediate 1-2b. Activation of the hydroxyl group of 1-2b using MsCl followed by the elimination in the presence of bases, such as DBU or the like, produces the unsaturated intermediates 1-2c. Hydrogenation of 1-2c gives the intermediate 1-2d.

Scheme 2
Compounds where "A" of Formula I is a cyclic alkyl or cyclic heteroalkyl moiety are synthesized as illustrated in Scheme 2. The synthesis of compounds 2-6 is used as an example.

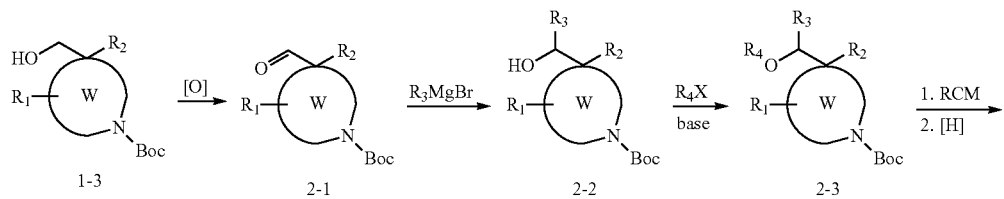

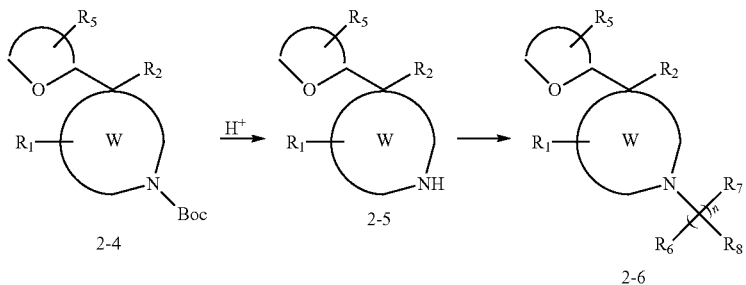

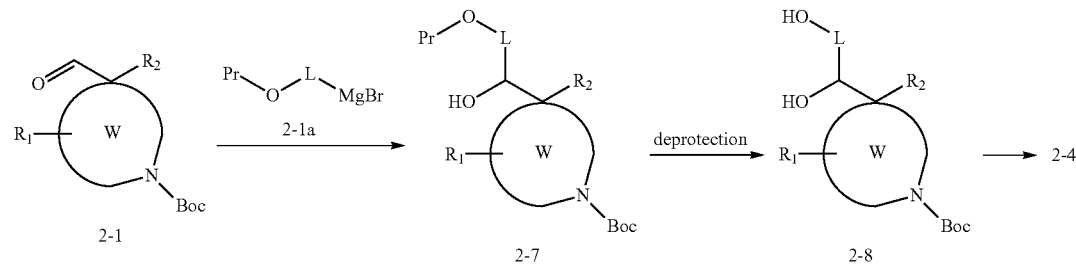

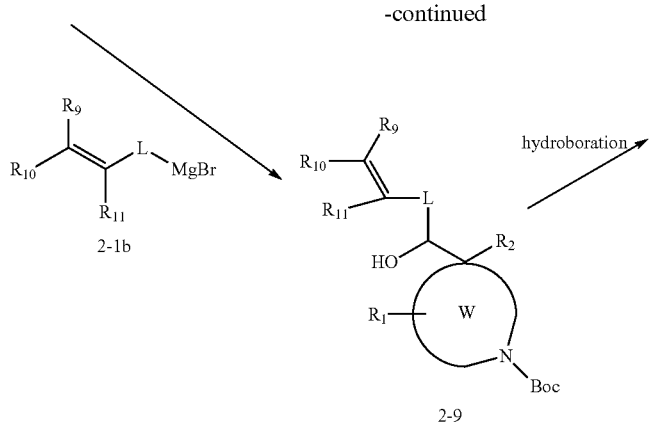

L: alkyl or heteroalkyl linkers; Pr: protection groups

Oxidation of 1-3 to 2-1 is carried out by Swern oxidation or other oxidants, such as Dess-Martin Periodiane or the like. Grignard reaction of aldehyde 2-1 with an unsaturated or a saturated Grignard reagent, followed by alkylation with an unsaturated or a saturated alkylating reagent under basic condition gives 2-3. Ring-closing metathesis (RCM) of 2-3 with a catalyst, such as Grubbs ruthenium-carbene complexes or the like, yields an unsaturated oxygen-containing heterocyclic 2-4 or a saturated oxygen-containing heterocyclic 2-4 after hydrogenation. Alternatively, the synthesis of 2-4 is achieved by a Grignard reaction of 2-1 with 2-1a or 2-1b, followed by either deprotection of the intermediate 2-7 or hydroboration of double bond of the intermediate 2-9 to give the corresponding diol 2-8. The diol 2-8 is converted to 2-4 by intramolecular cyclization under Mitsunobu reaction condition or displacement of the corresponding mesylates, tosylates, or the like.

Finally, the synthesis of 2-6 from 2-4 is achieved using the same methodology as the conversion of 1-4 to 1-6 in Scheme 1.

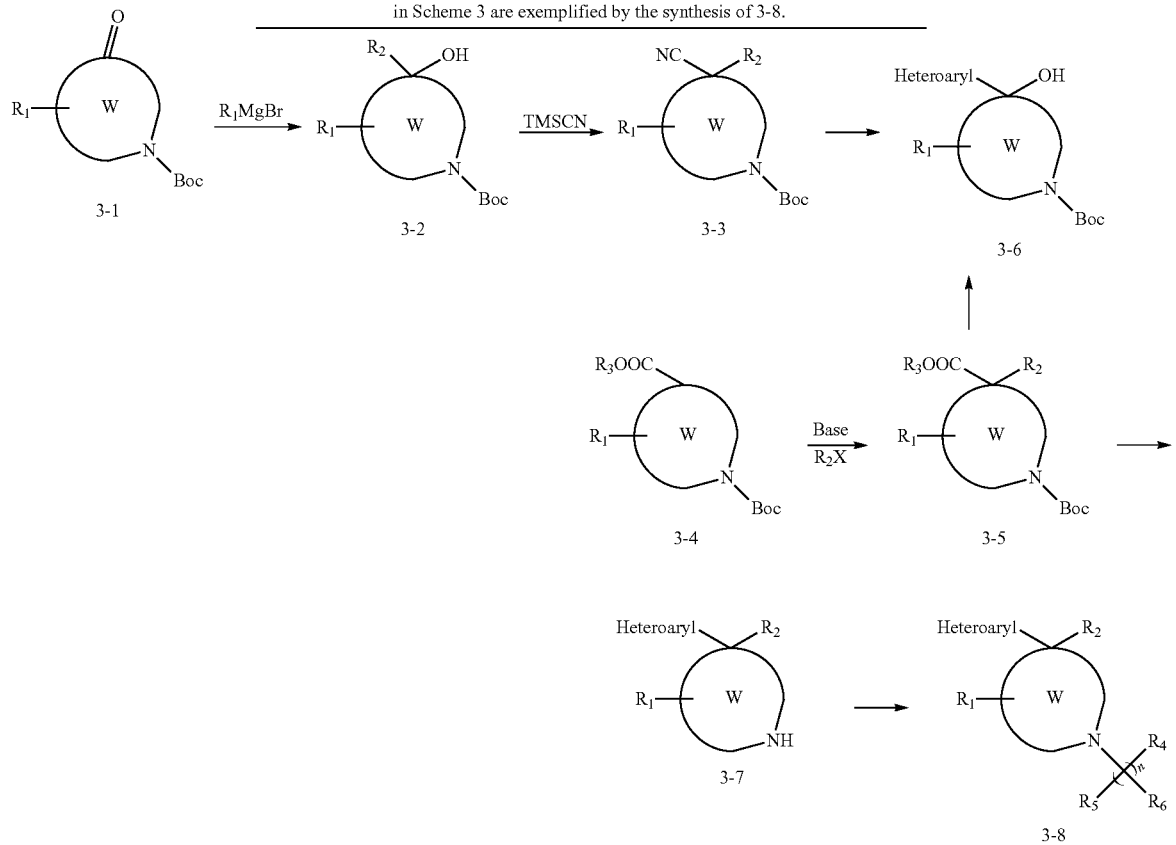

Scheme 3
Compounds where "A" of Formula I is a heteroaryl moiety are synthesized as illustrated in Scheme 3 are exemplified by the synthesis of 3-8.

-continued

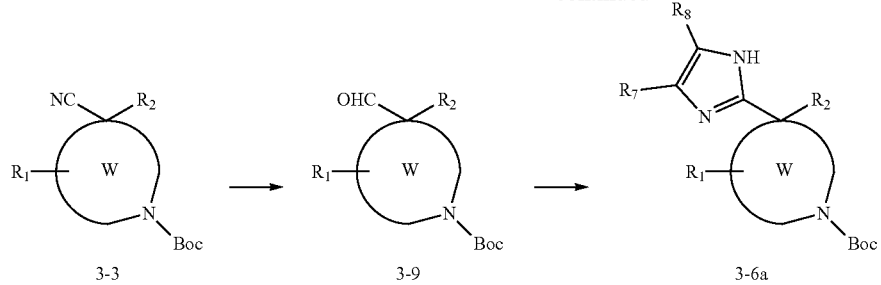

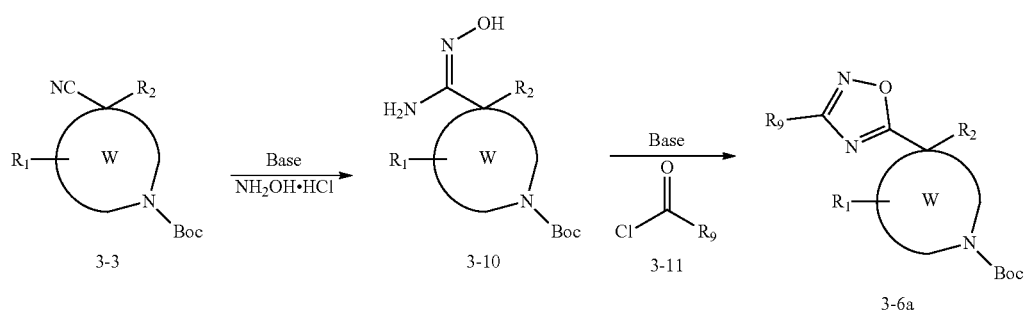

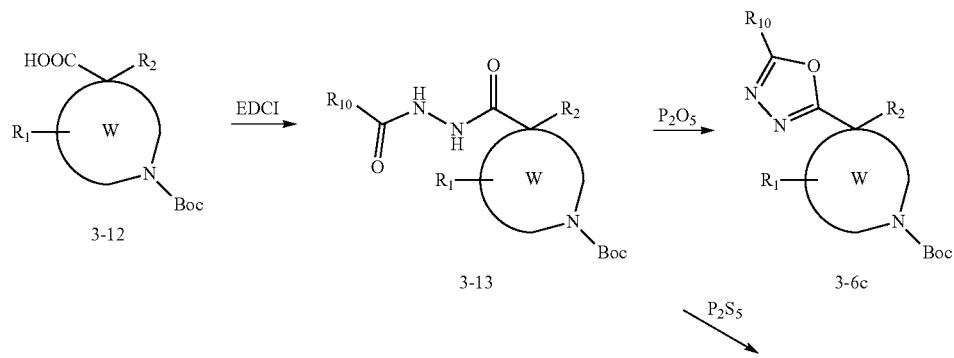

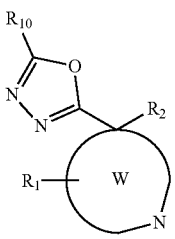

The cyano intermediate 3-3 and the ester intermediate 3-5 are prepared from substituted 3-2 by cynidation and 3-4 by alkylation as described in Scheme 1. The cyano group of 3-3 and the ester group of 3-5 are converted to heterocyclic rings such as imidazole, thiazole, thiadiazole, oxadiazole 3-6 (3-6a, 3-6b, 3-6c and 3-6d), etc. through the corresponding intermediates such as amide, thioamide, hydrazide, thiohydrazide or N-hydroxy-imidamide using the common methods exemplified in the scheme 3. The conversion of 3-6 to 3-8 is achieved using the methodology illustrated in Scheme 1.

Scheme 4
Compounds where "A" of Formula I is a heteroalkyl moiety are synthesized as illustrated in Scheme 4 and exemplified by the synthesis of 4-6.

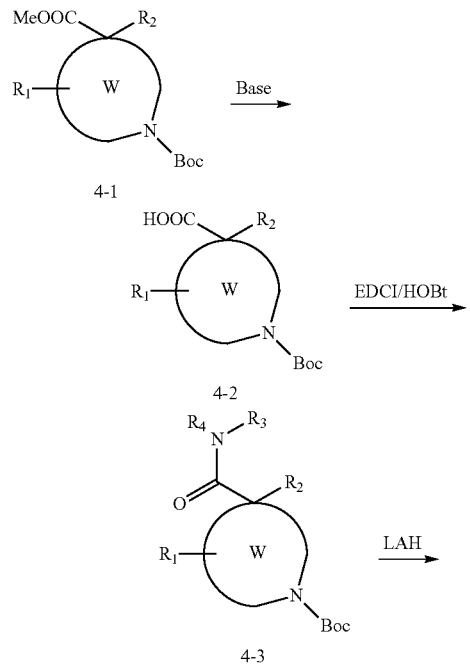

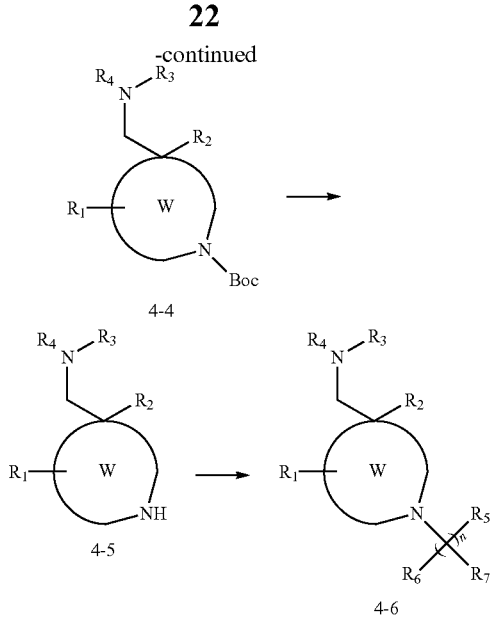

A suitable substituted cyclic amide 4-3 is prepared from the corresponding ester 4-1 by hydrolysis using bases, such as NaOH, LiOH, KOH, or the like, followed by coupling with an amine in the presence of coupling reagents, such as EDCl/HOBt, DCC, HATU, or the like. Reduction of 4-3 using $BH_3$ or $LiAlH_4$, followed by deprotection of Boc group of 4-4 and alkylation of 4-5 as described in Scheme 1 yields compound 4-6.

Scheme 5
As illustrated in Scheme 5, compounds where Y and Q of Formula I are certain moieties are synthesized.

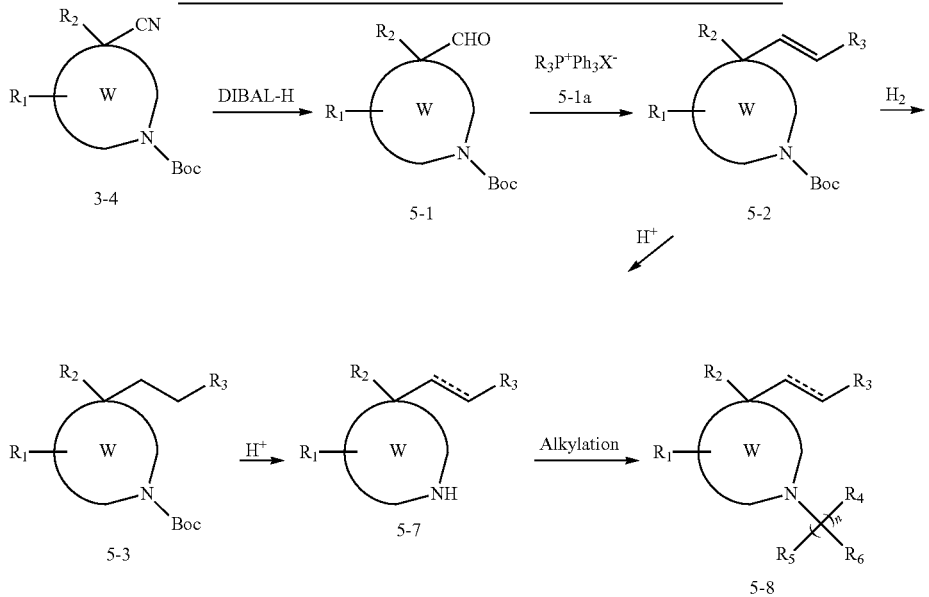

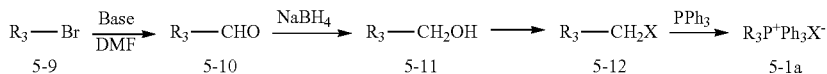

Reduction of CN group to aldehyde 5-1, followed by Wittig reaction with a quaternary phosphonium salt such as 5-1a produces compound 5-2. Hydrogenation of the double bond of 5-2 followed by deprotection or deprotection of 5-2 followed by the alkylation gives either an unsaturated or a saturated compound 5-8. The quaternary phosphonium salt 5-1a is prepared from a suitable bromide 5-9. Conversion of a suitable bromide 5-9 to the corresponding aldehyde 5-10, followed by reduction of the aldehyde with a suitable reducing agent, such as $NaBH_4$ or the like, gives alcohol 5-11. Halogenation of alcohol 5-11, followed by the treatment with $PPh_3$ gives a quaternary phosphonium salt 5-1a.

Scheme 6
As illustrated in Scheme 6, compounds where Y and Q of Formula I are other moieties than in Scheme 5 are synthesized.

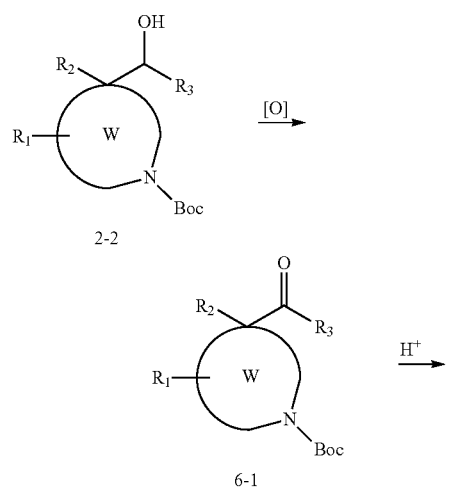

Scheme 7
As illustrated in Scheme 7, compounds where Z amd T of Formula I are particular moieties are synthesized.

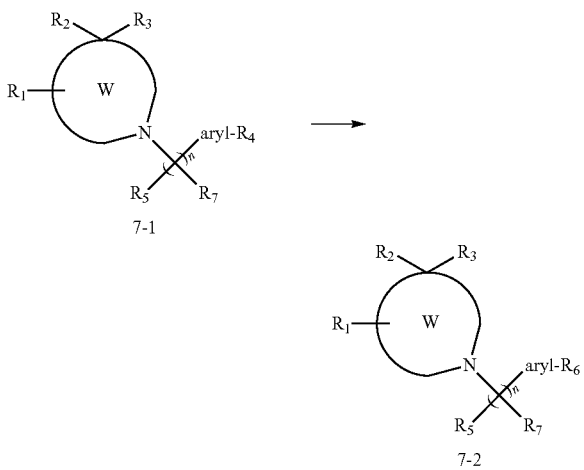

$R_4$ = Br, CN, $NO_2$, COOH, COOEt, pinacol boric ester, alkynyl
$R_6$ = alkynyl, aryl, heteroaryl The starting 7-1 is a group of intermediates which are prepared according to the schemes 1 to 6. The aryl group of 7-1 is a substituted or an unsubstituted aryl group, such as benzene, thiazolyl, thiophenyl, furanyl, imidazolyl, thiadiazolyl, oxadiazolyl, tetrazolyl. The $R_4$ is a functional group such as Br, I, CN, COOH, COOEt, boric acid. The conversion of $R_4$ to $R_6$ is achieved via Suzuki coupling of boric acid with Br or I, or the cyclization of hydrazide of ester with acid or the cyclization of N-hydroxy-imidamide with an acyl chloride.

Scheme 8
Scheme 8 illustrates one of the approaches for the synthesis of stereo isomers. In addition, the synthesis of the two enantiomerically pure isomers is also achieved by the chiral separation via chiral HPLC, chiral resolution, or column chromatography methods.

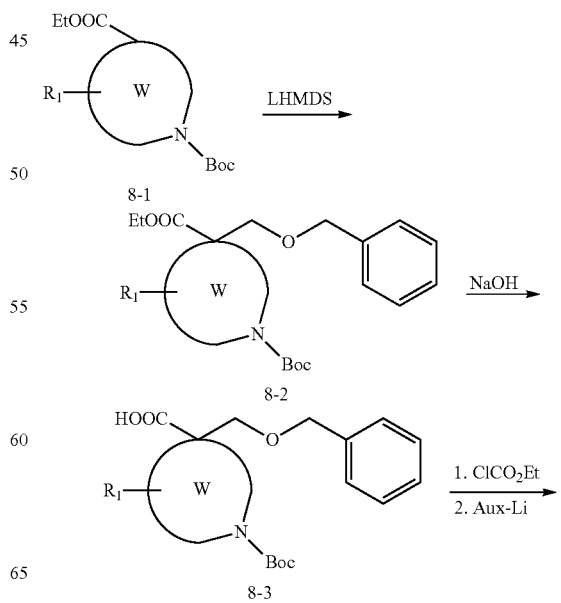

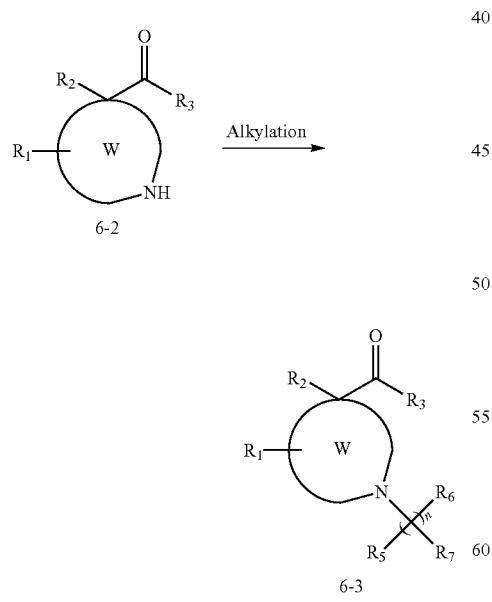

Alcohol 2-2 is oxidized with oxidants such as Dess-Martin Periodiane, PCC, or the like to form ketone 6-1. Deprotection of the Boc group of 6-1, followed by alkylation generates 6-3.

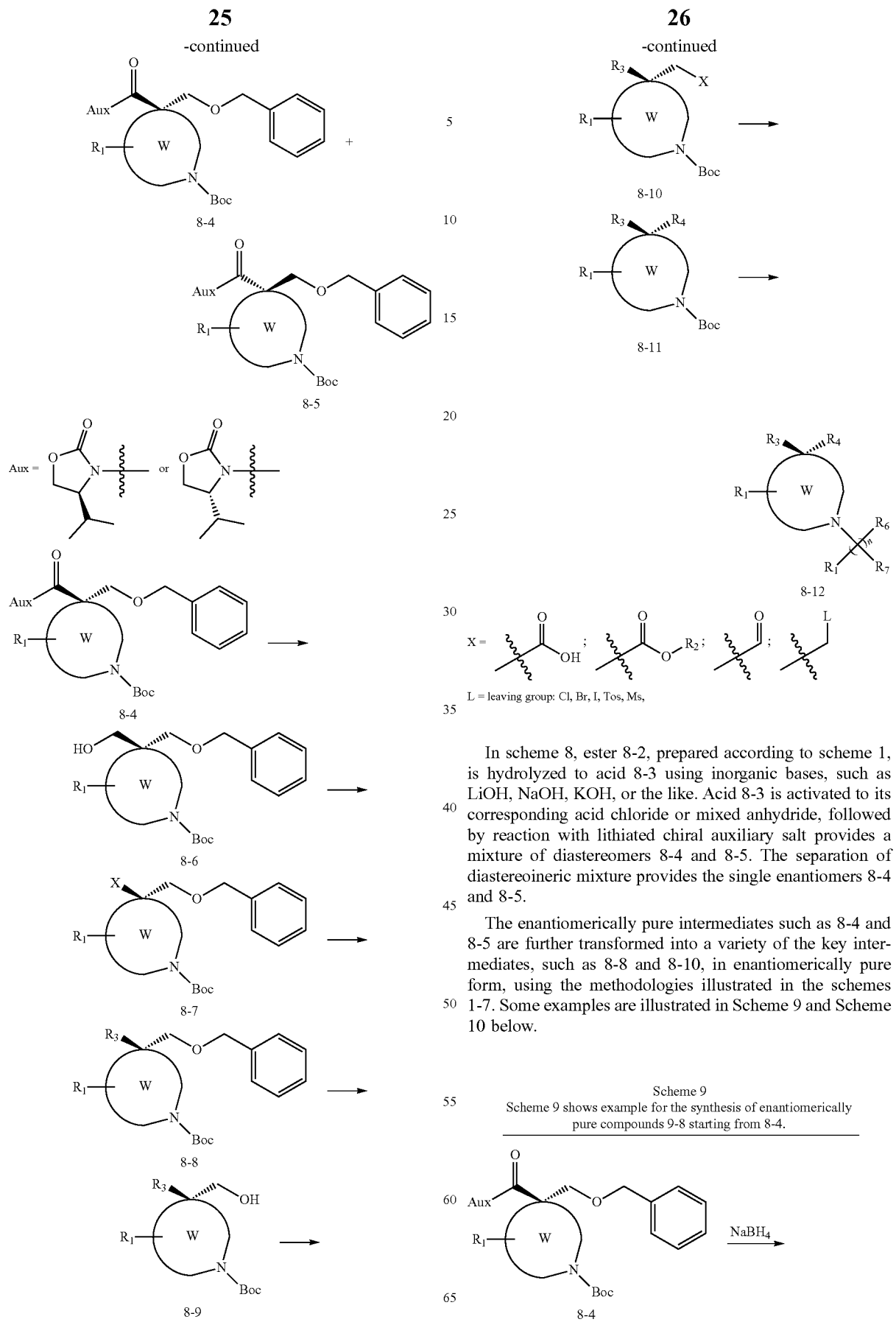

In scheme 8, ester 8-2, prepared according to scheme 1, is hydrolyzed to acid 8-3 using inorganic bases, such as LiOH, NaOH, KOH, or the like. Acid 8-3 is activated to its corresponding acid chloride or mixed anhydride, followed by reaction with lithiated chiral auxiliary salt provides a mixture of diastereomers 8-4 and 8-5. The separation of diastereoineric mixture provides the single enantiomers 8-4 and 8-5.

The enantiomerically pure intermediates such as 8-4 and 8-5 are further transformed into a variety of the key intermediates, such as 8-8 and 8-10, in enantiomerically pure form, using the methodologies illustrated in the schemes 1-7. Some examples are illustrated in Scheme 9 and Scheme 10 below.

Scheme 9
Scheme 9 shows example for the synthesis of enantiomerically pure compounds 9-8 starting from 8-4.

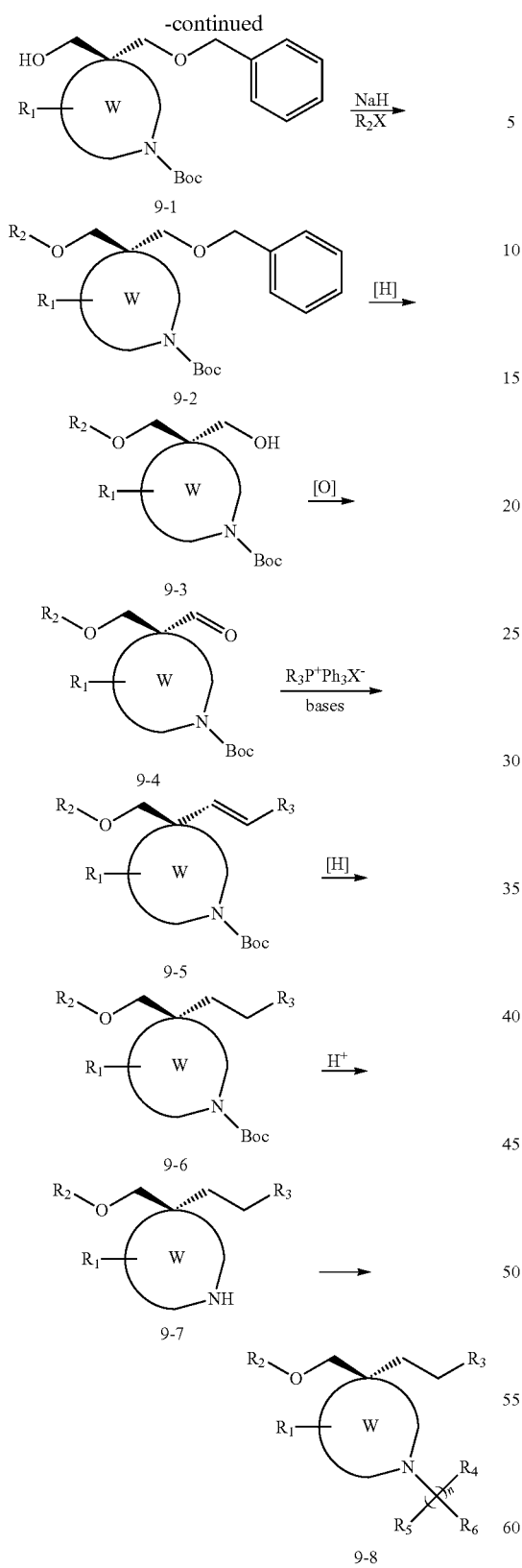

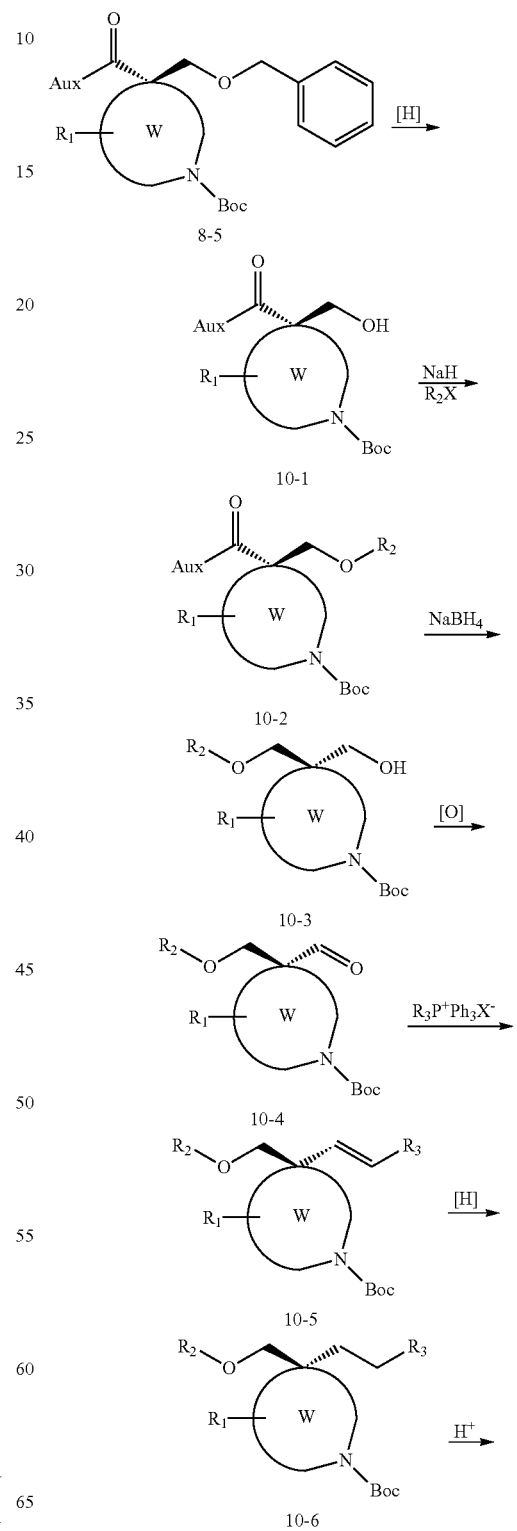

Using the same methodology as demonstrated in Scheme 9, the enantiomer of 9-8 is synthesized starting from the enantiomerically pure intermediate 8-5.

Scheme 10
Scheme 10 shows an example for the synthesis of enantiomerically pure compounds 10-8 starting from 8-5.

The enantiomerically pure intermediate 8-4 described in Scheme 8 is reduced using $NaBH_4$ to a chiral alcohol 9-1. The transformation of alcohol 9-1 to 9-8 is carried out according to the methodologies described in schemes 1 to 5.

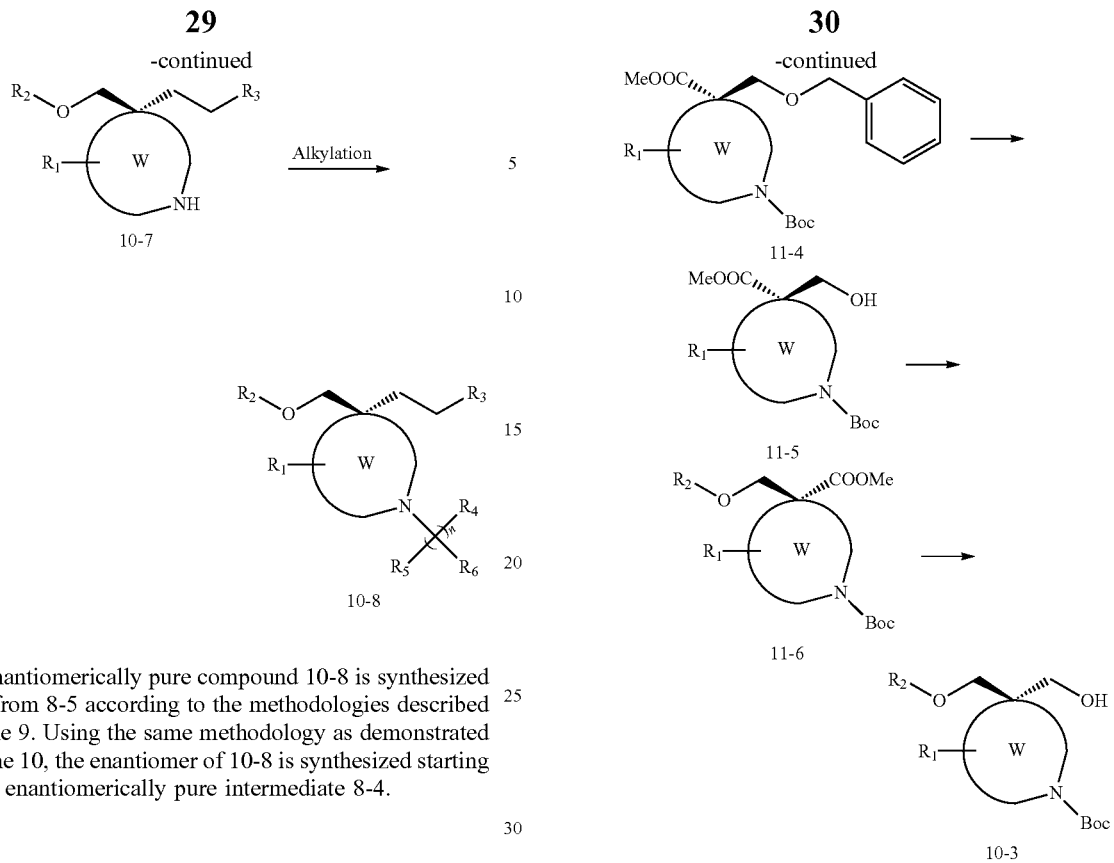

The enantiomerically pure compound 10-8 is synthesized starting from 8-5 according to the methodologies described in scheme 9. Using the same methodology as demonstrated in Scheme 10, the enantiomer of 10-8 is synthesized starting from the enantiomerically pure intermediate 8-4.

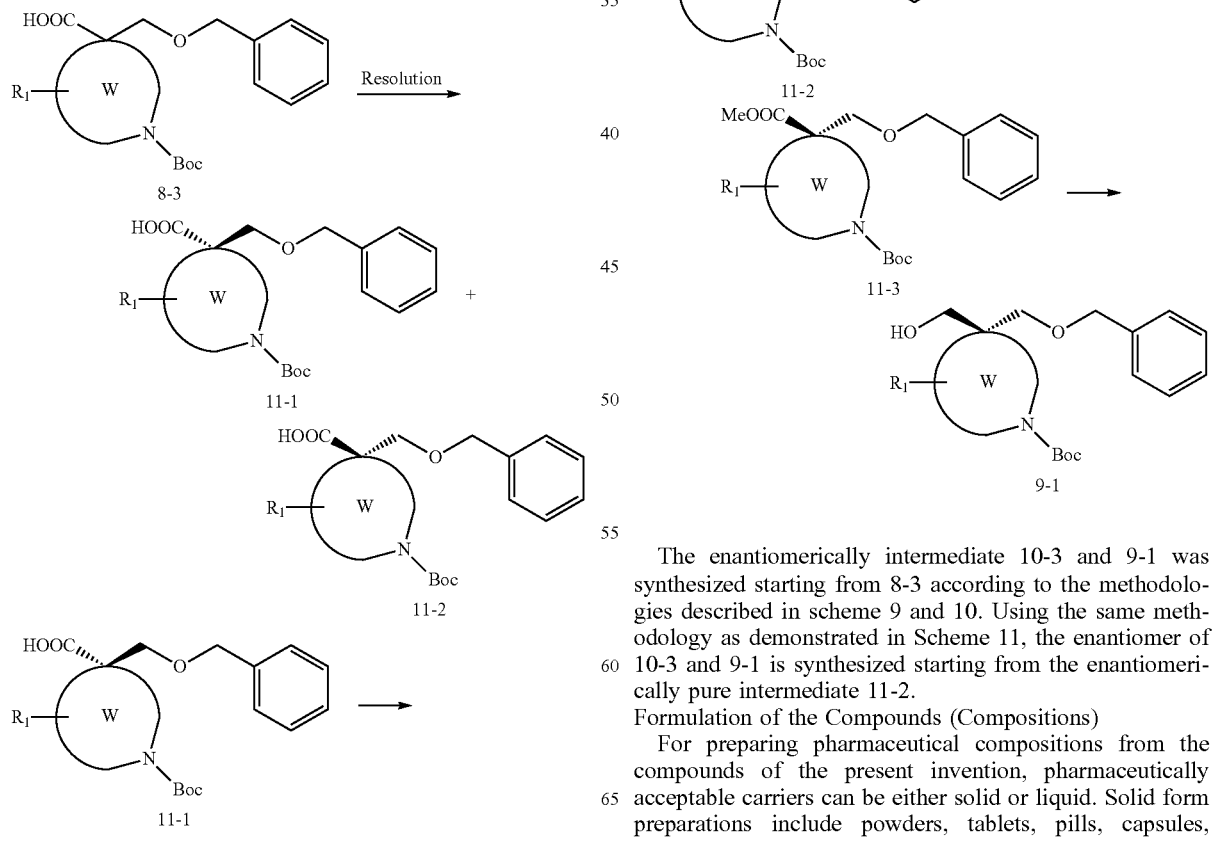

The enantiomerically intermediate 10-3 and 9-1 was synthesized starting from 8-3 according to the methodologies described in scheme 9 and 10. Using the same methodology as demonstrated in Scheme 11, the enantiomer of 10-3 and 9-1 is synthesized starting from the enantiomerically pure intermediate 11-2.

Formulation of the Compounds (Compositions)

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted to provide a pharmaceutically acceptable dosage of the active component.

EXAMPLES

The following examples are illustrative, but not limiting, of the methods and compositions described herein. Other suitable modifications and adaptations of the variety of conditions and parameters normally encountered in therapy and that are obvious to those skilled in the art are within the spirit and scope of the compounds and methods described herein.

In the examples below, unless otherwise stated, temperatures are given in degrees Celsius (° C.); operations were carried out at room or ambient temperature, "rt," or "RT," (typically a range of from about 18-25° C.); evaporation of solvent was carried out using a rotary evaporator under reduced pressure (typically, 4.5-30 mm Hg) with a bath temperature of up to 60° C.; the course of reactions was typically followed by thin layer chromatography (TLC) and reaction times are provided for illustration only; melting points are uncorrected; products exhibited satisfactory $^1$H-NMR and/or microanalytical data; yields are provided for illustration only; and the following conventional abbreviations are also used: mp (melting point), L (liter(s)), mL (milliliters), mmol (millimoles), g (grams), mg (milligrams), min (minutes), and h (hours).

Example 1

1. Synthesis of N-(4-((3-(ethoxymethyl)-3-phenethylpyrrolidin-1-yl)methyl)phenyl)acetamide

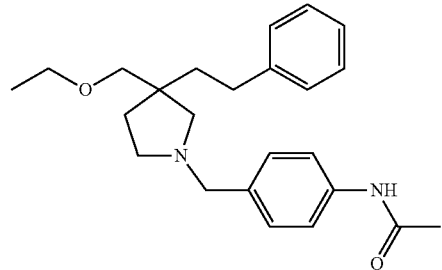 [SMILES: CCOCC1(CCc2ccccc2)CCN(Cc2ccc(NC(C)=O)cc2)C1]

1.1 Preparation of 1-tert-butyl 3-methyl 3-phenethylpyrrolidine-1,3-dicarboxylate To a solution of LHMDS (193.4 mL, 193.4 mmol, 1 M in THF solution) in anhydrous THF (350 mL) under N$_2$ atmosphere at −78° C. was added dropwise a solution of (2-iodoethyl)benzene (44.87 g, 193.4 mmol) and 1-tert-butyl 3-methyl pyrrolidine-1,3-dicarboxylate (22.2 g, 96.7 mmol) in anhydrous THF (350 mL) over 1.5 h. After the completion of addition, the mixture was stirred at −78° C. for 1 h, followed by stirring at −40° C. for 3 h before it was warmed to RT and stirred overnight. Upon completion of the reaction, the reaction was quenched with aqueous NH$_4$Cl and the resulting mixture was extracted with EtOAc. The organic layer was separated, washed with brine, and dried over anhydrous Na$_2$SO$_4$. After filtration and concentration under reduced pressure, the crude product was purified by silicagel column chromatography (Hexane:EtOAc=40:1) to give 19.06 g of 1-tert-butyl 3-methyl 3-phenethylpyrrolidine-1,3-dicarboxylate as a colorless oil. LC-MS (ESI+): m/z 356 [M+Na]$^+$.

1.2 Preparation of tert-butyl 3-(hydroxymethyl)-3-phenethylpyrrolidine-1-carboxylate To a solution of 1-tert-butyl 3-methyl 3-phenethylpyrrolidine-1,3-dicarboxylate (19.06 g, 57.2 mmol) in anhydrous THF (190 mL) under N$_2$ atmosphere at −10° C. was added lithium aluminum hydride (3.26 g, 85.8 mmol) in portions. The reaction mixture was stirred at −10° C. for 2 h before the reaction was quenched slowly by the addition of water (3.2 mL), 15% NaOH (3.2 mL) and water (9.6 mL). After stirred for 30 min, the mixture was extracted with EtOAc. The organic layer was washed with brine, dried over anhydrous Na$_2$SO$_4$, filtered and concentrated under a reduced pressure. The residue was purified by silica-gel column chromatography (Hexane:EtOAc=10:1) to give 18 g of tort-butyl 3-(hydroxymethyl)-3-phenethylpyrrolidine-1-carboxylate as a colorless oil. LC-MS (ESI+): m/z 328 [M+Na]$^+$.

1.3 Preparation of tert-butyl 3-(ethoxymethyl)-3-phenethylpyrrolidine-1-carboxylate To a solution of tert-butyl 3-(hydroxymethyl)-3-phenethylpyrrolidine-1-carboxylate (6 g, 19.7 mmol) in DMF (60 mL) at 0° C. was added NaH (1.6 g, 39.4 mmol, 60% in mineral oil) in portions and followed by addition of bromoethane (6.4 g, 59.1 mmol). The reaction mixture was allowed to warm to RT and stirred overnight. The reaction was quenched with water and extracted with EtOAc. The organic layer was washed with brine, dried over Na$_2$SO$_4$ and concentrated under a reduced pressure. The residue was purified by silica-gel column chromatography (Hexane:EtOAc=50:1) to give 6 g of tert-butyl 3-(ethoxymethyl)-3-phenethylpyrrolidine-1-carboxylate as a colorless oil. LC-MS (ESI+): m/z 334 [M+H]$^+$.

1.4 Preparation of 3-(ethoxymethyl)-3-phenethylpyrrolidine

To a solution of tert-butyl 3-(ethoxymethyl)-3-phenethylpyrrolidine-1-carboxylate (6 g, 18 mmol) in DCM (30 mL) at 0° C. was added TFA (6 mL) dropwise. The reaction mixture was warmed to RT and stirred for 5 h before it was quenched with water. After the pH of the mixture was adjusted to 8 with an aqueous Na$_2$CO$_3$ solution, the mixture was extracted with DCM. The organic layer was washed with brine, dried over Na$_2$SO$_4$ and concentrated in vacuo to afford 4.2 g of crude product 3-(ethoxymethyl)-3-phenethylpyrrolidine as an oil which was used directly for the next step without further purification. LC-MS (ESI+): m/z 234 [M+H]$^+$.

1.5 Preparation of N-(4-((3-(ethoxymethyl)-3-phenethylpyrrolidin-1-yl)methyl)phenyl)acetamide HCl To a mixture of 3-(ethoxymethyl)-3-phenethylpyrrolidine (100 mg, 0.42 mmol) and N-(4-formylphenyl)acetamide (81.5 mg, 0.50 mmol) in DCM (10 mL) at RT was added TEA (80.8 mg, 0.8 mmol). After the reaction mixture was stirred for 5 min, NaBH(OAc)$_3$ (356.2 mg, 1.68 mmol) was added and the resulting mixture was stirred overnight. Upon completion of the reaction, the mixture was treated with aqueous NaHCO$_3$ and extracted with DCM/MeOH (10:1). The organic layer was separated, dried over anhydrous Na$_2$SO$_4$ and concentrated in vacuo. After purification by silica-gel column chromatography, 42 mg of N-(4-((3-(ethoxymethyl)-3-phenethylpyrrolidin-1-yl)methyl)phenyl) acetamide was obtained. The product was dissolved in a solution of Et$_2$O/HCl (1 mL) and the mixture was stirred for 5 min before it was concentrated and washed with Et$_2$O twice to give 40 mg of N-(4-((3-(ethoxymethyl)-3-phenethylpyrrolidin-1-yl)methyl)phenyl)acetamide HCl salt as an yellow solid. LC-MS (ESI+): m/z 381 [M+H]$^+$.

2. Synthesis of N-(4-((3-(ethoxymethyl)-3-phenethylazetidin-1-yl)methyl)phenyl)acetamide

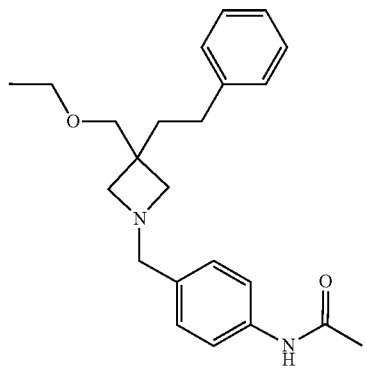 [SMILES: CCOCC1(CCc2ccccc2)CN(Cc2ccc(NC(C)=O)cc2)C1]

2.1 Preparation of 1-tert-butyl 3-methyl 3-(1-hydroxy-2-phenylethyl)azetidine-1,3-dicarboxylate To a solution of 1-tert-butyl 3-methyl azetidine-1,3-dicarboxylate (1 g, 4.6 mmol) in dry THF (20 mL) at −78° C. under N$_2$ atmosphere was added LDA (9.3 mmol) over 10 min. The reaction mixture was stirred at −78° C. for 1 h before a solution of 2-phenylacetaldehyde (720 mg, 6 mmol) in THF (10 mL) was added over 10 min. The reaction mixture was stirred at −78° C. for 30 min and then allowed to warm to RT over 1 h. Upon completion of the reaction, the reaction was quenched with water (20 mL) and extracted with EtOAc (50 mL×2). The combined organic phase was dried over Na$_2$SO$_4$ and concentrated under reduced pressure. The residue was purified by silica-gel column chromatography to give 800 mg of 1-tert-butyl 3-methyl 3-(1-hydroxy-2-phenylethyl)azetidine-1,3-dicarboxylate. LC-MS (ESI+): m/z 358 [M+Na]$^+$.

2.2 Preparation of 1-tert-butyl 3-methyl 3-(1-(methylsulfonyloxy)-2-phenylethyl)azetidine-1,3-dicarboxylate To a solution of 1-cert-butyl 3-methyl 3-(1-hydroxy-2-phenylethyl)azetidine-1,3-dicarboxylate (800 mg, 2.38 mmol) in DCM (20 mL) was added TEA (600 mg, 5.91 mmol) and MsCl (545 mg, 4.76 mmol). The reaction was stirred at RT for 24 h. Upon completion of the reaction, the reaction was quenched with water (20 mL) and extracted with DCM (100 mL×2). The combined organic phase was dried over Na$_2$SO$_4$ and concentrated to afford 900 mg of 1-tert-butyl 3-methyl 3-(1-(methylsulfonyloxy)-2-phenylethyl)azetidine-1,3-dicarboxylate, which was used directly for the next step without further purification. LC-MS (ESI+): m/z 414 [M+H]$^+$.

2.3 Preparation of (E)-1-tert-butyl 3-methyl 3-styrylazetidine-1,3-dicarboxylate To a solution of 1-tert-butyl 3-methyl 3-(1-(methylsulfonyloxy)-2-phenylethyl) azetidine-1,3-dicarboxylate (900 mg, 2.18 mmol) in toluene (40 mL) was added DBU (1 g, 6.62 mmol). The reaction was stirred at 60° C. overnight. Upon completion of the reaction, the reaction was quenched with water (30 mL) and extracted with EtOAc (100 mL×2). The combined organic phase was dried over Na$_2$SO$_4$ and concentrated under a reduced pressure. The residue was purified by silica-gel column chromatography to give 550 mg of (E)-1-tert-butyl 3-methyl 3-styrylazetidine-1,3-dicarboxylate. LC-MS (ESI+): m/z 340 [M+Na]$^+$.

2.4 Preparation of 1-tert-butyl 3-methyl 3-phenethylazetidine-1,3-dicarboxylate To a mixture of (E)-1-tert-butyl 3-methyl 3-styrylazetidine-1,3-dicarboxylate (500 mg, 1.58 mmol) and Pd/C (100 mg, 10%) in methanol (30 mL) was bubbled with hydrogen (1 atm) for 3 h. Upon completion of the reaction, the reaction mixture was filtered and the filtrate was concentrated to afford 500 mg of 1-tert-butyl 3-methyl 3-phenethylazetidine-1,3-dicarboxylate, which was used directly for the next step without further purification. LC-MS (ESI+): m/z 342 [M+Na]$^+$.

2.5 Preparation of tert-butyl 3-(hydroxymethyl)-3-phenethylazetidine-1-carboxylate The title compound was prepared from 1-tert-butyl 3-methyl 3-phenethylazetidine-1,3-dicarboxylate according to the procedure 1.2. LC-MS (ESI+): m/z 314 [M+Na]$^+$.

2.6 Preparation of tert-butyl 3-(ethoxymethyl)-3-phenethylazetidine-1-carboxylate The title compound was prepared from tert-butyl 3-(hydroxymethyl)-3-phenethylazetidine-1-carboxylate according to the procedure 1.3. LC-MS (ESI+): m/z 342 [M+Na]$^+$.

2.7 Preparation of 3-(ethoxymethyl)-3-phenethylazetidine

The title compound was prepared from tert-butyl 3-(ethoxymethyl)-3-phenethylazetidine-1-carboxylate according to the procedure 1.4. LC-MS (ESI+): m/z 220 [M+H]$^+$.

2.8 Preparation of N-(4-((3-(ethoxymethyl)-3-phenethylazetidin-1-yl)methyl)phenyl)acetamide The title compound was prepared from 3-(ethoxymethyl)-3-phenethylazetidine according to the procedure 1.5. LC-MS (ESI+): m/z 367 [M+H]$^+$.

3 Synthesis of N-(4-((4-(ethoxymethyl)-4-phenethylazepan-1-yl)methyl)phenyl)acetamide

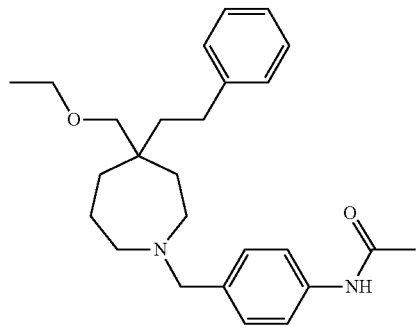 [SMILES: CCOCC1(CCc2ccccc2)CCCN(Cc2ccc(NC(C)=O)cc2)CC1]

3.1 Preparation of 1-(tert-butyl) 4-ethyl 5-oxoazepane-1,4-dicarboxylate

To a solution of tert-butyl 4-oxopiperidine-1-carboxylate (18.1 g, 90.87 mmol) in Et$_2$O (150 mL) under N$_2$ atmosphere at −78° C. was added dropwise ethyl 2-diazoacetate (10.38 g, 90.87 mmol) and BF$_3$/Et$_2$O (27.7 g, 90.87 mmol). The reaction mixture was stirred at −78° C. for 1 h. Upon completion of the reaction, the reaction was quenched with a saturated aqueous Na$_2$CO$_3$ solution and extracted with EtOAc (100 mL×3). The combined organic phase was washed with aqueous NaCl twice, dried over Na$_2$SO$_4$ and concentrated under reduced pressure. The residue was purified by silica-gel column chromatography to afford 23.66 g of 1-(tert-butyl) 4-ethyl 5-oxoazepane-1,4-dicarboxylate. LC-MS (ESI+): m/z 308 [M+Na]$^+$.

3.2 Preparation of 1-(tert-butyl) 4-ethyl 5-hydroxyazepane-1,4-dicarboxylate To a solution of 1-(tort-butyl) 4-ethyl 5-oxoazepane-1,4-dicarboxylate (21.5 g, 75.4 mmol) in MeOH/THF (60 mL/120 mL) under N$_2$ atmosphere at −78° C. was added NaBH$_4$ (2.85 g, 75.4 mmol) in portions. The mixture was stirred at −78° C. for 1 h. Upon completion of the reaction, the reaction was quenched with water (100 mL) and extracted with EtOAc (150 mL×3). The combined organic phase was dried over Na$_2$SO$_4$ and concentrated under reduced pressure. The residue was purified by silica-gel column chromatography to afford 15.49 g of 1-(tert-butyl) 4-ethyl 5-hydroxyazepane-1,4-dicarboxylate. LC-MS (ESI+): m/z 310 [M+Na]$^+$.

3.3 Preparation of 1-(tert-butyl) 4-ethyl 5-((methylsulfonyl)oxy)azepane-1,4-dicarboxylate To a solution of 1-(tert-butyl) 4-ethyl 5-hydroxyazepane-1,4-dicarboxylate (6.23 g, 21.68 mmol) in DCM (50 mL) was added TEA (5.47 g, 54.2 mmol) and MsCl (3.73 g, 32.52 mmol) under N$_2$ atmosphere at −15° C. The reaction mixture was stirred at −15° C. for 0.5 h before it was warmed to RT and stirred overnight. Upon completion, the reaction mixture was quenched with water (100 mL) and extracted with EtOAc (100 mL×3). The combined organic phase was dried over Na$_2$SO$_4$ and concentrated under reduced pressure. The residue was purified by silica-gel column chromatography to afford 5.0 g of 1-(tert-butyl) 4-ethyl 5-((methylsulfonyl)oxy)azepane-1,4-dicarboxylate as an yellow oil. LC-MS (ESI+): m/z 388 [M+Na]$^+$.

3.4 Preparation of 1-(tert-butyl) 4-ethyl 2,3,6,7-tetrahydro-1H-azepine-1,4-dicarboxylate A solution of 1-(tert-butyl) 4-ethyl 5-((methylsulfonyl)oxy)azepane-1,4-dicarboxylate (5.0 g, 13.7 mmol) and DBU (10 mL) in toluene (50 mL) was heated to 60° C. and stirred overnight. Upon completion of the reaction, the reaction mixture was quenched with water (70 mL) and extracted with EtOAc (100 mL×3). The combined organic phase was dried over Na$_2$SO$_4$ and concentrated under reduced pressure. The residue was purified by silica-gel column chromatography to afford 3.31 g of 1-(tert-butyl) 4-ethyl 2,3,6,7- tetrahydro-1H-azepine-1,4-dicarboxylate as a yellow oil. LC-MS (ESI+): m/z 292 [M+Na]+.

3.5 Preparation of 1-(tert-butyl) 4-ethyl azepane-1,4-dicarboxylate

The title compound was prepared from 1-(tert-butyl) 4-ethyl 2,3,6,7-tetrahydro-1H-azepine-1,4-dicarboxylate according to the procedure 2.4. LC-MS (ESI+): m/z 294 [M+Na]+.

3.6 Preparation of 1-(tert-butyl) 4-ethyl 4-phenethylazepane-1,4-dicarboxylate The title compound was prepared from 1-(tert-butyl) 4-ethyl azepane-1,4-dicarboxylate according to the procedure 1.1. LC-MS (ESI+): m/z 398 [M+Na]+.

3.7 Preparation of tert-butyl 4-(hydroxymethyl)-4-phenethylazepane-1-carboxylate The title compound was prepared from 1-(tert-butyl) 4-ethyl 4-phenethylazepane-1,4-dicarboxylate according to the procedure 1.2. LC-MS (ESI+): m/z 356 [M+Na]+.

3.8 Preparation of tert-butyl 4-(ethoxymethyl)-4-phenethylazepane-1-carboxylate The title compound was prepared from tert-butyl 4-(hydroxymethyl)-4-phenethylazepane-1-carboxylate according to the procedure 1.3. LC-MS (ESI+): m/z 362 [M+H]+.

3.9 Preparation of 4-(ethoxymethyl)-4-phenethylazepane

The title compound was prepared from tert-butyl 4-(ethoxymethyl)-4-phenethylazepane-1-carboxylate according to the procedure 1.4. LC-MS (ESI+): m/z 262 [M+H]+.

3.10 Preparation of N-(4-((4-(ethoxymethyl)-4-phenethylazepan-1-yl)methyl)phenyl)acetamide The title compound was prepared from 4-(ethoxymethyl)-4-phenethylazepane according to the procedure 1.5. LC-MS (ESI+): m/z 409 [M+H]+.

4 Synthesis of 4-(1-(3-(ethoxymethyl)-3-phenethylpyrrolidin-1-yl)ethyl)-1-methyl-1H-pyrazole

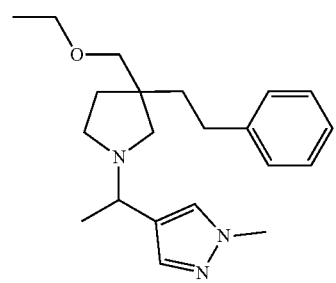 [SMILES: CCOCC1(CCc2ccccc2)CCN(C(C)c2cnn(C)c2)C1]

To a solution of 3-(ethoxymethyl)-3-phenethylpyrrolidine (155 mg, 0.66 mmol) and 1-methyl-1H-pyrazole-4-carbaldehyde (55 mg, 0.44 mmol) in dichloromethane (5 mL) at RT was added LiClO4 (23 mg, 0.22 mmol). The mixture was stirred at RT for 0.5 h before methylmagnesium bromide (0.66 mL, 0.66 mmol, 1M in THF) was added dropwise. The reaction mixture was stirred for 2 h. Upon completion of the reaction, the reaction mixture was quenched with water (20 mL) and extracted with EtOAc (15 mL×3). The combined organic phase was dried over Na2SO4 and concentrated under reduced pressure. The residue was purified by silica-gel column chromatography to give 21.8 mg of 4-(1-(3-(ethoxymethyl)-3-phenethylpyrrolidin-1-yl)ethyl)-1-methyl-1H-pyrazole as a yellow oil. LC-MS (ESI+): m/z 342 [M+H]+.

5 Synthesis of 3-(1-(3-(ethoxymethyl)-3-phenethylpyrrolidin-1-yl)ethyl)pyridine

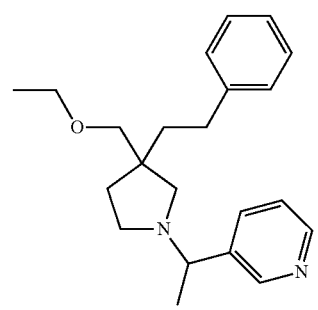 [SMILES: CCOCC1(CCc2ccccc2)CCN(C(C)c2cccnc2)C1]

5.1 Preparation of 3-(1-chloroethyl)pyridine

The title compound was prepared from 1-(pyridin-3-yl)ethanol according to the procedure 2.2. LC-MS (ESI+): m/z 142 [M+H]+.

5.2 Preparation of 3-(1-(3-(ethoxymethyl)-3-phenethylpyrrolidin-1-yl)ethyl)pyridine To a solution of 3-(ethoxymethyl)-3-phenethylpyrrolidine (50 mg, 0.21 mmol) in acetonitrile (10 mL) was added potassium carbonate (86 mg, 0.63 mmol) and 3-(1-chloroethyl)pyridine (30 mg, 0.21 mmol). The reaction mixture was stirred at 60° C. overnight. Upon completion of the reaction, the reaction mixture was quenched with water (20 mL) and extracted with DCM/MeOH=15:1 (20 mL×3). The combined organic phase was dried over Na2SO4 and concentrated under reduced pressure. The residue was purified by silica-gel column chromatography (DCM/MeOH=15:1) to give 25 mg of 3-(1-(3-(ethoxymethyl)-3-phenethylpyrrolidin-1-yl)ethyl)pyridine as a light yellow oil. LC-MS (ESI+): m/z 339 [M+H]+.

6 Synthesis of N-(4-((4-phenethyl-4-(tetrahydrofuran-2-yl)piperidin-1-yl)methyl)phenyl)acetamide

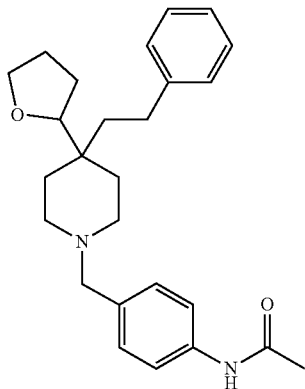 [SMILES: CC(=O)Nc1ccc(CN2CCC(CCc3ccccc3)(C3CCCO3)CC2)cc1]

6.1 Preparation of tert-butyl 4-formyl-4-phenethylpiperidine-1-carboxylate

To a solution of tert-butyl 4-(hydroxymethyl)-4-phenethylpiperidine-1-carboxylate (3 g, 9.4 mmol) in DCM (50 mL) was added Dess-Martin reagent (5.98 g, 14.1 mmol). The mixture was stirred at RT for 2 h. Upon completion of the reaction, the reaction mixture was quenched with aqueous sodium thiosulfate and sodium carbonate solution and stirred at RT for 0.5 h before it was extracted with DCM (30 mL×3). The combined organic phase was dried over $Na_2SO_4$ and concentrated under reduced pressure. The residue was purified by silica-gel column chromatography (EtOAc/hexane=1:6) to give 2.4 g of tert-butyl 4-formyl-4-phenethylpiperidine-1-carboxylate as a colorless oil. LC-MS (ESI+): m/z 318 $[M+H]^+$.

6.2 Preparation of tert-butyl 4(1-hydroxyallyl)-4-phenethylpiperidine-1-carboxylate To a solution of tert-butyl 4-formyl-4-phenethylpiperidine-1-carboxylate (200 mg, 0.63 mmol) in anhydrous ether (20 mL) under $N_2$ atmosphere at 0° C. was added vinylmagnesium bromide (0.7 mL, 1M in THF). The solution was stirred at 0° C. for 1 h. Upon completion of the reaction, the reaction mixture was quenched with water (10 mL) and extracted with EtOAc (100 mL×3). The combined organic phase was dried over $Na_2SO_4$ and concentrated under reduced pressure. The residue was purified by silica-gel column chromatography (EtOAc/hexane=1:10) to give 140 mg of tert-butyl 4-(1-hydroxyallyl)-4-phenethylpiperidine-1-carboxylate as a colorless oil. LC-MS (ESI+): m/z 346 $[M+H]^+$.

6.3 Preparation of tert-butyl 4-(1-hydroxyallyl)-4-phenethylpiperidine-1-carboxylate To a solution of tert-butyl 4-(1-hydroxyallyl)-4-phenethylpiperidine-1-carboxylate (140 mg, 0.57 mmol) in DMF (6 mL) under $N_2$ atmosphere at RT was added NaH (34 mg, 0.85 mmol, 60% in mineral oil). The mixture was stirred at RT for 0.5 h before 3-bromoprop-1-ene (102 mg, 0.85 mmol) was added. The reaction mixture was stirred at RT for 2 h. Upon completion, the reaction mixture was quenched with water (10 mL) and extracted with EtOAc (100 mL×3). The combined organic phase was dried over $Na_2SO_4$ and concentrated under reduced pressure. The residue was purified by silica-gel column chromatography (EtOAc/hexane=1:15) to give 180 mg of tert-butyl 4-(1-(allyloxy)but-3-en-1-yl)-4-phenethylpiperidine-1-carboxylate as a colorless oil. LC-MS (ESI+): m/z 386 $[M+H]^+$.

6.4 Preparation of tert-butyl 4-(2,5-dihydrofuran-2-yl)-4-phenethylpiperidine-1-carboxylate To a solution of 4-(1-(allyloxy)but-3-en-1-yl)-4-phenethylpiperidine-1-carboxylate (150 mg, 0.45 mmol.) in DCM (5 mL) at RT was added Grubbs II catalyst (15 mg) under $N_2$ atmosphere. The solution was stirred at RT for 3 h. Upon completion of the reaction, the reaction mixture was directly concentrated under reduced pressure. The residue was purified by silica-gel column chromatography (EtOAc/hexane=1:20) to give 120 mg of tert-butyl 4-(2,5-dihydrofuran-2-yl)-4-phenethylpiperidine-1-carboxylate as a colorless oil. LC-MS (ESI+): m/z 358 $[M+H]^+$.

6.5 Preparation of tert-butyl 4-phenethyl-4-(tetrahydrofuran-2-yl)piperidine-1-carboxylate The title compound was prepared from tert-butyl 4-(2,5-dihydrofuran-2-yl)-4-phenethylpiperidine-1-carboxylate according to the procedure 2.4. LC-MS (ESI+): m/z 360 $[M+H]^+$.

6.6 Preparation of 4-phenethyl-4-(tetrahydrofuran-2-yl)piperidine

The title compound was prepared from tert-butyl 4-phenethyl-4-(tetrahydrofuran-2-yl)piperidine-1-carboxylate according to the procedure 1.4. LC-MS (ESI+): m/z 260 $[M+H]^+$.

6.7 Preparation of N-(4-((4-phenethyl-4-(tetrahydrofuran-2-yl)piperidin-1-yl)methyl)phenyl)acetamide The title compound was prepared from 4-phenethyl-4-(tetrahydrofuran-2-yl)piperidine according to the procedure 1.5. LC-MS (ESI+): m/z 407 $[M+H]^+$.

7 Synthesis of N-(4-((4-(oxetan-2-yl)-4-phenethylpiperidin-1-yl)methyl)phenyl)acetamide

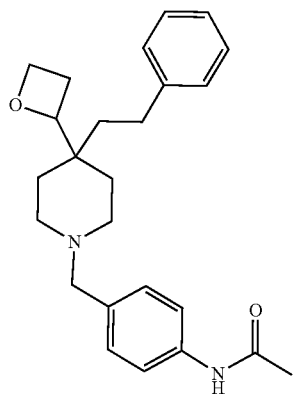 [SMILES: CC(=O)Nc1ccc(CN2CCC(CCc3ccccc3)(C3CCO3)CC2)cc1]

7.1 Preparation of tert-butyl 4-(oxiran-2-yl)-4-phenethylpiperidine-1-carboxylate To a mixture of trimethylsulfonium iodide (130 mg, 0.63 mmol) and NaH (38 mg, 0.96 mmol, 60% in mineral oil) in DMSO (5 was added tert-butyl 4-formyl-4-phenethylpiperidine-1-carboxylate (100 mg, 0.32 mmol). The reaction mixture was stirred at RT for 2 h. Upon completion of the reaction, the reaction mixture was quenched with water (5 mL) and extracted with EtOAc (10 mL×3). The combined organic phase was dried over $Na_2SO_4$ and concentrated under reduced pressure. The residue was purified by silica-gel column chromatography (EtOAc/hexane=1:10) to give 90 mg of tert-butyl 4-(oxiran-2-yl)-4-phenethylpiperidine-1-carboxylate as a colorless oil. LC-MS (ESI+): m/z 332 [M+H]$^+$.

7.2 Preparation of tert-butyl 4-(oxetan-2-yl)-4-phenethylpiperidine-1-carboxylate A solution of trimethylsulfoxonium iodide (123 mg, 0.56 mmol) and potassium tert-butylate (62 mg, 0.56 mmol) in 2-methylpropan-2-ol (5 mL) was stirred at 50° C. for 1 h. To the mixture was added a solution of tert-butyl 4-(oxiran-2-yl)-4-phenethylpiperidine-1-carboxylate (90 mg, 0.28 mmol) in 2-methylpropan-2-oi (2 mL). The reaction mixture was stirred at 50° C. for 48 h. Upon completion of the reaction, the reaction mixture was quenched with water (5 mL) and extracted with EtOAc (10 mL×3). The combined organic phase was dried over $Na_2SO_4$ and concentrated under reduced pressure. The residue was purified by silica-gel column chromatography (EtOAc/hexane=1:8) to give 30 mg of tert-butyl 4-(oxetan-2-yl)-4-phenethylpiperidine-1-carboxylate as a colorless oil. LC-MS (ESI+): m/z 346 [M+H]$^+$.

7.3 Preparation of 4-(oxetan-2-yl)-4-phenethylpiperidine

The title compound was prepared from tert-butyl 4-(oxetan-2-yl)-4-phenethylpiperidine-1-carboxylate according to the procedure 1.4. LC-MS (ESI+): m/z 246 [M+H]$^+$.

7.4 Preparation of N-(4-((4-(oxetan-2-yl)-4-phenethylpiperidin-1-yl)methyl)phenyl)acetamide The title compound was prepared from 4-(oxetan-2-yl)-4-phenethylpiperidine according to the procedure 1.5. LC-MS (ESI+): m/z 393 [M+H]$^+$.

8 Synthesis of N-(4-((3-(3,3-dimethyloxetan-2-yl)-3-phenethylpyrrolidin-1-yl)methyl)phenyl)acetamide

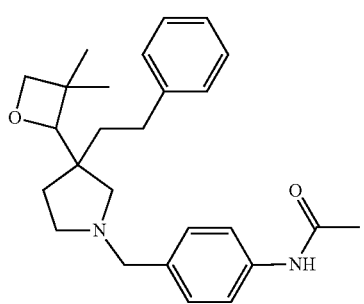 [SMILES: CC(=O)Nc1ccc(CN2CCC(CCc3ccccc3)(C3OCC3(C)C)C2)cc1]

8.1 Preparation of tert-butyl 3-(3-ethoxy-1-hydroxy-2,2-dimethyl-3-oxopropyl)-3-phenethylpyrrolidine-1-carboxylate To a solution of ethyl isobutyrate (383 mg, 3.3 mmol) in THF (5 mL) was added LHMDS (3.3 mL, 3.3 mmol, 1 M in THF solution) dropwise under $N_2$ atmosphere at 0° C. The mixture was stirred at 0° C. for 30 min before tert-butyl 3-formyl-3-phenethylpyrrolidine-1-carboxylate (500 mg, 1.6 mmol) in THF (2 mL) was added. Upon completion of the reaction, the reaction mixture was quenched with $NH_4Cl$ solution (8 mL) and extracted with EtOAc (10 mL×3). The combined organic phase was dried over $Na_2SO_4$ and concentrated under reduced pressure. The residue was purified by silica-gel column chromatography (hexane/EtOAc=6:1) to give 540 mg of tort-butyl 3-(3-ethoxy-1-hydroxy-2,2-dimethyl-3-oxopropyl)-3-phenethylpyrrolidine-1-carboxylate as an oil. LC-MS (ESI+): m/z 420 [M+H]$^+$.

8.2 Preparation of tert-butyl 3-(1,3-dihydroxy-2,2-dimethylpropyl)-3-phenethyl pyrrolidine-1-carboxylate To a solution of tert-butyl 3-(3-ethoxy-1-hydroxy-2,2-dimethyl-3-oxopropyl)-3-phenethylpyrrolidine-1-carboxylate (540 mg, 1.29 mmol) in THF (5 mL) under $N_2$ atmosphere at RT was added $LiAlH_4$ (64 mg, 1.67 mmol) in portions. The reaction mixture was stirred at RT for 30 min. Upon completion of the reaction, the reaction mixture was quenched with water (20 mL) and aqueous NaOH solution (0.5 ml, 1 eq). The resulting mixture was filtrated and the filtrate was extracted with EtOAc (30 mL×3). The combined organic phase was dried over $Na_2SO_4$ and concentrated under reduced pressure. The residue was purified by silica-gel column chromatography (hexane/EtOAc=3:1) to provide 320 mg of tert-butyl 3-(1,3-dihydroxy-2,2-dimethylpropyl)-3-phenethylpyrrolidine-1-carboxylate as an oil. LC-MS (ESI+): m/z 378 [M+H]$^+$.

8.3 Preparation of tert-butyl 3-(1-hydroxy-2,2-dimethyl-3-((methylsulfonyl)oxy) propyl)-3-phenethylpyrrolidine-1-carboxylate The title compound was prepared from tert-butyl 3-(1,3-dihydroxy-2,2-dimethylpropyl)-3-phenethyl pyrrolidine-1-carboxylate according to the procedure 2.2. LC-MS (ESI+): m/z 456 [M+H]$^+$.

8.4 Preparation of tert-butyl 3-(3,3-dimethyloxetan-2-yl)-3-phenethylpyrrolidine-1-carboxylate To a solution of 3-(1-hydroxy-2,2-dimethyl-3-((methylsulfonyl)oxy)propyl)-3-phenethyl pyrrolidine-1-carboxylate (300 mg, 0.66 mmol) in t-BuOH (10 mL) was added t-BuOK (222 mg, 1.98 mmol). The mixture was stirred at 35° C. for 2 h. Upon completion of the reaction, the reaction mixture was quenched with water (8 mL) and extracted with EtOAc (8 mL×3). The combined organic phase was dried over $Na_2SO_4$ and concentrated under reduced pressure. The residue was purified by silica column chromatography (hexane/EtOAc=3:1) to give 240 mg of tort-butyl 3-(3,3-dimethyloxetan-2-yl)-3-phenethylpyrrolidine-1-carboxylate as an oil. LC-MS (ESI+): m/z 360 [M+H]$^+$.

8.5 Preparation of 3-(3,3-dimethyloxetan-2-yl)-3-phenethylpyrrolidine

The title compound was prepared from tert-butyl 3-(3,3-dimethyloxetan-2-yl)-3-phenethylpyrrolidine-1-carboxylate according to the procedure 1.4. MS (ESI+): m/z 260 [M+H]+.

8.6 Preparation of N-(4-((3-(3,3-dimethyloxetan-2-yl)-3-phenethylpyrrolidin-1-yl) methyl)phenyl)acetamide The title compound was prepared from 3-(3,3-dimethyloxetan-2-yl)-3-phenethylpyrrolidine according to the procedure 1.5. MS (ESI+): m/z 407 [M+H]+.

9 Synthesis of N-(4-((4-(2-methoxyethyl)-4-phenethylpiperidin-1-yl)methyl)phenyl)acetamide

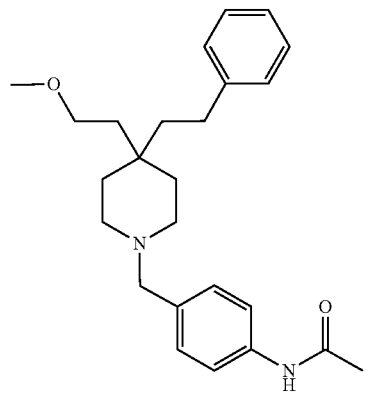 [SMILES: COCCC1(CCc2ccccc2)CCN(Cc2ccc(NC(C)=O)cc2)CC1]

9.1 Preparation of tert-butyl 4-(2-methoxyvinyl)-4-phenethylpiperidine-1-carboxylate To a solution of (ethoxymethyl)triphenylphosphonium chloride (357 mg, 1.04 mmol) in THF (5 mL) under N₂ atmosphere at 0° C. was added LHMDS (2 mL, 1M in THF solution). The mixture was stirred at 0° C. for 30 min before tert-butyl 4-formyl-4-phenethylpiperidine-1-carboxylate (300 mg, 0.95 mmol) in THF was added. After addition, the reaction mixture was allowed to warm to RT and stirred overnight. Upon completion of the reaction, the reaction mixture was quenched with saturated NH₄Cl solution (8 mL) and extracted with EtOAc (10 mL×3). The combined organic phase was washed with brine (10 mL), dried over Na₂SO₄ and concentrated under reduced pressure. The residue was purified by silica-gel column chromatography (EtOAc/hexane=1:10) to give 120 mg of tert-butyl 4-(2-methoxyvinyl)-4-phenethylpiperidine-1-carboxylate as a light yellow oil. LC-MS (ESI+): m/z 346 [M+H]+.

9.2 Preparation of tert-butyl 4-(2-methoxyethyl)-4-phenethylpiperidine-1-carboxylate The title compound was prepared from tert-butyl 4-(2-methoxyvinyl)-4-phenethylpiperidine-1-carboxylate according to the procedure 2.4. LC-MS (ESI+): m/z 348 [M+H]+.

9.3 Preparation of 4-(2-methoxyethyl)-4-phenethylpiperidine

The title compound was prepared from tert-butyl 4-(2-methoxyethyl)-4-phenethylpiperidine-1-carboxylate according to the procedure 1.4. LC-MS (ESI+): m/z 248 [M+H]+.

9.4 Preparation of N-(4-((4-(2-methoxyethyl)-4-phenethylpiperidin-1-yl)methyl)phenyl)acetamide The title compound was prepared from 4-(2-methoxyethyl)-4-phenethylpiperidine according to the procedure 1.5. LC-MS (ESI+): m/z 395 [M+H]+.

10 Synthesis of N-(4-((4-((difluoromethoxy)methyl)-4-phenethylpiperidin-1-yl) methyl)phenyl)acetamide

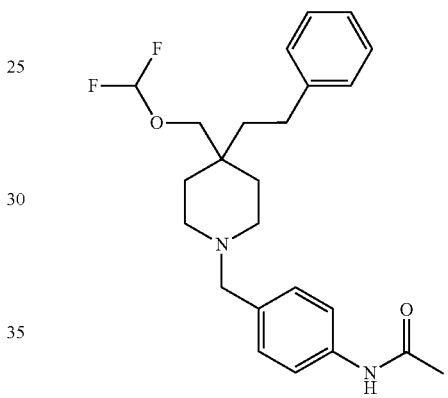

10.1 Preparation of tert-butyl 4-((difluoromethoxy)methyl)-4-phenethylpiperidine-1-carboxylate To a solution of tert-butyl 4-(hydroxymethyl)-4-phenethylpiperidine-1-carboxylate (0.30 g, 0.94 mmol) in CH₃CN (10 mL) at RT was added CuI (36 mg, 0.19 mmol). The mixture was heated to 45° C. before 2,2-difluoro-2-(fluorosulfonyl)acetic acid (0.34 g, 1.88 mmol) was added dropwise over 30 min. The reaction mixture was stirred at 45° C. for 2 h. Upon completion of the reaction, the solvent was removed under reduced pressure. The residue was neutralized with NaHCO₃ aqueous and extracted with EtOAc (3×50 mL). The combined organic phase was dried over anhydrous Na₂SO₄ and concentrated under reduced pressure. The residue was purified by silica-gel column chromatography (Hexane:EtOAc=40:1) to give 220 mg of tert-butyl 4-((difluoromethoxy)methyl)-4-phenethylpiperidine-1-carboxylate as a yellow oil. LC-MS (ESI+): m/z 270 [M+H-Boc]+.

10.2 Preparation of 4-((difluoromethoxy)methyl)-4-phenethylpiperidine

The title compound was prepared from tert-butyl 4-((difluoromethoxy)methyl)-4-phenethylpiperidine-1-carboxylate according to the procedure 1.4. LC-MS (ESI+): m/z 270 [M+H]+.

10.3 Preparation of N-(4-((4-((difluoromethoxy) methyl)-4-phenethylpiperidin-1-yl)methyl)phenyl) acetamide The title compound was prepared from 4-((difluoromethoxy)methyl)-4-phenethylpiperidine according to the procedure 1.5. LC-MS (ESI+): m/z 417 [M+H]+.

11 Synthesis of N-(4-((4-phenethyl-4-(pyridin-2-yl)piperidin-1-yl)methyl)phenyl)acetamide

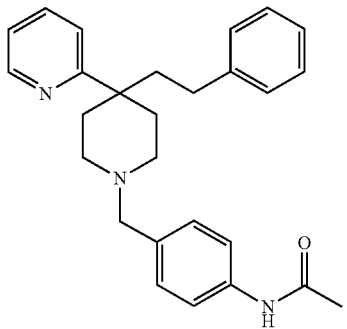 [SMILES: CC(=O)Nc1ccc(CN2CCC(CCc3ccccc3)(c3ccccn3)CC2)cc1]

11.1 Preparation of tert-butyl 4-cyano-4-(pyridin-2-yl)piperidine-1-carboxylate To a solution of 1-(tert-butoxycarbonyl)-4-cyano-2,3,4,5-tetrahydropyridin-1-ium (3.24 g, 15.43 mmol) and 2-fluoropyridine (1.65 g, 16.97 mmol) in THF (20 mL) at RT was added LHMDS (18.5 mL, 18.5 mmol, 1 M in THF solution). The reaction mixture was stirred at RT for 1.5 h. Upon completion of the reaction, the reaction mixture was quenched with water (50 mL) and extracted with EtOAc (50 mL×3). The combined organic phase was dried over anhydrous Na$_2$SO$_4$ and concentrated under reduced pressure. The residue was purified by silica-gel column chromatography to afford 4 g of tert-butyl 4-cyano-4-(pyridin-2-yl)piperidine-1-carboxylate. LC-MS (ESI+): m/z 288 [M+H]+.

11.2 Preparation of tert-butyl 4-formyl-4-(pyridin-2-yl)piperidine-1-carboxylate To a solution of tert-butyl 4-cyano-4-(pyridin-2-yl)piperidine-1-carboxylate (2.07 g, 7.2 mmol) in DCM (20 mL) and toluene (20 mL) under N$_2$ atmosphere at RT was added DIBAL-H (8 mL, 14.4 mmol, 1.5 M in toluene). The reaction mixture was stirred at RT for 1.5 h. Upon completion of the reaction, the reaction mixture was quenched with water (50 mL) and extracted with EtOAc (80 mL×3). The combined organic phase was dried over anhydrous Na$_2$SO$_4$ and concentrated under reduced pressure. The residue was purified by silica-gel column chromatography to afford 660 mg of tert-butyl 4-formyl-4-(pyridin-2-yl)piperidine-1-carboxylate. LC-MS (ESI+): m/z 291 [M+H]+.

11.3 Preparation of tert-butyl (E)-4-(pyridin-2-yl)-4-styrylpiperidine-1-carboxylate To a solution of benzyltriphenylphosphonium bromide (839.2 mg, 1.94 mmol) in THF (20 mL) at 0° C. under N$_2$ atmosphere was added NaH (129 mg, 3.22 mmol, 60% in mineral oil). The mixture was stirred at 0° C. for 10 min before a solution of tert-butyl 4-formyl-4-(pyridin-2-yl)piperidine-1-carboxylate (468 mg, 1.61 mmol) in THF was added. The reaction mixture was allowed to warm to RT and stirred overnight. Upon completion of the reaction, the reaction mixture was quenched with water (20 mL) and extracted with EtOAc (30 mL×3). The combined organic phase was dried over anhydrous Na$_2$SO$_4$ and concentrated under reduced pressure. The residue was purified by silica-gel column chromatography to afford 390 mg of tert-butyl (E)-4-(pyridin-2-yi)-4-styrylpiperidine-1-carboxylate. LC-MS (ESI+): m/z 387 [M+Na]+.

11.4 Preparation of tert-butyl 4-phenethyl-4-(pyridin-2-yl)piperidine-1-carboxylate The title compound was prepared from tert-butyl (E)-4-(pyridin-2-yl)-4-styrylpiperidine-1-carboxylate according to the procedure 2.4. LC-MS (ESI+): m/z 367 [M+H]+.

11.5 Preparation of 2-(4-phenethylpiperidin-4-yl)pyridine

The title compound was prepared from tert-butyl 4-phenethyl-4-(pyridin-2-yl)piperidine-1-carboxylate according to the procedure 1.4. LC-MS (ESI+): m/z 267 [M+H]+.

11.6 Preparation of N-(4-((4-phenethyl-4-(pyridin-2-yl)piperidin-1-yl)methyl)phenyl)acetamide To a mixture of 2-(4-phenethylpiperidin-4-yl)pyridine (100 mg, 0.37 mmol) and N-(4-formylphenyl)acetamide (123 mg, 0.75 mmol) in MeOH (5 mL) and water (1 mL) at RT was added Na$_2$CO$_3$ (80 mg, 0.75 mmol). The reaction mixture was stirred for 15 min before NaH$_3$BCN (24 mg, 0.37 mmol) was added. The reaction mixture was stirred at RT overnight. Upon completion of the reaction, the reaction mixture was quenched with water (20 mL) and extracted with DCM/MeOH (12:1, 30 mL×3). The combined organic phase was dried over anhydrous Na$_2$SO$_4$ and concentrated under reduced pressure. The residue was purified by silica-gel column chromatography to afford 25.5 mg of N-(4-((4-phenethyl-4-(pyridin-2-yl) piperidin-1-yl)methyl)phenyl) acetamide. The product was dissolved in a mixture solution of MeOH (1 mL) and Et$_2$O/HCl (2 mL) and the mixture was stirred for 20 min before concentrated and washed with Et$_2$O twice to afford 10.3 mg of N-(4-((4-phenethyl-4-(pyridin-2-yl)piperidin-1-yl) methyl)phenyl)acetamide HCl salt as a white solid. LC-MS (ESI+): m/z 414 [M+H]+.

12 Synthesis of N-(4-((4-phenethyl-4-(thiophen-2-yl)piperidin-1-yl)methyl)phenyl)acetamide

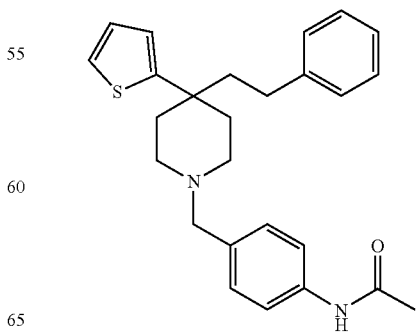

12.1 Preparation of tert-butyl 4-hydroxy-4-(thiophen-2-yl)piperidine-1-carboxylate To a solution of 2-bromothiophene (5.61 g, 34.4 mmol) in THF (100 mL) under N$_2$ atmosphere at −78° C. was added n-BuLi (15 mL, 37.6 mmol, 2.5 M in hexane) dropwise. The mixture was stirred at −78° C. for 60 min before it was allowed to warm to RT. After the reaction mixture was stirred at RT for 30 min, it was re-cooled to −78° C. and 1-(tert-butoxycarbonyl)-4-oxo-2,3,4,5-tetrahydropyridin-1-ium (6.23 g, 31.3 mmol) in THF was added dropwise. The reaction mixture was stirred at −78° C. for 1 h. Upon completion of the reaction, the reaction mixture was quenched with water (100 mL) and extracted with EtOAc (60 mL×3). The combined organic phase was dried over anhydrous Na$_2$SO$_4$ and concentrated under reduced pressure. The residue was purified by silica-gel column chromatography to afford 7.8 g of tert-butyl 4-hydroxy-4-(thiophen-2-yl)piperidine-1-carboxylate. LC-MS (ESI+): m/z 284 [M+H]$^+$.

12.2 Preparation of 4-(thiophen-2-yl)piperidine-4-carbonitrile

A solution of tert-butyl 4-hydroxy-4-(thiophen-2-yl)piperidine-1-carboxylate (7.8 g, 27.5 mmol) and I$_2$ (6.95 g, 27.5 mmol) in DCM (50 mL) was cooled to −25° C. and stirred for 30 min. To the mixture was added TMSCN (8.18 g, 82.7 mmol) in portions. The reaction mixture was stirred at −25° C. for 15 min. Upon completion of the reaction, the reaction mixture was concentrated to give 6.4 g of crude product, which was used directly for the next step without further purification. LC-MS (ESI+): m/z 193 [M+H]$^+$.

12.3 Preparation of tert-butyl 4-cyano-4-(thiophen-2-yl)piperidine-1-carboxylate To a mixture of 4-(thiophen-2-yl)piperidine-4-carbonitrile (6.4 g, 33.3 mmol) and Na$_2$CO$_3$ (7.07 g, 366.7 mmol) in THF (80 mL) and water (30 mL) at RT was added Boc$_2$O (13.3 g, 66.7 mmol) in portions. The reaction mixture was stirred at RT overnight. Upon completion of the reaction, the resulting mixture was extracted with EtOAc, dried over anhydrous Na$_2$SO$_4$ and concentrated under reduced pressure. The residue was purified by silica-gel column chromatography to afford 0.66 g of tert-butyl 4-cyano-4-(thiophen-2-yl)piperidine-1-carboxylate. LC-MS (ESI+): m/z 315 [M+H]$^+$.

12.4 Preparation of N-(4-((4-phenethyl-4-(thiophen-2-yl)piperidin-1-yl)methyl)phenyl)acetamide The title compound was prepared from tert-butyl 4-cyano-4-(thiophen-2-yl)piperidine-1-carboxylate according to the procedure 11.2, 11.3, 11.4, 11.5, 1.5. LC-MS (ESI+): m/z 419 [M+H]$^+$.

13 Synthesis of N-(4-((4-(1H-imidazol-2-yl)-4-phenethylpiperidin-1-yl)methyl)phenyl)acetainide

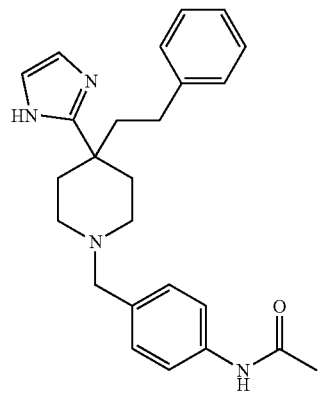 [SMILES: CC(=O)Nc1ccc(CN2CCC(CCc3ccccc3)(c3ncc[nH]3)CC2)cc1]

13.1 Preparation of tert-butyl 4-(1H-imidazol-2-yl)-4-phenethylpiperidine-1-carboxylate To a solution of tert-butyl 4-formyl-4-phenethylpiperidine-1-carboxylate (188 mg, 0.59 mmol) in MeOH (15 mL) was added ammonium hydroxide (0.6 mL, 4.90 mmol) and oxalaldehyde (0.07 mL, 5.9 mmol). The reaction mixture was stirred at RT overnight. Upon completion of the reaction, the reaction mixture was quenched with brine (10 mL) and extracted with EtOAc (20 mL×3). The combined organic phase was dried over anhydrous Na$_2$SO$_4$ and concentrated under reduced pressure. The residue was purified by silica-gel column chromatography (EtOAc/hexane=5:1 to 2:1) to give 163 mg of tort-butyl 4-(1H-imidazol-2-yl)-4-phenethylpiperidine-1-carboxylate as a white solid. LC-MS (ESI+): m/z 356 [M+H]$^+$.

13.2 Preparation of 4-(1H-imidazol-2-yl)-4-phenethylpiperidine

The title compound was prepared from tert-butyl 4-(1H-imidazol-2-yl)-4-phenethylpiperidine-1-carboxylate according to the procedure 12.2. LC-MS (ESI+): m/z 256 [M+H]$^+$.

13.3 Preparation of N-(4-((4-(1H-imidazol-2-yl)-4-phenethylpiperidin-1-yl)-methyl) phenyl)acetamide The title compound was prepared from 4-(1H-imidazol-2-yl)-4-phenethylpiperidine according to the procedure 1.5. LC-MS (ESI+): m/z 403 [M+H]$^+$.

14 Synthesis of N-(4-((4-(1,3,4-oxadiazol-2-yl)-4-phenethylpiperidin-1-yl)methyl)phenyl)acetamide

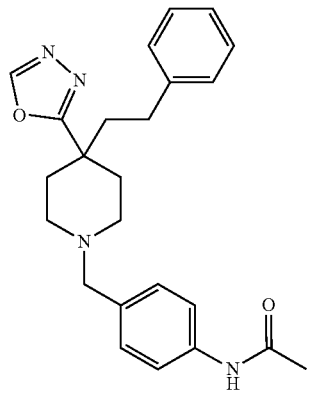 [SMILES: CC(=O)Nc1ccc(CN2CCC(CCc3ccccc3)(c3nnco3)CC2)cc1]

14.1 Preparation of tert-butyl 4-(2-formylhydrazine-1-carbonyl)-4-phenethylpiperidine-1-carboxylate To a solution of 1-(tert-butoxycarbonyl)-4-phenethylpiperidine-4-carboxylic acid (440 mg, 1.32 mmol), formohydrazide (79 mg, 1.32 mmol) and DIPEA (511 mg, 3.96 mmol) in DMF (3 mL) at RT was added HATU (552 mg, 1.45 mmol). The reaction mixture was stirred at 60° C. for 4 h. Upon completion of the reaction, the reaction mixture was quenched with water (20 mL) and extracted with DCM/MeOH (15:1). The combined organic phase was dried over anhydrous $Na_2SO_4$ and concentrated under reduced pressure. The residue was purified by (EtOAc/hexane=5:1 to 1:1) to afford 289.7 mg of tert-butyl 4-(2-formylhydrazine-1-carbonyl)-4-phenethylpiperidine-1-carboxylate. LC-MS (ESI+): m/z 376 [M+H]+.

14.2 Preparation of 2-(4-phenethylpiperidin-4-yl)-1,3,4-oxadiazole

A solution of tert-butyl 4-(2-formylhydrazine-1-carbonyl)-4-phenethylpiperidine-1-carboxylate (141 mg, 0.376 mmol) and $P_2O_5$ (213 mg, 1.5 mmol) was heated to 90° C. and stirred for 22 h. Upon completion of the reaction, the reaction mixture was poured into ice-water. After the pH of the mixture was adjusted to pH=8 with aqueous $Na_2CO_3$ solution, the mixture was extracted with DCM/MeOH (15:1). The organic phase was washed with brine, dried over $Na_2SO_4$ and concentrated under reduced pressure to afford 75 mg of the crude product, which was used directly for the next step without further purification. LC-MS (ESI+): m/z 258 [M+H]+.

14.3 Preparation of N-(4-((4-(1,3,4-oxadiazol-2-yl)-4-phenethylpiperidin-1-yl)methyl)phenyl)acetamide The title compound was prepared from 2-(4-phenethylpiperidin-4-yl)-1,3,4-oxadiazole according to the procedure 1.5. LC-MS (ESI+): m/z 405 [M+H]+.

15 Synthesis of N-(4-((4-phenethyl-4-(1,3,4-thiadiazol-2-yl)piperidin-1-yl)methyl)phenyl)acetamide

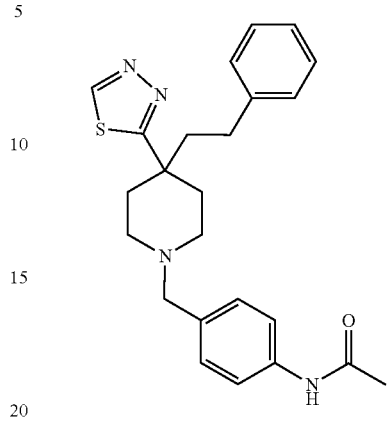

15.1 Preparation of 2-(4-phenethylpiperidin-4-yl)-1,3,4-thiadiazole

A solution of tert-butyl 4-(2-formylhydrazine-1-carbonyl)-4-phenethylpiperidine-1-carboxylate (380 mg, 1.01 mmol) and $P_2S_5$ (562 mg, 2.5 mmol) in toluene (5 mL) was heated to reflux and stirred for 30 min. Upon completion of the reaction, the pH of the mixture was adjusted to 8 with aqueous $Na_2CO_3$ solution and the mixture was extracted with DCM/MeOH (15:1). The organic phase was washed with brine, dried over $Na_2SO_4$ and concentrated under reduced pressure to afford 133 mg of the crude product, which was used directly for the next step without further purification. LC-MS (ESI+): m/z 274 [M+H]+.

15.2 Preparation of N-(4-((4-phenethyl-4-(1,3,4-thiadiazol-2-yl)piperidin-1-yl)methyl)phenyl)acetamide The title compound was prepared from 2-(4-phenethylpiperidin-4-yl)-1,3,4-thiadiazole according to the procedure 1.5. LC-MS (ESI+): m/z 421 [M+H]+.

16 Synthesis of N-(4-((4-(5-methyl-1,2,4-oxadiazol-3-yl)-4-phenethylpiperidin-1-yl)methyl)phenyl)acetamide

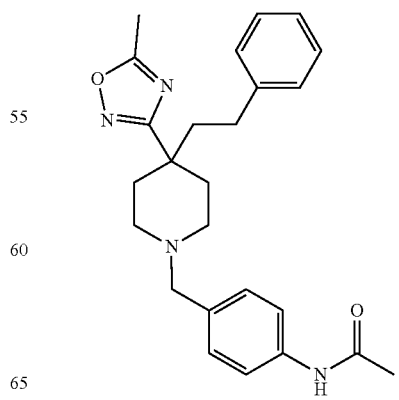

16.1 Preparation of tert-butyl 4-(N'-hydroxycarbamimidoyl)-4-phenethylpiperidine-1-carboxylate To a solution of tert-butyl-4-cyano-4-phenethylpiperidine-1-carboxylate (1.1 g, 3.44 mmol) in EtOH (15 mL) and H$_2$O (10 mL) was added hydroxylamine hydrochloride (2.4 g, 34.4 mmol) and sodium carbonate (1.8 g, 17.2 mmol). The reaction mixture was stirred at 80° C. overnight. Upon completion of the reaction, the reaction mixture was quenched with water (10 mL) and extracted with EtOAc (20 mL×3). The organic phase was dried over Na$_2$SO$_4$ and concentrated under reduced pressure. The residue was purified by silica-gel column chromatography (EtOAc/hexane=5:1-1:1) to give 337 mg of tert-butyl 4-(N'-hydroxycarbamimidoyl)-4-phenethylpiperidine-1-carboxylate as a white solid. LC-MS (ESI+): m/z 348 [M+H]$^+$.

16.2 Preparation of tert-butyl 4-(5-methyl-1,2,4-oxadiazol-3-yl)-4-phenethylpiperi-dine-1-carboxylate To a solution of tert-butyl 4-(N'-hydroxycarbainimidoyl)-4-phenethylpiperidine-1-carboxylate (196 mg, 0.6 mmol) in pyridine (6.5 mL) was added acetyl chloride (110 mg, 1.4 mmol). The reaction was stirred at 90° C. overnight. Upon completion of the reaction, the reaction mixture was quenched with water (10 mL) and extracted with EtOAc (15 mL×3). The organic phase was dried over Na$_2$SO$_4$ and concentrated under reduced pressure. The residue was purified by silica-gel column chromatography (EtOAc/hexane=10:1-5:1) to give 158 mg of tert-butyl 4-(5-methyl-1,2,4-oxadiazol-3-yl)-4-phenethylpiperidine-1-carboxylate as an oil. LC-MS (ESI+): m/z 372 [M+H]$^+$.

16.3 Preparation of 5-methyl-3-(4-phenethylpiperidin-4-yl)-1,2,4-oxadiazole

The title compound was prepared from tert-butyl 4-(5-methyl-1,2,4-oxadiazol-3-yl)-4-phenethylpiperi-dine-1-carboxylate according to the procedure 1.4. LC-MS (ESI+): m/z 272 [M+H]$^+$.

16.4 Preparation of N-(4-((4-(5-methyl-1,2,4-oxadiazol-3-yl)-4-phenethylpiperidin-1-yl)methyl)phenyl)acetamide The title compound was prepared from 5-methyl-3-(4-phenethylpiperidin-4-yl)-1,2,4-oxadiazole according to the procedure 1.5. LC-MS (ESI+): m/z 419 [M+H]$^+$.

17 Synthesis of N-(4-((4-((dimethylamino)methyl)-4-phenethylpiperidin-1-yl)methyl)phenyl)acetamide

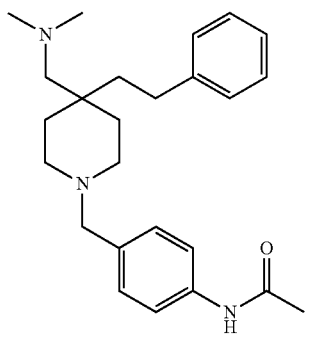 [SMILES: CC(=O)Nc1ccc(CN2CCC(CCc3ccccc3)(CN(C)C)CC2)cc1]

17.1 Preparation of 1-(cert-butoxycarbonyl)-4-phenethylpiperidine-4-carboxylic acid To a solution of 1-(tert-butyl) 4-ethyl 4-phenethylpiperidine-1,4-dicarboxylate (2.44 g, 6.75 mmol) in dioxane (30 mL), methanol (15 mL) and water (15 mL) at RT was added lithium hydroxide monohydrate (5.68 g, 135 mmol). The mixture was stirred at 50° C. overnight. Upon completion of the reaction, the reaction mixture was cooled to RT and quenched with 2M HCl solution until pH=3 before it was extracted with DCM/MeOH (12:1). The combined organic phase was dried over anhydrous Na$_2$SO$_4$ and concentrated under reduced pressure. The residue was purified by silica-gel column chromatography to afford 2.12 g of 1-(tert-butoxycarbonyl)-4-phenethylpiperidine-4-carboxylic acid. LC-MS (ESI-): m/z 332 [M-H]$^-$.

17.2 Preparation of tert-butyl 4-(dimethylcarbamoyl)-4-phenethylpiperidine-1-carboxylate To a solution of 1-(tert-butoxycarbonyl)-4-phenethylpiperidine-4-carboxylic acid (271.7 mg, 0.81 mmol) and dimethylamine hydrochloride (99.7 mg, 1.22 mmol) in DMF (6 mL) at RT was added HOBt (313.3 mg, 1.63 mmol), EDCl (220.2 mg, 1.63 mmol) and Et$_3$N (250 mg, 2.5 mmol). The reaction was stirred at 80° C. overnight. After cooled to rt, the reaction mixture was quenched with water (20 mL) and extracted with DCM (20 mL×3). The combined organic phase was dried over anhydrous Na$_2$SO$_4$ and concentrated under reduced pressure. The residue was purified by silica-gel column chromatography to afford 300 mg of tert-butyl 4-(dimethylcarbamoyl)-4-phenethylpiperidine-1-carboxylate. LC-MS (ESI+): m/z 361 [M+H]$^+$.

17.3 Preparation of N,N-dimethyl-4-phenethylpiperidine-4-carboxamide

The title compound was prepared from tert-butyl 4-(dimethylcarbamoyl)-4-phenethylpiperidine-1-carboxylate according to the procedure 1.4. LC-MS (ESI+): m/z 261 [M+H]$^+$.

17.4 Preparation of tert-butyl 4-((dimethylamino)methyl)-4-phenethylpiperidine-1-carboxylate To a solution of N,N-dimethyl-4-phenethylpiperidine-4-carboxamide (271 mg, 0.97 mmol) in THF (10 mL) under N$_2$ atmosphere at RT was added LiAlH$_4$ (75 mg, 1.95 mmol). The reaction was stirred at RT overnight. Upon completion of the reaction, the pH of the mixture was adjusted to 14 with 2 M NaOH solution and Boc$_2$O (312.6 mg, 1.56 mmol) in dioxane (20 mL) was added to the mixture. The reaction mixture was stirred overnight and then extracted with EtOAc (20 mL×3). The organic phase was washed with brine, dried over Na$_2$SO$_4$ and concentrated under reduced pressure. The residue was purified by silica-gel column chromatography to afford 210 mg of tert-butyl 4-((dimethylamino)methyl)-4-phenethylpiperidine-1-carboxylate. LC-MS (ESI+): m/z 347 [M+H]$^+$.

17.5 Preparation of N-(4-((4-((dimethylamino)methyl)-4-phenethylpiperidin-1-yl)methyl)phenyl)acetamide The title compound was prepared from tert-butyl 4-((dimethylamino)methyl)-4-phenethylpiperidine-1-carboxylate according to the procedure 1.4 and 1.5. LC-MS (ESI+): m/z 394 [M+H]$^+$.

18 Synthesis of 4-(2-(2,5-dimethylthiophen-3-yl)ethyl)-4-(ethoxymethyl)-1-((1-methyl-1H-pyrazol-4-yl)methyl)piperidine

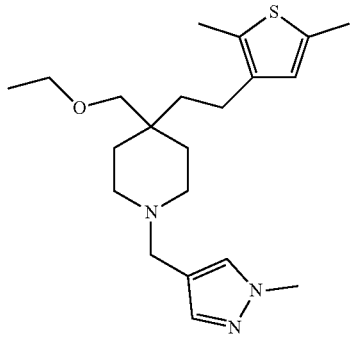 [SMILES: CCOCC1(CCc2cc(C)sc2C)CCN(Cc2cnn(C)c2)CC1]

18.1 Preparation of 3-bromo-2,5-dimethylthiophene

To a solution of 4-bromo-2-methylthiophene (2 g, 11.3 mmol) in THF (5 mL) under $N_2$ atmosphere at −78° C. was added lithium diisopropylamide (30 mL, 13.6 mmol, 1.2 eq.) in anhydrous THF. After stirred at −78° C. for 20 min, a solution of iodomethane (2.4 g, 16.9 mmol) in THF (10 mL) was added to the above reaction mixture. It was then allowed to warm to RT and stirred for 2 h. The reaction mixture was quenched with saturated ammonium chloride solution (5 mL), extracted with hexane (10 mL×3). The combined organic phase was washed with brine (10 mL), dried over $Na_2SO_4$ and concentrated. The residue was purified by silica-gel column chromatography (hexane) to give 1 g of 3-bromo-2,5-dimethylthiophene as a colorless oil. GC-MS: 190/192 (M).

18.2 Preparation of 2,5-dimethylthiophene-3-carbaldehyde

To a solution of 3-bromo-2,5-dimethylthiophene (1 g, 5.23 mmol) in THF (5 mL) under $N_2$ atmosphere at −78° C. was added n-butyllithium (2.5 mL, 6.25 mmol, 2.5 M in hexane). After 30 min, a solution of anhydrous DMF (421 mg, 5.76 mmol) in THF (2 mL) was added to the above mixture and stirred for 20 min. After quenched with water (5 mL), the aqueous solution was extracted with hexane (10 mL×3). The combined organic phase was washed with brine (10 mL), dried over $Na_2SO_4$. After filtration and concentration, the resulting oil was used directly for the next step without further purification. GC-MS: 140 (M+).

18.3 Preparation of (2,5-dimethylthiophen-3-yl)methanol

To a stirred solution of 2,5-dimethylthiophene-3-carbaldehyde (1 g, 7.14 mmol) in MeOH (5 mL) at RT was added $NaBH_4$ (542 mg, 14.28 mmol) in portions. After 1 h, a saturated ammonium chloride solution (10 mL) was added to quench the reaction and extracted with EtOAc (20 mL×3). The combined organic phase was dried over $Na_2SO_4$ and concentrated. The residue was purified by silica-gel column chromatography (EtOAc/hexane=1:6) to give 800 mg of (2,5-dimethylthiophen-3-yl)methanol as a colorless oil. GC-MS: 142 (M+).

18.4 Preparation of 3-(bromomethyl)-2,5-dimethylthiophene

To a solution of (2,5-dimethylthiophen-3-yl)methanol (2 g, 14.3 mmol) in $Et_2O$ (30 mL) at 0° C. was added tribromophosphine (0.679 mL). After stirred at 0° C. for 20 min, water was added to the reaction mixture and extracted with hexane (30 mL×3). The combined organic phase was dried over anhydrous $Na_2SO_4$ and concentrated to give 2 g of the crude product, which was used for the next step without further purification. GC-MS: 204/206 (M+).

18.5 Preparation of ((2,5-dimethylthiophen-3-yl)methyl)triphenylphosphonium bromide The above obtained crude product 3-(bromomethyl)-2,5-dimethylthiophene (2 g, 9.8 mmol) and triphenylphosphine (2.5 g, 9.8 mmol) in toluene (20 mL) was stirred at RT overnight. The precipitated white solid was filtered and washed with toluene (5 mL×3) to give 3.2 g of ((2,5-dimethylthiophen-3-yl)methyl)triphenylphosphonium bromide as a white solid, which was used directly for the next step without further purification. LC-MS (ESI+): m/z 387 $[M-Br]^+$.

18.6 Preparation of 4-(2-(2,5-dimethylthiophen-3-yl)ethyl)-4-(ethoxymethyl)-1-((1-methyl-1H-pyrazol-4-yl)methyl)piperidine The title compound was prepared according to the procedure 11.3, 11.4, 11.5 and 11.6. LC-MS (ESI+): m/z 376 $[M+H]^+$.

19 Synthesis of N-(4-((4-benzoyl-4-(pyridin-2-yl)piperidin-1-yl)methyl)phenyl)acetamide

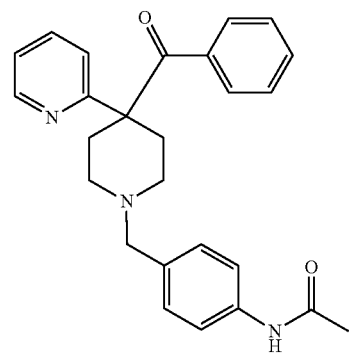 [SMILES: CC(=O)Nc1ccc(CN2CCC(C(=O)c3ccccc3)(c3ccccn3)CC2)cc1]

The title compound was prepared according to the procedure 6.2, 6.1, 1.4 and 1.5. LC-MS (ESI+): m/z 414 $[M+H]^+$.

20 Synthesis of N-(4-((4-(ethoxymethyl)-4-phenethylpiperidin-1-yl)methyl)phenyl)-2,2,2-trifluoroacetamide

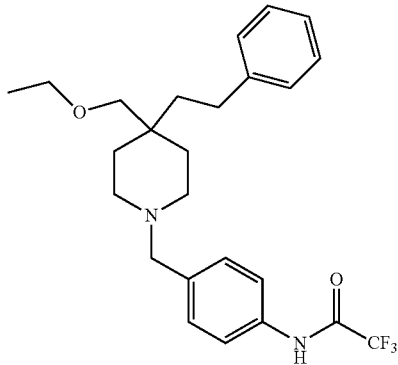 [SMILES: CCOCC1(CCc2ccccc2)CCN(Cc2ccc(NC(=O)C(F)(F)F)cc2)CC1]

20.1 Preparation of 4-(ethoxymethyl)-1-(4-nitrobenzyl)-4-phenethylpiperidine The title compound was prepared from 4-(ethoxymethyl)-4-phenethylpiperidine and 4-nitrobenzaldehyde according to the procedure 1.5. LC-MS (ESI+): m/z 383 [M+H]+.

20.2 Preparation of 4-((4-(ethoxymethyl)-4-phenethylpiperidin-1-yl)methyl)aniline To a solution of a saturated ammonium chloride solution (12 mL) in methanol (12 mL) at 60° C. was added Fe powder (58.4 mg, 1.04 mmol) and the mixture was stirred for 10 min. A solution of 4-(ethoxymethyl)-1-(4-nitrobenzyl)-4-phenethylpiperidine (100 mg, 0.26 mmol) in methanol (3 mL) was added to the above solution and stirred for 2 h. Upon completion of the reaction, the reaction mixture was filtered and concentrated. The residue was diluted with water (5 mL) and extracted with dichloromethane (20 mL×3). The combined organic phase was dried over $Na_2SO_4$, filtered and concentrated. The resulting oil was used directly for the next step without purification. LC-MS (ESI+): m/z 353 [M+H]+.

20.3 Preparation of N-(4-((4-(ethoxymethyl)-4-phenethylpiperidin-1-yl)methyl)phenyl)-2,2,2-trifluoroacetamide To a solution of 4-((4-(ethoxymethyl)-4-phenethylpiperidin-1-yl)methyl)aniline (58 mg, 0.16 mmol) and 2,2,2-trifluoroacetic acid (18.8 mg, 0.16 mmol) in DMF (3 mL) at RT was added HOBt (44.4 mg, 0.33 mmol), EDCl (63.2 mg, 0.33 mmol) and $Et_3N$ (50 mg, 0.49 mmol). The reaction was stirred at 80° C. overnight. After cooled to RT, water was added and extracted with DCM/MeOH (15:1, 30 mL×3). The combined organic phase was dried over anhydrous $Na_2SO_4$ and concentrated. The residue was purified by preparative TLC to afford 47.2 mg of N-(4-((4-(ethoxymethyl)-4-phenethylpiperidin-1-yl)methyl)phenyl)-2,2,2-trifluoroacetamide. The product was dissolved in a solution of MeOH (1 mL) and HCl/$Et_2O$ (2 mL). After stirred for 2 min, the solution was concentrated and washed with $Et_2O$ twice to afford 11.7 mg of N-(4-((4-(ethoxymethyl)-4-phenethylpiperidin-1-yl)methyl)phenyl)-2,2,2-trifluoroacetamide HCl salt as a yellow solid. LC-MS (ESI+): m/z 449 [M+H]+.

21 Synthesis of 4-((4-(ethoxymethyl)-4-phenethylpiperidin-1-yl)methyl)-N-(2,2,2-trifluoroethyl)aniline

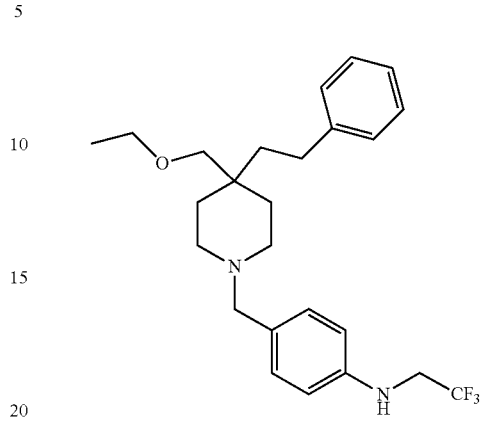

To a solution of N-(4-((4-(ethoxymethyl)-4-phenethylpiperidin-1-yl)methyl)phenyl)-2,2,2-trifluoroacetamide (25.5 mg, 0.056 mmol) in THF (5 mL) under a $N_2$ atmosphere at 0° C. was added $LiAlH_4$ (6.5 mg, 0.17 mmol) in portions. The reaction was stirred at 60° C. for 1 h. The completion of the reaction was monitored by TLC. The reaction was quenched with water slowly and adjusted pH to 9 with 10% NaOH aq., extracted with DCM/MeOH (12:1, 20 mL×3). The combined organic phase was dried over anhydrous $Na_2SO_4$, filtered and concentrated. The residue was purified by preparative TLC to afford 12.4 mg of 4-((4-(ethoxymethyl)-4-phenethylpiperidin-1-yl)methyl)-N-(2,2,2-trifluoroethyl)aniline. The product was dissolved in a solution of MeOH (1 mL) and HCl/$Et_2O$ (2 mL), and stirred for 2 min. The resulting suspension was concentrated and washed with $Et_2O$ twice to give 9.4 mg of 4-((4-(ethoxymethyl)-4-phenethylpiperidin-1-yl)methyl)-N-(2,2,2-trifluoroethyl)aniline HCl salt as a yellow solid. LC-MS (ESI+): m/z 435 [M+H]+.

22 Synthesis of 1-(4-((4-(ethoxymethyl)-4-phenethylpiperidin-1-yl)methyl)phenyl)-3-methylurea

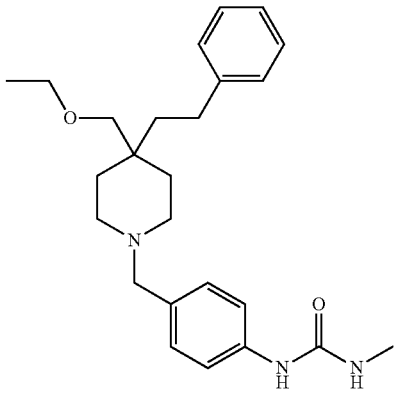 [SMILES: CCOCC1(CCc2ccccc2)CCN(Cc2ccc(NC(=O)NC)cc2)CC1]

22.1 Preparation of isocyanatomethane

Acetic Acid (2.02 g, 33.67 mmol) was dissolved in toluene (15 mL) in a reaction vessel fitted with a distillation head. Triethylamine (3.4 mg, 33.67 mmol) was added and the mixture was heated to 70° C. for 0.5 h. Diphenyl phosphorazidate (12 g, 43.77 mmol) was slowly added dropwise. After the addition was complete, the mixture was heated to 110° C. and stirred for 2 h. The product was collected as a solution in toluene by distillation, which used directly for the next step.

22.2 Preparation of 1-(4-((4-(ethoxymethyl)-4-phenethylpiperidin-1-yl)methyl)phenyl)-3-methylurea To a solution of 4-((4-(ethoxymethyl)-4-phenethylpiperidin-1-yl)methyl)aniline (52.3 mg, 0.14 mmol) in DCM (3 mL) at RT was added isocyanatomethane in toluene (0.5 mL, 0.22 mmol). After stirred overnight, the reaction mixture was concentrated. The residue was purified by preparative TLC to afford 15 mg of 1-(4-((4-(ethoxymethyl)-4-phenethylpiperidin-1-yl)methyl)phenyl)-3-methylurea. The product was dissolved in a solution of MeOH (1 mL) and HCl/Et$_2$O (2 mL), and stirred for 2 min. The resulting suspension was concentrated and washed with Et$_2$O twice to give 2.5 mg of 1-(4-((4-(ethoxymethyl)-4-phenethylpiperidin-1-yl)methyl)phenyl)-3-methylurea HCl salt as a yellow oil. LC-MS (ESI+): m/z 410 [M+H]$^+$.

23 Synthesis of N-(4-((3-(ethoxymethyl)-3-phenethylpyrrolidin-1-yl)methyl)phenyl)pyrimidin-2-amine

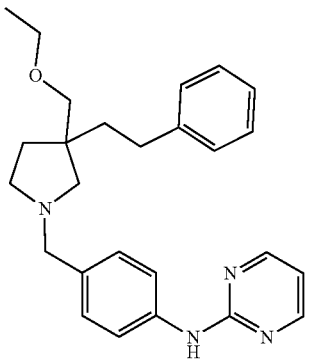 [SMILES: CCOCC1(CCc2ccccc2)CCN(Cc2ccc(Nc3ncccn3)cc2)C1]

To a solution of 1-(4-bromobenzyl)-3-(ethoxymethyl)-3-phenethylpyrrolidine (40 mg, 0.1 mmol) in toluene (5 mL) under a N$_2$ atmosphere was added pyrimidin-2-amine (15 mg, 0.15 mmol), BINAP (6 mg, 0.01 mmol), Pd(OAc)$_2$ (3 mg, 0.01 mmol) and t-BuOK (16 mg, 0.15 mmol). The reaction was stirred at 100° C. overnight. Upon completion of the reaction, water (10 mL) was added, extracted with ethyl acetate (10 mL×3). The combined organic phase was washed with brine (10 mL), dried over Na$_2$SO$_4$, filtered and concentrated. The residue was purified by silica-gel column chromatography (DCM:MeOH=15:1) to give 15 mg of N-(4-((3-(ethoxymethyl)-3-phenethylpyrrolidin-1-yl)methyl)phenyl)pyrimidin-2-amine as a colorless oil. LC-MS (ESI+): m/z 417 [M+H]$^+$.

24 Synthesis of 2-(4-((4-(ethoxymethyl)-4-phenethylpiperidin-1-yl)methyl)phenyl) thiazole

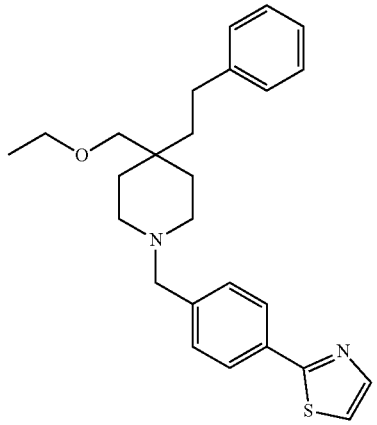 [SMILES: CCOCC1(CCc2ccccc2)CCN(Cc2ccc(-c3nccs3)cc2)CC1]

A suspension of 4-(ethoxymethyl)-4-phenethyl-1-(4-(4,4,5,5-tetramethyl-1,3,2-dioxaborolan-2-yl) benzyl)piperidine (100 mg, 0.22 mmol), 2-bromothiazole (53.1 mg, 0.32 mmol) and tetrakis(triphenylphosphine)palladium (12.5 mg, 0.01 mmol) in dioxane (10 mL) was stirred under a N$_2$ atmosphere at RT for 30 min. Sodium carbonate solution (69.9 mg in 8 mL H$_2$O, 0.66 mmol) was added. The reaction was stirred at 100° C. overnight. Upon completion of the reaction, it was quenched with water and extracted with dichloromethane (10 mL×3). The combined organic phase was dried over Na$_2$SO$_4$, filtered and concentrated. The resulting oil was purified by silica-gel column chromatography followed by treatment with HCl/Et2O (2 mL) to give 11.3 mg of 2-(4-((4-(ethoxymethyl)-4-phenethylpiperidin-1-yl)methyl)phenyl)thiazole HCl salt as a white solid. LC-MS (ESI+): m/z 421 [M+H]$^+$.

25 Synthesis of 2-(4-((4-(ethoxymethyl)-4-phenethylpiperidin-1-yl)methyl)phenyl)-1,3,4-oxadiazole

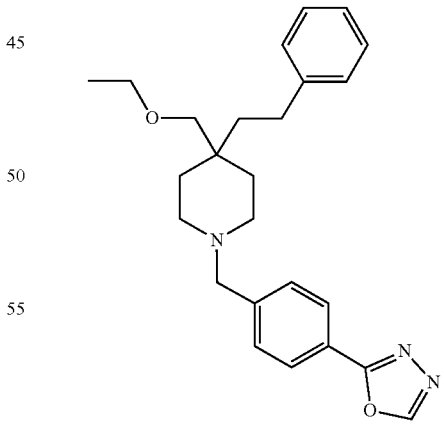

25.1 Preparation of 4-((4-(ethoxymethyl)-4-phenethylpiperidin-1-yl)methyl)-N'-formylbenzohydrazide To a solution of 4-((4-(ethoxymethyl)-4-phenethylpiperidin-1-yl)methyl)benzoic acid (690 mg, 1.81 mmol) and formohydrazide (108.5 mg, 1.81 mmol), DIPEA (701.3 mg, 5.42 mmol) in DMF (10 mL) at RT was added HATU (776.3 mg, 1.99 mmol). After stirred at 60° C. for 4 h, the reaction was quenched with water (30 mL) and extracted with DCM/MeOH (12:1, 20 mL×3). The combined organic phase was washed with brine, dried over anhydrous Na₂SO₄, filtered and concentrated. The residue was purified by silica-gel column chromatography to afford 780 mg of 4-((4-(ethoxymethyl)-4-phenethylpiperidin-1-yl)methyl)-N'-formylbenzohydrazide as an oil. LC-MS (ESI+): m/z 424 [M+H]⁺.

25.2 Preparation of 2-(4-((4-(ethoxymethyl)-4-phenethylpiperidin-1-yl)methyl)phenyl)-1,3,4-oxadiazole A solution of 4-((4-(ethoxymethyl)-4-phenethylpiperidin-1-yl)methyl)-N'-formylbenzohydrazide (178.7 mg, 0.42 mmol) and P₂O₅ (239.6 mg, 1.69 mmol in toluene (5 mL) was heated to reflux for 22 h. After cooled to 50° C., the reaction mixture was poured into ice-water and neutralized with aq. NaHCO₃ to pH=8, extracted with DCM/MeOH (12:1, 20 mL×3). The combined organic phase was dried over anhydrous Na₂SO₄ and concentrated. The residue was purified by preparative TLC to afford 40 mg of 2-(4-((4-(ethoxymethyl)-4-phenethylpiperidin-1-yl)methyl)phenyl)-1,3,4-oxadiazole as an oil. LC-MS (ESI+): m/z 406 [M+H]⁺.

26 Synthesis of 1-(4-((4-(ethoxymethyl)-4-phenethylpiperidin-1-yl)methyl)phenyl)ethanone

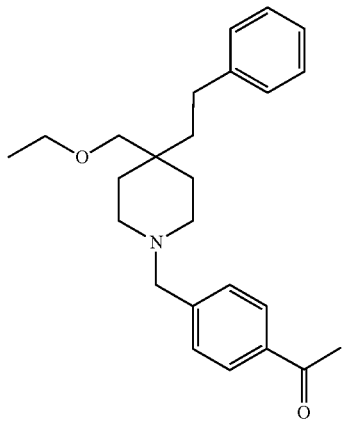 [SMILES: CCOCC1(CCc2ccccc2)CCN(Cc2ccc(C(C)=O)cc2)CC1]

26.1 Preparation of methyl 4-(2-methyl-1,3-dioxolan-2-yl)benzoate

To a solution of methyl 4-acetylbenzoate (9 g, 50.56 mmol) and ethylene glycol in toluene (180 mL) was added p-toluenesulfonic acid (961.8 mg, 5.5 mmol) in one portion. After heated with a Dean-Stark trap under reflux overnight, the reaction was then allowed to cool to RT and washed with a saturated aq. NaHCO₃ solution, water and brine. The organic layer was dried over Na₂SO₄, filtered and concentrated under reduced pressure. The residue was purified by flash column chromatography (DCM:hexane=1:3) to give 5 g of methyl 4-(2-methyl-1,3-dioxolan-2-yl)benzoate as a colorless oil.

26.2 Preparation of 4-(2-methyl-1,3-dioxolan-2-yl)benzaldehyde

To a solution of sodium dihydro-bis-(2-methoxyethoxy) aluminate (20 mL, 72 mmol, 70% in toluene solution) in THF (10 mL) at 0° C. was added 1-methylpiperazine (9 g, 90 mmol), followed by addition of methyl 4-(2-methyl-1,3-dioxolan-2-yl)benzoate (4 g, 18 mmol) in THF (10 mL) in dropwise at 0° C. After stirred at 0° C. for 1 h, the reaction mixture was poured into water and extracted with EtOAc. The combined organic layer was dried over anhydrous Na₂SO₄, filtered and concentrated under reduced pressure to afford 3.61 g of 4-(2-methyl-1,3-dioxolan-2-yl)benzaldehyde as an yellow oil, which was used directly for the next step.

26.3 Preparation of 4-(ethoxymethyl)-1-(4-(2-methyl-1,3-dioxolan-2-yl)benzyl)-4-phenethylpiperidine The title compound was prepared from 4-(2-methyl-1,3-dioxolan-2-yl)benzaldehyde according to the procedure 1.5. LC-MS (ESI+): m/z 424 [M+H]⁺.

26.4 Preparation of 1-(4-((4-(ethoxymethyl)-4-phenethylpiperidin-1-yl)methyl)phenyl)ethanone To a solution of 4-(ethoxymethyl)-1-(4-(2-methyl-1,3-dioxolan-2-yl)benzyl)-4-phenethylpiperidine (50 mg, 0.118 mmol) in acetone (3 mL) was added 5 N HCl (1.2 mL, 5.9 mmol) and the mixture was stirred at RT for 2 h. Upon completion of the reaction, acetone was removed under reduced pressure. The residual aqueous solution was extracted with MTBE (20 mL×3). The separated water layer was adjusted pH to 8 by addition of Na₂CO₃ aqueous solution and extracted with EtOAc (20 mL×3). The combined organic layer was washed with brine, dried over Na₂SO₄ and concentrated to afford 40 mg of crude 1-(4-((4-(ethoxymethyl)-4-phenethylpiperidin-1-yl)methyl)phenyl)ethanone. After purification by silica-gel column chromatography, the product was dissolved in a solution of HCl/Et₂O (2 mL) and stirred for 5 min. The resulting suspension was concentrated and washed with Et₂O twice to give 30 mg of 1-(4-((4-(ethoxymethyl)-4-phenethylpiperidin-1-yl)methyl)phenyl)ethanone HCl salt as a white solid. LC-MS (ESI+): m/z 380 [M+H]⁺.

27 Synthesis of 1-(4-(2H-1,2,3-triazol-4-yl)benzyl)-4-(ethoxymethyl)-4-phenethyl-piperidine

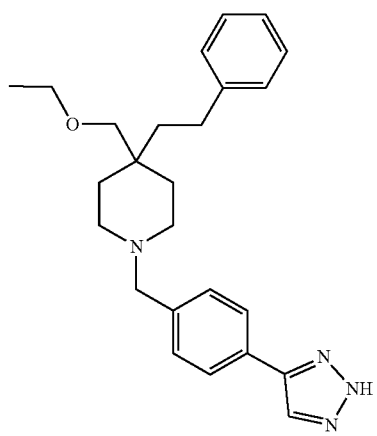 [SMILES: CCOCC1(CCc2ccccc2)CCN(Cc2ccc(-c3cn[nH]n3)cc2)CC1]

27.1 Preparation of 4-((trimethylsilyl)ethynyl)benzaldehyde

A suspension of 4-bromobenzaldehyde (1 g, 5 mmol), Pd(PPh$_3$)$_4$ (0.23 g, 0.2 mmol), CuI (95 mg, 0.5 mmol), triethylamine (2.02 g, 20 mmol) and ethynyltrimethylsilane (0.79 g, 8 mmol) in THF (20 mL) under a N$_2$ atmosphere was stirred at RT overnight. The mixture was filtered and the filtrate was concentrated. The residue was purified by silica-gel column chromatography to give 1.2 g of 4-((trimethylsilyl)ethynyl)benzaldehyde as a light brown solid.

27.2 Preparation of 4-(ethoxymethyl)-4-phenethyl-1-(4-((trimethylsilyl)ethynyl) benzyl) piperidine The title compound was prepared from 4-((trimethylsilyl)ethynyl)benzaldehyde according to the procedure 1.5. LC-MS (ESI+): m/z 434 [M+H]$^+$.

27.3 Preparation of 4-(ethoxymethyl)-1-(4-ethynylbenzyl)-4-phenethylpiperidine To a solution of 4-(ethoxymethyl)-4-phenethyl-1-(4-((trimethylsilyl)ethynyl)benzyl) piperidine (1 g, 2.3 mmol) in MeOH (15 mL) was added a pre-dissolved solution of KOH (136 mg, 2.4 mmol) in water (0.25 mL). The reaction mixture was stirred at RT for 1 h. After concentration, the residue was diluted with water and extracted with EtOAc (20 mL×3). The combined organic phase was dried over anhydrous Na$_2$SO$_4$, filtered and concentrated. The residue was purified by silica-gel column chromatography to give 820 mg of 4-(ethoxymethyl)-1-(4-ethynylbenzyl)-4-phenethylpiperidine as a brown oil. LC-MS (ESI+): m/z 362 [M+H]$^+$.

27.4 Preparation of 1-(4-(2H-1,2,3-triazol-4-yl)benzyl)-4-(ethoxymethyl)-4-phenethyl-piperidine To a solution of 4-(ethoxymethyl)-1-(4-ethynylbenzyl)-4-phenethylpiperidine (100 mg, 0.28 mmol) and azidotrimethylsilane (47.8 mg, 0.41 mmol) in N,N-dimethylformamide (4 mL) and MeOH (1 mL) under N$_2$ atmosphere at RT was added CuI (2.63 mg, 0.014 mmol). The mixture was stirred at 100° C. overnight. After cooled to RT, the reaction mixture was quenched by addition of ammonia aqueous solution and extracted with EtOAc (20 mL×3). The combined organic phase was dried over Na$_2$SO$_4$, filtered and concentrated. The residue was purified by silica-gel column chromatography to give 35 mg of 1-(4-(2H-1,2,3-triazol-4-yl)benzyl)-4-(ethoxymethyl)-4-phenethyl-piperidine as a yellow solid. LC-MS (ESI+): m/z 405 [M+H]$^+$.

28 Synthesis of 1-(4-(1H-tetrazol-5-yl)benzyl)-4-(ethoxymethyl)-4-phenethylpiperidine

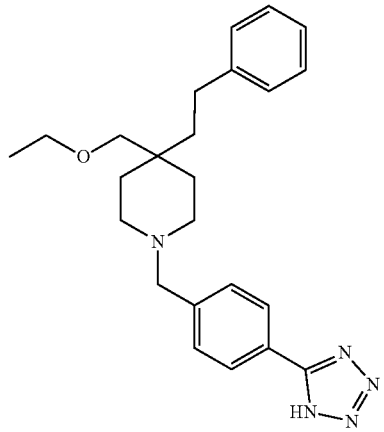 [SMILES: CCOCC1(CCc2ccccc2)CCN(Cc2ccc(-c3nnn[nH]3)cc2)CC1]

To a solution of 4-((4-(ethoxymethyl)-4-phenethylpiperidin-1-yl)methyl)benzonitrile (50 mg, 0.138 mmol) in DMF (3 mL) was added NaN$_3$ (54 mg, 0.83 mmol) and NH$_4$Cl (45 mg, 0.83 mmol). The reaction was stirred at 100° C. overnight. After cooled to RT, the reaction mixture was diluted with water (20 mL) and extracted with EtOAc (20 mL×3). The combined organic phase was dried over Na$_2$SO$_4$, filtered and concentrated. The residue was purified by preparative HPLC, followed by lyophilization and HCl salt formation in HCl/Et$_2$O solution to give 2.2 mg of 1-(4-(1H-tetrazol-5-yl)benzyl)-4-(ethoxymethyl)-4-phenethylpiperidine HCl salt as a white solid. LC-MS (ESI+): m/z 406 [M+H]$^+$.

29 Synthesis of 5-(4-((4-(ethoxymethyl)-4-phenethylpiperidin-1-yl)methyl)phenyl)-2,4-dihydro-3H-1,2,4-triazol-3-one

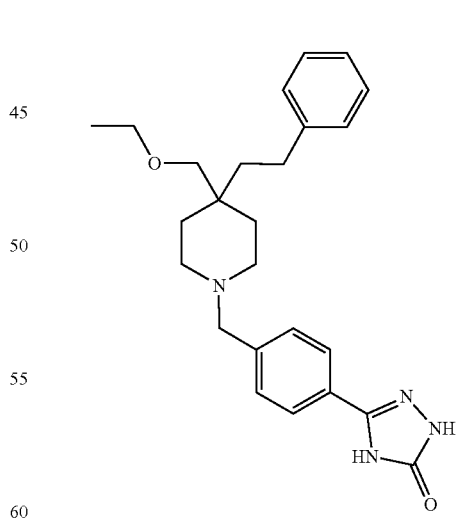

29.1 Preparation of 4-((4-(ethoxymethyl)-4-phenethylpiperidin-1-yl)methyl) benzohydrazide To a solution of methyl 4-((4-(ethoxymethyl)-4-phenethylpiperidin-1-yl)methyl)benzoate (500 mg, 1.26 mmol) in ethanol (20 mL) at RT was added hydrazine hydrate (7 mL). After stirred at 80° C. for 3 h. the reaction mixture was concentrated. The residue was purified by silica-gel column chromatography to give 800 mg of 4-((4-(ethoxymethyl)-4-phenethylpiperidin-1-yl)methyl) benzohydrazide as a solid. LC-MS (ESI+): m/z 396 [M+H]+.

29.2 Preparation of 5-(4-((4-(ethoxymethyl)-4-phenethylpiperidin-1-yl)methyl)phenyl)-1,3,4-oxadiazol-2-amine To a solution of 4-((4-(ethoxymethyl)-4-phenethylpiperidin-1-yl)methyl) benzohydrazide (700 mg, 1.77 mmol) in dioxane (20 mL) at RT was added a pre-prepared Na$_2$CO$_3$ aqueous solution (148.7 mg, 1.77 mmol) in H$_2$O (1 mL). After stirred for 10 min, cyanogen bromide (224 mg, 2.12 mmol) was added. After the reaction mixture was stirred at RT overnight, it was quenched by addition of water (30 mL) and extracted with EtOAc (20 mL×3). The combined organic phase was dried over Na$_2$SO$_4$, filtered and concentrated. The residue was purified by silica-gel column chromatography to give 144 mg of 5-(4-((4-(ethoxymethyl)-4-phenethylpiperidin-1-yl)methyl)phenyl)-1,3,4-oxadiazol-2-amine as a white solid. LC-MS (ESI+): m/z 421 [M+H]+.

29.3 Preparation of 1-(4-(5-ethoxy-4H-1,2,4-triazol-3-yl)benzyl)-4-(ethoxymethyl)-4-phenethylpiperidine To a solution of 5-(4-((4-(ethoxymethyl)-4-phenethylpiperidin-1-yl)methyl)phenyl)-1,3,4-oxadiazol-2-amine (110 mg, 0.26 mmol) in ethanol (20 mL) at RT was added potassium hydroxide (73.4 mg, 1.3 mmol). The reaction mixture was heated to reflux overnight. After cooled to RT, the mixture was concentrated under reduced pressure to remove EtOH and filtered. The filtrate was concentrated and purified by silica-gel column chromatography to give 65 mg of 1-(4-(5-ethoxy-4H-1,2,4-triazol-3-yl)benzyl)-4-(ethoxymethyl)-4-phenethylpiperidine as a white solid. LC-MS (ESI+): m/z 449 [M+H]+.

29.4 Preparation of 5-(4-((4-(ethoxymethyl)-4-phenethylpiperidin-1-yl)methyl)phenyl)-2,4-dihydro-3H-1,2,4-triazol-3-one A solution of 1-(4-(5-ethoxy-4H-1,2,4-triazol-3-yl) benzyl)-4-(ethoxymethyl)-4-phenethylpiperidine (50 mg, 0.11 mmol) in 10% HCl aqueous solution (10 mL) was heated to reflux overnight. After cooled to RT, the mixture was adjusted to pH=8 by addition of saturated Na$_2$CO$_3$ aqueous solution and extracted with dichloromethane (20 mL×3). The combined organic phase was dried over Na$_2$SO$_4$, filtered and concentrated. The residue was purified by silica-gel column chromatography to give 20 mg of 5-(4-((4-(ethoxymethyl)-4-phenethylpiperidin-1-yl)methyl)phenyl)-2,4-dihydro-3H-1,2,4-triazol-3-one as a white solid. LC-MS (ESI+): m/z 421 [M+H]+.

30. Synthesis of 5-((4-(ethoxymethyl)-4-phenethylpiperidin-1-yl)methyl)-1,3-dihydro-2H-benzo[d]imidazol-2-one

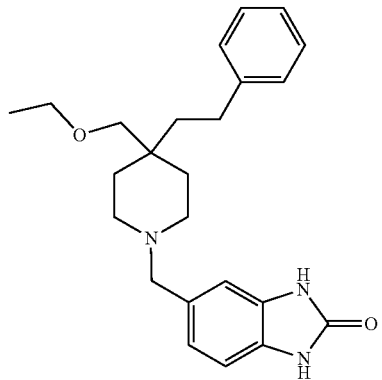 [SMILES: CCOCC1(CCc2ccccc2)CCN(Cc2ccc3[nH]c(=O)[nH]c3c2)CC1]

30.1 Preparation of 5-bromo-1,3-dihydro-2H-benzo[d]imidazol-2-one

To a solution of 4-bromobenzene-1,2-diamine (3 g, 16 mmol) in DMF (60 mL) was added CDI (3.1 g, 19.3 mmol). The reaction was stirred at 80° C. for 4 h. After the mixture was cooled to RT, water (100 mL) was added. The precipitate was collected by filtration and dried to give 4 g of 5-bromo-1,3-dihydro-2H-benzo[d]imidazol-2-one as a dark red solid. GC-MS: 212/214 (M).

30.2 Preparation of 5-vinyl-1,3-dihydro-2H-benzo[d]imidazol-2-one

To a solution of 5-bromo-1,3-dihydro-2H-benzo[d]imidazol-2-one (500 mg, 2.35 mmol), 4,4,5,5-tetramethyl-2-vinyl-1,3,2-dioxaborolane (542 mg, 3.52 mmol) and Pd(PPh$_3$)$_4$ (136 mg, 0.12 mmol) in dioxane (10 mL) under N$_2$ atmosphere was added Na$_2$CO$_3$ (1.1 g, 7.05 mmol). The reaction was stirred at 100° C. overnight. After the mixture was cooled to RT, water (20 mL) was added. The precipitate was collected by filtration and dried to give 150 mg of 5-vinyl-1,3-dihydro-2H-benzo[d]imidazol-2-one as a yellow solid. GC-MS: 160 (M).

30.3 Preparation of 2-oxo-2,3-dihydro-1H-benzo[d]imidazole-5-carbaldehyde

To a solution of 5-vinyl-1,3-dihydro-2H-benzo[d]imidazol-2-one (150 mg, 0.94 mmol) in dioxane (10 mL) and water (10 mL) was added OsO$_4$ (10 mg, 0.039 mmol) and NaIO$_4$ (600 mg, 2.82 mmol). After the reaction was stirred at RT for 3 h, water (10 mL) was added, extracted with ethyl acetate (10 mL×3) and washed with brine (10 mL). The combined organic phase was dried over Na$_2$SO$_4$, filtered and concentrated. The residue was purified by silica-gel column chromatography (DCM/MeOH=15:1-10:1) to give 37 mg of 2-oxo-2,3-dihydro-1H-benzo[d]imidazole-5-carbaldehyde as a solid. LC-MS (ESI-): m/z 161 [M−H]−.

30.4 Preparation of 5-((4-(ethoxymethyl)-4-phenethylpiperidin-1-yl)methyl)-1,3-dihydro-2H-benzo[d]imidazol-2-one The title compound was prepared from 2-oxo-2,3-dihydro-1H-benzo[d]imidazole-5-carbaldehyde according to the procedure 1.5. LC-MS (ESI+): m/z 394 [M+H]+.

31. Synthesis of N-(4-((4-(ethoxymethyl)-4-phenethylpiperidin-1-yl)methyl) cyclohexyl)acetamide

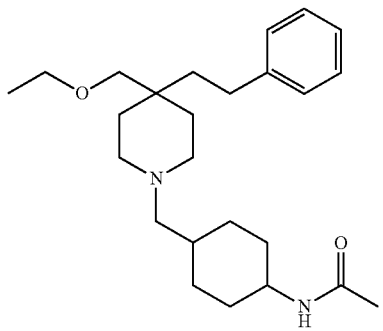 [SMILES: CCOCC1(CCc2ccccc2)CCN(CC2CCC(NC(C)=O)CC2)CC1]

31.1 Preparation of 4-(tert-butoxycarbonylamino)cyclohexanecarboxylic acid

To a solution of 4-aminocyclohexanecarboxylic acid (1.00 g, 6.99 mmol) in THF (20 mL) was added (Boc)$_2$O (1.68 g, 7.69 mmol) and 5 mL of saturated NaHCO$_3$ aqueous solution. After stirred at RT overnight, the mixture was adjusted to pH=3 with 10% HCl aqueous solution. The mixture was extracted with EtOAc (3×100 mL). The combined organic phase was dried over Na$_2$SO$_4$, filtered and concentrated in vacuo to give 2 g of 4-(tert-butoxycarbonylamino)cyclohexanecarboxylic acid as an oil, which was used directly for the next step. LC-MS (ESI−): m/z 242 [M−H]−.

31.2 Preparation of methyl 4-(tert-butoxycarbonylamino)cyclohexanecarboxylate To a solution of 4-(tert-butoxycarbonylamino)cyclohexanecarboxylic acid (1.70 g, 6.99 mmol) in MeOH (40 mL) at RT was added SOCl$_2$ (5 mL). After stirred at RT for 2 h, the reaction mixture was extracted with EtOAc (3×100 mL). The combined organic phase was washed with brine, dried over Na$_2$SO$_4$, filtered and concentrated in vacuo. The residue was purified by silica-gel column chromatography (Hexane:EtOAc=15:1) to give 1 g of methyl 4-(tert-butoxycarbonylamino)cyclohexanecarboxylate as an oil.

31.3 Preparation of tert-butyl 4-(hydroxymethyl)cyclohexylcarbamate

To a solution of methyl 4-(tert-butoxycarbonylamino)cyclohexanecarboxylate (0.90 g, 3.50 mmol) in THF (20 mL) was added LiAlH$_4$ (0.27 g, 7.00 mmol) in portions. After the reaction was stirred at RT for 20 min, 0.3 mL of water and 0.9 mL of 15% NaOH aqueous solution were added. The suspension was filtered. The filtrate was concentrated to give 930 mg of crude product as a yellow oil, which was used directly for the next step. LC-MS (ESI+): m/z 236 [M+Li]+.

31.4 Preparation of (4-(tert-butoxycarbonylamino)cyclohexyl)methyl 4-methylbenzenesulfonate To a solution of the above crude tert-butyl 4-(hydroxymethyl)cyclohexylcarbamate (0.90 g, 3.93 mmol) in DCM (90 mL) at 0° C. was added DMAP (14.0 mg, 3%) and Et$_3$N (0.79 g, 7.86 mmol). After 10 min, a suspension solution of TosCl (0.90 g, 4.72 mmol) in DCM was added. The mixture was stirred at RT overnight. The reaction mixture was then quenched with brine and extracted with EtOAc (3×100 mL). The combined organic layers were dried over Na$_2$SO$_4$, filtered and concentrated in vacuo. The residue was purified by silica-gel column chromatography (Hexane:EtOAc=20:1) to give 790 mg of (4-(tert-butoxycarbonylamino)cyclohexyl)methyl 4-methylbenzenesulfonate as an oil. LC-MS (ESI+): m/z 384 [M+H]+.

31.5 Preparation of tert-butyl 4-((4-(ethoxymethyl)-4-phenethylpiperidin-1-yl) methyl)cyclohexylcarbamate To a solution of 4-(ethoxymethyl)-4-phenethylpiperidine (0.18 mg, 0.72 mmol) and (4-(tert-butoxycarbonylamino)cyclohexyl)methyl 4-methylbenzenesulfonate (0.25 g, 0.65 mmol) in CH$_3$CN (10 mL) was added K$_2$CO$_3$ (0.18 g, 1.30 mmol). The mixture was stirred at 80° C. for 20 h. After cooled to RT, the mixture was diluted with brine and extracted with EtOAc (3×100 mL). The combined organic phase was dried over Na$_2$SO$_4$, filtered and concentrated in vacuo. The residue was purified by silica-gel column chromatography (Hexane:EtOAc=10:1) to give 170 mg of tert-butyl 4-((4-(ethoxymethyl)-4-phenethylpiperidin-1-yl)methyl)cyclohexylcarbamate as a yellow oil. LC-MS (ESI+): m/z 459 [M+H]+.

31.6 Preparation of 4-((4-(ethoxymethyl)-4-phenethylpiperidin-1-yl)methyl) cyclohexanamine The title compound was prepared from tert-butyl 4-((4-(ethoxymethyl)-4-phenethylpiperidin-1-yl) methyl)cyclohexylcarbamate according to the procedure 1.4. LC-MS (ESI+): m/z 359 [M+H]+.

31.7 Preparation of N-(4-((4-(ethoxymethyl)-4-phenethylpiperidin-1-yl)methyl) cyclohexyl)acetamide To a solution of 4-((4-(ethoxymethyl)-4-phenethylpiperidin-1-yl)methyl) cyclohexanamine (0.28 g, 0.47 mmol) in DCM (10 mL) at RT was added Et$_3$N (0.19 g, 1.89 mmol). CH$_3$COCl (44 mg, 0.56 mmol) was added dropwise. After stirred at RT for 1 h, the mixture was quenched with water and washed with saturated NaHCO$_3$ aqueous solution, followed by extraction with DCM (3×100 mL). The combined organic phase was dried over Na$_2$SO$_4$, filtered and concentrated in vacuo. The residue was purified by preparative TLC (EtOAc) to give an yellow oil, which was treated with HCl/Et$_2$O solution to give 32 mg of N-(4-((4-(ethoxymethyl)-4-phenethylpiperidin-1-yl)methyl) cyclohexyl)acetamide HCl salt as a white solid. LC-MS (ESI+): m/z 401 [M+H]+.

32. Synthesis of N-[4-(4-Ethoxymethyl-4-phenethyl-piperidin-1-yl)-phenyl]-acetamide

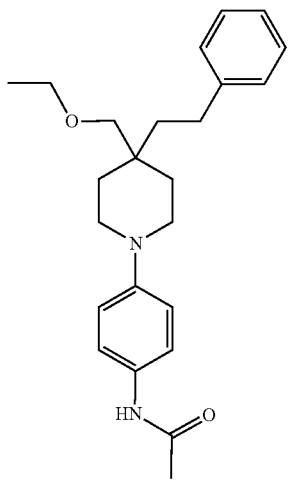 [SMILES: CCOCC1(CCc2ccccc2)CCN(c2ccc(NC(C)=O)cc2)CC1]

32.1 Preparation of 4-ethoxymethyl-1-(4-nitrophenyl)-4-phenethyl-piperidine

To a solution of 4-ethoxymethyl-4-phenethyl-piperidine (100 mg, 0.4 mmol) and 4-fluoronitrobenzene (70 mg, 0.5 mmol) in DMSO (5 mL) was added K$_2$CO$_3$ (100 mg, 0.75 mmol). The reaction was stirred at 90° C. overnight. After cooled to RT, the mixture was quenched with saturated NH$_4$Cl aqueous solution and extracted with EtOAc (20 mL×3). The combined organic phase was dried over Na$_2$SO$_4$ and concentrated in vacuo. The residue was purified by silica-gel column chromatography (EtOAc/MeOH=10:1) to give 200 mg of 4-ethoxymethyl-1-(4-nitrophenyl)-4-phenethyl-piperidine as a yellow solid. LC-MS (ESI+): m/z 369 [M+H]$^+$.

32.2 Preparation of 4-(4-ethoxymethyl-4-phenethyl-piperidin-1-yl)-phenylamine The title compound was prepared from 4-ethoxymethyl-1-(4-nitrophenyl)-4-phenethyl-piperidine according to the procedure 20.2. LC-MS (ESI+): m/z 339 [M+H]$^+$.

32.3 Preparation of N-[4-(4-ethoxymethyl-4-phenethyl-piperidin-1-yl)-phenyl]-acetamide The title compound was prepared from 4-(4-ethoxymethyl-4-phenethyl-piperidin-1-yl)-phenylamine according to the procedure 31.7. LC-MS (ESI+): m/z 381 [M+H]$^+$.

33. Synthesis of N-{4-[2-(4-Ethoxymethyl-4-phenethyl-piperidin-1-yl)-ethyl]-phenyl}-acetamide

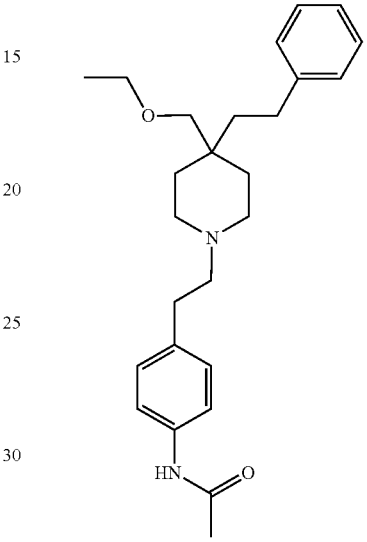

33.1 Preparation of 4-ethoxymethyl-1-[2-(4-nitrophenyl)-ethyl]-4-phenethyl-piperidine A solution of 4-ethoxymethyl-4-phenethyl-piperidine (150 mg, 0.6 mmol), toluene-4-sulfonic acid-2-(4-nitrophenyl)-ethyl ester (208 mg, 0.72 mmol) and K$_2$CO$_3$ (157 mg, 1.14 mmol) in CH$_3$CN (7 mL) was stirred at 60° C. overnight. The reaction mixture was quenched with saturated NH$_4$Cl aqueous solution and filtered. The filtrate was extracted with EtOAc (30 mL×3). The combined organic phase was dried over Na$_2$SO$_4$, filtered and concentrated in vacuo. The residue was purified by silica-gel column chromatography (EtOAc) to give 250 mg of 4-ethoxymethyl-1-[2-(4-nitro-phenyl)-ethyl]-4-phenethyl-piperidine as a yellow oil. LC-MS (ESI+): m/z 397 [M+H]$^+$.

33.2 Preparation of 4-[2-(4-ethoxymethyl-4-phenethyl-piperidin-1-yl)-ethyl]-phenylamine The title compound was prepared from 4-ethoxymethyl-1-[2-(4-nitro-phenyl)-ethyl]-4-phenethyl-piperidine according to the procedure 20.2. LC-MS (ESI+): m/z 367 [M+H]$^+$.

33.3 Preparation of N-{4-[2-(4-ethoxymethyl-4-phenethyl-piperidin-1-yl)-ethyl]-phenyl}-acetamide The title compound was prepared from 4-[2-(4-ethoxymethyl-4-phenethyl-piperidin-1-yl)-ethyl]-phenylamine according to the procedure 31.7. LC-MS (ESI+): m/z 409 μM+H]$^+$.

34. Synthesis of N-(4-((4-(ethoxymethyl)-4-phenethylpiperidin-1-yl)methyl)-2,6-dimethylphenyl)acetamide

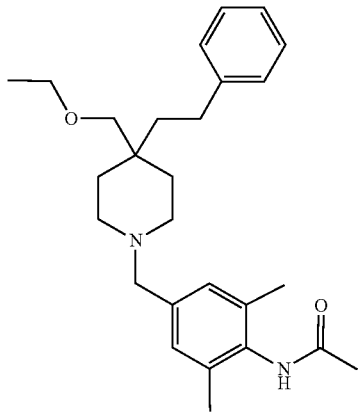 [SMILES: CCOCC1(CCc2ccccc2)CCN(Cc2cc(C)c(NC(C)=O)c(C)c2)CC1]

34.1 Preparation of 1,3,5-trimethyl-2-nitrobenzene

To a solution of mesitylene (3.23 g, 26.92 mmol) and con.H$_2$SO$_4$ (10 mL) at 0° C. was added fuming HNO$_3$ (1 mL). After the mixture was stirred at 0° C. for 2 h, ice water (30 mL) was added. The solution was extracted with n-hexane (50 mL×3), dried over Na$_2$SO$_4$, filtered and concentrated. The residue was purified by silica-gel column chromatography to afford 800 mg of 1,3,5-trimethyl-2-nitrobenzene.

34.2 Preparation of 3,5-dimethyl-4-nitrobenzoic acid

A solution of 1,3,5-trimethyl-2-nitrobenzene (800 mg, 4.84 mmol) and chromium (VI) oxide (1.65 g, 16.5 mmol) in acetic acid (10 mL) was stirred at RT for 4 h. The mixture was poured into ice water. The precipitated solid was collected by filtration and dried to give 362 mg of 3,5-dimethyl-4-nitrobenzoic acid. LC-MS (ESI−): m/z 194 [M−H]$^−$.

34.3 Preparation of (3,5-dimethyl-4-nitrophenyl)(4-(ethoxymethyl)-4-phenethylpiperidin-1-yl)methanone To a solution of 4-(ethoxymethyl)-4-phenethylpiperidine (458.5 mg, 1.85 mmol) and 3,5-dimethyl-4-nitrobenzoic acid (362 mg, 1.85 mmol) in DMF (10 mL) at RT was added. EDCl (712.8 mg, 3.71 mmol), HOBt (501.2 mg, 3.71 mmol) and Et$_3$N (562.5 mg, 5.60 mmol). The reaction was stirred at 80° C. overnight. Upon completion of the reaction, the reaction was cooled to RT and water (10 mL) was added. The aqueous solution was extracted with EtOAc (30 mL×3). The combined organic phase was dried over Na$_2$SO$_4$ and concentrated. The residue was purified by silica-gel column chromatography to afford 570 mg of (3,5-dimethyl-4-nitrophenyl)(4-(ethoxymethyl)-4-phenethylpiperidin-1-yl)methanone. LC-MS (ESI+): m/z 425 [M+H]$^+$.

34.4 Preparation of 1-(3,5-dimethyl-4-nitrobenzyl)-4-(ethoxymethyl)-4-phenethylpiperidine To a solution of (3,5-dimethyl-4-nitrophenyl)(4-(ethoxymethyl)-4-phenethylpiperidin-1-yl)methanone (577 mg, 1.36 mmol) in THF (20 mL) under a N$_2$ atmosphere at RT was added LiAlH$_4$ (129.2 mg, 3.40 mmol). After stirred at RT for 0.5 h, the reaction mixture was quenched with water, followed by addition of NaOH aqueous solution to adjust pH to 9 and extracted with EtOAc (30 mL×3). The combined organic layer was dried over Na$_2$SO$_4$, filtered and concentrated. The residue was purified by silica-gel column chromatography to afford 274.8 mg of 1-(3,5-dimethyl-4-nitrobenzyl)-4-(ethoxymethyl)-4-phenethylpiperidine. LC-MS (ESI+): m/z 411 [M+H]$^+$.

34.5 Preparation of 4-((4-(ethoxymethyl)-4-phenethylpiperidin-1-yl)methyl)-2,6-dimethylaniline The title compound was prepared from 1-(3,5-dimethyl-4-nitrobenzyl)-4-(ethoxymethyl)-4-phenethylpiperidine according to the procedure 20.2. LC-MS (ESI+): m/z 381 [M+H]$^+$.

34.6 Preparation of N-(4-((4-(ethoxymethyl)-4-phenethylpiperidin-1-yl)methyl)-2,6-dimethylphenyl)acetamide The title compound was prepared from 4-((4-(ethoxymethyl)-4-phenethylpiperidin-1-yl)methyl)-2,6-dimethylaniline according to the procedure 31.7 LC-MS (ESI+): m/z 423 [M+H]$^+$.

35. Synthesis of (R)-3-((3-(ethoxymethyl)-3-(2-(5-methylthiophen-3-yl)ethyl)pyrrolidin-1-yl)methyl)pyridine and (S)-3-((3-(ethoxymethyl)-3-(2-(5-methylthiophen-3-yl)ethyl)pyrrolidin-1-yl)methyl)pyridine

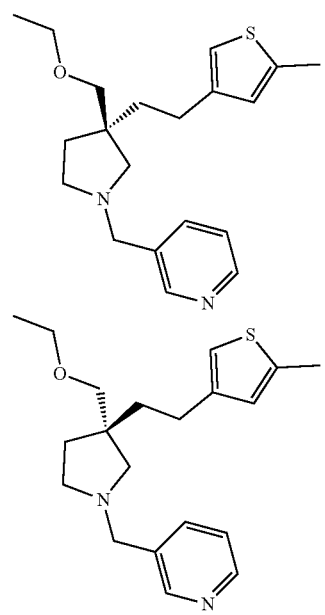

35.1 Preparation of 1-tert-butyl 3-methyl 3-((benzyloxy)methyl)pyrrolidine-1,3-dicarboxylate To a solution of LHMDS (1.18 L, 1.18 mol, 1.0 M in THF solution) in THF (1 L) at −78° C. under N$_2$ atmosphere was added a solution of 1-tert-butyl 3-methyl pyrrolidine-1,3- dicarboxylate (180 g, 0.786 mol) and ((chloromethoxy)methyl)benzene (184 g, 1.18 mol) in THF (0.5 L). The mixture was then allowed to warm to RT slowly and stirred at RT overnight. The reaction was then quenched with water (1.5 L) and extracted with EtOAc (2×1 L). The combined organic phase was washed with brine (2×1.5 L), dried over $Na_2SO_4$, filtered and concentrated in vacuo. The residue was purified by flash column chromatography (EtOAc:Hexane=1:40-1:20-1:10) to provide 260 g of 1-tert-butyl 3-methyl 3-((benzyloxy)methyl)pyrrolidine-1,3-dicarboxylate as a yellow oil. LC-MS (ESI+): m/z 350 [M+H]$^+$.

35.2 Preparation of 3-((benzyloxy)methyl)-1-(tert-butoxycarbonyl)pyrrolidine-3-carboxylic acid To a solution of 1-tert-butyl 3-methyl 3-((benzyloxy)methyl)pyrrolidine-1,3-dicarboxylate (290 g, 0.83 mol) in MeOH (800 mL) was added a solution of NaOH (66.5 g, 1.66 mol) in $H_2O$ (800 mL). The reaction was stirred at RT for 2 h. The solvent was removed and the aqueous phase was adjust pH to 5-6 using 10% HCl aqueous solution. The mixture was extracted with DCM:MeOH (2×1 L). The combined organic layer was washed with brine (2×1.5 L), dried over $Na_2SO_4$, filtered and concentrated in vacuo. The residue was washed with n-Hexane to provide 195 g of 3-((benzyloxy)methyl)-1-(tert-butoxycarbonyl)pyrrolidine-3-carboxylic acid as an off-white solid. LC-MS (ESI−): m/z 334 [M−H]$^-$.

35.3 Preparation of tert-butyl (R)-3-((benzyloxy)methyl)-3-((S)-4-isopropyl-2-oxooxazolidine-3-carbonyl)pyrrolidine-1-carboxylate and tert-butyl (S)-3-((benzyloxy)methyl)-3-((S)-4-isopropyl-2-oxooxazolidine-3-carbonyl)pyrrolidine-1-carboxylate To a solution of 3-((benzyloxy)methyl)-1-(tert-butoxycarbonyl)pyrrolidine-3-carboxylic acid (70 g, 0.21 mol) and TEA (43.4 mL, 0.31 mol) in THF (700 mL) under $N_2$ atmosphere at 0° C. was added methyl carbonochloridate (17.8 mL, 0.23 mol) dropwise. The reaction mixture was stirred at 0° C. for 1 h and filtered. The filtration was concentrated in vacuo to provide the crude mixed anhydride, which was dissolved in THF (400 mL) for further use.

To a solution of (S)-4-isopropyloxazolidin-2-one (30 g, 0.23 mol) in THF (700 mL) under $N_2$ atmosphere at −78° C. was added n-BuLi (100 mL, 0.25 mol, 2.5 M in hexane) dropwise. The reaction mixture was stirred at −78° C. for 2 h. To the solution was added the pre-prepared solution of mixed anhydride in THF (400 mL).

After stirred at −78° C. for 1 h, the reaction mixture was quenched with water (500 mL) and extracted with EtOAc (2×500 mL). The combined organic layer was washed with brine (2×800 mL), dried over $Na_2SO_4$, filtered and concentrated in vacuo. The residue was purified by flash column chromatography (EtOAc:n-hexane=1:40-1:20-1:10) to provide 15 g of tert-butyl (R)-3-((benzyloxy)methyl)-3-((S)-4-isopropyl-2-oxooxazolidine-3-carbonyl)pyrrolidine-1-carboxylate as off-white solid and 23 g of tert-butyl (S)-3-((benzyloxy)methyl)-3-((S)-4-isopropyl-2-oxooxazolidine-3-carbonyl)pyrrolidine-1-carboxylate as an oil. LC-MS (ESI+): m/z 447 [M+H]$^+$.

35.4 Preparation of tert-butyl (S)-3-((benzyloxy)methyl)-3-(hydroxymethyl)pyrrolidine-1-carboxylate To a solution of tert-butyl (R)-3-((benzyloxy)methyl)-3-((S)-4-isopropyl-2-oxooxazolidine-3-carbonyl)pyrrolidine-1-carboxylate (2 g, 4.48 mmol) in THF:MeOH (1:1, 20 mL) was added $NaBH_4$ (340 mg, 8.96 mmol) in portions. After the reaction was stirred at RT for 2 h, a saturated $NH_4Cl$ aqueous solution was added. The mixture was extracted with EtOAc (20 mL×3). The combined organic phase was dried over $Na_2SO_4$, filtered and concentrated. The residue was purified by silica-gel column chromatography (EtOAc/hexane=1:3) to give 1.2 g of tert-butyl (S)-3-((benzyloxy)methyl)-3-(hydroxymethyl)pyrrolidine-1-carboxylate as a colorless oil. LC-MS (ESI+): m/z 322 [M+H]$^+$.

35.5 Preparation of tert-butyl (S)-3-((benzyloxy)methyl)-3-(ethoxymethyl)pyrrolidine-1-carboxylate To a solution of tert-butyl (S)-3-((benzyloxy)methyl)-3-(hydroxymethyl)pyrrolidine-1-carboxylate (1.2 g, 3.4 mmol) in DMF (30 mL) under $N_2$ atmosphere at RT was added NaH (275 mg, 6.9 mmol). After the reaction was stirred at RT for 0.5 h, bromoethane (440 mg, 4.1 mmol) was added dropwise. After the reaction was stirred at RT for 12 h, water (50 mL) was added. The aqueous solution was extracted with EtOAc (20 mL×3). The combined organic layer was dried over $Na_2SO_4$ and concentrated. The residue was purified by silica-gel column chromatography (EtOAc/hexane=1:6) to give 1.2 g of (tert-butyl (S)-3-((benzyloxy)methyl)-3-(ethoxymethyl)pyrrolidine-1-carboxylate as a colorless oil. LC-MS (ESI+): m/z 350 [M+H]$^+$.

35.6 Preparation of tert-butyl (R)-3-(ethoxymethyl)-3-(hydroxymethyl)pyrrolidine-1-carboxylate A solution of (tert-butyl (S)-3-((benzyloxy)methyl)-3-(ethoxymethyl)pyrrolidine-1-carboxylate (1.2 g, 3.4 mmol) and Pd/C (100 mg) in MeOH (20 mL) was kept under a hydrogen atmosphere at 1 atm for 12 h. Upon completion of the reaction, Pd/C was removed by filtration and the filtrate was concentrated. The residue was purified by silica-gel column chromatography (EtOAc/hexane=1:1) to give 900 mg of tert-butyl (R)-3-(ethoxymethyl)-3-(hydroxymethyl)pyrrolidine-1-carboxylate as a colorless oil. LC-MS (ESI+): m/z 260 [M+H]$^+$.

35.7 Preparation of tert-butyl (R)-3-(ethoxymethyl)-3-formylpyrrolidine-1-carboxylate To a solution of tert-butyl (R)-3-(ethoxymethyl)-3-(hydroxymethyl)pyrrolidine-1-carboxylate (900 mg, 3.4 mmol) in DCM (5 mL) was added. Dess-Martin Periodiane (2.1 g, 5.1 mmol,). After the reaction was stirred at RT for 1 h, sodium thiosulfate solution (10 mL) was added and stirred for additional 0.5 h. The aqueous solution was extracted with DCM (20 mL×3), dried over anhydrous $Na_2SO_4$, filtered and concentrated. The residue was purified by silica-gel column chromatography (EtOAc/hexane=1:3) to give 800 mg of tert-butyl (R)-3-(ethoxymethyl)-3-formylpyrrolidine-1-carboxylate as a colorless oil. LC-MS (ESI+): m/z 258 [M+H]$^+$.

35.8 Preparation of tert-butyl (S)-3-(ethoxymethyl)-3-(2-(5-methylthiophen-3-yl)vinyl)pyrrolidine-1-carboxylate To a solution of ((5-methylthiophen-3-yl)methyl)triphenylphosphonium bromide (500 mg, 1.11 mmol) in DCM (10 mL) under $N_2$ atmosphere at 0° C. was added a solution of 50% NaOH (88 mg, 2.22 mmol) in water. After 30 min, tert-butyl (R)-3-(ethoxymethyl)-3-formylpyrrolidine-1-carboxylate (287 mg, 1.11 mmol) in DCM (5 mL) was added.

Upon completion of the reaction, water was added to dilute the mixture and extracted with DCM (20 mL×3). The combined organic phase was dried over Na₂SO₄, filtered and concentrated. The residue was purified by silica-gel column chromatography to give 280 mg of tert-butyl (S)-3-(ethoxymethyl)-3-(2-(5-methylthiophen-3-yl)vinyl) pyrrolidine-1-carboxylate as a colorless oil. LC-MS (ESI+): m/z 352 [M+H]⁺.

35.9 Preparation of tert-butyl (R)-3-(ethoxymethyl)-3-(2-(5-methylthiophen-3-yl)ethyl)pyrrolidine-1-carboxylate A solution of tert-butyl (S)-3-(ethoxymethyl)-3-(2-(5-methylthiophen-3-yl)vinyl) pyrrolidine-1-carboxylate (280 mg, 0.79 mmol) and Pd/C (30 mg) in MeOH (10 mL) was kept under hydrogen atmosphere at 1 atm for 2 h. Upon completion of the reaction, Pd/C was removed by filtration. After concentration, the residue was purified by silica-gel column chromatography (EtOAc/hexane=1:1) to give 280 mg of tert-butyl (R)-3-(ethoxymethyl)-3-(2-(5-methylthiophen-3-yl)ethyl)pyrrolidine-1-carboxylate as a colorless oil. LC-MS (ESI+): m/z 354 [M+H]⁺.

35.10 Preparation of (R)-3-(ethoxymethyl)-3-(2-(5-methylthiophen-3-yl)ethyl)pyrrolidine To a solution of tort-butyl (R)-3-(ethoxymethyl)-3-(2-(5-methylthiophen-3-yl)ethyl)pyrrolidine-1-carboxylate (280 mg) in dichloromethane (5 mL) was added trifluoroacetic acid (0.5 mL). After the reaction mixture was stirred at RT for 2 h, saturated Na₂CO₃ aqueous solution was added to adjust pH to 8. The aqueous solution was extracted with DCM/MeOH=(15:1, 20 mL×3). The combined organic phase was dried over Na₂SO₄, filtered and concentrated. The resulting oil was used directly for the next step without further purification. LC-MS (ESI+): m/z 254 [M+H]⁺.

35.11 Preparation of (R)-3-((3-(ethoxymethyl)-3-(2-(5-methylthiophen-3-yl)ethyl)pyrrolidin-1-yl)methyl)pyridine To a solution of (R)-3-(ethoxymethyl)-3-(2-(5-methylthiophen-3-yl)ethyl)pyrrolidine (50 mg, 0.2 mmol) and nicotinaldehyde (42 mg, 0.4 mmol) in DCM (6 mL) was added Et₃N (0.1 mL). The reaction mixture was stirred at RT for 10 min. Sodium triacetoxyhydroborate (130 mg, 0.6 mmol) was added. After stirred at RT overnight the reaction mixture was quenched with a saturated NH₄Cl aqueous solution (0.5 mL) and diluted with water (5 mL). The mixture was extracted with DCM (15 mL×3). The combined organic phase was dried over Na₂SO₄, filtered and concentrated. The residue was purified by preparative TLC (DCM/MeOH=15:1) to give 30 mg of (R)-3-((3-(ethoxymethyl)-3-(2-(5-methylthiophen-3-yl)ethyl)pyrrolidin-1-yl)methyl)pyridine as a light yellow oil. LC-MS (ESI+): m/z 345 [M+H]⁺.

35.12 Preparation of (S)-3-((3-(ethoxymethyl)-3-(2-(5-methylthiophen-3-yl)ethyl)pyrrolidin-1-yl)methyl)pyridine The title compound was prepared from tort-butyl (S)-3-((benzyloxy)methyl)-3-((S)-4-isopropyl-2-oxooxazolidine-3-carbonyl)pyrrolidine-1-carboxylate according to the procedure 35.4 to 35.11. LC-MS (ESI+): m/z 345 [M+H]⁺.

36. Synthesis of (R)-3-((benzyloxy)methyl)-1-(tert-butoxycarbonyl)pyrrolidine-3-carboxylic acid and (S)-3-((benzyloxy)methyl)-1-(tert-butoxycarbonyl)pyrrolidine-3-carboxylic acid

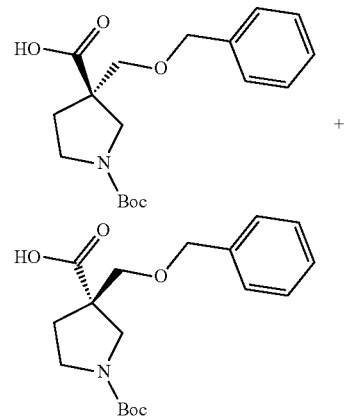

To a solution of 3-((benzyloxy)methyl)-1-(tert-butoxycarbonyl)pyrrolidine-3-carboxylic acid (658 g, 1.96 mol) in i-PrOH:acetone=1:1 (8 L) at RT was added (R)-1-phenylethanamine (237 g, 1.96 mol) and the solution was stirred at RT overnight. The precipitated solid was collected by filtration and dried to yield 285 g of white solid. The solid was then recrystallized twice in i-PrOH:acetone 1:1 (1.6 L, 1.3 L) to give 196 g of (R)-3-((benzyloxy)methyl)-1-(tert-butoxycarbonyl)pyrrolidine-3-carboxylic acid as amine salt.

The mother liquor was combined and concentrated. The resulting crude product was washed with MTBE to afford 390 g of white solid. The white solid was dissolved in i-PrOH:acetone=1:1 (4.6 L) (S)-1-phenylethanamine (155 g, 1.3 mol) was added to the above solution and stirred at RT overnight. The precipitated solid was collected by filtration and dried under reduced pressure to yield 303 g of white solid. The solid was then recrystallized twice in i-PrOH:acetone=1:1 (1.7 L, 1.5 L) to give 227 g of (S)-3-((benzyloxy)methyl)-1-(tert-butoxycarbonyl)pyrrolidine-3-carboxylic acid as amine salt.

220 g of (R)-3-((benzyloxy)methyl)-1-(tert-butoxycarbonyl)pyrrolidine-3-carboxylic acid amine salt was dissolved in DCM:H₂O=1:1 (2 L). 1M HCl solution was added to adjust pH to 4 and the solution was extracted with DCM (1 L×3). The combined organic phase was dried over Na₂SO₄, filtered, concentrated and slurried with MTBE to afford 160 g (R)-3-((benzyloxy)methyl)-1-(tert-butoxycarbonyl)pyrrolidine-3-carboxylic acid as white solid.

The absolute (R) and (S) configuration was determined by an X-ray crystal structure analysis of (R)-3-((benzyloxy)methyl)-1-(tert-butoxycarbonyl)pyrrolidine-3-carboxylic acid and (S)-3-((benzyloxy)methyl)-1-(tert-butoxycarbonyl)pyrrolidine-3-carboxylic acid.

The (R) and (S) acid was derivated to their corresponding methyl ester to determine the ee value by chiral HPLC analysis under the following conditions: ChIRALCEL OJ-R; Mobile phase: ACN/H₂O; Flow rate: 1.0 mL/min; Temperature: RT.

The X-ray of (S)-3-((benzyloxy)methyl)-1-(tert-butoxycarbonyl)pyrrolidine-3-carboxylic acid is shown in FIG. 1 and Table 1 below shows it properties.

TABLE 1

| Crystal data and structure refinement | |
|---|---|
| Identification code | cu_20180103sgy1_0m_a |
| Empirical formula | C18 H25 N O5 |
| Formula weight | 335.39 |
| Temperature | 153(2) K |
| Wavelength | 1.54178 Å |
| Crystal system | Orthorhombic |
| Space group | $P2_12_12_1$ |
| Unit cell dimensions | a = 6.4758(3) Å  α = 90°. |
| | b = 10.9588(4) Å  β = 90°. |
| | c = 25.9930(10) Å  γ = 90°. |
| Volume | 1844.65(13) Å$^3$ |
| Z | 4 |
| Density (calculated) | 1.208 Mg/m$^3$ |
| Absorption coefficient | 0.722 mm$^{-1}$ |
| F(000) | 720 |
| Crystal size | 0.260 × 0.190 × 0.180 mm$^3$ |
| Theta range for data collection | 4.378 to 68.153°. |
| Index ranges | −6 <= h <= 7, −12 <= k <= 13, |
| | −30 <= l <= 31 |
| Reflections collected | 8642 |
| Independent reflections | 3274 [R(int) = 0.0218] |
| Completeness to theta = 67.679° | 99.1% |
| Refinement method | Full-matrix least-squares on F$^2$ |
| Data/restraints/parameters | 3274/0/221 |
| Goodness-of-fit on F$^2$ | 1.079 |
| Final R indices [I > 2sigma(I)] | R1 = 0.0295, wR2 = 0.0785 |
| R indices (all data) | R1 = 0.0299, wR2 = 0.0788 |
| Absolute structure parameter | 0.08(5) |
| Extinction coefficient | n/a |
| Largest diff. peak and hole | 0.172 and −0.174 e · Å$^{-3}$ |

Figure 2:
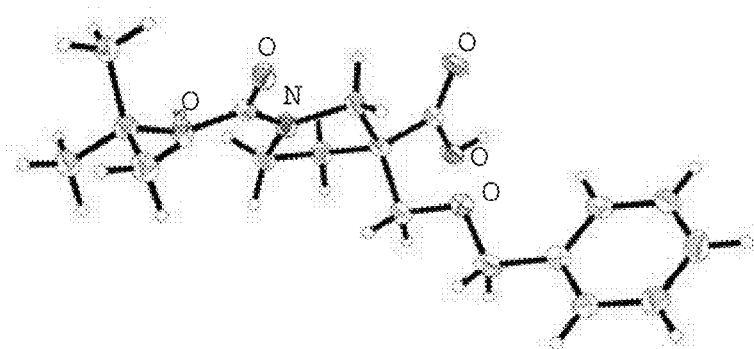
FIG. 2 is an X-ray crystallography depiction of (R)-3-((benzyloxy)methyl)-1-(tert-butoxycarbonyl)pyrrolidine-3-carboxylic acid.

The X-ray of (R)-3-((benzyloxy)methyl)-1-(tert-butoxycarbonyl)pyrrolidine-3-carboxylic acid is shown in FIG. 2, and its properties are shown in Table 2 below.

TABLE 2

| Crystal data and structure refinement | |
|---|---|
| Identification code | cu_20180103sgy2_0m_a |
| Empirical formula | C18 H25 NO 5 |
| Formula weight | 335.39 |
| Temperature | 153(2) K |
| Wavelength | 1.54178 Å |
| Crystal system | Orthorhombic |
| Space group | $P2_12_12_1$ |
| Unit cell dimensions | a = 6.4767(5) Å  α = 90°. |
| | b = 10.9368(7) Å  β = 90°. |
| | c = 25.9500(16) Å  γ = 90°. |
| Volume | 1838.2(2) Å$^3$ |
| Z | 4 |
| Density (calculated) | 1.212 Mg/m$^3$ |
| Absorption coefficient | 0.724 mm$^{-1}$ |
| F(000) | 720 |
| Crystal size | 0.220 × 0.180 × 0.160 mm$^3$ |
| Theta range for data collection | 3.406 to 68.367°. |
| Index ranges | −5 <= h <= 7, −13 <= k <= 13, |
| | −28 <= l <= 31 |
| Reflections collected | 5373 |
| Independent reflections | 2961 [R(int) = 0.0589] |
| Completeness to theta = 67.679° | 97.4% |
| Refinement method | Full-matrix least-squares on F$^2$ |
| Data/restraints/parameters | 2961/0/221 |
| Goodness-of-fit on F$^2$ | 1.089 |
| Final R indices [I > 2sigma(I)] | R1 = 0.0865, wR2 = 0.2382 |
| R indices (all data) | R1 = 0.0887, wR2 = 0.2411 |
| Absolute structure parameter | −0.04(10) |
| Extinction coefficient | n/a |
| Largest diff. peak and hole | 0.562 and −0.309 e · Å$^{-3}$ |

37. Synthesis of 1-(tert-butyl) 3-methyl (R)-3-((benzyloxy)methyl)pyrrolidine-1,3-dicarboxylate

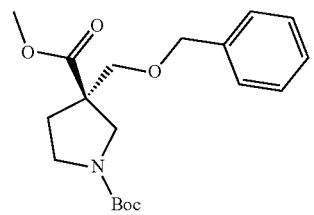 [SMILES: COC(=O)[C@]1(COCc2ccccc2)CCN(C(=O)OC(C)(C)C)C1]

To a solution of (R)-3-((benzyloxy)methyl)-1-(tert-butoxycarbonyl)pyrrolidine-3-carboxylic acid (169 g, 0.5 mol) in DMF (1.5 L) was added $K_2CO_3$ (150 g, 1.0 mol). The solution was stirred at RT for 10 min. MeI (86 g, 0.6 mol) was added and the reaction mixture was stirred for 4 h. Upon completion of the reaction, water (4 L) was added and the aqueous solution was extracted with EtOAc (500 mL×3). The combined organic layer was washed with brine (300 mL) and dried over $Na_2SO_4$, filtered and concentrated to give 184.9 g of (R)-1-tert-butyl 3-methyl 3-((benzyloxy)methyl)pyrrolidine-1,3-dicarboxylate as a colorless oil. LC-MS (ESI+): m/z 350 [M+H]$^+$.

38. Synthesis of (R)-5-(2-(3-(ethoxymethyl)-3-phenethylpyrrolidin-1-yl)propan-2-yl)-2-methylpyridine

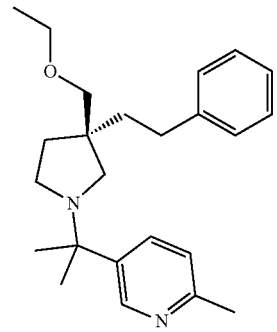 [SMILES: CCOC[C@]1(CCc2ccccc2)CCN(C(C)(C)c2ccc(C)nc2)C1]

38.1 Preparation of (R)-(3-(ethoxymethyl)-3-phenethylpyrrolidin-1-yl)(6-methylpyridin-3-yl)methanone

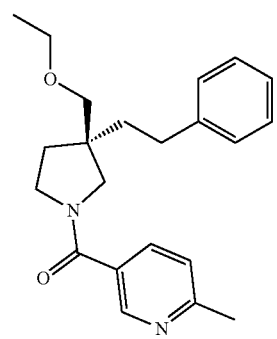 [SMILES: CCOC[C@]1(CCc2ccccc2)CCN(C(=O)c2ccc(C)nc2)C1]

To a solution of (R)-3-(ethoxymethyl)-3-phenethylpyrrolidine (205 mg, 0.88 mmol) and 6-methylnicotinic acid (157 mg, 1.43 mmol) in DMF (3 mL) was added HOBt (297 mg, 2.2 mmol) and EDCl (422 mg, 2.2 mmol). After stirred at RT overnight, the reaction mixture was quenched with sodium hydroxide solution (2 N, 15 mL), extracted with EtOAc (35 mL×3), and washed with brine (20 mL). The organic phase was dried over $Na_2SO_4$, filtered and concentrated. The residue was purified by silica column chromatography (EtOAc/n-hexane=10:1-1:1) to give 198 mg of (R)-(3-(ethoxymethyl)-3-phenethylpyrrolidin-1-yl)(6-methylpyridin-3-yl)methanone. LC-MS (ESI+): m/z 353 [M+H]⁺.

38.2 Preparation of (R)-5-(2-(3-(ethoxymethyl)-3-phenethylpyrrolidin-1-yl)propan-2-yl)-2-methylpyridine

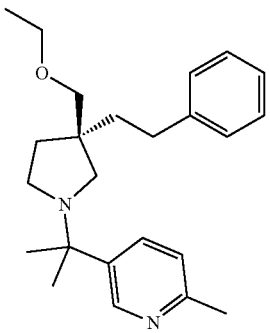 [SMILES: CCOC[C@]1(CCc2ccccc2)CCN(C(C)(C)c2ccc(C)nc2)C1]

To a solution of (R)-(3-(ethoxymethyl)-3-phenethylpyrrolidin-1-yl)(6-methylpyridin-3-yl)methanone (198 mg, 0.56 mmol) in THF (10 mL) under $N_2$ atmosphere at −10° C. was added a solution of titanium (IV) isopropoxide (208 mg, 0.73 mmol) in THF (5 mL) in dropwise. MeMgI (1.25 mL, 3.5 M, 4.38 mmol) was then added to the above solution. After stirred at 10° C. overnight, the reaction mixture was quenched with saturated $NH_4Cl$ solution (8 mL), extracted with EtOAc (10 mL×3) and washed with brine (10 mL). The organic phase was dried over $Na_2SO_4$, and concentrated. The residue was purified by silica column chromatography (EtOAc/n-hexane=10:1-1:1) to give 32 mg of (R)-5-(2-(3-(ethoxymethyl)-3-phenethylpyrrolidin-1-yl)propan-2-yl)-2-methylpyridine. LC-MS (ESI+): m/z 367 [M+H]⁺.

39. Synthesis of (R)-5-(1-(3-(ethoxymethyl)-3-(2-(thiophen-2-yl)ethyl)pyrrolidin-1-yl)cyclopropyl)-2-methylpyridine

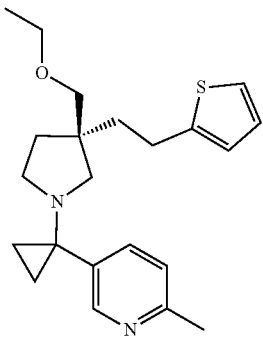 [SMILES: CCOC[C@]1(CCc2cccs2)CCN(C2(c3ccc(C)nc3)CC2)C1]

To a solution of (R)-(3-(ethoxymethyl)-3-(2-(thiophen-2-yl)ethyl)pyrrolidin-1-yl)(6-methylpyridin-3-yl)methanone (190 mg, 0.53 mmol) in THF (5 mL) under $N_2$ atmosphere at −10° C. was added a solution of titanium (IV) isopropoxide (165.0 mg, 0.58 mmol) in THF (10 mL). After stirring for 15 minutes, a solution of EtMgI (3.0 M in ethyl ether, 1.12 mL, 3.36 mmol) in toluene (15 mL) was added. The resulting solution was warmed to reflux for 15 min. After cooled to 8° C., the reaction mixture was quenched with water, neutralized with $Na_2CO_3$ solution and extracted with EtOAc (15 mL×3). The combined organic layers were washed with brine, dried over $Na_2SO_4$ and concentrated. The residue was purified by chromatography to give 19.0 mg of (R)-5-(1-(3-(ethoxymethyl)-3-(2-(thiophen-2-yl)ethyl)pyrrolidin-1-yl)cyclopropyl)-2-methylpyridine as a light yellow oil. LC-MS (ESI+): m/z 371 [M+H]⁺.

40. Synthesis of 5-(1-(4-(ethoxymethyl)-4-phenethylpiperidin-1-yl)cyclohexyl)-2-methylpyridine

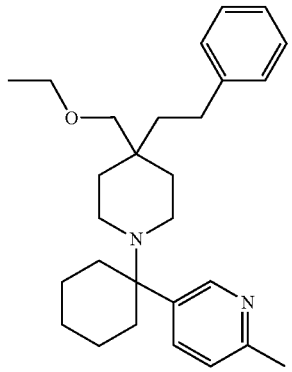 [SMILES: CCOCC1(CCc2ccccc2)CCN(C2(c3ccc(C)nc3)CCCCC2)CC1]

To a solution of (4-(ethoxymethyl)-4-phenthylpiridin-1-yl)(6-methylpyridin-3-yl)methanone (230 mg, 0.63 mmol) in toluene (10 mL) under $N_2$ atmosphere at RT was added pentane-1,5-diyl-dimagnesium dibromide (1.1 mL, 3.5 M, 3.77 mmol). After completion of addition, the reaction mixture was warmed to 90° C. and stirred for 15 min. After cooled to RT, the reaction mixture was quenched with saturated $NH_4Cl$ solution (8 mL), extracted with EtOAc (10 mL×3) and washed with brine (10 mL). The organic phase was dried over $Na_2SO_4$, filtered and concentrated. The residue was purified by silica column chromatography to give 10.7 mg of 5-(1-(4-(ethoxymethyl)-4-phenethylpiperidin-1-1)cyclohexyl)-2-methylpyridine. LC-MS (ESI+): m/z 421 [M+H]⁺.

41. Synthesis of (S)-5-((3-(ethoxymethyl)-3-(phenoxymethyl)pyrrolidin-1-yl) methyl)-2-methylpyridine

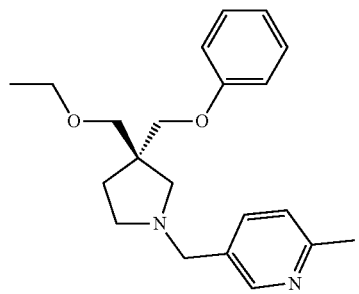 [SMILES: CCOC[C@]1(COc2ccccc2)CCN(Cc2ccc(C)nc2)C1]

41.1 Preparation of tert-butyl (S)-3-(ethoxymethyl)-3-(((methylsulfonyl)oxy)methyl)pyrrolidine-1-carboxylate

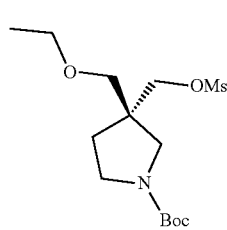 [SMILES: CCOC[C@]1(COS(C)(=O)=O)CCN(C(=O)OC(C)(C)C)C1]

To a solution of tert-butyl (R)-3-(ethoxymethyl)-3-(hydroxymethyl)pyrrolidine-1-carboxylate (410 mg, 1.58 mmol) in THF (5 mL) under $N_2$ atmosphere at 0° C. was added $Et_3N$ (319.8 mg, 3.17 mmol) and the solution was stirred for 10 min. MsCl (362 mg, 3.17 mmol) was added and the reaction mixture was stirred at RT for 2 h. Upon completion of the reaction, aqueous $NH_4Cl$ (10 ml) was added. The aqueous solution was extracted with EtOAc (10 mL×3) and washed with brine (10 mL). The organic phase was dried over $Na_2SO_4$, filtered and concentrated. The crude product was used for the next step without further purification. LC-MS (ESI+): m/z 338 [M+H]$^+$.

41.2 Preparation of tert-butyl (S)-3-(ethoxymethyl)-3-(phenoxymethyl)pyrrolidine-1-carboxylate

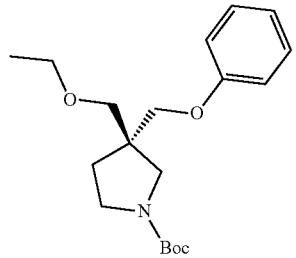 [SMILES: CCOC[C@]1(COc2ccccc2)CCN(C(=O)OC(C)(C)C)C1]

To a solution of phenol (119 mg, 1.26 mmol) in DMF (5 ml) under $N_2$ atmosphere was added NaH (151.9 mg, 6.3 mmol). After the reaction mixture was stirred for 10 min, (S)-tert-butyl 3-(ethoxymethyl)-3-(((methylsulfonyl)oxy)methyl) pyrrolidine-1-carboxylate (533 mg, 1.58 mmol) in DMF (5 ml) was added. The reaction mixture was stirred at 60° C. overnight. Upon completion of the reaction, water (10 ml) was added. The aqueous solution was extracted with EtOAc (10 mL×3) and washed with brine (10 mL). The combined organic phase was dried over $Na_2SO_4$, filtered and concentrated. The residue was purified by silica column chromatography (EtOAc/n-Hex=1:100-1:50) to give 381.6 mg of tert-butyl (S)-3-(ethoxymethyl)-3-(phenoxymethyl) pyrrolidine-1-carboxylate. LC-MS (ESI+): m/z 336 [M+H]$^+$.

41.3 Preparation of (S)-5-((3-(ethoxymethyl)-3-(phenoxymethyl)pyrrolidin-1-yl)methyl)-2-methylpyridine

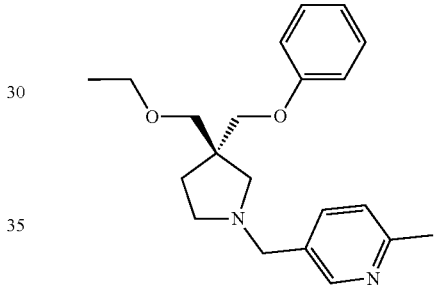

The title compound was prepared from tert-butyl (S)-3-(ethoxymethyl)-3-(phenoxymethyl) pyrrolidine-1-carboxylate according to the procedure 1.4 and 1.5. LC-MS (ESI+): m/z 341 [M+H]$^+$.

42. Synthesis of (R)—N-((3-(ethoxymethyl)-1-((6-methylpyridin-3-yl)methyl) pyrrolidin-3-yl)methyl)-N-methylaniline

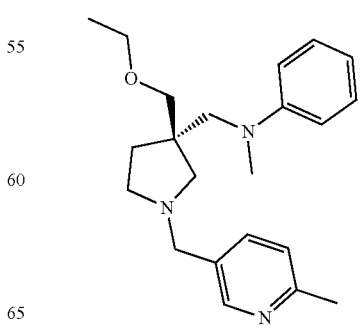

42.1 Preparation of (S)-tert-butyl 3-(ethoxymethyl)-3-((methyl(phenyl)amino)methyl) pyrrolidine-1-carboxylate

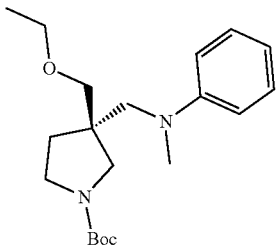 [SMILES: CCOC[C@]1(CN(C)c2ccccc2)CCN(C(=O)OC(C)(C)C)C1]

To a solution of N-methylaniline (166 mg, 1.56 mmol) and tert-butyl (S)-3-(ethoxymethyl)-3-formylpyrrolidine-1-carboxylate (400 mg, 1.56 mmol) in DCM (8 mL) at RT was added Et$_3$N (2 mL) and NaBH (OAc)$_3$ (1.32 g, 6.2 mmol). The reaction mixture was stirred at room temperature overnight. Upon completion of the reaction, saturated Na$_2$CO$_3$ solution (10 mL) was added. The aqueous solution was extracted with DCM:MeOH=15:1 (15 mL×3) and washed with brine (10 mL). The organic phase was dried over Na$_2$SO$_4$, filtered and concentrated. The residue was purified by silica column chromatography (EtOAc/n-hexane=1:50-1:20) to give 149 mg of (S)-tert-butyl 3-(ethoxymethyl)-3-((methyl(phenyl)amino)methyl) pyrrolidine-1-carboxylate. LC-MS (ESI+): m/z 349 [M+H]$^+$.

42.2 Preparation of (R)—N-((3-(ethoxymethyl)-1-((6-methylpyridin-3-yl)methyl) pyrrolidin-3-yl) methyl)-N-methylaniline

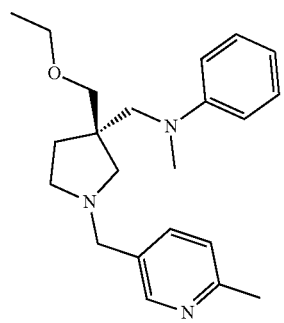 [SMILES: CCOC[C@]1(CN(C)c2ccccc2)CCN(Cc2ccc(C)nc2)C1]

The title compound was prepared from (S)-tert-butyl 3-(ethoxymethyl)-3-((methyl(phenyl)amino)methyl) pyrrolidine-1-carboxylate according to the procedure 1.4 and 1.5. LC-MS (ESI+): m/z 354 [M+H]$^+$.

43. Synthesis of (R)-5-((3-(ethoxymethyl)-3-(2-(thiophen-2-yl)ethyl)pyrrolidin-1-yl)methyl)pyridin-2(1H)-one

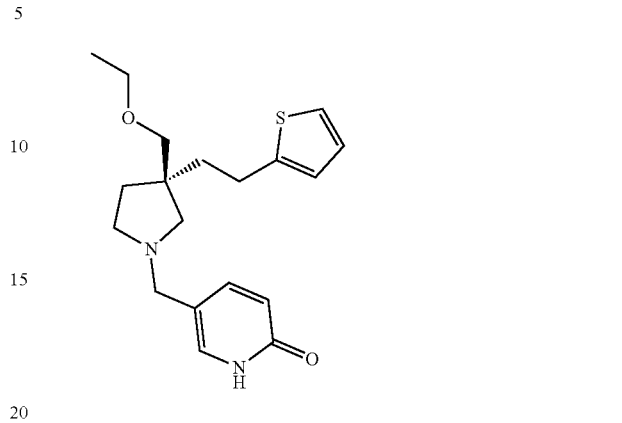

A solution of (R)-5-((3-(ethoxymethyl)-3-(2-(thiophen-2-yl)ethyl)pyrrolidin-1-yl)methyl)-2-methoxypyridine (45 mg, 0.13 mmol), LiCl (52 mg, 1.25 mmol) and p-TSA (240 mg, 1.25 mmol) in DMF (10 mL) was stirred at 120° C. for 1 h. Upon completion of the reaction, the reaction mixture was quenched by the addition of water (30 mL), saturated NaHCO$_3$ solution (30 mL) and extracted with EtOAc (30 mL×3). The combined organic phase was dried over Na$_2$SO$_4$, filtered and concentrated. The residue was purified by silica column chromatography to afford 31 mg of (R)-5-((3-(ethoxymethyl)-3-(2-(thiophen-2-yl)ethyl)pyrrolidin-1-yl)methyl)pyridin-2(1H)-one. LC-MS (ESI+): m/z 347 [M+H]$^+$.

44. Synthesis of (R)-2-(2-(3-(ethoxymethyl)-1-(2-(6-methylpyridin-3-yl)propan-2-yl)pyrrolidin-3-yl) ethyl)pyrimidin-4(3H)-one

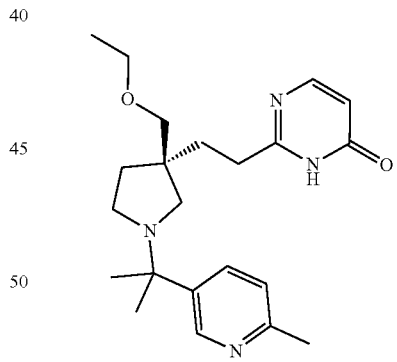

A solution of (S)-2-(2-(3-(ethoxymethyl)-1-(2-(6-methylpyridin-3-yl)propan-2-yl)pyrrolidin-3-yl)ethyl)-4-methoxypyrimidine (39.8 mg, 0.1 mmol), LiCl (42 mg, 1.0 mmol) and p-TSA (172 mg, 1.0 mmol) in DMF (5 mL) was stirred at 120° C. for 1 h. Upon completion of the reaction, the reaction mixture was quenched by the addition of water (30 mL), saturated NaHCO$_3$ solution (30 mL) and extracted with EtOAc (30 mL×3). The combined organic phase was dried over Na$_2$SO$_4$, filtered and concentrated. The residue was purified by silica column chromatography to afford 23 mg of (R)-2-(2-(3-(ethoxymethyl)-1-(2-(6-methylpyridin-3-yl)propan-2-yl)pyrrolidin-3-yl)ethyl)pyrimidin-4(3H)-one. LC-MS (ESI+): m/z 385 [M+H]$^+$.

45. Synthesis of (R)-8-(2-(3-(ethoxymethyl)-1-(2-(6-methylpyridin-3-yl)propan-2-yl) pyrrolidin-3-yl) ethyl)-7H-purine

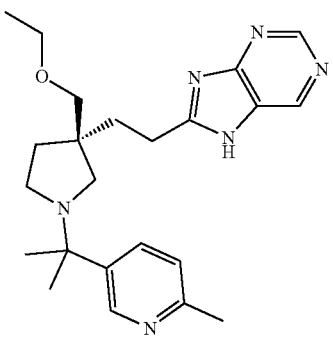 [SMILES: CCOC[C@]1(CCc2nc3ncncc3[nH]2)CCN(C(C)(C)c2ccc(C)nc2)C1]

45.1 Preparation of 8-methyl-7H-purine

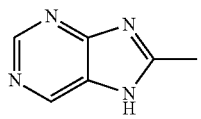

A solution of 4,5-dimethylthiazole (500 mg, 4.55 mmol) in acetic acid (30 mL) was stirred by microwave initiation at 140° C. for 10 min. Upon completion of the reaction, acetic acid was removed under reduced pressure to afford 550 mg of 8-methyl-7H-purine as a red solid.

45.2 Preparation of 7-(4-methoxybenzyl)-8-methyl-7H-purine

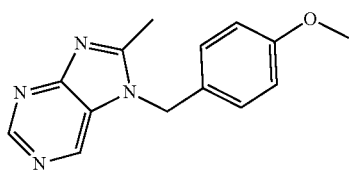 [SMILES: COc1ccc(Cn2c(C)nc3ncncc32)cc1]

A solution of 8-methyl-7H-purine (1.5 g, 11.19 mmol) and 1-(chloromethyl)-4-methoxybenzene (1.9 g, 12.31 mmol) and K$_2$CO$_3$ (4.6 g, 33.58 mmol) in DMF (50 mL) was stirred at RT for 12 h. Upon completion of the reaction, the reaction mixture was quenched with water (250 mL) and extracted with EtOAc (150 mL×3). The combined organic phase was dried over Na$_2$SO$_4$, filtered and concentrated. The residue was purified by silica column chromatography (EtOAc/n-hexane=1:1) to afford 900 mg of 7-(4-methoxybenzyl)-8-methyl-7H-purine. LC-MS (ESI+): m/z 255 [M+H]$^+$.

45.3 Preparation of tert-butyl (S)-3-(ethoxymethyl)-3-(2-(7-(4-methoxybenzyl)-7H-purin-8-yl)vinyl) pyrrolidine-1-carboxylate

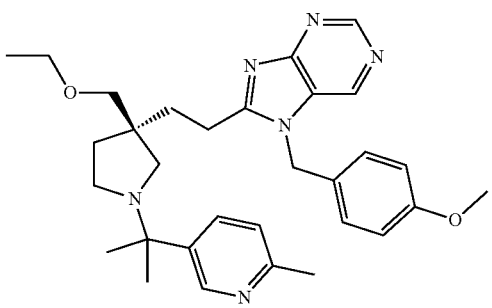 [SMILES: CCOC[C@]1(CCc2nc3ncncc3n2Cc2ccc(OC)cc2)CCN(C(C)(C)c2ccc(C)nc2)C1]

To a solution of 7-(4-methoxybenzyl)-8-methyl-7H-purine (200 mg, 0.78 mmol) and tert-butyl (S)-3-(ethoxymethyl)-3-formylpyrrolidine-1-carboxylate (250 mg, 0.78 mmol) in DMF (5 mL) under N$_2$ atmosphere at RT was added t-ButOK (250 mg, 2.34 mmol). After stirred for 3 h, the reaction mixture was quenched by the addition of water (300 mL), NH$_4$Cl saturated solution (30 mL) and extracted with EtOAc (50 mL×3). The combined organic phase was dried over Na$_2$SO$_4$, filtered and concentrated. The residue was purified by silica column chromatography to give 350 mg of tert-butyl (S)-3-(ethoxymethyl)-3-(2-(7-(4-methoxybenzyl)-7H-purin-8-yl)vinyl)pyrrolidine-1-carboxylate. LC-MS (ESI+): m/z 494 [M+H]$^+$.

45.4 Preparation of (R)-8-(2-(3-(ethoxymethyl)-1-(2-(6-methylpyridin-3-yl)propan-2-yl)pyrrolidin-3-yl)ethyl)-7-(4-methoxybenzyl)-7H-purine The title compound was prepared from tert-butyl (S)-3-(ethoxymethyl)-3-(2-(7-(4-methoxybenzyl)-7H-purin-8-yl)vinyl)pyrrolidine-1-carboxylate according to the procedure 2.4, 1.4, 38.1 and 38.2. LC-MS (ESI+): m/z 529 [M+H]$^+$.

45.5 Preparation of (R)-8-(2-(3-(ethoxymethyl)-1-(2-(6-methylpyridin-3-yl)propan-2-yl)pyrrolidin-3-yl)ethyl)-7H-purine

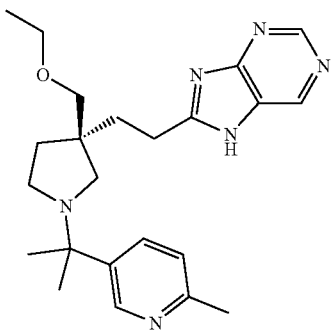 [SMILES: CCOC[C@]1(CCc2nc3ncncc3[nH]2)CCN(C(C)(C)c2ccc(C)nc2)C1]

A solution of (R)-8-(2-(3-(ethoxymethyl)-1-(2-(6-methylpyridin-3-yl)propan-2-yl)pyrrolidin-3-yl) ethyl)-7-(4-methoxybenzyl)-7H-purine (52 mg, 0.01 mmol) in TFA (20 mL) were stirred at 80° C. for 0.5 h. Upon completion of the reaction, TFA was removed under reduced pressure and the residue was diluted with MeOH (10 mL) and NH$_3$.H$_2$O (20 mL). The aqueous solution was extracted with DCM (50 mL×3). The combined organic phase was dried over NaSO$_4$, filtered and concentrated. The residue was purified by silica column chromatography (DCM/MeOH=5:1) to afford 28.4 mg of (R)-8-(2-(3-(ethoxymethyl)-1-(2-(6-methylpyridin-3-yl)propan-2-yl)pyrrolidin-3-yl)ethyl)-7-(4-methoxybenzyl)-7H-purine.

A solution of (R)-8-(2-(3-(ethoxymethyl)-1-(2-(6-methylpyridin-3-yl)propan-2-yl)pyrrolidin-3-yl)ethyl)-7H-purine (28 mg, 0.09 mmol) and citrate acid (13 mg, 0.09 mmol) in MeOH (2 mL) was stirred at RT for 2 h. The solution was concentrated under reduced pressure and the resulting solid was slurried in anhydrous diethyl ether for 0.5 h. The solid was collected and dried to afford 29 mg of (R)-8-(2-(3-(ethoxymethyl)-1-(2-(6-methylpyridin-3-yl)propan-2-yl)pyrrolidin-3-yl)ethyl)-7H-purine citrate. LC-MS (ESI+): m/z 409 [M+H]$^+$.

46. Synthesis of (R)-5-(2-(3-(ethoxymethyl)-3-(2-(5-fluorothiophen-2-yl)ethyl)pyrrolidin-1-yl)propan-2-yl)-2-methylpyridine and (S)-5-(2-(3-(ethoxymethyl)-3-(2-(5-fluorothiophen-2-yl)ethyl)pyrrolidin-1-yl)propan-2-yl)-2-methylpyridine

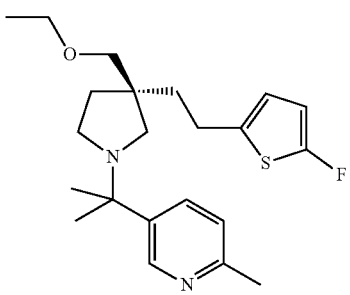

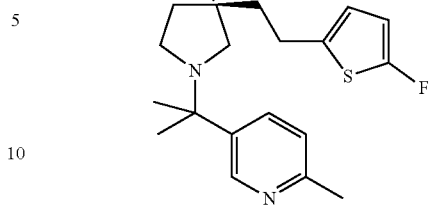

46.1 Preparation of tert-butyl (S)-3-((benzyloxy)methyl)-3-(hydroxymethyl)pyrrolidine-1-carboxylate To a solution of (R)-3-((benzyloxy)methyl)-1-(tert-butoxycarbonyl)pyrrolidine-3-carboxylic acid (40 g, 119.2 mmol) in THF (200 ml) under N$_2$ atmosphere at 0° C. was added BH$_3$ (238 ml, in THF) in dropwise. The reaction was allowed to warm to RT and stirred for 2 hrs. Upon completion of the reaction, the mixture was concentrated under reduced pressure to afford 42 g of tert-butyl (S)-3-((benzyloxy)methyl)-3-(hydroxymethyl)pyrrolidine-1-carboxylate, which was used for the next step without further purification. LC-MS (ESI+): m/z 322 [M+H]$^+$.

46.2 Preparation of tert-butyl (R)-3-((benzyloxy)methyl)-3-formylpyrrolidine-1-carboxylate To a solution of tert-butyl (S)-3-((benzyloxy)methyl)-3-(hydroxymethyl)pyrrolidine-1-carboxylate (42 g, 130.7 mmol) in acetone (250 ml) was added IBX (73 g, 261.3 mmol). The mixture was warmed to 40° C. and stirred for overnight. Upon completion of the reaction, the mixture was filtered and concentrated under reduced pressure. The resulting residue was purified by silica-gel column chromatography (PE/EtOAc=8/1) to afford 34.9 g of tert-butyl (R)-3-((benzyloxy)methyl)-3-formylpyrrolidine-1-carboxylate. LC-MS (ESI+): m/z 320 [M+H]$^+$.

46.3 Preparation of tert-butyl (S)-3-((benzyloxy)methyl)-3-(2-(5-fluorothiophen-2-yl)ethyl)pyrrolidine-1-carboxylate The title compound was prepared from tert-butyl (R)-3-((benzyloxy)methyl)-3-formylpyrrolidine-1-carboxylate according to the procedure 35.8 and 35.9. LC-MS (ESI+): m/z 420 [M+H]$^+$.

46.4 Preparation of tert-butyl (S)-3-(2-(5-fluorothiophen-2-yl)ethyl)-3-(hydroxymethyl)pyrrolidine-1-carboxylate To a solution of tert-butyl (S)-3-((benzyloxy)methyl)-3-(2-(5-fluorothiophen-2-yl)ethyl)pyrrolidine-1-carboxylate (24 g, 57.3 mmol) in THF (240 ml) at −78° C. was added BBr$_3$ (172 ml, 172 mmol, 1M in DCM). Upon completion of the reaction, the mixture was quenched with aqueous Na$_2$CO$_3$. Boc$_2$O (25 g, 114.6 mmol) was added to the above aqueous solution. After stirred at RT for 1 h, the mixture was diluted with water (200 ml) and extracted with DCM (100 ml×3). The combined organic layers were dried over Na$_2$SO$_4$, concentrated and the resulting residue was purified by silica-gel column chromatography (PE/EtOAc=3/1) to afford 9.3 g of tert-butyl (S)-3-(2-(5-fluorothiophen-2-yl)

ethyl)-3-(hydroxymethyl)pyrrolidine-1-carboxylate. LC-MS (ESI+): m/z 330 [M+H]+.

46.5 Preparation of (S)-5-(2-(3-(ethoxymethyl)-3-(2-(5-fluorothiophen-2-yl)ethyl)pyrrolidin-1-yl)propan-2-yl)-2-methylpyridine The title compound was prepared from tert-butyl (S)-3-(2-(5-fluorothiophen-2-yl)ethyl)-3-(hydroxymethyl)pyrrolidine-1-carboxylate according to the procedure 1.3, 1.4, 38.1 and 38.2. LC-MS (ESI+): m/z 391 [M+H]+.

46.6 Preparation of (S)-5-(2-(3-(ethoxymethyl)-3(2-(5-fluorothiophen-2-yl)ethyl)pyrrolidin-1-yl)propan-2-yl)-2-methylpyridine The title compound could be prepared from (S)-3-((benzyloxy)methyl)-1-(tert-butoxycarbonyl)pyrrolidine-3-carboxylic acid according to the procedure 46.1, 1.3, 35.6, 35.7, 35.8, 35.9, 35.10, 38.1 and 38.2. LC-MS (ESI+): m/z 391 [M+H]+.

46.7 Preparation of (R)-5-(2-(3-(ethoxymethyl)-3-(2-(5-fluorothiophen-2-yl)ethyl)pyrrolidin-1-yl)propan-2-yl)-2-methylpyridine The title compound was prepared from (S)-3-((benzyloxy)methyl)-1-(tert-butoxycarbonyl)pyrrolidine-3-carboxylic acid or (R)-3-((benzyloxy)methyl)-1-(tert-butoxycarbonyl)pyrrolidine-3-carboxylic acid according to the procedures of 46.1 to 46.5 or 46.6. LC-MS (ESI+): m/z 391 [M+H]+.

Example 2

Antinociception and Hot Plate Test
Animals
Male Sprague Dawley rats (200 g~300 g) were maintained on a 12-hour light/dark cycle with Purina rodent chow and water available ad libitum, and they were housed in groups of two until testing.
Hot Plate Test
The hot plate test is adapted from that described previously (Tyers, 1980). Male Sprague-Dawley rats (200-300 g) were acclimated to the vivarium for 48 hours. Animals were placed individually on a heated surface (52° C.) and the time interval (seconds) between placement and a licking of the hind paw was recorded as the predrug latency response. This same procedure was repeated 30 minutes after s.c. administration of a compound. All compounds were administered s.c. in a volume of 2 ml/100 g. The cutoff time, designed to prevent injury to the animals, was 30 seconds (with vehicle latencies of approximately 8~15 seconds). The percent maximum possible antinociceptive effect [% maximum possible effect (MPE)] was determined using the formula:

Percent MPE=(Post drug latency−baseline latency)/(30−baseline latency)×100

The redrug latency of each animal and cutoff time is used the predrug latency of each animal and cutoff time as noted above. Experimenter was blind to the treatment of animals during behavioral observations.

Example 3

Antinociception and Warm-Water Tail-Flick Test
Animals
Male C57BL/6 mice (20-30 g; 6-12 wk) were maintained on a 12-h light/dark cycle with rodent chow and water available ad libitum, and they were housed separately until testing.
Warm-Water Tail-Flick Test
Antinociception was assessed using the 55° C. warm-water tail-flick test. The latency to the first sign of a rapid tail flick was taken as the behavioral endpoint (Jannsen et al., 1963). Each mouse was first tested for baseline latency by immersing its tail in the water and recording the time to response. Mice not responding within 2 s were excluded from further testing. Mice were then s.c. administered the test compound and tested for antinociception at 30 min, 60 min, 90 min, and 120 min time points afterward. Antinociception was calculated using the following formula: percentage of antinociception=100×(test latency−control latency)/(20−control latency). To avoid tissue damage, a maximum score was assigned (100%) to animals that failed to respond within 20 s.
Results
The list of certain compounds and their data of the present invention is set forth in Table below.

TABLE III

| Compound. | Structure | Name | MS (ESI+): [M + H]+ | H-NMR |
|---|---|---|---|---|
| 1 | 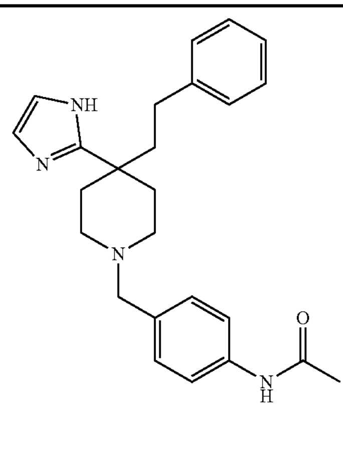 | N-(4-((4-(1H-imidazol-2-yl)-4-phenethylpiperidin-1-yl)methyl)phenyl)acetamide | 403 | 1H NMR (300 MHz, MeOD): δ 7.55 (d, J = 8.4 Hz, 2H), 7.30 (d, J = 8.4 Hz, 2H), 7.23-7.20 (m, 2H), 7.17-7.00 (m, 5H), 3.60 (s, 2H), 2.92 (d, J = 12.6 Hz, 2H), 2.45 (d, J = 7.5 Hz, 2H), 2.76-2.22 (m, 4H), 2.13 (s, 3H), 1.90-1.82 (m, 4H) |

TABLE III-continued

| Compound. | Structure | Name | MS (ESI+): [M + H]+ | H-NMR |
|---|---|---|---|---|
| 2 | 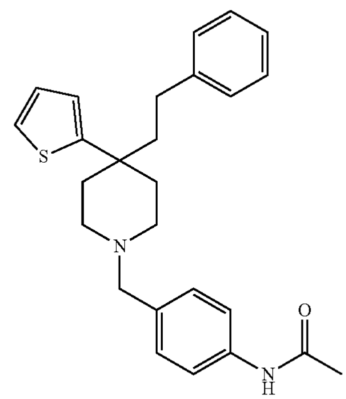 [SMILES: CC(=O)Nc1ccc(CN2CCC(CCc3ccccc3)(c3cccs3)CC2)cc1] | N-(4-((4-phenethyl-4-(thiophen-2-yl)piperidin-1-yl)methyl)phenyl)acetamide | 419 | $^1$H NMR (300 MHz, MeOD): δ 7.54 (d, J = 8.4 Hz, 2H), 7.33-7.07 (m, 6H), 7.03-6.94 (m, 4H), 3.51 (s, 2H), 2.78-2.75 (m, 2H), 2.46-2.43 (m, 2H), 2.39-2.20 (m, 4H), 2.12 (s, 3H), 1.94-1.81 (m, 4H). |
| 3 | 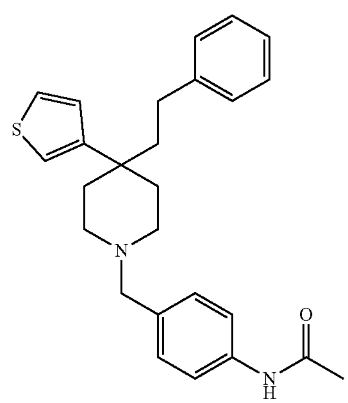 [SMILES: CC(=O)Nc1ccc(CN2CCC(CCc3ccccc3)(c3ccsc3)CC2)cc1] | N-(4-((4-phenethyl-4-(thiophen-3-yl)piperidin-1-yl)methyl)phenyl)acetamide | 419 | $^1$H NMR (300 MHz, MeOD): δ 7.53 (d, J = 8.4 Hz, 2H), 7.34-7.26 (m, 3H), 7.22-7.12 (m, 3H), 7.10-6.96 (m, 4H), 3.52 (s, 2H), 2.79-2.75 (m, 2H), 2.46-2.22 (m, 6H), 2.13 (s, 3H), 1.97-1.82 (m, 4H). |
| 4 | 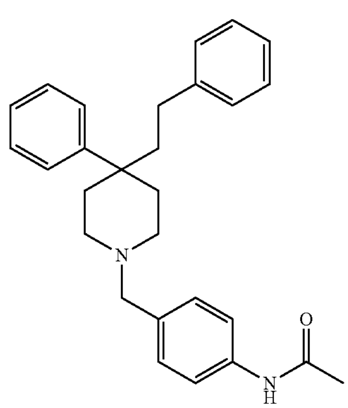 [SMILES: CC(=O)Nc1ccc(CN2CCC(CCc3ccccc3)(c3ccccc3)CC2)cc1] | N-(4-((4-phenethyl-4-phenylpiperidin-1-yl)methyl)phenyl)acetamide | 413 | $^1$H NMR (300 MHz, MeOD): δ 7.61 (d, J = 8.1 Hz, 2H), 7.45-7.43 (m, 4H), 7.38-7.27 (m, 3H), 7.21-7.09 (m, 3H), 6.97 (d, J = 6.9 Hz, 2H), 3.89 (s, 2H), 3.12-3.08 (m, 2H), 2.76-2.73 (m, 2H), 2.49-2.44 (m, 2H), 2.24-2.18 (m, 2H), 2.14 (s, 3H), 2.06-1.94 (m, 2H), 1.90-1.85 (m, 2H). |

TABLE III-continued

| Compound. | Structure | Name | MS (ESI+): [M + H]+ | H-NMR |
|---|---|---|---|---|
| 5 | 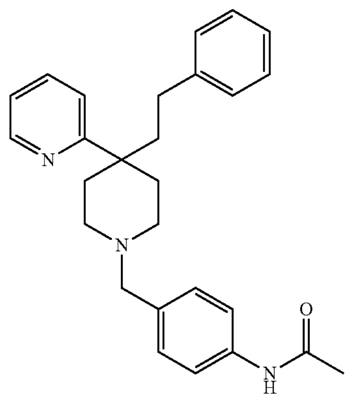 [SMILES: CC(=O)Nc1ccc(CN2CCC(CCc3ccccc3)(c3ccccn3)CC2)cc1] | N-(4-((4-phenethyl-4-(pyridin-2-yl)piperidin-1-yl)methyl)phenyl)acetamide | 414 | $^1$H NMR (300 MHz, MeOD): δ 8.62 (d, J = 3.9 Hz, 1H), 7.86-7.83 (m, 1H), 7.63-7.54 (m, 3H), 7.38-7.29 (m, 3H), 7.20-7.09 (m, 3H), 6.98 (d, J = 6.9 Hz, 2H), 3.89 (s, 2H), 3.15-3.11 (m, 2H), 2.72- 2.67 (m, 4H), 2.23-2.17 (m, 2H), 2.14 (s, 3H), 2.05-1.93 (m, 4H) |
| 6 | 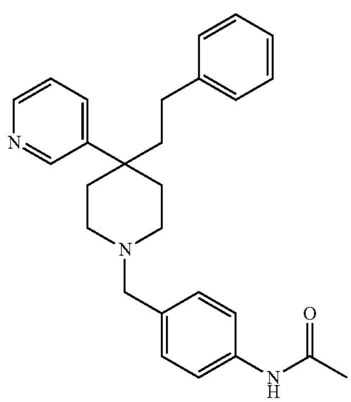 [SMILES: CC(=O)Nc1ccc(CN2CCC(CCc3ccccc3)(c3cccnc3)CC2)cc1] | N-(4-((4-phenethyl-4-(pyridin-3-yl)piperidin-1-yl)methyl)phenyl)acetamide | 414 | $^1$H NMR (300 MHz, MeOD): δ 8.60 (d, J = 1.8 Hz, 1H), 8.44 (d, J = 3.6 Hz, 1H), 7.92 (d, J = 8.1 Hz, 1H), 7.54-7.46 (m, 3H), 7.28 (d, J = 8.4 Hz, 2H), 7.21-7.08 (m, 3H), 6.98 (d, J = 7.2 Hz, 2H), 3.51 (s, 2H), 2.76-2.74 (m, 2H), 2.35-2.32 (m, 4H), 2.26-2.20 (m, 2H), 2.12 (s, 3H), 2.03-1.91 (m, 4H). |
| 7 | 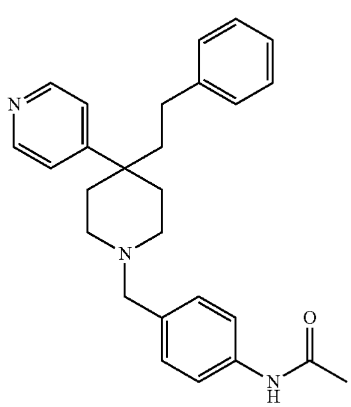 [SMILES: CC(=O)Nc1ccc(CN2CCC(CCc3ccccc3)(c3ccncc3)CC2)cc1] | N-(4-((4-phenethyl-4-(pyridin-4-yl)piperidin-1-yl)methyl)phenyl)acetamide | 414 | $^1$HNMR (300 MHz, MeOD): δ 8.52 (d, J = 6.0 Hz, 2H), 7.53 (d, J = 8.4 Hz, 2H), 7.47 (d, J = 6.0 Hz, 2H), 7.31-7.28 (m, 2H), 7.20-7.15 (m, 2H), 7.12-7.07 (m, 1H), 6.97 (d, J = 6.9 Hz, 2H), 3.49 (s, 2H), 2.85-2.73 (m, 2H), 2.31-2.17 (m, 6H), 2.12 (s, 3H), 1.98-1.86 (m, 4H). |

TABLE III-continued

| Compound. | Structure | Name | MS (ESI+): [M + H]+ | H-NMR |
|---|---|---|---|---|
| 8 | 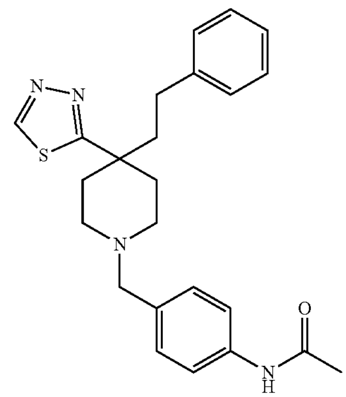 [SMILES: CC(=O)Nc1ccc(CN2CCC(CCc3ccccc3)(c3nncs3)CC2)cc1] | N-(4-((4-phenethyl-4-(1,3,4-thiadiazol-2-yl)piperidin-1-yl)methyl)phenyl)acetamide | 443 [M + Na]+ | $^1$H NMR (300 MHz, MeOD): δ 9.47 (s, 1H), 7.51 (d, J = 8.4 Hz, 2H), 7.27-7.21 (m, 4H), 7.19-7.12 (m, 1H), 7.09-7.03 (m, 2H), 3.44 (s, 2H), 2.80-2.76 (m, 2H), 2.43-2.34 (m, 4H), 2.29-2.18 (m, 2H), 2.12 (s, 3H), 2.08-2.03 (m, 4H) |
| 9 | 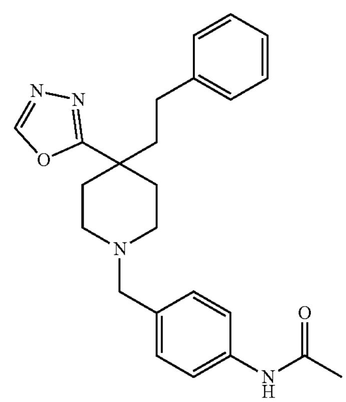 [SMILES: CC(=O)Nc1ccc(CN2CCC(CCc3ccccc3)(c3nnco3)CC2)cc1] | N-(4-((4-(1,3,4-oxadiazol-2-yl)-4-phenethylpiperidin-1-yl)methyl)phenyl)acetamide | 405 | $^1$H NMR (300 MHz, MeOD): δ 8.91 (s, 1H), 7.53 (d, J = 8.4 Hz, 2H), 7.32-7.19 (m, 4H), 7.15-7.06 (m, 3H), 3.52 (s, 2H), 2.88-2.84 (m, 2H), 2.44-2.37 (m, 4H), 2.26-2.17 (m, 2H), 2.13 (s, 3H), 2.04-1.87 (m, 4H) |
| 10 | 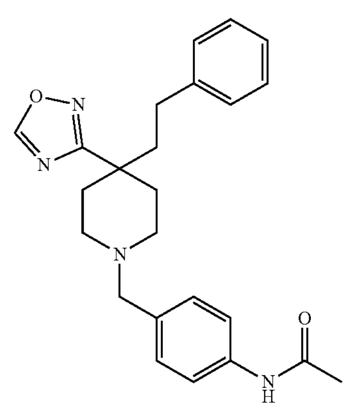 [SMILES: CC(=O)Nc1ccc(CN2CCC(CCc3ccccc3)(c3ncon3)CC2)cc1] | N-(4-((4-(1,2,4-oxadiazol-3-yl)-4-phenethylpiperidin-1-yl)methyl)phenyl)acetamide | 405 | $^1$H NMR (300 MHz, MeOD): δ 9.20 (s, 1H), 7.55-7.52 (d, J = 8.4 Hz, 2H), 7.29-7.19 (m, 4H), 7.15-7.04 (m, 3H), 3.52 (s, 2H), 2.86-2.82 (m, 2H), 2.45-2.23 (m, 6H), 2.13 (s, 3H), 1.91-1.82 (m, 4H) |

TABLE III-continued

| Compound. | Structure | Name | MS (ESI+): [M + H]+ | H-NMR |
|---|---|---|---|---|
| 11 | 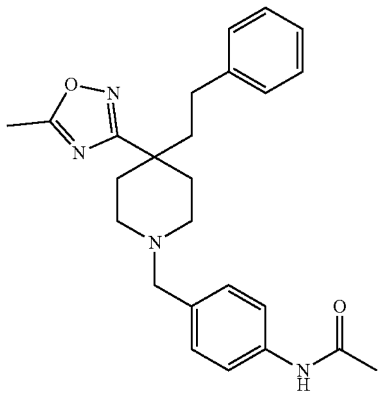 [SMILES: CC(=O)Nc1ccc(CN2CCC(CCc3ccccc3)(c3noc(C)n3)CC2)cc1] | N-(4-((4-(5-methyl-1,2,4-oxadiazol-3-yl)-4-phenethylpiperidin-1-yl)methyl)phenyl)acetamide | 419 | ¹H NMR (300 MHz, MeOD): δ 7.57 (d, J = 8.4 Hz, 2H), 7.32 (d, J = 8.4 Hz, 2H), 7.24-7.06 (m, 5H), 3.74 (s, 2H), 3.01-2.98 (m, 2H), 2.60 (s, 3H), 2.45-2.37 (m, 6H), 2.13 (s, 3H), 1.83-1.98 (m, 4H) |
| 12 | 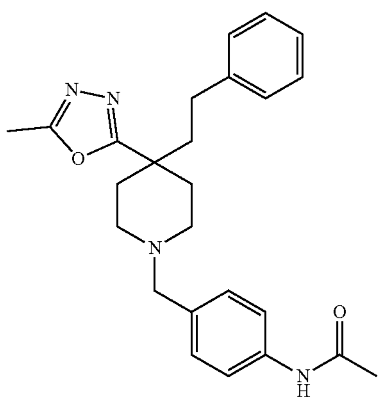 [SMILES: CC(=O)Nc1ccc(CN2CCC(CCc3ccccc3)(c3nnc(C)o3)CC2)cc1] | N-(4-((4-(5-methyl-1,3,4-oxadiazol-2-yl)-4-phenethylpiperidin-1-yl)methyl)phenyl)acetamide | 419 | ¹H NMR (300 MHz, MeOD): δ 7.52 (d, J = 8.4 Hz, 2H), 7.28-7.00 (m, 7H), 3.48 (s, 2H), 2.83-2.79 (m, 2H), 2.47-2.43 (m, 5H), 2.39-2.35 (m, 2H), 2.24-2.16 (m, 2H), 2.13 (s, 3H), 2.04-1.99 (m, 2H), 1.91-1.81 (m, 2H) |
| 13 | 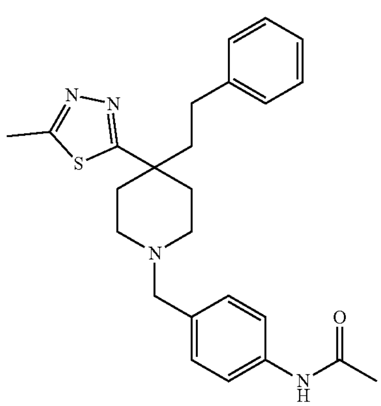 [SMILES: CC(=O)Nc1ccc(CN2CCC(CCc3ccccc3)(c3nnc(C)s3)CC2)cc1] | N-(4-((4-(5-methyl-1,3,4-thiadiazol-2-yl)-4-phenethylpiperidin-1-yl)methyl)phenyl)acetamide | 435 | ¹H NMR (300 MHz, MeOD): δ 7.56 (d, J = 8.4 Hz, 2H), 7.31 (d, J = 8.4 Hz, 2H), 7.24-7.19 (m, 2H), 7.15-7.05 (m, 3H), 3.67 (s, 2H), 3.01-2.92 (m, 2H), 2.79 (s, 2H), 2.49-2.38 (m, 7H), 2.17 (s, 3H), 2.05-1.90 (m, 4H) |

TABLE III-continued

| Compound. | Structure | Name | MS (ESI+): [M + H]+ | H-NMR |
|---|---|---|---|---|
| 14 | 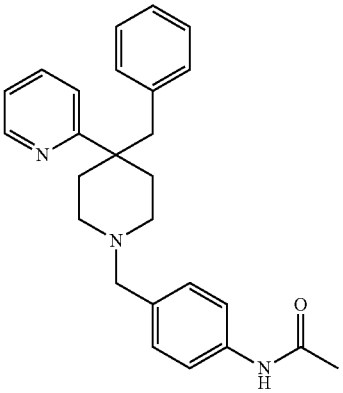 [SMILES: CC(=O)Nc1ccc(CN2CCC(Cc3ccccc3)(c3ccccn3)CC2)cc1] | N-(4-((4-benzyl-4-(pyridin-2-yl)piperidin-1-yl)methyl)phenyl)acetamide | 400 | $^1$H NMR (300 MHz, CDCl$_3$): δ 9.3 (S, 1H), 8.60 (d, J = 3.6 Hz, 1H), 7.73 (d, J = 7.8 Hz, 2H), 7.61-7.56 (m, 1H), 7.46 (d, J = 8.1 Hz, 2H), 7.20-7.03 (m, 4H), 6.89 (d, J = 8.4 Hz, 1H), 6.50 (d, J = 9.9 Hz, 2H), 3.88 (s, 2H), 3.29-3.26 (m, 2H), 2.97 (s, 2H), 2.62-2.35 (m, 6H), 2.25 (s, 3H) |
| 15 | 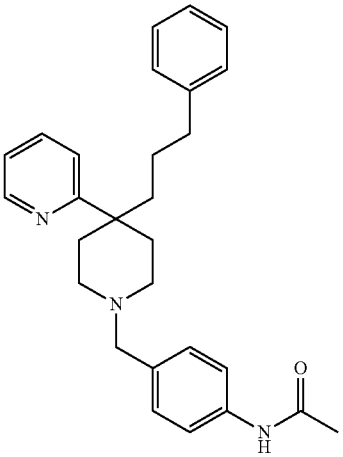 [SMILES: CC(=O)Nc1ccc(CN2CCC(CCCc3ccccc3)(c3ccccn3)CC2)cc1] | N-(4-((4-(3-phenylpropyl)-4-(pyridin-2-yl)piperidin-1-yl)methyl)phenyl)acetamide | 428 | $^1$H NMR (300 MHz, MeOD): δ 8.55- (d, J = 3.9 Hz, 1H), 7.80-7.78- (m, 1H), 7.61 (d, J = 8.4 Hz, 2H), 7.45 (d, J = 8.1 Hz, 1H), 7.35 (d, J = 8.4 Hz, 2H), 7.29-7.10 (m, 4H), 6.99 (d, J = 6.9 Hz, 2H), 3.96 (s, 2H), 3.18-3.14 (m, 2H), 2.73-2.59 (m, 4H), 2.46-2.41 (m, 2H), 2.14 (s, 3H), 1.95-1.66 (m, 4H), 1.31-1.23 (m, 2H) |
| 16 | 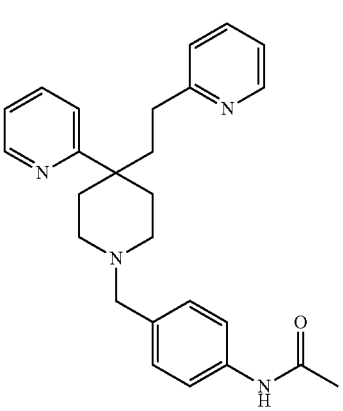 [SMILES: CC(=O)Nc1ccc(CN2CCC(CCc3ccccn3)(c3ccccn3)CC2)cc1] | N-(4-((4-(pyridin-2-yl)-4-(2-(pyridin-2-yl)ethyl)piperidin-1-yl)methyl)phenyl)acetamide | 415 | $^1$H NMR (300 MHz, MeOD): δ 8.60- (d, J = 3.6 Hz, 1H), 8.35- (d, J = 4.5 Hz, 1H), 7.87-7.81- (m, 1H), 7.70-7.54- (m, 4H), 7.36 (d, J = 8.4 Hz, 2H), 7.31-7.29 (m, 1H), 7.27-7.17 (m, 1H), 7.08 (d, J = 7.8 Hz, 1H), 3.93 (s, 2H), 3.36-3.32 (m, 2H), 3.19-3.15 (m, 4H), 2.45-2.41 (m, 2H), 2.14 (s, 3H), 2.14-2.03 (m, 4H) |

TABLE III-continued

| Compound. | Structure | Name | MS (ESI+): [M + H]+ | H-NMR |
|---|---|---|---|---|
| 17 | 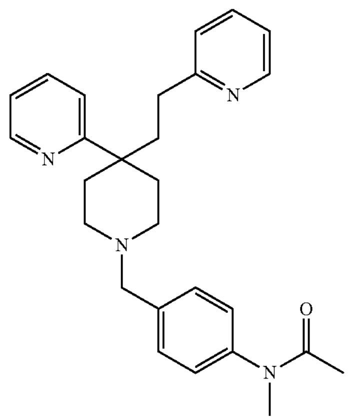 [SMILES: CC(=O)N(C)c1ccc(CN2CCC(CCc3ccccn3)(c3ccccn3)CC2)cc1] | N-methyl-N-(4-((4-phenethyl-4-(pyridin-2-yl)piperidin-1-yl)methyl)phenyl)acetamide | 428 | $^1$H NMR (300 MHz, CDCl$_3$): δ 8.64 (d, J = 3.3 Hz, 1H), 7.73-7.62 (m, 3H), 7.35 (d, J = 7.9 Hz, 1H), 7.21-7.11 (m, 6H), 6.99 (d, J = 6.9 Hz, 2H), 3.96-3.75 (m, 2H), 3.27 (s, 3H), 2.64-2.46 (m, 4H), 2.28-2.20 (m, 2H), 2.02-1.96 (m, 2H), 1.88 (s, 3H), 1.62-1.48 (m, 4H). |
| 18 | 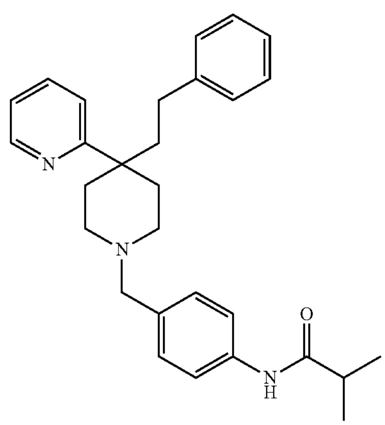 [SMILES: CC(C)C(=O)Nc1ccc(CN2CCC(CCc3ccccc3)(c3ccccn3)CC2)cc1] | N-(4-((4-phenethyl-4-(pyridin-2-yl)piperidin-1-yl)methyl)phenyl)isobutyramide | 442 | $^1$H NMR (300 MHz, MeOD): δ 8.60 (d, J = 3.9 Hz, 1H), 7.83-7.79 (m, 1H), 7.60 (d, J = 8.4 Hz, 2H), 7.51 (d, J = 7.8 Hz, 1H), 7.33-7.26 (m, 3H), 7.19-7.08 (m, 3H), 6.96 (d, J = 7.2 Hz, 2H), 3.71 (s, 2H), 2.98-2.94 (m, 2H), 2.67-2.51 (m, 5H), 2.22-2.16 (m, 2H), 2.01-1.91 (m, 4H), 1.20 (d, J = 6.9 Hz, 6H) |
| 19 | 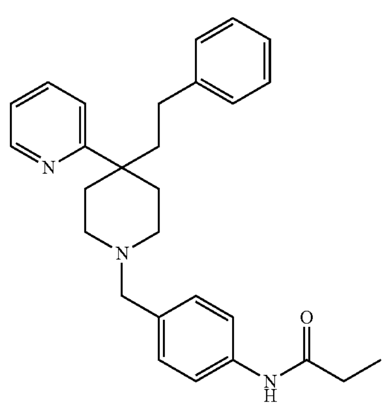 [SMILES: CCC(=O)Nc1ccc(CN2CCC(CCc3ccccc3)(c3ccccn3)CC2)cc1] | N-(4-((4-phenethyl-4-(pyridin-2-yl)piperidin-1-yl)methyl)phenyl)propionamide | 428 | $^1$H NMR (300 MHz, MeOD): δ 8.60 (d, J = 4.2 Hz, 1H), 7.83-7.80 (m, 1H), 7.59-7.50 (m, 3H), 7.32-7.26 (m, 3H), 7.20-7.09 (m, 3H), 6.96 (d, J = 7.2 Hz, 2H), 3.67 (s, 2H), 2.95-2.91 (m, 2H), 2.57-2.36 (m, 6H), 2.22-2.16 (m, 2H), 2.00-1.92 (m, 4H), 1.21 (t, J = 7.5 Hz, 3H). |

TABLE III-continued

| Compound. | Structure | Name | MS (ESI+): [M + H]+ | H-NMR |
|---|---|---|---|---|
| 20 | 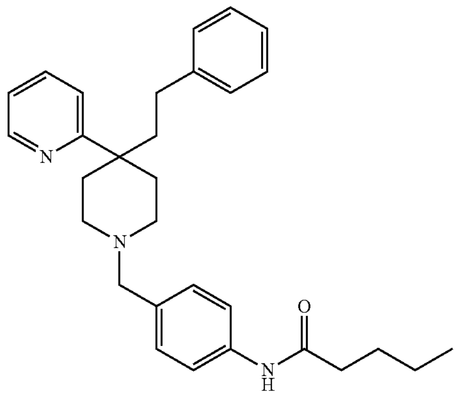 [SMILES: CCCCC(=O)Nc1ccc(CN2CCC(CCc3ccccc3)(c3ccccn3)CC2)cc1] | N-(4-((4-phenethyl-4-(pyridin-2-yl)piperidin-1-yl)methyl)phenyl)pentanamide | 456 | $^1$H NMR (300 MHz, MeOD): δ 8.61 (d, J = 3.9 Hz, 1H), 7.88-7.83 (m, 1H), 7.64 (d, J = 8.4 Hz, 2H), 7.56-7.53 (m, 1H), 7.39-7.31 (m, 3H), 7.18-7.09 (m, 3H), 6.97 (d, J = 6.9 Hz, 2H), 3.95 (s, 2H), 3.20-3.15 (m, 2H), 2.79-2.69 (m, 4H), 2.42-2.36 (m, 2H), 2.21-2.18 (m, 2H), 2.03-1.96 (m, 4H), 1.71-1.66 (m, 2H), 1.45-1.38 (m, 2H), 0.97 (t, J = 7.2 Hz, 3H). |
| 21 | 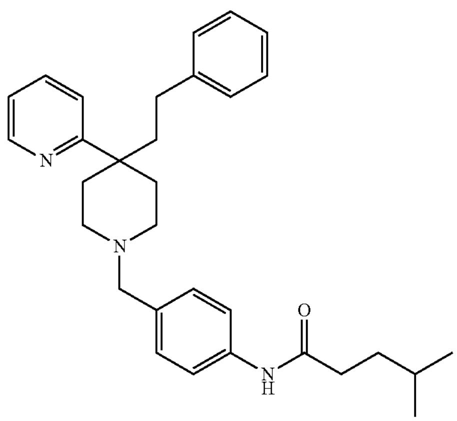 [SMILES: CC(C)CCC(=O)Nc1ccc(CN2CCC(CCc3ccccc3)(c3ccccn3)CC2)cc1] | 4-methyl-N-(4-((4-phenethyl-4-(pyridin-2-yl)piperidin-1-yl)methyl)phenyl)pentanamide | 470 | $^1$H NMR (300 MHz, MeOD): δ 8.59 (d, J = 3.9 Hz, 1H), 7.86-7.81 (m, 1H), 7.59-7.50 (m, 3H), 7.32-7.29 (m, 3H), 7.19-7.08 (m, 3H), 6.96 (d, J = 7.2 Hz, 2H), 3.66 (s, 2H), 2.94-2.89 (m, 2H), 2.51-2.36 (m, 6H), 2.22-2.16 (m, 2H), 1.97-1.91 (m, 4H), 1.62-1.58 (m, 3H), 0.96 (d, J =6.0 Hz, 6H). |
| 22 | 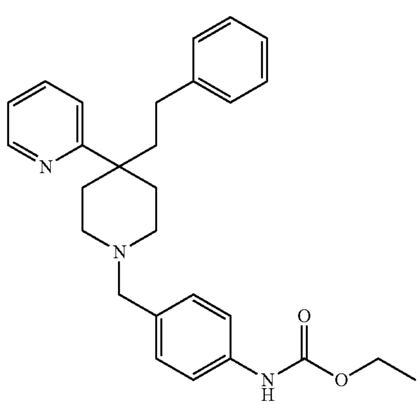 [SMILES: CCOC(=O)Nc1ccc(CN2CCC(CCc3ccccc3)(c3ccccn3)CC2)cc1] | ethyl 4-((4-phenethyl-4-(pyridin-2-yl)piperidin-1-yl)methyl)phenylcarbamate | 444 | $^1$H NMR (300 MHz, MeOD): δ 8.60 (d, J = 4.2 Hz, 1H), 7.86-7.80 (m, 1H), 7.52 (d, J = 8.1 Hz, 1H), 7.44 (d, J = 8.1 Hz, 2H), 7.30-7.25 (m, 3H), 7.20-7.09 (m, 3H), 6.97 (d, J = 7.2 Hz, 2H), 4.20 (q, J = 6.9 Hz, 2H), 3.63 (s, 2H), 2.92-2.88 (m, 2H), 2.56-2.41 (m, 4H), 2.22-2.17 (m, 2H), 1.97-1.91 (m, 4H), 1.31 (t, J = 6.9 Hz, 3H). |

TABLE III-continued

| Compound. | Structure | Name | MS (ESI+): [M + H]+ | H-NMR |
|---|---|---|---|---|
| 23 | 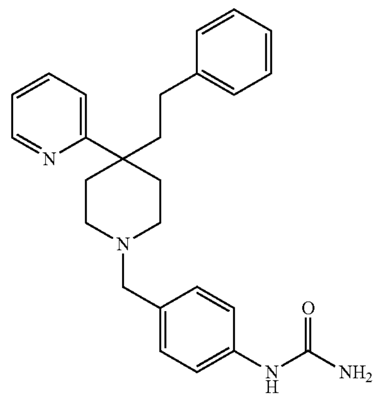 [SMILES: NC(=O)Nc1ccc(CN2CCC(CCc3ccccc3)(c3ccccn3)CC2)cc1] | 1-(4-((4-phenethyl-4-(pyridin-2-yl)piperidin-1-yl)methyl)phenyl)urea | 415 | ¹H NMR (300 MHz, MeOD): δ 8.60 (d, J = 3.9 Hz, 1H), 7.85-7.80 (m, 1H), 7.52 (d, J = 7.8 Hz, 1H), 7.41-7.25 (m, 5H), 7.19-7.06 (m, 3H), 6.96 (d, J = 6.9 Hz, 2H), 3.72 (s, 2H), 3.03-2.80 (m, 2H), 2.71-2.30 (m, 4H), 2.22-2.17 (m, 2H), 2.05-1.93 (m, 4H). |
| 24 | 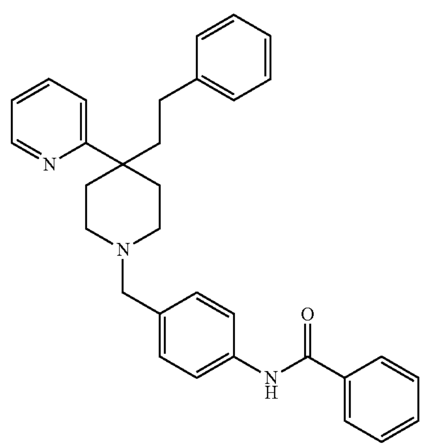 [SMILES: O=C(Nc1ccc(CN2CCC(CCc3ccccc3)(c3ccccn3)CC2)cc1)c1ccccc1] | N-(4-((4-phenethyl-4-(pyridin-2-yl)piperidin-1-yl)methyl)phenyl)benzamide | 476 | ¹H NMR (300 MHz, MeOD): δ 8.60 (d, J = 3.9 Hz, 1H), 7.94 (d, J = 7.2 Hz, 2H), 7.84-7.74 (m, 3H), 7.58-7.48 (m, 4H), 7.38 (d, J = 8.4 Hz, 2H), 7.29-7.08 (m, 4H), 6.96 (d, J = 7.5 Hz, 2H), 3.73 (s, 2H), 2.99-2.95 (m, 2H), 2.61-2.49 (m, 4H), 2.21-2.15 (m, 2H), 2.01-1.91 (m, 4H) |
| 25 | 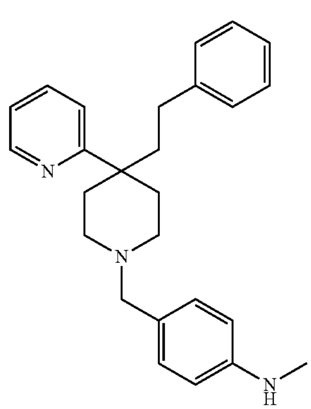 [SMILES: CNc1ccc(CN2CCC(CCc3ccccc3)(c3ccccn3)CC2)cc1] | N-methyl-4-((4-phenethyl-4-(pyridin-2-yl)piperidin-1-yl)methyl)aniline | 386 | ¹H NMR (300 MHz, MeOD): δ 8.60 (d, J = 3.9 Hz, 1H), 7.83-7.79 (m, 1H), 7.51 (d, J = 7.8 Hz, 1H), 7.29-7.26 (m, 1H), 7.20-7.08 (m, 5H), 6.96 (d, J = 6.9 Hz, 2H), 6.60 (d, J = 8.7 Hz, 2H), 3.64 (s, 2H), 3.33-3.32 (m, 2H), 2.76 (s, 3H), 2.58-2.51 (m, 4H), 2.22-2.16 (m, 2H), 2.00-1.91 (m, 4H) |

TABLE III-continued

| Compound. | Structure | Name | MS (ESI+): [M + H]+ | H-NMR |
|---|---|---|---|---|
| 26 | 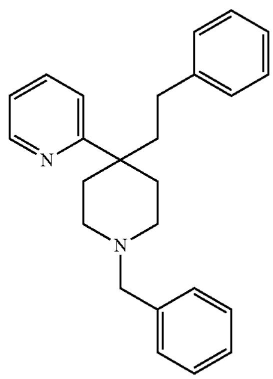 [SMILES: c1ccc(CCC2(c3ccccn3)CCN(Cc3ccccc3)CC2)cc1] | 2-(1-benzyl-4-phenethylpiperidin-4-yl)pyridine | 357 | ¹H NMR (300 MHz, MeOD): δ 8.60 (d, J = 3.9 Hz, 1H), 7.87-7.82 (m, 1H), 7.55 (d, J = 8.1 Hz, 1H), 7.38 (s, 5H), 7.32-7.28 (m, 1H), 7.20-7.07 (m, 3H), 6.97 (d, J = 6.9 Hz, 2H), 3.80 (s, 2H), 3.03-2.99 (m, 2H), 2.60-2.56 (m, 4H), 2.23-2.17 (m, 2H), 2.02-1.93 (m, 4H) |
| 27 | 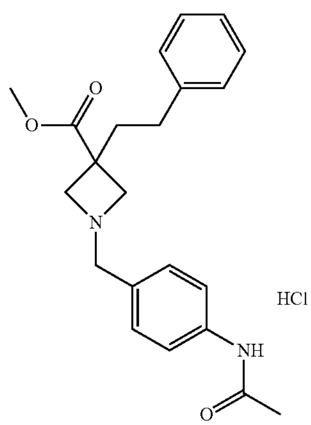 [SMILES: COC(=O)C1(CCc2ccccc2)CN(Cc2ccc(NC(C)=O)cc2)C1 ; Cl] | methyl 1-(4-acetamidobenzyl)-3-phenethylazetidine-3-carboxylate HCl | 367 | ¹H NMR (300 MHz, MeOD): δ 7.68 (d, J = 8.4 Hz, 2H), 7.40 (d, J = 8.4 Hz, 2H), 7.32-7.19 (m, 5H), 4.38-4.32 (m, 4H), 4.02 (d, J = 11.4 Hz, 2H), 3.82 (s, 3H), 2.59-2.54 (m, 2H), 2.34-3.29 (m, 2H), 2.15 (s, 3H). |
| 28 | 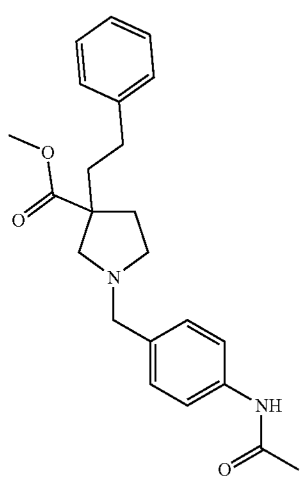 [SMILES: COC(=O)C1(CCc2ccccc2)CCN(Cc2ccc(NC(C)=O)cc2)C1] | methyl 1-(4-acetamidobenzyl)-3-phenethylpyrrolidine-3-carboxylate | 381 | ¹H NMR (300 MHz, CDCl₃): δ 7.63 (brs, 1H), 7.47 (d, J = 8.4 Hz, 2H), 7.30-7.28 (m, 4H), 7.21-7.14 (m, 3H), 3.70 (s, 3H), 3.62 (s, 2H), 3.05 (d, J = 9.9 Hz, 1H), 2.69-2.62 (m, 2H), 2.59-2.40 (m, 4H), 2.18 (s, 3H), 2.08-2.01 (m, 2H), 1.86-1.77 (m, 1H) |

TABLE III-continued

| Compound. | Structure | Name | MS (ESI+): [M + H]+ | H-NMR |
|---|---|---|---|---|
| 29 | 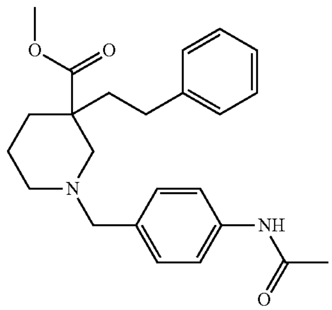 [SMILES: COC(=O)C1(CCc2ccccc2)CCCN(Cc2ccc(NC(C)=O)cc2)C1] | methyl 1-(4-acetamidobenzyl)-3-phenethylpiperidine-3-carboxylate | 395 | ¹H NMR (300 MHz, CDCl₃): δ 7.45- (d, J = 7.8 Hz, 2H), 7.29-7.11- (m, 7H), 3.69 (s, 3H), 3.52-3.36 (m, 2H), 2.91 (s, 1H), 2.57-2.39 (m, 2H), 2.36-2.30 (m, 1H), 2.28-2.19 (m, 5H), 2.04-1.97 (m, 1H), 1.96-1.95 (m, 1H), 1.87-1.66 (m, 4H) |
| 30 | 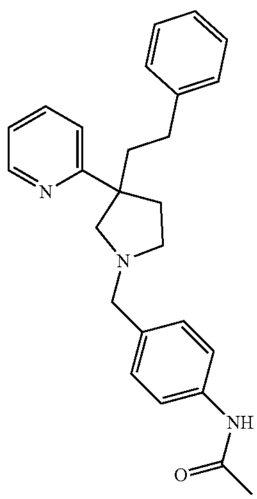 [SMILES: CC(=O)Nc1ccc(CN2CCC(CCc3ccccc3)(c3ccccn3)C2)cc1] | N-(4-((3-phenethyl-3-(pyridin-2-yl)pyrrolidin-1-yl)methyl)phenyl)acetamide | 400 | ¹H NMR (300 MHz, MeOD): δ 8.56 (d, J = 3.0 Hz, 1H), 7.84 (t, J = 7.50 Hz, 1H), 7.61-7.51 (m, 3H), 7.40-7.28 (m, 3H), 7.20-6.98 (m, 5H), 4.11-3.95 (m, 2H), 3.73 (d, J = 9.0 Hz, 1H), 3.22-3.07 (m, 3H), 2.54-2.50 (m, 1H), 2.34-2.15 (m, 5H), 2.13 (s, 3H). |
| 31 | 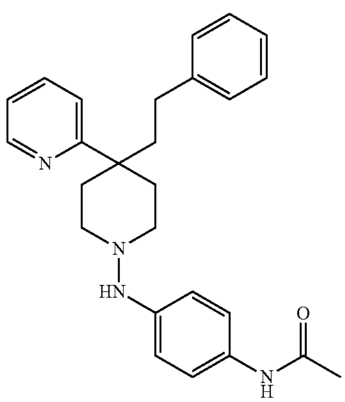 [SMILES: CC(=O)Nc1ccc(NN2CCC(CCc3ccccc3)(c3ccccn3)CC2)cc1] | N-(4-(4-phenethyl-4-(pyridin-2-yl)piperidin-1-ylamino)phenyl)acetamide | 415 | ¹H NMR (300 MHz, MeOD): δ 8.60 (d, J = 3.9 Hz, 1H), 7.80-7.86 (m, 1H), 7.55 (d, J = 8.1 Hz, 1H), 7.16-7.30 (m, 5H), 7.07-7.12 (m, 1H), 6.99 (d, J = 7.2 Hz, 2H), 6.85 (d, J = 8.7 Hz, 2H), 2.94-2.97 (m, 2H), 2.50-2.54 (m, 4H), 2.19-2.25 (m, 2H), 2.08 (s, 3H), 1.96-2.05 (m, 4H). |
| 32 | 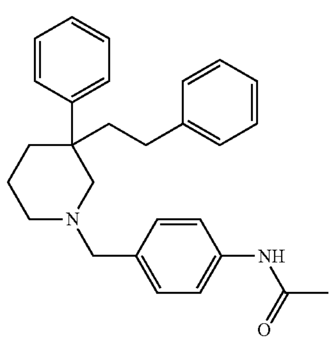 [SMILES: CC(=O)Nc1ccc(CN2CCCC(CCc3ccccc3)(c3ccccc3)C2)cc1] | N-(4-((3-phenethyl-3-(pyridin-2-yl)piperidin-1-yl)methyl)phenyl)acetamide | 414 | |

TABLE III-continued

| Compound. | Structure | Name | MS (ESI+): [M + H]+ | H-NMR |
|---|---|---|---|---|
| 33 | 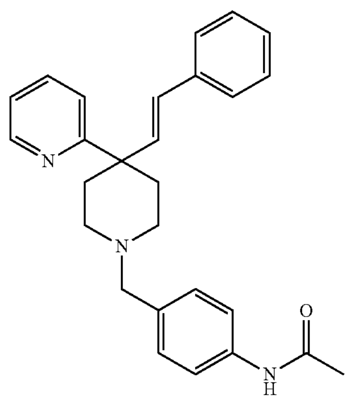 | (E)-N-(4-((4-(pyridin-2-yl)-4-styrylpiperidin-1-yl)methyl)phenyl)acetamide | 412 | ¹H NMR (300 MHz, MeOD): δ 8.60 (d, J = 3.9 Hz, 1H), 7.83-7.78 (m, 1H), 7.65 (d, J = 8.4 Hz, 2H), 7.52 (d, J = 8.1 Hz, 1H), 7.48-7.35 (m, 4H), 7.31-7.18 (m, 4H), 6.38-6.32 (m, 2H), 4.11 (s, 2H), 3.31-3.22 (m, 2H), 3.20-3.04 (m, 2H), 2.78-2.63 (m, 2H), 2.45-2.34 (m, 2H), 2.14 (s, 3H) |
| 34 | 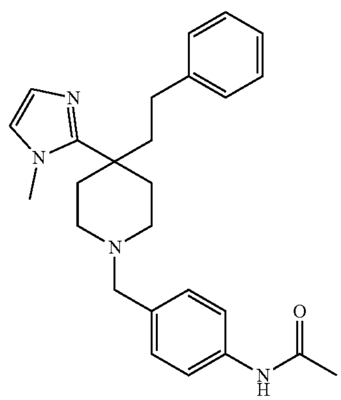 [SMILES: CC(=O)Nc1ccc(CN2CCC(CCc3ccccc3)(c3nccn3C)CC2)cc1] | N-(4-((4-(1-methyl-1H-imidazol-2-yl)-4-phenethylpiperidin-1-yl)methyl)phenyl)acetamide | 417 | ¹H NMR (300 MHz, MeOD): δ 7.70 (d, J = 8.5 Hz, 2H), 7.45 (d, J = 8.5 Hz, 2H), 7.22 (t, J = 7.2 Hz, 2H), 7.15-7.03 (m, 5H), 4.47 (s, 2H), 3.44-3.28 (m, 4H), 3.12 (s, 3H), 2.61 (d, J = 15.5 Hz, 2H), 2.34-2.19 (m, 4H), 2.16 (s, 3H), 2.03-1.97 (m, 2H). |
| 35 | 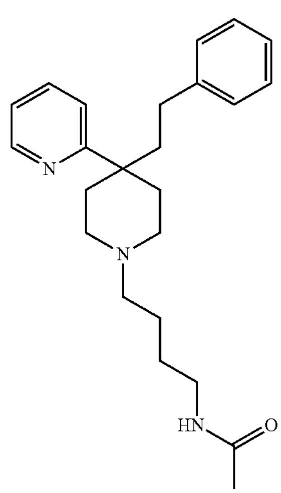 [SMILES: CC(=O)NCCCCN1CCC(CCc2ccccc2)(c2ccccn2)CC1] | N-(4-(4-phenethyl-4-(pyridin-2-yl)piperidin-1-yl)butyl)acetamide | 380 | ¹H NMR (300 MHz, MeOD): δ 8.63 (d, J = 3.9 Hz, 1H), 7.87-7.89 (m, 1H), 7.58 (d, J = 8.1 Hz, 1H), 7.32-7.37 (m, 1H), 7.11-7.22 (m, 3H), 6.99 (d, J = 7.2 Hz, 2H), 3.56-3.60 (m, 1H), 3.17-3.21 (m, 3H), 2.69-2.94 (m, 4H), 2.20-2.26 (m, 2H), 1.99-2.06 (m, 5H), 1.94 (s, 3H), 1.67-1.70 (m, 2H), 1.51-1.57 (m, 3H). |

TABLE III-continued

| Compound. | Structure | Name | MS (ESI+): [M + H]+ | H-NMR |
|---|---|---|---|---|
| 36 | 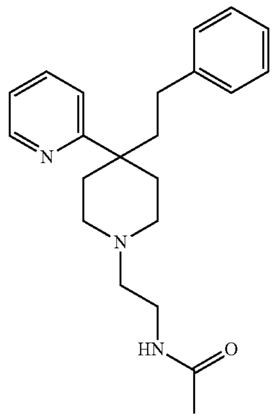 [SMILES: CC(=O)NCCN1CCC(CCc2ccccc2)(c2ccccn2)CC1] | N-(2-(4-phenethyl-4-(pyridin-2-yl)piperidin-1-yl)ethyl)acetamide | 352 | ¹H NMR (300 MHz, MeOD): δ 8.62 (d, J = 4.2 Hz, 1H), 7.82-7.88 (m, 1H), 7.56 (d, J = 7.8 Hz, 1H), 7.28-7.32 (m, 1H), 7.10-7.21 (m, 3H), 6.99 (d, J = 6.9 Hz, 2H), 3.42 (t, J = 6.3 Hz, 2H), 3.32-3.33 (m, 2H), 2.79 (t, J = 6.3 Hz, 2H), 2.63-2.71 (m, 4H), 2.20-2.25 (m, 2H), 1.99-2.04 (m, 4H), 1.96 (s, 3H). |
| 37 | 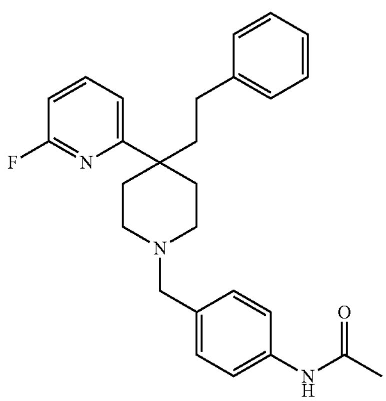 [SMILES: CC(=O)Nc1ccc(CN2CCC(CCc3ccccc3)(c3cccc(F)n3)CC2)cc1] | N-(4-((4-(6-fluoropyridin-2-yl)-4-phenethylpiperidin-1-yl)methyl)phenyl)acetamide | 432 | ¹H NMR (300 MHz, CDCl₃): δ 7.78-7.75- (m, 1H), 7.46-7.43- (d, J = 6.9 Hz, 2H), 7.29 (s, 1H), 7.24-7.15- (m, 5H), 7.02 (d, J = 6.9 Hz, 2H), 6.79-6.70 (m, 1H), 3.4 (s, 2H), 2.75-2.62 (m, 2H), 2.41-2.36 (m, 2H), 2.28-2.22 (m, 4H), 2.18 (s, 3H), 1.99-1.93 (m, 4H) |
| 38 | 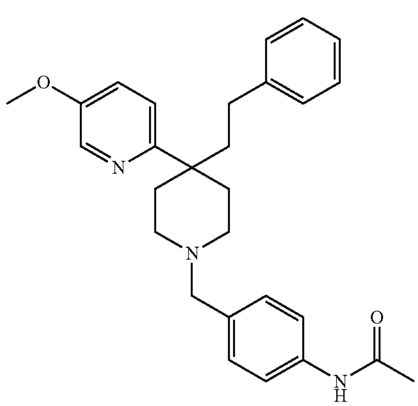 [SMILES: COc1ccc(C2(CCc3ccccc3)CCN(Cc3ccc(NC(C)=O)cc3)CC2)nc1] | N-(4-((4-(5-methoxypyridin-2-yl)-4-phenethylpiperidin-1-yl)methyl)phenyl)acetamide | 444 | ¹H NMR (300 MHz, MeOD): δ 8.29-8.28 (d, J =2.4 Hz, 1H), 7.59-7.56 (d, J = 8.4 Hz, 2H), 7.46-7.38 (m, 2H), -7.34-7.31 (d, J = 8.4 Hz, 2H), 7.20-7.15 (m, 2H), 7.11-7.06 (m, 1H), -6.98-6.96 (d, J = 7.2 Hz, 2H), 3.9 (s, 3H), 3.7 (s, 2H), 3.02-2.98 (d, J = 10.8 Hz, 2H), 2.58-2.54 (m, 4H), 2.23-2.18 (m, 2H), 2.13 (s, 3H), 1.97-1.89 (m, 4H). |

TABLE III-continued

| Compound. | Structure | Name | MS (ESI+): [M + H]+ | H-NMR |
|---|---|---|---|---|
| 39 | 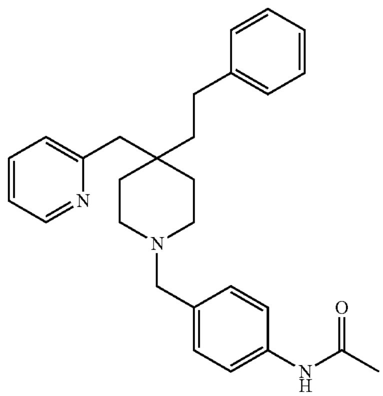 [SMILES: CC(=O)Nc1ccc(CN2CCC(CCc3ccccc3)(Cc3ccccn3)CC2)cc1] | N-(4-((4-phenethyl-4-(pyridin-2-ylmethyl)piperidin-1-yl)methyl)phenyl)acetamide | 428 | $^1$H NMR (300 MHz, CD$_3$OD): δ 8.83 (d, J = 6.0 Hz, 1H), 8.65-8.58 (m, 1H), 8.06-8.02 (m, 2H), 7.68-7.66 (m, 2H), 7.58-7.46 (m, 2H), 7.32 (d, J = 4.2 Hz, 3H), 7.25-7.17 (m, 2H), 4.27 (s, 2H), 3.54-3.47 (m, 2H), 3.31 (s, 2H), 3.26-3.21 (m, 2H), 2.77-2.72 (m, 2H), 2.15 (s, 3H), 1.96-1.80 (m, 6H) |
| 40 | 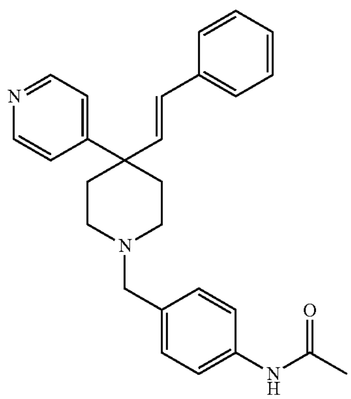 [SMILES: CC(=O)Nc1ccc(CN2CCC(/C=C/c3ccccc3)(c3ccncc3)CC2)cc1] | (E)-N-(4-((4-(pyridin-4-yl)-4-styrylpiperidin-1-yl)methyl)phenyl)acetamide | 412 | |
| 41 | 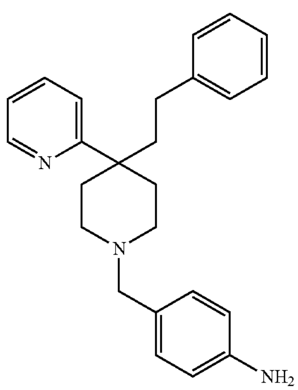 [SMILES: Nc1ccc(CN2CCC(CCc3ccccc3)(c3ccccn3)CC2)cc1] | 4-((4-phenethyl-4-(pyridin-2-yl)piperidin-1-yl)methyl)aniline | 372 | $^1$H NMR (300 MHz, CDCl$_3$): δ 8.61 (d, J = 3.9 Hz, 1H), 7.73 (t, J = 6.9 Hz, 1H), 7.34 (d, J = 8.1 Hz, 3H), 7.23-7.09 (m, 4H), 6.96 (d, J = 6.9 Hz, 2H), 6.65 (d, J = 8.1 Hz, 2H), 3.85 (s, 2H), 3.32-3.27 (m, 2H), 2.66-2.47 (m, 6H), 2.25-2.19 (m, 2H), 1.99-1.94 (m, 2H) |
| 42 | 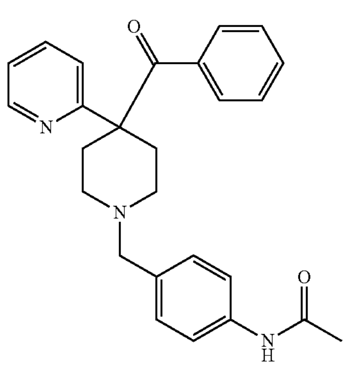 [SMILES: CC(=O)Nc1ccc(CN2CCC(C(=O)c3ccccc3)(c3ccccn3)CC2)cc1] | N-(4-((4-benzoyl-4-(pyridin-2-yl)piperidin-1-yl)methyl)phenyl)acetamide | 414 | $^1$H NMR (300 MHz, MeOD): δ 8.62 (d, J = 4.3 Hz, 1H), 7.83 (t, J = 7.0 Hz, 1H), 7.59 (d, J = 8.4 Hz, 2H), 7.45 (d, J = 8.6 Hz, 4H), 7.37-7.27 (m, 5H), 3.85 (s, 2H), 3.07 (m, 2H), 2.77 (t, J = 10.7 Hz, 2H), 2.63-2.46 (m, 4H), 2.14 (s, 3H). |

TABLE III-continued

| Compound. | Structure | Name | MS (ESI+): [M + H]+ | H-NMR |
|---|---|---|---|---|
| 43 | 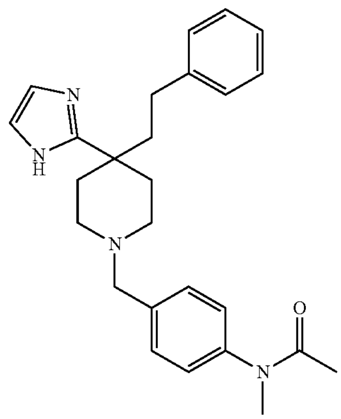 [SMILES: CC(=O)N(C)c1ccc(CN2CCC(CCc3ccccc3)(c3ncc[nH]3)CC2)cc1] | N-(4-((4-(1H-imidazol-2-yl)-4-phenethylpiperidin-1-yl)methyl)phenyl)-N-methylacetamide | 417 | ¹H NMR (300 MHz, MeOD): δ 7.76 (d, J = 8.4 Hz, 2H), 7.54 (d, J = 8.4 Hz, 2H), 7.24-7.08 (m, 7H), 4.69 (s, 2H), 3. 51-3.60 (m, 2H), 3.27-3.54 (m, 2H), 2.91 (s, 3H), 2.65-2.43 (m, 4H), 2.31-2.28 (m, 2H), 2.17-2.12 (m, 5H) |
| 44 | 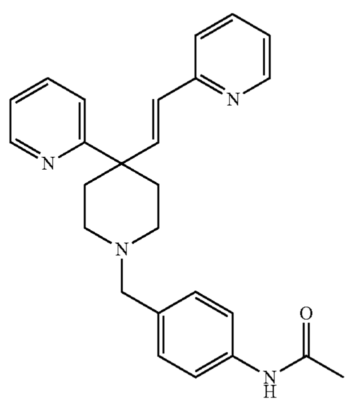 [SMILES: CC(=O)Nc1ccc(CN2CCC(/C=C/c3ccccn3)(c3ccccn3)CC2)cc1] | (E)-N-(4-((4-(pyridin-2-yl)-4-(2-(pyridin-2-yl)vinyl)piperidin-1-yl)methyl)phenyl)acetamide | 413 | ¹H NMR (300 MHz, MeOD): δ 8.57 (d, J = 3.9 Hz, 1H), 8.43 (d, J = 4.2 Hz, 1H), 7.85-7.73 (m, 2H), 7.59-7.52 (m, 3H), 7.45 (d, J = 7.8 Hz, 1H), 7.34 (d, J = 8.4 Hz, 2H), 7.29-7.22 (m, 2H), 6.82 (d, J = 16.4 Hz, 1H), 6.42 (d, J = 16.6 Hz, 1H), 3.77 (s, 2H), 2.96-2.93 (m, 2H), 2.85-2.65 (m, 2H), 2.65-2.52 (m, 2H), 2.34-2.26 (m, 2H), 2.14 (s, 3H). |
| 45 | 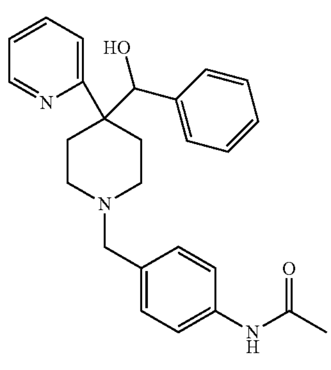 [SMILES: CC(=O)Nc1ccc(CN2CCC(c3ccccn3)(C(O)c3ccccc3)CC2)cc1] | N-(4-((4-(hydroxy(phenyl)methyl)-4-(pyridin-2-yl)piperidin-1-yl)methyl)phenyl)acetamide | 416 | ¹H NMR (300 MHz, MeOD): δ 8.51 (d, J = 4.2 Hz, 1H), 7.74-7.68 (m, 1H), 7.55 (d, J = 8.4 Hz, 2H), 7.29 (m, 4H), 7.11 (m, 3H), 6.78 (d, J = 6.0 Hz, 2H), 4.71 (s, 1H), 3.67 (s, 2H), 3.05 (d, J = 11.6 Hz, 2H), 2.65-2.50 (m, 2H), 2.38-2.13 (m, 4H), 2.13 (s, 3H). |

TABLE III-continued

| Compound. | Structure | Name | MS (ESI+): [M + H]⁺ | H-NMR |
|---|---|---|---|---|
| 46 | 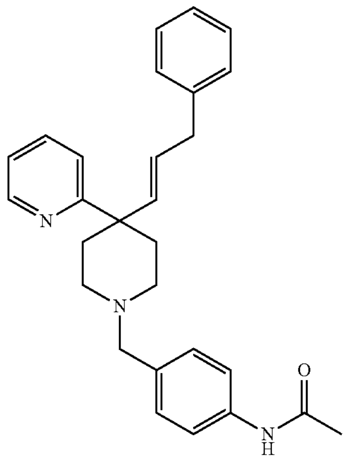 [SMILES: CC(=O)Nc1ccc(CN2CCC(/C=C/Cc3ccccc3)(c3ccccn3)CC2)cc1] | (E)-N-(4-((4-(3-phenylprop-1-enyl)-4-(pyridin-2-yl)piperidin-1-yl)methyl)phenyl)acetamide | 426 | ¹H NMR (300 MHz, MeOD): δ 8.50 (d, J = 4.0 Hz, 1H), 7.78-7.75 (m, 1H), 7.55-7.51 (m, 3H), 7.31 (d, J = 8.4 Hz, 2H), 7.25-7.07 (m, 4H), 6.75 (d, J = 6.7 Hz, 2H), 5.88 (d, J = 11.3 Hz, 1H), 5.62-4.87 (m, 1H), 3.57 (s, 2H), 2.93 (d, J = 7.5 Hz, 2H), 2.75 (m, 2H), 2.59 (t, J = 10.1 Hz, 2H), 2.29-2.13 (m, 4H), 2.13 (s, 3H). |
| 47 | 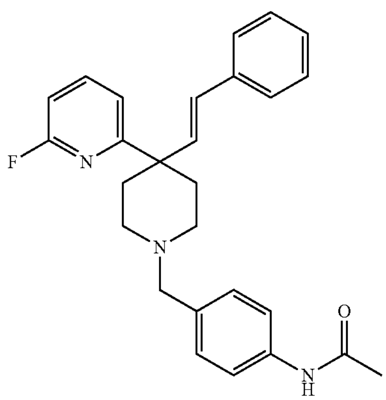 [SMILES: CC(=O)Nc1ccc(CN2CCC(/C=C/c3ccccc3)(c3cccc(F)n3)CC2)cc1] | (E)-N-(4-((4-(6-fluoropyridin-2-yl)-4-styrylpiperidin-1-yl)methyl)phenyl)acetamide | 430 | ¹H NMR (300 MHz, CDCl₃): δ 7.61-7.58 (m, 1H), 7.43 (d, J = 7.8 Hz, 2H), 7.28-7.23 (m, 2H), 7.09-7.03 (m, 4H), 6.88-6.85 (m, 2H), 6.68-6.66 (m, 2H), 5.90 (d, J = 12.3 Hz, 1H), 3.50 (s, 2H), 2.52-2.38 (m, 4H), 2.18 (s, 3H), 1.97-2.02 (m, 4H). |
| 48 | 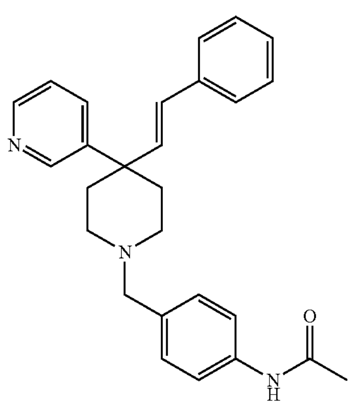 [SMILES: CC(=O)Nc1ccc(CN2CCC(/C=C/c3ccccc3)(c3cccnc3)CC2)cc1] | (E)-N-(4-((4-(pyridin-3-yl)-4-styrylpiperidin-1-yl)methyl)phenyl)acetamide | | |

TABLE III-continued

| Compound. | Structure | Name | MS (ESI+): [M + H]+ | H-NMR |
|---|---|---|---|---|
| 49 | 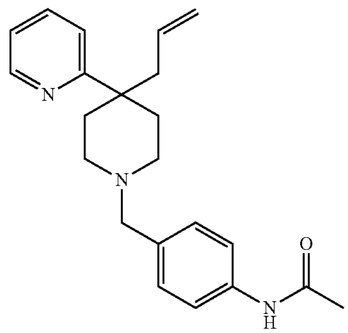 [SMILES: C=CCC1(c2ccccn2)CCN(Cc2ccc(NC(C)=O)cc2)CC1] | N-(4-((4-allyl-4-(pyridin-2-yl)piperidin-1-yl)methyl)phenyl)acetamide | 350 | $^{1}$H NMR (300 MHz, CDCl$_3$): δ 8.62 (d, J = 3.9 Hz, 1H), 7.65 (t, J = 7.4 Hz, 1H), 7.48 (d, J = 8.1 Hz, 2H), 7.34-7.23 (m, 3H), 7.15-7.11 (m, 1H), 5.43-5.34 (m, 1H), 4.91-4.84 (m, 2H), 2.76 (brs, 2H), 2.43-2.38 (m, 4H), 2.31-2.24 (m, 2H), 2.20 (s, 3H), 2.02-1.68 (m, 4H). |
| 50 | 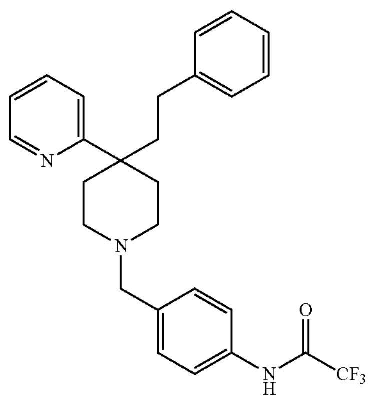 [SMILES: O=C(Nc1ccc(CN2CCC(CCc3ccccc3)(c3ccccn3)CC2)cc1)C(F)(F)F] | 2,2,2-trifluoro-N-(4-((4-phenethyl-4-(pyridin-2-yl)piperidin-1-yl)methyl)phenyl)acetamide | 468 | $^{1}$H NMR (300 MHz, MeOD): δ 8.60 (d, J = 3.9 Hz, 1H), 7.86-7.81 (m, 1H), 7.67 (d, J = 8.4 Hz, 2H), 7.53 (d, J = 8.1 Hz, 1H), 7.42 (d, J = 8.4 Hz, 2H), 7.31-7.27 (m, 1H), 7.06-7.20 (m, 3H), 6.97 (d, J = 6.9 Hz, 2H), 3.74 (s, 2H), 2.95-2.99 (m, 2H), 2.48-2.55 (m, 4H), 2.17-2.23 (m, 2H), 1.93-2.02 (m, 4H). |
| 51 | 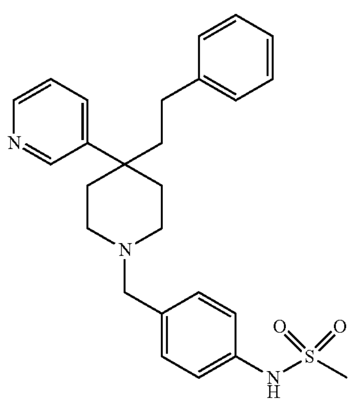 [SMILES: CS(=O)(=O)Nc1ccc(CN2CCC(CCc3ccccc3)(c3cccnc3)CC2)cc1] | N-(4-((4-phenethyl-4-(pyridin-2-yl)piperidin-1-yl)methyl)phenyl)methanesulfonamide | 450 | $^{1}$H NMR (300 MHz, MeOD): δ 8.59 (d, J = 3.9 Hz, 1H), 7.79-7.84 (m, 1H), 7.51 (d, J = 7.8 Hz, 1H), 7.06-7.32 (m, 8H), 6.96 (d, J = 7.2 Hz, 2H), 3.52 (s, 2H), 2.95 (s, 3H), 2.76-2.80 (m, 2H), 2.47-2.52 (m, 2H), 2.28-2.35 (m, 2H), 2.16-2.22 (m, 2H), 1.93-1.96 (s, 4H). |
| 52 | 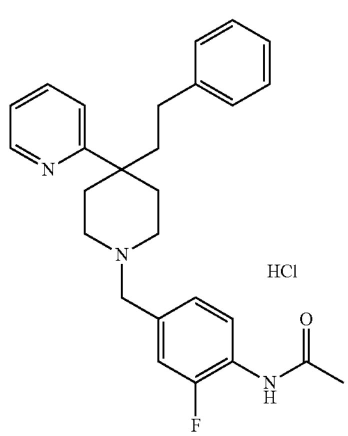 [SMILES: CC(=O)Nc1ccc(CN2CCC(CCc3ccccc3)(c3ccccn3)CC2)cc1F ; Cl] | N-(2-fluoro-4-((4-phenethyl-4-(pyridin-2-yl)piperidin-1-yl)methyl)phenyl)acetamide HCl | 432 | $^{1}$H NMR (300 MHz, CDCl$_3$): δ 8.85-8.71 (m, 1H), 8.58 (m, 1H), 8.21-7.98 (m, 3H), 7.55-7.26 (m, 2H), 7.25-7.01 (m, 5H), 4.45-4.27 (m, 2H), 3.54-3.49 (m, 3H), 2.98-2.94 (m, 2H), 2.62-2.41 (m, 4H), 2.23-2.17 (m, 5H), 1.98-1.92 (m, 4H). |

TABLE III-continued

| Compound. | Structure | Name | MS (ESI+): [M + H]+ | H-NMR |
|---|---|---|---|---|
| 53 | 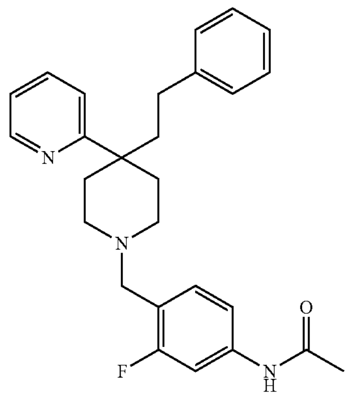 [SMILES: CC(=O)Nc1ccc(CN2CCC(CCc3ccccc3)(c3ccccn3)CC2)c(F)c1] | N-(3-fluoro-4-((4-phenethyl-4-(pyridin-2-yl)piperidin-1-yl)methyl)phenyl)acetamide | 432 | $^1$H NMR (300 MHz, MeOD): δ 8.59 (d, J = 4.0 Hz, 1H), 7.82 (t, J = 6.9 Hz, 1H), 7.54 (t, J = 11.2 Hz, 2H), 7.35-7.06 (m, 6H), 6.96 (d, J = 7.1 Hz, 2H), 3.61 (s, 2H), 2.86-2.82 (m, 2H), 2.55-2.35 (m, 4H), 2.20-2.16 (m, 2H), 2.13 (s, 3H), 2.03-1.90 (m, 4H). |
| 54 | 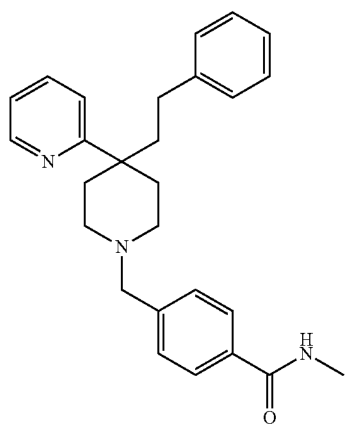 [SMILES: CNC(=O)c1ccc(CN2CCC(CCc3ccccc3)(c3ccccn3)CC2)cc1] | N-methyl-4-((4-phenethyl-4-(pyridin-2-yl)piperidin-1-yl)methyl)benzamide | 414 | $^1$H NMR (300 MHz, CDCl$_3$): δ 8.65 (d, J = 3.9 Hz, 1H), 7.74-7.67 (m, 3H), 7.45 (d, J = 7.8 Hz, 2H), 7.33 (d, J = 7.8 Hz, 1H), 7.24-7.13 (m, 4H), 7.01 (d, J = 7.2 Hz, 2H), 6.28 (s, 1H), 3.59 (s, 2H), 3.02 (d, J = 4.8 Hz, 3H), 2.85-2.78 (m, 2H), 2.50 (d, J = 12.9 Hz, 2H), 2.37-2.21 (m, 4H), 2.08-1.94 (m, 4H). |
| 55 | 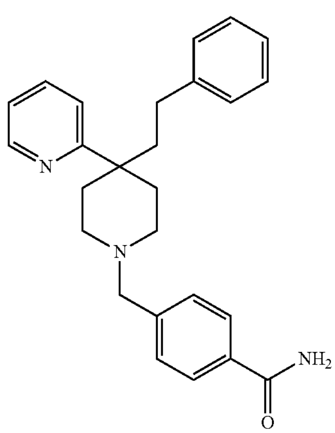 [SMILES: NC(=O)c1ccc(CN2CCC(CCc3ccccc3)(c3ccccn3)CC2)cc1] | 4-((4-phenethyl-4-(pyridin-2-yl)piperidin-1-yl)methyl)benzamide | 400 | $^1$H NMR (300 MHz, CDCl$_3$): δ 8.65 (s, 1H), 7.77 (d, J = 7.8 Hz, 2H), 7.68 (t, J = 7.4 Hz, 1H), 7.42 (d, J = 7.8 Hz, 2H), 7.33 (d, J = 8.1 Hz, 1H), 7.24-7.11 (m, 4H), 7.02 (d, J = 7.2 Hz, 2H), 6.11-5.83 (m, 2H), 3.50 (s, 2H), 2.69-2.68 (m, 2H), 2.46 (d, J = 6.0 Hz, 2H), 2.23 (d, J = 9.6 Hz, 4H), 2.00-1.91 (m, 4H). |

TABLE III-continued

| Compound. | Structure | Name | MS (ESI+): [M + H]⁺ | H-NMR |
|---|---|---|---|---|
| 56 | 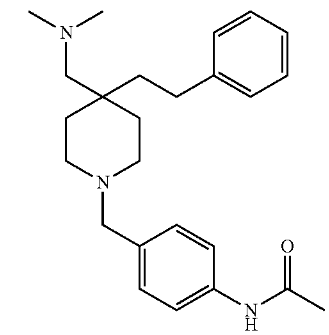 [SMILES: CC(=O)Nc1ccc(CN2CCC(CCc3ccccc3)(CN(C)C)CC2)cc1] | N-(4-((4-((dimethylamino)methyl)-4-phenethylpiperidin-1-yl)methyl)phenyl)acetamide | 394 | $^1$H NMR (300 MHz, MeOD): δ 7.54 (d, J = 8.4 Hz, 2H), 7.31-7.12 (m, 7H), 3.55 (s, 2H), 2.60-2.44 (m, 6H), 2.34 (s, 8H), 2.13 (s, 3H), 1.74-1.70 (m, 2H), 1.69-1.61 (m, 4H). |
| 57 | 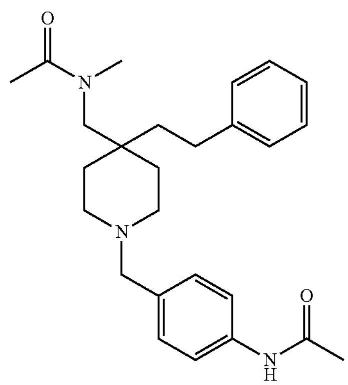 [SMILES: CC(=O)Nc1ccc(CN2CCC(CCc3ccccc3)(CN(C)C(C)=O)CC2)cc1] | N-((1-(4-acetamidobenzyl)-4-phenethylpiperidin-4-yl)methyl)-N-methylacetamide | 422 | $^1$H NMR (300 MHz, MeOD): δ 7.66 (d, J = 8.4 Hz, 2H), 7.45 (d, J = 8.4 Hz, 2H), 7.38-7.13 (m, 5H), 4.06 (s, 2H), 3.49 (s, 2H), 3.23-3.14 (m, 5H), 3.00-2.96 (m, 2H), 2.66-2.61 (m, 2H), 2.14 (s, 6H), 1.74-1.66 (m, 6H). |
| 58 | 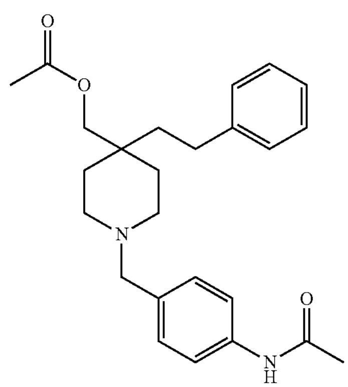 [SMILES: CC(=O)Nc1ccc(CN2CCC(CCc3ccccc3)(COC(C)=O)CC2)cc1] | (1-(4-acetamidobenzyl)-4-phenethylpiperidin-4-yl)methyl acetate | 409 | $^1$H NMR (300 MHz, CDCl$_3$): δ 7.46 (d, J = 8.1 Hz, 2H), 7.35-7.17 (m, 7H), 4.09 (s, 2H), 3.51 (s, 2H), 2.58-2.44 (m, 6H), 2.19 (s, 3H), 2.10 (s, 3H), 1.72-1.59 (m, 6H). |
| 59 | 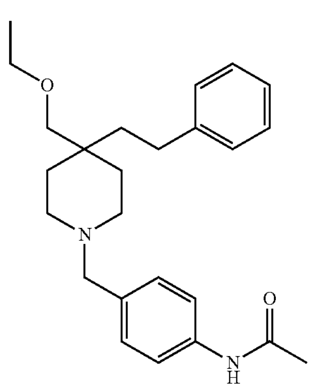 [SMILES: CCOCC1(CCc2ccccc2)CCN(Cc2ccc(NC(C)=O)cc2)CC1] | N-(4-((4-(ethoxymethyl)-4-phenethylpiperidin-1-yl)methyl)phenyl)acetamide | 395 | $^1$H NMR (300 MHz, CDCl$_3$): δ 7.54 (d, J = 7.5 Hz, 2H), 7.40 (d, J = 7.2 Hz, 2H), 7.32-7.28 (m, 2H), 7.19 (d, J = 7.2 Hz, 3H), 3.68 (s, 2H), 3.51-3.45 (m, 4H), 3.32 (s, 2H), 2.66-2.52 (m, 4H), 2.21 (s, 3H), 1.73-1.61 (m, 6H), 1.21 (t, J = 7.1 Hz, 3H). |

TABLE III-continued

| Compound. | Structure | Name | MS (ESI+): [M + H]+ | H-NMR |
|---|---|---|---|---|
| 60 | 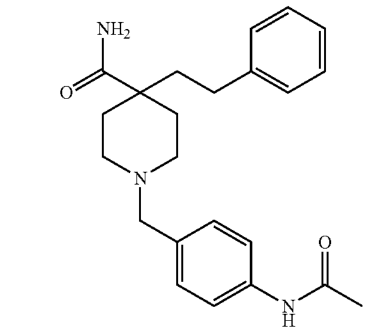 [SMILES: CC(=O)Nc1ccc(CN2CCC(CCc3ccccc3)(C(N)=O)CC2)cc1] | 1-(4-acetamidobenzyl)-4-phenethylpiperidine-4-carboxamide | 380 | $^1$H NMR (300 MHz, MeOD): δ 7.58 (d, J = 8.4 Hz, 2H), 7.34 (d, J = 8.4 Hz, 2H), 7.31-7.23 (m, 2H), 7.17-7.14 (m, 3H), 3.78 (s, 2H), 3.18-2.96 (m, 2H), 2.60-2.51 (m, 4H), 2.28-2.24 (m, 2H), 2.13 (s, 3H), 1.83-1.77 (m, 2H), 1.71-1.63 (m, 2H). |
| 61 | 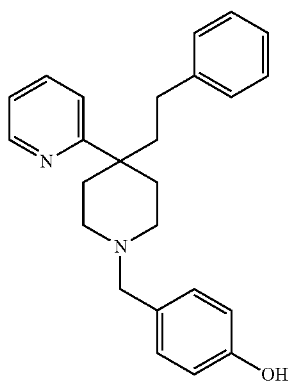 [SMILES: Oc1ccc(CN2CCC(CCc3ccccc3)(c3ccccn3)CC2)cc1] | 4-((4-phenethyl-4-(pyridin-2-yl)piperidin-1-yl)methyl)phenol | 373 | $^1$H NMR (300 MHz, MeOD): δ 8.63 (d, J = 4.8 Hz, 1H), 7.87 (t, J = 7.1 Hz, 1H), 7.57 (d, J = 7.8 Hz, 1H), 7.34-7.10 (m, 6H), 6.98 (d, J = 6.9 Hz, 2H), 6.83 (d, J = 8.4 Hz, 2H), 3.99 (s, 2H), 3.32-3.24 (m, 2H), 2.82-2.68 (m, 4H), 2.25-2.20 (m, 2H), 2.05-1.97 (m, 4H). |
| 62 | 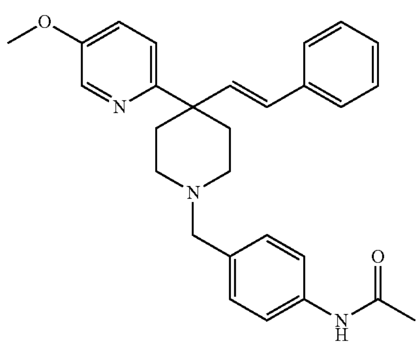 [SMILES: COc1ccc(C2(/C=C/c3ccccc3)CCN(Cc3ccc(NC(C)=O)cc3)CC2)nc1] | (E)-N-(4-((4-(5-methoxypyridin-2-yl)-4-styrylpiperidin-1-yl)methyl)phenyl)acetamide | 442 | $^1$H NMR (300 MHz, MeOD): δ 8.24 (d, J = 1.6 Hz, 1H), 7.58 (d, J = 8.4 Hz, 2H), 7.51-7.16 (m, 9H), 6.37-6.25 (m, 2H), 3.87 (s, 3H), 3.75 (s, 2H), 2.96-2.90 (m, 2H), 2.85-2.65 (m, 2H), 2.60-2.48 (m, 2H), 2.25-2.18 (m, 2H), 2.13 (s, 3H). |
| 63 | 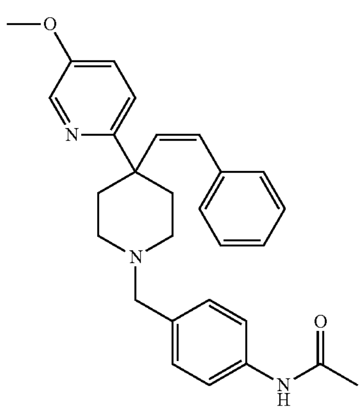 [SMILES: COc1ccc(C2(/C=C\c3ccccc3)CCN(Cc3ccc(NC(C)=O)cc3)CC2)nc1] | (Z)-N-(4-((4-(5-methoxypyridin-2-yl)-4-styrylpiperidin-1-yl)methyl)phenyl)acetamide | 442 | $^1$H NMR (300 MHz, MeOD): δ 8.14 (s, 1H), 7.59 (d, J = 8.4 Hz, 2H), 7.34 (d, J = 8.4 Hz, 2H), 7.29-7.15 (m, 2H), 7.11-7.09 (m, 3H), 6.78-6.77 (m, 2H), 6.69 (d, J = 12.5 Hz, 1H), 5.94 (d, J = 12.5 Hz, 1H), 3.85 (s, 3H), 3.82 (s, 2H), 2.90-2.75 (m, 4H), 2.24-2.15 (m, 2H), 2.14 (s, 3H), 2.10-2.02 (m, 2H). |

TABLE III-continued

| Compound. | Structure | Name | MS (ESI+): [M + H]+ | H-NMR |
|---|---|---|---|---|
| 64 | 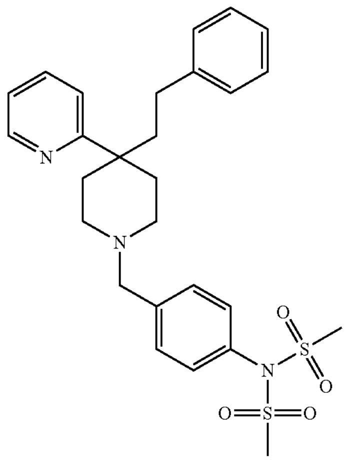 [SMILES: CS(=O)(=O)N(c1ccc(CN2CCC(CCc3ccccc3)(c3ccccn3)CC2)cc1)S(C)(=O)=O] | N-(methylsulfonyl)-N-(4-((4-phenethyl-4-(pyridin-2-yl)piperidin-1-yl)methyl)phenyl)methanesulfonamide | 528 | $^1$H NMR (300 MHz, MeOD): δ 8.60 (d, J = 4.2 Hz, 1H), 7.85-7.81 (t, 1H), 7.54-7.42 (m, 5H), 7.30-7.26 (m, 1H), 7.20-7.06 (m, 3H), 6.97 (d, J = 7.2 Hz, 2H), 3.70 (s, 2H), 3.44 (s, 6H), 2.97-2.87 (m, 2H), 2.56-2.42 (m, 4H), 2.23-2.17 (m, 2H), 1.98-1.93 (m, 4H). |
| 65 | 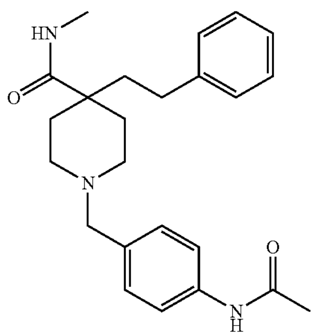 [SMILES: CNC(=O)C1(CCc2ccccc2)CCN(Cc2ccc(NC(C)=O)cc2)CC1] | 1-(4-acetamidobenzyl)-N-methyl-4-phenethylpiperidine-4-carboxamide | 394 | $^1$H NMR (300 MHz, MeOD): δ 7.63 (d, J = 8.4 Hz, 2H), 7.40 (d, J = 8.4 Hz, 2H), 7.27-7.22 (m, 2H), 7.17-7.12 (m, 3H), 3.98 (s, 2H), 3.23-3.13 (m, 2H), 2.79 (s, 3H), 2.74-2.70 (m, 2H), 2.51-2.45 (m, 2H), 2.34-2.29 (m, 2H), 2.14 (s, 3H), 1.83-1.72 (m, 4H). |
| 66 | 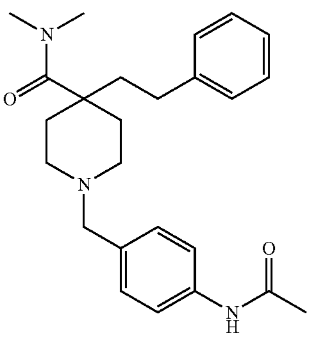 [SMILES: CC(=O)Nc1ccc(CN2CCC(CCc3ccccc3)(C(=O)N(C)C)CC2)cc1] | 1-(4-acetamidobenzyl)-N,N-dimethyl-4-phenethylpiperidine-4-carboxamide | 408 | $^1$H NMR (300 MHz, MeOD): δ 7.61 (d, J = 8.4 Hz, 2H), 7.38 (d, J = 8.4 Hz, 2H), 7.29-7.24 (m, 2H), 7.18-7.15 (m, 3H), 3.89 (s, 2H), 3.15-3.02 (m, 8H), 2.77-2.69 (m, 2H), 2.52-2.46 (m, 4H), 2.14 (s, 3H), 2.01-1.98 (m, 2H), 1.77-1.70 (m, 2H). |
| 67 | 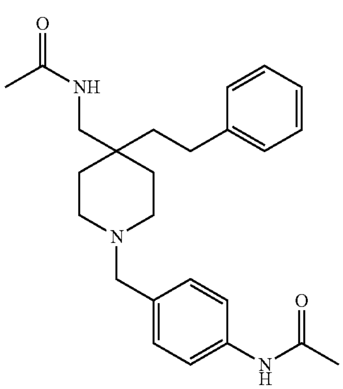 [SMILES: CC(=O)NCC1(CCc2ccccc2)CCN(Cc2ccc(NC(C)=O)cc2)CC1] | N-((1-(4-acetamidobenzyl)-4-phenethylpiperidin-4-yl)methyl)acetamide | 408 | $^1$H NMR (300 MHz, MeOD): δ 7.56 (d, J = 8.4 Hz, 2H), 7.32 (d, J = 8.4 Hz, 2H), 7.27-7.11 (m, 5H), 3.65 (s, 2H), 3.32 (s, 2H), 2.71-2.55 (m, 6H), 2.13 (s, 3H), 1.99 (s, 3H), 1.60-1.54 (m, 6H). |

TABLE III-continued

| Compound. | Structure | Name | MS (ESI+): [M + H]+ | H-NMR |
|---|---|---|---|---|
| 68 | 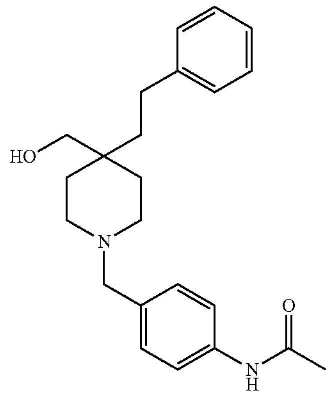 [SMILES: CC(=O)Nc1ccc(CN2CCC(CO)(CCc3ccccc3)CC2)cc1] | N-(4-((4-(hydroxymethyl)-4-phenethylpiperidin-1-yl)methyl)phenyl)acetamide | 367 | $^1$H NMR (300 MHz, MeOD) δ 7.62 (d, J = 8.4 Hz, 2H), 7.39 (d, J = 8.4 Hz, 2H), 7.35-7.28 (m, 2H), 7.20 (m, 3H), 3.65 (s, 2H), 3.57 (s, 2H), 2.64-2.42 (m, 6H), 2.21 (s, 3H), 1.80-1.51 (m, 6H). |
| 69 | 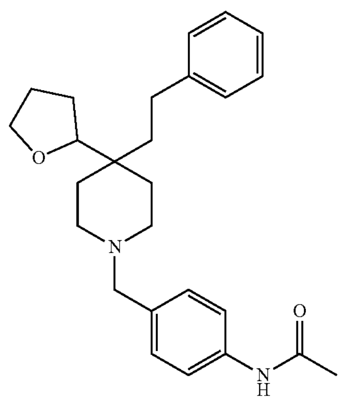 [SMILES: CC(=O)Nc1ccc(CN2CCC(CCc3ccccc3)(C3CCCO3)CC2)cc1] | N-(4-((4-phenethyl-4-(tetrahydrofuran-2-yl)piperidin-1-yl)methyl)phenyl)acetamide | 407 | $^1$H NMR (300 MHz, MeOD): δ 7.55 (d, J = 8.4 Hz, 2H), 7.32-7.25 (m, 4H), 7.23-7.14 (m, 3H), 3.90-3.72 (m, 3H), 3.6 (s, 2H), 2.79-2.74 (m, 2H), 2.60-2.38 (m, 4H), 2.13 (s, 3H), 1.90-1.72 (m, 7H), 1.60-1.54 (m, 3H). |
| 70 | 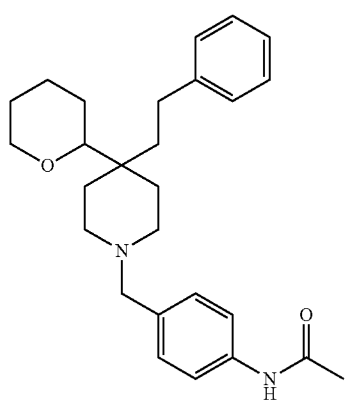 [SMILES: CC(=O)Nc1ccc(CN2CCC(CCc3ccccc3)(C3CCCCO3)CC2)cc1] | N-(4-((4-phenethyl-4-(tetrahydro-2H-pyran-2-yl)piperidin-1-yl)methyl)phenyl)acetamide | 421 | $^1$H NMR (300 MHz, MeOD): δ 7.54 (d, J = 8.4 Hz, 2H), 7.31-7.25 (m, 4H), 7.23-7.14 (m, 3H), 4.00 (d, J = 7.5 Hz, 1H), 3.56 (s, 2H), 3.40-3.32 (m, 1H), 3.23 (d, J = 10.5 Hz, 1H), 2.70-2.65 (m, 3H), 2.49-2.36 (m, 3H), 2.13 (s, 3H), 1.93-1.72 (m, 4H), 1.66-1.52 (m, 8H). |
| 71 | 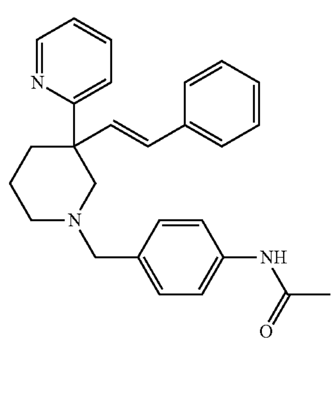 [SMILES: CC(=O)Nc1ccc(CN2CCCC(/C=C/c3ccccc3)(c3ccccn3)C2)cc1] | (E)-N-(4-((3-(pyridin-2-yl)-3-styrylpiperidin-1-yl)methyl)phenyl)acetamide | | |

TABLE III-continued

| Compound. | Structure | Name | MS (ESI+): [M + H]+ | H-NMR |
|---|---|---|---|---|
| 72 | 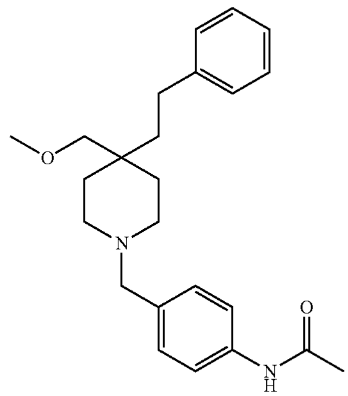 [SMILES: COCC1(CCc2ccccc2)CCN(Cc2ccc(NC(C)=O)cc2)CC1] | N-(4-((4-(methoxymethyl)-4-phenethylpiperidin-1-yl)methyl)phenyl)acetamide | 381 | $^1$H NMR (300 MHz, CDCl$_3$): δ 7.51 (d, J = 7.8 Hz, 2H), 7.36-7.27 (m, 4H), 7.20 (d, J = 6.6 Hz, 3H), 3.59 (s, 2H), 3.36 (s, 3H), 3.28 (s, 2H), 2.57-2.25 (m, 6H), 2.20 (s, 3H), 1.72-1.66 (m, 6H). |
| 73 | 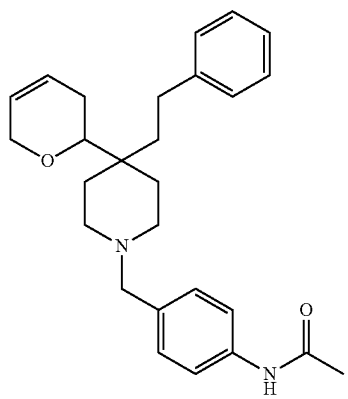 [SMILES: CC(=O)Nc1ccc(CN2CCC(CCc3ccccc3)(C3CC=CCO3)CC2)cc1] | N-(4-((4-(3,6-dihydro-2H-pyran-2-yl)-4-phenethylpiperidin-1-yl)methyl)phenyl)acetamide | 419 | $^1$H NMR (300 MHz, MeOD): δ 7.54 (d, J = 8.4 Hz, 2H), 7.31-7.23 (m, 4H), 7.19-7.12 (m, 3H), 5.92-5.82 (m, 1H), 5.74-5.73 (m, 1H), 4.27-4.07 (m, 2H), 3.56-3.49 (m, 3H), 2.72-2.68 (m, 3H), 2.67-2.45 (m, 3H), 2.31-2.19 (m, 1H), 2.13 (s, 3H), 1.99-1.80 (m, 4H), 1.67-1.54 (m, 3H). |
| 74 | 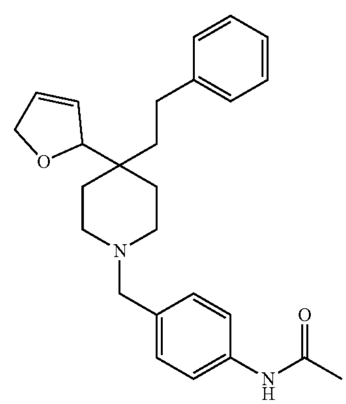 [SMILES: CC(=O)Nc1ccc(CN2CCC(CCc3ccccc3)(C3C=CCO3)CC2)cc1] | N-(4-((4-(2,5-dihydrofuran-2-yl)-4-phenethylpiperidin-1-yl)methyl)phenyl)acetamide | 405 | $^1$H NMR (300 MHz, MeOD): δ 7.45 (d, J = 8.4 Hz, 2H), 7.31-7.28 (m, 3H), 7.21-7.17 (m, 4H), 6.01-5.99 (m, 1H), 5.90-5.88 (m, 1H), 4.85 (s, 1H), 4.67-4.65 (m, 2H), 3.59 (s, 2H), 2.77-2.56 (m, 4H), 2.31-2.24 (m, 2H), 2.19 (s, 3H), 1.76-1.46 (m, 6H). |
| 75 | 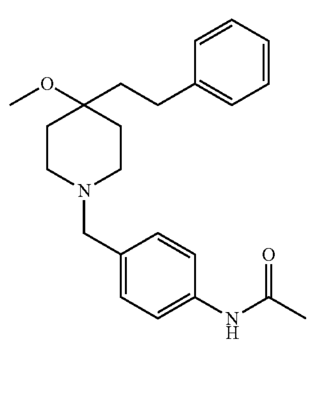 [SMILES: COC1(CCc2ccccc2)CCN(Cc2ccc(NC(C)=O)cc2)CC1] | N-(4-((4-methoxy-4-phenethylpiperidin-1-yl)methyl)phenyl)acetamide | 367 | $^1$H NMR (300 MHz, MeOD): δ 7.71 (d, J = 8.4 Hz, 2H), 7.48 (d, J = 8.4 Hz, 2H), 7.30-7.15 (m, 5H), 4.30 (s, 2H), 3.55-3.17 (m, 7H), 2.71-2.60 (m, 2H), 2.19-1.16 (m, 5H), 1.85-1.68 (m, 4H). |

TABLE III-continued

| Compound. | Structure | Name | MS (ESI+): [M + H]+ | H-NMR |
|---|---|---|---|---|
| 76 | 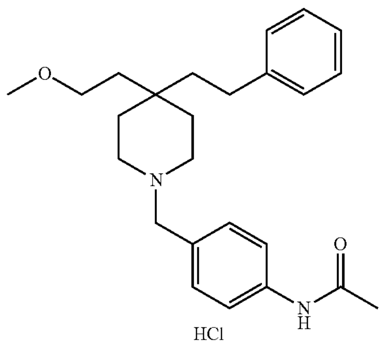 [SMILES: COCCC1(CCc2ccccc2)CCN(Cc2ccc(NC(C)=O)cc2)CC1 ; Cl] | N-(4-((4-(2-methoxyethyl)-4-phenethylpiperidin-1-yl)methyl)phenyl)acetamide HCl | 395 | ¹H NMR (300 MHz, MeOD): δ 7.70 (d, J = 7.2 Hz, 2H), 7.49-7.45 (m, 2H), 7.29-7.24 (m, 3H), 7.20-7.17 (m, 2H), 4.30 (s, 2H), 3.55-3.51 (m, 2H), 3.35-3.17 (m, 7H), 2.76-2.55 (m, 2H), 2.16 (s, 3H), 1.96-1.60 (m, 8H). |
| 77 | 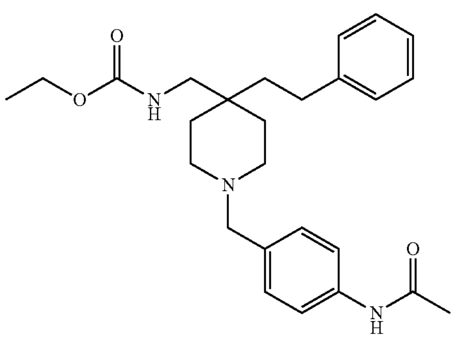 [SMILES: CCOC(=O)NCC1(CCc2ccccc2)CCN(Cc2ccc(NC(C)=O)cc2)CC1] | ethyl (1-(4-acetamidobenzyl)-4-phenethylpiperidin-4-yl)methylcarbamate | 438 | ¹H NMR (300 MHz, MeOD): δ 7.56 (d, J = 8.4 Hz, 2H), 7.33 (d, J = 8.4 Hz, 2H), 7.27-7.12 (m, 5H), 4.09 (q, J = 7.2 Hz, 2H), 3.66 (s, 2H), 3.18 (s, 2H), 2.72-2.54 (m, 6H), 2.18 (s, 3H), 1.59-1.55 (m, 6H), 1.25 (t, J = 7.2 Hz, 3H). |
| 78 | 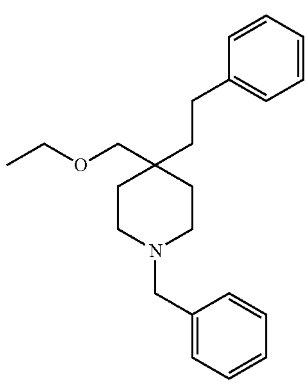 [SMILES: CCOCC1(CCc2ccccc2)CCN(Cc2ccccc2)CC1] | 1-benzyl-4-(ethoxymethyl)-4-phenethylpiperidine | 338 | ¹H NMR (300 MHz, MeOD): δ 7.49-7.46 (m, 5H), 7.36-7.16 (m, 5H), 4.12 (s, 2H), 3.51 (q, J = 7.2 Hz, 2H), 3.06 (s, 4H), 2.61-2.55 (m, 2H), 1.84-1.69 (m, 6H), 1.35-1.30 (m, 2H). 1.21 (t, J = 7.2 Hz, 3H). |
| 79 | 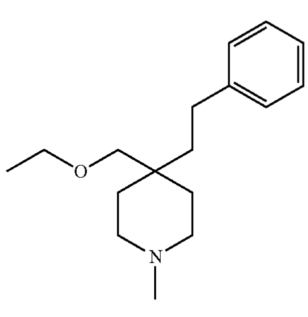 [SMILES: CCOCC1(CCc2ccccc2)CCN(C)CC1] | 4-(ethoxymethyl)-1-methyl-4-phenethylpiperidine | 262 | ¹H NMR (300 MHz, CDCl₃): δ 7.32-7.18 (m, 5H), 3.53-3.46 (m, 2H), 3.37 (s, 2H), 2.94-2.89 (m, 4H), 2.60-2.54 (m, 5H), 1.88-1.86 (m, 4H), 1.75-1.72 (m, 2H), 1.22 (t, J = 7.1 Hz, 3H). |

TABLE III-continued

| Compound. | Structure | Name | MS (ESI+): [M + H]+ | H-NMR |
|---|---|---|---|---|
| 80 | 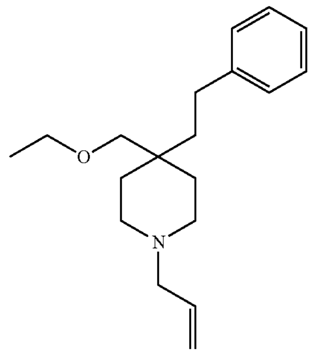 [SMILES: C=CCN1CCC(CCc2ccccc2)(COCC)CC1] | 1-allyl-4-(ethoxymethyl)-4-phenethylpiperidine | 288 | ¹H NMR (300 MHz, CDCl₃): δ 7.32-7.19 (m, 5H), 6.07-5.94 (m, 1H), 5.31-5.25 (m, 2H), 3.50 (q, J = 6.9 Hz, 2H), 3.31 (s, 2H), 3.19 (d, J = 6.6 Hz, 2H), 2.67-2.47 (m, 6H), 1.74-1.68 (m, 6H), 1.22 (t, J = 7.1 Hz, 3H). |
| 81 | 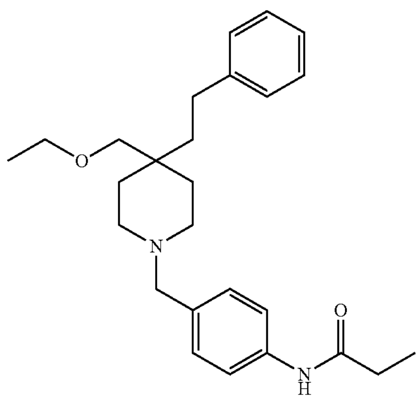 [SMILES: CCOCC1(CCc2ccccc2)CCN(Cc2ccc(NC(=O)CC)cc2)CC1] | N-(4-((4-(ethoxymethyl)-4-phenethylpiperidin-1-yl)methyl)phenyl)propionamide | 409 | ¹H NMR (300 MHz, MeOD): δ 7.70 (d, J = 7.8 Hz, 2H), 7.48 (d, J = 7.8 Hz, 2H), 7.26-7.16 (m, 5H), 4.23 (s, 2H), 3.53-3.50 (m, 2H), 3.41 (s, 2H), 3.33-3.04 (m, 4H), 2.58-2.55 (m, 2H), 2.46-2.39 (m, 2H), 1.87-1.73 (m, 6H), 1.27-1.20 (m, 6H). |
| 82 | 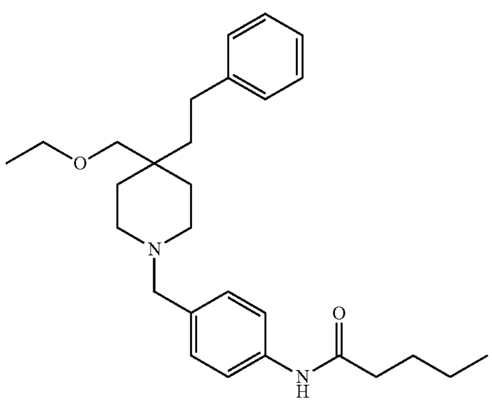 [SMILES: CCCCC(=O)Nc1ccc(CN2CCC(CCc3ccccc3)(COCC)CC2)cc1] | N-(4-((4-(ethoxymethyl)-4-phenethylpiperidin-1-yl)methyl)phenyl)pentanamide | 437 | ¹H NMR (300 MHz, MeOD): δ 7.65 (d, J = 8.4 Hz, 2H), 7.41 (d, J = 8.1 Hz, 2H), 7.25-7.15 (m, 5H), 4.00 (s, 2H), 3.49 (q, J = 6.9 Hz, 2H), 3.38 (s, 2H), 3.08-2.98 (m, 4H), 2.59-2.53 (m, 2H), 2.42-2.37 (m, 2H), 1.80-1.76 (m, 2H), 1.71-1.64 (m, 6H), 1.46-1.38 (m, 2H), 1.20 (t, J = 6.9 Hz, 3H), 0.97 (t, J = 7.5 Hz, 3H). |
| 83 | 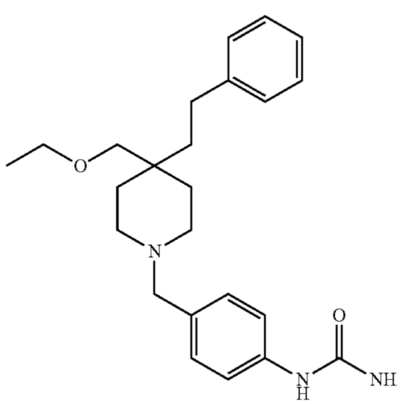 [SMILES: CCOCC1(CCc2ccccc2)CCN(Cc2ccc(NC(N)=O)cc2)CC1] | 1-(4-((4-(ethoxymethyl)-4-phenethylpiperidin-1-yl)methyl)phenyl)urea | 396 | ¹H NMR (300 MHz, MeOD): δ 7.38 (d, J = 8.4 Hz, 2H), 7.28-7.22 (m, 4H), 7.17-7.11 (m, 3H), 3.61 (s, 2H), 3.49 (q, J = 6.9 Hz, 2H), 3.33 (s, 2H), 2.59-2.51 (m, 6H), 1.71-1.52 (m, 6H), 1.20 (t, J = 6.9 Hz, 3H). |

TABLE III-continued

| Compound. | Structure | Name | MS (ESI+): [M + H]+ | H-NMR |
|---|---|---|---|---|
| 84 | 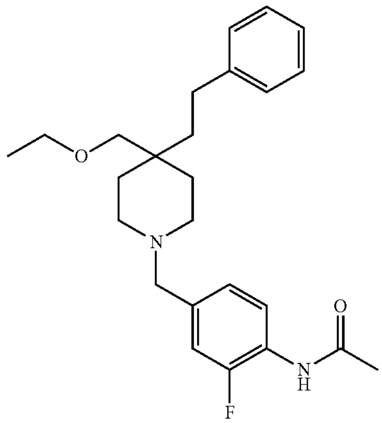 [SMILES: CCOCC1(CCc2ccccc2)CCN(Cc2ccc(NC(C)=O)c(F)c2)CC1] | N-(4-((4-(ethoxymethyl)-4-phenethylpiperidin-1-yl)methyl)-2-fluorophenyl)acetamide | 413 | $^1$H NMR (300 MHz, MeOD): δ 8.07 (t, J = 8.3 Hz, 1H), 7.37-7.14 (m, 7H), 4.19 (s, 2H), 3.53 (q, J = 6.9 Hz, 2H), 3.47 (s, 2H), 3.21-3.06 (m, 4H), 2.62-2.56 (m, 2H), 2.20 (s, 3H), 1.93-1.86 (m, 2H), 1.76-1.71 (m, 4H), 1.21 (t, J = 6.9 Hz, 3H). |
| 85 | 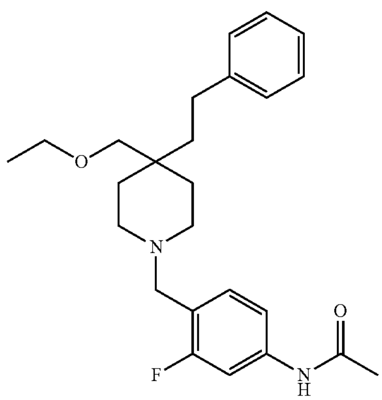 [SMILES: CCOCC1(CCc2ccccc2)CCN(Cc2ccc(NC(C)=O)cc2F)CC1] | N-(4-((4-(ethoxymethyl)-4-phenethylpiperidin-1-yl)methyl)-3-fluorophenyl)acetamide | 413 | $^1$H NMR (300 MHz, CDCl$_3$): δ 7.60-7.32 (m, 4H), 7.19 (d, J = 6.00 Hz, 3H), 7.08 (d, J = 7.80 Hz, 1H), 3.65 (brs, 2H), 3.52-3.45 (m, 2H), 3.35 (s, 2H), 2.56-2.52 (m, 4H), 2.21 (s, 3H), 1.72-1.66 (m, 8H), 1.21 (t, J = 6.9 Hz, 3H). |
| 86 | 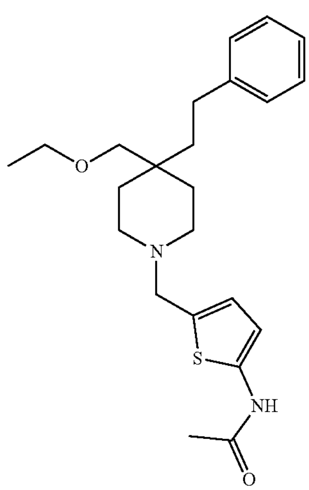 | N-(5-((4-(ethoxymethyl)-4-phenethylpiperidin-1-yl)methyl)thiophen-2-yl)acetamide HCl | 401 | $^1$H NMR (300 MHz, MeOD): δ 7.28-7.11 (m, 6H), 6.75-6.73 (m, 1H), 4.50-4.48 (m, 2H), 3.55-3.42 (m, 3H), 3.36-3.31 (m, 8H), 2.62-2.57 (m, 2H), 2.17-1.65 (m, 6H), 1.24-1.17 (m, 3H). |

TABLE III-continued

| Compound. | Structure | Name | MS (ESI+): [M + H]⁺ | H-NMR |
|---|---|---|---|---|
| 87 | 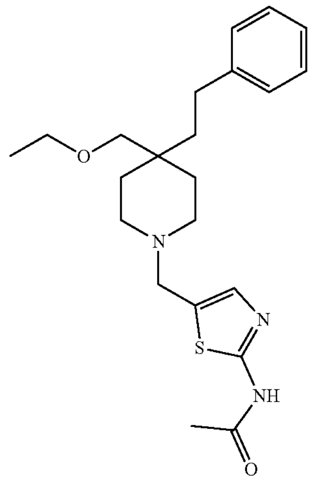 [SMILES: CCOCC1(CCc2ccccc2)CCN(Cc2cnc(NC(C)=O)s2)CC1] | N-(5-((4-(ethoxymethyl)-4-phenethylpiperidin-1-yl)methyl)thiazol-2-yl)acetamide | 402 | ¹H NMR (300 MHz, MeOD): δ 7.66-7.65 (d, J = 2.1 Hz, 1H), 7.28-7.26 (m, 3H), 7.18-7.16 (m, 2H), 3.55-3.40 (m, 6H), 3.24-3.19 (m, 2H), 2.62-2.57 (m, 2H), 2.52 (s, 3H), 2.06-1.63 (m, 8H), 1.32-1.17 (m, 3H). |
| 88 | 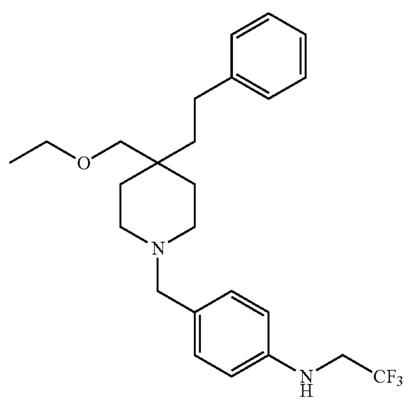 [SMILES: CCOCC1(CCc2ccccc2)CCN(Cc2ccc(NCC(F)(F)F)cc2)CC1] | 4-((4-(ethoxymethyl)-4-phenethylpiperidin-1-yl)methyl)-N-(2,2,2-trifluoroethyl)aniline | 435 | ¹H NMR (300 MHz, MeOD): δ 7.28-7.15 (m, 7H), 6.76 (d, J = 8.4 Hz, 2H), 3.89-3.80 (m, 4H), 3.54-3.47 (q, 2H), 3.37 (s, 2H), 3.02-2.91 (m, 4H), 2.59-2.53 (m, 2H), 1.82-1.64 (m, 6H), 1.20 (t, J = 6.9 Hz, 3H). |
| 89 | 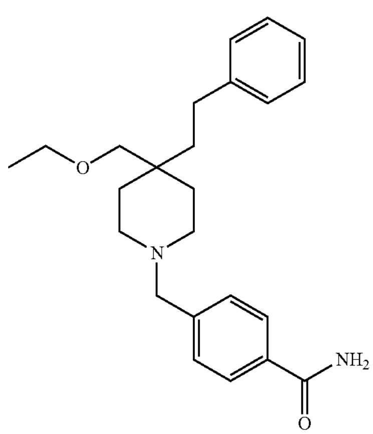 [SMILES: CCOCC1(CCc2ccccc2)CCN(Cc2ccc(C(N)=O)cc2)CC1] | 4-((4-(ethoxymethyl)-4-phenethylpiperidin-1-yl)methyl)benzamide | 381 | ¹H NMR (300 MHz, CDCl₃): δ 7.78 (d, J = 8.1 Hz, 2H), 7.44 (d, J = 7.8 Hz, 2H), 7.32-7.28 (m, 2H), 7.21-7.16 (m, 3H), 3.60 (s, 2H), 3.51 (q, J = 14.1, 7.2 Hz, 2H), 2.59-2.46 (m, 6H), 1.74-1.53 (m, 8H), 1.18 (t, J = 7.0 Hz, 3H). |

TABLE III-continued

| Compound. | Structure | Name | MS (ESI+): [M + H]+ | H-NMR |
|---|---|---|---|---|
| 90 | 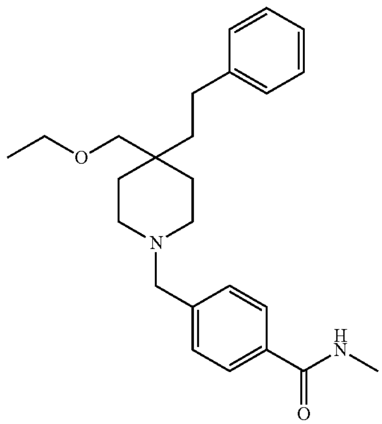 [SMILES: CCOCC1(CCc2ccccc2)CCN(Cc2ccc(C(=O)NC)cc2)CC1] | 4-((4-(ethoxymethyl)-4-phenethylpiperidin-1-yl)methyl)-N-methylbenzamide | 395 | ¹H NMR (300 MHz, CDCl₃): δ 7.75 (d, J = 7.8 Hz, 2H), 7.48 (d, J = 7.8 Hz, 2H), 7.32-7.27 (m, 2H), 7.20-7.18 (m, 3H), 6.26 (brs, 1H), 3.70 (s, 2H), 3.52-3.45 (q, J = 13.8 Hz, 2H), 3.32 (s, 2H), 3.03 (d, J = 4.8 Hz, 3H), 2.79-2.52 (m, 6H), 1.73-1.67 (m, 6H), 1.21 (t, J = 6.9 Hz, 3H). |
| 91 | 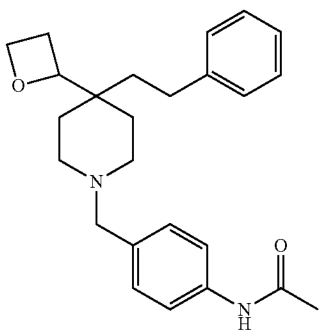 [SMILES: CC(=O)Nc1ccc(CN2CCC(CCc3ccccc3)(C3CCO3)CC2)cc1] | N-(4-((4-(oxetan-2-yl)-4-phenethylpiperidin-1-yl)methyl)phenyl)acetamide | 393 | ¹H NMR (300 MHz, MeOD): δ 7.55 (d, J = 8.7 Hz, 2H), 7.33-7.26 (m, 4H), 7.23-7.15 (m, 3H), 4.93-4.91 (m, 1H), 4.67-4.65 (m, 1H), 4.39-4.36 (m, 1H), 3.61 (s, 2H), 2.83-2.78 (m, 2H), 2.67-2.37 (m, 6H), 2.13 (s, 3H), 1.83-1.76 (m, 3H), 1.60-1.52 (m, 3H). |
| 92 | 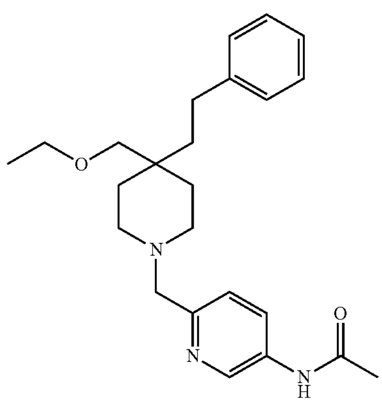 | N-(6-((4-(ethoxymethyl)-4-phenethylpiperidin-1-yl)methyl)pyridin-3-yl)acetamide | 396 | ¹H NMR (300 MHz, CDCl₃): δ 8.54 (d, J = 2.1 Hz, 1H), 8.11 (d, J = 8.4 Hz, 1H), 7.55-752 (m, 1H), 7.44 (d, J = 8.4 Hz, 1H), 7.32-7.26 (m, 2H), 7.19 (d, J = 7.2 Hz, 2H), 3.70 (s, 2H), 3.52-3.45 (m, 2H), 3.31 (s, 2H), 2.58-2.52 (m, 4H), 2.27 (s, 3H), 1.98-1.60 (m, 8H), 1.21 (t, J = 6.9 Hz, 1H). |
| 93 | 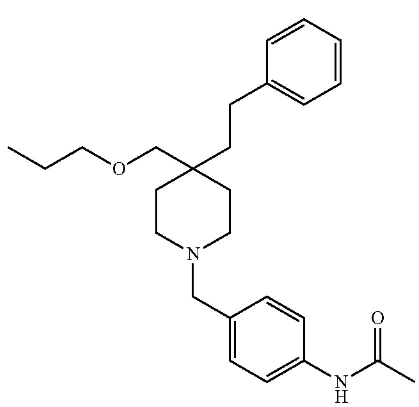 [SMILES: CCCOCC1(CCc2ccccc2)CCN(Cc2ccc(NC(C)=O)cc2)CC1] | N-(4-((4-phenethyl-4-(propoxymethyl)piperidin-1-yl)methyl)phenyl)acetamide | 409 | ¹H NMR (300 MHz, CDCl₃): δ 7.48 (d, J = 8.1 Hz, 2H), 7.35-7.27 (m, 4H), 7.19 (d, J = 6.6 Hz, 3H), 3.56 (s, 2H), 3.38 (q, J = 6.9 Hz, 2H), 3.30 (s, 2H), 2.58-2.52 (m, 4H), 2.20 (s, 3H), 1.71-1.55 (m, 10H), 0.96 (t, J = 7.1 Hz, 3H). |

TABLE III-continued

| Compound. | Structure | Name | MS (ESI+): [M + H]+ | H-NMR |
|---|---|---|---|---|
| 94 | 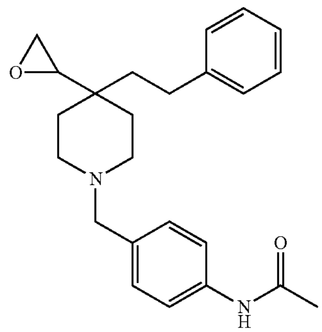 [SMILES: CC(=O)Nc1ccc(CN2CCC(CCc3ccccc3)(C3CO3)CC2)cc1] | N-(4-((4-(oxiran-2-yl)-4-phenethylpiperidin-1-yl)methyl)phenyl)acetamide | 379 | ¹H NMR (300 MHz, MeOD): δ 7.58 (d, J = 8.7 Hz, 2H), 7.36 (d, J = 8.4 Hz, 2H), 7.21-7.09 (m, 5H), 3.92-3.60 (m, 4H), 2.94-2.73 (m, 7H), 2.13 (s, 3H), 2.05-1.47 (m, 6H). |
| 95 | 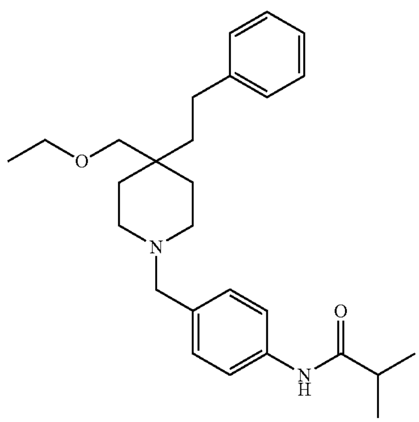 [SMILES: CCOCC1(CCc2ccccc2)CCN(Cc2ccc(NC(=O)C(C)C)cc2)CC1] | N-(4-((4-(ethoxymethyl)-4-phenethylpiperidin-1-yl)methyl)phenyl)isobutyramide | 423 | ¹H NMR (300 MHz, MeOD): δ 7.69 (d, J = 8.4 Hz, 2H), 7.46 (d, J = 8.4 Hz, 2H), 7.28-7.12 (m, 5H), 4.15 (s, 2H), 3.54-3.47 (q, J = 13.8 Hz, 2H), 3.39 (s, 2H), 3.19-3.08 (m, 4H), 2.69-2.54 (m, 3H), 1.90-1.81 (m, 2H), 1.77-1.68 (m, 4H), 1.22-1.17 (m, 9H). |
| 96 | 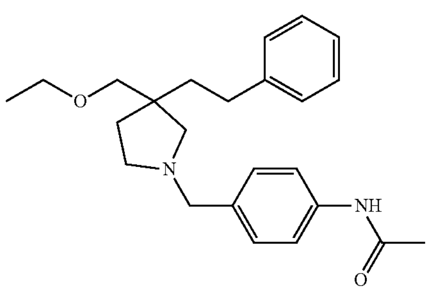 [SMILES: CCOCC1(CCc2ccccc2)CCN(Cc2ccc(NC(C)=O)cc2)C1] | N-(4-((3-(ethoxymethyl)-3-phenethylpyrrolidin-1-yl)methyl)phenyl)acetamide | 381 | ¹H NMR (300 MHz, MeOD): δ 7.52 (d, J = 8.4 Hz, 2H), 7.30 (d, J = 8.4 Hz, 2H), 7.27-7.22 (m, 2H), 7.17-7.13 (m, 3H), 3.61 (s, 2H), 3.50 (q, J = 7.0 Hz, 2H), 3.35 (s, 2H), 2.68-2.57 (m, 5H), 2.38 (d, J = 9.9 Hz, 1H), 2.13 (s, 3H), 1.78-1.68 (m, 4H), 1.20 (t, J = 6.9 Hz, 3H). |
| 97 | 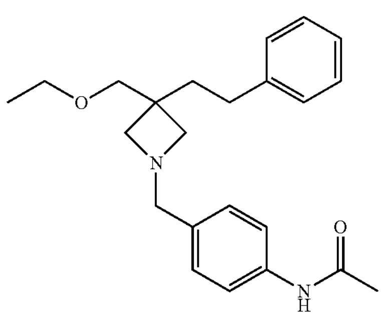 | N-(4-((3-(ethoxymethyl)-3-phenethylazetidin-1-yl)methyl)phenyl)acetamide HCl | 367 | ¹H NMR (300 MHz, MeOD): δ 7.68 (d, J = 8.4 Hz, 2H), 7.40 (d, J = 8.4 Hz, 2H), 7.39-7.21 (m, 5H), 4.31 (d, J = 22.8 Hz, 2H), 4.12-3.95 (m, 2H), 3.87 (d, J = 10.5 Hz, 2H), 3.75-3.60 (m, 2H), 3.49 (s, 2H), 2.69-2.54 (m, 2H), 2.15 (s, 3H), 2.10-1.95 (m, 2H), 1.40-1.20 (m, 3H). |

TABLE III-continued

| Compound. | Structure | Name | MS (ESI+): [M + H]+ | H-NMR |
|---|---|---|---|---|
| 98 | 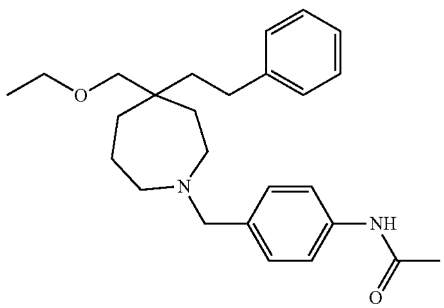 [SMILES: CCOCC1(CCc2ccccc2)CCCN(Cc2ccc(NC(C)=O)cc2)CC1] | N-(4-((4-(ethoxymethyl)-4-phenethylazepan-1-yl)methyl)phenyl)acetamide | 409 | ¹H NMR (300 MHz, MeOD): δ 7.60 (d, J = 8.4 Hz, 2H), 7.36 (d, J = 8.4 Hz, 2H), 7.26-7.13 (m, 5H), 3.83 (s, 2H), 3.50-3.43 (q, J = 13.8 Hz, 2H), 3.20 (s, 2H), 2.86-2.83 (m, 4H), 2.54-2.48 (m, 2H), 2.13 (s, 3H), 1.77-1.54 (m, 8H), 1.19 (t, J = 6.9 Hz, 3H). |
| 99 | 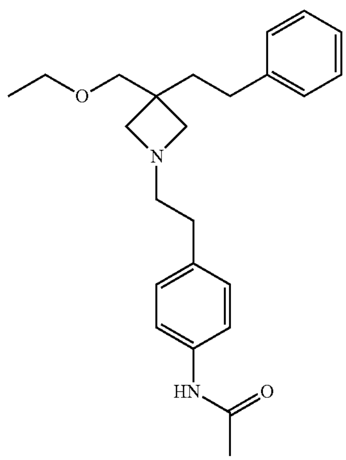 [SMILES: CCOCC1(CCc2ccccc2)CN(CCc2ccc(NC(C)=O)cc2)C1] | N-(4-(2-(3-(ethoxymethyl)-3-phenethylazetidin-1-yl)ethyl)phenyl)acetamide | 381 | ¹H NMR (300 MHz, MeOD): δ 7.73 (d, J = 8.1 Hz, 1H), 7.55 (d, J = 8.1 Hz, 2H), 7.29-7.19 (m, 6H), 4.10 (d, J = 10.8 Hz, 1H), 3.94 (s, 2H), 3.83 (d, J =10.8 Hz, 1H), 3.69-3.61 (m, 3H), 3.47-3.32 (m, 3H), 2.89-2.87 (m, 2H), 2.62-2.56 (m, 2H), 2.13 (s, 3H), 2.08-2.02 (m, 2H), 1.32-1.25 (m, 3H). |
| 100 | 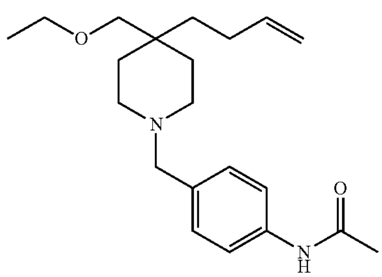 [SMILES: C=CCCC1(COCC)CCN(Cc2ccc(NC(C)=O)cc2)CC1] | N-(4-((4-(but-3-enyl)-4-(ethoxymethyl)piperidin-1-yl)methyl)phenyl)acetamide | 345 | ¹H NMR (300 MHz, CDCl₃): δ 7.45 (d, J = 8.1 Hz, 2H), 7.30 (d, J = 8.1 Hz, 1H), 7.18 (brs, 1H), 5.85-5.79 (m, 1H), 5.05-4.92 (m, 2H), 3.51 (s, 2H), 3.47 (q, J = 6.9 Hz, 2H), 3.22 (s, 2H), 2.43 (s, 4H), 2.19 (s, 3H), 2.04-1.96 (m, 2H), 1.61-1.53 (m, 6H), 1.18 (t, J = 6.9 Hz, 3H). |
| 101 | 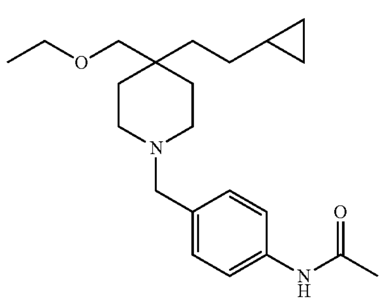 [SMILES: CCOCC1(CCC2CC2)CCN(Cc2ccc(NC(C)=O)cc2)CC1] | N-(4-((4-(2-cyclopropylethyl)-4-(ethoxymethyl)piperidin-1-yl)methyl)phenyl)acetamide | 359 | ¹H NMR (300 MHz, MeOD): δ 7.71 (d, J = 8.7 Hz, 2H), 7.47 (d, J = 8.7 Hz, 2H), 4.28 (d, J = 6.3 Hz, 2H), 3.65 (q, J = 6.9 Hz, 2H), 3.50-3.42 (m, 4H), 3.32-3.14 (m, 2H), 2.15 (s, 3H), 1.74-1.38 (m, 6H), 1.22-1.12 (m, 6H), 0.48-0.43 (m, 2H), 0.07-0.01 (m, 2H). |

TABLE III-continued

| Compound. | Structure | Name | MS (ESI+): [M + H]⁺ | H-NMR |
|---|---|---|---|---|
| 102 | 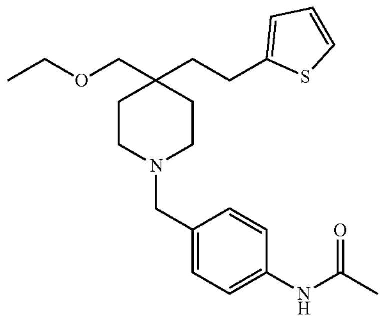 | N-(4-((4-(ethoxymethyl)-4-(2-(thiophen-2-yl)ethyl)piperidin-1-yl)methyl)phenyl)acetamide HCl | 401 | ¹H NMR (300 MHz, MeOD): δ 7.70 (d, J = 8.4 Hz, 2H), 7.45 (d, J = 8.4 Hz, 2H), 7.19-7.15 (m , 1H), 6.96-6.81 (m, 2H), 4.29 (s, 2H), 3.67-3.55 (m, 3H), 3.33-3.10 (m, 5H), 2.90-2.85 (m, 2H), 2.15 (s, 3H), 2.05-1.66 (m, 6H), 1.20 (t, J = 6.9 Hz, 3H). |
| 103 | 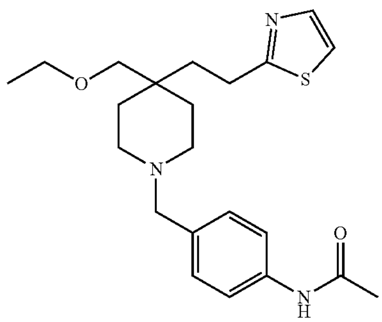 | N-(4-((4-(ethoxymethyl)-4-(2-(thiazol-2-yl)ethyl)piperidin-1-yl)methyl)phenyl)acetamide HCl | 402 | ¹H NMR (300 MHz, MeOD): δ 8.15 (dd, J = 10.5 , 3.6 Hz, 1H), 7.97 (dd, J = 6.3, 3.9 Hz, 1H), 7.71 (d, J = 8.1 Hz, 2H), 7.53 (d, J = 8.1 Hz, 2H), 4.35 (d, J = 12.6 Hz, 2H), 3.57-3.47 (m, 4H), 3.32-3.31 (m, 2H), 3.25-3.17 (m, 2H), 2.20-2.15 (m, 5H), 2.04-1.80 (m, 6H), 1.21 (t, J = 6.9 Hz, 3H). |
| 104 | 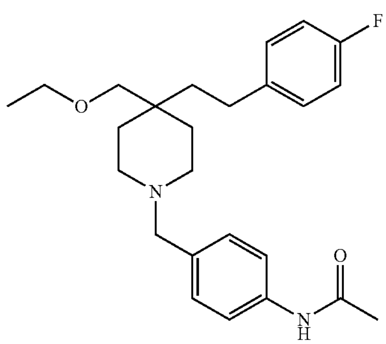 [SMILES: CCOCC1(CCc2ccc(F)cc2)CCN(Cc2ccc(NC(C)=O)cc2)CC1] | N-(4-((4-(ethoxymethyl)-4-(4-fluoro-phenethyl)piperidin-1-yl)methyl)phenyl)acetamide | 413 | 1H NMR (300 MHz, MeOD): δ 7.57 (d, J = 8.4 Hz, 2H), 7.35 (d, J = 8.4 Hz, 2H), 7.20-7.16 (m, 2H), 7.01-6.95 (m, 2H), 3.74 (s, 2H), 3.50 (q, J = 6.9 Hz, 2H), 3.32 (s, 2H), 2.76-2.68 (m, 4H), 2.58-2.52 (m, 2H), 2.14 (s, 3H), 1.71-1.61 (m, 6H), 1.20 (t, J = 6.9 Hz, 3H). |
| 105 | 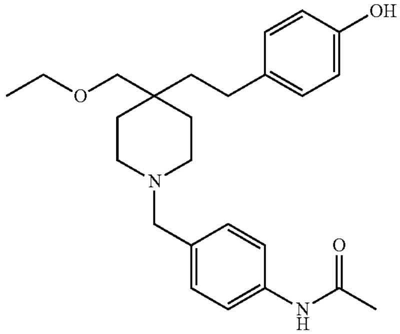 | N-(4-((4-(ethoxymethyl)-4-(4-hydroxy-phenethyl)piperidin-1-yl)methyl)phenyl)acetamide HCl | 411 | ¹H NMR (300 MHz, MeOD): δ 7.70 (d, J = 8.4 Hz, 2H), 7.45 (d, J = 8.4 Hz, 2H), 7.07 (d, J = 8.4 Hz, 1H), 6.96 (d, J = 8.4 Hz, 1H), 6.70 (t, J = 8.7 Hz, 2H), 4.28 (s, 2H), 3.54-3.46 (m, 3H), 3.36-3.32 (m, 2H), 3.33-3.10 (m, 3H), 2.52-2.46 (m, 2H), 2.16 (s, 3H), 1.97-1.61 (m, 6H), 1.20 (t, J = 6.9 Hz, 3H). |

TABLE III-continued

| Compound. | Name | MS (ESI+): [M + H]+ | H-NMR |
|---|---|---|---|
| 106 | N-(4-((4-(ethoxymethyl)-4-(4-methoxyphenethyl)piperidin-1-yl)methyl)phenyl)acetamide HCl | 425 | ¹H NMR (300 MHz, MeOD): δ 7.70 (d, J = 8.4 Hz, 2H), 7.47 (d, J = 8.4 Hz, 2H), 7.11 (d, J =8.7 Hz 2H), 6.84 (d, J = 8.7 Hz, 2H), 4.28 (s, 2H), 3.77 (s, 3H), 3.53 (q, J = 6.9 Hz, 2H), 3.33-3.10 (m, 6H), 2.56-2.50 (m, 2H), 2.15 (s, 3H), 2.16-1.66 (m, 6H), 1.20 (t, J = 6.9 Hz, 3H). |
| 107 | N-(4-((4-((difluoromethoxy)methyl)-4-phenethylpiperidin-1-yl)methyl)phenyl)acetamide | 417 | ¹H NMR (300 MHz, MeOD): δ 7.71 (d, J = 8.4 Hz, 2H), 7.48 (d, J = 8.4 Hz, 2H), 7.29-7.17 (m, 5H), 6.75-6.21 (m, 1H), 4.31 (s, 2H), 4.06 (s, 1H), 3.78 (s, 1H), 3.32 (s, 2H), 3.24-3.09 (m, 2H), 2.64-2.58 (m, 2H), 2.16 (s, 3H), 2.05-1.65 (m, 6H) |
| 108 | 5-((4-(ethoxymethyl)-4-phenethylpiperidin-1-yl)methyl)-1H-benzo[d]imidazol-2(3H)-one | 394 | ¹H NMR (300 MHz, MeOD): δ 7.27-7.18 (m, 7H), 7.02 (s, 1H), 3.59 (s, 2H), 3.50 (q, J = 7.1 Hz, 2H)), 3.47-3.30 (m, 2H), 3.12-3.10 (m, 1H), 2.59-2.52 (m, 5H), 1.75-1.52 (m, 6H), 1.20 (t, J = 7.1 Hz, 3H). |
| 109 | 5-((4-(ethoxymethyl)-4-phenethylpiperidin-1-yl)methyl)indolin-2-one | 393 | 1H NMR (300 MHz, MeOD): δ 7.39-7.14 (m, 7H), 6.99 (d, J = 7.8 Hz, 1H), 4.24 (s, 1H), 3.65-3.42 (m, 3H), 3.33-3.32 (m, 3H), 3.23-3.15 (m, 4H), 2.62-2.56 (m, 2H), 1.99-1.77 (m, 6H), 1.21 (t, J = 6.9 Hz, 3H). |

TABLE III-continued

| Compound. | Structure | Name | MS (ESI+): [M + H]+ | H-NMR |
|---|---|---|---|---|
| 110 | 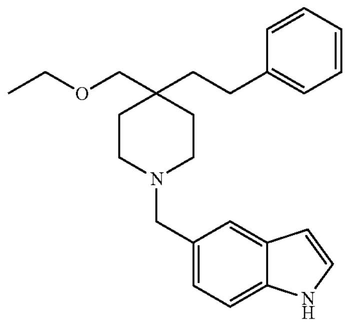 [SMILES: CCOCC1(CCc2ccccc2)CCN(Cc2ccc3[nH]ccc3c2)CC1] | 5-((4-(ethoxymethyl)-4-phenethylpiperidin-1-yl)methyl)-1H-indole | 377 | ¹H NMR (300 MHz, MeOD): δ 7.72 (s, 1H), 7.51-7.16 (m, 8H), 6.54 (s, 1H), 4.37 (d, J = 6.9 Hz, 2H), 3.52 (q, J = 6.9 Hz, 2H), 3.42 (s, 2H), 3.28-3.21 (m, 4H), 2.61-2.55 (m, 2H), 1.92-1.72 (m, 6H), 1.87 (t, J = 6.9 Hz, 3H). |
| 111 | 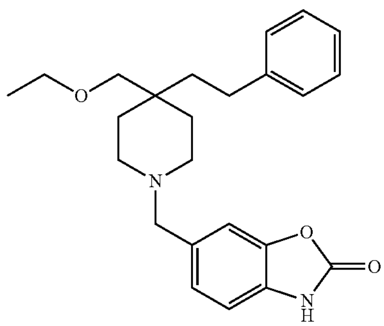 [SMILES: CCOCC1(CCc2ccccc2)CCN(Cc2ccc3[nH]c(=O)oc3c2)CC1] | 6-((4-(ethoxymethyl)-4-phenethylpiperidin-1-yl)methyl)benzo[d]oxazol-2(3H)-one | 395 | ¹H NMR (300 MHz, MeOD): δ 7.29-7.01 (m, 8H), 3.79 (s, 2H), 3.50 (q, J = 7.0 Hz, 2H), 3.34-3.33 (m, 2H), 2.81-2.71 (m, 4H), 2.55-2.52 (m, 2H), 1.71-1.58 (m, 6H), 1.21 (t, J = 7.0 Hz, 3H). |
| 112 | 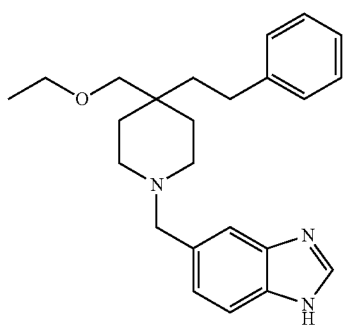 [SMILES: CCOCC1(CCc2ccccc2)CCN(Cc2ccc3[nH]cnc3c2)CC1] | 5-((4-(ethoxymethyl)-4-phenethylpiperidin-1-yl)methyl)-1H-benzo[d]imidazole | 378 | ¹H NMR (300 MHz, MeOD): δ 8.36 (s, 1H), 7.89 (s, 1H), 7.75 (d, J = 8.1 Hz, 1H), 7.48 (d, J = 8.1 Hz, 1H), 7.26-7.16 (m, 5H), 4.49 (s, 2H), 3.66-3.48 (m, 4H), 3.33-3.32 (m, 4H), 2.62-2.56 (m, 2H), 2.05-1.62 (m, 6H), 1.18 (t, J = 6.9 Hz, 3H). |
| 113 | 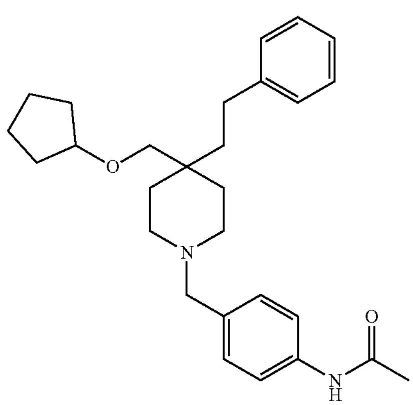 [SMILES: CC(=O)Nc1ccc(CN2CCC(CCc3ccccc3)(COC3CCCC3)CC2)cc1] | N-(4-((4-(cyclopentyloxymethyl)-4-phenethylpiperidin-1-yl)methyl)phenyl)acetamide | 435 | ¹H NMR (300 MHz, CDCl₃): δ 7.79 (brs, 1H), 7.57 (d, J = 8.1 Hz, 2H), 7.41 (d, J = 8.1 Hz, 2H), 7.31-7.27 (m, 2H), 7.26-7.16 (m, 3H), 3.84 (s, 1H), 3.71 (s, 2H), 3.28 (s, 2H), 2.69-2.52 (m, 6H), 2.22 (s, 3H), 1.72-1.54 (m, 14H). |

TABLE III-continued

| Compound. | Structure | Name | MS (ESI+): [M + H]+ | H-NMR |
|---|---|---|---|---|
| 114 | 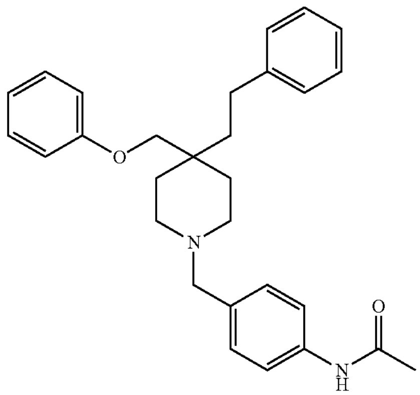 [SMILES: CC(=O)Nc1ccc(CN2CCC(CCc3ccccc3)(COc3ccccc3)CC2)cc1] | N-(4-((4-phenethyl-4-(phenoxymethyl)piperidin-1-yl)methyl)phenyl)acetamide | 443 | $^1$H NMR (300 MHz, MeOD): δ 7.62 (d, J = 8.7 Hz, 2H), 7.39 (d, J = 8.5 Hz, 2H), 7.32-7.22 (m, 4H), 7.15 (d, J = 7.2 Hz, 3H), 6.96 (d, J = 7.2 Hz, 3H), 3.94 (s, 4H), 2.93 (s, 4H), 2.63-2.57 (m, 2H), 2.15 (s, 3H), 1.90-1.81 (m, 6H). |
| 115 | 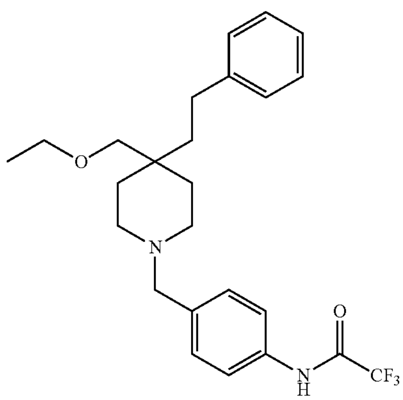 [SMILES: CCOCC1(CCc2ccccc2)CCN(Cc2ccc(NC(=O)C(F)(F)F)cc2)CC1] | N-(4-((4-(ethoxymethyl)-4-phenethylpiperidin-1-yl)methyl)phenyl)-2,2,2-trifluoroacetamide | 449 | $^1$H NMR (300 MHz, CDCl$_3$): δ 7.89 (s, 1H), 7.53 (d, J = 8.7 Hz, 2H), 7.39 (d, J = 8.4 Hz, 2H), 7.26-7.17 (m, 5H), 3.53-3.46 (m, 4H), 3.31 (s, 2H), 2.58-2.24 (m, 6H), 1.73-1.53 (m, 6H), 1.27 (t, J = 6.9 Hz, 3H). |
| 116 | 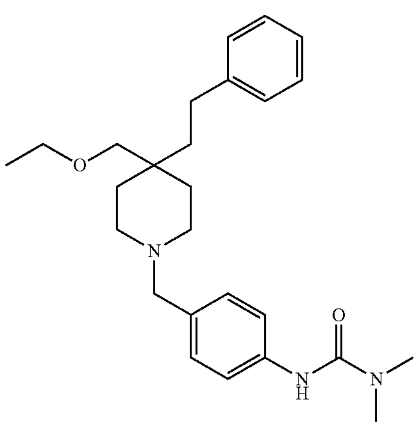 [SMILES: CCOCC1(CCc2ccccc2)CCN(Cc2ccc(NC(=O)N(C)C)cc2)CC1] | 3-(4-((4-(ethoxymethyl)-4-phenethylpiperidin-1-yl)methyl)phenyl)-1,1-dimethylurea | 424 | $^1$H NMR (300 MHz, MeOD): δ 7.43 (d, J = 8.7 Hz, 2H), 7.32 (d, J = 8.7 Hz, 2H), 7.28-7.23 (m, 2H), 7.19-7.15 (m, 3H), 3.85 (s, 2H), 3.51 (q, J = 6.9 Hz, 2H), 3.37 (s, 2H), 3.03 (s, 6H), 2.91-2.83 (m, 4H), 2.59-2.54 (m, 2H), 1.76-1.61 (m, 6H), 1.21 (t, J = 6.9 Hz, 3H). |

TABLE III-continued

| Compound. | Structure | Name | MS (ESI+): [M + H]+ | H-NMR |
|---|---|---|---|---|
| 117 | 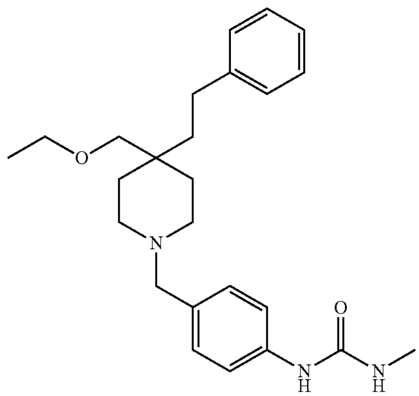 [SMILES: CCOCC1(CCc2ccccc2)CCN(Cc2ccc(NC(=O)NC)cc2)CC1] | 1-(4-((4-(ethoxymethyl)-4-phenethylpiperidin-1-yl)methyl)phenyl)-3-methylurea | 410 | ¹H NMR (300 MHz, MeOD): δ 7.49 (d, J = 8.7 Hz, 2H), 7.37 (d, J = 8.4 Hz, 2H), 7.30-7.16 (m, 3H), 7.09-7.04 (m, 2H), 4.17 (s, 2H), 3.51 (q, J = 6.9 Hz, 2H), 3.40 (s, 2H), 3.21-3.13 (m, 4H), 2.78 (s, 3H), 2.60-2.54 (m, 2H), 1.93-1.61 (m, 6H), 1.20 (t, J = 6.9 Hz, 3H). |
| 118 | 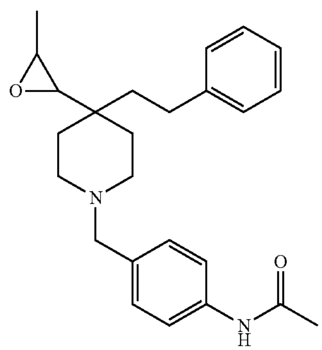 [SMILES: CC(=O)Nc1ccc(CN2CCC(CCc3ccccc3)(C3OC3C)CC2)cc1] | N-(4-((4-(3-methyloxiran-2-yl)-4-phenethylpiperidin-1-yl)methyl)phenyl)acetamide | 393 | ¹H NMR (300 MHz, MeOD): δ 7.64 (d, J = 8.4 Hz, 2H), 7.42 (d, J = 8.4 Hz, 2H), 7.23-7.08 (m, 5H), 4.02 (s, 2H), 3.42-3.38 (m, 2H), 3.32-2.85 (m, 6H), 2.63-2.52 (m, 1H), 2.14 (s, 3H), 1.95-1.64 (m, 5H), 1.46 (t, J = 6.9 Hz, 3H). |
| 119 | 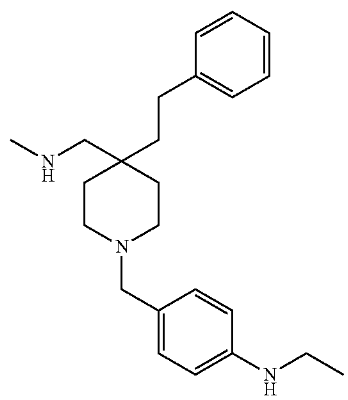 [SMILES: CCNc1ccc(CN2CCC(CCc3ccccc3)(CNC)CC2)cc1] | N-ethyl-4-((4-((methylamino)methyl)-4-phenethylpiperidin-1-yl)methyl)aniline | 366 | ¹H NMR (300 MHz, MeOD): δ 7.28-7.22 (m, 4H), 7.17-7.07 (m, 3H), 6.62 (d, J = 8.4 Hz, 2H), 3.41 (s, 2H), 3.12 (q, J = 6.9 Hz, 2H), 2.56-2.44 (m, 8H), 2.38 (s, 3H), 1.67-1.54 (m, 6H), 1.22 (t, J = 6.9 Hz, 3H). |
| 120 | 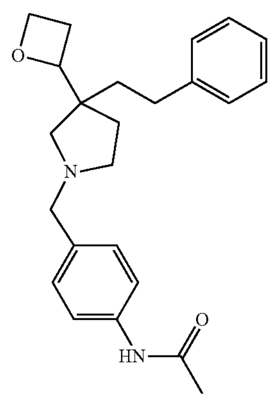 [SMILES: CC(=O)Nc1ccc(CN2CCC(CCc3ccccc3)(C3CCO3)C2)cc1] | N-(4-((3-(oxetan-2-yl)-3-phenethylpyrrolidin-1-yl)methyl)phenyl)acetamide | 379 | ¹H NMR (300 MHz, CDCl₃): δ 7.47-7.45 (m, 2H), 7.34-7.29 (m, 3H), 7.26-7.24 (m, 1H), 7.19-7.14 (m, 3H), 4.90-4.84 (m, 1H), 4.68-4.66 (m, 1H), 4.39-4.29 (m, 1H), 3.67-3.64 (m, 2H), 2.83-2.47 (m, 6H), 2.19-2.18 (m, 3H), 2.05-1.63 (m, 6H). |

TABLE III-continued

| Compound. | Structure | Name | MS (ESI+): [M + H]+ | H-NMR |
|---|---|---|---|---|
| 121 | 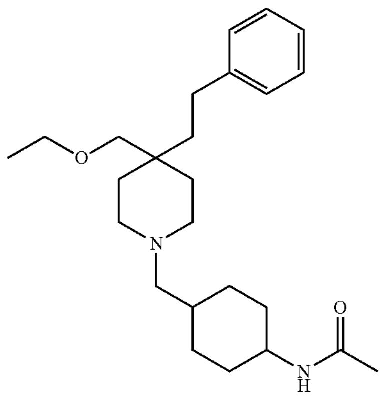 | N-(4-((4-(ethoxymethyl)-4-phenethylpiperidin-1-yl)methyl)cyclohexyl)acetamide HCl | 401 | ¹H NMR (300 MHz, CD3OD): δ 7.16-7.28 (m, 5H), 3.95 (brs, 1H), 3.57-3.46 (m, 6H), 3.33-3.09 (m, 4H), 2.63-2.57 (m, 2H), 2.03-1.99 (m, 9H), 1.88-1.64 (m, 7H), 1.51-1.48 (m, 2H), 1.27-1.21 (m, 3H) |
| 122 | 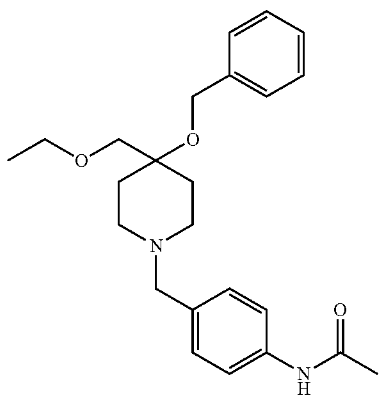 [SMILES: CCOCC1(OCc2ccccc2)CCN(Cc2ccc(NC(C)=O)cc2)CC1] | N-(4-((4-(benzyloxy)-4-(ethoxymethyl)piperidin-1-yl)methyl)phenyl)acetamide | 397 | ¹H NMR (300 MHz, MeOD): δ 7.70 (d, J = 8.7 Hz, 2H), 7.46 (d, J = 8.4 Hz, 2H), 7.31-7.30 (m, 5H), 4.53 (s, 2H), 4.29 (s, 2H), 3.57-3.52 (m, 4H), 3.33-3.19 (m, 4H), 2.23-2.17 (m, 5H), 2.15-1.80 (m, 2H), 1.20 (t, J = 6.9 Hz, 3H). |
| 123 | 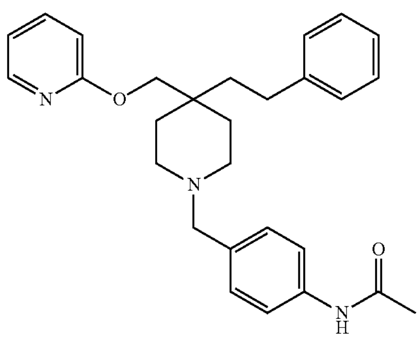 [SMILES: CC(=O)Nc1ccc(CN2CCC(CCc3ccccc3)(COc3ccccn3)CC2)cc1] | N-(4-((4-phenethyl-4-((pyridin-2-yloxy)methyl)piperidin-1-yl)methyl)phenyl)acetamide | 444 | ¹H NMR (300 MHz, MeOD): δ 8.13 (d, J = 1.5 Hz, 1H), 7.70-7.64 (m, 1H), 7.54 (d, J = 8.4 Hz, 2H), 7.29 (d, J = 8.1 Hz, 2H), 7.31-7.18 (m, 2H), 7.13-7.09 (m, 3H), 6.97-6.93 (m, 1H), 6.82 (d, J = 8.4, 1H), 4.22 (s, 2H), 3.55 (s, 2H), 2.59-2.55 (m, 6H), 2.12 (s, 3H), 1.79-1.62 (m, 6H). |
| 124 | 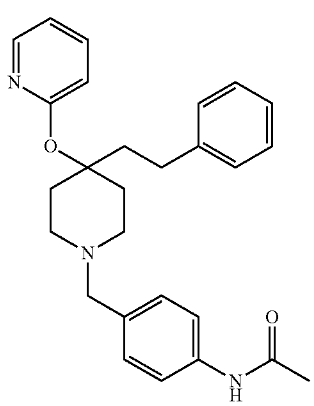 [SMILES: CC(=O)Nc1ccc(CN2CCC(CCc3ccccc3)(Oc3ccccn3)CC2)cc1] | N-(4-((4-phenethyl-4-(pyridin-2-yloxy)piperidin-1-yl)methyl)phenyl)acetamide | 430 | ¹H NMR (300 MHz, MeOD): δ 8.13 (d, J = 1.5 Hz, 1H), 7.70-7.64 (m, 1H), 7.56 (d, J = 6.9 Hz, 2H), 7.33 (d, J = 8.4 Hz, 2H), 7.21-7.16 (m, 3H), 7.12-6.92 (m, 3H), 6.80 (d, J = 8.4 Hz, 1H), 3.69 (s, 2H), 2.87-2.84 (m, 2H), 2.65-2.57 (m, 6H), 2.43-2.37 (m, 2H), 2.13 (s, 3H), 1.83-1.80 (m, 2H). |

TABLE III-continued

| Compound. | Structure | Name | MS (ESI+): [M + H]+ | H-NMR |
|---|---|---|---|---|
| 125 | 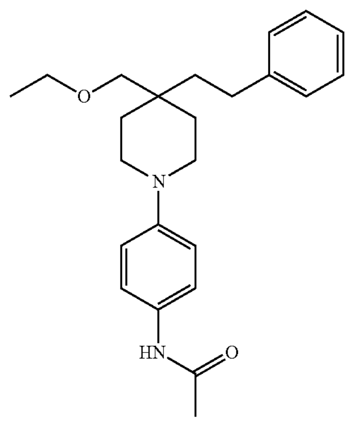 [SMILES: CCOCC1(CCc2ccccc2)CCN(c2ccc(NC(C)=O)cc2)CC1] | N-(4-(4-(ethoxymethyl)-4-phenethylpiperidin-1-yl)phenyl)acetamide | 381 | $^1$H NMR (300 MHz, MeOD): δ 7.82 (d, J = 9.0 Hz, 2H), 7.65 (d, J = 9.0 Hz, 2H), 7.32-7.18 (m, 5H), 3.63-3.56 (m, 8H), 2.69-2.63 (m, 2H), 2.19-2.13 (m, 5H), 2.01-1.92 (m, 4H), 1.27 (t, J = 6.9 Hz, 3H). |
| 126 | 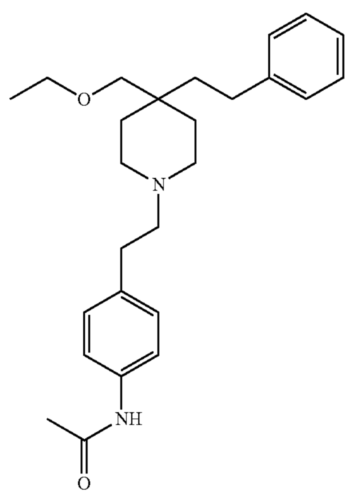 [SMILES: CCOCC1(CCc2ccccc2)CCN(CCc2ccc(NC(C)=O)cc2)CC1] | N-(4-(2-(4-(ethoxymethyl)-4-phenethylpiperidin-1-yl)ethyl)phenyl)acetamide | 409 | $^1$H NMR (300 MHz, MeOD): δ 7.55 (d, J = 6.9 Hz, 2H), 7.29-7.24 (m, 5H), 7.20-7.18 (m, 2H), 3.69-3.08 (m, 12H), 2.58-2.50 (m, 2H), 2.13 (s, 3H), 1.86-1.59 (m, 6H), 1.26 (t, J = 7.5 Hz, 3H) |
| 127 | 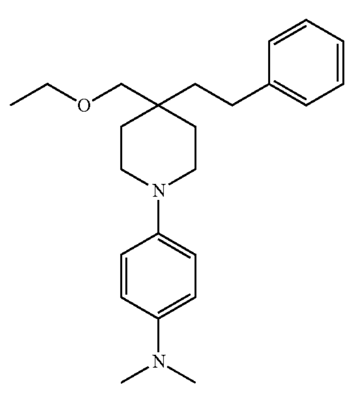 [SMILES: CCOCC1(CCc2ccccc2)CCN(c2ccc(N(C)C)cc2)CC1] | 4-(4-(ethoxymethyl)-4-phenethylpiperidin-1-yl)-N,N-dimethylaniline | 367 | $^1$H NMR (300 MHz, CDCl3): δ 7.32-7.28 (m, 2H), 7.22-7.19 (m, 3H), 6.95 (d, J = 9.0 Hz, 2H), 6.77 (d, J = 9.6 Hz, 2H), 3.51 (q, J = 7.2 Hz, 2H), 3.36 (s, 2H), 3.15-3.02 (m, 4H), 2.88 (s, 6H), 2.63-2.58 (m, 2H), 1.79-1.66 (m, 6H), 1.23 (t, J = 6.9 Hz, 3H). |

TABLE III-continued

| Compound. | Structure | Name | MS (ESI+): [M + H]+ | H-NMR |
|---|---|---|---|---|
| 128 | 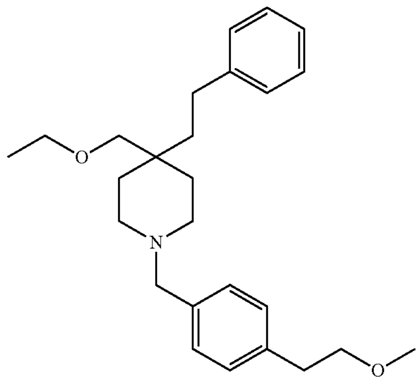 [SMILES: CCOCC1(CCc2ccccc2)CCN(Cc2ccc(CCOC)cc2)CC1] | 4-(ethoxymethyl)-1-(4-(2-methoxyethyl)benzyl)-4-phenethylpiperidine | 396 | 1H NMR (300 MHz, CD$_3$OD): δ 7.46-7.36 (m, 4H), 7.28-7.17 (m, 5H), 4.30 (s, 2H), 3.64 (t, J = 6.6 Hz, 2H), 3.52 (q, J = 6.9 Hz, 2H), 3.33-3.31 (m, 9H), 2.92 (t, J = 6.6 Hz, 2H), 2.62-2.56 (m, 2H), 1.98-1.65 (m, 6H), 1.21 (t, J = 6.9 Hz, 3H) |
| 129 | 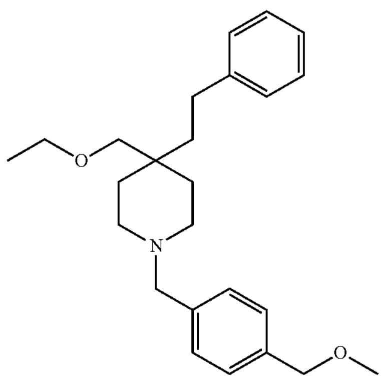 [SMILES: CCOCC1(CCc2ccccc2)CCN(Cc2ccc(COC)cc2)CC1] | 4-(ethoxymethyl)-1-(4-(methoxymethyl)benzyl)-4-phenethylpiperidine HC | 382 | 1H NMR (300 MHz, MeOD): δ 7.54-7.47 (m, 4H), 7.29-7.23 (m, 3H), 7.18-7.15 (m, 2H), 4.53 (s, 2H), 4.34 (s, 2H), 3.55-3.48 (m, 3H), 3.42 (s, 3H), 3.37-3.20 (m, 5H), 2.62-2.56 (m, 2H), 2.04-1.60 (m, 6H), 1.19 (t, J = 3.0 Hz, 3H). |
| 130 | 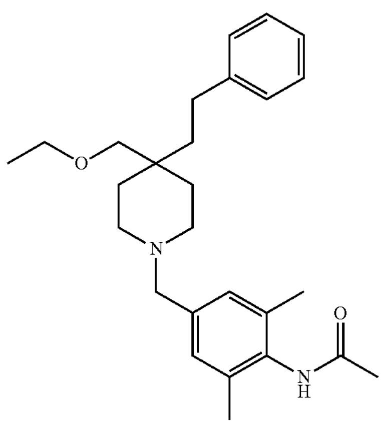 [SMILES: CCOCC1(CCc2ccccc2)CCN(Cc2cc(C)c(NC(C)=O)c(C)c2)CC1] | N-(4-((4-(ethoxymethyl)-4-phenethylpiperidin-1-yl)methyl-2,6-dimethylphenyl)acetamide | 423 | $^1$H NMR (300 MHz, MeOD): δ 7.29-7.16 (m, 7H), 4.15 (s, 2H), 3.54 (q, J = 6.9 Hz, 2H), 3.41 (s, 2H), 3.26-3.12 (m, 4H), 2.61-2.55 (m, 2H), 2.26 (s, 6H), 2.20 (s, 3H), 1.86-1.70 (m, 6H), 1.22 (t, J = 6.9 Hz, 3H). |
| 131 | 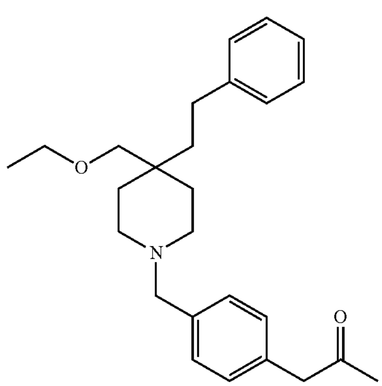 [SMILES: CCOCC1(CCc2ccccc2)CCN(Cc2ccc(CC(C)=O)cc2)CC1] | 1-(4-((4-(ethoxymethyl)-4-phenethylpiperidin-1-yl)methyl)phenyl)propan-2-one | 394 | $^1$H NMR (300 MHz, MeOD): δ 7.33 (d, J = 8.1 Hz, 2H), 7.28-7.15 (m, 7H), 3.77 (s, 2H), 3.61 (s, 2H), 3.51 (q, J = 6.9 Hz, 2H), 3.33 (s, 2H), 2.58-2.52 (m, 6H), 2.16 (s, 3H), 1.69-1.55 (m, 6H), 1.22 (t, J = 6.9 Hz, 3H). |

TABLE III-continued

| Compound. | Structure | Name | MS (ESI+): [M + H]+ | H-NMR |
|---|---|---|---|---|
| 132 | 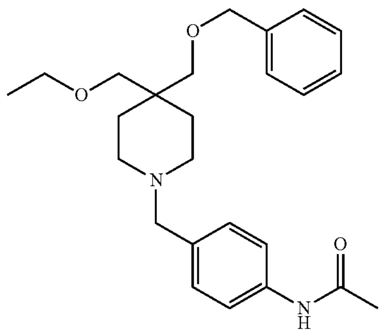 | N-(4-((4-(benzyloxymethyl)-4-(ethoxymethyl)piperidin-1-yl)methyl)phenyl)acetamide HCl | 411 | ¹H NMR (300 MHz, MeOD): δ 7.69 (d, J = 8.4 Hz, 2H), 7.46-7.41 (m, 2H), 7.36-7.29 (m, 5H), 4.51 (d, J = 14.1 Hz, 2H), 4.25 (d, J = 11.2 Hz, 2H), 3.55-3.44 (m, 4H), 3.34-3.32 (m, 4H), 3.31-3.26 (m, 2H), 2.15 (s, 3H), 2.12-1.80 (m, 4H), 1.42 (t, J = 7.2 Hz, 3H). |
| 133 | 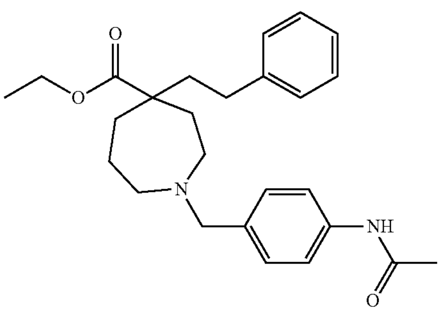 [SMILES: CCOC(=O)C1(CCc2ccccc2)CCCN(Cc2ccc(NC(C)=O)cc2)CC1] | ethyl 1-(4-acetamidobenzyl)-4-phenethylazepane-4-carboxylate | 423 | ¹H NMR (300 MHz, MeOD): δ 7.52 (d, J = 8.4 Hz, 2H), 7.28-7.22 (m, 4H), 7.13 (t, J = 8.2 Hz, 3H), 4.14 (q, J = 7.1 Hz, 2H), 3.66-3.57 (m, 2H), 2.66-2.60 (m, 4H), 2.49-2.43 (m, 2H), 2.23-2.20 (m, 2H), 2.12 (s, 3H), 1.87-1.66 (m, 6H), 1.26 (t, J = 7.0 Hz, 3H). |
| 134 | 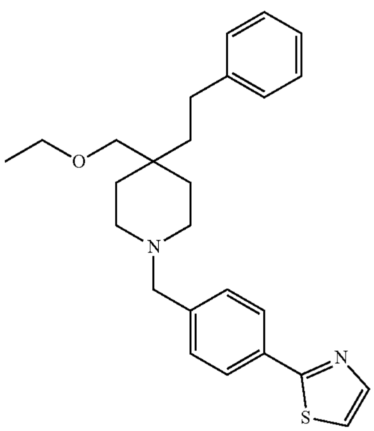 | 2-(4-((4-(ethoxymethyl)-4-phenethylpiperidin-1-yl)methyl)phenyl)thiazole | 421 | ¹H NMR (300 MHz, MeOD): δ 8.02 (d, J = 8.4 Hz, 2H), 7.91 (d, J = 3.3 Hz, 1H), 7.68 (d, J = 3.3 Hz, 1H), 7.60 (d, J = 8.4 Hz, 2H), 7.26-7.15 (m, 6H), 4.07 (s, 2H), 3.51 (q, J = 6.9 Hz, 2H), 3.39 (s, 2H), 3.02-2.94 (m, 4H), 2.60-2.54 (m, 2H), 1.82-1.68 (m, 6H), 1.21 (t, J = 6.9 Hz, 3H). |
| 135 | 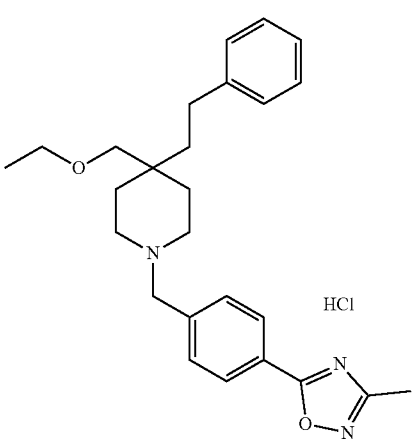 [SMILES: CCOCC1(CCc2ccccc2)CCN(Cc2ccc(-c3nc(C)no3)cc2)CC1 ; Cl] | 5-(4-((4-(ethoxymethyl)-4-phenethylpiperidin-1-yl)methyl)pheny)-3-methyl-1,2,4-oxadiazole HCl | 420 | 1H NMR (300 MHz, MeOD): δ 8.26 (dd, J = 8.4, 2.4 Hz, 2H), 7.77 (dd, J = 8.1, 5.1 Hz, 2H), 7.26 (t, J = 5.4 Hz, 3H), 7.18 (d, J = 6.9 Hz, 2H), 4.46 (s, 2H), 3.57-3.50 (m, 3H), 3.40-3.31 (m, 4H), 2.62-2.57 (m, 2H), 2.46 (s, 3H), 2.01 (d, J = 6 Hz, 1H), 1.90-1.87(m, 3H), 1.85-1.63 (m, 1H), 1.23-1.18 (m, 3H) |

TABLE III-continued

| Compound. | Structure | Name | MS (ESI+): [M + H]+ | H-NMR |
|---|---|---|---|---|
| 136 | HCl | 3-(4-((4-(ethoxymethyl)-4-phenethylpiperidin-1-yl)methyl)phenyl)-1,2,4-oxadiazole HCl | 406 | 1H NMR (300 MHz, MeOD): δ 9.34 (s, 1H), 8.26 (d, J = 8.1 Hz, 2H), 7.73 (d, J = 8.1 Hz, 2H), 7.26-7.18 (m, 5H), 4.43 (s, 2H), 3.67-3.53 (m, 6H), 3.24-3.19 (m, 2H), 2.63-2.57 (m, 2H), 2.06-2.01 (m, 1H), 1.86-1.70 (m, 5H), 1.23 (t, J = 6.3 Hz, 3H) |
| 137 | 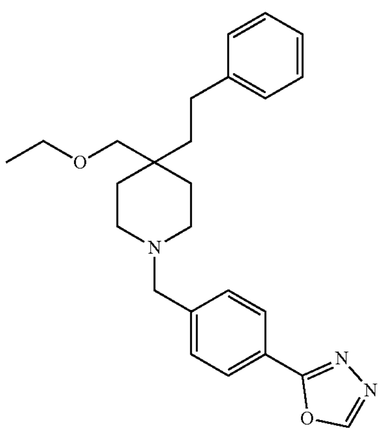 [SMILES: CCOCC1(CCc2ccccc2)CCN(Cc2ccc(-c3nnco3)cc2)CC1] | 2-(4-((4-(ethoxymethyl)-4-phenethylpiperidin-1-yl)methyl)phenyl)-1,3,4-oxadiazole | 406 | $^1$H NMR (300 MHz, MeOD): δ 9.02 (s, 1H), 8.08 (d, J = 8.4 Hz, 2H), 7.61 (d, J = 8.4 Hz, 2H), 7.27-7.14 (m, 5H), 3.74 (s, 2H), 3.51 (q, J = 6.9 Hz, 2H), 3.36-3.32 (m, 2H), 2.63-2.53 (m, 6H), 1.71-1.59 (m, 6H), 1.21 (t, J = 6.9 Hz, 3H). |
| 138 | 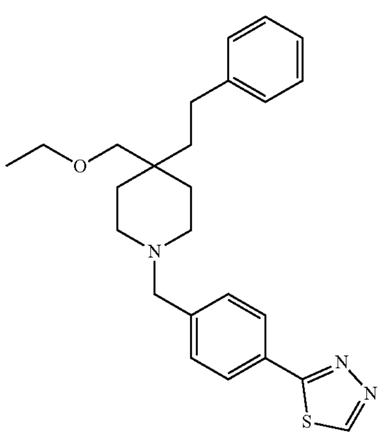 | 2-(4-((4-(ethoxymethyl)-4-phenethylpiperidin-1-yl)methyl)phenyl)-1,3,4-thiadiazole | 422 | $^1$H NMR (300 MHz, MeOD): δ 9.45 (s, 1H), 8.01 (d, J = 8.4 Hz, 2H), 7.58 (d, J = 8.4 Hz, 2H), 7.26-7.13 (m, 5H), 3.83 (s, 2H), 3.48 (q, J = 6.9 Hz, 2H), 3.34-3.32 (m, 2H), 2.80-2.63 (m, 4H), 2.56-2.51 (m, 2H), 1.71-1.60 (m, 6H), 1.19 (t, J = 6.9 Hz, 3H). |

TABLE III-continued

| Compound. | Structure | Name | MS (ESI+): [M + H]+ | H-NMR |
|---|---|---|---|---|
| 139 | 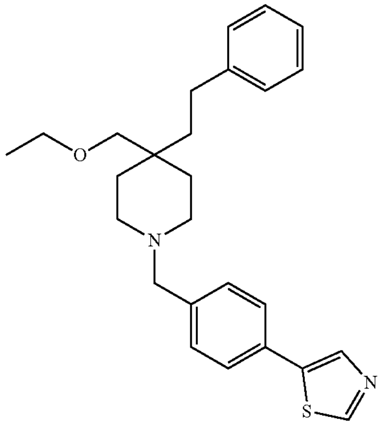 | 5-(4-((4-(ethoxymethyl)-4-phenethylpiperidin-1-yl)methyl)phenyl)thiazole | 421 | ¹H NMR (300 MHz, MeOD): δ 8.98 (s, 1H), 8.20 (s, 1H), 7.69 (d, J = 8.1 Hz, 2H), 7.49 (d, J = 8.1 Hz, 2H), 7.25 (t, J = 7.5 Hz, 2H), 7.16 (t, J = 6.9 Hz, 3H), 3.84 (s, 2H), 3.52 (q, J = 6.9 Hz, 2H), 3.31 (m, 2H), 2.77 (m, 4H), 2.58-2.52 (m, 2H), 1.74-1.63 (m, 6H), 1.23 (t, J = 6.9 Hz, 3H). |
| 140 | 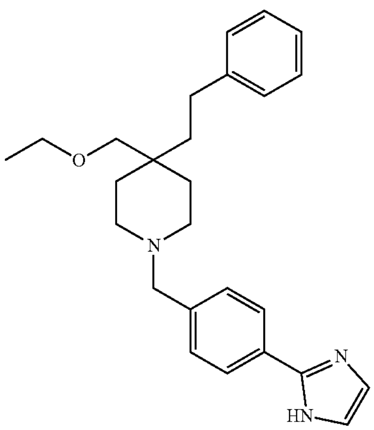 [SMILES: CCOCC1(CCc2ccccc2)CCN(Cc2ccc(-c3ncc[nH]3)cc2)CC1] | 1-(4-(1H-imidazol-2-yl)benzyl)-4-(ethoxymethyl)-4-phenethylpiperidine | 404 | ¹H NMR (300 MHz, MeOD): δ 7.95 (d, J = 8.40 Hz, 2H), 7.57 (d, J = 8.40 Hz, 2H), 7.29-7.18 (m, 7H), 4.12 (s, 2H), 3.52 (q, J = 6.9 Hz, 2H), 3.40 (s, 2H), 3.09-3.05 (m, 4H), 2.61-2.55 (m, 2H), 1.87-1.66 (m, 6H), 1.21 (t, J = 6.9 Hz, 3H). |
| 141 | 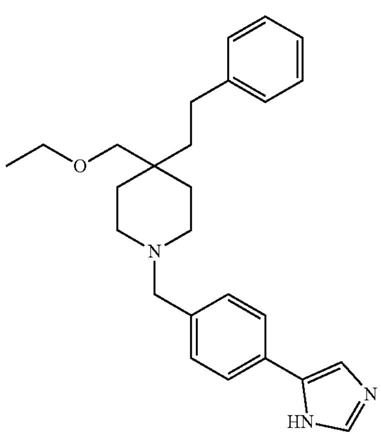 [SMILES: CCOCC1(CCc2ccccc2)CCN(Cc2ccc(-c3cnc[nH]3)cc2)CC1] | 1-(4-(1H-imidazol-5-yl)benzyl)-4-(ethoxymethyl)-4-phenethylpiperidine | 404 | ¹H NMR (300 MHz, MeOD): δ 7.78 (t, J = 3.90 Hz, 3H), 7.51-7.46 (m, 3H), 7.24-7.13 (m, 5H), 4.09 (s, 2H), 3.50 (q, J = 6.9 Hz, 2H), 3.48 (s, 2H), 3.09-3.04 (m, 4H), 2.58-2.52 (m, 2H), 1.84-1.64 (m, 6H), 1.18 (t, J = 6.9 Hz, 3H). |

TABLE III-continued

| Compound. | Structure | Name | MS (ESI+): [M + H]+ | H-NMR |
|---|---|---|---|---|
| 142 | 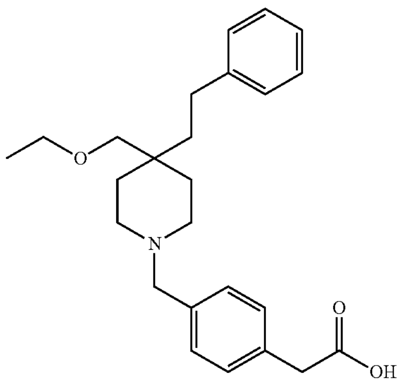 [SMILES: CCOCC1(CCc2ccccc2)CCN(Cc2ccc(CC(=O)O)cc2)CC1] | 2-(4-((4-(ethoxymethyl)-4-phenethylpiperidin-1-yl)methyl)phenyl)acetic acid | 396 | ¹H NMR (300 MHz, MeOD): δ 7.40-7.37 (m, 4H), 7.29-7.13 (m, 5H), 4.15 (s, 2H), 3.55-3.48 (m, 4H), 3.38 (s, 2H), 3.15-3.12 (m, 4H), 2.60-2.54 (m, 2H), 1.89-1.66 (m, 6H), 1.21 (t, J = 6.9 Hz, 3H). |
| 143 | 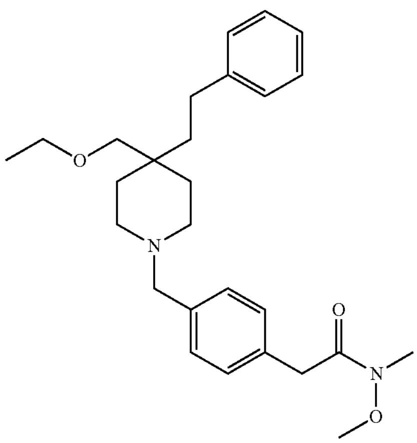 [SMILES: CCOCC1(CCc2ccccc2)CCN(Cc2ccc(CC(=O)N(C)OC)cc2)CC1] | 2-(4-((4-(ethoxymethyl)-4-phenethylpiperidin-1-yl)methyl)phenyl)-N-methoxy-N-methylacetamide | 439 | ¹H NMR (300 MHz, CDCl3): δ 7.32-7.28 (m, 6H), 7.23-7.18 (m, 3H), 3.77 (s, 2H), 3.62 (s, 3H), 3.50-3.45 (m, 4H), 3.30 (s, 2H), 3.21 (s, 3H), 2.58-2.52 (m, 2H), 2.47-2.38 (m, 2H), 1.73-1.67 (m, 2H), 1.65-1.47 (m, 6H), 1.21 (t, J = 6.9 Hz, 3H). |
| 144 | 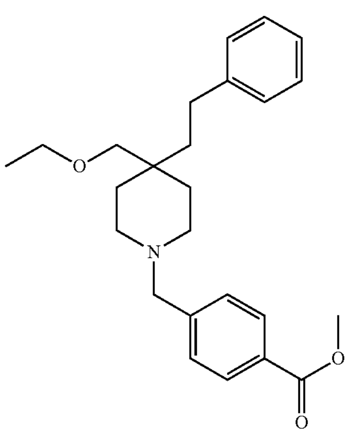 [SMILES: CCOCC1(CCc2ccccc2)CCN(Cc2ccc(C(=O)OC)cc2)CC1] | methyl 4-((4-(ethoxymethyl)-4-phenethylpiperidin-1-yl)methyl)benzoate | 396 | ¹H NMR (300 MHz, MeOD): δ 8.14 (d, J = 6.0 Hz, 2H), 7.67 (d, J = 6.0 Hz, 2H), 7.25-7.19 (m, 5H), 4.42 (s, 2H), 3.95 (s, 3H), 3.70-3.52 (m, 3H), 3.49-3.09 (m, 5H), 2.62-2.57 (m, 2H), 1.99-1.64 (m, 6H), 1.21 (t, J = 7.5 Hz, 3H). |

TABLE III-continued

| Compound. | Structure | Name | MS (ESI+): [M + H]+ | H-NMR |
|---|---|---|---|---|
| 145 | 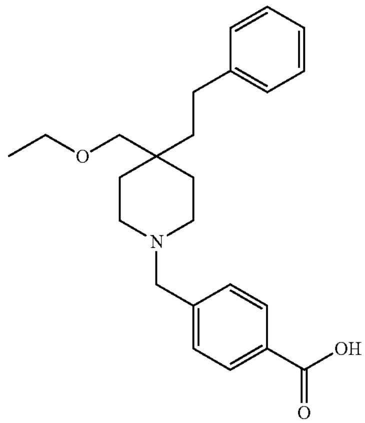 [SMILES: CCOCC1(CCc2ccccc2)CCN(Cc2ccc(C(=O)O)cc2)CC1] | 4-((4-(ethoxymethyl)-4-phenethylpiperidin-1-yl)methyl)benzoic acid | 382 | ¹H NMR (300 MHz, MeOD): δ 8.15-8.12 (m, 2H), 7.70-7.66 (m, 2H), 7.26-7.15 (m, 5H), 4.43 (s, 2H), 3.58-3.48 (m, 3H), 3.33-3.25 (m, 5H), 2.65-2.56 (m, 2H), 2.04-1.60 (m, 6H), 1.23-1.18 (m, 3H). |
| 146 | 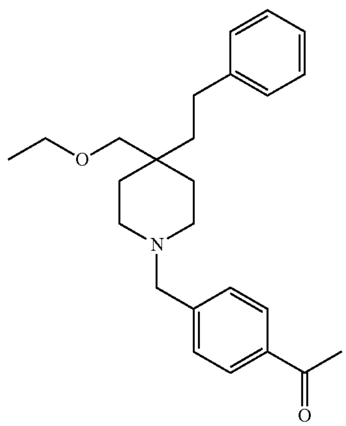 [SMILES: CCOCC1(CCc2ccccc2)CCN(Cc2ccc(C(C)=O)cc2)CC1] | 1-(4-((4-(ethoxymethyl)-4-phenethylpiperidin-1-yl)methyl)phenyl)ethanone | 380 | ¹H NMR (300 MHz, MeOD): δ 7.99-7.91 (m, 2H), 7.50-7.43 (m, 2H), 7.32-7.27 (m, 2H), 7.21-7.16 (m, 3H), 3.57 (s, 2H), 3.51 (q, J = 6.9 Hz, 2H), 3.31 (s, 2H), 2.63 (s, 3H), 2.61-2.59 (m, 2H), 2.58-2.44 (m, 4H), 1.74-1.52 (m, 6H), 1.22 (t, J = 6.9 Hz, 3H). |
| 147 | 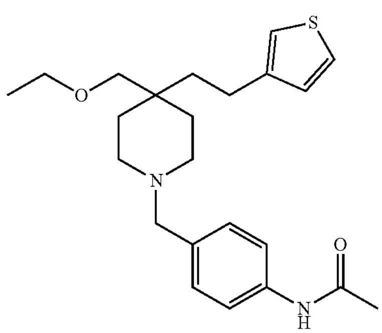 [SMILES: CCOCC1(CCc2ccsc2)CCN(Cc2ccc(NC(C)=O)cc2)CC1] | N-(4-((4-(ethoxymethyl)-4-(2-(thiophen-3-yl)ethyl)piperidin-1-yl)methyl)phenyl)acetamide | 401 | ¹H NMR (300 MHz, CD3OD): δ 7.72-7.68 (m, 2H), 7.50-7.46 (m, 2H), 7.34-7.32 (m, 1H), 7.10-6.91 (m, 2H), 4.29 (s, 2H), 3.51 (q, J = 6.9 Hz, 2H), 3.43-3.38 (m, 2H), 3.34-3.18 (m, 4H), 2.67-2.61 (m, 2H), 2.16 (s, 3H), 1.89-1.80 (m, 4H), 1.69-1.61 (m, 2H), 1.17 (t, J = 6.9 Hz, 3H) |
| 148 | 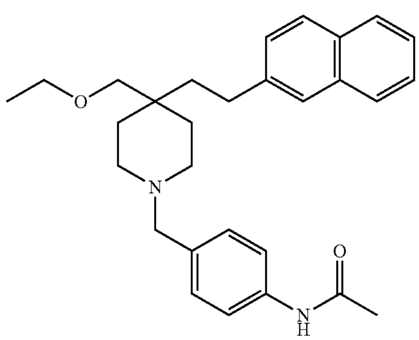 [SMILES: CCOCC1(CCc2ccc3ccccc3c2)CCN(Cc2ccc(NC(C)=O)cc2)CC1] | N-(4-((4-(ethoxymethyl)-4-(2-(naphthalen-2-yl)ethyl)piperidin-1-yl)methyl)phenyl)acetamide | 445 | 1H NMR (300 MHz, CD3OD): δ 7.71-7.82 (m, 2H), 7.68-7.70 (m, 4H), 7.42-7.50 (m, 5H), 4.36-4.25 (m, 2H), 3.61-3.57 (m, 2H), 3.54-3.51 (m, 2H), 3.21-3.19 (m, 2H), 2.80-2.72 (m, 2H), 2.16 (s, 3H), 2.10-2.03 (m, 2H), 1.95-1.85 (m, 4H), 1.81-1.74 (m, 2H), 1.18 (t, J = 6.9 Hz, 3H) |

TABLE III-continued

| Compound. | Structure | Name | MS (ESI+): [M + H]+ | H-NMR |
|---|---|---|---|---|
| 149 | 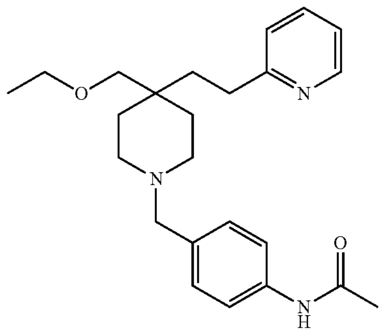 [SMILES: CCOCC1(CCc2ccccn2)CCN(Cc2ccc(NC(C)=O)cc2)CC1] | N-(4-((4-(ethoxymethyl)-4-(2-(pyridin-2-yl)ethyl)piperidin-1-yl)methyl)phenyl)acetamide | 396 | $^1$H NMR (300 MHz, MeOD): δ 8.46 (d, J = 4.9 Hz, 1H), 7.78-7.69 (m, 1H), 7.68 (d, J = 8.5 Hz, 2H), 7.45 (d, J = 8.5 Hz, 2H), 7.34 (d, J = 7.8 Hz, 1H), 7.27 (m, 1H), 4.19 (s, 2H), 3.52 (q, J = 7.2 Hz, 2H), 3.41 (s, 2H), 3.19 (m, 4H), 2.80-2.74 (m, 2H), 2.15 (s, 3H), 1.89-1.74 (m, 6H), 1.20 (t, J = 7.0 Hz, 3H). |
| 150 | 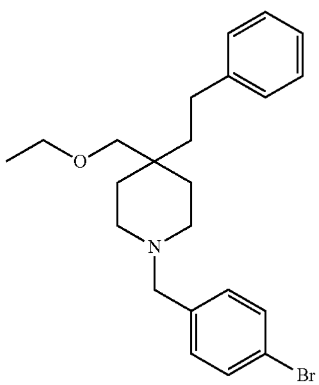 [SMILES: CCOCC1(CCc2ccccc2)CCN(Cc2ccc(Br)cc2)CC1] | 1-(4-bromobenzyl)-4-(ethoxymethyl)-4-phenethylpiperidine | 417, 419 | $^1$H NMR (300 MHz, MeOD): δ 7.68 (d, J = 9.0 Hz, 2H), 7.46 (d, J = 9.0 Hz, 2H), 7.26-7.18 (m, 5H), 3.53-3.46 (m, 4H), 3.33 (s, 3H), 2.62-2.56 (m, 2H), 2.54-2.37 (m, 4H), 1.73-1.61 (m, 6H), 1.21 (t, J = 6.9 Hz, 3H). |
| 151 | 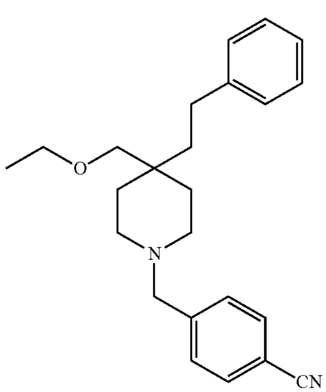 [SMILES: CCOCC1(CCc2ccccc2)CCN(Cc2ccc(C#N)cc2)CC1] | 4-((4-(ethoxymethyl)-4-phenethylpiperidin-1-yl)methyl)benzonitrile | 363 | $^1$H NMR (300 MHz, CDCl$_3$): δ 7.61 (d, J = 8.1 Hz, 2H), 7.46 (d, J = 8.1 Hz, 2H), 7.33-7.19 (m, 5H), 3.55 (s, 2H), 3.50 (q, J = 6.9 Hz, 2H), 3.31 (s, 2H), 2.59-2.06 (m, 6H), 1.74-1.54 (m, 6H), 1.22 (t, J = 6.9 Hz, 3H). |

TABLE III-continued

| Compound. | Structure | Name | MS (ESI+): [M + H]+ | H-NMR |
|---|---|---|---|---|
| 152 | 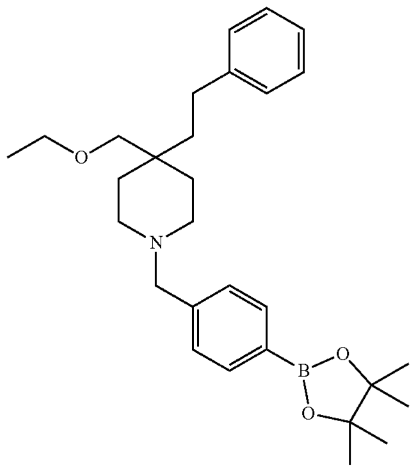 [SMILES: CCOCC1(CCc2ccccc2)CCN(Cc2ccc(B3OC(C)(C)C(C)(C)O3)cc2)CC1] | 4-(ethoxymethyl)-4-phenethyl-1-(4-(4,4,5,5-tetramethyl-1,3,2-dioxaborolan-2-yl)benzyl)piperidine | 464 | $^1$H NMR (300 MHz, DMSO-d$_6$): δ 7.76 (d, J = 7.8 Hz, 2H), 7.57 (t, J = 6.3 Hz, 2H), 7.30-7.15 (m, 5H), 4.35-4.33 (m, 2H), 3.49-3.42 (m, 3H), 3.32-3.06 (m, 6H), 1.76-1.67 (m, 7H), 1.31-1.19 (m, 12H), 1.16-1.12 (m, 3H). |
| 153 | 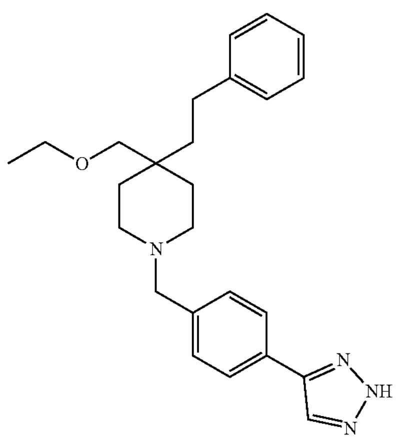 [SMILES: CCOCC1(CCc2ccccc2)CCN(Cc2ccc(-c3cn[nH]n3)cc2)CC1] | 1-(4-(2H-1,2,3-triazol-4-yl)benzyl)-4-(ethoxymethyl)-4-phenethylpiperidine | 405 | $^1$H NMR (300 MHz, MeOD): δ 8.24 (s, 1H), 7.96 (d, J = 6.5 Hz, 2H), 7.58 (d, J = 6.3 Hz, 2H), 7.28-7.17 (m, 5H), 4.17 (s, 2H), 3.53 (q, J = 6.9 Hz, 2H), 3.42 (s, 2H), 3.11-3.06 (m, 2H), 2.68-2.58 (m, 4H), 1.96-1.72 (m, 6H), 1.22 (t, J = 6.9 Hz, 3H). |
| 154 | 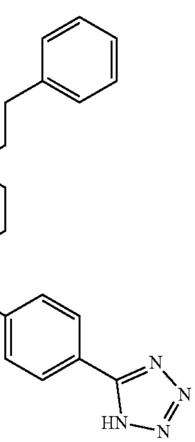 | 1-(4-(1H-tetrazol-5-yl)benzyl)-4-(ethoxymethyl)-4-phenethylpiperidine HCl | 406 | 1H NMR (300 MHz, MeOD): δ 8.2 (d, J = 6.6 Hz, 2H), 7.78 (dd, J = 7.8, 4.2 Hz, 2H), 7.28-7.15 (m, 5H), 4.45 (s, 2H), 3.57-3.53 (m, 4H), 3.31-3.19 (m, 4H), 2.63-2.57 (m, 2H), 1.90-1.63 (m, 6H), 1.21 (t, J = 6.9 Hz, 3H). |

TABLE III-continued

| Compound. | Structure | Name | MS (ESI+): [M + H]+ | H-NMR |
|---|---|---|---|---|
| 155 | 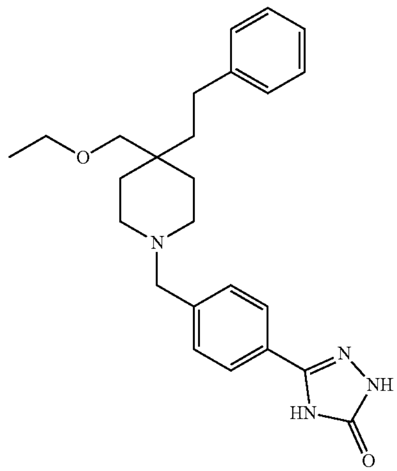 [SMILES: CCOCC1(CCc2ccccc2)CCN(Cc2ccc(-c3n[nH]c(=O)[nH]3)cc2)CC1] | 3-(4-((4-(ethoxymethyl)-4-phenethylpiperidin-1-yl)methyl)phenyl)-1H-1,2,4-triazol-5(4H)-one | 421 | ¹H NMR (300 MHz, MeOD): δ 7.76 (d, J = 8.4 Hz, 2H), 7.47 (d, J = 8.1 Hz, 2H), 7.26-7.12 (m, 5H), 3.66 (s, 2H), 3.548 (q, J = 6.9 Hz, 2H), 3.32-3.30 (m, 2H), 2.56-2.51 (m, 6H), 1.68-1.53 (m, 6H), 1.19 (t, J = 6.9 Hz, 3H). |
| 156 | 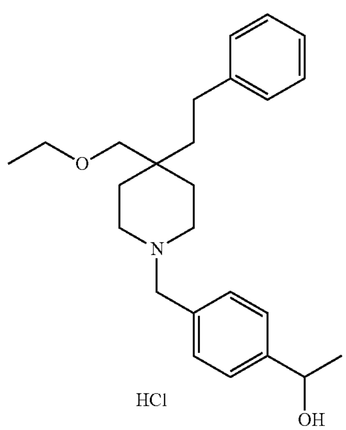 [SMILES: CCOCC1(CCc2ccccc2)CCN(Cc2ccc(C(C)O)cc2)CC1 ; Cl] | 1-(4-((4-(ethoxymethyl)-4-phenethylpiperidin-1-yl)methyl)phenyl)ethanol HCl | 382.3 | H-NMR (300 MHz, MeOD): δ 7.60-7.50 (m, 4H), 7.29-7.15 (m, 5H), 4.33 (s, 2H), 3.55-3.49 (m, 3H), 3.33-3.10 (m, 5H), 2.62-2.56 (m, 2H), 2.05-1.97 (m, 1H), 1.90-1.55 (m, 6H), 1.50-1.40 (m, 3H), 1.23-1.17 (m, 3H). |
| 157 | 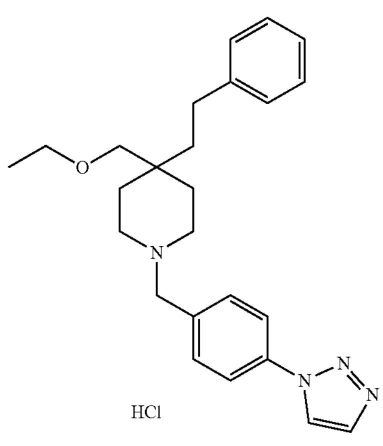 [SMILES: CCOCC1(CCc2ccccc2)CCN(Cc2ccc(-n3ccnn3)cc2)CC1 ; Cl] | 1-(4-(1H-1,2,3-triazol-1-yl)benzyl-4-(ethoxymethyl)-4-phenethylpiperidine HCl | 442 | ¹H NMR (300 MHz, MeOD): δ 8.69 (s, 1H), 8.07-8.01 (m, 3H), 7.84-7.79 (m, 2H), 7.29-7.18 (m, 5H), 4.46 (s, 2H), 3.58-3.51 (m, 3H), 3.38-3.31 (m, 3H), 2.60-2.57 (m, 2H), 2.10-1.95 (m, 2H), 1.89-1.85 (m, 6H), 1.24-1.18 (m, 3H). |

TABLE III-continued

| Compound. | Structure | Name | MS (ESI+): [M + H]+ | H-NMR |
|---|---|---|---|---|
| 158 | 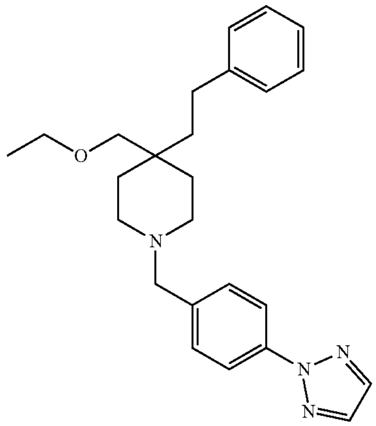 [SMILES: CCOCC1(CCc2ccccc2)CCN(Cc2ccc(-n3nccn3)cc2)CC1] | 1-(4-(2H-1,2,3-triazol-2-yl)benzyl-4-(ethoxymethyl)-4-phenethylpiperidine | 405 | $^1$H NMR (300 MHz, MeOD): δ 8.58 (d, J = 1.1 Hz, 1H), 7.94-7.91 (m, 3H), 7.66 (d, J = 8.5 Hz, 2H), 7.26-7.14 (m, 5H), 3.96 (s, 2H), 3.52 (q, J = 7.0 Hz, 2H), 3.35 (s, 2H), 2.90-2.85 (m, 4H), 2.67-2.55 (m, 2H), 1.75-1.68 (m, 6H), 1.21 (t, J = 7.0 Hz, 3H). |
| 159 | 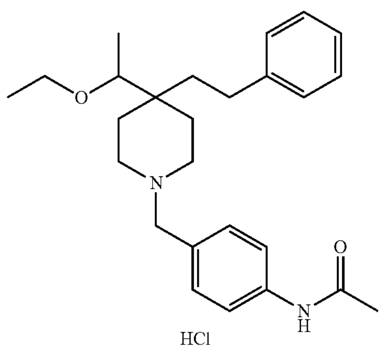 [SMILES: CCOC(C)C1(CCc2ccccc2)CCN(Cc2ccc(NC(C)=O)cc2)CC1 ; Cl] | N-(4-((4-(1-ethoxyethyl)-4-phenethylpiperidin-1-yl)methyl)phenyl)acetamide HCl | 409 | $^1$H NMR (300 MHz, MeOD): δ 7.70 (d, J = 8.4 Hz, 2H), 7.49-7.45 (m, 2H), 7.32-7.15 (m, 5H), 4.28 (s, 2H), 3.74-3.68 (m, 1H), 3.38-3.32 (m, 2H), 3.15-3.13 (m, 2H), 2.65-2.53 (m, 2H), 2.16-1.94 (m, 7H), 1.77-1.62 (m, 4H), 1.22-1.12 (m, 6H). |
| 160 | 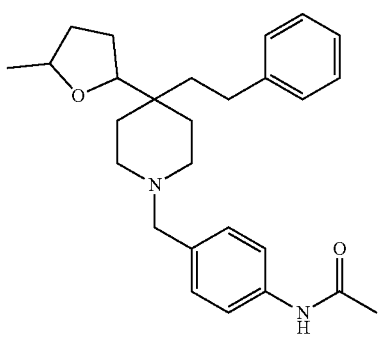 [SMILES: CC(=O)Nc1ccc(CN2CCC(CCc3ccccc3)(C3CCC(C)O3)CC2)cc1] | N-(4-((4-(5-methyltetrahydro-furan-2-yl)-4-phenethylpiperidin-1-yl)methyl)phenyl)acetamide | 421 | $^1$H NMR (300 MHz, MeOD): δ 7.62 (d, J = 8.4 Hz, 2H), 7.39 (d, J = 8.7 Hz, 2H), 7.28-7.14 (m, 5H), 4.12-3.92 (m, 4H), 3.15-3.12 (m, 2H), 2.89-2.81 (m, 2H), 2.59-2.57 (m, 2H), 2.13 (s, 3H), 1.99-1.81 (m, 6H), 1.66-1.60 (m, 4H), 1.19 (d, J = 6.0 Hz, 3H). |
| 161 | 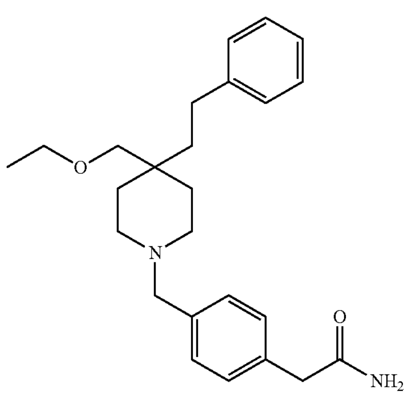 [SMILES: CCOCC1(CCc2ccccc2)CCN(Cc2ccc(CC(N)=O)cc2)CC1] | 2-(4-((4-(ethoxymethyl)-4-phenethylpiperidin-1-yl)methyl)phenyl)acetamide | 395 | $^1$H NMR (300 MHz, MeOD): δ 7.40-7.37 (m, 4H), 7.34-7.15 (m, 5H), 3.87 (s, 2H), 3.55-3.47 (m, 4H), 3.37 (s, 2H), 2.88-2.79 (m, 4H), 2.59-2.53 (m, 2H), 1.75-1.61 (m, 6H), 1.20 (t, J = 7.0 Hz, 3H). |

TABLE III-continued

| Compound. | Structure | Name | MS (ESI+): [M + H]+ | H-NMR |
|---|---|---|---|---|
| 162 | 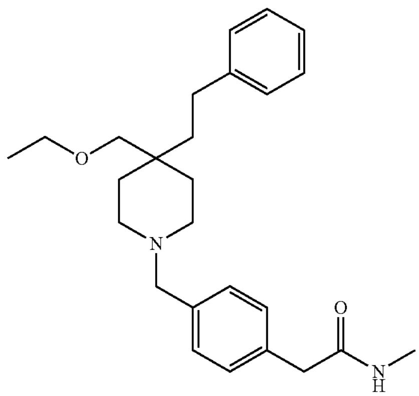 [SMILES: CCOCC1(CCc2ccccc2)CCN(Cc2ccc(CC(=O)NC)cc2)CC1] | 2-(4-((4-(ethoxymethyl)-4-phenethylpiperidin-1-yl)methyl)phenyl)-N-methylacetamide | 409 | ¹H NMR (300 MHz, MeOD): δ 7.33-7.22 (m, 6H), 7.17-7.14 (m, 3H), 3.57 (s, 2H), 3.50-3.46 (m, 4H), 3.33 (s, 2H), 2.73 (s, 3H), 2.57-2.52 (m, 6H), 1.69-1.52 (m, 6H), 1.21 (t, J = 7.0 Hz, 3H). |
| 163 | 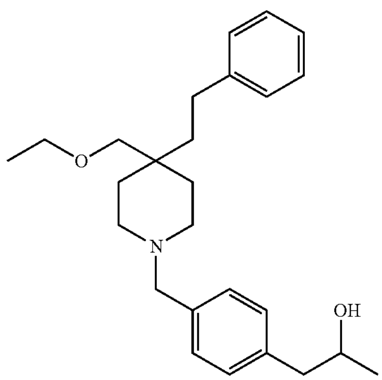 [SMILES: CCOCC1(CCc2ccccc2)CCN(Cc2ccc(CC(C)O)cc2)CC1] | 1-(4-((4-(ethoxymethyl)-4-phenethylpiperidin-1-yl)methyl)phenyl)propan-2-ol | 396 | ¹H NMR (300 MHz, MeOD): δ 7.3-7.15 (m, 9H), 4.05-3.93 (m, 1H), 3.82 (s, 2H), 3.52-3.46 (m, 2H), 3.37 (s, 2H), 2.79-2.77 (m, 6H), 2.59-2.53 (m, 2H), 1.74-1.62 (m, 6H), 1.23-1.15 (m, 6H). |
| 164 | 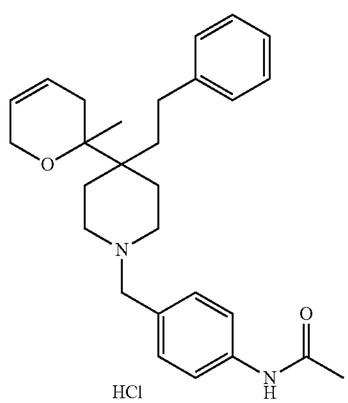 [SMILES: CC(=O)Nc1ccc(CN2CCC(CCc3ccccc3)(C3(C)CC=CCO3)CC2)cc1 ; Cl] | N-(4-((4-(2-methyl-3,6-dihydro-2H-pyran-2-yl)-4-phenethylpiperidin-1-yl)methyl)phenyl)acetamide HCl | 433 | 1H NMR (300 MHz, MeOD): δ 7.70 (d, J = 8.5 Hz, 2H), 7.48 (d, J = 8.5 Hz, 2H), 7.34-7.13 (m, 5H), 5.79-5.77 (m, 2H), 4.28 (s, 2H), 4.24-4.01 (m, 2H), 3.34 (m, 2H), 3.13 (m, 2H), 2.95-2.52 (m, 3H), 2.46 (m, 1H), 2.15 (s, 3H), 2.10-1.88 (m, 6H), 1.30 (s, 3H) |
| 165 | 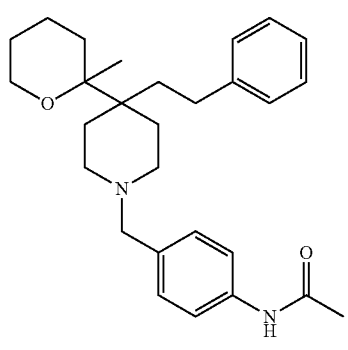 [SMILES: CC(=O)Nc1ccc(CN2CCC(CCc3ccccc3)(C3(C)CCCCO3)CC2)cc1] | N-(4-((4-(2-methyltetrahydro-2H-pyran-2-yl)-4-phenethylpiperidin-1-yl)methyl)phenyl)acetamide | 435 | ¹H NMR (300 MHz, CDCl₃): δ 7.48-7.37 (m, 3H), 7.32-7.20 (m, 3H), 7.19-7.12 (m, 3H), 3.68-3.61 (m, 2H), 3.52 (s, 2H), 2.87-2.65 (m, 4H), 2.26-2.04 (m, 5H), 2.00-1.80 (m, 2H), 1.77-1.66 (m, 4H), 1.54-1.41 (m, 4H), 1.27-1.22 (m, 5H). |

TABLE III-continued

| Compound. | Structure | Name | MS (ESI+): [M + H]+ | H-NMR |
|---|---|---|---|---|
| 166 | 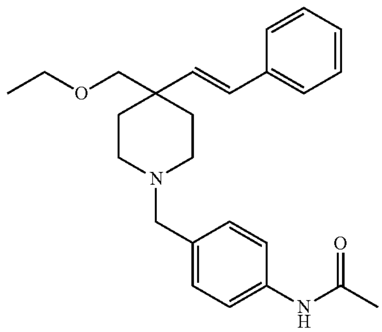 [SMILES: CCOCC1(/C=C/c2ccccc2)CCN(Cc2ccc(NC(C)=O)cc2)CC1] | (E)-N-(4-((4-(ethoxymethyl)-4-(2-(pyridin-2-yl)vinyl)piperidin-1-yl)methyl)phenyl)acetamide | 394 | $^1$H NMR (300 MHz, MeOD): δ 8.50 (d, J = 4.8 Hz, 1H), 7.82 (td, J = 7.8, 1.8 Hz, 1H), 7.64 (d, J = 8.4 Hz, 2H), 7.53 (d, J = 8.1 Hz, 1H), 7.41 (d, J = 8.4 Hz, 2H), 7.32-7.28 (m, 1H), 6.65 (s, 2H), 4.08 (s, 2H), 3.53-3.47 (m, 2H), 3.38-3.63 (m, 2H), 3.33-3.21 (m, 2H), 3.05-2.96 (m, 2H), 1.17 (t, J = 6.9 Hz, 3H). |
| 167 | 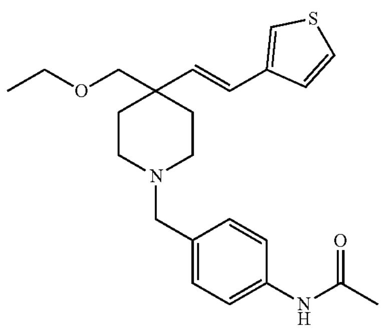 [SMILES: CCOCC1(/C=C/c2ccsc2)CCN(Cc2ccc(NC(C)=O)cc2)CC1] | (E)-N-(4-((4-(ethoxymethyl)-4-(2-(thiophen-3-yl)vinyl)piperidin-1-yl)methyl)phenyl)acetamide | 399 | |
| 168 | 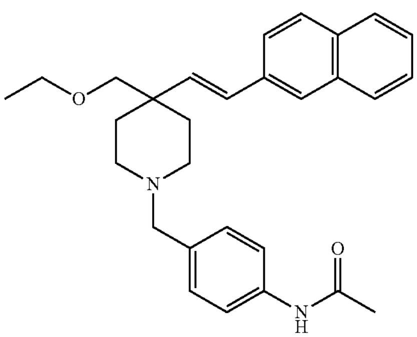 [SMILES: CCOCC1(/C=C/c2ccc3ccccc3c2)CCN(Cc2ccc(NC(C)=O)cc2)CC1] | (E)-N-(4-((4-(ethoxymethyl)-4-(2-(naphthalen-2-yl)vinyl)piperidin-1-yl)methyl)phenyl)acetamide | 443 | |
| 169 | 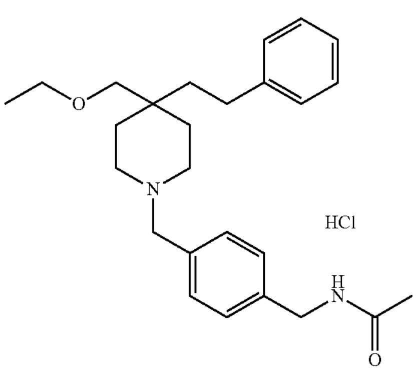 [SMILES: CCOCC1(CCc2ccccc2)CCN(Cc2ccc(CNC(C)=O)cc2)CC1 ; Cl] | N-(4-((4-(ethoxymethyl)-4-phenethylpiperidin-1-yl)methyl)benzyl)acetamide HCl | 409 | $^1$H NMR (300 MHz, MeOD): δ 7.52-7.48 (m, 2H), 7.44-7.41 (m, 2H), 7.29-7.15 (m, 5H), 4.41 (s, 2H), 4.32 (s, 2H), 3.55-3.50 (m, 4H), 3.32-3.19 (m, 3H), 2.62-2.56 (m, 2H), 2.02-1.98 (m, 4H), 1.88-1.59 (m, 6H), 1.19-1.17 (m, 3H). HCl salt |

TABLE III-continued

| Compound. | Structure | Name | MS (ESI+): [M + H]⁺ | H-NMR |
|---|---|---|---|---|
| 170 | 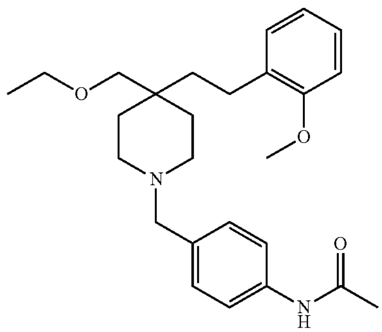 [SMILES: CCOCC1(CCc2ccccc2OC)CCN(Cc2ccc(NC(C)=O)cc2)CC1] | N-(4-((4-(ethoxymethyl)-4-(2-methoxyphenethyl)piperidin-1-yl)methyl)phenyl)acetamide | 425 | ¹H NMR (300 MHz, MeOD): δ 7.70 (d, J = 7.8 Hz, 2H), 7.47 (dd, J = 8.7, 2.4 Hz, 2H), 7.18-7.13 (m, 2H), 6.94-6.84 (m, 2H), 4.29 (s, 2H), 3.82 (d, J = 6.0 Hz, 3H), 3.55-3.51 (m, 3H), 3.44-3.31 (m, 5H), 2.59-2.56 (m, 2H), 2.16 (s, 3H), 2.10-1.92 (m, 1H), 1.86-1.50 (m, 5H), 1.23-1.17 (m, 3H). |
| 171 | 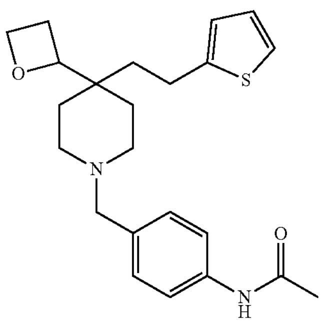 [SMILES: CC(=O)Nc1ccc(CN2CCC(CCc3cccs3)(C3CCO3)CC2)cc1] | N-(4-((4-(oxetan-2-yl)-4-(2-(thiophen-2-yl)ethyl)piperidin-1-yl)methyl)phenyl)acetamide | 399 | ¹H NMR (300 MHz, MeOD): δ 7.54 (d, J = 9.0 Hz, 2H), 7.31 (d, J = 6.0 Hz, 2H), 7.15 (d, J = 6.0 Hz, 1H), 6.89 (d, J = 9.0 Hz, 1H), 6.81-6.80 (m, 1H), 4.90-4.86 (m, 1H), 4.66-4.64 (m, 1H), 4.38-4.35 (m, 1H), 3.64 (s, 2H), 2.85-2.65 (m, 5H), 2.53-2.44 (m, 3H), 2.12 (s, 3H), 1.88-1.75 (m, 4H), 1.56-1.52 (m, 2H). |
| 172 | 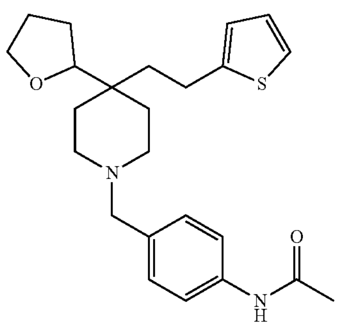 [SMILES: CC(=O)Nc1ccc(CN2CCC(CCc3cccs3)(C3CCCO3)CC2)cc1] | N-(4-((4-(tetrahydrofuran-2-yl)-4-(2-(thiophen-2-yl)ethyl)piperidin-1-yl)methyl)phenyl)acetamide | 413 | ¹H NMR (300 MHz, MeOD): δ 7.58 (d, J = 9.0 Hz, 2H), 7.35 (d, J = 9.0 Hz, 2H), 7.15 (d, J = 6.0 Hz, 1H), 6.90-6.87 (m, 1H), 6.82-6.80 (m, 1H), 3.85-3.72 (m, 5H), 2.93-2.84 (m, 4H), 2.82-2.65 (m, 2H), 2.12 (s, 3H), 1.92-1.62 (m, 8H), 1.60-1.48 (m, 2H). |
| 173 | 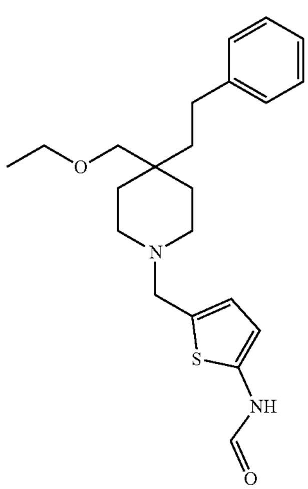 [SMILES: CCOCC1(CCc2ccccc2)CCN(Cc2ccc(NC=O)s2)CC1] | N-(5-((4-(ethoxymethyl)-4-phenethylpiperidin-1-yl)methyl)thiophen-2-yl)formamide | 387 | ¹H NMR (300 MHz, MeOD): δ 8.28 (s, 1H), 7.27-7.23 (m, 5H), 6.88 (d, J = 3.8 Hz, 1H), 6.67-6.59 (m, 1H), 4.01-3.97 (m, 2H), 3.50 (q, J = 7.0 Hz, 2H), 3.36 (s, 2H), 2.84-2.78 (m, 4H), 2.58-2.53 (m, 2H), 1.73-1.65 (m, 6H), 1.21 (t, J = 7.0 Hz, 3H). |

TABLE III-continued

| Compound. | Structure | Name | MS (ESI+): [M + H]+ | H-NMR |
|---|---|---|---|---|
| 174 | 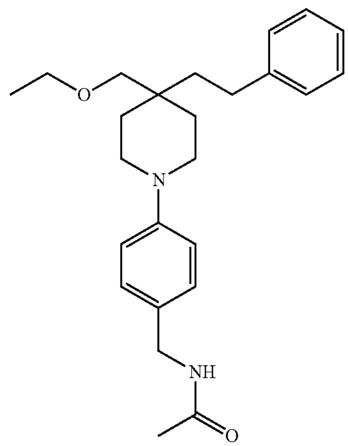 [SMILES: CCOCC1(CCc2ccccc2)CCN(c2ccc(CNC(C)=O)cc2)CC1] | N-(4-(4-(ethoxymethyl)-4-phenethylpiperidin-1-yl)benzyl)acetamide | 395 | ¹H NMR (300 MHz, CDCl₃): δ 7.32-7.26 (m, 2H), 7.22-7.17 (m, 5H), 6.91 (d, J = 8.7 Hz, 2H), 5.78 (brs, 1H), 4.33 (d, J = 5.4 Hz, 2H), 3.52 (q, J = 6.9 Hz, 2H), 3.37 (s, 2H), 3.23-3.13 (m, 4H), 2.64-2.58 (m, 2H), 2.00 (s, 3H), 1.79-1.63 (m, 6H), 1.24 (t, J = 7.0 Hz, 3H). |
| 175 | 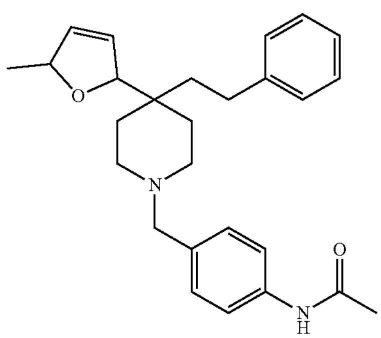 [SMILES: CC(=O)Nc1ccc(CN2CCC(CCc3ccccc3)(C3C=CC(C)O3)CC2)cc1] | N-(4-((4-(5-methyl-2,5-dihydrofuran-2-yl)-4-phenethylpiperidin-1-yl)methyl)phenyl)acetamide | 419 | ¹H NMR (300 MHz, MeOD): δ 7.68 (d, J = 8.4 Hz, 2H), 7.46 (d, J = 8.7 Hz, 2H), 7.28-7.17 (m, 5H), 6.05-5.90 (m, 2H), 4.19 (s, 2H), 3.36-3.08 (m, 4H), 2.71-2.56 (m, 2H), 2.15 (s, 3H), 1.97-1.74 (m, 8H), 1.35-1.24 (m, 3H). |
| 176 | 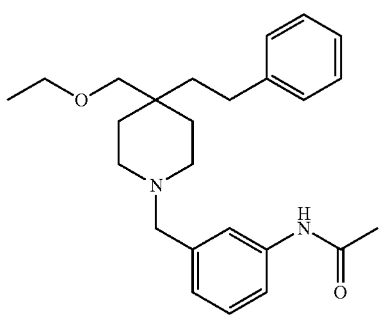 [SMILES: CCOCC1(CCc2ccccc2)CCN(Cc2cccc(NC(C)=O)c2)CC1] | N-(3-((4-(ethoxymethyl)-4-phenethylpiperidin-1-yl)methyl)phenyl)acetamide | 395 | ¹H NMR (300 MHz, CDCl₃) δ 7.56 (d, J = 8.1 Hz, 1H), 7.42 (m, 2H), 7.32-7.29 (m, 1H), 7.26 (d, J = 4.3 Hz, 1H), 7.23-7.15 (m, 3H), 7.08 (d, J = 7.6 Hz, 1H), 3.55 (s, 2H), 3.48 (q, J = 7.0 Hz, 2H), 3.31 (s, 2H), 2.58-2.50 (m, 6H), 2.18 (s, 3H), 1.73-1.52 (m, 6H), 1.22 (t, J = 7.0 Hz, 3H). |
| 177 | 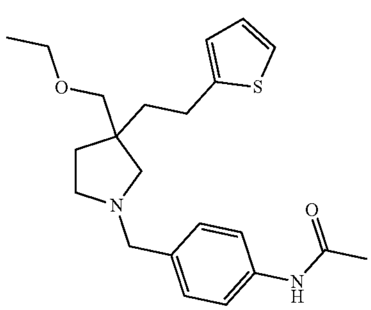 [SMILES: CCOCC1(CCc2cccs2)CCN(Cc2ccc(NC(C)=O)cc2)C1] | N-(4-((3-(ethoxymethyl)-3-(2-(thiophen-2-yl)ethyl)pyrrolidin-1-yl)methyl)phenyl)acetamide | 387 | 1H NMR (300 MHz, MeOD): δ 7.56 (d, J = 9.0 Hz, 2H), 7.33 (d, J = 9.0 Hz, 2H), 7.16-7.13 (m, 1H), 6.89-6.86 (m, 1H), 6.80-6.79 (m, 1H), 3.82 (s, 2H), 3.54-3.47 (m, 2H), 3.36-3.34 (m, 4H), 2.83-2.78 (m, 4H), 2.12 (s, 3H), 1.89-1.78 (m, 4H), 1.19 (t, J = 7.0 Hz, 3H). |

TABLE III-continued

| Compound. | Structure | Name | MS (ESI+): [M + H]+ | H-NMR |
|---|---|---|---|---|
| 178 | 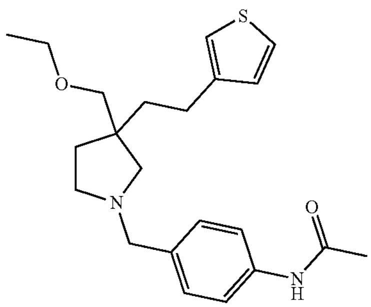 [SMILES: CCOCC1(CCc2ccsc2)CCN(Cc2ccc(NC(C)=O)cc2)C1] | N-(4-((3-(ethoxymethyl)-3-(2-(thiophen-3-yl)ethyl)pyrrolidin-1-yl)methyl)phenyl)acetamide | 387 | $^1$H NMR (300 MHz, MeOD): δ 7.65 (d, J = 9.0 Hz, 2H), 7.42 (d, J = 9.0 Hz, 2H), 7.32-7.29 (m, 1H), 7.03 (s, 1H), 6.97-6.95 (m, 1H), 4.22-4.17 (m, 2H), 3.57-3.41 (m, 2H), 3.31 (s, 2H), 3.27-3.17 (m, 2H), 3.08-2.85(m, 2H), 2.64 (t, J = 6.0 Hz, 2H), 2.13 (s, 3H), 2.11-1.88 (m, 4H), 1.21 (t, J = 9.0 Hz, 3H). |
| 179 | 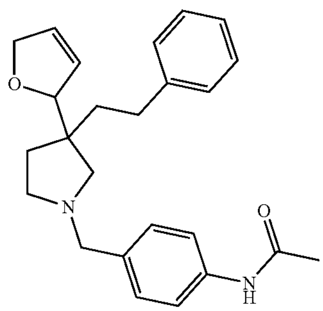 [SMILES: CC(=O)Nc1ccc(CN2CCC(CCc3ccccc3)(C3C=CCO3)C2)cc1] | N-(4-((3-(2,5-dihydrofuran-2-yl)-3-phenethylpyrrolidin-1-yl)methyl)phenyl)acetamide | 391 | $^1$H NMR (300 MHz, MeOD): δ 7.55 (dd, J = 8.4, 1.5 Hz, 2H), 7.32 (d, J = 8.7 Hz, 2H), 7.23-7.12 (m, 5H), 6.10-6.08 (m, 1H), 5.93-5.86 (m, 1H), 4.91 (m, 1H), 4.61-4.57 (m, 2H), 3.79-3.73 (m, 2H), 2.92-2.55 (m, 6H), 2.11 (s, 3H), 1.95-1.72 (m, 4H) |
| 180 | 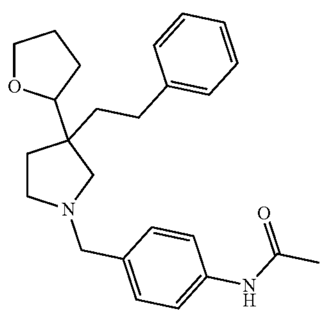 [SMILES: CC(=O)Nc1ccc(CN2CCC(CCc3ccccc3)(C3CCCO3)C2)cc1] | N-(4-((3-phenethyl-3-(tetrahydrofuran-2-yl)pyrrolidin-1-yl)methyl)phenyl)acetamide | 393 | $^1$H NMR (300 MHz, MeOD): δ 7.59 (d, J = 9.0 Hz, 2H), 7.39 (d, J = 9.0 Hz, 2H), 7.27-7.14 (m, 5H), 4.12-3.76 (m, 4H), 3.12-2.61 (m, 5H), 2.13 (s, 3H), 2.04-1.71 (m, 10H). |
| 181 | 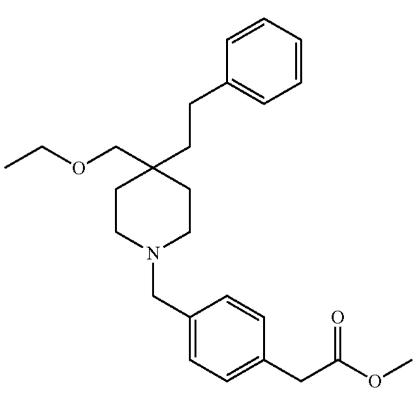 [SMILES: CCOCC1(CCc2ccccc2)CCN(Cc2ccc(CC(=O)OC)cc2)CC1] | methyl 2-(4-((4-(ethoxymethyl)-4-phenethylpiperidin-1-yl)methyl)phenyl)acetate | 410 | $^1$H NMR (300 MHz, MeOD): δ 7.50-7.40 (m, 4H), 7.27-7.14 (m, 5H), 4.32 (s, 2H), 3.73 (s, 2H), 3.70 (s, 3H), 3.52 (q, J = 6.9 Hz, 2H), 3.34-3.31 (m, 6H), 2.62-2.56 (m, 2H), 2.15-1.52 (m, 6H), 1.20 (t, J = 6.9 Hz, 3H). |

TABLE III-continued

| Compound. | Name | MS (ESI+): [M + H]+ | H-NMR |
|---|---|---|---|
| 182 | N-(4-((4-(2,5-dihydrofuran-2-yl)-4-(2-(thiophen-2-yl)ethyl)piperidin-1-yl)methyl)phenyl)acetamide | 411 | ¹H NMR (300 MHz, MeOD): δ 7.57 (d, J = 9.0 Hz, 2H), 7.34 (d, J = 9.0 Hz, 2H), 7.15 (d, J = 6.0 Hz, 1H), 6.90-6.87 (m, 1H), 6.81-6.80 (m, 1H), 6.09-6.06 (m, 1H), 5.95-5.94 (m, 1H), 4.81-4.76 (m, 1H), 4.62-4.60 (m, 2H), 3.79 (s, 2H), 2.91-2.81 (m, 4H), 2.82-2.55 (m, 2H), 2.12 (s, 3H), 1.81-1.73 (m, 4H), 1.62-1.48 (m, 2H). |
| 183 | N-(4-((4-(pyridin-2-yl)-4-(2-(thiophen-2-yl)ethyl)piperidin-1-yl)methyl)phenyl)acetamide | 420 | 1H NMR (300 MHz, MeOD): δ 8.61-8.59 (dd, J = 3.3, 0.3 Hz, 1H), 7.84-7.83 (m, 1H), 7.61-7.52 (m, 3H), 7.35-7.29 (m, 3H), 7.10-7.08 (m, 1H), 6.83-6.80 (m, 1H), 6.64-6.62 (m, 1H), 3.90 (s, 2H), 3.09 (m, 2H), 2.80-2.60 (m, 4H), 2.46-2.41 (m, 2H), 2.12 (s, 3H), 2.06-1.94 (m, 4H). |
| 184 | N-(4-((4-(pyridin-2-yl)-4-(2-(thiophen-3-yl)ethyl)piperidin-1-yl)methyl)phenyl)acetamide | 420 | ¹H NMR (300 MHz, MeOD): δ 8.57-8.55 (m, 1H), 7.80-7.79 (m, 1H), 7.56-7.47 (m, 3H), 7.29-7.19 (m, 4H), 6.83-6.74 (m, 2H), 3.62 (s, 2H), 2.96-2.81 (m, 2H), 2.68-2.39 (m, 4H), 2.24-2.20 (m, 2H), 2.11 (s, 3H), 2.01-1.92 (m, 4H). |
| 185 | N-(4-((4-(oxetan-2-yl)-4-(2-(thiophen-3-yl)ethyl)piperidin-1-yl)methyl)phenyl)acetamide | 399 | ¹H NMR (300 MHz, MeOD): δ 7.67 (dd, J = 6.9, 0.9 Hz, 2H), 7.45 (d, J = 9.00 Hz, 2H), 7.32-7.30 (m, 1H), 7.06 (s, 1H), 6.98 (d, J = 6.00 Hz, 1H), 4.92 (s, 1H), 4.67-4.63 (m, 1H), 4.39-4.34 (m, 1H), 4.25 (s, 2H), 3.51-3.34 (m, 2H), 3.32-3.29 (m, 2H), 2.66-2.53 (m, 4H), 2.14 (s, 3H), 2.11-1.69 (m, 6H). |

TABLE III-continued

| Compound. | Structure | Name | MS (ESI+): [M + H]+ | H-NMR |
|---|---|---|---|---|
| 186 | 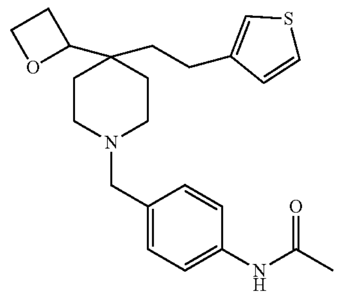 [SMILES: CC(=O)Nc1ccc(CN2CCC(CCc3ccsc3)(C3CCO3)CC2)cc1] | N-(4-((4-(tetrahydrofuran-2-yl)-4-(2-(thiophen-3-yl)ethyl)piperidin-1-yl)methyl)phenyl)acetamide | 413 | ¹H NMR (300 MHz, MeOD): δ 7.62 (dd, J = 6.9, 0.9 Hz, 2H), 7.43 (d, J = 9.00 Hz, 2H), 7.06 (d, J = 3.00 Hz, 1H), 7.06-6.98 (m, 2H), 4.18 (s, 2H), 3.82-3.71 (m, 3H), 3.35 (s, 2H), 3.12-3.09 (m, 2H), 2.67-2.63 (m, 2H), 2.13 (s, 3H), 1.99-1.88 (m, 6H), 1.76-1.65 (m, 4H). |
| 187 | 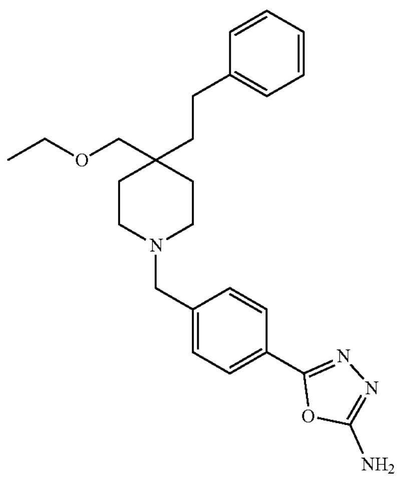 [SMILES: CCOCC1(CCc2ccccc2)CCN(Cc2ccc(-c3nnc(N)o3)cc2)CC1] | 5-(4-((4-(ethoxymethyl)-4-phenethylpiperidin-1-yl)methyl)phenyl)-1,3,4-oxadiazol-2-amine | 421 | ¹H NMR (300 MHz, MeOD): δ 7.86 (d, J = 8.4 Hz, 2H), 7.50 (d, J = 8.4 Hz, 2H), 7.23-7.20 (m, 2H), 7.18-7.09 (m, 3H), 3.64 (s, 2H), 3.49 (q, J = 6.9 Hz, 2H), 3.33 (s, 2H), 2.57-2.51 (m, 6H), 1.75-1.47 (m, 6H), 1.19 (t, J = 7.0 Hz, 3H). |
| 188 | 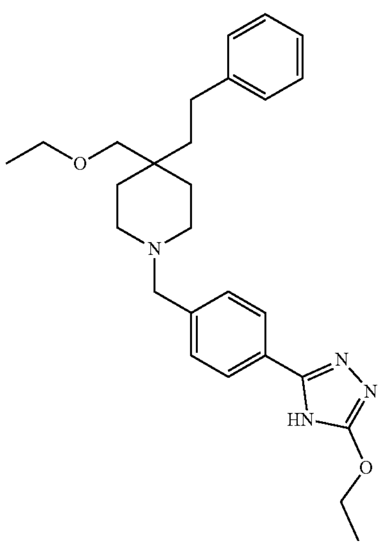 [SMILES: CCOCC1(CCc2ccccc2)CCN(Cc2ccc(-c3nnc(OCC)[nH]3)cc2)CC1] | 1-(4-(5-ethoxy-4H-1,2,4-triazol-3-yl)benzyl)-4-(ethoxymethyl)-4-phenethylpiperidine | 449 | ¹H NMR (300 MHz, MeOD): δ 7.95 (d, J = 9.0 Hz, 2H), 7.54 (d, J = 9.0 Hz, 2H), 7.24-7.13 (m, 5H), 4.41 (q, J = 6.9 Hz, 2H), 3.94 (s, 2H), 3.49 (q, J = 6.9 Hz, 2H), 3.31 (s, 2H), 2.86 (m, 4H), 2.58-2.52 (m, 2H), 1.74-1.64 (m, 6H), 1.43 (t, J = 7.1 Hz, 3H), 1.19 (t, J = 7.0 Hz, 3H). |

TABLE III-continued

| Compound. | Structure | Name | MS (ESI+): [M + H]+ | H-NMR |
|---|---|---|---|---|
| 189 | 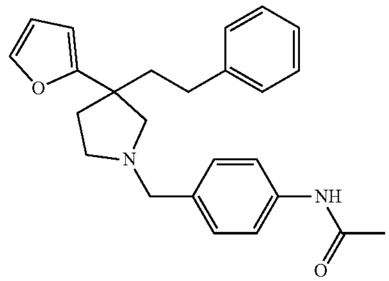 [SMILES: CC(=O)Nc1ccc(CN2CCC(CCc3ccccc3)(c3ccco3)C2)cc1] | N-(4-((3-(furan-2-yl)-3-phenethylpyrrolidin-1-yl)methyl)phenyl)acetamide | 389 | $^1$H NMR (300 MHz, MeOD): δ 7.52 (d, J = 9.0 Hz, 2H), 7.45 (s, 1H), 7.28 (d, J = 9.0 Hz, 2H), 7.20-7.04 (m, 5H), 6.35 (dd, J = 3.2, 1.9 Hz, 1H), 6.20 (d, J = 3.0 Hz, 1H), 3.71-3.70 (m, 2H), 3.32 (s, 2H), 3.06 (d, J = 9.0 Hz, 1H), 2.86-2.76 (m, 3H), 2.36-2.25 (m, 2H), 2.06 (s, 3H), 2.03-1.98 (m, 2H). |
| 190 | 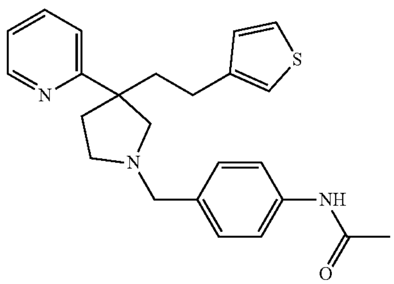 [SMILES: CC(=O)Nc1ccc(CN2CCC(CCc3ccsc3)(c3ccccn3)C2)cc1] | N-(4-((3-(pyridin-2-yl)-3-(2-(thiophen-3-yl)ethyl)pyrrolidin-1-yl)methyl)phenyl)acetamide | 406 | $^1$H NMR (300 MHz, MeOD): δ 8.52 (d, J = 4.2 Hz, 1H), 7.83-7.77 (m, 1H), 7.56 (d, J = 8.4 Hz, 2H), 7.48 (d, J = 8.1 Hz, 1H), 7.35 (d, J = 8.4 Hz, 2H), 7.29-7.21 (m, 2H), 6.86 (s, 1H), 6.80 (d, J = 4.8 Hz, 1H), 3.90 (q, J = 6.9 Hz, 2H), 3.54-3.51 (m, 1H), 3.12-2.89 (m, 3H), 2.56-2.41 (m, 1H), 2.38-2.14 (m, 5H), 2.12 (s, 3H). |
| 191 | 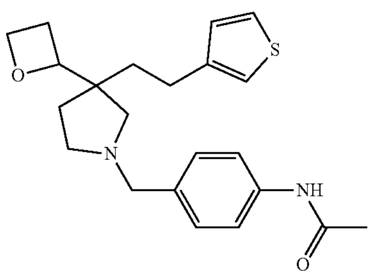 [SMILES: CC(=O)Nc1ccc(CN2CCC(CCc3ccsc3)(C3CCO3)C2)cc1] | N-(4-((3-(oxetan-2-yl)-3-(2-(thiophen-3-yl)ethylpyrrolidin-1-yl)methyl)phenyl)acetamide | 385 | $^1$H NMR (300 MHz, MeOD): δ 7.65-7.59 (m, 2H), 7.44-7.32 (m, 2H), 7.31-7.29 (m, 1H), 7.03 (d, J = 1.5 Hz, 1H), 6.95-6.93 (m, 1H), 4.96-4.92 (m, 1H), 4.75-4.65 (m, 1H), 4.48-4.39 (m, 1H), 4.28-4.09 (m, 2H), 3.31-3.30 (m, 2H), 3.16-2.89 (m, 2H), 2.62-2.53 (m, 4H), 2.12 (s, 3H), 2.12-1.78 (m, 4H). |
| 192 | 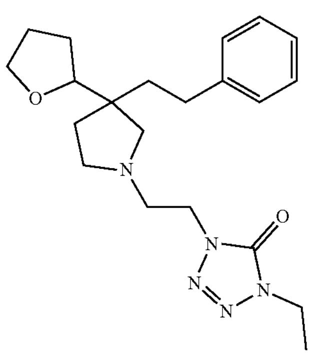 [SMILES: CCn1nnn(CCN2CCC(CCc3ccccc3)(C3CCCO3)C2)c1=O] | 1-ethyl-4-(2-(3-phenethyl-3-(tetrahydrofuran-2-yl)pyrrolidin-1-yl)ethyl)-1H-tetrazol-5(4H)-one | 386 | $^1$H NMR (300 MHz, MeOD): δ 7.28-7.17 (m, 5H), 4.49-4.41 (m, 2H), 4.05-3.92 (m, 3H), 3.90-3.58 (m, 6H), 3.01-2.86 (m, 1H), 2.69-2.60 (m, 2H), 2.30-2.20 (m, 1H), 2.05-1.99 (m, 4H), 1.90-1.59 (m, 4H), 1.45-1.40 (m, 3H). |

TABLE III-continued

| Compound. | Structure | Name | MS (ESI+): [M + H]+ | H-NMR |
|---|---|---|---|---|
| 193 | 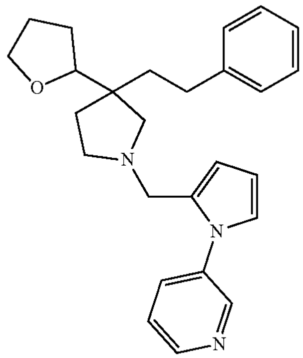 [SMILES: c1ccc(CCC2(C3CCCO3)CCN(Cc3cccn3-c3cccnc3)C2)cc1] | 3-(2-((3-phenethyl-3-(tetrahydrofuran-2-yl)pyrrolidin-1-yl)methyl)-1H-pyrrol-1-yl)pyridine | 402 | ¹H NMR (300 MHz, MeOD): δ 8.74 (s, 1H), 8.45 (d, J = 3.7 Hz, 1H), 8.06 (dd, J = 5.4, 2.8 Hz, 1H), 7.48 (dd, J =8.2, 4.8 Hz, 1H), 7.28-7.18 (m, 2H), 7.13-7.11 (m, 3H), 6.93-6.94 (m, 1H), 6.25 (dd, J = 7.7, 4.7 Hz, 2H), 3.83-3.18 (m, 4H), 2.47-2.55 (m, 6H), 1.86-1.80 (m, 3H), 1.62-1.54 (m, 6H). |
| 194 | 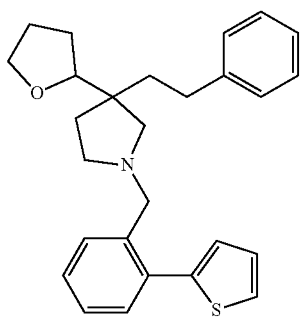 [SMILES: c1ccc(CCC2(C3CCCO3)CCN(Cc3ccccc3-c3cccs3)C2)cc1] | 3-phenethyl-3-(tetrahydrofuran-2-yl)-1-(2-(thiophen-2-yl)benzyl)pyrrolidine | 418 | ¹H NMR (300 MHz, MeOD): δ 7.59-7.57 (m, 2H), 7.52-7.49 (m, 3H), 7.29-7.16 (m, 7H), 4.49-4.34 (m, 2H), 3.91-3.37 (m, 3H), 3.20-3.01 (m, 2H), 2.63-2.59 (m, 3H), 1.98-1.91 (m, 5H), 1.89-1.81 (m, 4H). |
| 195 | 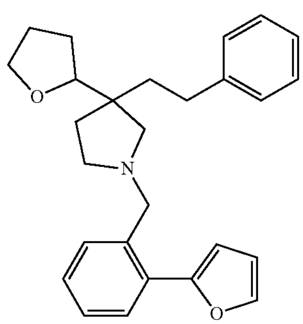 [SMILES: c1ccc(CCC2(C3CCCO3)CCN(Cc3ccccc3-c3ccco3)C2)cc1] | 1-(2-(furan-2-yl)benzyl)-3-phenethyl-3-(tetrahydrofuran-2-yl)pyrrolidine | 402 | 1H NMR (300 MHz, MeOD): δ 7.82 (dd, J = 8.7, 4.6 Hz, 2H), 7.63-7.51 (m, 2H), 7.48 (dd, J = 10.7, 4.4 Hz, 1H), 7.36-7.16 (m, 5H), 6.97 (d, J = 3.3 Hz, 1H), 6.70 (dd, J = 3.4, 1.9 Hz, 1H), 4.58 (t, J = 10.3 Hz, 2H), 4.05 (dd, J = 9.4, 6.2 Hz, 1H), 3.91-3.80 (m, 1H), 3.78-3.69 (m, 1H), 3.68-3.60 (m, 2H), 3.55-3.36 (m, 2H), 2.78-2.66 (m, 1H), 2.65-2.53 (m, 1H), 2.27-2.12 (m, 1H), 2.05-1.86 (m, 6H), 1.68-1.58 (m, 1H). |
| 196 | 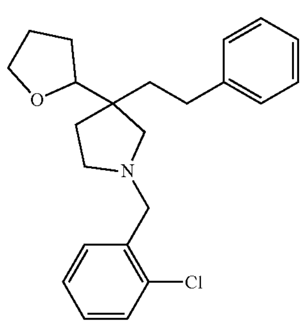 [SMILES: Clc1ccccc1CN1CCC(CCc2ccccc2)(C2CCCO2)C1] | 1-(2-chlorobenzyl)-3-phenethyl-3-(tetrahydrofuran-2-yl)pyrrolidine | 370 | ¹H NMR (300 MHz, MeOD): δ 7.56-7.55 (m, 1H), 7.47-7.36 (m, 1H), 7.35-7.16 (m, 7H), 3.99-3.76 (m, 5H), 2.94-2.65 (m, 6H), 1.96-1.75 (m, 8H). |

TABLE III-continued

| Compound. | Structure | Name | MS (ESI+): [M + H]+ | H-NMR |
|---|---|---|---|---|
| 197 | 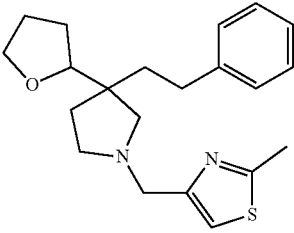 [SMILES: Cc1nc(CN2CCC(CCc3ccccc3)(C3CCCO3)C2)cs1] | 2-methyl-4-((3-phenethyl-3-(tetrahydrofuran-2-yl)pyrrolidin-1-yl)methyl)thiazole | 357 | ¹H NMR (400 MHz, MeOD): δ 7.61-7.59 (m, 1H), 7.31-7.19 (m, 5H), 4.77-4.47 (m, 2H), 4.04-3.96 (m, 2H), 3.84-3.54 (m, 4H), 3.37-3.33 (m, 2H), 2.77 (s, 3H), 2.70-2.66 (m, 2H), 2.44-2.33 (m, 1H), 2.05-1.82 (m, 6H). |
| 198 | 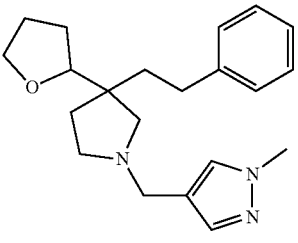 [SMILES: Cn1cc(CN2CCC(CCc3ccccc3)(C3CCCO3)C2)cn1] | 1-methyl-4-((3-phenethyl-3-(tetrahydrofuran-2-yl)pyrrolidin-1-yl)methyl)-1H-pyrazole | 340 | ¹H NMR (300 MHz, MeOD): δ 7.82 (d, J = 9.0 Hz, 1H), 7.63 (d, J = 7.2 Hz, 1H), 7.32-7.19 (m, 5H), 4.62-4.21 (m, 2H), 4.01-3.79 (m, 5H), 3.41-3.34 (m, 2H), 3.21-3.05 (m, 2H), 2.70-2.66 (m, 2H), 2.38-2.18 (m, 2H), 2.07-1.84 (m, 6H), 1.81-1.50 (m, 1H). |
| 199 | 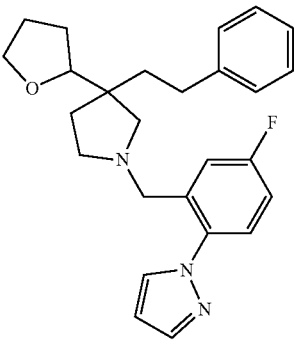 [SMILES: Fc1ccc(-n2cccn2)c(CN2CCC(CCc3ccccc3)(C3CCCO3)C2)c1] | 1-(4-fluoro-2-((3-phenethyl-3-(tetrahydrofuran-2-yl)pyrrolidin-1-yl)methyl)phenyl)-1H-pyrazole | 420 | ¹H NMR (300 MHz, MeOD): δ 8.11 (d, J = 9.5 Hz, 1H), 7.80 (s, 1H), 7.64-7.41 (m, 2H), 7.23-7.15 (m, 6H), 6.59 (s, 1H), 3.95-3.64 (m, 5H), 3.46-3.42 (m, 1H), 2.69-2.63 (m, 3H), 2.35-2.32 (m, 1H), 2.05-1.56 (m, 9H). |
| 200 | 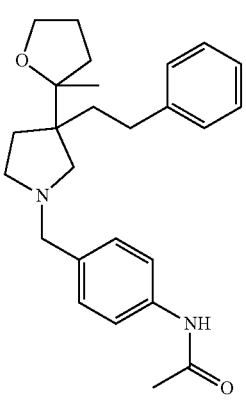 [SMILES: CC(=O)Nc1ccc(CN2CCC(CCc3ccccc3)(C3(C)CCCO3)C2)cc1] | N-(4-((3-(2-methyltetrahydrofuran-2-yl)-3-phenethylpyrrolidin-1-yl)methyl)phenyl)acetamide | 407 | ¹H NMR (300 MHz, MeOD): δ 7.68-6.64 (m, 2H), 7.47-7.43 (m, 2H), 7.29-7.16 (m, 5H), 4.34-4.25 (m, 1H), 4.17-4.13 (m, 1H), 3.89-3.85 (m, 2H), 3.48-3.89 (m, 1H), 3.23-2.91 (m, 3H), 2.67-2.61 (m, 2H), 2.13-1.93 (m, 7H), 1.79-1.69 (m, 4H), 1.17 (d, J = 12.0 Hz, 3H). |

TABLE III-continued

| Compound. | Structure | Name | MS (ESI+): [M + H]+ | H-NMR |
|---|---|---|---|---|
| 201 | 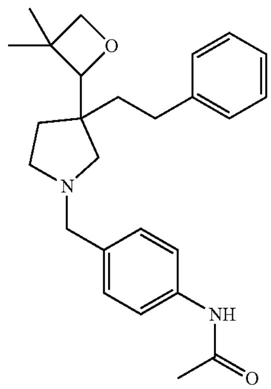 [SMILES: CC(=O)Nc1ccc(CN2CCC(CCc3ccccc3)(C3OCC3(C)C)C2)cc1] | N-(4-((3-(3,3-dimethyloxetan-2-yl)-3-phenethylpyrrolidin-1-yl)methyl)phenyl)acetamide | 407 | $^1$H NMR (400 MHz, MeOD): δ 7.58-7.54 (m, 2H), 7.39-7.31 (m, 2H), 7.20-7.15 (m, 2H), 7.08 (d, J = 7.2 Hz, 3H), 4.81-4.59 (m, 1H), 4.27-4.01 (m, 4H), 3.32-3.10 (m, 3H), 2.71-2.45 (m, 3H), 2.04 (s, 3H), 1.95-1.70 (m, 4H), 1.28 (s, 3H), 1.19 (s, 3H). |
| 202 | 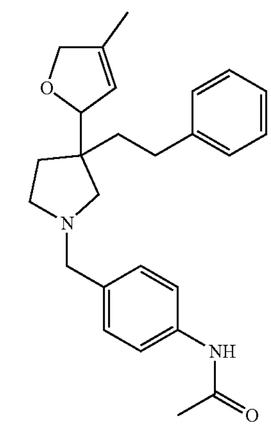 [SMILES: CC(=O)Nc1ccc(CN2CCC(CCc3ccccc3)(C3C=C(C)CO3)C2)cc1] | N-(4-((3-(4-methyl-2,5-dihydrofuran-2-yl)-3-phenethylpyrrolidin-1-yl)methyl)phenyl)acetamide | 406 | $^1$H NMR (300 MHz, MeOD): δ 7.59 (t, J = 8.4 Hz, 2H), 7.37 (d, J = 8.5 Hz, 2H), 7.29-7.12 (m, 5H), 5.51 (s, 1H), 4.58-4.36 (m, 2H), 4.10-3.88 (m, 2H), 3.05-2.63 (m, 7H), 2.18-2.11 (m, 3H), 2.08-1.90 (m, 2H), 1.85-1.70 (m, 6H). |
| 203 | 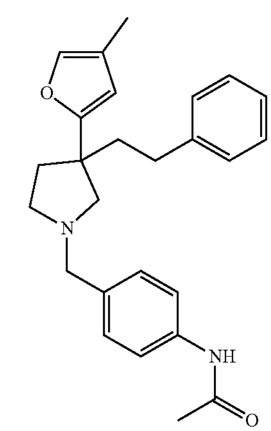 [SMILES: CC(=O)Nc1ccc(CN2CCC(CCc3ccccc3)(c3cc(C)co3)C2)cc1] | N-(4-((3-(4-methylfuran-2-yl)-3-phenethylpyrrolidin-1-yl)methyl)phenyl)acetamide | 403 | $^1$H NMR (300 MHz, MeOD): δ 7.81-7.65 (m, 1H), 7.57-7.30 (m, 3H), 7.22-7.05 (m, 6H), 6.12 (s, 1H), 3.88-3.86 (m, 2H), 2.89 (m, 4H), 2.38-2.01 (m, 12H). |

TABLE III-continued

| Compound. | Structure | Name | MS (ESI+): [M + H]+ | H-NMR |
|---|---|---|---|---|
| 204 | 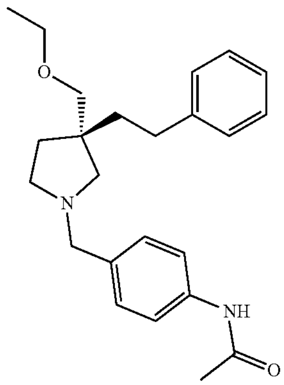 [SMILES: CCOC[C@@]1(CCc2ccccc2)CCN(Cc2ccc(NC(C)=O)cc2)C1] | (S)-N-(4-((3-(ethoxymethyl)-3-phenethylpyrrolidin-1-yl)methyl)phenyl)acetamide | 381 | $^1$H NMR (300 MHz, MeOD): δ 7.66 (d, J = 8.7 Hz, 2H), 7.43 (d, J = 8.4 Hz, 2H), 7.27-7.15 (m, 5H), 4.26 (d, J = 12.9 Hz, 1H), 4.22 (d, J = 12.9 Hz, 1H), 3.56-3.53 (m, 2H), 3.44-3.41 (m, 3H), 3.22-3.29 (m, 2H), 3.06 (d, J = 11.9 Hz, 1H), 2.63-2.55 (m, 2H), 2.13 (s, 3H), 2.04-1.99 (m, 2H), 1.87-1.81 (m, 2H), 1.21 (t, J = 7.0 Hz, 3H). |
| 205 | 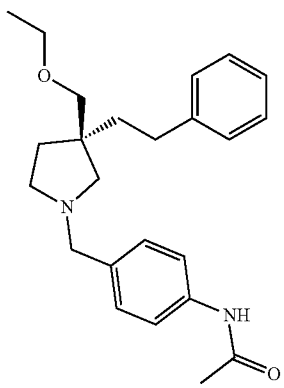 [SMILES: CCOC[C@]1(CCc2ccccc2)CCN(Cc2ccc(NC(C)=O)cc2)C1] | (R)-N-(4-((3-(ethoxymethyl)-3-phenethylpyrrolidin-1-yl)methyl)phenyl)acetamide | 381 | $^1$H NMR (300 MHz, MeOD): δ 7.59 (d, J = 8.4 Hz, 2H), 7.36 (d, J = 8.4 Hz, 2H), 7.24-7.14 (m, 5H), 3.95-3.92 (m, 2H), 3.52 (q, J = 6.9 Hz, 2H), 3.39 (s, 2H), 3.12-2.90 (m, 3H), 2.74 (d, J = 10.7 Hz, 1H), 2.59-2.53 (m, 2H), 2.12 (s, 3H), 1.86-1.76 (m, 4H), 1.20 (t, J = 7.0 Hz, 3H). |
| 206 | 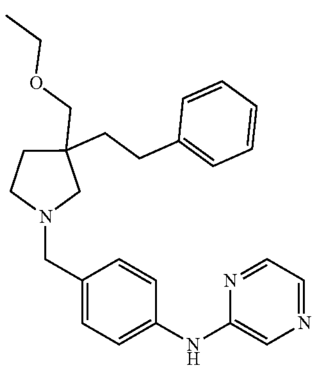 [SMILES: CCOCC1(CCc2ccccc2)CCN(Cc2ccc(Nc3cnccn3)cc2)C1] | N-(4-((3-(ethoxymethyl)-3-phenethylpyrrolidin-1-yl)methyl)phenyl)pyrazin-2-amine | 417 | $^1$H NMR (300 MHz, MeOD): δ 8.14 (d, J = 1.2 Hz, 1H), 8.10 (dd, J = 2.7, 1.4 Hz, 1H), 7.83 (d, J = 2.8 Hz, 1H), 7.74-7.71 (d, J = 7.5 Hz, 2H), 7.36-7.33 (d, J = 8.4 Hz, 2H), 7.24-7.12 (m, 5H), 3.86-3.85 (m, 2H), 3.52-3.46 (m, 2H), 3.32 (s, 2H), 2.97-2.85 (m, 3H), 2.67 (d, J = 10.8 Hz, 1H), 2.55-2.50 (m, 2H), 1.82-1.75 (m, 4H), 1.19 (t, J = 7.0 Hz, 3H). |
| 207 | 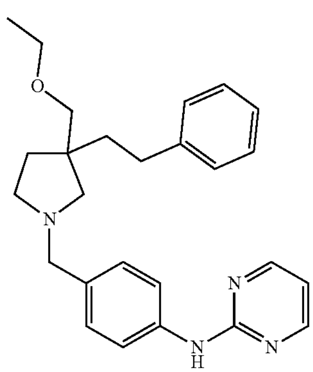 [SMILES: CCOCC1(CCc2ccccc2)CCN(Cc2ccc(Nc3ncccn3)cc2)C1] | N-(4-((3-(ethoxymethyl)-3-phenethylpyrrolidin-1-yl)methyl)phenyl)pyrimidin-2-amine | 417 | $^1$H NMR (300 MHz, MeOD): δ 8.65 (d, J = 3.9 Hz, 2H), 7.98 (dd, J = 6.6, 1.8 Hz, 2H), 7.61-7.57 (m, 2H), 7.29-7.08 (m, 6H), 4.46-4.34 (m, 2H), 3.62-3.37 (m, 8H), 2.65-2.62 (m, 2H), 2.22-1.78 (m, 4H), 1.21 (t, J = 7.0 Hz, 3H). |

TABLE III-continued

| Compound. | Structure | Name | MS (ESI+): [M + H]+ | H-NMR |
|---|---|---|---|---|
| 208 | 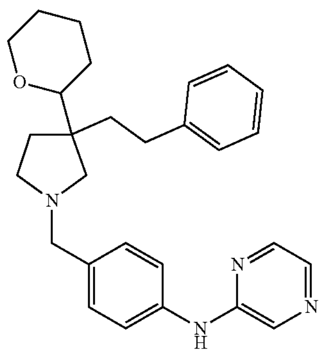 [SMILES: c1ccc(CCC2(C3CCCCO3)CCN(Cc3ccc(Nc4cnccn4)cc3)C2)cc1] | N-(4-((3-phenethyl-3-(tetrahydro-2H-pyran-2-yl)pyrrolidin-1-yl)methyl)phenyl)acetamide | 407 | ¹H NMR (400 MHz, MeOD): δ 7.71 (dd, J = 6.3, 2.1 Hz, 2H), 7.50-7.42 (m, 2H), 7.29-7.18 (m, 5H), 4.45-4.02 (m, 3H), 3.72-3.46 (m, 4H), 3.34-3.01 (m, 2H), 2.63-2.16 (m, 4H), 2.17 (s, 3H), 1.94-1.60 (m, 5H), 1.59-1.55 (m, 3H). |
| 209 | 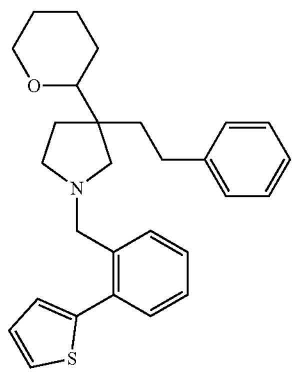 [SMILES: c1ccc(CCC2(C3CCCCO3)CCN(Cc3ccccc3-c3cccs3)C2)cc1] | 3-phenethyl-3-(tetrahydro-2H-pyran-2-yl)-1-(2-(thiophen-2-yl)benzyl)pyrrolidine | 432 | ¹H NMR (300 MHz, MeOD): δ 7.65-7.61 (m, 2H), 7.51-7.61 (m, 3H), 7.29-7.15 (m, 7H), 4.49 (s, 2H), 3.98-3.91 (m, 1H), 3.41-3.22 (m, 5H), 2.94-2.74 (m, 1H), 2.58-2.53 (m, 2H), 2.28-2.04 (m, 2H), 1.89-1.51 (m, 8H). |
| 210 | 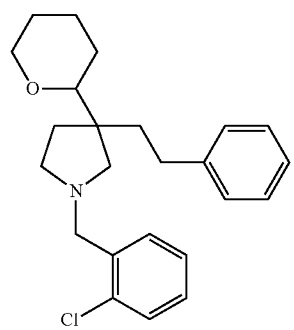 [SMILES: Clc1ccccc1CN1CCC(CCc2ccccc2)(C2CCCCO2)C1] | 1-(2-chlorobenzyl)-3-phenethyl-3-(tetrahydro-2H-pyran-2-yl)pyrrolidine | 384 | ¹H NMR (300 MHz, MeOD): δ 7.57-7.49 (m, 2H), 7.41-7.18 (m, 7H), 4.72 (s, 1H), 4.14-4.04 (m, 2H), 3.41-3.34 (m, 2H), 3.15-2.58 (m, 5H), 2.28-2.04 (m, 2H), 1.84-1.28 (m, 8H). |
| 211 | 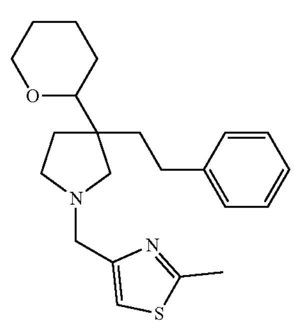 [SMILES: Cc1nc(CN2CCC(CCc3ccccc3)(C3CCCCO3)C2)cs1] | 2-methyl-4-((3-phenethyl-3-(tetrahydro-2H-pyran-2-yl)pyrrolidin-1-yl)methyl)thiazole | 371 | ¹H NMR (300 MHz, MeOD): δ 7.59-7.58 (m, 1H), 7.31-7.20 (m, 5H), 4.51-4.38 (m, 2H), 4.14-4.04 (m, 1H), 3.73-3.45 (m, 5H), 3.23-3.20 (m, 1H), 2.76 (s, 3H), 2.65-2.26 (m, 4H), 1.94-1.59 (m, 8H). |

TABLE III-continued

| Compound. | Name | MS (ESI+): [M + H]⁺ | H-NMR |
|---|---|---|---|
| 212 | 4-((3-phenethyl-3-(tetrahydrofuran-2-yl)pyrrolidin-1-yl)methyl)-1H-pyrazole | 326 | |
| 213 | 1-methyl-4-((3-phenethyl-3-(tetrahydro-2H-pyran-2-yl)pyrrolidin-1-yl)methyl)-1H-pyrazole | 354 | $^1$H NMR (300 MHz, MeOD): δ 7.81 (d, J = 7.5 Hz, 1H), 7.62 (d, J = 6.6 Hz, 1H), 7.30-7.19 (m, 5H), 4.51-4.38 (m, 3H), 3.89 (s, 3H), 3.64-3.44 (m, 4H), 2.74-2.61 (m, 2H), 2.45-2.31 (m, 2H), 2.15-1.74 (m, 6H), 1.57-1.31 (m, 4H). |
| 214 | 1-methyl-3-((3-phenethyl-3-(tetrahydrofuran-2-yl)pyrrolidin-1-yl)methyl)-1H-pyrazole | 340 | $^1$H NMR (300 MHz, MeOD): δ 7.65-7.55 (m, 1H), 7.31-7.19 (m, 6H), 4.53-4.35 (m, 2H), 4.15-4.05 (m, 1H), 3.78-3.55 (m, 4H), 3.25-3.21 (m, 1H), 2.75 (s, 3H), 2.67-2.25 (m, 3H), 1.94-1.59 (m, 8H) |
| 215 | 1-methyl-5-((3-phenethyl-3-(tetrahydrofuran-2-yl)pyrrolidin-1-yl)methyl)-1H-pyrazole | 340 | |
| 216 | N-(4-((3-(3-methyl-2,5-dihydrofuran-2-yl)-3-phenethylpyrrolidin-1-yl)methyl)phenyl)acetamide | 405 | $^1$H NMR (400 MHz, MeOD): δ 7.55-7.53 (m, 2H), 7.29 (d, J = 8.3 Hz, 2H), 7.25-7.23 (m, 2H), 7.16-7.12 (m, 3H), 5.68-5.66 (m, 1H), 4.69-4.67 (m, 1H), 4.49-4.47 (m, 2H), 3.64-3.61 (m, 2H), 2.79-2.52 (m, 6H), 2.13 (s, 3H), 2.12-2.00 (m, 1H), 1.93-1.61 (m, 6H). |

TABLE III-continued

| Compound. | Structure | Name | MS (ESI+): [M + H]+ | H-NMR |
|---|---|---|---|---|
| 217 | 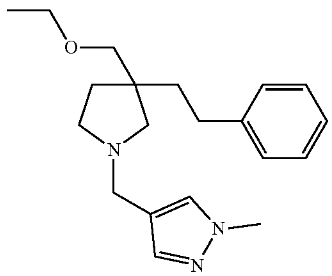 [SMILES: CCOCC1(CCc2ccccc2)CCN(Cc2cnn(C)c2)C1] | 4-((3-(ethoxymethyl)-3-phenethylpyrrolidin-1-yl)methyl)-1-methyl-1H-pyrazole | 328 | ¹H NMR (300 MHz, MeOD): δ 7.71 (s, 1H), 7.54(s, 1H), 7.28-7.15 (m, 5H), 3.98-3.97 (m, 2H), 3.89 (s, 3H), 3.54 (q, J = 6.9 Hz, 2H), 3.49-3.31 (m, 2H), 3.29-3.07 (m, 3H), 2.87-2.75 (m, 1H), 2.57-2.54 (m, 2H), 1.91-1.77 (m, 4H), 1.20 (t, J =6.9 Hz, 3H). |
| 218 | 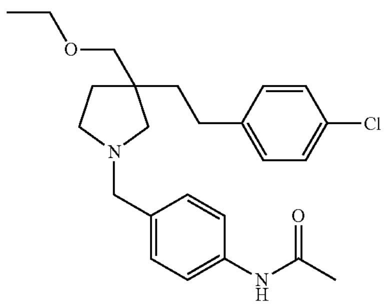 [SMILES: CCOCC1(CCc2ccc(Cl)cc2)CCN(Cc2ccc(NC(C)=O)cc2)C1] | N-(4-((3-(2-chlorophenethyl)-3-(ethoxymethyl)pyrrolidin-1-yl)methyl)phenyl)acetamide | 416 | ¹H NMR (300 MHz, MeOD): δ 7.58-7.52 (m, 2H), 7.49-7.30 (m, 2H), 7.27-7.22 (m, 2H), 7.17-7.14 (m, 2H), 3.88-3.82 (m, 2H), 3.52-3.47 (m, 2H), 3.37 (s, 2H), 2.82-2.59 (m, 2H), 2.58-2.52 (m, 2H), 2.12 (s, 3H), 2.11-2.01 (m, 2H), 1.83-1.75 (m, 4H), 1.21 (t, J = 6.9 Hz, 3H). |
| 219 | 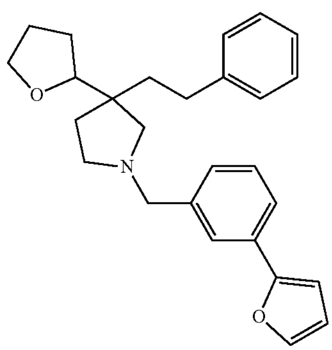 [SMILES: c1ccc(CCC2(C3CCCO3)CCN(Cc3cccc(-c4ccco4)c3)C2)cc1] | 1-(3-(furan-2-yl)benzyl-3-phenethyl-3-(tetrahydrofuran-2-yl)pyrrolidine | 402 | ¹H NMR (300 MHz, MeOD): δ 7.85-7.83 (m, 1H), 7.76 (d, J = 7.6 Hz, 1H), 7.60-7.58 (m, 1H), 7.47 (t, J =1.1 Hz, 1H), 7.36 (dd, J = 7.7, 3.9 Hz, 1H), 7.25-7.14 (m, 5H), 6.86-6.84 (m, 1H), 6.56-6.53 (m, 1H), 4.37-4.22 (m, 1H), 4.14 (d, J = 12.8 Hz, 1H), 3.96-3.86 (m, 2H), 3.83-3.71 (m, 1H), 3.49-3.33 (m, 1H), 3.25-3.00 (m, 2H), 2.74-2.55 (m, 2H), 2.18-2.00 (m, 2H), 2.04-1.73 (m, 6H), 1.66-1.48 (m, 1H). |
| 220 | 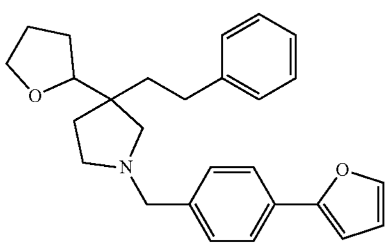 [SMILES: c1ccc(CCC2(C3CCCO3)CCN(Cc3ccc(-c4ccco4)cc3)C2)cc1] | 1-(4-(furan-2-yl)benzyl-3-phenethyl-3-(tetrahydrofuran-2-yl)pyrrolidine | 402 | ¹H NMR (300 MHz, MeOD): δ 7.71 (dd, J =8.3, 2.1 Hz, 2H), 7.56-7.55 (m, 1H), 7.42 (d, J = 6.3 Hz, 2H), 7.25-7.23 (m, 2H), 7.21-7.13 (m, 3H), 6.80-6.77 (m, 1H), 6.52-6.50 (m, 1H), 3.94-3.84 (m, 4H), 3.76 (m, 1H), 2.99 (m, 2H), 2.87-2.75 (m, 1H), 2.64-2.62 (m, 2H), 1.97-1.91 (m, 6H), 1.80-1.66 (m, 2H), 1.63-1.52 (m, 1H). |
| 221 | 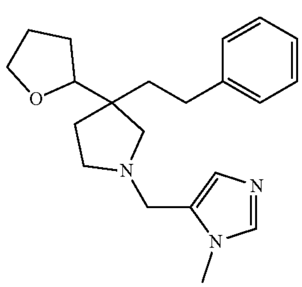 [SMILES: Cn1cncc1CN1CCC(CCc2ccccc2)(C2CCCO2)C1] | 1-methyl-5-((3-phenethyl-3-(tetrahydrofuran-2-yl)pyrrolidin-1-yl)methyl)-1H-imidazole | 340 | ¹H NMR (300 MHz, MeOD): δ 7.57 (s, 1H), 7.25-7.12 (m, 5H), 6.84 (s, 1H), 3.86-3.72 (m, 2H), 3.71 (s, 3H), 3.61-3.59 (m, 3H), 2.66-2.44 (m, 6H), 1.92-1.62 (m, 8H). |

TABLE III-continued

| Compound. | Structure | Name | MS (ESI+): [M + H]+ | H-NMR |
|---|---|---|---|---|
| 222 | 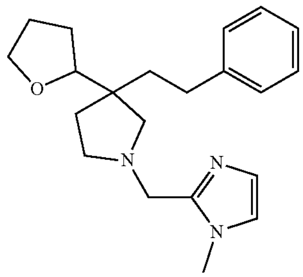 [SMILES: Cn1ccnc1CN1CCC(CCc2ccccc2)(C2CCCO2)C1] | 1-methyl-2-((3-phenethyl-3-(tetrahydrofuran-2-yl)pyrrolidin-1-yl)methyl)-1H-imidazole | 340 | ¹H NMR (300 MHz, MeOD): δ 7.30-7.22 (m, 5H), 7.19-7.17 (m, 1H), 7.11-7.09 (m, 1H), 4.14-3.94 (m, 4H), 3.77 (d, J = 7.8 Hz, 3H), 3.34-3.32 (m, 1H), 2.95-2.80 (m, 3H), 2.75-2.56 (m, 2H), 2.20-2.05 (m, 2H), 2.03-1.92 (m, 3H), 1.89-1.68 (m, 3H), 1.59-1.50 (m, 1H). |
| 223 | 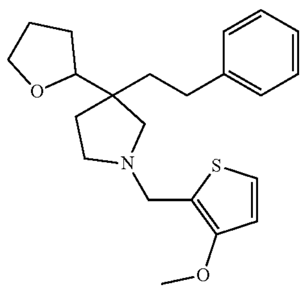 [SMILES: COc1ccsc1CN1CCC(CCc2ccccc2)(C2CCCO2)C1] | 1-((3-methoxythiophen-2-yl)methyl)-3-phenethyl-3-(tetrahydrofuran-2-yl)pyrrolidine | 372 | |
| 224 | 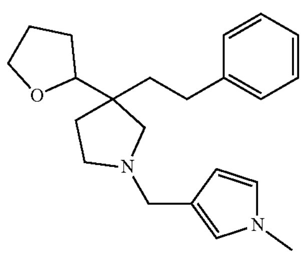 [SMILES: Cn1ccc(CN2CCC(CCc3ccccc3)(C3CCCO3)C2)c1] | 1-methyl-3-((3-phenethyl-3-(tetrahydrofuran-2-yl)pyrrolidin-1-yl)methyl)-1H-pyrrole | 339 | ¹H NMR (300 MHz, MeOD): δ 7.28-7.16 (m, 5H), 6.85 (d, J = 6.9 Hz, 1H), 6.71 (t, J = 2.4 Hz, 1H), 6.18 (dd, J = 4.9, 2.7 Hz, 1H), 4.29-4.16 (m, 1H), 4.11-3.82 (m, 3H), 3.82-3.72 (m, 1H), 3.66 (s, 3H), 3.39-3.30 (m, 1H), 3.20-3.07 (s, 2H), 2.65-2.59 (m, 2H), 2.29-1.89 (m, 5H), 1.83-1.46 (m, 4H). |
| 225 | 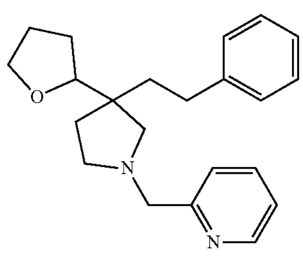 [SMILES: c1ccc(CCC2(C3CCCO3)CCN(Cc3ccccn3)C2)cc1] | 2-((3-phenethyl-3-(tetrahydrofuran-2-yl)pyrrolidin-1-yl)methyl)pyridine | 337 | ¹H NMR (300 MHz, MeOD): δ 8.47 (dd, J = 1.5, 0.9 Hz, 1H), 7.83 (dd, J = 9.6, 1.8 Hz, 1H), 7.54 (d, J = 7.8 Hz, 1H), 7.32-7.23 (m, 1H), 7.23-7.12 (m, 5H), 3.99-3.81 (m, 2H), 3.82-3.66 (m, 3H), 2.87-2.53 (m, 6H), 1.93-1.67 (m, 8H). |
| 226 | 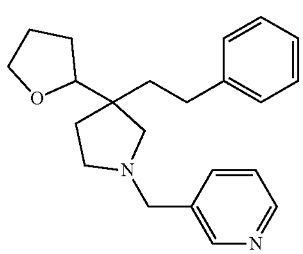 [SMILES: c1ccc(CCC2(C3CCCO3)CCN(Cc3cccnc3)C2)cc1] | 3-((3-phenethyl-3-(tetrahydrofuran-2-yl)pyrrolidin-1-yl)methyl)pyridine | 337 | ¹H NMR (300 MHz, MeOD): δ 8.56 (s, 1H), 8.55-8.45 (m, 1H), 7.87-7.77 (m, 1H), 7.45-7.32 (m, 1H), 7.27-7.13 (m, 5H), 3.91-3.75 (m, 5H), 2.86-2.60 (m, 6H), 1.97-1.72 (m, 8H). |

TABLE III-continued

| Compound. | Structure | Name | MS (ESI+): [M + H]+ | H-NMR |
|---|---|---|---|---|
| 227 | 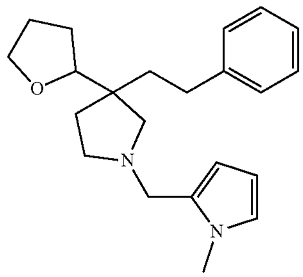 [SMILES: Cn1cccc1CN1CCC(CCc2ccccc2)(C2CCCO2)C1] | 1-methyl-2-((3-phenethyl-3-(tetrahydrofuran-2-yl)pyrrolidin-1-yl)methyl)-1H-pyrrole | 339 | ¹H NMR (300 MHz, MeOD): δ 7.28-7.15 (m, 5H), 6.75 (d, J = 2.4 Hz, 1H), 6.25 (s, 1H), 6.07 (d, J = 2.7 Hz, 1H), 4.11 (s, 2H), 3.97-3.92 (m, 2H), 3.87 (s, 1H), 3.68 (s, 3H), 3.30-3.09 (m, 4H), 2.82-2.60 (m, 2H), 2.03-1.80 (m, 4H), 1.78-1.75 (m, 4H). |
| 228 | 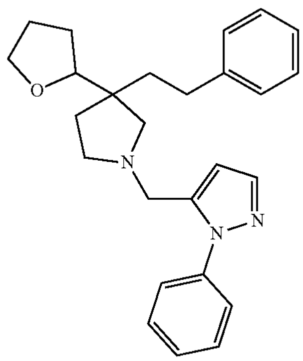 [SMILES: c1ccc(CCC2(C3CCCO3)CCN(Cc3ccnn3-c3ccccc3)C2)cc1] | 5-((3-phenethyl-3-(tetrahydrofuran-2-yl)pyrrolidin-1-yl)methyl)-1-phenyl-1H-pyrazole | 402 | ¹H NMR (300 MHz, MeOD): δ 7.64-7.61 (m, 3H), 7.61-7.41 (m, 3H), 7.26-7.21 (m, 2H), 7.15-7.13 (m, 3H), 6.47 (s, 1H), 3.81-3.80 (m, 3H), 3.66 (s, 2H), 2.61-2.42 (m, 6H), 1.97-1.64 (m, 8H). |
| 229 | 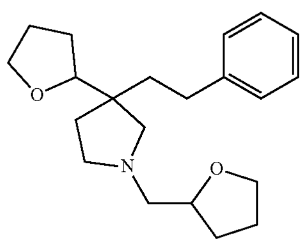 [SMILES: c1ccc(CCC2(C3CCCO3)CCN(CC3CCCO3)C2)cc1] | 3-phenethyl-3-(tetrahydrofuran-2-yl)-1-((tetrahydrofuran-2-yl)methyl)pyrrolidine | 330 | ¹HNMR (300 MHz, MeOD): δ 7.27-7.17 (m, 5H), 4.11-3.78 (m, 6H), 3.59-3.13 (m, 6H), 2.70-2.65 (m, 2H), 2.13-2.01 (m, 3H), 1.98-1.83 (m, 7H), 1.81-1.79 (m, 2H). |
| 230 | 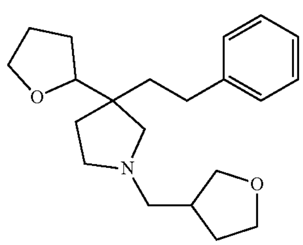 [SMILES: c1ccc(CCC2(C3CCCO3)CCN(CC3CCOC3)C2)cc1] | 3-phenethyl-3-(tetrahydrofuran-2-yl)-1-((tetrahydrofuran-3-yl)methyl)pyrrolidine | 330 | ¹HNMR (300 MHz, MeOD): δ 7.27-7.17 (m, 5H), 5.49 (s, 2H), 3.98-3.45 (m, 9H), 3.32-3.13 (m, 2H), 2.71-2.66 (m, 3H), 2.03-1.82 (m, 10H). |
| 231 | 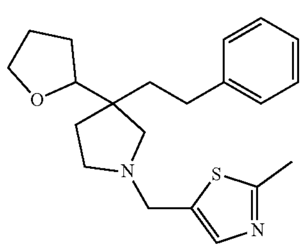 [SMILES: Cc1ncc(CN2CCC(CCc3ccccc3)(C3CCCO3)C2)s1] | 2-methyl-5-((3-phenethyl-3-(tetrahydrofuran-2-yl)pyrrolidin-1-yl)methyl)thiazole | 367 | ¹HNMR (300 MHz, MeOD): δ 7.47 (s, 1H), 7.26-7.13 (m, 5H), 3.92-3.74 (m, 5H), 2.67-2.33 (m, 8H), 2.06-1.62 (m, 9H). |

TABLE III-continued

| Compound. | Structure | Name | MS (ESI+): [M + H]+ | H-NMR |
|---|---|---|---|---|
| 232 | 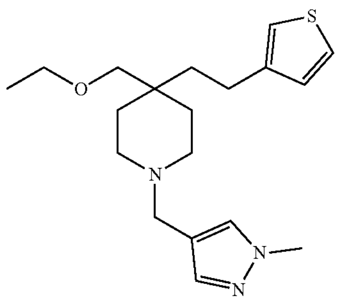 [SMILES: CCOCC1(CCc2ccsc2)CCN(Cc2cnn(C)c2)CC1] | 4-(ethoxymethyl)-1-((1-methyl-1H-pyrazol-4-yl)methyl)-4-(2-(thiophen-3-yl)ethyl)piperidine | 348 | ¹H NMR (300 MHz, MeOD): δ 7.55 (s, 1H), 7.43 (s, 1H), 7.28 (dd, J = 4.9, 2.9 Hz, 1H), 6.97 (d, J = 2.1 Hz, 1H), 6.92 (d, J = 4.9 Hz, 1H), 3.86 (s, 3H), 3.52-3.42 (m, 4H), 3.29 (s, 2H), 2.61-2.51 (m, 6H), 1.70-1.48 (m, 6H), 1.17 (t, J = 7.0 Hz, 3H). |
| 233 | 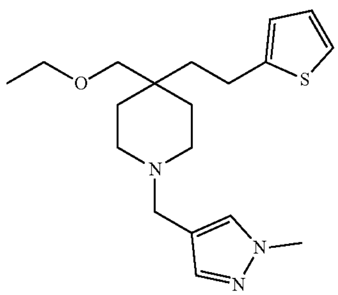 [SMILES: CCOCC1(CCc2cccs2)CCN(Cc2cnn(C)c2)CC1] | 4-(ethoxymethyl)-1-((1-methyl-1H-pyrazol-4-yl)methyl)-4-(2-(thiophen-2-yl)ethyl)piperidine | 348 | ¹H NMR (300 MHz, MeOD): δ 7.68 (s, 1H), 7.52 (s, 1H), 7.15 (dd, J = 5.1, 1.2 Hz, 1H), 6.88 (dd, J = 5.1, 3.6 Hz, 1H), 6.80 (dd, J = 3.4, 1.0 Hz, 1H), 3.88 (d, J = 6.7 Hz, 3H), 3.85 (s, 2H), 3.48 (q, J = 7.0 Hz, 2H), 3.34 (s, 2H), 2.87-2.77 (m, 6H), 1.79-1.67 (m, 4H), 1.65-1.58 (m, 2H), 1.18 (t, J = 7.0 Hz, 3H). |
| 234 | 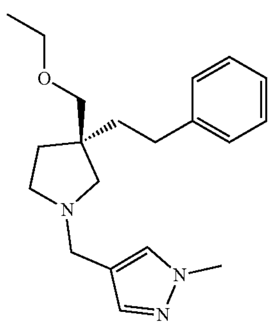 [SMILES: CCOC[C@]1(CCc2ccccc2)CCN(Cc2cnn(C)c2)C1] | (R)-4-((3-(ethoxymethyl)-3-phenethylpyrrolidin-1-yl)methyl)-1-methyl-1H-pyrazole | 328 | ¹H NMR (300 MHz, MeOD): δ 7.71 (s, 1H), 7.54 (s, 1H), 7.27-7.22 (m, 2H), 7.18-7.14 (m, 3H), 4.00-3.98 (m, 2H), 3.89 (s, 3H), 3.50 (d, J = 7.2 Hz, 2H), 3.40-3.31 (m, 2H), 3.19-3.09 (m, 3H), 2.86-2.82 (m, 1H), 2.59-2.55 (m, 2H), 1.98-1.77 (m, 4H), 1.20 (t, J = 7.0 Hz, 3H). |
| 235 | 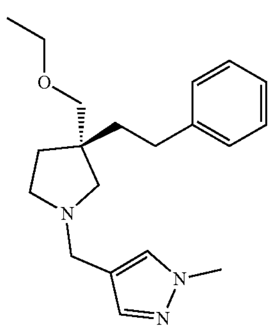 [SMILES: CCOC[C@@]1(CCc2ccccc2)CCN(Cc2cnn(C)c2)C1] | (S)-4-((3-(ethoxymethyl)-3-phenethylpyrrolidin-1-yl)methyl)-1-methyl-1H-pyrazole | 328 | ¹H NMR (300 MHz, MeOD): δ 7.67 (s, 1H), 7.51 (s, 1H), 7.29-7.07 (m, 5H), 3.91-3.80 (m, 5H), 3.56-3.46 (m, 2H), 3.43-3.35 (m, 2H), 3.10-2.88 (m, 3H), 2.72 (d, J = 12.0 Hz, 1H), 2.60-2.51 (m, 2H), 1.92-1.67 (m, 4H), 1.17 (t, J = 6.9 Hz, 3H). |
| 236 | 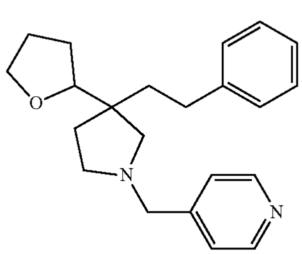 [SMILES: c1ccc(CCC2(C3CCCO3)CCN(Cc3ccncc3)C2)cc1] | 4-((3-phenethyl-3-(tetrahydrofuran-2-yl)pyrrolidin-1-yl)methyl)pyridine | 337 | ¹H NMR (300 MHz, MeOD): δ 8.46 (dd, J = 4.8, 1.5 Hz, 1H), 7.45-7.43 (m, 2H), 7.27-7.13 (m, 5H), 3.86-3.67 (m, 5H), 2.70-2.35 (m, 6H), 1.94-1.67 (m, 8H). |

TABLE III-continued

| Compound. | Structure | Name | MS (ESI+): [M + H]+ | H-NMR |
|---|---|---|---|---|
| 237 | 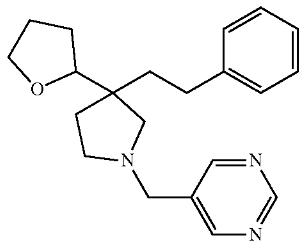 [SMILES: c1ccc(CCC2(C3CCCO3)CCN(Cc3cncnc3)C2)cc1] | 5-((3-phenethyl-3-(tetrahydrofuran-2-yl)pyrrolidin-1-yl)methyl)pyrimidine | 338 | 1H NMR (300 MHz, MeOD): δ 9.06 (s, 1H), 8.78 (s, 2H), 7.26-7.12 (m, 5H), 3.95-3.92 (m, 2H), 3.75-3.64 (m, 3H), 2.97-2.45 (m, 6H), 1.93-1.81 (m, 5H), 1.74-1.64 (m, 3H). |
| 238 | 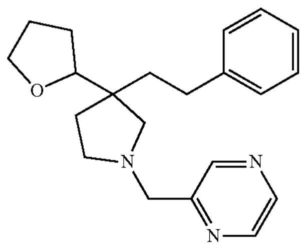 [SMILES: c1ccc(CCC2(C3CCCO3)CCN(Cc3cnccn3)C2)cc1] | 2-((3-phenethyl-3-(tetrahydrofuran-2-yl)pyrrolidin-1-yl)methyl)pyrazine | 338 | $^1$H NMR (300 MHz, MeOD): δ 8.72 (d, J = 6.0 Hz, 1H), 8.59-8.50 (m, 2H), 7.27-7.13 (m, 5H), 3.95-3.64 (m, 5H), 2.97-2.59 (m, 6H), 2.00-1.69 (m, 8H). |
| 239 | 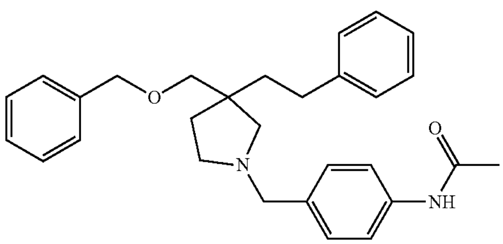 [SMILES: CC(=O)Nc1ccc(CN2CCC(CCc3ccccc3)(COCc3ccccc3)C2)cc1] | N-(4-((3-(benzyloxymethyl)-3-phenethylpyrrolidin-1-yl)methyl)phenyl)acetamide | 443 | $^1$H NMR (300 MHz, MeOD): δ 7.53-7.49 (m, 2H), 7.34-7.20 (m, 9H), 7.14-7.10 (m, 3H), 4.50 (s, 2H), 3.57-3.56 (m, 2H), 3.37 (s, 2H), 2.61-2.32 (m, 6H), 2.11 (s, 3H), 1.90-1.65 (m, 4H). |
| 240 | 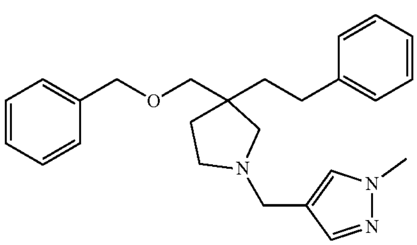 [SMILES: Cn1cc(CN2CCC(CCc3ccccc3)(COCc3ccccc3)C2)cn1] | 4-((3-(benzyloxymethyl)-3-phenethylpyrrolidin-1-yl)methyl)-1-methyl-1H-pyrazole | 390 | $^1$H NMR (300 MHz, MeOD) δ 7.97 (d, J = 6.0 Hz, 1H), 7.75 (d, J = 10.5 Hz, 1H), 7.57 (d, J = 11.4 Hz, 1H), 7.39-7.13 (m, 9H), 4.58-4.53 (m, 3H), 4.28-4.23 (m, 2H), 4.04 (s, 2H), 3.92-3.88 (m, 3H), 3.54-3.42 (m, 4H), 2.58-2.45 (m, 2H), 2.20-1.75 (m, 3H) |
| 241 | 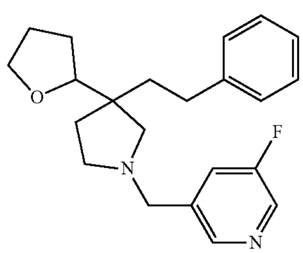 | 3-fluoro-5-((3-phenethyl-3-(tetrahydrofuran-2-yl)pyrrolidin-1-yl)methyl)pyridine | 355 | $^1$H NMR (300 MHz, MeOD): δ 8.40-8.37 (m, 2H), 7.66 (d, J = 9.0 Hz, 1H), 7.26-7.13 (m, 5H), 3.87-3.74 (m, 3H), 3.72 (s, 2H), 2.71-2.49 (m, 6H), 1.94-1.67 (m, 8H). |
| 242 | 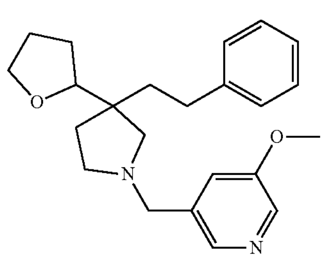 [SMILES: COc1cncc(CN2CCC(CCc3ccccc3)(C3CCCO3)C2)c1] | 3-methoxy-5-((3-phenethyl-3-(tetrahydrofuran-2-yl)pyrrolidin-1-yl)methyl)pyridine | 367 | $^1$H NMR (300 MHz, MeOD): δ 8.13-8.11 (m, 2H), 7.45 (dd, J = 4.5, 1.8 Hz, 1H), 7.45-7.43 (m, 2H), 7.26-7.12 (m, 3H), 3.93-3.74 (m, 6H), 3.66 (s, 2H), 2.71-2.47 (m, 6H), 1.93-1.65 (m, 8H). |

TABLE III-continued

| Compound. | Structure | Name | MS (ESI+): [M + H]+ | H-NMR |
|---|---|---|---|---|
| 243 | 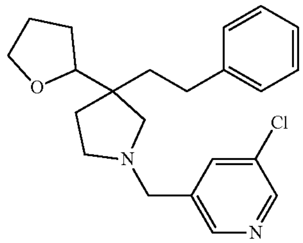 [SMILES: Clc1cncc(CN2CCC(CCc3ccccc3)(C3CCCO3)C2)c1] | 3-chloro-5-((3-phenethyl-3-(tetrahydrofuran-2-yl)pyrrolidin-1-yl)methyl)pyridine | 371 | ¹H NMR (300 MHz, MeOD): δ 8.45 (s, 2H), 7.89 (s, 1H), 7.26-7.12 (m, 5H), 3.95-3.92 (m, 2H), 3.75-3.64 (m, 3H), 2.71-2.57 (m, 4H), 2.55-2.47 (m, 2H), 1.92-1.65 (m, 8H). |
| 244 | 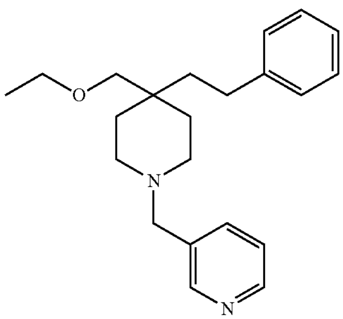 [SMILES: CCOCC1(CCc2ccccc2)CCN(Cc2cccnc2)CC1] | 3-((4-(ethoxymethyl)-4-phenethylpiperidin-1-yl)methyl)pyridine | 339 | ¹H NMR (300 MHz, MeOD): δ 8.50 (d, J = 1.5 Hz, 1H), 8.45 (dd, J = 4.8, 1.5 Hz, 1H), 7.85 (d, J = 7.8 Hz, 1H), 7.43 (m, 1H), 7.26-7.21 (m, 2H), 7.16-7.12 (m, 3H), 3.59 (s, 2H), 3.48 (q, J = 6.9 Hz, 2H), 3.32-3.30 (m, 2H), 2.56-2.47 (m, 6H), 1.68-1.53 (m, 6H), 1.20 (t, J = 6.9 Hz, 3H). |
| 245 | 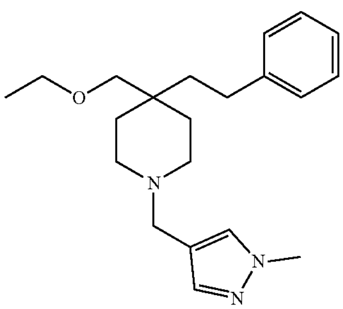 [SMILES: CCOCC1(CCc2ccccc2)CCN(Cc2cnn(C)c2)CC1] | 4-(ethoxymethyl)-1-((1-methyl-1H-pyrazol-4-yl)methyl)-4-phenethylpiperidine | 342 | ¹H NMR (300 MHz, MeOD): δ 7.58 (s, 1H), 7.45 (s, 1H), 7.26-7.21 (m, 2H), 7.16-7.13 (m, 3H), 3.87 (s, 3H), 3.58 (s, 2H), 3.48 (q, J = 6.9 Hz, 2H), 3.32-3.30 (m, 2H), 2.61-2.51 (m, 6H), 1.67-1.56 (m, 6H), 1.19 (t, J = 6.9 Hz, 3H). |
| 246 | 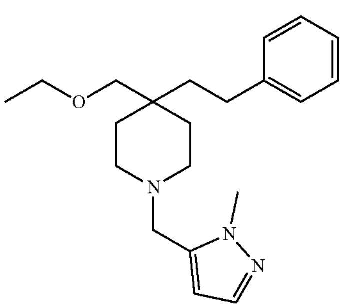 [SMILES: CCOCC1(CCc2ccccc2)CCN(Cc2ccnn2C)CC1] | 4-(ethoxymethyl)-1-((1-methyl-1H-pyrazol-5-yl)methyl)-4-phenethylpiperidine | 342 | ¹H NMR (300 MHz, MeOD): δ 7.59 (s, 1H), 7.26-7.21 (m, 2H), 7.16-7.13 (m, 3H), 6.87 (s, 1H), 3.70 (s, 3H), 3.54-3.47 (m, 4H), 3.45-3.32 (m, 2H), 2.56-2.47 (m, 6H), 1.68-1.49 (m, 6H), 1.20 (t, J = 6.9 Hz, 3H). |
| 247 | 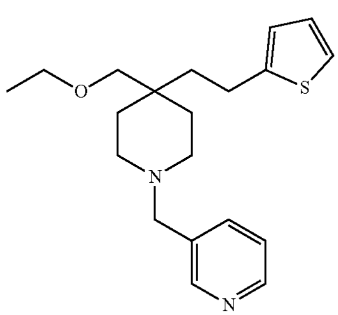 [SMILES: CCOCC1(CCc2cccs2)CCN(Cc2cccnc2)CC1] | 3-((4-(ethoxymethyl)-4-(2-(thiophen-2-yl)ethyl)piperidin-1-yl)methyl)pyridine | 345 | ¹H NMR (300 MHz, MeOD): δ 8.52 (d, J = 1.6 Hz, 1H), 8.47 (dd, J = 4.9, 1.6 Hz, 1H), 7.86 (d, J = 7.8 Hz, 1H), 7.45-7.44 (m, 1H), 7.14 (dd, J = 5.2, 1.2 Hz, 1H), 6.88 (dd, J = 5.1, 3.4 Hz, 1H), 6.78 (dd, J = 3.4, 1.0 Hz, 1H), 3.68 (s, 2H), 3.48 (q, J = 7.0 Hz, 2H), 3.32 (s, 2H), 2.82-2.76 (m, 2H), 2.59-2.54 (m, 4H), 1.79-1.73 (m, 2H), 1.69-1.59 (m, 2H), 1.54-1.50 (m, 2H), 1.18 (t, J = 7.0 Hz, 3H). |

TABLE III-continued

| Compound. | Structure | Name | MS (ESI+): [M + H]+ | H-NMR |
|---|---|---|---|---|
| 248 | 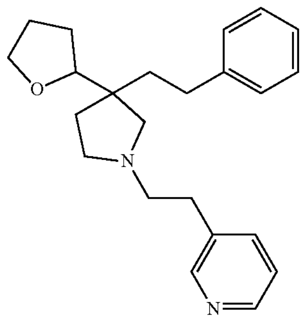 [SMILES: c1ccc(CCC2(C3CCCO3)CCN(CCc3cccnc3)C2)cc1] | 3-(2-(3-phenethyl-3-(tetrahydrofuran-2-yl)pyrrolidin-1-yl)ethyl)pyridine | 351 | ¹H NMR (300 MHz, CDCl₃) δ 8.50 (s, 2H), 7.70 (s, 1H), 7.27-7.13 (m, 6H), 4.12 (d, J = 6.3 Hz, 1H), 3.88-3.21 (m, 7H), 3.11-2.88 (m, 1H), 2.68-2.49 (m, 2H), 2.21-1.54 (m, 4H), 1.26-0.97 (m, 4H). |
| 249 | 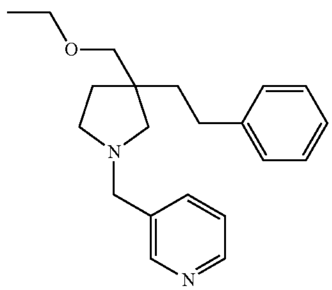 [SMILES: CCOCC1(CCc2ccccc2)CCN(Cc2cccnc2)C1] | 3-((3-(ethoxymethyl)-3-phenethylpyrrolidin-1-yl)methyl)pyridine | 325 | ¹H NMR (300 MHz, MeOD): δ 8.52 (d, J = 1.7 Hz, 1H), 8.45 (dd, J = 4.9, 1.6 Hz, 1H), 7.84 (d, J = 7.8 Hz, 1H), 7.44-7.41 (m, 1H), 7.25-7.12 (m, 5H), 3.69 (s, 2H), 3.49 (q, J = 7.0 Hz, 2H), 3.34 (s, 2H), 2.68-2.53 (m, 5H), 2.37 (d, J = 9.6 Hz, 1H), 1.76-1.67 (m, 4H), 1.18 (t, J =7.0 Hz, 3H). |
| 250 | 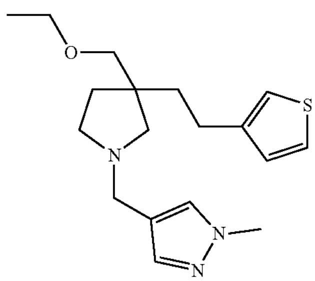 [SMILES: CCOCC1(CCc2ccsc2)CCN(Cc2cnn(C)c2)C1] | 4-((3-(ethoxymethyl)-3-(2-(thiophen-3-yl)ethyl)pyrrolidin-1-yl)methyl)-1-methyl-1H-pyrazole | 334 | ¹H NMR (300 MHz, MeOD): δ 7.58 (s, 1H), 7.45 (s, 1H), 7.29 (dd, J = 4.9, 3.0 Hz, 1H), 6.99 (d, J = 1.8 Hz, 1H), 6.94 (dd, J = 4.9, 1.2 Hz, 1H), 3.87 (s, 3H), 3.64 (s, 2H), 3.49 (q, J = 7.0 Hz, 2H), 3.33-3.30 (m, 2H), 2.77-2.46 (m, 6H), 1.90-1.67 (m, 4H), 1.18 (t, J = 7.0 Hz, 3H). |
| 251 | 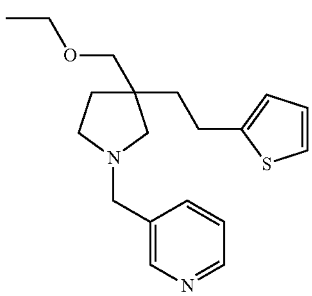 [SMILES: CCOCC1(CCc2cccs2)CCN(Cc2cccnc2)C1] | 3-((3-(ethoxymethyl)-3-(2-(thiophen-2-yl)ethyl)pyrrolidin-1-yl)methyl)pyridine | 331 | ¹H NMR (300 MHz, MeOD): δ 8.51 (d, J = 1.7 Hz, 1H), 8.43 (dd, J = 4.9, 1.5 Hz, 1H), 7.84 (d, J = 7.8 Hz, 1H), 7.41 (dd, J = 7.8, 4.9 Hz, 1H), 7.13 (dd, J = 5.1, 1.1 Hz, 1H), 6.87 (dd, J = 5.1, 3.4 Hz, 1H), 6.78 (dd, J = 3.3, 0.9 Hz, 1H), 3.64 (s, 2H), 3.51-3.44 (m, 2H), 3.37-3.32 (m, 2H), 2.80 (t, J = 8.4 Hz, 2H), 2.63-2.53 (m, 3H), 2.24 (d, J = 9.6 Hz, 1H), 1.86-1.68 (m, 2H), 1.66 (t, J = 6.8 Hz, 2H), 1.17 (t, J = 7.0 Hz, 3H). |
| 252 | 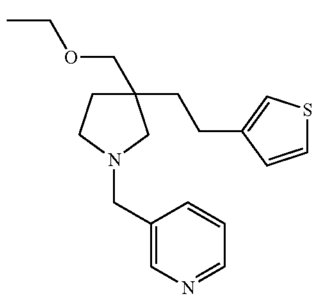 [SMILES: CCOCC1(CCc2ccsc2)CCN(Cc2cccnc2)C1] | 3-(3-(ethoxymethyl)-3-(2-(thiophen-3-yl)ethyl)pyrrolidin-1-yl)methyl)pyridine | 331 | ¹H NMR (300 MHz, MeOD): δ 8.52 (d, J = 1.7 Hz, 1H), 8.46 (dd, J = 4.9, 1.6 Hz, 1H), 7.85 (d, J = 7.8 Hz, 1H), 7.43 (d, J = 5.1 Hz, 1H), 7.28 (dd, J = 4.9, 3.0 Hz, 1H), 6.99-6.98 (m, 1H), 6.93 (dd, J = 4.9, 1.2 Hz, 1H), 3.71 (s, 2H), 3.48 (q, J = 7.0 Hz, 2H), 3.33 (d, J = 5.1 Hz, 2H), 2.70-2.57 (m, 5H), 2.39 (d, J = 9.8 Hz, 1H), 1.80-1.77 (m, 2H), 1.69 (t, J = 6.9 Hz, 2H), 1.17 (t, J = 7.0 Hz, 3H). |

TABLE III-continued

| Compound. | Structure | Name | MS (ESI+): [M + H]+ | H-NMR |
|---|---|---|---|---|
| 253 | 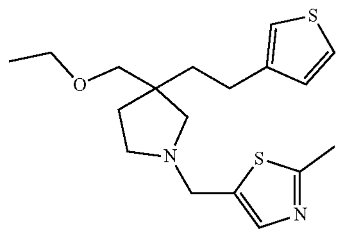 [SMILES: CCOCC1(CCc2ccsc2)CCN(Cc2cnc(C)s2)C1] | 5-((3-(ethoxymethyl)-3-(2-(thiophen-3-yl)ethyl)pyrrolidin-1-yl)methyl)-2-methylthiazole | 351 | ¹H NMR (300 MHz, MeOD): δ 7.27 (dd, J = 4.9, 2.9 Hz, 1H), 7.22 (s, 1H), 6.98 (d, J = 1.9 Hz, 1H), 6.93 (dd, J = 4.9, 1.2 Hz, 1H), 3.74 (s, 2H), 3.48 (q, J = 7.0 Hz, 2H), 3.36 (s, 2H), 2.72-2.70 (m, 2H), 2.68 (s, 3H), 2.64-2.54 (m, 3H), 2.47-2.44 (m, 1H), 1.81-1.73 (m, 2H), 1.68 (t, J = 6.8 Hz, 2H), 1.18 (t, J = 7.0 Hz, 3H). |
| 254 | 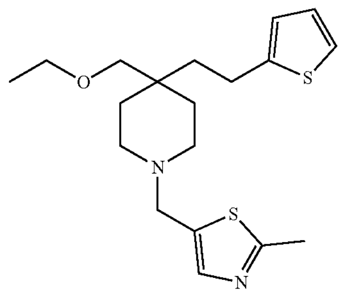 [SMILES: CCOCC1(CCc2cccs2)CCN(Cc2cnc(C)s2)CC1] | 5-(4-(ethoxymethyl)-4-(2-(thiophen-2-yl)ethyl)piperidin-1-yl)methyl)-2-methylthiazole | 365 | ¹H NMR (300 MHz, MeOD): δ 7.24 (s, 1H), 7.13 (dd, J =5.2, 1.2 Hz, 1H), 6.87 (dd, J = 5.1, 3.4 Hz, 1H), 6.77 (dd, J = 3.4, 0.9 Hz, 1H), 3.65 (s, 2H), 3.47 (q, J = 6.9 Hz, 2H), 3.31 (d, ./= 1.6 Hz, 2H), 2.80-2.74 (m, 2H), 2.68 (s, 3H), 2.55-2.51 (m, 4H), 1.76-1.69 (m, 2H), 1.62-1.46 (m, 4H), 1.18 (t, J = 7.0 Hz, 3H). |
| 255 | 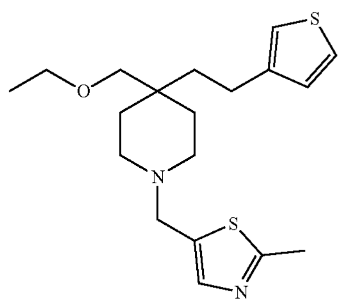 [SMILES: CCOCC1(CCc2ccsc2)CCN(Cc2cnc(C)s2)CC1] | 5-((4-(ethoxymethyl)-4-(2-(thiophen-3-yl)ethyl)piperidin-1-yl)methyl)-2-methylthiazole | 365 | ¹H NMR (300 MHz, MeOD): δ 7.63 (d, J = 8.1 Hz, 1H), 7.32-7.29 (m, 1H), 7.07-6.93 (m, 2H), 4.38 (s, 2H), 3.52-3.41 (m, 3H), 3.40-3.32 (m, 2H), 3.29-3.10 (m, 3H), 2.73 (d, J = 1.7 Hz, 3H), 2.65-2.60 (m, 2H), 2.02-1.89 (m, 1H), 1.87-1.80 (m, 3H), 1.69-1.63 (m, 2H), 1.19 (t, J = 7.0 Hz, 3H). |
| 256 | 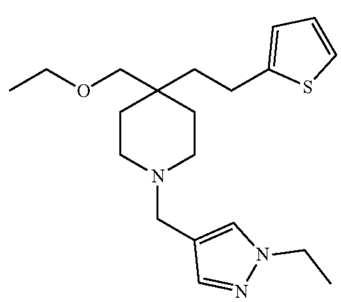 [SMILES: CCOCC1(CCc2cccs2)CCN(Cc2cnn(CC)c2)CC1] | 4-(ethoxymethyl)-1-((1-ethyl-1H-pyrazol-4-yl)methyl)-4-(2-(thiophen-2-yl)ethyl)piperidine | 362 | ¹H NMR (300 MHz, MeOD): δ 7.71 (s, 1H), 7.52 (s, 1H), 7.15 (dd, J = 5.1, 1.2 Hz, 1H), 6.88 (dd, J = 5.1, 3.4 Hz, 1H), 6.79 (dd, J = 3.4, 0.9 Hz, 1H), 4.18 (q, J = 7.0 Hz, 2H), 3.79 (s, 2H), 3.48 (q, J = 7.0 Hz, 2H), 3.33 (s, 2H), 2.83-2.77 (m, 6H), 1.79-1.69 (m, 4H), 1.65-1.62 (m, 2H), 1.44 (t, J = 7.3 Hz, 3H), 1.18 (t, J = 7.0 Hz, 3H). |
| 257 | 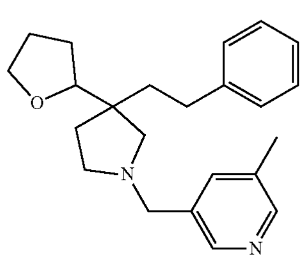 [SMILES: Cc1cncc(CN2CCC(CCc3ccccc3)(C3CCCO3)C2)c1] | 3-methyl-5-((3-phenethyl-3-(tetrahydrofuran-2-yl)pyrrolidin-1-yl)methyl)pyridine | 351 | ¹H NMR (300 MHz, MeOD): δ 8.30 (d, J = 11.2 Hz, 2H), 7.67 (s, 1H), 7.26-7.13 (m, 5H), 3.90-3.83 (m, 2H), 3.74-3.65 (m, 1H), 3.65 (s, 2H), 2.73-2.54 (m, 6H), 2.36 (s, 3H), 1.93-1.65 (m, 8H). |

TABLE III-continued

| Compound. | Structure | Name | MS (ESI+): [M + H]+ | H-NMR |
|---|---|---|---|---|
| 258 | 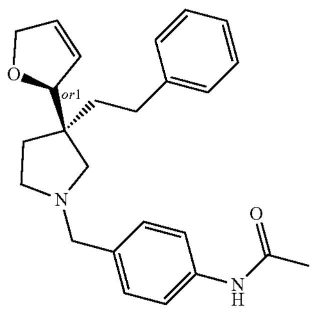 [SMILES: CC(=O)Nc1ccc(CN2CC[C@@](CCc3ccccc3)([C@@H]3C=CCO3)C2)cc1] | N-(4-(((R)-3-((S)-2,5-dihydrofuran-2-yl)-3-phenethylpyrrolidin-1-yl)methyl)phenyl)acetamide | 391 | $^1$H NMR (300 MHz, MeOD): δ 7.68 (d, J = 8.4 Hz, 2H), 7.45 (d, J = 8.4 Hz, 2H), 7.32-7.15 (m, 5H), 6.23-6.04 (m, 1H), 6.01-5.94 (m, 1H), 5.06 (m, 1H), 4.88-4.32 (m, 4H), 3.68-3.34 (m, 2H), 3.16 (d, J = 12.6 Hz, 1H), 3.06-2.83 (m, 1H), 2.71-2.66 (m, 2H), 2.30-2.27 (m, 1H), 2.13 (s, 3H), 2.12-2.11 (m, 1H), 1.82-1.78 (m, 2H). |
| 259 | 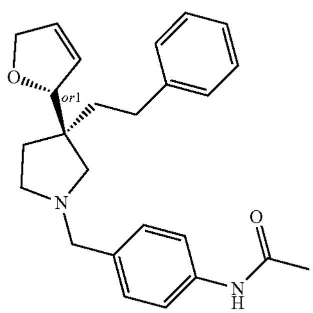 [SMILES: CC(=O)Nc1ccc(CN2CC[C@@](CCc3ccccc3)([C@H]3C=CCO3)C2)cc1] | N-(4-(((R)-3-((R)-2,5-dihydrofuran-2-yl)-3-phenethylpyrrolidin-1-yl)methyl)phenyl)acetamide | 391 | $^1$H NMR (300 MHz, MeOD): δ 7.67 (d, J = 8.4 Hz, 2H), 7.44 (t, J = 8.6 Hz, 2H), 7.27-7.17 (m, 5H), 6.12-6.19 (d, J = 6.6 Hz, 1H), 6.01-5.89 (m, 1H), 5.03-5.10 (m, 1H), 4.88-4.64 (m, 2H), 4.44-4.14 (m, 2H), 3.49-3.34 (m, 3H), 3.22-3.29 (m, 1H), 2.69-2.66 (m, 2H), 2.14 (s, 3H), 2.09-1.83 (m, 4H). |
| 260 | 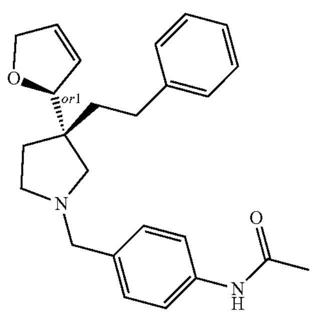 [SMILES: CC(=O)Nc1ccc(CN2CC[C@](CCc3ccccc3)([C@@H]3C=CCO3)C2)cc1] | N-(4-((3-((S)-2,5-dihydrofuran-2-yl)-3-phenethylpyrrolidin-1-yl)methyl)phenyl)acetamide N-(4-(((S)-3-((S)-2,5-dihydrofuran-2-yl)-3-phenethylpyrrolidin-1-yl)methyl)phenyl)acetamide | 391 | $^1$H NMR (300 MHz, MeOD) δ 7.67 (d, J = 8.1 Hz, 2H), 7.54 (d, J = 7.2 Hz, 2H), 7.27-7.15 (m, 5H), 6.15-5.85 (m, 1H), 5.93-5.86 (m, 1H), 5.10-4.94 (m, 1H), 4.65-4.19 (m, 4H), 3.49-3.31 (m, 1H), 3.16 (d, J = 12.5 Hz, 1H), 3.03-2.86 (m, 1H), 2.71-2.66 (m, 2H), 2.26-2.30 (m, 2H), 2.13 (s, 3H), 1.83-1.78 (m, 3H). |
| 261 | 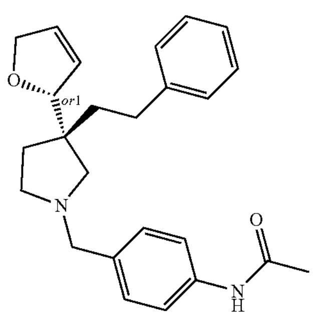 [SMILES: CC(=O)Nc1ccc(CN2CC[C@](CCc3ccccc3)([C@H]3C=CCO3)C2)cc1] | N-(4-(((S)-3-((R)-2,5-dihydrofuran-2-yl)-3-phenethylpyrrolidin-1-yl)methyl)phenyl)acetamide | 391 | $^1$H NMR (300 MHz, MeOD): δ 7.68 (d, J = 8.4 Hz, 2H), 7.45 (t, J = 8.9 Hz, 2H), 7.27-7.17 (m, 5H), 6.28-6.12 (m, 1H), 6.01-5.84 (m, 1H), 5.02-4.95 (m, 1H), 4.69-4.71 (m, 2H), 4.49-4.11 (m, 2H), 3.39-3.35 (m, 1H), 3.32-3.31 (m, 1H), 3.29-3.26 (m, 2H), 2.67 (m, 2H), 2.21-2.08 (m, 3H), 1.92-1.83 (m, 4H). |
| 262 | 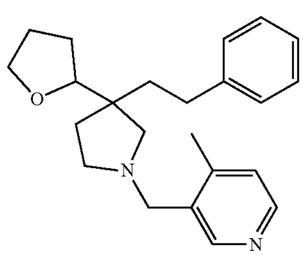 [SMILES: Cc1ccncc1CN1CCC(CCc2ccccc2)(C2CCCO2)C1] | 4-methyl-3-((3-phenethyl-3-(tetrahydrofuran-2-yl)pyrrolidin-1-yl)methyl)pyridine | 351 | $^1$H NMR (300 MHz, MeOD): δ 8.36 (s, 1H), 8.28 (d, J = 4.8 Hz, 1H), 7.26-7.12 (m, 6H), 3.95-3.92 (m, 3H), 3.63 (s, 2H), 2.67-2.57 (m, 6H), 2.48 (s, 3H), 1.92-1.65 (m, 8H). |

TABLE III-continued

| Compound. | Structure | Name | MS (ESI+): [M + H]+ | H-NMR |
|---|---|---|---|---|
| 263 | 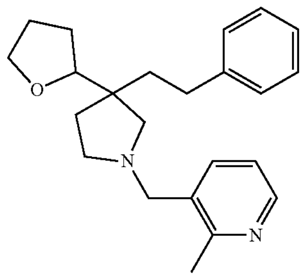 [SMILES: Cc1ncccc1CN1CCC(CCc2ccccc2)(C2CCCO2)C1] | 2-methyl-3-((3-phenethyl-3-(tetrahydrofuran-2-yl)pyrrolidin-1-yl)methyl)pyridine | 351 | $^1$H NMR (300 MHz, CDCl$_3$): δ 8.38 (d, J = 3.9 Hz, 1H), 7.59 (d, J = 7.2 Hz, 1H), 7.30-7.27 (m, 2H), 7.26-7.15 (m, 3H), 7.11-7.06 (m, 1H), 3.88-3.83 (m, 2H), 3.75-3.72 (m, 1H), 3.55 (s, 2H), 2.73-2.42 (m, 9H), 1.88-1.78 (m, 5H), 1.72-1.63 (m, 3H). |
| 264 | 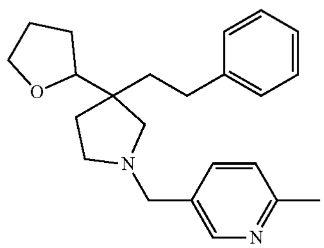 [SMILES: Cc1ccc(CN2CCC(CCc3ccccc3)(C3CCCO3)C2)cn1] | 2-methyl-5-((3-phenethyl-3-(tetrahydrofuran-2-yl)pyrrolidin-1-yl)methyl)pyridine | 351 | $^1$H NMR (300 MHz, MeOD): δ 8.37 (s, 1H), 7.79 (d, J = 9.0 Hz, 1H), 7.26-7.13 (m, 6H), 3.97-3.74 (m, 3H), 3.72 (s, 2H), 2.81-2.79 (m, 4H), 2.56 (s, 3H), 2.49-2.37 (m, 2H), 1.94-1.67 (m, 8H). |
| 265 | 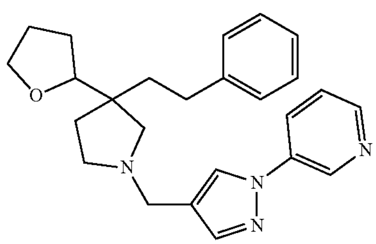 [SMILES: c1ccc(CCC2(C3CCCO3)CCN(Cc3cnn(-c4cccnc4)c3)C2)cc1] | 3-(4-((3-phenethyl-3-(tetrahydrofuran-2-yl)pyrrolidin-1-yl)methyl)-1H-pyrazol-1-yl)pyridine | 403 | $^1$H NMR (300 MHz, MeOD): δ 9.06-9.04 (m, 1H), 8.55-8.52 (m, 2H), 8.27-8.24 (m, 1H), 7.91 (d, J = 3.0 Hz, 1H), 7.59-7.42 (m, 1H), 7.25-7.14 (m, 5H), 4.26-4.18 (m, 2H), 3.93-3.71 (m, 3H), 3.45-3.29 (m, 4H), 2.68-2.63 (m, 2H), 2.00-1.78 (m, 8H). |
| 266 | 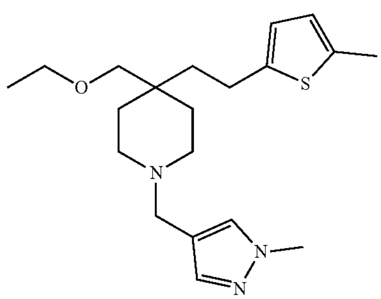 [SMILES: CCOCC1(CCc2ccc(C)s2)CCN(Cc2cnn(C)c2)CC1] | 4-(ethoxymethyl)-1-((1-methyl-1H-pyrazol-4-yl)methyl)-4-(2-(5-methylthiophen-2-yl)ethyl)piperidine | 362 | $^1$H NMR (300 MHz, MeOD): δ 7.59 (s, 1H), 7.46 (s, 1H), 6.53-6.50 (m, 2H), 3.87 (s, 3H), 3.60 (s, 2H), 3.46 (q, J = 7.0 Hz, 2H), 3.31 (s, 2H), 2.71-2.61 (m, 6H), 2.39 (s, 3H), 1.73-1.50 (m, 6H), 1.17 (t, J = 7.0 Hz, 3H). |
| 267 | 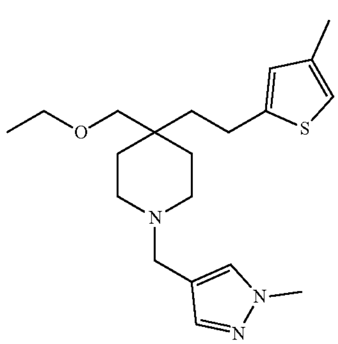 [SMILES: CCOCC1(CCc2cc(C)cs2)CCN(Cc2cnn(C)c2)CC1] | 4-(ethoxymethyl)-1-((1-methyl-1H-pyrazol-4-yl)methyl)-4-(2-(4-methylthiophen-2-yl)ethyl)piperidine | 362 | $^1$H NMR (300 MHz, MeOD): δ 7.58 (s, 1H), 7.45 (s, 1H), 6.69 (s, 1H), 6.59 (s, 1H), 3.87 (s, 3H), 3.57 (s, 2H), 3.47 (q, J = 7.0 Hz, 2H), 3.29 (s, 2H), 2.74-2.58 (m, 6H), 2.18 (s, 3H), 1.74-1.51 (m, 6H), 1.16 (t, J = 7.0 Hz, 3H). |

TABLE III-continued

| Compound. | Structure | Name | MS (ESI+): [M + H]+ | H-NMR |
|---|---|---|---|---|
| 268 | 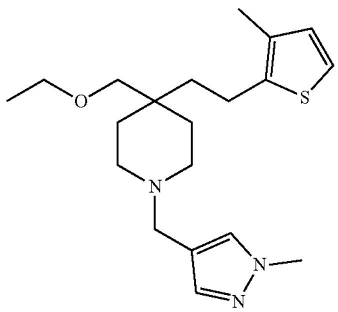 [SMILES: CCOCC1(CCc2sccc2C)CCN(Cc2cnn(C)c2)CC1] | 4-(ethoxymethyl)-1-((1-methyl-1H-pyrazol-4-yl)methyl)-4-(2-(3-methylthiophen-2-yl)ethyl)piperidine | 362 | $^1$H NMR (300 MHz, MeOD): δ 7.82 (s, 1H), 7.61 (s, 1H), 7.04 (d, J = 5.1 Hz, 1H), 6.74 (d, J = 5.1 Hz, 1H), 4.19 (s, 2H), 3.92 (s, 3H), 3.52 (q, J = 6.9 Hz, 2H), 3.41 (s, 2H), 3.25-3.02 (m, 4H), 2.74-2.68 (m, 2H), 2.14 (s, 3H), 1.92-1.62 (m, 6H), 1.19 (t, J = 7.0 Hz, 3H). |
| 269 | 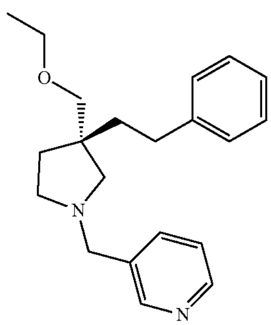 [SMILES: CCOC[C@@]1(CCc2ccccc2)CCN(Cc2cccnc2)C1] | (S)-3-(3-(ethoxymethyl)-3-phenethylpyrrolidin-1-yl)methyl)pyridine | 325 | $^1$H NMR (300 MHz, CDCl$_3$): δ 8.55 (d, J = 1.5 Hz, 1H), 8.49 (dd, J = 4.8, 1.8 Hz, 1H), 7.66 (d, J = 7.5 Hz, 1H), 7.29-7.14 (m, 6H), 3.59 (s, 2H), 3.48 (q, J = 6.9 Hz, 2H), 3.31 (q, J = 8.8 Hz, 2H), 2.63-2.50 (m, 5H), 2.30-2.27 (m, 1H), 1.81-1.73 (m, 2H), 1.68-1.61 (m, 2H), 1.19 (t, J = 7.0 Hz, 3H). |
| 270 | 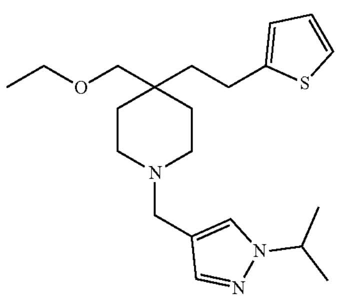 [SMILES: CCOCC1(CCc2cccs2)CCN(Cc2cnn(C(C)C)c2)CC1] | 4-(ethoxymethyl)-1-((1-isopropyl-1H-pyrazol-4-yl)methyl)-4-(2-(thiophen-2-yl)ethyl)piperidine HCl | 376 | $^1$H NMR (300 MHz, MeOD): δ 7.97 (d, J = 3.4 Hz, 1H), 7.70 (d, J = 4.0 Hz, 1H), 7.19-7.14 (m, 1H), 6.91-6.80 (m, 2H), 4.58-4.50 (m, 1H), 4.24 (s, 2H), 3.52-3.41 (m, 3H), 3.38-3.31 (m, 3H), 3.24-3.01 (m, 2H), 2.85-2.80 (m, 2H), 1.94-1.68 (m, 6H), 1.51 (dd, J = 6.7, 1.6 Hz, 6H), 1.18 (t, J = 7.0 Hz, 3H). |
| 271 | 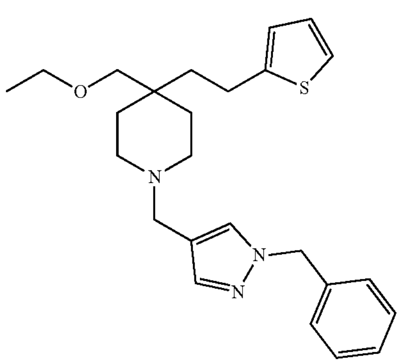 [SMILES: CCOCC1(CCc2cccs2)CCN(Cc2cnn(Cc3ccccc3)c2)CC1] | 1-((1-benzyl-1H-pyrazol-4-yl)methyl)-4-(ethoxymethyl)-4-(2-(thiophen-2-yl)ethyl)piperidine | 424 | $^1$H NMR (300 MHz, MeOD): δ 7.68 (s, 1H), 7.51 (s, 1H), 7.31-7.28 (m, 3H), 7.23-7.16 (m, 2H), 7.14 (dd, J = 5.1, 1.1 Hz, 1H), 6.88 (dd, J = 5.1, 3.4 Hz, 1H), 6.78-6.76 (m, 1H), 5.34 (s, 2H), 3.59 (s, 2H), 3.46 (q, J = 7.0 Hz, 2H), 3.35-3.31 (m, 2H), 2.81-2.75 (m, 2H), 2.65-2.44 (m, 4H), 1.76-1.54 (m, 6H), 1.17 (t, J = 7.0 Hz, 3H). |

TABLE III-continued

| Compound | Name | MS (ESI+): [M + H]+ | H-NMR |
|---|---|---|---|
| 272 | 3-((3-(2,5-dihydrofuran-2-yl)-3-(2-(thiophen-yl)ethyl)pyrrolidin-1-yl)methyl)pyridine | 341 | $^1$H NMR (300 MHz, CDCl$_3$): δ 8.55 (s, 1H), 8.51 (d, J = 4.2 Hz, 1H), 7.77 (brs, 1H), 7.29-7.24 (m, 2H), 6.93 (s, 2H), 6.05-5.95 (m, 1H), 5.84-5.82 (m, 1H), 4.97-4.81 (m, 1H), 4.64 (s, 2H), 3.65 (s, 2H), 2.78-2.40 (m, 6H), 1.97-1.67 (m, 4H). |
| 273 | 2,6-dimethyl-3-((3-phenethyl-3-(tetrahydrofuran-2-yl)pyrrolidin-1-yl)methyl)pyridine | 365 | $^1$H NMR (300 MHz, MeOD): δ 7.63 (d, J = 7.8 Hz, 1H), 7.26-7.11 (m, 6H), 3.91-3.29 (m, 5H), 2.84-2.65 (m, 6H), 2.56 (s, 3H), 2.48 (s, 3H), 1.96-1.71 (m, 8H). |
| 274 | 2-methoxy-5-((3-phenethyl-3-(tetrahydrofuran-2-yl)pyrrolidin-1-yl)methyl)pyridine | 367 | $^1$H NMR (300 MHz, MeOD): δ 8.13 (d, J = 2.1 Hz, 2H), 7.63 (dd, J = 8.4, 2.4 Hz, 2H), 7.27-7.16 (m, 2H), 6.76 (d, J = 9.0 Hz, 2H), 4.63 (s, 4H), 3.94-3.89 (m, 6H), 2.86-2.57 (m, 2H), 1.92-1.65 (m, 10H). |
| 275 | (S)-3-((3-(ethoxymethyl)-3-(2-(thiophen-2-yl)ethyl)pyrrolidin-1-yl)methyl)pyridine | 331 | $^1$H NMR (300 MHz, CDCl$_3$): δ 8.54 (s, 1H), 8.49-8.47 (m, 1H), 7.66 (d, J = 7.5 Hz, 1H), 7.26-7.24 (m, 1H), 7.11-7.09 (m, 1H), 6.92-6.89 (m, 1H), 6.79-6.78 (m, 1H), 3.59 (s, 2H), 3.47 (q, J = 6.9 Hz, 2H), 3.31-3.23 (m, 2H), 2.87-2.81 (m, 2H), 2.62-2.51 (m, 3H), 2.35-2.27 (m, 1H), 1.95-1.83 (m, 2H), 1.68-1.64 (m, 2H), 1.18 (t, J = 6.9 Hz, 3H). |

TABLE III-continued

| Compound. | Structure | Name | MS (ESI+): [M + H]+ | H-NMR |
|---|---|---|---|---|
| 276 | 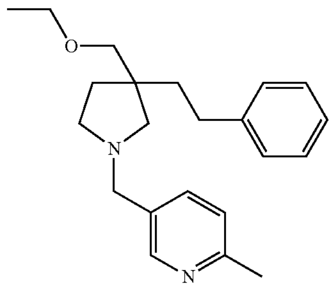 [SMILES: CCOCC1(CCc2ccccc2)CCN(Cc2ccc(C)nc2)C1] | 5-((3-(ethoxymethyl)-3-phenethylpyrrolidin-1-yl)methyl)-2-methylpyridine | 339 | $^1$H NMR (300 MHz, MeOD): δ 8.40 (s, 1H), 7.74 (dd, J = 7.8, 2.1 Hz, 1H), 7.32-7.13 (m, 6H), 3.76 (s, 2H), 3.50 (q, J = 6.9 Hz, 2H), 3.36-3.31 (m, 3H), 2.79-2.47 (m, 8H), 1.78-1.72 (m, 4H), 1.19 (t, J = 6.9 Hz, 3H). |
| 277 | 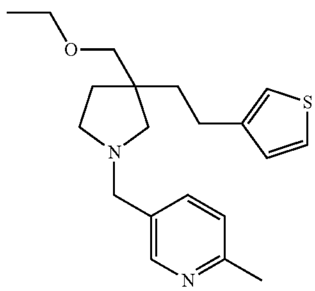 [SMILES: CCOCC1(CCc2ccsc2)CCN(Cc2ccc(C)nc2)C1] | 5-((3-(ethoxymethyl)-3-(2-(thiophen-3-yl)ethyl)pyrrolidin-1-yl)methyl)-2-methylpyridine | 345 | $^1$H NMR (300 MHz, CDCl$_3$): δ 8.42 (s, 1H), 7.92 (s, 1H), 7.22-7.17 (m, 2H), 6.94 (s, 2H), 3.84 (s, 2H), 3.51-3.31 (m, 4H), 2.91-2.76 (m, 4H), 2.59-2.55 (m, 5H), 2.00-1.84 (m, 4H), 1.20 (t, J = 6.9 Hz, 3H). |
| 278 | 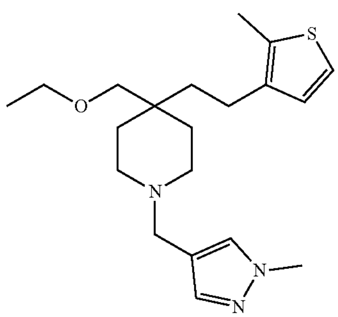 [SMILES: CCOCC1(CCc2ccsc2C)CCN(Cc2cnn(C)c2)CC1] | 4-(ethoxymethyl)-1-((1-methyl-1H-pyrazol-4-yl)methyl)-4-(2-(2-methylthiophen-3-yl)ethyl)piperidine | 362 | $^1$H NMR (300 MHz, MeOD): δ 7.82 (s, 1H), 7.61 (s, 1H), 7.03 (d, J = 5.1 Hz, 1H), 6.81 (d, J = 4.5 Hz, 1H), 4.22 (s, 2H), 3.92 (s, 3H), 3.54-3.42 (m, 3H), 3.40-3.12 (m, 5H), 2.53-2.47 (m, 2H), 2.34 (s, 3H), 2.04-1.60 (m, 6H), 1.18 (t, J = 7.0 Hz, 3H). |
| 279 | 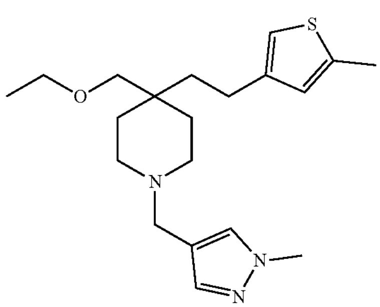 [SMILES: CCOCC1(CCc2csc(C)c2)CCN(Cc2cnn(C)c2)CC1] | 4-(ethoxymethyl)-1-((1-methyl-1H-pyrazol-4-yl)methyl)-4-(2-(5-methylthiophen-3-yl)ethyl)piperidine | 362 | $^1$H NMR (300 MHz, MeOD): δ 7.54 (s, 1H), 7.42 (s, 1H), 6.63 (d, J = 27.0 Hz, 1H), 6.58 (s, 1H), 3.86 (s, 3H), 3.50-3.42 (m, 4H), 3.313.27 (m, 2H), 2.70-2.65 (m, 1H), 2.572.38 (m, 8H), 1.72-1.44 (m, 6H), 1.17 (t, J = 7.0 Hz, 3H). |
| 280 | 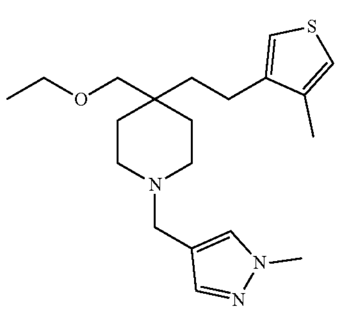 [SMILES: CCOCC1(CCc2cscc2C)CCN(Cc2cnn(C)c2)CC1] | 4-(ethoxymethyl)-1-((1-methyl-1H-pyrazol-4-yl)methyl)-4-(2-(4-methylthiophen-3-yl)ethyl)piperidine | 362 | $^1$H NMR (300 MHz, MeOD): δ 7.81 (s, 1H), 7.60 (s, 1H), 6.98-6.93 (m, 2H), 4.17 (s, 2H), 3.91 (s, 3H), 3.49 (q, J = 6.9 Hz, 2H), 3.40 (s, 2H), 3.29-3.09 (m, 4H), 2.53-2.48 (m, 2H), 2.17 (s, 3H), 1.91-1.65 (m, 6H), 1.16 (t, J = 7.0 Hz, 3H). |

TABLE III-continued

| Compound. | Structure | Name | MS (ESI+): [M + H]+ | H-NMR |
|---|---|---|---|---|
| 281 | 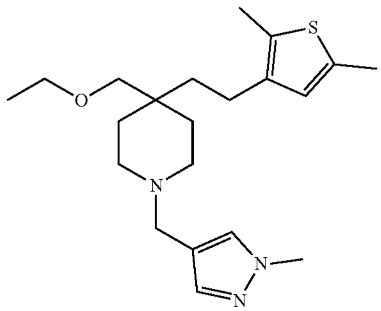 [SMILES: CCOCC1(CCc2cc(C)sc2C)CCN(Cc2cnn(C)c2)CC1] | 4-(2-(2,5-dimethylthiophen-3-yl)ethyl)-4-(ethoxymethyl)-1-((1-methyl-1H-pyrazol-4-yl)methyl)piperidine | 376 | $^1$H NMR (300 MHz, MeOD):δ 7.54 (s, 1H), 7.42 (s, 1H), 6.40 (s, 1H), 3.86 (s, 3H), 3.47 (q, J = 7.0 Hz, 2H), 3.43 (s, 2H), 3.28 (s, 2H), 2.47-2.42 (m, 4H), 2.39-2.33 (m, 5H), 2.26 (s, 3H), 1.68-1.50 (m, 6H), 1.18 (t, J = 7.0 Hz, 3H). |
| 282 | 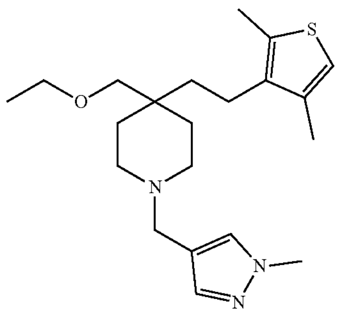 [SMILES: CCOCC1(CCc2c(C)csc2C)CCN(Cc2cnn(C)c2)CC1] | 4-(2-(2,4-dimethylthiophen-3-yl)ethyl)-4-(ethoxymethyl)-1-((1-methyl-1H-pyrazol-4-yl)methyl)piperidine | 376 | $^1$H NMR (300 MHz, MeOD): δ 7.55 (s, 1H), 7.42 (s, 1H), 6.65 (s, 1H), 3.86 (s, 3H), 3.53-3.34 (m, 4H), 2.54-2.38 (m, 6H), 2.30 (s, 3H), 2.10-2.02 (m, 3H), 1.63-1.58 (m, 8H), 1.17 (t, J = 6.9 Hz, 3H). |
| 283 | 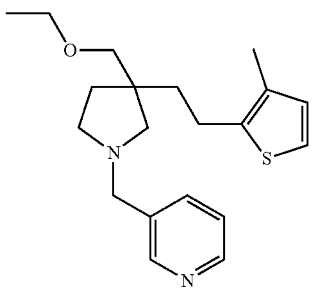 [SMILES: CCOCC1(CCc2sccc2C)CCN(Cc2cccnc2)C1] | 3-((3-(ethoxymethyl)-3-(2-(3-methylthiophen-2-yl)ethyl)pyrrolidin-1-yl)methyl)pyridine | 345 | $^1$H NMR (300 MHz, MeOD): δ 8.54 (d, J = 1.5 Hz, 1H), 8.50 (dd, J = 5.1, 1.5 Hz, 1H), 7.87 (d, J = 9.0 Hz, 1H), 7.46-7.42 (m, 1H), 7.01 (d, J = 5.1 Hz, 1H), 6.73 (d, J = 5.1 Hz, 1H), 3.78 (s, 2H), 3.51 (q, J = 6.9 Hz, 2H), 3.67 (s, 2H), 2.81-2.54 (m, 5H), 2.43-2.30 (m, 1H), 2.12 (s, 3H), 1.89-1.58 (m, 4H), 1.19 (t, J = 6.9 Hz, 3H). |
| 284 | 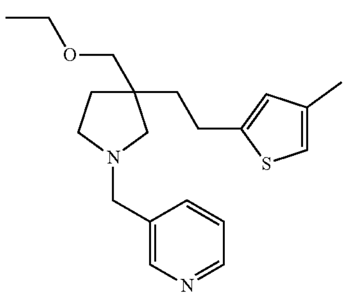 [SMILES: CCOCC1(CCc2cc(C)cs2)CCN(Cc2cccnc2)C1] | 3-((3-(ethoxymethyl)-3-(2-(4-methylthiophen-2-yl)ethyl)pyrrolidin-1-yl)methyl)pyridine | 345 | $^1$H NMR (300 MHz, MeOD): δ 8.51 (d, J = 1.5 Hz, 1H), 8.43 (dd, J = 5.1, 1.5 Hz, 1H), 7.83 (d, J = 9.0 Hz, 1H), 7.42 (d, J = 9.0 Hz, 1H), 6.68 (s, 1H), 6.58 (s, 1H), 3.64-3.57 (s, 4H), 3.50 (q, J = 6.9 Hz, 2H), 2.81-2.54 (m, 5H), 2.43-2.30 (m, 1H), 2.12 (s, 3H), 1.89-1.78 (m, 2H), 1.75-1.58(m, 2H), 1.17 (t, J = 6.9 Hz, 3H). |
| 285 | 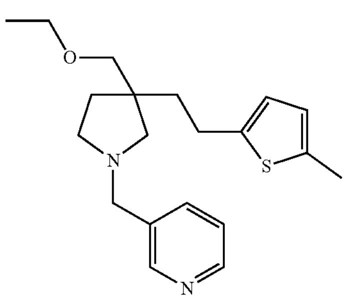 [SMILES: CCOCC1(CCc2ccc(C)s2)CCN(Cc2cccnc2)C1] | 3-((3-(ethoxymethyl)-3-(2-(5-methylthiophen-2-yl)ethyl)pyrrolidin-1-yl)methyl)pyridine | 345 | $^1$H NMR (300 MHz, MeOD): δ 8.55 (d, J = 1.8 Hz, 1H), 8.49 (dd, J = 4.9, 1.5 Hz, 1H), 7.88 (d, J = 7.9 Hz, 1H), 7.45 (dd, J = 7.8, 5.0 Hz, 1H), 6.54-6.50 (m, 2H), 3.85 (s, 2H), 3.50 (q, J = 7.0 Hz, 2H), 3.34-3.32 (m, 2H), 2.84-2.68 (m, 5H), 2.54 (d, J = 10.3 Hz, 1H), 2.38 (s, 3H), 1.86-1.74 (m, 4H), 1.18 (t, J = 7.0 Hz, 3H). |

TABLE III-continued

| Compound. | Structure | Name | MS (ESI+): [M + H]+ | H-NMR |
|---|---|---|---|---|
| 286 | 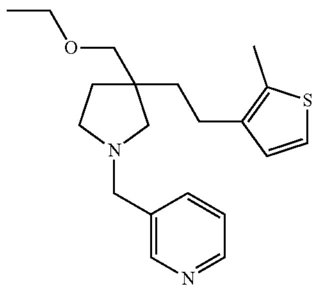 [SMILES: CCOCC1(CCc2ccsc2C)CCN(Cc2cccnc2)C1] | 3-((3-(ethoxymethyl)-3-(2-(2-methylthiophen-yl)ethyl)pyrrolidin-1-yl)methyl)pyridine | 345 | ¹H NMR (300 MHz, MeOD): δ 8.54 (d, J = 1.8 Hz, 1H), 8.47 (dd, J =4.9, 1.5 Hz, 1H), 7.87 (t, J = 3.9 Hz, 1H), 7.44 (dd, J = 7.8, 5.0 Hz, 1H), 7.00 (d, J = 5.2 Hz, 1H), 6.77 (d, J = 5.2 Hz, 1H), 3.78 (s, 2H), 3.50 (q, J = 7.0 Hz, 2H), 3.36-3.33 (m, 2H), 2.78-2.66 (m, 3H), 2.51-2.45 (m, 3H), 2.32 (s, 3H), 1.76-1.64 (m, 4H), 1.16 (t, J = 7.0 Hz, 3H). |
| 287 | 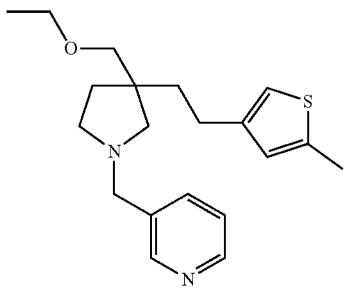 [SMILES: CCOCC1(CCc2csc(C)c2)CCN(Cc2cccnc2)C1] | 3-((3-(ethoxymethyl)-3-(2-(5-methylthiophen-yl)ethyl)pyrrolidin-1-yl)methyl)pyridine | 345 | ¹H NMR (300 MHz, MeOD): δ 8.51 (d, J = 1.5 Hz, 1H), 8.43 (dd, J = 4.8, 1.5 Hz, 1H), 7.83 (d, J = 7.8 Hz, 1H), 7.43-7.41 (m, 1H), 6.68-6.59 (m, 1H), 6.51 (s, 1H), 3.64 (s, 2H), 3.47 (q, J = 6.9 Hz, 2H), 2.63-2.29 (m, 11H), 1.79-1.63 (m, 4H), 1.17 (t, J = 9.0 Hz, 3H). |
| 288 | 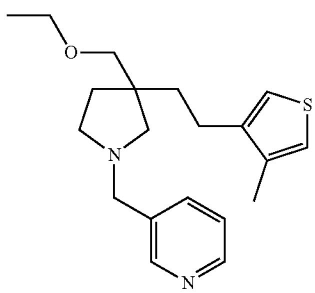 [SMILES: CCOCC1(CCc2cscc2C)CCN(Cc2cccnc2)C1] | 3-((3-(ethoxymethyl)-3-(2-(4-methylthiophen-yl)ethyl)pyrrolidin-1-yl)methyl)pyridine | 345 | ¹H NMR (300 MHz, MeOD): δ 8.57 (d, J = 1.8 Hz, 1H), 8.51 (dd, J = 4.8, 1.8 Hz, 1H), 7.90 (d, J = 7.8 Hz, 1H), 7.46 (dd, J = 4.8, 0.3 Hz, 1H), 6.94-6.92 (m, 2H), 3.91 (s, 2H), 3.51 (q, J = 7.0 Hz, 2H), 3.39 (s, 2H), 2.88-2.80 (m, 3H), 2.61 (d, J = 10.2 Hz, 1H), 2.51-2.47 (m, 2H), 2.16 (s, 3H), 1.83-1.75 (m, 4H), 1.19 (t, J = 6.9 Hz, 3H). |
| 289 | 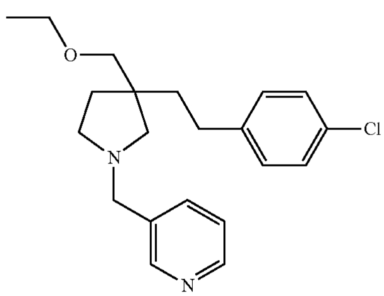 [SMILES: CCOCC1(CCc2ccc(Cl)cc2)CCN(Cc2cccnc2)C1] | 3-((3-(4-chlorophenethyl)-3-(ethoxy-methyl)pyrrolidin-1-yl)methyl)pyridine | 359 | ¹H NMR (300 MHz, MeOD): δ 8.51 (d, J = 1.5 Hz, 1H), 8.43 (d, J = 4.8, 1.5 Hz, 1H), 7.82 (d, J = 1.5 Hz, 1H), 7.44-7.42 (m, 1H), 7.20-7.02 (m, 4H), 3.65 (s, 2H), 3.50 (q, J = 6.9 Hz, 2H), 3.45-3.34 (m, 2H), 2.83-2.48 (m, 6H), 1.89-1.78 (m, 4H), 1.18 (t, J = 6.9 Hz, 3H). |
| 290 | 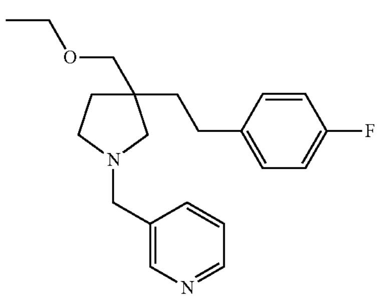 | 3-((3-(ethoxy-methyl)-3-(4-fluoro-phenethyl)pyrrolidin-1-yl)methyl)pyridine | 343 | ¹H NMR (300 MHz, MeOD): δ 9.51 (d, J = 5.7 Hz, 1H), 9.32 (t, J = 9.0 Hz, 1H), 7.86 (d, J = 1.5 Hz, 1H), 7.50-7.32 (m, 1H), 7.20-7.02 (m, 2H), 7.01-6.83 (m, 2H), 3.76 (s, 2H), 3.61 (q, J = 6.9 Hz, 2H), 3.36-3.34 (m, 2H), 2.83-2.48 (m, 6H), 1.89-1.78 (m, 4H), 1.17 (t, J = 6.9 Hz, 3H). |

TABLE III-continued

| Compound. | Structure | Name | MS (ESI+): [M + H]⁺ | H-NMR |
|---|---|---|---|---|
| 291 | 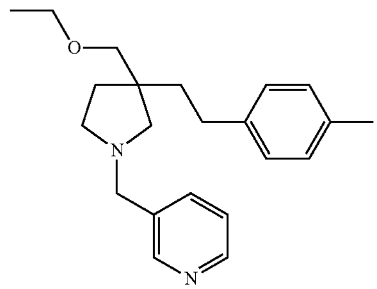 [SMILES: CCOCC1(CCc2ccc(C)cc2)CCN(Cc2cccnc2)C1] | 3-((3-(ethoxymethyl)-3-(4-methylphenethyl)pyrrolidin-1-yl)methyl)pyridine | 339 | ¹H NMR (300 MHz, MeOD): δ 8.51 (d, J = 1.5 Hz, 1H), 8.43 (dd, J = 4.8, 1.5 Hz, 1H), 7.83 (d, J = 9.0 Hz, 1H), 7.44-7.42 (m, 1H), 7.20-7.02 (m, 4H), 3.65 (s, 2H), 3.52-3.47 (q, J = 7.2 Hz, 2H), 3.45-3.34 (m, 2H), 2.83-2.48 (m, 5H), 2.43-2.30 (m, 1H), 2.32 (s, 3H), 1.89-1.78 (m, 4H), 1.18 (t, J = 6.9 Hz, 3H). |
| 292 | 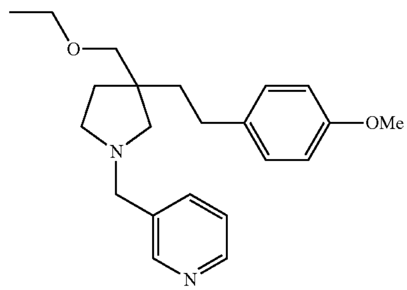 [SMILES: CCOCC1(CCc2ccc(OC)cc2)CCN(Cc2cccnc2)C1] | 3-((3-(ethoxymethyl)-3-(4-methoxyphenethyl)pyrrolidin-1-yl)methyl)pyridine | 355 | ¹H NMR (300 MHz, MeOD): δ 8.60 (s, 1H), 8.55 (dd, J = 5.1, 1.5 Hz, 1H), 7.92 (d, J = 7.8 Hz, 1H), 7.51-7.48 (m, 1H), 7.08 (d, J = 8.7 Hz, 2H), 6.80 (dd, J = 6.9, 2.1 Hz, 2H), 4.06-4.05 (m, 2H), 3.75 (s, 3H), 3.53 (q, J = 6.9 Hz, 2H), 3.29 (s, 2H), 3.20-2.87 (m, 3H), 2.80-2.47 (m, 3H), 1.89-1.78 (m, 4H), 1.20 (t, J = 6.9 Hz, 3H). |
| 293 | 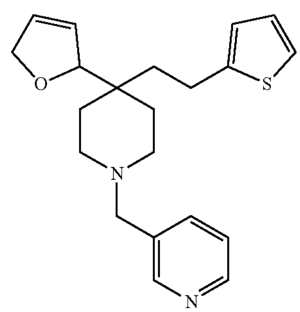 [SMILES: C1=CC(C2(CCc3cccs3)CCN(Cc3cccnc3)CC2)OC1] | 3-((4-(2,5-dihydrofuran-2-yl)-4-(2-(thiophen-2-yl)ethyl)piperidin-1-yl)methyl)pyridine | 355 | ¹H NMR (300 MHz, CDCl₃): δ 8.54-8.50 (m, 2H), 7.68 (brs, 1H), 7.24 (s, 1H), 7.12-7.10 (m, 1H), 6.92 (dd, J = 5.1, 3.3 Hz, 1H), 6.78 (d, J = 2.7 Hz, 1H), 6.00 (dd, J = 6.3, 1.8 Hz, 1H), 5.87-5.84 (m, 1H), 4.82-4.76 (m, 1H), 4.65-4.63 (m, 2H), 3.53 (s, 2H), 2.85-2.79 (m, 2H), 2.71-2.59 (m, 2H), 2.28-2.22 (m, 2H), 1.82-1.59 (m, 6H). |
| 294 | 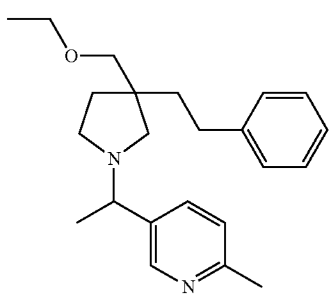 [SMILES: CCOCC1(CCc2ccccc2)CCN(C(C)c2ccc(C)nc2)C1] | 5-(1-(3-(ethoxymethyl)-3-phenethyl-pyrrolidin-1-yl)ethyl)-2-methylpyridine | 353 | ¹H NMR (300 MHz, CDCl₃): δ 8.40 (t, J = 2.4 Hz, 1H), 7.56-7.54 (m, 1H), 7.29-7.08 (m, 6H), 3.50-3.43 (m, 2H), 3.29-3.28 (m, 2H), 3.19-3.17 (m, 1H), 2.77-2.51 (m, 6H), 2.47-2.39 (m, 2H), 2.25-2.22 (m, 1H), 1.77-1.62 (m, 4H), 1.34 (d, J = 6.6 Hz, 3H), 1.18 (t, J = 7.0 Hz, 3H). |
| 295 | 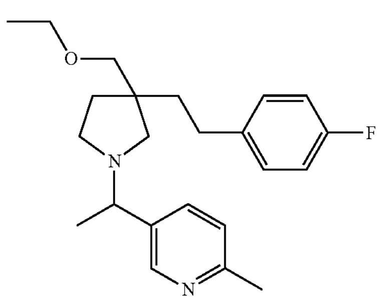 [SMILES: CCOCC1(CCc2ccc(F)cc2)CCN(C(C)c2ccc(C)nc2)C1] | 5-(1-(3-(ethoxymethyl)-3-(4-fluorophenethyl)pyrrolidin-1-yl)ethyl)-2-methylpyridine | 371 | ¹H NMR (300 MHz, MeOD): δ 8.34 (d, J = 2.1 Hz, 1H), 7.73 (dd, J = 8.0, 2.3 Hz, 1H), 7.27 (d, J = 8.1 Hz, 1H), 7.18-7.11 (m, 2H), 6.98-6.91 (m, 2H), 3.51-3.44 (m, 2H), 3.31-3.30 (m, 2H), 2.72-2.65 (m, 1H), 2.54-2.50 (m, 6H), 2.43-2.40 (m, 2H), 2.33-2.14 (m, 1H), 1.72-1.62 (m, 4H), 1.38 (d, J = 6.6 Hz, 3H), 1.17 (t, J = 7.0 Hz, 3H). |

TABLE III-continued

| Compound. | Structure | Name | MS (ESI+): [M + H]+ | H-NMR |
|---|---|---|---|---|
| 296 | 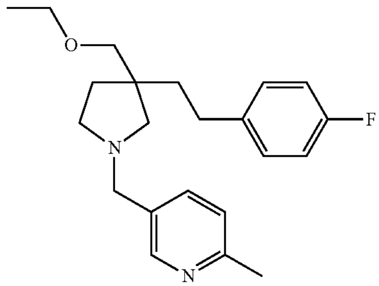 [SMILES: CCOCC1(CCc2ccc(F)cc2)CCN(Cc2ccc(C)nc2)C1] | 5-((3-(ethoxymethyl)-3-(4-fluorophenethyl)pyrrolidin-1-yl)methyl)-2-methylpyridine | 357 | ¹H NMR (300 MHz, MeOD): δ 8.48 (s, 1H), 7.84-7.81 (m, 1H), 7.37 (d, J = 8.1 Hz, 1H), 7.19(dd, J = 8.7, 5.7 Hz, 1H), 6.97 (t, J = 9.0 Hz, 1H), 4.11-4.09 (m, 2H), 3.52 (q, J = 6.9 Hz, 1H), 3.41 (s, 2H), 3.15-2.81 (m, 4H), 2.58-2.56 (m, 5H), 1.90-1.78 (m, 4H), 1.20 (t, J = 6.9 Hz, 3H). |
| 297 | 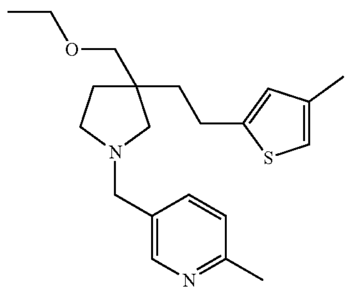 [SMILES: CCOCC1(CCc2cc(C)cs2)CCN(Cc2ccc(C)nc2)C1] | 5-((3-(ethoxymethyl)-3-(2-(4-methylthiophen-2-yl)ethyl)pyrrolidin-1-yl)methyl)-2-methylpyridine | 359 | ¹H NMR (300 MHz, MeOD): δ 8.36 (d, J = 1.5 Hz, 1H), 7.71 (d, J = 7.5 Hz, 1H), 7.27 (d, J = 8.1 Hz, 1H), 6.68 (s, 1H), 6.58 (s, 1H), 3.60 (s, 2H), 3.50 (q, J = 6.9 Hz, 2H), 3.34-3.05 (m, 2H), 2.81-2.54 (m, 5H), 2.52 (s, 3H), 2.43-2.30 (m, 1H), 2.12 (s, 3H), 1.89-1.63 (m, 4H), 1.17 (t, J = 6.9 Hz, 3H). |
| 298 | 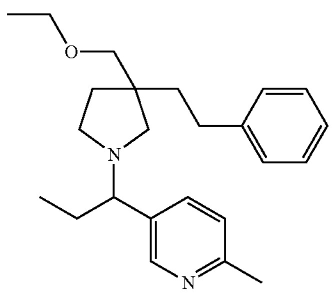 [SMILES: CCOCC1(CCc2ccccc2)CCN(C(CC)c2ccc(C)nc2)C1] | 5-(1-(3-(ethoxymethyl)-3-phenethylpyrrolidin-1-yl)propyl)-2-methylpyridine | 367 | ¹H NMR (300 MHz, MeOD): δ 8.44 (s, 1H), 7.83 (d, J = 8.7 Hz, 1H), 7.42 (d, J = 6.0 Hz, 1H), 7.22-7.16 (m, 5H), 4.01-3.87 (m, 1H), 3.52 (q, J = 6.9 Hz, 2H), 3.40 (s, 2H), 3.11-2.90 (m, 2H), 62-2.51 (m, 5H), 2.20-1.60 (m, 8H), 1.19 (t, J = 6.7 Hz, 3H), 0.74 (t, J = 7.1 Hz, 3H). |
| 299 | 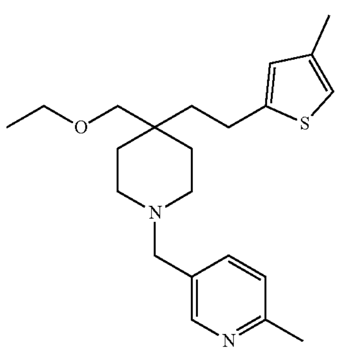 [SMILES: CCOCC1(CCc2cc(C)cs2)CCN(Cc2ccc(C)nc2)CC1] | 5-((4-(ethoxymethyl)-4-(2-(4-methylthiophen-2-yl)ethyl)piperidin-1-yl)methyl)-2-methylpyridine | 373 | ¹H NMR (300 MHz, MeOD):δ 8.44 (d, J = 1.8 Hz, 1H), 7.80 (dd, J = 8.1, 2.1 Hz, 1H), 7.35 (d, J = 8.1 Hz, 1H), 6.70 (s, 1H), 6.61 (s, 1H), 3.91 (s, 2H), 3.48 (q, J = 7.0 Hz, 2H), 3.37-3.31 (m, 2H), 2.83-2.80 (m, 4H), 2.72-2.69 (m, 2H), 2.54 (s, 3H), 2.17(s, 3H), 1.78-1.57 (m, 6H), 1.18 (t, J = 6.9 Hz, 3H). |
| 300 | 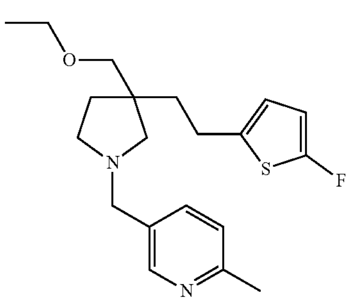 [SMILES: CCOCC1(CCc2ccc(F)s2)CCN(Cc2ccc(C)nc2)C1] | 5-((3-(ethoxymethyl)-3-(2-(5-fluorothiophen-2-yl)ethyl)pyrrolidin-1-yl)methyl)-2-methylpyridine | 363 | ¹H NMR (300 MHz, MeOD): δ 8.44 (d, J = 1.8 Hz, 1H), 7.79 (dd, J = 8.1, 2.1 Hz, 1H), 7.34 (d, J = 8.1 Hz, 1H), 6.42 (t, J = 3.6 Hz, 1H), 6.29 (dd, J = 3.9, 2.1 Hz, 1H), 4.04-3.83 (m, 2H), 3.51 (q, J = 7.0 Hz, 2H), 3.36 (s, 2H), 3.00-2.87 (m, 3H), 2.69-2.66 (m, 3H), 2.54 (s, 3H), 1.89-1.76 (m, 4H), 1.18 (t, J = 6.9 Hz, 3H). |

TABLE III-continued

| Compound. | Structure | Name | MS (ESI+): [M + H]+ | H-NMR |
|---|---|---|---|---|
| 301 | 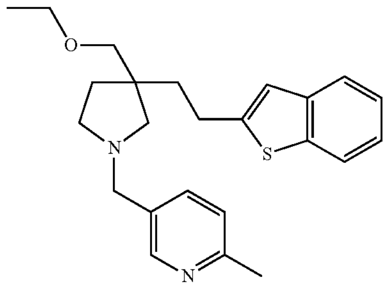 [SMILES: CCOCC1(CCc2cc3ccccc3s2)CCN(Cc2ccc(C)nc2)C1] | 5-((3-(2-(benzo[b]thiophen-2-yl)ethyl)-3-(ethoxymethyl)pyrrolidin-1-yl)methyl)-2-methylpyridine | 395 | $^1$H NMR (300 MHz, CDCl$_3$): δ 8.42 (d, J = 1.5 Hz, 1H), 7.74 (d, J = 7.5 Hz, 1H), 7.64 (d, J = 7.2 Hz, 1H), 7.32-7.20 (m, 4H), 7.02 (s, 1H), 4.14-3.90 (m, 2H), 3.57-3.30 (m, 6H), 2.97-2.86 (m, 2H), 2.57 (s, 3H), 2.19-1.87 (m, 6H), 1.22 (t, J = 7.0 Hz, 3H). |
| 302 | 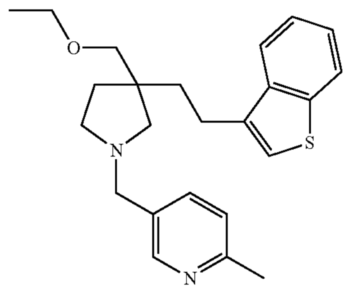 [SMILES: CCOCC1(CCc2csc3ccccc23)CCN(Cc2ccc(C)nc2)C1] | 5-((3-(2-(benzo[b]thiophen-3-yl)ethyl)-3-(ethoxymethyl)pyrrolidin-1-yl)methyl)-2-methylpyridine | 395 | $^1$H NMR (300 MHz, CDCl$_3$): δ 8.43 (s, 1H), 7.84 (d, J = 7.2 Hz, 1H), 7.73 (d, J = 6.9 Hz, 1H), 7.40-7.31 (m, 2H), 7.22 (d, J = 8.1 Hz, 2H), 7.12(s, 1H), 4.11-3.87 (m, 2H), 3.60-3.38 (m, 4H), 3.21-2.90 (m, 2H), 2.84-2.79 (m, 2H), 2.57 (s, 3H), 2.10-2.00 (m, 6H), 1.25 (t, J = 7.0 Hz, 3H). |
| 303 | 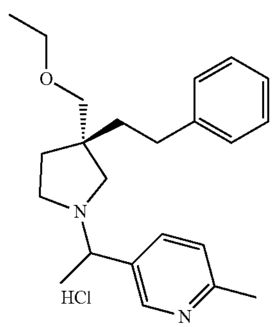 [SMILES: CCOC[C@@]1(CCc2ccccc2)CCN(C(C)c2ccc(C)nc2)C1 ; Cl] | 5-(1-((S)-3-(ethoxymethyl)-3-phenethylpyrrolidin-1-yl)ethyl)-2-methylpyridine HCl | 353 | $^1$H NMR (300 MHz, MeOD): δ 9.04 (s, 1H), 8.75 (t, J = 5.1 Hz, 1H), 8.02 (d, J = 8.7 Hz, 1H), 7.28-7.15 (m, 5H), 4.71-4.69 (m, 1H), 3.90-3.39 (m, 6H), 3.29-3.01 (m, 2H), 2.83 (s, 3H), 2.65-2.60 (m, 2H), 2.19-1.88 (m, 4H), 1.84 (d, J = 6.9 Hz, 3H), 1.28-1.11 (m, 3H). |
| 304 | 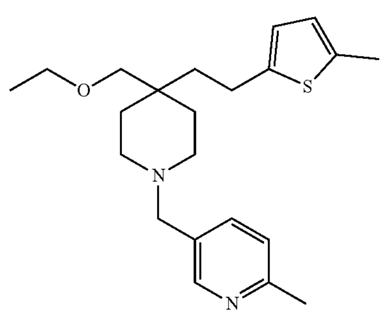 [SMILES: CCOCC1(CCc2ccc(C)s2)CCN(Cc2ccc(C)nc2)CC1] | 5-((4-(ethoxymethyl)-4-(2-(5-methylthiophen-2-yl)ethyl)piperidin-1-yl)methyl)-2-methylpyridine | 373 | $^1$H NMR (300 MHz, MeOD): δ 8.46 (d, J = 1.8 Hz, 1H), 7.82 (dd, J = 8.1, 2.1 Hz, 1H), 7.37 (d, J = 8.1 Hz, 1H), 6.55-6.51 (m, 2H), 4.01 (s, 2H), 3.48 (q, J = 6.9 Hz, 2H), 3.33 (s, 2H), 3.01-2.89 (m, 4H), 2.80-2.68 (m, 2H), 2.55 (s, 3H), 2.39 (s, 3H), 1.78-1.58 (m, 6H), 1.17 (t, J = 6.9 Hz, 3H). |
| 305 | 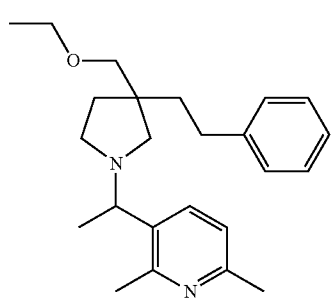 [SMILES: CCOCC1(CCc2ccccc2)CCN(C(C)c2ccc(C)nc2C)C1] | 3-(1-(3-(ethoxymethyl)-3-phenethylpyrrolidin-1-yl)ethyl)-2,6-dimethylpyridine | 367 | $^1$H NMR (300 MHz, MeOD): δ 7.78 (dd, J = 7.8, 2.1 Hz, 1H), 7.26-7.20 (m, 2H), 7.16-7.09 (m, 4H), 3.53-3.46 (m, 3H), 3.35-3.32 (m, 2H), 2.78-2.66 (m, 1H), 2.57-2.51 (m, 5H), 2.49-2.38 (m, 5H), 2.26 (d, J = 9.6 Hz, 1H), 1.75-1.63 (m, 4H), 1.31 (d, J = 6.6 Hz, 3H), 1.21-1.67 (m, 3H). |

TABLE III-continued

| Compound. | Structure | Name | MS (ESI+): [M + H]+ | H-NMR |
|---|---|---|---|---|
| 306 | 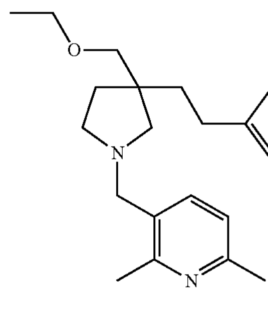 | 3-((3-(ethoxymethyl)-3-(2-(thiophen-3-yl)ethyl)pyrrolidin-1-yl)methyl)-2,6-dimethylpyridine | 359 | $^1$H NMR (300 MHz, MeOD): δ 7.57 (d, J = 7.8 Hz, 1H), 7.27 (dd, J = 4.9, 3.0 Hz, 1H), 7.06 (d, J = 7.8 Hz, 1H), 6.96 (d, J = 1.8 Hz, 1H), 6.92 (d, J = 4.9 Hz, 1H), 3.56 (s, 2H), 3.47 (q, J = 7.0 Hz, 2H), 3.35 (s, 2H), 2.66-2.47 (m, 8H), 2.46 (s, 3H), 2.29 (d, J = 9.4 Hz, 1H), 1.83-1.71 (m, 2H), 1.63 (t, J = 6.9 Hz, 2H), 1.17 (t, J = 7.0 Hz, 3H). |
| 307 | 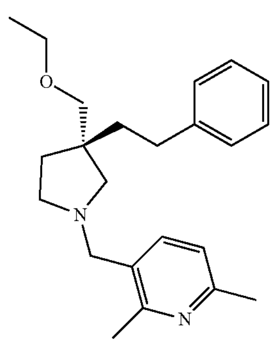 [SMILES: CCOC[C@@]1(CCc2ccccc2)CCN(Cc2ccc(C)nc2C)C1] | (S)-3-((3-(ethoxymethyl)-3-phenethylpyrrolidin-1-yl)methyl)-2,6-dimethylpyridine | 353 | $^1$H NMR (300 MHz, MeOD): δ 7.57 (d, J = 7.8 Hz, 1H), 7.25-7.14 (m, 2H), 7.12-7.05 (m, 4H), 3.58 (s, 2H), 3.48 (q, J = 6.9 Hz, 2H), 3.35-3.29 (m, 2H), 2.64-2.56 (m, 8H), 2.47 (s, 3H), 2.35-2.28 (m, 1H), 1.78-1.63 (m, 4H), 1.18 (t, J = 6.9 Hz, 3H). |
| 308 | 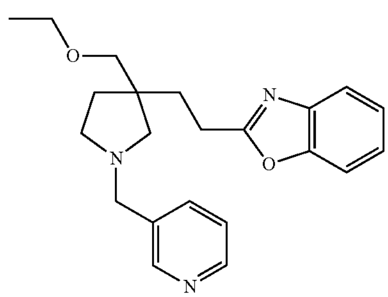 [SMILES: CCOCC1(CCc2nc3ccccc3o2)CCN(Cc2cccnc2)C1] | 2-(2-(3-(ethoxymethyl)-1-(pyridin-3-ylmethyl)pyrrolidin-3-yl)ethyl)benzo[d]oxazole | 366 | $^1$H NMR (300 MHz, MeOD): δ 8.50 (s, 1H), 8.43 (dd, J = 4.9, 1.5 Hz, 1H), 7.82 (d, , J = 7.8 Hz, 1H), 7.62-7.54 (m, 2H), 7.40-7.33 (m, 3H), 3.66 (s, 2H), 3.42 (q, J = 7.2 Hz, 3H), 3.36-3.35 (m, 2H), 2.98 (t, J = 7.5 Hz, 2H), 2.65-2.55 (m, 2H), 2.57 (d, J = 9.7 Hz, 1H), 2.36 (d, J = 9.7 Hz, 1H), 2.07-2.00 (m, 2H), 1.69 (t, J = 7.5 Hz, 2H), 1.10 (t, J = 7.0 Hz, 3H). |
| 309 | 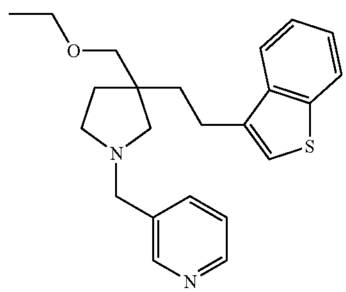 [SMILES: CCOCC1(CCc2csc3ccccc23)CCN(Cc2cccnc2)C1] | 3-((3-(2-(benzo[b]thiophen-3-yl)ethyl)-3-(ethoxymethyl)pyrrolidin-1-yl)methyl)pyridine | 381 | $^1$H NMR (300 MHz, MeOD): δ 8.56 (s, 1H), 8.50-8.49 (m, 1H), 7.89-7.77 (m, 3H), 7.47-7.43 (m, 1H), 7.37-7.31 (m, 2H), 7.21 (s, 1H), 3.87 (s, 2H), 3.55 (q, J = 6.9 Hz, 2H), 3.46-3.39 (m, 2H), 2.88-2.79 (m, 5H), 2.75-2.63 (m, 1H), 2.18-1.95 (m, 2H), 1.89-1.79 (m, 2H), 1.22 (t, J = 6.9 Hz, 3H). |

TABLE III-continued

| Compound | Structure | Name | MS (ESI+): [M + H]+ | H-NMR |
|---|---|---|---|---|
| 310 | 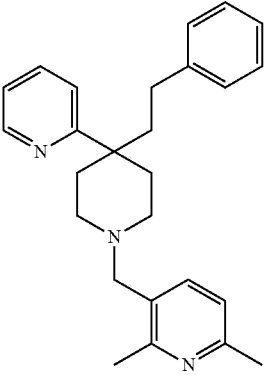 [SMILES: Cc1ccc(CN2CCC(CCc3ccccc3)(c3ccccn3)CC2)c(C)n1] | 2,6-dimethyl-3-((4-phenethyl-4-(pyridin-2-yl)piperidin-1-yl)methyl)pyridine | 386 | ¹H NMR (300 MHz, MeOD): δ 8.60 (dd, J = 4.9, 1.0 Hz, 1H), 7.84 (t, J = 3.9 Hz, 1H), 7.65 (d, J = 7.8 Hz, 1H), 7.54 (d, J = 8.1 Hz, 1H), 7.31-7.27 (m, 1H), 7.16-7.08 (m, 4H), 6.98-6.95 (m, 2H), 3.77 (s, 2H), 3.00-2.97 (m, 2H), 2.61-2.54 (m, 7H), 2.49 (s, 3H), 2.22-2.17 (m, 2H), 1.99-1.93 (m, 4H). |
| 311 | 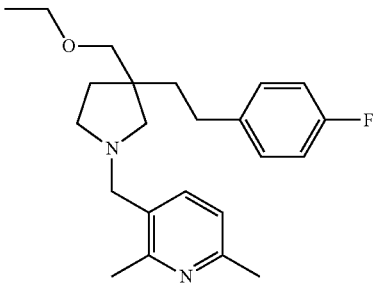 [SMILES: CCOCC1(CCc2ccc(F)cc2)CCN(Cc2ccc(C)nc2C)C1] | 3-((3-(ethoxymethyl)-3-(4-fluoro-phenethyl)pyrrolidin-1-yl)methyl)-2,6-dimethylpyridine | 371 | ¹H NMR (300 MHz, MeOD): δ 7.58 (d, J = 7.8 Hz, 1H), 7.19-7.14 (m, 2H), 7.09-7.06 (m, 1H), 7.00-6.94 (m, 2H), 3.59 (s, 2H), 3.46 (q, J = 6.9 Hz, 2H), 3.36-3.34 (m, 4H), 2.61 (s, 3H), 2.48 (s, 3H), 2.33-2.29 (m, 4H), 1.89-1.78 (m, 4H), 1.19 (t, J = 7.2 Hz, 3H). |
| 312 | 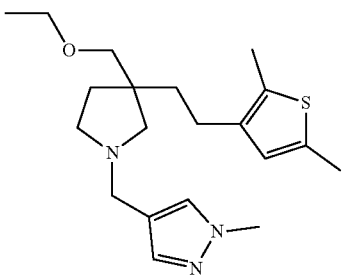 [SMILES: CCOCC1(CCc2cc(C)sc2C)CCN(Cc2cnn(C)c2)C1] | 4-((3-(2-(2,5-dimethylthiophen-3-yl)ethyl)-3-(ethoxymethyl)pyrrolidin-1-yl)methyl)-1-methyl-1H-pyrazole | 362 | ¹H NMR (300 MHz, MeOD): δ 7.81 (s, 1H), 7.61 (s, 1H), 6.46 (s, 1H), 5.49 (s, 1H), 4.27-4.16 (m, 2H), 3.91 (s, 3H), 3.58-3.49 (m, 2H), 3.56-3.26 (m, 5H), 3.04 (d, J = 11.6 Hz, 1H), 2.43 (t, J = 8.4 Hz, 2H), 2.33 (s, 3H), 2.26 (s, 3H), 2.06-1.92 (m, 2H), 1.80-1.66 (m, 2H), 1.20 (t, J = 6.9 Hz, 3H). |
| 313 | 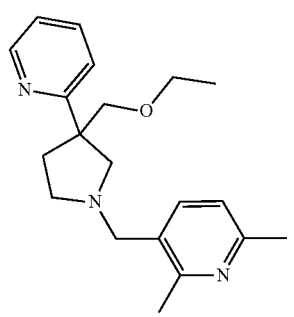 [SMILES: CCOCC1(c2ccccn2)CCN(Cc2ccc(C)nc2C)C1] | 3-((3-(ethoxymethyl)-3-(pyridin-2-yl)pyrrolidin-1-yl)methyl)-2,6-dimethylpyridine | 326 | ¹H NMR (300 MHz, MeOD): δ 8.39 (d, J = 3.7 Hz, 1H), 7.73-7.58 (m, 2H), 7.31 (d, J = 7.9 Hz, 1H), 7.23-7.11 (m, 1H), 7.04 (d, J = 7.8 Hz, 1H), 3.86 (s, 2H), 3.63-3.51 (m, 2H), 3.38-3.25 (m, 2H), 3.24-3.17 (m, 2H), 3.04-2.73 (m, 2H), 2.48 (s, 3H), 2.39 (s, 3H), 2.28-2.05 (m, 2H), 0.96 (t, J = 6.9 Hz, 3H). |

TABLE III-continued

| Compound. | Structure | Name | MS (ESI+): [M + H]+ | H-NMR |
|---|---|---|---|---|
| 314 | 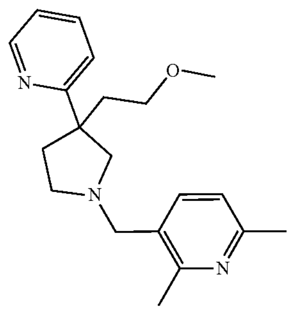 [SMILES: COCCC1(c2ccccn2)CCN(Cc2ccc(C)nc2C)C1] | 3-((3-(2-methoxyethyl)-3-(pyridin-2-yl)pyrrolidin-1-yl)methyl)-2,6-dimethylpyridine | 326 | $^1$H NMR (300 MHz, MeOD): δ 8.47-8.45 (m, 1H), 7.53 (t, J = 1.8 Hz, 1H), 7.39 (d, J = 7.8 Hz, 1H), 7.19 (m, 1H), 7.04-7.02 (m, 1H), 6.86 (d, J = 7.8 Hz, 1H), 3.51 (d, J = 2.1 Hz, 2H), 3.10 (s, 3H), 3.08-2.93 (m, 2H), 2.76-1.97 (m, 14H). |
| 315 | 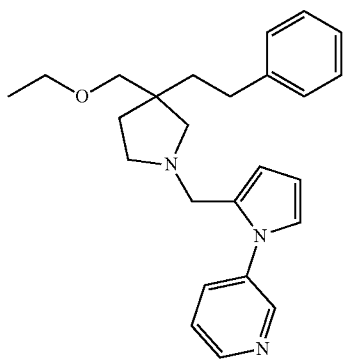 [SMILES: CCOCC1(CCc2ccccc2)CCN(Cc2cccn2-c2cccnc2)C1] | 3-(2-((3-(ethoxymethyl)-3-phenethylpyrrolidin-1-yl)methyl)-1H-pyrrol-1-yl)pyridine | 390 | $^1$H NMR (300 MHz, MeOD): δ 8.74 (s, 1H), 8.47-8.45 (m, 1H), 8.11-8.01 (m, 1H), 7.50-7.48 (m, 1H), 7.25-7.09 (m, 5H), 6.91 (d, J = 2.4 Hz, 1H), 6.23 (s, 2H), 3.52-3.38 (m, 4H), 3.35-3.29 (m, 2H), 2.51-2.41 (m, 5H), 2.30-2.15 (m, 1H), 1.65-1.53 (m, 4H), 1.17 (t, J = 6.9 Hz, 3H). |
| 316 | 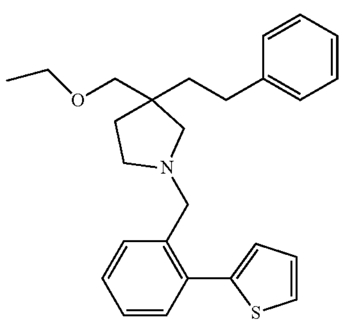 [SMILES: CCOCC1(CCc2ccccc2)CCN(Cc2ccccc2-c2cccs2)C1] | 3-(ethoxymethyl)-3-phenethyl-1-(2-(thiophen-2-yl)benzyl)pyrrolidine | 406 | $^1$H NMR (300 MHz, MeOD): δ 7.59-7.56 (m, 1H), 7.53-7.42 (m, 4H), 7.28-7.22 (m, 3H), 7.21-7.14 (m, 4H), 4.10 (s, 2H), 3.50 (q, J = 7.0 Hz, 2H), 3.36-3.31 (m, 2H), 2.88-2.73 (m, 3H), 2.58-2.51 (m, 3H), 1.82-1.72 (m, 4H), 1.18 (t, J = 6.9 Hz, 3H). |
| 317 | 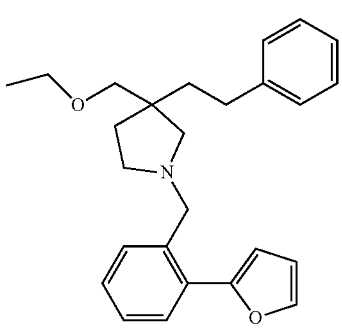 [SMILES: CCOCC1(CCc2ccccc2)CCN(Cc2ccccc2-c2ccco2)C1] | 3-(ethoxymethyl)-1-(2-(furan-2-yl)benzyl)-3-phenethylpyrrolidine | 390 | $^1$H NMR (300 MHz, MeOD): δ 7.77-7.74 (m, 2H), 7.55-7.49 (m, 2H), 7.43-7.40 (m, 1H), 7.29-7.20 (m, 5H), 6.90-6.88 (m, 1H), 6.64-6.62 (m, 1H), 4.32-4.27 (m, 2H), 3.54-3.38 (m, 4H), 3.34-2.87 (m, 4H), 2.85-2.75 (m, 2H), 2.04-1.95 (m, 2H), 1.89-1.72 (m, 2H), 1.17 (t, J = 6.9 Hz, 3H). |

TABLE III-continued

| Compound. | Structure | Name | MS (ESI+): [M + H]+ | H-NMR |
|---|---|---|---|---|
| 318 | 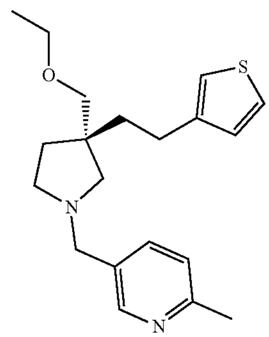 [SMILES: CCOC[C@@]1(CCc2ccsc2)CCN(Cc2ccc(C)nc2)C1] | (S)-5-((3-(ethoxymethyl)-3-(2-(thiophen-3-yl)ethyl)pyrrolidin-1-yl)methyl)-2-methylpyridine | 345 | ¹H NMR (300 MHz, MeOD): δ 8.42 (d, J = 1.9 Hz, 1H), 7.77 (dd, J = 8.0, 2.1 Hz, 1H), 7.34-7.29 (m, 2H), 7.01-6.95 (m, 2H), 3.83 (s, 2H), 3.51 (q, J = 7.0 Hz, 2H), 3.37 (s, 2H), 2.89-2.80 (m, 2H), 2.76 (d, J = 10.3 Hz, 1H), 2.65-2.57 (m, 3H), 2.55 (s, 3H), 1.89-1.76 (m, 4H), 1.19 (t, J = 6.9 Hz, 3H). |
| 319 | 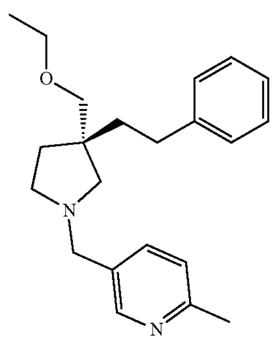 [SMILES: CCOC[C@@]1(CCc2ccccc2)CCN(Cc2ccc(C)nc2)C1] | (S)-5-((3-(ethoxymethyl)-3-phenethylpyrrolidin-1-yl)methyl)-2-methylpyridine | 339 | ¹H NMR (300 MHz, MeOD): δ 8.33 (s, 1H), 7.68 (d, J = 7.5 Hz, 1H), 7.24-7.05 (m, 6H), 3.77 (s, 2H), 3.50 (q, J = 6.9 Hz, 2H), 3.21 (s, 2H), 2.84-2.70 (m, 3H), 2.52-2.44 (m, 6H), 1.73-1.60 (m, 4H), 1.10 (t, J = 6.9 Hz, 3H). |
| 320 | 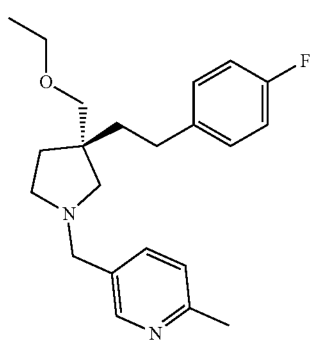 [SMILES: CCOC[C@@]1(CCc2ccc(F)cc2)CCN(Cc2ccc(C)nc2)C1] | (S)-5-((3-(ethoxymethyl)-3-(4-fluorophenethyl)pyrrolidin-1-yl)methyl)-2-methylpyridine | 357 | ¹H NMR (300 MHz, MeOD): δ 8.41 (d, J = 3.1 Hz, 1H), 7.76 (dd, J = 8.0, 2.3 Hz, 1H), 7.32 (d, J = 8.0 Hz, 1H), 7.21-7.15 (m, 2H), 7.00-6.94 (m, 2H), 3.80 (s, 2H), 3.51 (q, J = 6.9 Hz, 2H), 3.37-3.32 (m, 2H), 2.82-2.71 (m, 3H), 2.61-2.51 (m, 6H), 1.81-1.73 (m, 4H), 1.20 (t, J = 6.9 Hz, 3H). |
| 321 | 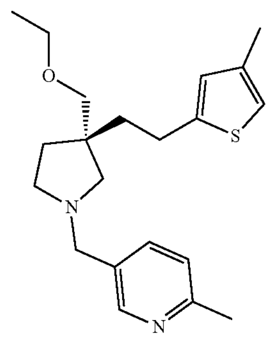 [SMILES: CCOC[C@@]1(CCc2cc(C)cs2)CCN(Cc2ccc(C)nc2)C1] | (S)-5-((3-(ethoxymethyl)-3-(2-(4-methylthiophen-2-yl)ethyl)pyrrolidin-1-yl)methyl)-2-methylpyridine | 359 | ¹H NMR (300 MHz, MeOD): δ 8.38 (d, J = 1.8 Hz, 1H), 7.73 (dd, J = 8.1, 2.1 Hz, 1H), 7.30 (d, J = 8.1 Hz, 1H), 6.70 (s, 1H), 6.60 (s, 1H), 3.67 (s, 2H), 3.50 (q, J = 6.9 Hz, 2H), 3.33-3.32 (m, 2H), 2.77-2.63 (m, 4H), 2.59 (d, J = 9.9 Hz, 1H), 2.53 (s, 3H), 2.38 (d, J = 9.6 Hz, 1H), 2.18 (d, J = 0.9 Hz, 3H), 1.91-1.76 (m, 2H), 1.69 (t, J = 7.2 Hz, 2H), 1.19 (t, J = 6.9 Hz, 3H). |

TABLE III-continued

| Compound. | Structure | Name | MS (ESI+): [M + H]+ | H-NMR |
|---|---|---|---|---|
| 322 | 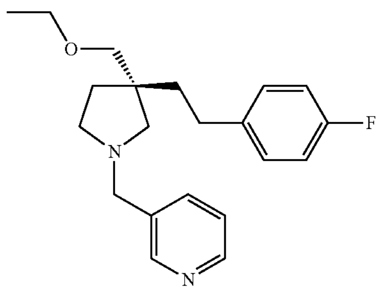 [SMILES: CCOC[C@@]1(CCc2ccc(F)cc2)CCN(Cc2cccnc2)C1] | (S)-3-((3-(ethoxymethyl)-3-(4-fluoro phenethyl)pyrrolidin-1-yl)methyl)pyridine | 343 | $^1$H NMR (300 MHz, MeOD): δ 8.50 (s, 1H), 8.44-8.42 (m, 1H), 7.83 (d, J = 7.8 Hz, 1H), 7.41 (dd, J = 7.5, 4.8 Hz, 1H), 7.18-7.13 (m, 2H), 6.98-6.92 (m, 2H), 3.65 (s, 2H), 3.48 (q, J = 7.2 Hz, 2H), 3.34-3.30 (m, 2H), 2.66-2.53 (m, 5H), 2.34-2.31 (d, J = 9.6 Hz, 1H), 1.75-1.65 (m, 4H), 1.18 (t, J =7.2 Hz, 3H) |
| 323 | 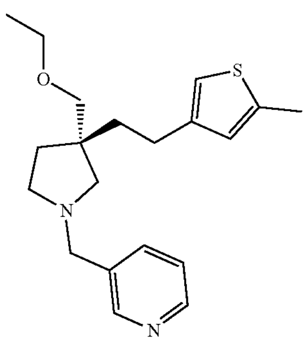 [SMILES: CCOC[C@@]1(CCc2csc(C)c2)CCN(Cc2cccnc2)C1] | (S)-3-((3-(ethoxymethyl)-3-(2-(5-methylthiophen-3-yl)ethyl)pyrrolidin-1-yl)methyl)pyridine | 345 | $^1$H NMR (300 MHz, MeOD): δ 8.42 (d, J = 1.8 Hz, 1H), 8.35 (dd, J = 4.8, 1.5 Hz, 1H), 7.74 (d, J = 7.8 Hz, 1H), 7.32 (dd, J = 7.8, 4.8 Hz, 1H), 6.59 (s, 1H), 6.49 (s, 1H), 3.60 (s, 2H), 3.37 (q, J = 6.9 Hz, 2H), 3.22-3.19 (m, 2H), 2.59-2.50 (m, 3H), 2.40 (t, J = 8.4 Hz, 2H), 2.31-2.29 (m, 4H), 1.70-1.55 (m, 4H), 1.07 (t, J = 6.9 Hz, 3H). |
| 324 | 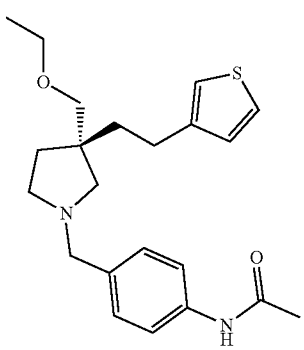 [SMILES: CCOC[C@@]1(CCc2ccsc2)CCN(Cc2ccc(NC(C)=O)cc2)C1] | (S)-N-(4-((3-(ethoxymethyl)-3-(2-(thiophen-3-yl)ethyl)pyrrolidin-1-yl)methyl)phenyl)acetamide | 387 | $^1$H NMR (300 MHz, MeOD): δ 7.55 (d, J = 8.7 Hz, 2H), 7.32 (d, J = 8.7 Hz, 2H), 7.21 (dd, J = 5.1, 3.0 Hz, 1H), 6.94 (s, 1H), 6.86 (d, J = 4.8 Hz, 1H), 4.11-4.07 (m, 2H), 3.45 (q, J = 6.9 Hz, 2H), 3.31 (s, 2H), 3.24-3.22 (m, 1H), 3.21-3.06 (m, 2H), 2.88 (d, J = 11.6 Hz, 1H), 2.54 (t, J = 7.8 Hz, 2H), 2.04 (s, 3H), 1.93-1.75 (m, 4H), 1.10 (t, J = 6.9 Hz, 3H). |
| 325 | 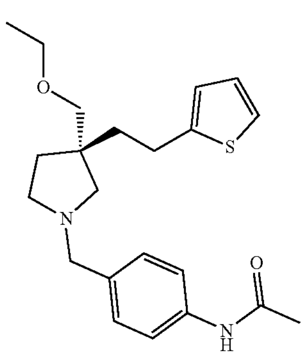 [SMILES: CCOC[C@@]1(CCc2cccs2)CCN(Cc2ccc(NC(C)=O)cc2)C1] | (R)-N-(4-((3-(ethoxymethyl)-3-(2-(thiophen-2-yl)ethyl)pyrrolidin-1-yl)methyl)phenyl)acetamide | 387 | $^1$H NMR (300 MHz, MeOD): δ 7.61 (d, J = 8.4 Hz, 2H), 7.38 (d, J = 8.7 Hz, 2H), 7.12 (dd, J = 5.1, 0.9 Hz, 1H), 6.84 (dd, J = 5.1, 1.8 Hz, 1H), 6.78 (d, J = 3.3 Hz, 1H), 4.54 (s, 2H), 4.22-4.17 (m, 2H), 3.48 (q, J = 6.9 Hz, 2H), 3.37-3.34 (m, 2H), 3.25-3.18 (m, 1H), 3.00 (d, J = 11.7 Hz, 1H), 2.78 (t, J = 7.8 Hz, 2H), 2.09 (s, 3H), 1.98-1.86 (m, 4H), 1.13 (t, J = 6.9 Hz, 3H). |

TABLE III-continued

| Compound. | Name | MS (ESI+): [M + H]+ | H-NMR |
|---|---|---|---|
| 326 | (S)-3-((3-(ethoxymethyl)-3-(2-(thiophen-2-yl)ethyl)pyrrolidin-1-yl)methyl)pyridine | 331 | ¹H NMR (300 MHz, CDCl₃): δ 8.54 (s, 1H), 8.49-8.47 (m, 1H), 7.66 (d, J = 7.5 Hz, 1H), 7.26-7.24 (m, 1H), 7.11-7.09 (m, 1H), 6.92-6.89 (m, 1H), 6.79-6.78 (m, 1H), 3.59 (s, 2H), 3.47 (q, J = 6.9 Hz, 2H), 3.31-3.23 (m, 2H), 2.87-2.81 (m, 2H), 2.62-2.51 (m, 3H), 2.35-2.27 (m, 1H), 1.95-1.83 (m, 2H), 1.68-1.64 (m, 2H), 1.18 (t, J = 6.9 Hz, 3H). |
| 327 | 3-(1-(4-(ethoxymethyl)-4-phenethylpiperidin-1-yl)ethyl)pyridine | 353 | ¹H NMR (300 MHz, MeOD): δ 8.51 (d, J = 1.8 Hz, 1H), 8.45 (dd, J = 4.8, 1.8 Hz, 1H), 7.86 (d, J = 7.8 Hz, 1H), 7.44 (dd, J = 4.8, 1.8 Hz, 1H), 7.27-7.22 (m, 2H), 7.15-7.12 (m, 3H), 3.57 (q, J = 6.9 Hz, 1H), 3.47 (q, J = 6.9 Hz, 2H), 3.30 (s, 2H), 2.55-2.49 (m, 4H), 2.46-2.34 (m, 2H), 1.64-1.53 (m, 6H), 1.44 (d, J = 6.9 Hz, 3H), 1.19 (t, J = 6.9 Hz, 3H). |
| 328 | 2,6-dimethyl-3-(1-(4-phenethyl-4-(pyridin-2-yl)piperidin-1-yl)ethyl)pyridine | 400 | ¹H NMR (300 MHz, CDCl₃): δ 8.60 (d, J = 3.9 Hz, 1H), 8.27 (d, J = 7.5 Hz, 1H), 7.72 (td, J = 7.8, 1.8 Hz, 1H), 7.32 (d, J = 7.8 Hz, 1H), 7.25-7.05 (m, 5H), 6.96 (d, J = 7.2 Hz, 2H), 4.08-3.99 (m, 1H), 3.85-3.61 (m, 1H), 3.49 (s, 1H), 3.12-2.93 (m, 1H), 2.81-2.61 (m, 2H), 2.60-2.43 (m, 8H), 2.42-2.17 (m, 3H), 2.05-1.90 (m, 2H), 1.70 (d, J = 6.3 Hz, 3H). |
| 329 | (S)-3-((3-(ethoxymethyl)-3-(2-(4-methylthiophen-2-yl)ethyl)pyrrolidin-1-yl)methyl)-2,6-dimethylpyridine | 373 | ¹H NMR (300 MHz, MeOD): δ 7.72 (d, J = 7.8 Hz, 1H), 7.18 (d, J = 7.8 Hz, 1H), 6.72 (d, J = 0.9 Hz, 1H), 6.63 (s, 1H), 4.01 (s, 2H), 3.54 (q, J = 6.9 Hz, 2H), 3.40 (s, 2H), 3.07-2.92 (m, 3H), 2.80-2.72 (m, 3H), 2.60 (s, 3H), 2.52 (s, 3H), 2.18 (s, 3H), 1.96-1.86 (m, 4H), 1.21 (t, J = 6.9 Hz, 3H). |

TABLE III-continued

| Compound. | Structure | Name | MS (ESI+): [M + H]+ | H-NMR |
|---|---|---|---|---|
| 330 | 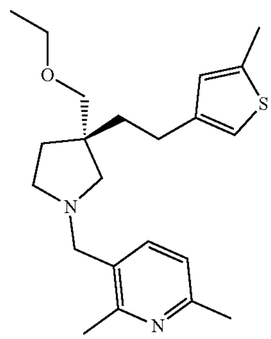 [SMILES: CCOC[C@@]1(CCc2csc(C)c2)CCN(Cc2ccc(C)nc2C)C1] | (S)-3-((3-(ethoxymethyl)-3-(2-(5-methylthiophen-yl)ethyl)pyrrolidin-1-yl)methyl)-2,6-dimethylpyridine | 373 | ¹H NMR (300 MHz, MeOD): δ 7.58 (d, J = 7.8 Hz, 1H), 7.05 (d, J = 7.8 Hz, 1H), 6.61 (s, 1H), 6.51 (s, 1H), 3.85 (s, 2H), 3.41 (q, J = 6.9 Hz, 2H), 3.27 (s, 2H), 2.91-2.75 (m, 3H), 2.56 (d, J = 10.5 Hz, 1H), 2.48 (s, 3H), 2.45-2.36 (m, 5H), 2.31 (s, 3H), 1.76-1.64 (m, 4H), 1.09 (t, J = 6.9 Hz, 3H). |
| 331 | 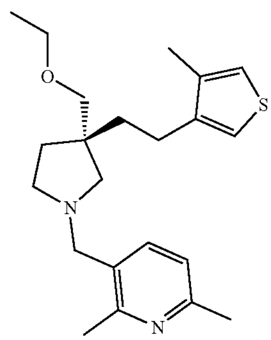 [SMILES: CCOC[C@@]1(CCc2cscc2C)CCN(Cc2ccc(C)nc2C)C1] | (S)-3-((3-(ethoxymethyl)-3-(2-(4-methylthiophen-3-yl)ethyl)pyrrolidin-1-yl)methyl)-2,6-dimethylpyridine | 373 | ¹H NMR (300 MHz, MeOD): δ 7.69 (d, J = 7.8 Hz, 1H), 7.16 (d, J = 7.8 Hz, 1H), 6.96 (s, 1H), 6.95 (s, 1H), 3.93 (s, 2H), 3.54 (q, J = 6.9 Hz, 2H), 3.42 (s, 2H), 2.98-2.86 (m, 3H), 2.68-2.65 (m, 1H), 2.55 (s, 3H), 2.52-2.50 (m, 5H), 2.19 (s, 3H), 1.88-1.77 (m, 4H), 1.21 (t, J = 6.9 Hz, 3H). |
| 332 | 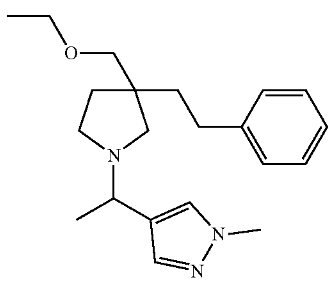 [SMILES: CCOCC1(CCc2ccccc2)CCN(C(C)c2cnn(C)c2)C1] | 4-(1-(3-(ethoxymethyl)-3-phenethylpyrrolidin-1-yl)ethyl)-1-methyl-1H-pyrazole | 342 | ¹H NMR (300 MHz, CDCl₃): δ 7.77 (d, J = 8.1 Hz, 1H), 7.39 (d, J = 5.4 Hz, 1H), 7.19-7.05 (m, 5H), 4.37-4.14 (m, 1H), 3.85 (s, 3H), 3.62-3.37 (m, 4H), 3.34 (s, 2H), 3.18-3.14 (m, 2H), 2.59-2.39 (m, 2H), 2.11-1.90 (m, 2H), 1.89-1.72 (m, 2H), 1.67 (dd, J = 6.9, 2.7 Hz, 3H), 1.16 (t, J = 6.9 Hz, 3H). |
| 333 | 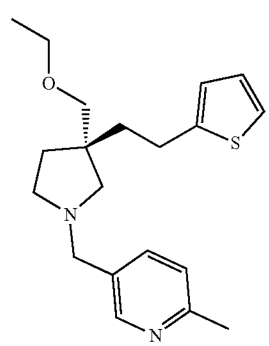 [SMILES: CCOC[C@@]1(CCc2cccs2)CCN(Cc2ccc(C)nc2)C1] | (S)-5-((3-(ethoxymethyl)-3-(2-(thiophen-2-yl)ethyl)pyrrolidin-1-yl)methyl)-2-methylpyridine | 345 | ¹H NMR (300 MHz, MeOD): δ 8.26 (d, J = 2.4 Hz, 1H), 7.63 (dd, J = 8.0, 2.1 Hz, 1H), 7.17 (t, J = 9.8 Hz, 1H), 7.04 (dd, J = 5.1, 1.1 Hz, 1H), 6.77 (dd, J = 5.1, 3.3 Hz, 1H), 6.68 (d, J = 2.6 Hz, 1H), 3.57 (s, 2H), 3.39 (q, J = 6.9 Hz, 2H), 3.23 (s, 2H), 2.70 (t, J = 8.1 Hz, 2H), 2.70-2.48 (m, 3H), 2.42 (s, 3H), 2.29 (d, J = 9.9 Hz, 1H), 1.79-1.71 (m, 2H), 1.59 (t, J = 6.9 Hz, 2H), 1.08 (t, J = 6.9 Hz, 3H). |

TABLE III-continued

| Compound. | Structure | Name | MS (ESI+): [M + H]+ | H-NMR |
|---|---|---|---|---|
| 334 | 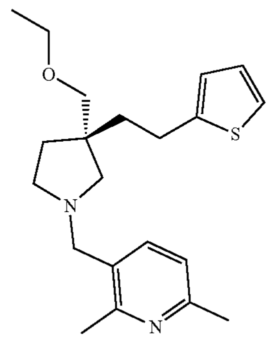 [SMILES: CCOC[C@@]1(CCc2cccs2)CCN(Cc2ccc(C)nc2C)C1] | (S)-3-((3-(ethoxymethyl)-3-(2-(thiophen-2-yl)ethyl)pyrrolidin-1-yl)methyl)-2,6-dimethylpyridine | 359 | $^1$H NMR (300 MHz, MeOD): δ 7.51 (d, J = 7.5 Hz, 1H), 7.04-7.00 (m, 2H), 6.77 (s, 1H), 6.68 (s, 1H), 3.59 (s, 2H), 3.40 (q, J = 6.9 Hz, 2H), 3.24 (s, 2H), 2.73-2.68 (m, 2H), 2.62-2.52 (m, 3H), 2.45 (s, 3H), 2.38-2.24 (m, 4H), 1.77-1.74 (m, 2H), 1.60 (t, J = 6.4 Hz, 2H), 1.08 (t, J = 6.9 Hz, 3H). |
| 335 | 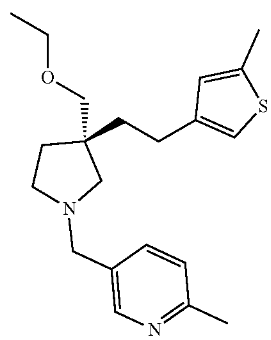 [SMILES: CCOC[C@@]1(CCc2csc(C)c2)CCN(Cc2ccc(C)nc2)C1] | (S)-5-((3-(ethoxymethyl)-3-(2-(5-methylthiophen-3-yl)ethyl)pyrrolidin-1-yl)methyl)-2-methylpyridine | 359 | $^1$H NMR (300 MHz, MeOD): δ 8.27 (d, J = 1.8 Hz, 1H), 7.62 (dd, J = 7.8, 2.1 Hz, 1H), 7.19 (d, J = 7.8 Hz, 1H), 6.58 (s, 1H), 6.49 (s, 1H), 3.58 (s, 2H), 3.37 (q, J = 6.9 Hz, 2H), 3.22-3.20 (m, 2H), 2.63-2.51 (m, 3H), 2.48-2.42 (m, 5H), 2.39-2.30 (m, 4H), 1.71-1.57 (m, 4H), 1.07 (d, J = 6.9 Hz, 3H). |
| 336 | 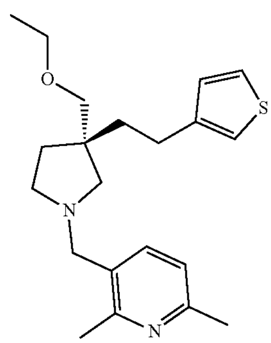 [SMILES: CCOC[C@@]1(CCc2ccsc2)CCN(Cc2ccc(C)nc2C)C1] | (S)-3-((3-(ethoxymethyl)-3-(2-(thiophen-3-yl)ethyl)pyrrolidin-1-yl)methyl)-2,6-dimethylpyridine | 359 | $^1$H NMR (300 MHz, MeOD): δ 7.54 (d, J = 7.5 Hz, 1H), 7.17 (t, J = 3.9 Hz, 1H), 7.01 (d, J = 6.9 Hz, 1H), 6.88-6.82 (m, 2H), 3.7 (s, 2H), 3.39 (q, J = 6.9 Hz, 2H), 3.28-3.20 (m, 2H), 2.79-2.59 (m, 3H), 2.53-2.34 (m, 6H), 2.32 (s, 3H), 1.79-1.62 (m, 4H), 1.18 (t, J = 7.0 Hz, 3H) |
| 337 | 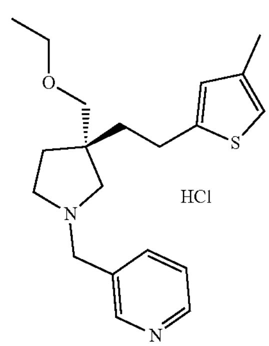 [SMILES: CCOC[C@@]1(CCc2cc(C)cs2)CCN(Cc2cccnc2)C1 ; Cl] | (S)-3-(3-(ethoxymethyl)-3-(2-(4-methylthiophen-2-yl)ethyl)pyrrolidin-1-yl)methyl)pyridine HCl | 345 | $^1$H NMR (300 MHz, MeOD): δ 9.16 (s, 1H), 8.91-8.83 (m, 2H), 8.14-8.09 (m, 1H), 6.64-6.55 (m, 2H), 4.63 (s, 2H), 3.63-3.35 (m, 8H), 2.70-2.67 (m, 2H), 2.06 (s, 3H), 1.90-1.82 (m, 4H), 1.15 (t, J = 7.0 Hz, 3H), |

TABLE III-continued

| Compound. | Name | MS (ESI+): [M + H]+ | H-NMR |
|---|---|---|---|
| 338 | 2-(3-(ethoxymethyl)-3-phenethylpyrrolidin-1-yl)-1-(6-methylpyridin-3-yl)ethanol | 369 | ¹H NMR (300 MHz, MeOD): δ 8.74 (s, 1H), 8.54-8.51 (d, J = 7.5 Hz, 1H), 7.89-7.86 (d, J = 7.9 Hz, 1H), 7.15-7.06 (m, 5H), 5.28 (s, 1H), 3.83-3.67 (m, 2H), 3.55-3.35 (m, 8H), 2.72 (s, 3H), 2.57-2.51 (m, 2H), 2.09-2.05 (m, 2H), 1.89-1.73 (m, 2H), 1.21-1.16 (m, 3H). |
| 339 | N,2,6-trimethyl-N-(4-phenethyl-4-(pyridin-2-yl)piperidin-1-yl)pyridin-3-amine | 401 | ¹H NMR (300 MHz, MeOD): δ 8.60 (d, J = 3.9 Hz, 1H), 7.84 (t, J = 7.5 Hz, 1H), 7.54 (d, J = 8.1 Hz, 1H), 7.36-7.27 (m, 2H), 7.20-7.09 (m, 4H), 6.97 (d, J = 6.9 Hz, 2H), 2.88-2.85 (m, 2H), 2.73-2.68 (m, 5H), 2.58 (s, 3H), 2.48-2.40 (m, 5H), 2.21-2.15 (m, 2H), 1.96-1.88 (m, 4H). |
| 340 | 4-((3-(ethoxymethyl)-3-phenethylpyrrolidin-1-yl)methyl)-2-methylthiazole | 345 | ¹H NMR (300 MHz, MeOD): δ 7.41 (s, 1H), 7.18-7.05 (m, 5H), 4.18 (s, 2H), 3.49 (q, J = 6.9 Hz, 2H), 3.36 (s, 2H), 3.24-3.09 (m, 4H), 2.63 (s, 3H), 2.53-2.46 (m, 2H), 1.96-1.90 (m, 2H), 1.78-1.69 (m, 2H), 1.14 (t, J = 6.9 Hz, 3H) |
| 341 | 4-(1-(3-(ethoxymethyl)-3-phenethylpyrrolidin-1-yl)ethyl)-2-methylthiazole | 359 | ¹H NMR (300 MHz, MeOD): δ 7.41 (s, 1H), 7.18-7.07 (m, 5H), 4.41-4.38 (m, 1H), 3.45 (q, J = 6.9 Hz, 2H), 3.37-3.29 (m, 4H), 3.16-3.12 (m, 2H), 2.61 (s, 3H), 2.48 (t, J = 8.4 Hz, 2H), 1.93-1.65 (m, 4H), 1.59-1.57 (m, 3H), 1.15 (t, J = 6.9 Hz, 3H) |

TABLE III-continued

| Compound. | Name | MS (ESI+): [M + H]+ | H-NMR |
|---|---|---|---|
| 342 | 2-(3-(ethoxymethyl)-phenethylpyrrolidin-1-yl)-2-(6-methylpyridin-3-yl)ethanol | 369 | $^1$H NMR (300 MHz, MeOD): δ 8.98-8.93 (m, 1H), 8.74-8.65 (m, 1H), 7.96-7.94 (d, J = 8.4 Hz, 1H), 7.17-7.08 (m, 5H), 4.73-4.62 (m, 2H), 4.19-4.14 (m, 1H), 3.91-3.83 (m, 2H), 3.53-3.42 (m, 5H), 3.05-3.28 (m, 1H), 2.76 (s, 3H), 2.57-2.49 (m, 2H), 2.00-1.68 (m, 4H). 1.16-1.12 (m, 3H) |
| 343 | 3-(2-(3-(ethoxymethyl)-3-phenethylpyrrolidin-1-yl)propan-2-yl)pyridine | 353 | N/A |
| 344 | (S)-5-(3-(ethoxymethyl)-3-(2-(5-fluorothiophen-2-yl)ethyl)pyrrolidin-1-yl)methyl)-2-methylpyridine | 363 | $^1$H NMR (300 MHz, MeOD): δ 8.31 (s, 1H), 7.66 (dd, J = 7.8, 2.1 Hz, 1H), 7.22 (d, J = 7.8 Hz, 1H), 6.31 (t, J = 3.3 Hz, 1H), 6.19-6.17 (m, 1H), 3.74 (s, 2H), 3.40 (q, J = 7.0 Hz, 2H), 3.24 (s, 3H), 2.75-2.55 (m, 5H), 2.48 (s, 3H), 1.73-1.62 (m, 4H), 1.08 (t, J = 6.9 Hz, 3H) |
| 345 | (S)-3-((3-(ethoxymethyl)-3-(2-(5-fluorothiophen-2-yl)ethyl)pyrrolidin-1-yl)methyl)pyridine | 349 | $^1$H NMR (300 MHz, MeOD): δ 8.78 (s, 1H), 8.52 (d, J = 4.5 Hz, 1H), 7.92 (d, J = 8.1 Hz, 1H), 7.50-7.45 (m, 1H), 6.43 (br s, 1H), 6.29 (br s, 1H), 3.94 (s, 2H), 3.51 (q, J = 7.0 Hz, 2H), 3.32 (s, 2H), 2.92-2.58 (m, 6H), 1.90-1.75 (m, 4H), 1.19 (t, J = 6.9 Hz, 3H) |
| 346 | 5-(1-(3-(ethoxymethyl)-3-phenethylpyrrolidin-1-yl)ethyl)-2-methylthiazole | 359 | $^1$H NMR (300 MHz, CDCl$_3$): δ 7.37 (s, 1H), 7.29-7.25 (m, 2H), 7.19-7.14 (m, 3H), 3.65-3.63 (m, 1H), 3.47 (q, J = 6.9 Hz, 2H), 3.32-3.24 (m, 2H), 2.73-2.67 (m, 1H), 2.66 (s, 3H), 2.59-2.43 (m, 4H), 2.36-2.27 (m, 1H), 1.79-1.70 (m, 2H), 1.65-1.61 (m, 2H), 1.41 (d, J = 6.3 Hz, 3H), 1.18 (t, J = 6.9 Hz, 3H). |

TABLE III-continued

| Compound. | Structure | Name | MS (ESI+): [M + H]+ | H-NMR |
|---|---|---|---|---|
| 347 | 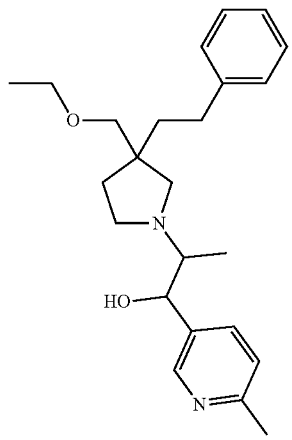 [SMILES: CCOCC1(CCc2ccccc2)CCN(C(C)C(O)c2ccc(C)nc2)C1] | 2-(3-(ethoxymethyl)-3-phenethylpyrrolidin-1-yl)-1-(6-methylpyridin-3-yl)propan-1-ol | 383 | $^1$H NMR (300 MHz, MeOD): δ 8.75 (s, 1H), 8.50 (d, J = 8.1 Hz, 1H), 7.90 (d, J = 8.2 Hz, 1H), 7.27-7.01 (m, 5H), 4.89-4.82 (m, 1H), 3.72-3.05 (m, 9H), 2.73 (s, 3H), 2.57 (dd, J = 16.1, 8.3 Hz, 2H), 2.21-2.00 (m, 2H), 1.88-1.72 (m, 2H), 1.32-1.15 (m, 6H). |
| 348 | 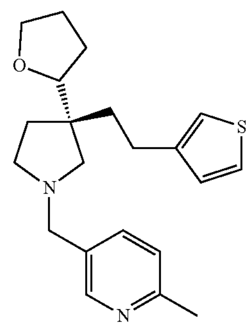 [SMILES: Cc1ccc(CN2CC[C@](CCc3ccsc3)(C3CCCO3)C2)cn1] | 2-methyl-5-(((S)-3-((S)-tetrahydrofuran-2-yl)-3-(2-(thiophen-3-yl)ethyl)pyrrolidin-1-yl)methyl)pyridine | 357 | $^1$H NMR (300 MHz, MeOD): δ 9.05-9.01 (m, 1H), 8.81-8.65 (m, 1H), 8.07-8.02 (m, 1H), 7.36-7.31 (m, 1H), 7.09-7.01 (m, 2H), 4.81-4.59 (m, 2H), 4.02-3.33 (m, 7H), 2.86 (s, 3H), 2.84-2.69 (m, 2H), 2.05-1.89 (m, 8H) |
| 349 | 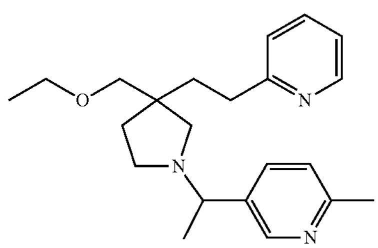 [SMILES: CCOCC1(CCc2ccccn2)CCN(C(C)c2ccc(C)nc2)C1] | 5-(1-(3-(ethoxymethyl)-3-(2-(pyridin-2-yl)ethyl)pyrrolidin-1-yl)ethyl)-2-methylpyridine | 354 | $^1$H NMR (300 MHz, MeOD): δ 8.35-8.23 (m, 2H), 7.71-7.57 (m, 2H), 7.27-7.06 (m, 3H), 3.46-3.31 (m, 3H), 3.24-3.20 (m, 2H), 2.82-2.50 (m, 4H), 2.49-2.28 (m, 5H), 1.75-1.71 (m, 2H), 1.64-1.59 (m, 2H), 1.33 (d, J = 6.6 Hz, 3H), 1.06 (m, 3H). |
| 350 | 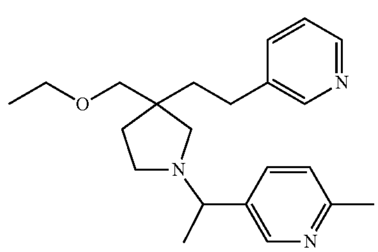 [SMILES: CCOCC1(CCc2cccnc2)CCN(C(C)c2ccc(C)nc2)C1] | 5-(1-(3-(ethoxymethyl)-3-(2-(pyridin-3-yl)ethyl)pyrrolidin-1-yl)ethyl)-2-methylpyridine | 354 | $^1$H NMR (300 MHz, MeOD): δ 8.28-8.23 (m, 3H), 7.69-7.59 (m, 2H), 7.27-7.19 (m, 2H), 3.43-3.35 (m, 3H), 3.26-3.21 (m, 3H), 2.77 (m, 1H), 2.53-2.46 (m, 4H), 2.43 (s, 3H), 1.69-1.61 (m, 4H), 1.36-1.34 (m, 3H). 1.09-1.05 (m, 3H) |
| 351 | 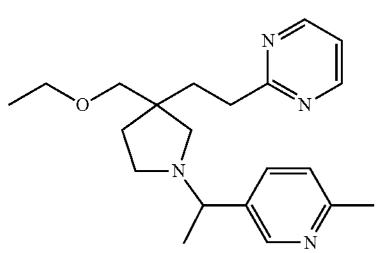 [SMILES: CCOCC1(CCc2ncccn2)CCN(C(C)c2ccc(C)nc2)C1] | 2-(2-(3-(ethoxymethyl)-1-(1-(6-methylpyridin-3-yl)ethyl)pyrrolidin-3-yl)ethyl)pyrimidine | 355 | $^1$H NMR (300 MHz, MeOD): δ 8.61-8.58 (m, 2H), 8.26 (d, J = 1.5 Hz, 1H), 7.65 (d, J = 8.1 Hz, 1H), 7.29-7.11 (m, 2H), 3.30-3.22 (m, 6H), 2.85-2.68 (m, 3H), 2.48-2.27 (m, 5H), 1.84 (t, J = 6.9 Hz, 2H), 1.59 (t, J = 6.9 Hz, 2H), 1.29 (t, J = 6.6 Hz, 3H), 1.08-1.02 (m, 3H). |

TABLE III-continued

| Compound. | Structure | Name | MS (ESI+): [M + H]+ | H-NMR |
|---|---|---|---|---|
| 352 | 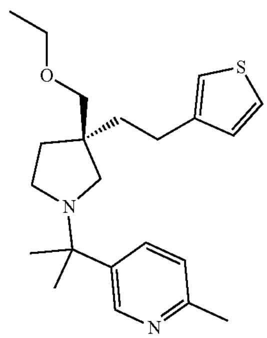 [SMILES: CCOC[C@]1(CCc2ccsc2)CCN(C(C)(C)c2ccc(C)nc2)C1] | (R)-5-(2-(3-(ethoxymethyl)-3-(2-(thiophen-3-yl)ethyl)pyrrolidin-1-yl)propan-2-yl)-2-methylpyridine | 373 | ¹H NMR (300 MHz, MeOD): δ 8.48 (d, J = 1.8 Hz, 1H), 7.81 (dd, J = 8.1, 2.1 Hz, 1H), 7.21-7.17 (m, 2H), 6.88 (s, 1H), 6.82 (d, J = 4.8 Hz, 1H), 3.36 (q, J = 6.9 Hz, 2H), 3.32-3.25 (m, 2H), 2.71 (s, 2H), 2.57 (d, J = 8.9 Hz, 1H), 2.48 (t, J = 8.4 Hz, 2H), 2.42 (s, 3H), 2.37 (s, 1H), 1.73-1.50 (m, 4H), 1.43 (s, 6H), 1.05 (t, J = 7.0 Hz, 3H). |
| 353 | 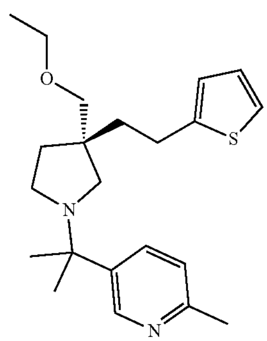 [SMILES: CCOC[C@@]1(CCc2cccs2)CCN(C(C)(C)c2ccc(C)nc2)C1] | (S)-5-(2-(3-(ethoxymethyl)-3-(2-(thiophen-2-yl)ethyl)pyrrolidin-1-yl)propan-2-yl)-2-methylpyridine | 373 | ¹H NMR (300 MHz, MeOD): δ 8.57 (d, J = 2.2 Hz, 1H), 7.92 (dd, J = 8.3, 2.5 Hz, 1H), 7.29 (d, J = 8.3 Hz, 1H), 7.06 (dd, J =5.1, 1.1 Hz, 1H), 6.78 (dd, J = 5.1, 3.6 Hz, 1H), 6.69 (d, J =3.3 Hz, 1H), 3.35 (q, J = 7.0 Hz, 2H), 3.23-3.21 (m, 2H), 3.01 (t, J = 6.9 Hz, 2H), 2.90 (d, J = 11.1 Hz, 1H), 2.71-2.65 (m, 3H), 2.45 (s, 3H), 1.81-1.66 (m, 4H), 1.63 (s, 6H), 1.03 (t, J = 7.0 Hz, 3H). |
| 354 | 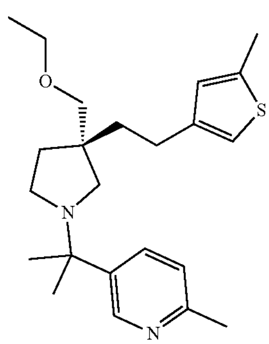 [SMILES: CCOC[C@@]1(CCc2csc(C)c2)CCN(C(C)(C)c2ccc(C)nc2)C1] | (S)-5-(2-(3-(ethoxymethyl)-3-(2-(5-methylthiophen-3-yl)ethyl)pyrrolidin-1-yl)propan-2-yl)-2-methylpyridine | 387 | ¹H NMR (300 MHz, MeOD): δ 8.56 (d, J = 2.2 Hz, 1H), 7.91 (dd, J = 8.3, 2.5 Hz, 1H), 7.28 (d, J = 8.3 Hz, 1H), 6.60 (s, 1H), 6.49 (s, 1H), 3.34 (q, J = 7.0 Hz, 2H), 3.22-3.21 (m, 2H), 2.97 (t, J = 6.7 Hz, 2H), 2.83 (d, J = 10.9 Hz, 1H), 2.61 (d, J = 10.7 Hz, 1H), 2.45 (s, 3H), 2.37 (t, J = 8.3 Hz, 2H), 2.31 (s, 3H), 1.78-1.57 (m, 10H), 1.03 (t, J = 7.0 Hz, 3H). |
| 355 | 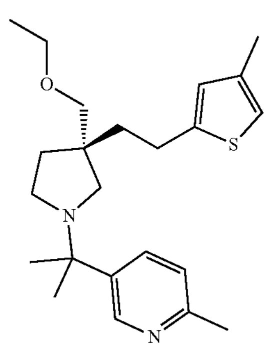 [SMILES: CCOC[C@@]1(CCc2cc(C)cs2)CCN(C(C)(C)c2ccc(C)nc2)C1] | (S)-5-(2-(3-(ethoxymethyl)-3-(2-(4-methylthiophen-2-yl)ethyl)pyrrolidin-1-yl)propan-2-yl)-2-methylpyridine | 387 | ¹H NMR (300 MHz, MeOD): δ 8.63 (d, J = 2.2 Hz, 1H), 7.96 (dd, J = 8.2, 2.4 Hz, 1H), 7.35 (d, J = 8.2 Hz, 1H), 6.71 (s, 1H), 6.60 (s, 1H), 3.47 (q, J = 6.9 Hz, 2H), 3.36-3.33 (m, 2H), 2.94-2.91 (m, 2H), 2.81 (d, J = 10.2 Hz, 1H), 2.72 (t, J = 8.4 Hz, 2H), 2.61-2.58 (m, 1H), 2.55 (s, 3H), 2.18 (s, 3H), 1.85-1.68 (m, 4H), 1.62 (s, 6H), 1.16 (t, J = 7.0 Hz, 3H). |

TABLE III-continued

| Compound. | Structure | Name | MS (ESI+): [M + H]+ | H-NMR |
|---|---|---|---|---|
| 356 | 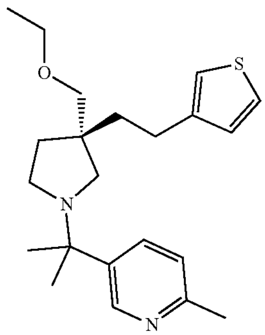 [SMILES: CCOC[C@@]1(CCc2ccsc2)CCN(C(C)(C)c2ccc(C)nc2)C1] | (S)-5-(2-(3-(ethoxymethyl)-3-(2-(thiophen-3-yl)ethyl)pyrrolidin-1-yl)propan-2-yl)-2-methylpyridine | 373 | $^1$H NMR (300 MHz, MeOD): δ 8.62 (d, J = 2.1 Hz, 1H), 7.95 (dd, J = 8.4, 2.4 Hz, 1H), 7.35-7.29 (m, 2H), 6.99 (d, J = 1.8 Hz, 1H), 6.94 (dd, J = 5.1, 1.2 Hz, 1H), 3.47 (q, J = 6.9 Hz, 2H), 3.36-3.33 (m, 2H), 2.89 (s, 2H), 2.76 (d, J = 9.8 Hz, 1H), 2.62-2.54 (m, 6H), 1.82-1.68 (m, 4H), 1.59 (s, 6H), 1.16 (t, J = 7.0 Hz, 3H). |
| 357 | 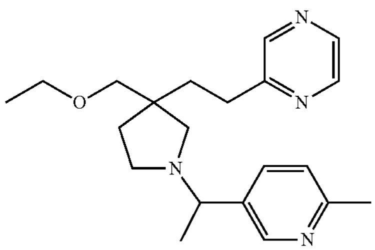 | 2-(2-(3-(ethoxymethyl)-1-(1-(6-methylpyridin-3-yl)ethyl)pyrrolidin-3-yl)ethyl)pyrazine HCl | 355 | $^1$H NMR (300 MHz, MeOD): δ 9.15 (s, 1H), 8.91 (d, J = 8.4 Hz, 1H), 8.78-8.60 (m, 3H), 8.08 (d, J = 8.1 Hz, 1H), 3.95-3.42 (m, 10H), 3.19-2.92 (m, 1H), 2.86 (s, 3H), 2.25-2.03 (m, 4H), 1.88 (d, J = 6.3 Hz, 3H), 1.23 (t, J = 7.0 Hz, 3H) |
| 358 | 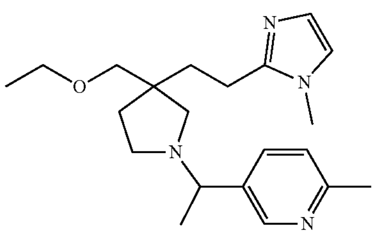 [SMILES: CCOCC1(CCc2nccn2C)CCN(C(C)c2ccc(C)nc2)C1] | 5-(1-(3-(ethoxymethyl)-3-(2-(1-methyl-1H-imidazol-2-yl)ethyl)pyrrolidin-1-yl)ethyl)-2-methylpyridine | 357 | $^1$H NMR (300 MHz, MeOD): δ 8.29 (d, J = 1.8 Hz, 1H), 7.68 (d, J = 9.3 Hz, 1H), 7.23 (d, J = 8.1, 1H), 6.90-6.88 (m, 1H), 6.76-6.74 (m, 1H), 3.57-3.56 (m, 3H), 3.45-3.40 (m, 2H), 3.28-3.26 (m, 2H), 2.66-2.50 (m, 4H), 2.46 (s, 3H), 2.40-2.17 (m, 3H), 1.74-1.71 (m, 2H), 1.62-1.58 (m, 2H), 1.34-1.32 (m, 3H), 1.14-1.07 (m, 3H) |
| 359 | 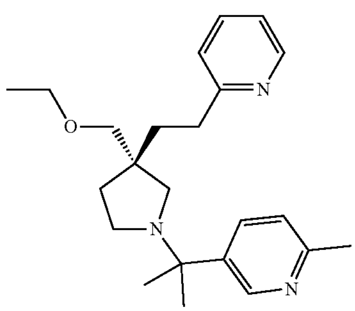 [SMILES: CCOC[C@@]1(CCc2ccccn2)CCN(C(C)(C)c2ccc(C)nc2)C1] | (S)-5-(2-(3-(ethoxymethyl)-3-(2-(pyridin-2-yl)ethyl)pyrrolidin-1-yl)propan-2-yl)-2-methylpyridine | 358 | $^1$H NMR (300 MHz, MeOD): δ 9.10 (s, 1H), 8.93 (dd, J = 8.7, 2.1 Hz, 1H), 8.62 (d, J = 5.7 Hz, 1H), 8.41 (t, J = 7.8 Hz, 1H), 7.95 (d, J = 8.7 Hz, 2H), 7.82 (t, J = 6.9 Hz, 1H), 3.49-3.29 (m, 8H), 3.01-2.95 (m, 2H), 2.74 (s, 3H), 2.05-1.94 (m, 4H), 1.89 (s, 6H), 1.05 (t, J = 6.9 Hz, 3H) |
| 360 | 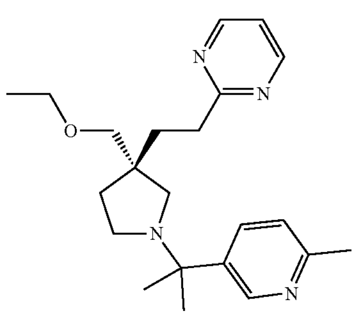 [SMILES: CCOC[C@@]1(CCc2ncccn2)CCN(C(C)(C)c2ccc(C)nc2)C1] | (S)-2-(2-(3-(ethoxymethyl)-1-(2-(6-methylpyridin-3-yl)propan-2-yl)pyrrolidin-3-yl)ethyl)pyrimidine | 369 | $^1$H NMR (300 MHz, MeOD): δ 8.72 (d, J = 5.0 Hz, 2H), 8.56 (d, J = 2.1 Hz, 1H), 7.91 (dd, J = 8.2, 2.4 Hz, 1H), 7.34 (t, J = 5.0 Hz, 1H), 7.28 (d, J = 8.2 Hz, 1H), 3.46 (q, J = 7.0 Hz, 2H), 3.36-3.33 (m, 2H), 2.92 (t, J = 8.2 Hz, 2H), 2.72-2.62 (m, 2H), 2.61 (d, J = 9.4 Hz, 1H), 2.52 (s, 3H), 2.41 (d, J = 8.7 Hz, 1H), 1.96-1.89 (m, 2H), 1.65 (t, J = 6.8 Hz, 2H), 1.48 (s, 6H), 1.15 (t, J = 6.9 Hz, 3H). |

TABLE III-continued

| Compound. | Structure | Name | MS (ESI+): [M + H]+ | H-NMR |
|---|---|---|---|---|
| 361 | 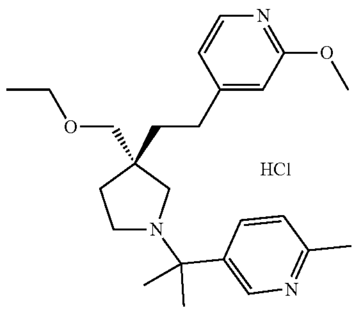 [SMILES: CCOC[C@@]1(CCc2ccnc(OC)c2)CCN(C(C)(C)c2ccc(C)nc2)C1 ; Cl] | (S)-4-(2-(3-(ethoxymethyl)-1-(2-(6-methylpyridin-3-yl)propan-2-yl)pyrrolidin-3-yl)ethyl)-2-methoxypyridine HCl | 398 | $^1$H NMR (300 MHz, MeOD): δ 9.24 (s, 1H), 9.08 (d, J = 8.4 Hz, 1H), 8.27-8.23 (m, 1H), 8.08 (d, J = 8.4 Hz, 1H), 7.62 (s, 1H), 7.46 (d, J = 6.0 Hz, 1H), 4.26 (s, 3H), 3.67-3.28 (m, 8H), 2.97-2.87 (m, 5H), 2.17-2.02 (m, 10H), 1.26-1.20 (m, 3H). |
| 362 | 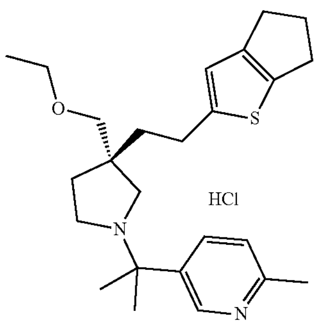 [SMILES: CCOC[C@@]1(CCc2cc3c(s2)CCC3)CCN(C(C)(C)c2ccc(C)nc2)C1 ; Cl] | (S)-5-(2-(3-(2-(5,6-dihydro-4H-cyclopenta[b]thiophen-2-yl)ethyl)-3-(ethoxymethyl)pyrrolidin-1-yl)propan-2-yl)-2-methylpyridine HCl | 413 | $^1$H NMR (300 MHz, MeOD): δ 8.95-8.89 (m, 1H), 8.61-8.58 (m, 1H), 7.79-7.76 (m, 1H), 6.43 (s, 1H), 3.50-3.25 (m, 6H), 2.67-2.53 (m, 11H), 2.30-2.26 (m, 2H), 1.97-1.71 (m, 10H), 1.08-1.04 (m, 3H) |
| 363 | 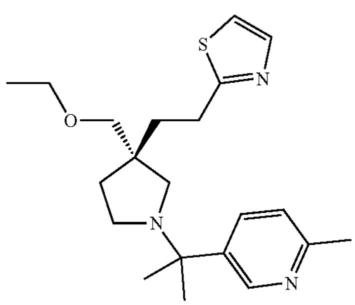 [SMILES: CCOC[C@@]1(CCc2nccs2)CCN(C(C)(C)c2ccc(C)nc2)C1] | (S)-2-(2-(3-(ethoxymethyl)-1-(2-(6-methylpyridin-3-yl)propan-2-yl)pyrrolidin-3-yl)ethyl)thiazole | 374 | $^1$H NMR (300 MHz, MeOD): δ 8.44 (d, J = 2.0 Hz, 1H), 7.79 (dd, J = 8.1, 2.3 Hz, 1H), 7.55 (d, J = 3.4 Hz, 1H), 7.34 (d, J = 3.4 Hz, 1H), 7.17 (d, J = 8.2 Hz, 1H), 3.36 (q, J = 7.0 Hz, 2H), 3.25-3.21 (m, 2H), 2.92 (t, J = 8.0 Hz, 2H), 2.59 (s, 2H), 2.47 (d, J = 7.8 Hz, 1H), 2.41 (s, 3H), 2.27 (d, J = 9.3 Hz, 1H), 1.86-1.74 (m, 2H), 1.53 (t, J = 6.8 Hz, 2H), 1.36 (s, 6H), 1.05 (t, J = 7.0 Hz, 3H). |
| 364 | 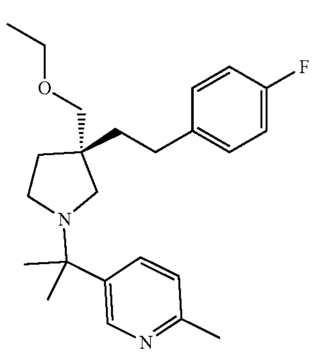 [SMILES: CCOC[C@@]1(CCc2ccc(F)cc2)CCN(C(C)(C)c2ccc(C)nc2)C1] | (S)-5-(2-(3-(ethoxymethyl)-3-(4-fluorophenethyl)pyrrolidin-1-yl)propan-2-yl)-2-methylpyridine | 385 | $^1$H NMR (300 MHz, MeOD): δ 8.55 (d, J = 2.1 Hz, 1H), 7.87 (dd, J = 8.2, 2.4 Hz, 1H), 7.26 (d, J = 8.2 Hz, 1H), 7.16-7.12 (m, 2H), 7.00-6.94 (m, 2H), 3.48 (q, J = 7.0 Hz, 2H), 3.36-3.33 (m, 2H), 2.68-2.62 (m, 2H), 2.57-2.50 (m, 6H), 2.31 (d, J = 9.2 Hz, 1H), 1.73-1.66 (m, 2H), 1.61 (t, J = 6.9 Hz, 2H), 1.44 (s, 6H), 1.18 (t, J = 7.0 Hz, 3H). |

TABLE III-continued

| Compound. | Structure | Name | MS (ESI+): [M + H]+ | H-NMR |
|---|---|---|---|---|
| 365 | 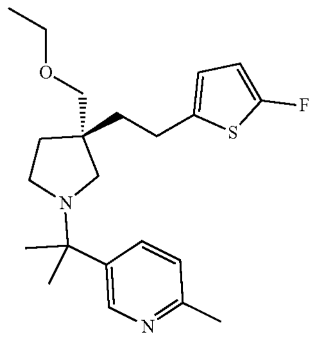 [SMILES: CCOC[C@@]1(CCc2ccc(F)s2)CCN(C(C)(C)c2ccc(C)nc2)C1] | (S)-5-(2-(3-(ethoxymethyl)-3-(2-(5-fluorothiophen-2-yl)ethyl)pyrrolidin-1-yl)propan-2-yl)-2-methylpyridine | 391 | ¹H NMR (300 MHz, MeOD): δ 8.58 (d, J = 1.7 Hz, 1H), 7.91 (dd, J = 8.2, 2.3 Hz, 1H), 7.31 (d, J = 8.1 Hz, 1H), 6.41 (t, J = 3.5 Hz, 1H), 6.30 (dd, J = 3.8, 2.2 Hz, 1H), 3.47 (q, J = 7.0 Hz, 2H), 3.30-3.27 (m, 2H), 2.77-2.72 (m, 2H), 2.71-2.60 (m, 3H), 2.53 (s, 3H), 2.45-2.42 (m, 1H), 1.82-1.58 (m, 4H), 1.52 (s, 6H), 1.17 (t, J = 7.0 Hz, 3H). |
| 366 | 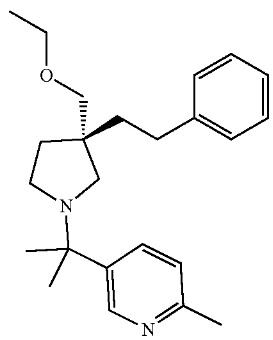 [SMILES: CCOC[C@@]1(CCc2ccccc2)CCN(C(C)(C)c2ccc(C)nc2)C1] | (S)-5-(2-(3-(ethoxymethyl)-3-phenethylpyrrolidin-1-yl)propan-2-yl)-2-methylpyridine | 367 | ¹H NMR (300 MHz, MeOD): δ 8.46 (d, J = 1.8 Hz, 1H), 7.79 (dd, J = 8.2, 2.3 Hz, 1H), 7.19-7.11 (m, 3H), 7.05-7.00 (m, 3H), 3.37 (q, J = 7.0 Hz, 2H), 3.25-3.21 (m, 2H), 2.62 (s, 2H), 2.48-2.38 (m, 6H), 2.30 (s, 1H), 1.68-1.50 (m, 4H), 1.38 (s, 6H), 1.07 (t, J = 7.0 Hz, 3H). |
| 367 | 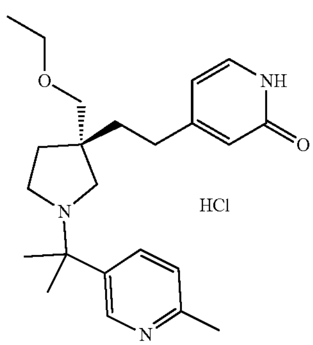 [SMILES: CCOC[C@@]1(CCc2cc[nH]c(=O)c2)CCN(C(C)(C)c2ccc(C)nc2)C1 ; Cl] | (S)-4-(2-(3-(ethoxymethyl)-1-(2-(6-methylpyridin-3-yl)propan-2-yl)pyrrolidin-3-yl)ethyl)pyridin-2(1H)-one HCl | 384 | ¹H NMR (300 MHz, MeOD): δ 9.10-9.09 (m, 1H), 8.92-8.88 (m, 1H), 7.95 (d, J = 8.4 Hz, 1H), 7.68 (d, J = 6.3 Hz, 1H), 6.82-6.72 (m, 2H), 3.50-3.20 (m, 9H), 2.75 (s, 3H), 2.60-2.55 (m, 2H), 2.02-1.82 (m, 10H), 1.14-1.06 (m, 3H). |
| 368 | 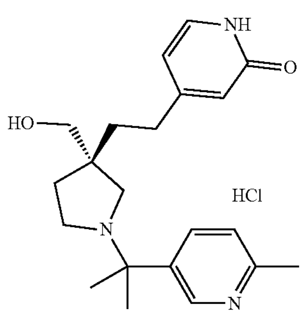 [SMILES: Cc1ccc(C(C)(C)N2CC[C@@](CO)(CCc3cc[nH]c(=O)c3)C2)cn1 ; Cl] | (S)-4-(2-(3-(hydroxymethyl)-1-(2-(6-methylpyridin-3-yl)propan-2-yl)pyrrolidin-3-yl)ethyl)pyridin-2(1H)-one HCl | 356 | ¹H NMR (300 MHz, MeOD): δ 9.21 (s, 1H), 9.04 (d, J = 7.8 Hz, 1H), 8.07 (d, J = 7.8 Hz, 1H), 7.88 (s, 1H), 7.07-7.00 (m, 2H), 3.95-3.49 (m, 5H), 3.33-3.09 (m, 1H), 2.87 (s, 3H), 2.82-2.74 (m, 2H), 2.22-2.02 (m, 10H). |

TABLE III-continued

| Compound. | Structure | Name | MS (ESI+): [M + H]+ | H-NMR |
|---|---|---|---|---|
| 369 | 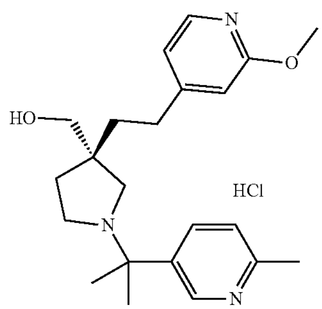 [SMILES: COc1cc(CC[C@]2(CO)CCN(C(C)(C)c3ccc(C)nc3)C2)ccn1 ; Cl] | (S)-(3-(2-(2-methoxypyridin-4-yl)ethyl)-1-(2-(6-methylpyridin-3-yl)propan-2-yl)pyrrolidin-3-yl)methanol HCl | 370 | ¹H NMR (300 MHz, MeOD): δ 9.23 (s, 1H), 9.08 (d, J = 7.8 Hz, 1H), 8.25 (t, J = 5.7 Hz, 1H), 8.08 (d, J = 8.4 Hz, 1H), 7.68 (d, J = 9.0 Hz, 1H), 7.53-7.48 (m, 1H), 4.30 (s, 3H), 3.68-3.40 (m, 4H), 3.33-3.25 (m, 2H), 3.00-2.88 (m, 5H), 2.17-2.01 (m, 10H). |
| 370 | 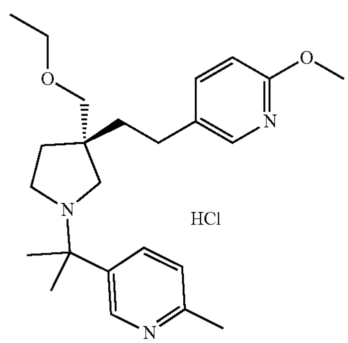 [SMILES: CCOC[C@@]1(CCc2ccc(OC)nc2)CCN(C(C)(C)c2ccc(C)nc2)C1 ; Cl] | (S)-5-(2-(3-(ethoxymethyl)-1-(2-(6-methylpyridin-3-yl)propan-2-yl)pyrrolidin-3-yl)ethyl)-2-methoxypyridine HCl | 398 | ¹H NMR (300 MHz, MeOD): δ 8.84-8.77 (m, 1H), 8.39-8.24 (m, 1H), 7.90-7.81 (m, 1H), 7.62-7.46 (m, 2H), 6.72 (d, J = 8.4 Hz, 1H), 3.80 (s, 3H), 3.43-3.25 (m, 7H), 3.06-2.90 (m, 1H), 2.59 (s, 3H), 2.47-2.35 (m, 2H), 2.01-1.87 (m, 2H), 1.83 (s, 6H), 1.78-1.49 (m, 2H), 1.03 (t, J = 6.9 Hz, 3H). |
| 371 | 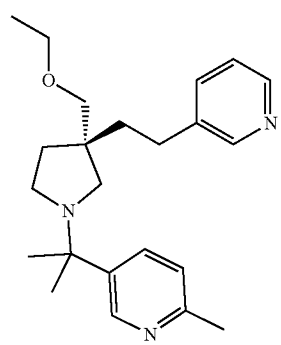 [SMILES: CCOC[C@@]1(CCc2cccnc2)CCN(C(C)(C)c2ccc(C)nc2)C1] | (S)-5-(2-(3-(ethoxymethyl)-3-(2-(pyridin-3-yl)ethyl)pyrrolidin-1-yl)propan-2-yl)-2-methylpyridine | 368 | ¹H NMR (300 MHz, MeOD): δ 8.52 (s, 1H), 8.30 (s, 2H), 7.85 (d, J = 6.0 Hz, 1H), 7.62 (d, J = 7.8 Hz, 1H), 7.31-7.22 (m, 2H), 3.41 (q, J = 6.9 Hz, 2H), 3.27-3.25 (m, 2H), 2.27-2.52 (m, 5H), 2.46-2.30 (m, 4H), 1.75-1.54 (m, 4H), 1.46 (s, 6H), 1.10 (t, J = 6.9 Hz, 3H). |
| 372 | 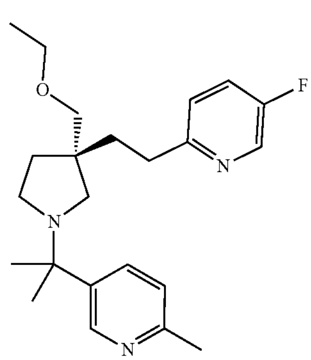 [SMILES: CCOC[C@@]1(CCc2ccc(F)cn2)CCN(C(C)(C)c2ccc(C)nc2)C1] | (S)-2-(2-(3-(ethoxymethyl)-1-(2-(6-methylpyridin-3-yl)propan-2-yl)pyrrolidin-3-yl)ethyl)-5-fluoropyridine | 386 | ¹H NMR (300 MHz, MeOD) : δ 8.50 (s, 1H), 8.22 (d, J = 2.7 Hz, 1H), 7.83 (dd, J =8.1, 2.4 Hz, 1H), 7.48-7.41 (m, 1H), 7.22 (dd, J = 8.6, 4.7 Hz, 2H), 3.36 (q, J = 6.9 Hz, 2H), 3.24 (d, J = 6.6 Hz, 2H), 2.76 (s, 2H), 2.64 (t, J = 8.4 Hz, 3H), 2.50-2.44 (m, 1H), 2.43 (s, 3H), 1.78-1.58 (m, 4H), 1.47 (s, 6H), 1.05 (t, J = 7.0 Hz, 3H). |

TABLE III-continued

| Compound. | Structure | Name | MS (ESI+): [M + H]+ | H-NMR |
|---|---|---|---|---|
| 373 | 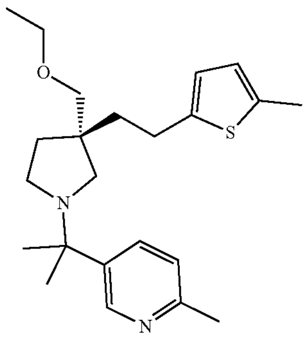 [SMILES: CCOC[C@@]1(CCc2ccc(C)s2)CCN(C(C)(C)c2ccc(C)nc2)C1] | (S)-5-(2-(3-(ethoxymethyl)-3-(2-(5-methylthiophen-2-yl)ethyl)pyrrolidin-1-yl)propan-2-yl)-2-methylpyridine | 387 | ¹H NMR (300 MHz, MeOD): δ 8.45 (d, J = 2.1 Hz, 1H), 7.79 (dd, J = 8.2, 2.4 Hz, 1H), 7.17 (d, J = 8.4 Hz, 1H), 6.41 (s, 2H), 3.36 (q, J = 7.0 Hz, 2H), 3.18-3.15 (m, 2H), 2.60-2.47 (m, 5H), 2.41 (s, 3H), 2.28-2.26 (m, 4H), 1.69-1.60 (m, 2H), 1.54-1.49 (m, 2H), 1.38 (s, 6H), 1.05 (t, J = 7.1 Hz, 3H). |
| 374 | 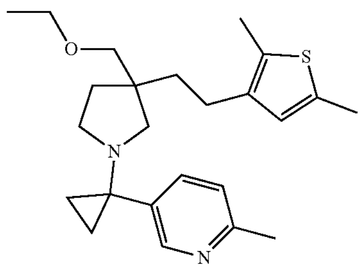 [SMILES: CCOCC1(CCc2cc(C)sc2C)CCN(C2(c3ccc(C)nc3)CC2)C1] | 5-(1-(3-(2-(2,5-dimethylthiophen-3-yl)ethyl)-3-(ethoxymethyl)pyrrolidin-1-yl)cyclopropyl)-2-methylpyridine | 399 | ¹H NMR (300 MHz, CDCl₃): δ 8.35 (s, 1H), 7.40 (d, J = 7.8 Hz, 1H), 7.04 (d, J = 7.8 Hz, 1H), 6.33 (s, 1H), 3.35 (d, J = 6.6 Hz, 2H), 3.06 (t, J = 8.0 Hz, 2H), 2.47 (s, 6H), 2.29 (s, 3H), 2.26-2.17 (m, 3H), 2.16 (s, 3H), 1.57 (s, 2H), 1.37 (d, J = 8.5 Hz, 2H), 1.08 (t, J = 6.6 Hz, 3H), 0.88-0.79 (m, 2H), 0.68 (s, 2H). |
| 375 | 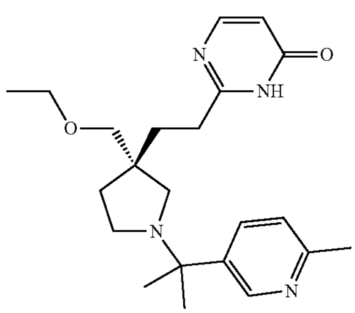 [SMILES: CCOC[C@@]1(CCc2nccc(=O)[nH]2)CCN(C(C)(C)c2ccc(C)nc2)C1] | (S)-2-(2-(3-(ethoxymethyl)-1-(2-(6-methylpyridin-3-yl)propan-2-yl)pyrrolidin-3-yl)ethyl)pyrimidin-4(3H)-one | 385 | ¹H NMR (300 MHz, MeOD): δ 9.11 (s, 1H), 8.94 (d, J = 8.4 Hz, 1H), 7.96 (d, J = 8.7 Hz, 1H), 7.90 (d, J = 7.8 Hz, 1H), 6.51 (d, J = 7.8 Hz, 1H), 3.49-3.38 (m, 4H), 3.38-3.25 (m, 4H), 2.89-2.78 (m, 2H), 2.75 (s, 3H), 2.08-1.94 (m, 4H), 1.90 (s, 6H), 1.12 (t, J = 7.2 Hz, 3H). |
| 376 | 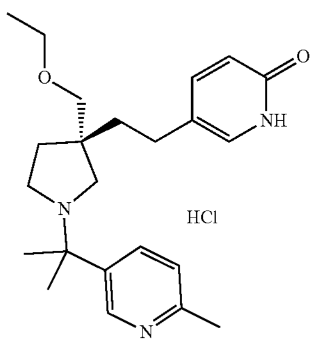 [SMILES: CCOC[C@@]1(CCc2ccc(=O)[nH]c2)CCN(C(C)(C)c2ccc(C)nc2)C1 ; Cl] | (S)-5-(2-(3-(ethoxymethyl)-1-(2-(6-methylpyridin-3-yl)propan-2-yl)pyrrolidin-3-yl)ethyl)pyridin-2(1H)-one HCl | 384 | ¹H NMR (300 MHz, MeOD): δ 9.10-9.09 (m, 1H), 8.98-8.91 (m, 1H), 8.11 (dd, J = 9.0, 2.4 Hz, 1H), 7.98-7.92 (m, 2H), 7.05-6.99 (m, 1H), 3.50-3.27 (m, 7H), 3.15-2.98 (m, 1H), 2.76 (s, 3H), 2.59-2.50 (m, 2H), 2.06-1.94 (m, 2H), 1.89 (s, 6H), 1.85-1.79 (m, 2H), 1.11 (t, J = 6.9 Hz, 3H). |

TABLE III-continued

| Compound. | Structure | Name | MS (ESI+): [M + H]⁺ | H-NMR |
|---|---|---|---|---|
| 377 | 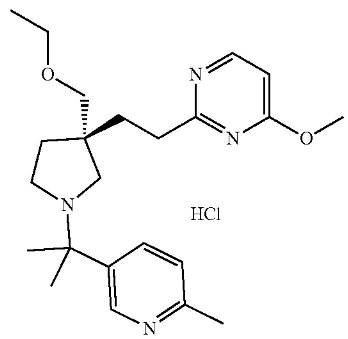 [SMILES: CCOC[C@@]1(CCc2nccc(OC)n2)CCN(C(C)(C)c2ccc(C)nc2)C1 ; Cl] | (S)-2-(2-(3-(ethoxymethyl)-1-(2-(6-methylpyridin-3-yl)propan-2-yl)pyrrolidin-3-yl)ethyl)-4-methoxypyrimidine HCl | 399 | ¹H NMR (300 MHz, MeOD): δ 9.11 (s, 1H), 8.95 (d, J = 8.4 Hz, 1H), 8.53 (d, J = 6.9 Hz, 1H), 7.96 (d, J = 8.7 Hz, 1H), 7.13 (d, J = 6.9 Hz, 1H), 4.14 (s, 3H), 3.48-3.32 (m, 8H), 3.10-2.98 (m, 2H), 2.75 (s, 3H), 2.15-2.00 (m, 4H), 1.91 (s, 6H), 1.11 (t, J = 7.2 Hz, 3H). |
| 378 | 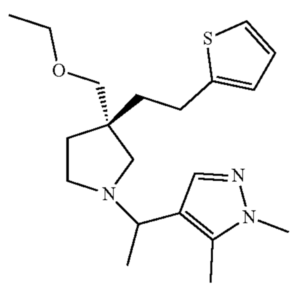 [SMILES: CCOC[C@@]1(CCc2cccs2)CCN(C(C)c2cnn(C)c2C)C1] | 4-(1-((S)-3-(ethoxymethyl)-3-(2-(thiophen-2-yl)ethyl)pyrrolidin-1-yl)ethyl)-1,5-dimethyl-1H-pyrazole | 362 | ¹H NMR (300 MHz, MeOD): δ 7.48 (s, 1H), 7.13-7.03 (m, 1H), 6.81-6.78 (m, 1H), 6.72 (s, 1H), 4.15 (s, 1H), 3.45-3.38 (m, 2H), 3.30 (q, J = 9.4 Hz, 2H), 3.20-3.09 (m, 4H), 2.98 (s, 2H), 2.72 (t, J = 8.4 Hz, 3H), 2.22 (s, 3H), 1.90-1.68 (m, 4H), 1.51 (d, J = 6.6 Hz, 3H), 1.08 (t, J = 6.3 Hz, 3H). |
| 379 | 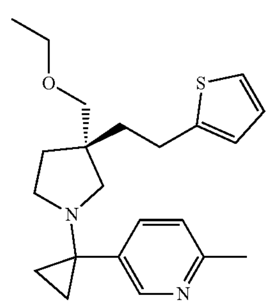 [SMILES: CCOC[C@@]1(CCc2cccs2)CCN(C2(c3ccc(C)nc3)CC2)C1] | (S)-5-(1-(3-(ethoxymethyl)-3-(2-(thiophen-2-yl)ethyl)pyrrolidin-1-yl)cyclopropyl)-2-methylpyridine | 371 | ¹H NMR (300 MHz, CDCl₃): δ 8.43 (s, 1H), 7.49 (d, J = 6.9 Hz, 1H), 7.20-7.04 (m, 2H), 6.88 (dd, J = 5.1, 3.4 Hz, 1H), 6.73 (d, J = 2.7 Hz, 1H), 3.39 (d, J = 6.6 Hz, 2H), 3.16-3.10 (m, 2H), 2.76-2.67 (m, 2H), 2.56 (s, 2H), 2.54 (s, 3H), 2.30 (s, 2H), 1.71 (s, 4H), 1.12 (t, J = 6.4 Hz, 3H), 1.06-0.90 (m, 2H), 0.77 (s, 2H). |
| 380 | 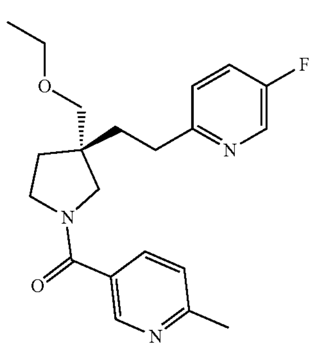 [SMILES: CCOC[C@@]1(CCc2ccc(F)cn2)CCN(C(=O)c2ccc(C)nc2)C1] | (S)-(3-(ethoxymethyl)-3-(2-(5-fluoropyridin-2-yl)ethyl)pyrrolidin-1-yl)(6-methylpyridin-3-yl)methanone | 372 | ¹H NMR (300 MHz, MeOD): δ 8.48 (dd, J = 10.2, 1.8 Hz, 1H), 8.23-8.20 (m, 1H), 7.79-7.75 (m, 1H), 7.50-7.38 (m, 1H), 7.32-7.19 (m, 2H), 3.67-3.40 (m, 4H), 3.38-3.23 (m, 4H), 2.80-2.73 (m, 1H), 2.71-2.60 (m, 1H), 2.49 (s, 3H), 1.95-1.67 (m, 4H), 1.14-1.02 (m, 3H). |

TABLE III-continued

| Compound. | Structure | Name | MS (ESI+): [M + H]⁺ | H-NMR |
|---|---|---|---|---|
| 381 | 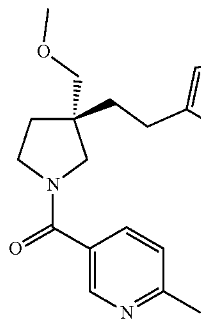 | (S)-(3-(methoxymethyl)-3-(2-(5-methylthiophen-3-yl)ethyl)pyrrolidin-1-yl)(6-methylpyridin-3-yl)methanone | 359 | ¹H NMR (300 MHz, MeOD): δ 8.55 (dd, J = 11.1, 1.8 Hz, 1H), 7.85-7.81 (m, 1H), 7.38 (d, J = 8.1 Hz, 1H), 6.74-6.57 (m, 2H), 3.66-3.58 (m, 2H), 3.42-3.37 (m, 3H), 3.32-3.30 (m, 2H), 3.29-3.22 (m, 2H), 2.58-2.45 (m, 5H), 2.41-2.38 (m, 3H), 1.85-1.73 (m, 4H). |
| 382 | 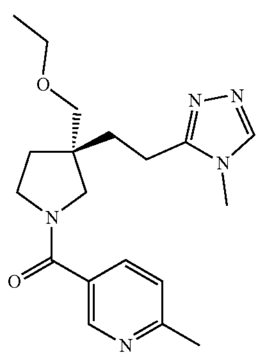 [SMILES: CCOC[C@@]1(CCc2nncn2C)CCN(C(=O)c2ccc(C)nc2)C1] | (S)-(3-(ethoxymethyl)-3-(2-(4-methyl-4H-1,2,4-triazol-yl)ethyl)pyrrolidin-1-yl)(6-methylpyridin-3-yl)methanone | 380 [M + Na]⁺ | ¹H NMR (300 MHz, MeOD) : δ 8.62-8.60 (m, 1H), 8.38 (d, J = 9.9 Hz, 1H), 7.92-7.89 (m, 1H), 7.42 (d, J = 8.1 Hz, 1H), 3.80-3.59 (m, 6H), 3.58-3.36 (m, 5H), 2.90-2.83 (m, 2H), 2.60 (s, 3H), 2.08-1.83 (m, 4H), 1.25-1.12 (m, 3H). |
| 383 | 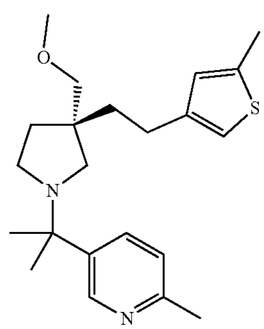 [SMILES: COC[C@@]1(CCc2csc(C)c2)CCN(C(C)(C)c2ccc(C)nc2)C1] | (S)-5-(2-(3-(methoxymethyl)-3-(2-(5-methylthiophen-3-yl)ethyl)pyrrolidin-1-yl)propan-2-yl)-2-methylpyridine | 373 | ¹H NMR (300 MHz, MeOD) : δ 8.64 (d, J = 2.1 Hz, 1H), 7.97 (dd, J = 8.1, 2.4 Hz, 1H), 7.36 (d, J = 8.1 Hz, 1H), 6.70 (s, 1H), 6.60 (s, 1H), 3.31 (s, 3H), 3.28 (s, 2H), 3.02-2.94 (m, 2H), 2.91-2.81 (m, 1H), 2.63-2.59 (m, 1H), 2.55 (s, 3H), 2.48 (t, J = 8.3 Hz, 2H), 2.42 (s, 3H), 1.83-1.70 (m, 4H), 1.65 (s, 6H). |
| 384 | 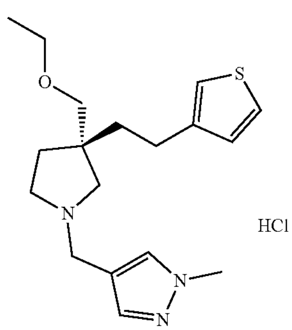 [SMILES: CCOC[C@@]1(CCc2ccsc2)CCN(Cc2cnn(C)c2)C1 ; Cl] | (S)-4-((3-(ethoxymethyl)-3-(2-(thiophen-3-yl)ethyl)pyrrolidin-1-yl)methyl)-1-methyl-1H-pyrazole HCl | 334 | ¹H NMR (300 MHz, MeOD): δ 7.86 (d, J = 7.5 Hz, 1H), 7.65 (d, J = 3.9 Hz, 1H), 7.39-7.26 (m, 1H), 7.15-6.90 (m, 2H), 4.36-4.19 (m, 2H), 3.92 (s, 3H), 3.68-3.36 (m, 6H), 3.30-3.21 (m, 1H), 3.02-2.88 (m, 1H), 2.67-2.64 (m, 2H), 2.11-1.79 (m, 4H), 1.28-1.10 (m, 3H). |

TABLE III-continued

| Compound. | Structure | Name | MS (ESI+): [M + H]+ | H-NMR |
|---|---|---|---|---|
| 385 | 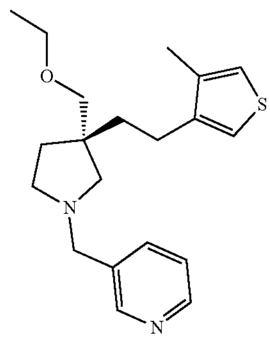 [SMILES: CCOC[C@@]1(CCc2cscc2C)CCN(Cc2cccnc2)C1] | (S)-3-((3-(ethoxymethyl)-3-(2-(4-methylthiophen-3-yl)ethyl)pyrrolidin-1-yl)methyl)pyridine | 345 | $^1$H NMR (300 MHz, MeOD): δ 8.53 (s, 1H), 8.46 (d, J = 4.5 Hz, 1H), 7.85 (d, J = 7.8 Hz, 1H), 7.44-7.40 (m, 1H), 6.92 (s, 2H), 3.73 (s, 2H), 3.50 (q, J = 6.9 Hz, 2H), 3.35 (d, J = 8.1 Hz, 2H), 2.79-2.66 (m, 2H), 2.63 (d, J = 9.9 Hz, 1H), 2.49 (t, J = 8.0 Hz, 2H), 2.42 (d, J = 9.9 Hz, 1H), 2.16 (s, 3H), 1.83-1.65 (m, 4H), 1.18 (t, J = 6.9 Hz, 3H). |
| 386 | 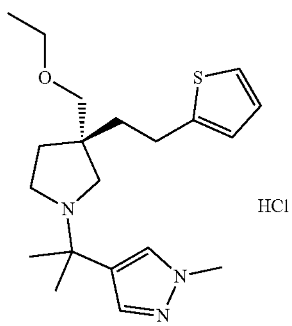 [SMILES: CCOC[C@@]1(CCc2cccs2)CCN(C(C)(C)c2cnn(C)c2)C1 ; Cl] | (S)-4-(2-(3-(ethoxymethyl)-3-(2-(thiophen-2-yl)ethyl)pyrrolidin-1-yl)propan-2-yl)-1-methyl-1H-pyrazole HCl | 362 | $^1$H NMR (300 MHz, MeOD): δ 7.87 (d, J = 5.1 Hz, 1H), 7.65 (d, J = 9.0 Hz, 1H), 7.08 (dd, J = 5.1, 1.2 Hz, 1H), 6.85-6.77 (m, 1H), 6.74-6.70 (m, 1H), 3.83-3.78 (m, 3H), 3.52-3.39 (m, 2H), 3.38-3.28 (m, 2H), 3.17-3.02 (m, 4H), 2.77-2.70 (m, 1H), 2.63-2.51 (m, 1H), 1.99-1.86 (m, 2H), 1.79 (m, 2H), 1.67 (s, 6H), 1.25-1.20 (m, 3H). |
| 387 | 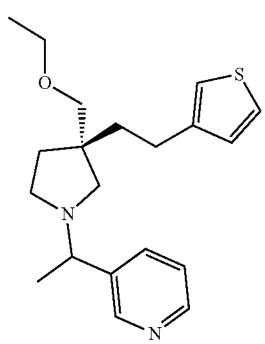 [SMILES: CCOC[C@@]1(CCc2ccsc2)CCN(C(C)c2cccnc2)C1] | 3-(1-((S)-3-(ethoxymethyl)-3-(2-(thiophen-3-yl)ethyl)pyrrolidin-1-yl)ethyl)pyridine | 345 | $^1$H NMR (300 MHz, MeOD): δ 8.41 (s, 1H), 8.33 (dd, J = 4.9, 1.5 Hz, 1H), 7.75 (d, J = 7.8 Hz, 1H), 7.31 (dd, J = 7.9, 4.9 Hz, 1H), 7.20-7.15 (m, 1H), 6.88 (s, 1H), 6.83 (t, J = 4.8 Hz, 1H), 3.44-3.33 (m, 2H), 3.23 (m, 2H), 2.70-2.58 (m, 1H), 2.54-2.44 (m, 2H), 2.33 (m, 2H), 2.26-2.08 (m, 2H), 1.67 (m, 2H), 1.58-1.54 (m, 2H), 1.30 (d, J = 6.6 Hz, 3H), 1.11-1.04 (m, 3H). |
| 388 | 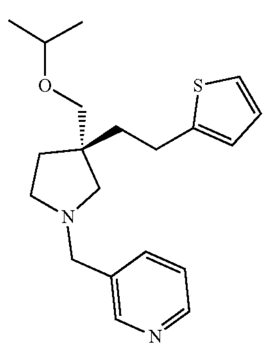 [SMILES: CC(C)OC[C@@]1(CCc2cccs2)CCN(Cc2cccnc2)C1] | (S)-3-((3-(isopropoxymethyl)-3-(2-(thiophen-2-yl)ethyl)pyrrolidin-1-yl)methyl)pyridine | 345 | $^1$H NMR (300 MHz, MeOD): δ 8.51 (s, 1H), 8.43 (d, J = 3.9 Hz, 1H), 7.83 (d, J = 7.8 Hz, 1H), 7.41 (dd, J = 7.8, 4.9 Hz, 1H), 7.13 (d, J = 5.1 Hz, 1H), 6.92-6.84 (m, 1H), 6.77 (d, J = 3.0 Hz, 1H), 3.65 (s, 2H), 3.58-3.49 (m, 1H), 3.39-3.29 (m, 2H), 2.80 (t, J = 8.6 Hz, 2H), 2.68-2.51 (m, 3H), 2.35-2.31 (m, 1H), 1.91-1.75 (m, 2H), 1.65 (t, J = 6.8 Hz, 2H), 1.13-0.89 (m, 6H). |

TABLE III-continued

| Compound. | Structure | Name | MS (ESI+): [M + H]+ | H-NMR |
|---|---|---|---|---|
| 389 | 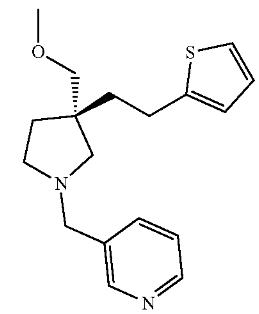 [SMILES: COC[C@@]1(CCc2cccs2)CCN(Cc2cccnc2)C1] | (S)-3-((3-(methoxymethyl)-3-(2-(thiophen-2-yl)ethyl)pyrrolidin-1-yl)methyl)pyridine | 317 | $^1$H NMR (300 MHz, MeOD): δ 8.50 (s, 1H), 8.43 (dd, J = 4.9, 1.4 Hz, 1H), 7.83 (d, J = 7.8 Hz, 1H), 7.41 (dd, J = 7.8, 5.0 Hz, 1H), 7.13 (dd, J = 5.1, 1.0 Hz, 1H), 6.87 (dd, J = 5.1, 3.5 Hz, 1H), 6.78 (d, J = 3.3 Hz, 1H), 3.64 (s, 2H), 3.33 (s, 3H), 3.30-3.27 (m, 2H), 2.85-2.79 (m, 2H), 2.70-2.62 (m, 2H), 2.54-2.53 (m, 1H), 2.33-2.32 (m, 1H), 1.90-1.76 (m, 2H), 1.66 (t, J = 6.9 Hz, 2H). |
| 390 | 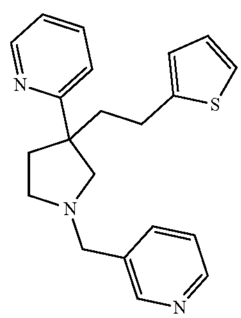 [SMILES: c1ccc(C2(CCc3cccs3)CCN(Cc3cccnc3)C2)nc1] | 2-(1-(pyridin-3-ylmethyl)-3-(2-(thiophen-2-yl)ethyl)pyrrolidin-3-yl)pyridine | 350 | $^1$H NMR (300 MHz, MeOD): δ 8.51 (d, J = 6.0 Hz, 2H), 8.45 (d, J = 3.6 Hz, 1H), 7.86-7.76 (m, 2H), 7.46-7.40 (m, 2H), 7.25 (t, J = 5.9 Hz, 1H), 7.10 (d, J = 5.1 Hz, 1H), 6.83-6.81 (m, 1H), 6.65 (s, 1H), 3.77 (s, 2H), 3.23-3.18 (m, 1H), 2.87-2.82 (m, 2H), 2.80-2.71 (m, 1H), 2.48-2.39 (m, 3H), 2.28-2.22 (m, 2H), 2.19-2.10 (m, 1H). |
| 391 | 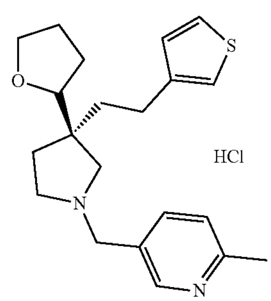 [SMILES: Cc1ccc(CN2CC[C@@](CCc3ccsc3)(C3CCCO3)C2)cn1 ; Cl] | 2-methyl-5-(((3R)-3-(tetrahydrofuran-2-yl)-3-(2-(thiophen-3-yl)ethyl)pyrrolidin-1-yl)methyl)pyridine HCl | 357 | $^1$H NMR (300 MHz, MeOD): δ 9.17-9.01 (m, 1H), 8.85-8.60 (m, 1H), 8.10-8.02 (m, 1H), 7.36-7.31 (m, 1H), 7.09-7.01 (m, 2H), 4.92-4.59 (m, 2H), 4.02-3.78 (m, 4H), 3.59-3.36 (m, 3H), 2.86-2.80 (m, 3H), 2.76-2.69 (m, 2H), 2.38-2.25 (m, 1H), 2.12-1.90 (m, 6H), 1.80-1.50 (m, 1H). |
| 392 | 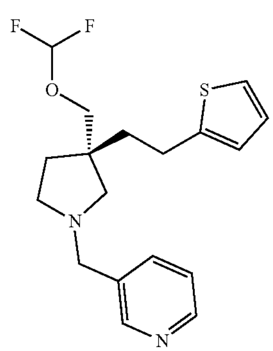 [SMILES: FC(F)OC[C@@]1(CCc2cccs2)CCN(Cc2cccnc2)C1] | (S)-3-((3-((difluoromethoxy)methyl)-3-(2-(thiophen-2-yl)ethyl)pyrrolidin-1-yl)methyl)pyridine | 353 | $^1$H NMR (300 MHz, MeOD): δ 8.50-8.42 (m, 2H), 7.83 (d, J = 7.8 Hz, 1H), 7.41 (dd, J = 7.5, 5.1 Hz, 1H), 7.14 (dd, J = 5.1, 1.2 Hz, 1H), 6.88 (dd, J = 5.1, 3.6 Hz, 1H), 6.79 (d, J = 2.4 Hz, 1H), 6.63-6.12 (m, 1H), 3.79 (q, J = 9.3 Hz, 2H), 3.66 (s, 2H), 2.83 (t, J = 8.6 Hz, 2H), 2.75-2.53 (m, 3H), 2.36-2.33 (m, 1H), 1.96-1.82 (m, 2H), 1.79-1.64 (m, 2H). |

TABLE III-continued

| Compound. | Name | MS (ESI+): [M + H]+ | H-NMR |
|---|---|---|---|
| 393 | 3-((3-ethoxy-3-(2-(thiophen-2-yl)ethyl)pyrrolidin-1-yl)methyl)pyridine | 317 | ¹H NMR (300 MHz, MeOD): δ 8.53 (d, J = 1.5 Hz, 1H), 8.46 (dd, J = 4.9, 1.5 Hz, 1H), 7.86 (d, J = 7.8 Hz, 1H), 7.46-7.43 (m, 1H), 7.16 (dd, J = 5.3, 1.1 Hz, 1H), 6.90 (dd, J = 5.1, 3.3 Hz, 1H), 6.83-6.81 (m, 1H), 3.73-3.70 (m, 2H), 3.46-3.43 (m, 2H), 2.88-2.78 (m, 4H), 2.56-2.52 (m, 2H), 2.07-2.01 (m, 3H), 1.88-1.77 (m, 1H), 1.19 (t, J = 6.9 Hz, 3H). |
| 394 | 3-((3-(ethoxymethyl)-3-(2-(thiophen-2-yl)ethyl)azetidin-1-yl)methyl)pyridine | 317 | ¹H NMR (300 MHz, MeOD): δ 8.42-8.38 (m, 2H), 7.73 (d, J = 8.1 Hz, 1H), 7.34 (dd, J = 7.8, 4.8 Hz, 1H), 7.07 (dd, J = 5.0, 0.8 Hz, 1H), 6.87-6.70 (m, 2H), 3.80 (s, 2H), 3.55-3.42 (m, 4H), 3.36-3.32 (m, 2H), 3.22-3.18 (m, 2H), 2.85-2.66 (m, 2H), 2.00-1.94 (m, 2H), 1.25-1.02 (m, 3H). |
| 395 | (S)-3-(1-(3-(ethoxymethyl)-3-(2-(thiophen-2-yl)ethyl)pyrrolidin-1-yl)cyclopropyl)pyridine | 357 | ¹H NMR (300 MHz, CDCl₃): δ 8.54 (d, J = 1.8 Hz, 1H), 8.48 (dd, J = 7.8, 1.5 Hz, 1H), 7.64-7.53 (m, 1H), 7.24 (d, J = 5.1 Hz, 1H), 7.07 (dd, J = 5.3, 1.1 Hz, 1H), 6.88 (dd, J = 5.1, 3.3 Hz, 1H), 6.74 (d, J = 2.4 Hz, 1H), 3.42-3.37 (m, 2H), 3.15-3.13 (m, 2H), 2.81-2.68 (m, 2H), 2.56-2.49 (m, 3H), 2.31-2.27 (m, 1H), 1.90-1.66 (m, 2H), 1.49-1.45 (m, 2H), 1.14 (t, J = 7.1 Hz, 3H), 1.02-0.95 (m, 2H), 0.80-0.76 (m, 2H). |
| 396 | 2-(1-(2-(pyridin-3-yl)propan-2-yl)-4-(2-(thiophen-2-yl)ethyl)piperidin-4-yl)pyridine | 392 | ¹H NMR (300 MHz, MeOD): δ 8.70 (d, J = 1.8 Hz, 1H), 8.57-8.49 (m, 1H), 8.36 (dd, J = 4.8, 1.5 Hz, 1H), 8.03-7.94 (m, 1H), 7.81-7.77 (m, 1H), 7.46 (d, J = 8.1 Hz, 1H), 7.37 (dd, J = 8.0, 4.8 Hz, 1H), 7.26-7.17 (m, 2H), 6.82 (d, J = 1.8 Hz, 1H), 6.75 (dd, J = 4.8, 0.9 Hz, 1H), 2.64-2.62 (m, 2H), 2.44-2.26 (m, 4H), 2.21-2.18 (m, 2H), 2.04-1.91 (m, 2H), 1.90-1.81 (m, 2H), 1.33 (s, 6H). |

TABLE III-continued

| Compound. | Structure | Name | MS (ESI+): [M + H]+ | H-NMR |
|---|---|---|---|---|
| 397 | 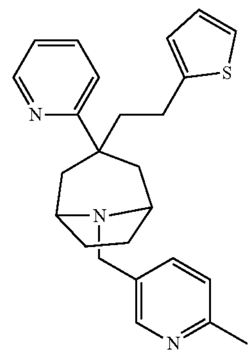 [SMILES: Cc1ccc(CN2C3CCC2CC(CCc2cccs2)(c2ccccn2)C3)cn1] | 8-((6-methylpyridin-3-yl)methyl)-3-(pyridin-2-yl)-3-(2-(thiophen-2-yl)ethyl)-8-azabicyclo[3.2.1]octane | 404 | $^1$H NMR (300 MHz, MeOD): δ 8.51-8.50 (m, 1H), 8.41 (s, 1H), 7.85-7.70 (m, 2H), 7.40 (d, J = 8.1 Hz, 1H), 7.31 (d, J = 8.1 Hz, 1H), 7.25 (dd, J = 7.0, 5.3 Hz, 1H), 7.15-7.07 (m, 1H), 6.83 (dd, J = 5.0, 3.5 Hz, 1H), 6.65 (d, J = 3.0 Hz, 1H), 3.88 (d, J = 3.3 Hz, 2H), 3.65 (s, 2H), 2.60-2.51 (m, 5H), 2.50-2.41 (m, 2H), 2.39-2.21 (m, 6H), 2.17-2.08 (m, 2H). |
| 398 | 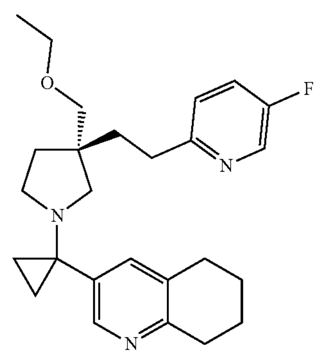 [SMILES: CCOC[C@@]1(CCc2ccc(F)cn2)CCN(C2(c3cnc4c(c3)CCCC4)CC2)C1] | (S)-3-(1-(3-(ethoxymethyl)-3-(2-(5-fluoropyridin-2-yl)ethyl)pyrrolidin-1-yl)cyclopropyl)-5,6,7,8-tetrahydroquinoline | 424 | $^1$H NMR (300 MHz, MeOD): δ 8.29 (d, J = 2.7 Hz, 1H), 8.18 (d, J = 1.8 Hz, 1H), 7.59-7.49 (m, 1H), 7.44 (s, 1H), 7.27 (dd, J = 8.6, 4.5 Hz, 1H), 3.39 (q, J = 7.0 Hz, 2H), 3.22-3.13 (m, 2H), 2.91-2.77 (m, 4H), 2.73-2.64 (m, 2H), 2.63-2.51 (m, 3H), 2.36-2.32 (m, 1H), 1.97-1.77 (m, 4H), 1.76-1.59 (m, 2H), 1.51 (t, J = 6.8 Hz, 2H), 1.11 (t, J = 7.1 Hz, 3H), 1.03-0.95 (m, 2H), 0.78-0.77 (m, 2H). |
| 399 | 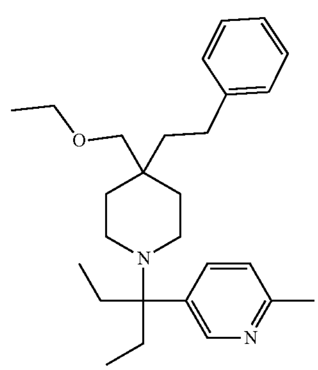 [SMILES: CCOCC1(CCc2ccccc2)CCN(C(CC)(CC)c2ccc(C)nc2)CC1] | 5-(3-(4-(ethoxymethyl)-4-phenethylpiperidin-1-yl)pentan-3-yl)-2-methylpyridine | 409 | $^1$H NMR (300 MHz, CDCl$_3$): δ 8.55 (d, J = 1.9 Hz, 1H), 7.63 (dd, J = 8.1, 2.3 Hz, 1H), 7.38-7.23 (m, 2H), 7.17 (d, J = 6.6 Hz, 3H), 7.09 (d, J = 8.1 Hz, 1H), 3.45 (q, J = 7.0 Hz, 2H), 3.34-3.18 (m, 2H), 2.60-2.47 (m, 9H), 1.87-1.79 (m, 4H), 1.67-1.57 (m, 2H), 1.54-1.39 (m, 4H), 1.19 (t, J = 6.9 Hz, 3H), 0.80 (t, J = 7.4 Hz, 6H). |
| 400 | 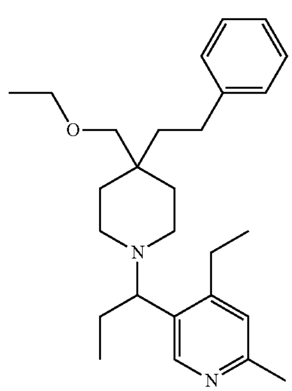 [SMILES: CCOCC1(CCc2ccccc2)CCN(C(CC)c2cnc(C)cc2CC)CC1] | 5-(1-(4-(ethoxymethyl)-4-phenethylpiperidin-1-yl)propyl)-4-ethyl-2-methylpyridine | 409 | $^1$H NMR (300 MHz, CDCl$_3$): δ 8.40 (s, 1H), 7.32-7.22 (m, 2H), 7.21-7.12 (m, 3H), 6.96 (s, 1H), 3.45 (q, J = 6.9 Hz, 3H), 3.28 (s, 2H), 2.69 (q, J = 7.5 Hz, 2H), 2.60-2.46 (m, 7H), 2.37-2.22 (m, 2H), 2.01-1.69 (m, 4H), 1.69-1.59 (m, 2H), 1.52-1.44 (m, 2H), 1.27-1.16 (m, 6H), 0.72 (t, J = 7.4 Hz, 3H). |

TABLE III-continued

| Compound. | Name | MS (ESI+): [M + H]⁺ | H-NMR |
|---|---|---|---|
| 401 | 5-(1-(4-(ethoxymethyl)-4-phenethylpiperidin-1-yl)cyclohexyl-2-methylpyridine | 421 | ¹H NMR (300 MHz, CDCl₃): δ 8.45 (d, J = 2.1 Hz, 1H), 7.49 (dd, J = 8.1, 2.1 Hz, 1H), 7.23 (d, J = 7.5 Hz, 2H), 7.19-7.05 (m, 4H), 3.2-3.35 (m, 2H), 3.11 (s, 2H), 2.55 (s, 3H), 2.49-2.41 (m, 2H), 2.30-2.22 (m, 4H), 2.01-1.95 (m, 4H), 1.69-1.60 (m, 4H), 1.57-1.41 (m, 8H), 1.20-1.07 (m, 3H). |
| 402 | (S)-5-(2-(3-(2-ethoxypropan-2-yl)-3-(2-(thiophen-2-yl)ethyl)pyrrolidin-1-yl)propan-2-yl)-2-methylpyridine | 401 | ¹H NMR (300 MHz, MeOD): δ 8.69 (s, 1H), 8.02 (d, J = 7.8 Hz, 1H), 7.39 (d, J = 8.4 Hz, 1H), 7.16 (d, J = 5.1 Hz, 1H), 6.96-6.85 (m, 1H), 6.80 (s, 1H), 3.43-3.38 (m, 2H), 3.30-2.91 (m, 6H), 2.54 (s, 3H), 2.31-1.96 (m, 2H), 1.76 (s, 8H), 1.18-1.10 (m, 6H), 1.10-1.02 (m, 3H). |
| 403 | 3-(1-((S)-3-(2-ethoxypropan-2-yl)-3-(2-(thiophen-2-yl)ethyl)pyrrolidin-1-yl)ethyl)-2,6-dimethylpyridine | 401 | ¹H NMR (300 MHz, MeOD): δ 8.25 (d, J = 6.0 Hz, 1H), 7.27 (d, J = 6.6 Hz, 1H), 7.20-7.15 (m, 1H), 6.91-6.85 (m, 2H), 3.90 (d, J = 12.8 Hz, 1H), 3.78-3.57 (m, 2H), 3.49-3.40 (m, 4H), 3.09-2.85 (m, 2H), 2.52 (d, J = 5.4 Hz, 3H), 2.32 (d, J = 2.7 Hz, 3H), 2.01-1.74 (m, 4H), 1.26-1.06 (m, 12H). |
| 404 | (S)-3-((3-(ethoxymethyl)-3-(2-(thiophen-2-yl)ethyl)pyrrolidin-1-yl)methyl)-2,4-dimethylpyridine | 359 | ¹H NMR (300 MHz, MeOD): δ 8.02 (d, J = 5.1 Hz, 1H), 7.02 (dd, J =5.1, 1.1 Hz, 1H), 6.97 (d, J = 5.1 Hz, 1H), 6.76 (dd, J = 5.1, 3.4 Hz, 1H), 6.68-6.60 (m, 1H), 3.55 (s, 2H), 3.39-3.33 (m, 2H), 3.21-3.12 (m, 2H), 2.69 (t, J = 8.3 Hz, 2H), 2.49 (s, 3H), 2.47-2.38 (m, 3H), 2.33 (s, 3H), 2.23-2.21 (m, 1H), 1.80-1.64 (m, 2H), 1.50 (t, J = 6.9 Hz, 2H), 1.05 (t, J = 7.0 Hz, 3H). |

TABLE III-continued

| Compound. | Structure | Name | MS (ESI+): [M + H]+ | H-NMR |
|---|---|---|---|---|
| 405 | 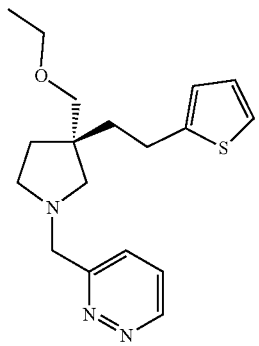 [SMILES: CCOC[C@@]1(CCc2cccs2)CCN(Cc2cccnn2)C1] | (S)-3-((3-(ethoxymethyl)-3-(2-(thiophen-2-yl)ethyl)pyrrolidin-1-yl)methyl)pyridazine | 332 | ¹H NMR (300 MHz, MeOD): δ 9.00 (dd, J = 4.9, 1.6 Hz, 1H), 7.74 (dd, J = 8.5, 1.6 Hz, 1H), 7.62 (dd, J = 8.5, 4.9 Hz, 1H), 7.04 (dd, J = 5.1, 1.1 Hz, 1H), 6.78 (dd, J = 5.1, 3.4 Hz, 1H), 6.74-6.64 (m, 1H), 3.86 (s, 2H), 3.39 (q, J = 7.0 Hz, 2H), 3.25 (d, J = 2.3 Hz, 2H), 2.75-2.70 (m, 2H), 2.67-2.57 (m, 2H), 2.55-2.52 (m, 1H), 2.35-2.33 (m, 1H), 1.77-1.75 (m, 2H), 1.60 (t, J = 6.9 Hz, 2H), 1.08 (t, J = 7.0 Hz, 3H). |
| 406 | 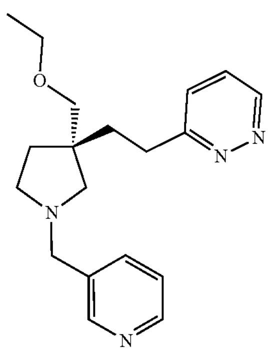 [SMILES: CCOC[C@@]1(CCc2cccnn2)CCN(Cc2cccnc2)C1] | (S)-3-(2-(3-(ethoxymethyl)-1-(pyridin-3-ylmethyl)pyrrolidin-3-yl)ethyl)pyridazine | 327 | ¹H NMR (300 MHz, MeOD): δ 9.02 (t, J = 3.3 Hz, 1H), 8.53 (s, 1H), 8.47 (s, 1H), 7.86 (d, J = 7.8 Hz, 1H), 7.64 (d, J = 3.2 Hz, 2H), 7.47-7.37 (m, 1H), 3.76 (s, 2H), 3.48 (q, J = 7.0 Hz, 2H), 3.38 (s, 2H), 2.99-2.91 (m, 2H), 2.81-2.68 (m, 2H), 2.49-2.47 (m, 1H), 2.04-1.96 (m, 1H), 1.97-1.85 (m, 2H), 1.76 (t, J = 6.9 Hz, 2H), 1.17 (t, J = 7.0 Hz, 3H). |
| 407 | 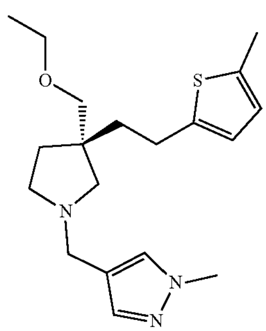 [SMILES: CCOC[C@@]1(CCc2ccc(C)s2)CCN(Cc2cnn(C)c2)C1] | (S)-4-((3-(ethoxymethyl)-3-(2-(5-methylthiophen-2-yl)ethyl)pyrrolidin-1-yl)methyl)-1-methyl-1H-pyrazole | 348 | ¹H NMR (300 MHz, MeOD): δ 7.53 (s, 1H), 7.42 (s, 1H), 6.52 (d, J = 3.6 Hz, 2H), 3.86 (s, 3H), 3.52 (s, 2H), 3.48-3.45 (m, 2H), 3.33-3.28 (m, 2H), 2.65 (m, 5H), 2.38 (s, 3H), 2.36-2.34 (m, 1H), 1.89-1.72 (m, 2H), 1.68-1.62 (m, 2H), 1.17 (t, J = 7.0 Hz, 3H). |
| 408 | 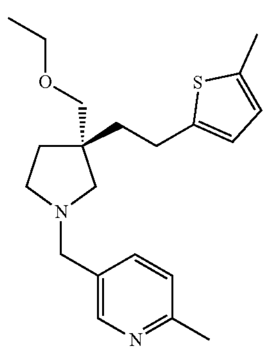 [SMILES: CCOC[C@@]1(CCc2ccc(C)s2)CCN(Cc2ccc(C)nc2)C1] | (S)-5-((3-(ethoxymethyl)-3-(2-(5-methylthiophen-2-yl)ethyl)pyrrolidin-1-yl)methyl)-2-methylpyridine | 359 | ¹H NMR (300 MHz, MeOD): δ 8.35 (d, J = 2.0 Hz, 1H), 7.71 (dd, J = 8.0, 2.2 Hz, 1H), 7.27 (d, J = 8.0 Hz, 1H), 6.60-6.41 (m, 2H), 3.60 (s, 2H), 3.47 (q, J = 7.0 Hz, 2H), 3.31-3.28 (m, 2H), 2.76-2.69 (m, 2H), 2.68-2.59 (m, 2H), 2.58-2.50 (m, 4H), 2.38 (s, 3H), 2.32-2.30 (m, 1H), 1.88-1.73 (m, 2H), 1.64 (t, J =6.8 Hz, 2H), 1.17 (t, J = 7.0 Hz, 3H). |

TABLE III-continued

| Compound. | Structure | Name | MS (ESI+): [M + H]+ | H-NMR |
|---|---|---|---|---|
| 409 | 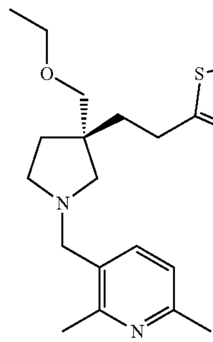 | (S)-3-((3-(ethoxymethyl)-3-(2-(5-methylthiophen-2-yl)ethyl)pyrrolidin-1-yl)methyl)-2,6-dimethylpyridine | 373 | ¹H NMR (300 MHz, MeOD): δ 7.57 (d, J = 1.1 Hz, 1H), 7.06 (d, J = 7.8 Hz, 1H), 6.50 (s, 2H), 3.56 (s, 2H), 3.47 (q, J = 7.0 Hz, 2H), 3.36-3.31 (m, 2H), 2.76-2.69 (m, 2H), 2.63-2.60 (m, 2H), 2.53 (s, 3H), 2.52-2.49 (m, 1H), 2.47 (s, 3H), 2.38 (s, 3H), 2.31-2.28 (m, 1H), 1.82-1.75 (m, 2H), 1.62 (t, J = 6.9 Hz, 2H), 1.16 (t, J = 7.0 Hz, 3H). |
| 410 | 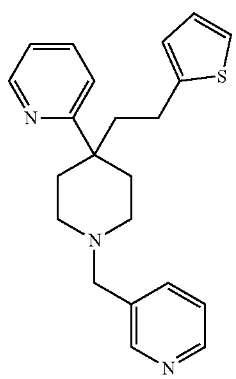 [SMILES: c1ccc(C2(CCc3cccs3)CCN(Cc3cccnc3)CC2)nc1] | 2-(1-(pyridin-3-ylmethyl)-4-(2-(thiophen-2-yl)ethyl)piperidin-4-yl)pyridine | 364 | ¹H NMR (300 MHz, MeOD): δ 8.56 (dd, J = 4.9, 1.0 Hz, 1H), 8.47 (d, J = 1.5 Hz, 1H), 8.43 (dd, J = 4.9, 1.5 Hz, 1H), 7.80-7.77 (m, 2H), 7.49 (d, J = 8.1 Hz, 1H), 7.40 (dd, J = 7.4, 5.0 Hz, 1H), 7.29-7.20 (m, 1H), 7.07 (dd, J = 5.2, 1.1 Hz, 1H), 6.80 (dd, J = 5.1, 3.5 Hz, 1H), 6.62 (d, J = 2.5 Hz, 1H), 3.49 (s, 2H), 2.76-2.61 (m, 2H), 2.55-2.35 (m, 4H), 2.30-2.18 (m, 2H), 2.09-1.98 (m, 2H), 1.96-1.82 (m, 2H). |
| 411 | 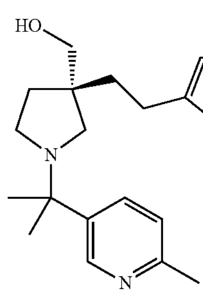 | (S)-(1-(2-(6-methylpyridin-3-yl)propan-2-yl)-3-(2-(thiophen-2-yl)ethyl)pyrrolidin-3-yl)methanol | 345 | ¹H NMR (300 MHz, MeOD): δ 8.53 (d, J = 2.0 Hz, 1H), 7.86 (dd, J = 8.2, 2.2 Hz, 1H), 7.25 (d, J = 8.2 Hz, 1H), 7.13 (d, J = 5.1 Hz, 1H), 6.92-6.84 (m, 1H), 6.78 (d, J = 3.3 Hz, 1H), 3.46 (s, 2H), 2.85-2.75 (m, 2H), 2.66-2.60 (m, 2H), 2.55 (d, J = 9.3 Hz, 1H), 2.50 (s, 3H), 2.34 (d, J = 9.3 Hz, 1H), 1.82-1.73 (m, 2H), 1.67-1.54 (m, 2H), 1.44 (s, 6H). |
| 412 | 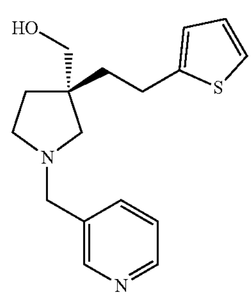 [SMILES: OC[C@@]1(CCc2cccs2)CCN(Cc2cccnc2)C1] | (S)-(1-(pyridin-3-ylmethyl)-3-(2-(thiophen-2-yl)ethyl)pyrrolidin-3-yl)methanol | 303 | ¹H NMR (300 MHz, MeOD): δ 8.51 (s, 1H), 8.43 (dd, J = 4.9, 1.5 Hz, 1H), 7.83 (d, J = 7.8 Hz, 1H), 7.43-7.41 (m, 1H), 7.19-7.11 (m, 1H), 6.89-6.86 (m, 1H), 6.80 (d, J = 3.3 Hz, 1H), 3.65 (s, 2H), 3.48 (s, 2H), 2.89-2.81 (m, 2H), 2.66-2.55 (m, 3H), 2.34 (d, J = 9.6 Hz, 1H), 1.88-1.81 (m, 2H), 1.67 (t, J = 6.9 Hz, 2H). |

TABLE III-continued

| Compound. | Structure | Name | MS (ESI+): [M + H]+ | H-NMR |
|---|---|---|---|---|
| 413 | 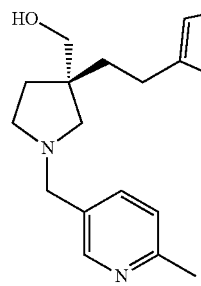 | (S)-(1-((6-methylpyridin-3-yl)methyl)-3-(2-(thiophen-2-yl)ethyl)pyrrolidin-3-yl)methanol | 317 | $^1$H NMR (300 MHz, MeOD): δ 8.35 (d, J = 1.8 Hz, 1H), 7.71 (dd, J = 8.0, 2.1 Hz, 1H), 7.27 (d, J = 8.0 Hz, 1H), 7.13 (dd, J = 5.4, 1.2 Hz, 1H), 6.89-6.87 (m, 1H), 6.80 (d, J = 2.4 Hz, 1H), 3.60 (s, 2H), 3.47 (s, 2H), 2.88-2.77 (m, 2H), 2.70-2.60 (m, 1H), 2.60-2.53 (m, 2H), 2.51 (s, 3H), 2.32 (d, J = 9.6 Hz, 1H), 1.87-1.84 (m, 2H), 1.67 (t, J = 6.9 Hz, 2H). |
| 414 | 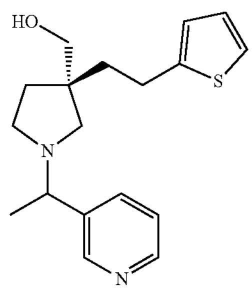 [SMILES: CC(c1cccnc1)N1CC[C@@](CO)(CCc2cccs2)C1] | ((3S)-1-(1-(pyridin-3-yl)ethyl)-3-(2-(thiophen-2-yl)ethyl)pyrrolidin-3-yl)methanol | 317 | $^1$H NMR (300 MHz, MeOD): δ 8.50 (s, 1H), 8.42 (d, J = 3.9 Hz, 1H), 7.85 (d, J = 7.8 Hz, 1H), 7.42-7.38 (m, 1H), 7.13 (d, J = 5.1 Hz, 1H), 6.92-6.84 (m, 1H), 6.79 (s, 1H), 3.47 (d, J = 7.8 Hz, 2H), 3.38-3.31 (m, 1H), 2.83-2.81 (m, 2H), 2.73-2.58 (m, 1H), 2.50-2.38 (m, 2H), 2.28 (d, J = 9.6 Hz, 1H), 1.85-1.80 (m, 2H), 1.78-1.66 (m, 2H), 1.40 (d, J = 6.6 Hz, 3H). |
| 415 | 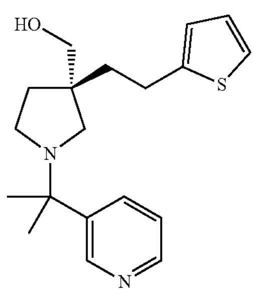 [SMILES: CC(C)(c1cccnc1)N1CC[C@@](CO)(CCc2cccs2)C1] | (S)-1-(2-(pyridin-3-yl)propan-2-yl)-3-(2-(thiophen-2-yl)ethyl)pyrrolidin-3-yl)methanol | 331 | $^1$H NMR (300 MHz, MeOD): δ 8.69 (d, J = 1.5 Hz, 1H), 8.37 (d, J = 4.8 Hz, 1H), 8.02-7.93 (m, 1H), 7.41-7.39 (m, 1H), 7.14-7.11 (m, 1H), 6.89-6.86 (m, 1H), 6.79 (d, J = 2.4 Hz, 1H), 3.53-3.41 (m, 2H), 2.81 (t, J = 8.4 Hz, 2H), 2.64-2.60 (m, 2H), 2.55 (d, J = 9.0 Hz, 1H), 2.33 (d, J = 9.0 Hz, 1H), 1.84-1.78 (m, 2H), 1.64-1.59 (m, 2H), 1.45 (s, 6H). |
| 416 | 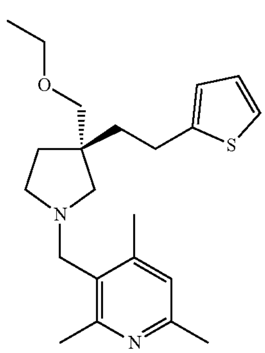 [SMILES: CCOC[C@@]1(CCc2cccs2)CCN(Cc2c(C)cc(C)nc2C)C1] | (S)-3-((3-(ethoxymethyl)-3-(2-(thiophen-2-yl)ethyl)pyrrolidin-1-yl)methyl)-2,4,6-trimethylpyridine | 373 | $^1$H NMR (300 MHz, MeOD): δ 7.13-7.11 (m, 1H), 6.93 (s, 1H), 6.88-6.85 (m, 1H), 6.75 (d, J = 3.3 Hz, 1H), 3.60 (s, 2H), 3.49-3.42 (m, 2H), 3.28-3.27 (m, 2H), 2.79 (t, J = 8.4 Hz, 2H), 2.61-2.48 (m, 6H), 2.39 (d, J = 7.8 Hz, 6H), 2.30 (d, J = 9.3 Hz, 1H), 1.90-1.73 (m, 2H), 1.59 (t, J = 6.9 Hz, 2H), 1.15 (t, J = 7.0 Hz, 3H). |

TABLE III-continued

| Compound. | Name | MS (ESI+): [M + H]⁺ | H-NMR |
|---|---|---|---|
| 417 | 2-(1-((1-methyl-1H-pyrazol-4-yl)methyl)-4-phenethylpiperidin-4-yl)pyridine | 361 | $^1$H NMR (300 MHz, MeOD): δ 8.57-8.55 (m, 1H), 7.80-7.76 (m, 1H), 7.50-7.48 (m, 2H), 7.38 (s, 1H), 7.31-7.21 (m, 1H), 7.18-7.13 (m, 2H), 7.09-7.07 (m, 1H), 6.96-6.93 (m, 2H), 3.84 (s, 3H), 3.37 (s, 2H), 2.78-2.64 (m, 2H), 2.50-2.44 (m, 2H), 2.29-2.12 (m, 4H), 1.98-1.82 (m, 4H). |
| 418 | 5-(((2S,6S)-4-(4-fluorophenethyl)-2,6-dimethyl-4-(pyridin-2-yl)piperidin-1-yl)methyl)-2-methylpyridine | 418 | $^1$H NMR (300 MHz, MeOD): δ 8.55 (d, J = 3.9 Hz, 1H), 8.34 (s, 1H), 7.79-7.72 (m, 2H), 7.56 (d, J = 7.8 Hz, 1H), 7.25 (t, J = 6.9 Hz, 2H), 6.97-6.85 (m, 4H), 3.91 (d, J = 14.1 Hz, 1H), 3.43 (d, J = 14.1 Hz, 1H), 3.19-3.05 (m, 1H), 2.91-2.82 (m, 1H), 2.65 (d, J = 13.8 Hz, 1H), 2.49 (s, 3H), 2.45-2.35 (m, 2H), 2.03-1.94 (m, 2H), 1.81-1.69 (m, 2H), 1.57-1.53 (m, 1H), 1.23 (d, J = 6.3 Hz, 3H), 0.37 (d, J = 6.9 Hz, 3H). |
| 419 | (R)-5-((3-(ethoxymethyl)-3-(phenoxymethyl)pyrrolidin-1-yl)methyl)-2-methylpyridine | 341 | $^1$H NMR (300 MHz, MeOD): δ 8.36 (s, 1H), 7.72 (dd, J = 8.0, 1.9 Hz, 1H), 7.28-7.21 (m, 3H), 6.91-6.81 (m, 3H), 3.87 (s, 2H), 3.64 (s, 2H), 3.46 (q, J = 7.1 Hz, 4H), 2.68-2.63 (m, 2H), 2.59-2.45 (m, 5H), 1.78-1.73 (m, 2H), 1.11 (t, J = 6.9 Hz, 3H). |
| 420 | (S)-2-(2-(3-(ethoxymethyl)-1-(pyridin-3-ylmethyl)pyrrolidin-3-yl)ethyl)pyridine | 326 | $^1$H NMR (300 MHz, MeOD): δ 8.52 (s, 1H), 8.46-8.39 (m, 2H), 7.85 (d, J = 8.1 Hz, 1H), 7.74 (t, J = 7.8 Hz, 1H), 7.42 (dd, J = 7.8, 5.0 Hz, 1H), 7.30 (d, J = 7.8 Hz, 1H), 7.27-7.21 (m, 1H), 3.73 (s, 2H), 3.48 (dd, J = 14.0, 7.0 Hz, 2H), 3.38-3.30 (m, 2H), 2.80-2.63 (m, 5H), 2.42 (d, J = 9.9 Hz, 1H), 1.88-1.80 (m, 2H), 1.73 (t, J = 6.9 Hz, 2H), 1.17 (t, J = 6.9 Hz, 3H). |

TABLE III-continued

| Compound. | Structure | Name | MS (ESI+): [M + H]⁺ | H-NMR |
|---|---|---|---|---|
| 421 | 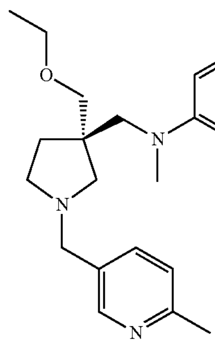 | (S)-N-((3-(ethoxymethyl)-1-((6-methylpyridin-3-yl)methyl)pyrrolidin-3-yl)methyl)-N-methylaniline | 354 | ¹H NMR (300 MHz, MeOD): δ 8.36 (s, 1H), 7.71 (dd, J = 7.9, 2.0 Hz, 1H), 7.26 (d, J = 7.9 Hz, 1H), 7.07 (t, J = 7.9 Hz, 2H), 6.78 (d, J = 8.4 Hz, 2H), 6.57 (t, J = 7.2 Hz, 1H), 3.59 (q, J = 12.6 Hz, 2H), 3.49-3.42 (m, 2H), 3.38-3.30 (m, 3H), 3.27-3.25 (m, 1H), 2.93 (s, 3H), 2.77-2.75 (m, 1H), 2.58 (d, J = 9.7 Hz, 1H), 2.55-2.44 (m, 4H), 2.20 (d, J = 9.9 Hz, 1H), 1.68 (t, J = 6.9 Hz, 2H), 1.20 (t, J = 6.9 Hz, 3H). |
| 422 | 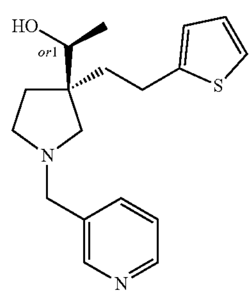 [SMILES: C[C@H](O)[C@]1(CCc2cccs2)CCN(Cc2cccnc2)C1] | (S)-1-((R)-1-(pyridin-3-ylmethyl)-3-(2-(thiophen-2-yl)ethyl)pyrrolidin-3-yl)ethan-1-ol | 317 | ¹H NMR (300 MHz, MeOD): δ 8.51 (s, 1H), 8.43 (d, J = 4.5 Hz, 1H), 7.84 (d, J = 7.7 Hz, 1H), 7.43-7.39 (m, 1H), 7.18-7.11 (m, 1H), 6.94-6.84 (m, 1H), 6.80 (s, 1H), 3.79-3.75 (m, 1H), 3.66-3.56 (m, 2H), 2.88-2.81 (m, 2H), 2.69-2.59 (m, 3H), 2.46-2.34 (m, 1H), 2.03-1.53 (m, 4H), 1.20-1.12 (m, 3H). |
| 423 | 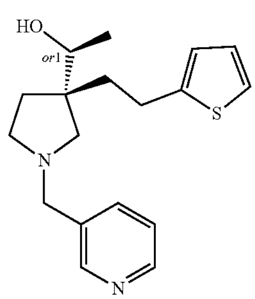 [SMILES: C[C@H](O)[C@@]1(CCc2cccs2)CCN(Cc2cccnc2)C1] | (S)-1-((S)-1-(pyridin-3-ylmethyl)-3-(2-(thiophen-2-yl)ethyl)pyrrolidin-3-yl)ethan-1-ol | 317 | ¹H NMR (300 MHz, MeOD): δ 8.51 (s, 1H), 8.43 (d, J = 4.5 Hz, 1H), 7.84 (d, J = 7.8 Hz, 1H), 7.41 (dd, J = 7.2, 4.8 Hz, 1H), 7.18-7.11 (m, 1H), 6.89-6.84 (m, 1H), 6.80 (s, 1H), 3.80-3.75 (m, 1H), 3.66-3.56 (m, 2H), 2.88-2.81 (m, 2H), 2.69-2.60 (m, 3H), 2.46-2.38 (m, 1H), 2.03-1.53 (m, 4H), 1.19-1.12 (m, 3H). |
| 424 | 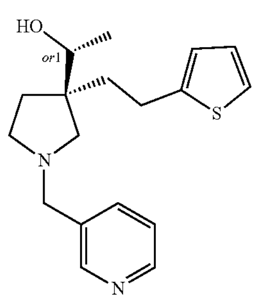 [SMILES: C[C@@H](O)[C@]1(CCc2cccs2)CCN(Cc2cccnc2)C1] | (R)-1-((R)-1-(pyridin-3-ylmethyl)-3-(2-(thiophen-2-yl)ethyl)pyrrolidin-3-yl)ethan-1-ol | 317 | ¹H NMR (300 MHz, MeOD): δ 8.51 (s, 1H), 8.45 (d, J = 3.6 Hz, 1H), 7.84 (d, J = 7.9 Hz, 1H), 7.44-7.40 (m, 1H), 7.14 (d, J = 5.1 Hz, 1H), 6.94-6.85 (m, 1H), 6.79 (d, J = 2.6 Hz, 1H), 3.82 (q, J = 6.2 Hz, 1H), 3.70 (s, 2H), 2.91-2.80 (m, 2H), 2.78-2.58 (m, 3H), 2.46-2.42 (m, 1H), 2.09-1.94 (m, 1H), 1.93-1.72 (m, 2H), 1.69-1.52 (m, 1H), 1.14 (d, J = 6.3 Hz, 3H). |

TABLE III-continued

| Compound. | Structure | Name | MS (ESI+): [M + H]+ | H-NMR |
|---|---|---|---|---|
| 425 | 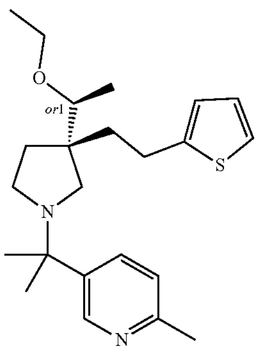 [SMILES: CCO[C@@H](C)[C@@]1(CCc2cccs2)CCN(C(C)(C)c2ccc(C)nc2)C1] | 5-(2-((S)-3-((S or R)-1-ethoxyethyl)-3-(2-(thiophen-2-yl)ethyl)pyrrolidin-1-yl)propan-2-yl)-2-methylpyridine | 387 | ¹H NMR (300 MHz, MeOD): δ 8.54 (d, J = 2.1 Hz, 1H), 7.87 (dd, J = 8.2, 1.7 Hz, 1H), 7.25 (d, J = 8.2 Hz, 1H), 7.13 (d, J = 5.1 Hz, 1H), 6.93-6.85 (m, 1H), 6.77 (s, 1H), 3.71-3.57 (m, 1H), 2.99-2.83 (m, 2H), 2.70-2.52 (m, 5H), 2.49 (s, 3H), 2.41-2.30 (m, 1H), 1.99-1.74 (m, 2H), 1.74-1.56 (m, 2H), 1.43 (s, 6H), 1.20-1.04 (m, 6H). |
| 426 | 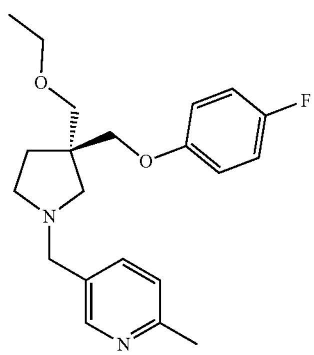 [SMILES: CCOC[C@@]1(COc2ccc(F)cc2)CCN(Cc2ccc(C)nc2)C1] | (R)-5-((3-(ethoxymethyl)-3-((4-fluorophenoxy)methyl)pyrrolidin-1-yl)methyl)-2-methylpyridine | 359 | ¹H NMR (300 MHz, MeOD): δ 8.36 (d, J = 1.5 Hz, 1H), 7.72 (dd, J = 7.8, 2.1 Hz, 1H), 7.27 (d, J = 8.0 Hz, 1H), 6.97 (t, J = 8.7 Hz, 2H), 6.92-6.85 (m, 2H), 3.90-3.82 (m, 2H), 3.64 (s, 2H), 3.53-3.40 (m, 4H), 2.73-2.61 (m, 2H), 2.58-2.45 (m, 5H), 1.74 (t, J = 6.9 Hz, 2H), 1.11 (t, J = 6.9 Hz, 3H). |
| 427 | 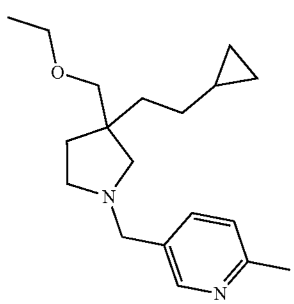 [SMILES: CCOCC1(CCC2CC2)CCN(Cc2ccc(C)nc2)C1] | 5-((3-(2-cyclopropylethyl)-3-(ethoxymethyl)pyrrolidin-1-yl)methyl)-2-methylpyridine | 303 | ¹H NMR (300 MHz, MeOD): δ 8.38 (d, J = 1.7 Hz, 1H), 7.74 (dd, J = 8.0, 2.1 Hz, 1H), 7.30 (d, J = 8.0 Hz, 1H), 3.71 (s, 2H), 3.51 (q, J = 7.0 Hz, 2H), 3.30-3.14 (m, 2H), 2.81-2.59 (m, 3H), 2.53 (s, 3H), 2.45-2.28 (m, 1H), 1.79-1.49 (m, 4H), 1.20-1.05 (m, 5H), 0.75-0.54 (m, 1H), 0.48-0.26 (m, 2H), 0.09-0.07 (m, 2H). |
| 428 | 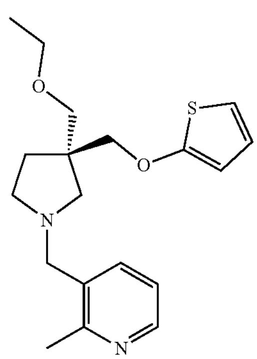 [SMILES: CCOC[C@@]1(COc2cccs2)CCN(Cc2cccnc2C)C1] | (S)-3-((3-(ethoxymethyl)-3-(2-(thiophen-2-yl)ethyl)pyrrolidin-1-yl)methyl)-2-methylpyridine | 345 | ¹H NMR (300 MHz, MeOD): δ 8.29-8.27 (m, 1H), 7.71 (d, J = 7.5 Hz, 1H), 7.22 (dd, J = 7.8, 5.2 Hz, 1H), 7.13-7.12 (m, 1H), 6.88-6.86 (m, 1H), 6.77 (d, J = 3.0 Hz, 1H), 3.62 (s, 2H), 3.48 (q, J = 6.9 Hz, 2H), 3.39-3.32 (m, 2H), 2.79 (t, J = 8.4 Hz, 2H), 2.67-2.48 (m, 6H), 2.32 (d, J = 9.3 Hz, 1H), 1.96-1.73 (m, 2H), 1.65 (t, J = 6.9 Hz, 2H), 1.17 (t, J = 6.9 Hz, 3H). |

TABLE III-continued

| Compound. | Name | MS (ESI+): [M + H]+ | H-NMR |
|---|---|---|---|
| 429 | 5-((3-(ethoxymethyl)-3-(2-(thiophen-2-yl)ethyl)azetidin-1-yl)methyl)-2-methylpyridine | 331 | ¹H NMR (300 MHz, MeOD): δ 8.35-8.27 (m, 1H), 7.71 (d, J = 7.5 Hz, 1H), 7.24-7.20 (m, 1H), 7.13 (d, J = 4.5 Hz, 1H), 6.87 (dd, J = 5.1, 3.3 Hz, 1H), 6.77 (d, J = 3.0 Hz, 1H), 3.62 (s, 2H), 3.48 (q, J = 6.9 Hz, 2H), 3.39-3.32 (m, 2H), 2.79 (q, J = 8.4 Hz, 2H), 2.67-2.48 (m, 4H), 2.32 (d, J = 9.3 Hz, 1H), 1.96-1.73 (m, 2H), 1.65 (t, J = 6.9 Hz, 2H), 1.17 (t, J = 6.9 Hz, 3H). |
| 430 | (S)-4-((3-(ethoxymethyl)-3-(2-(thiophen-2-yl)ethyl)pyrrolidin-1-yl)methyl)-1-methyl-1H-pyrazole HCl | 334 | ¹H NMR (300 MHz, MeOD): δ 7.83 (d, J = 5.1 Hz, 1H), 7.62 (s, 1H), 7.25-7.13 (m, 1H), 7.00-6.78 (m, 2H), 4.41-4.17 (m, 2H), 3.92 (s, 3H), 3.71-3.34 (m, 6H), 3.30-3.12 (m, 2H), 2.95-2.80 (m, 2H), 2.22-1.99 (m, 2H), 1.97-1.81 (m, 2H), 1.20 (q, J = 6.9 Hz, 3H). |
| 431 | 5-(2-(3-(2-cyclopropylethyl)-3-(ethoxymethyl)pyrrolidin-1-yl)propan-2-yl)-2-methylpyridine | 331 | ¹H NMR (300 MHz, MeOD): δ 8.52 (d, J = 1.9 Hz, 1H), 7.84 (dd, J = 8.2, 2.4 Hz, 1H), 7.24 (d, J = 8.1 Hz, 1H), 3.50-3.37 (m, 2H), 3.19 (q, J = 8.8 Hz, 2H), 2.66-2.54 (m, 2H), 2.51 (s, 3H), 2.46 (d, J = 9.1 Hz, 1H), 2.22 (d, J = 9.1 Hz, 1H), 1.61-1.44 (m, 4H), 1.32-1.27 (m, 6H), 1.19-1.06 (m, 5H), 0.69-0.52 (m, 1H), 0.40-0.37 (m, 2H), 0.13-0.08 (m, 2H). |
| 432 | 2-methyl-5-((4-phenethyl-4-(pyridin-2-yl)piperidin-1-yl)methyl)pyridine | 372 | ¹H NMR (300 MHz, MeOD): δ 8.57 (dd, J = 4.8, 1.2 Hz, 1H), 8.32 (d, J = 1.8 Hz, 1H), 7.80-7.79 (m, 1H), 7.69 (dd, J = 8.1, 2.1 Hz, 1H), 7.50 (d, J = 8.1 Hz, 1H), 7.30-7.21 (m, 2H), 7.18-7.15 (m, 2H), 7.09-7.07 (m, 1H), 6.95 (d, J = 6.9 Hz, 2H), 3.46 (s, 2H), 2.78-2.60 (m, 2H), 2.50 (s, 3H), 2.43-2.40 (m, 2H), 2.31-2.12 (m, 4H), 1.99-1.86 (m, 4H). |

TABLE III-continued

| Compound. | Structure | Name | MS (ESI+): [M + H]+ | H-NMR |
|---|---|---|---|---|
| 433 | 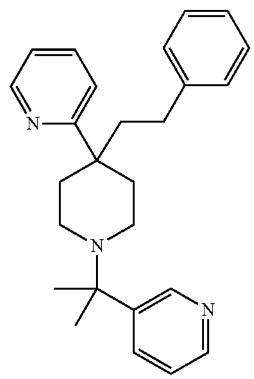 [SMILES: CC(C)(c1cccnc1)N1CCC(CCc2ccccc2)(c2ccccn2)CC1] | 2-(4-phenethyl-1-(2-(pyridin-3-yl)propan-2-yl)piperidin-4-yl)pyridine | 386 | ¹H NMR (300 MHz, MeOD): δ 8.70 (d, J = 2.4 Hz, 1H), 8.56-8.54 (m, 1H), 8.36 (dd, J = 4.8, 1.5 Hz, 1H), 7.99 (d, J = 8.1 Hz, 1H), 7.86-7.79 (m, 1H), 7.48 (d, J = 7.8 Hz, 1H), 7.39-7.36 (m, 1H), 7.25-7.24 (m, 1H), 7.16 (t, J = 7.2 Hz, 2H), 7.09-7.06 (m, 1H), 6.95 (d, J = 6.9 Hz, 2H), 2.71-2.58 (m, 2H), 2.35-2.30 (m, 4H), 2.18-2.13 (m, 2H), 1.98-1.82 (m, 4H), 1.36-1.29 (m, 6H). |
| 434 | 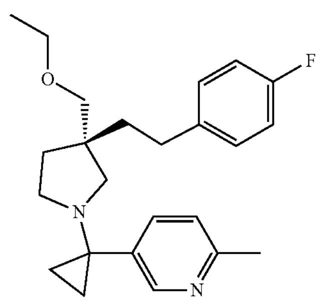 [SMILES: CCOC[C@@]1(CCc2ccc(F)cc2)CCN(C2(c3ccc(C)nc3)CC2)C1] | (S)-5-(1-(3-(ethoxymethyl)-3-(4-fluorophenethyl)pyrrolidin-1-yl)cyclopropyl)-2-methylpyridine | 383 | ¹H NMR (300 MHz, MeOD): δ 8.34 (d, J = 1.8 Hz, 1H), 7.65 (dd, J = 7.8, 2.1 Hz, 1H), 7.28 (d, J = 8.1 Hz, 1H), 7.09-7.06 (m, 2H), 6.96-6.90 (m, 2H), 3.40 (q, J = 7.2 Hz, 2H), 3.24-3.17 (m, 2H), 2.68-2.53 (m, 3H), 2.50-2.48 (m, 3H), 2.45-2.43 (m, 2H), 2.33 (d, J = 9.3 Hz, 1H), 1.59-1.45 (m, 4H), 1.12 (t, J = 6.9 Hz, 3H), 1.01-0.98 (m, 2H), 0.80-0.78 (m, 2H). |
| 435 | 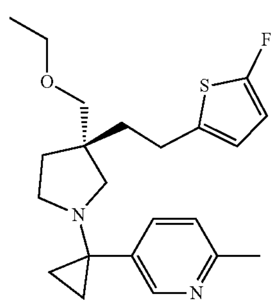 [SMILES: CCOC[C@@]1(CCc2ccc(F)s2)CCN(C2(c3ccc(C)nc3)CC2)C1] | (S)-5-(1-(3-(ethoxymethyl)-3-(2-(5-fluorothiophen-2-yl)ethylpyrrolidin-1-yl)cyclopropyl)-2-methylpyridine | 389 | ¹H NMR (300 MHz, MeOD): δ 8.34 (d, J = 1.8 Hz, 1H), 7.65 (dd, J = 7.8, 2.1 Hz, 1H), 7.28 (d, J = 8.1 Hz, 1H), 6.34-6.33 (m, 1H), 6.26 (dd, J =3.8, 2.1 Hz, 1H), 3.46-3.32 (m, 2H), 3.15 (q, J = 9.3 Hz, 2H), 2.68-2.54 (m, 5H), 2.51 (s, 3H), 2.31 (d, J = 9.3 Hz, 1H), 1.78-1.55 (m, 2H), 1.54-1.40 (m, 2H), 1.11 (t, J = 6.9 Hz, 3H), 1.01-0.98 (m, 2H), 0.80-0.79 (m, 2H). |
| 436 | 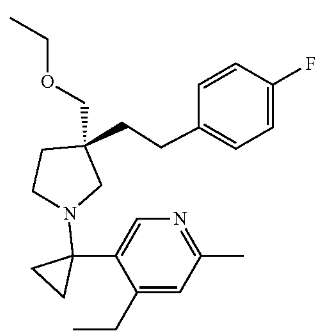 [SMILES: CCOC[C@@]1(CCc2ccc(F)cc2)CCN(C2(c3cnc(C)cc3CC)CC2)C1] | (S)-5-(1-(3-(ethoxymethyl)-3-(4-fluorophenethyl)pyrrolidin-1-yl)cyclopropyl)-4-ethyl-2-methylpyridine | 411 | ¹H NMR (300 MHz, CDCl₃): δ 8.30 (s, 1H), 7.17-6.99 (m, 3H), 6.92 (t, J = 8.7 Hz, 2H), 3.42 (q, J = 7.0 Hz, 2H), 3.15 (q, J = 8.7 Hz, 2H), 2.85 (q, J = 7.5 Hz, 2H), 2.66-2.39 (m, 8H), 2.23 (d, J = 8.7 Hz, 1H), 1.69-1.53 (m, 2H), 1.44 (t, J = 6.9 Hz, 2H), 1.25-1.20 (m, 3H), 1.15 (t, J = 6.9 Hz, 3H), 1.04-1.02 (m, 2H), 0.88-0.71 (m, 2H). |

TABLE III-continued

| Compound. | Structure | Name | MS (ESI+): [M + H]⁺ | H-NMR |
|---|---|---|---|---|
| 437 | 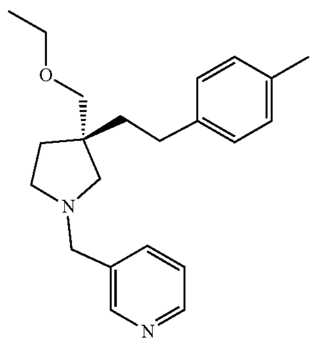 [SMILES: CCOC[C@@]1(CCc2ccc(C)cc2)CCN(Cc2cccnc2)C1] | (S)-3-((3-(ethoxymethyl)-3-(4-methyl-phenethyl)pyrrolidin-1-yl)methyl)pyridine | 339 | ¹H NMR (300 MHz, MeOD): δ 8.50 (d, J = 1.5 Hz, 1H), 8.44 (dd, J = 8.1, 1.5 Hz, 1H), 7.84 (d, J = 7.8 Hz, 1H), 7.41 (dd, J = 7.5, 4.5 Hz, 1H), 7.09-6.98 (m, 4H), 3.65 (s, 2H), 3.48 (q, J = 6.9 Hz, 2H), 3.34-3.30 (m, 2H), 2.72-2.46 (m, 5H), 2.32 (d, J = 9.6 Hz, 1H), 2.27 (s, 3H), 1.81-1.62 (m, 4H), 1.18 (t, J = 6.9 Hz, 3H). |
| 438 | 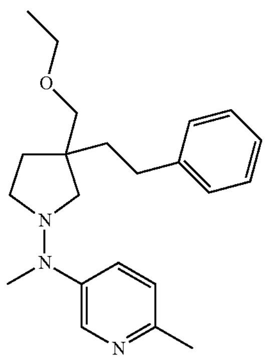 [SMILES: CCOCC1(CCc2ccccc2)CCN(N(C)c2ccc(C)nc2)C1] | N-(3-(ethoxymethyl)-3-phenethylpyrrolidin-1-yl)-N,6-dimethylpyridin-3-amine | 354 | ¹H NMR (300 MHz, MeOD): δ 8.16 (d, J = 2.7 Hz, 1H), 7.31-7.06 (m, 7H), 3.54 (q, J = 7.2 Hz, 2H), 3.42 (q, J = 8.7 Hz, 2H), 2.93-2.87 (m, 2H), 2.91-2.81 (m, 4H), 2.67-2.60 (m, 3H), 2.38 (s, 3H), 1.84-1.69 (m, 4H), 1.22 (t, J = 6.9 Hz, 3H). |
| 439 | 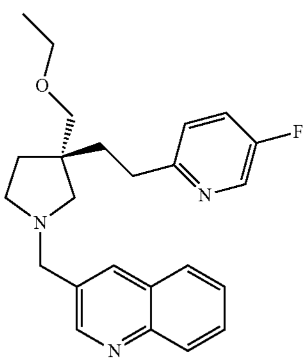 [SMILES: CCOC[C@@]1(CCc2ccc(F)cn2)CCN(Cc2cnc3ccccc3c2)C1] | (S)-3-((3-(ethoxymethyl)-3-(2-(5-fluoropyridin-2-yl)ethyl)pyrrolidin-1-yl)methyl)quinoline | 394 | ¹H NMR (300 MHz, MeOD): δ 8.86 (d, J = 2.1 Hz, 1H), 8.30 (d, J = 3.3 Hz, 2H), 8.02 (d, J = 8.4 Hz, 1H), 7.95 (d, J = 8.4 Hz, 1H), 7.80-7.73 (m, 1H), 7.64-7.62 (m, 1H), 7.52-7.51 (m, 1H), 7.34-7.29 (m, 1H), 3.84 (s, 2H), 3.47 (q, J = 7.0 Hz, 2H), 3.35-3.30 (m, 2H), 2.82-2.60 (m, 5H), 2.40 (d, J = 9.6 Hz, 1H), 1.90-1.79 (m, 2H), 1.71 (t, J = 6.9 Hz, 2H), 1.15 (t, J = 6.9 Hz, 3H). |
| 440 | 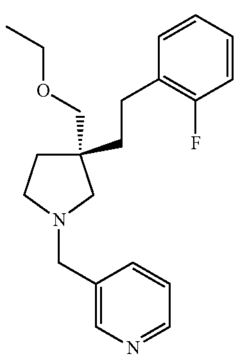 [SMILES: CCOC[C@@]1(CCc2ccccc2F)CCN(Cc2cccnc2)C1] | (S)-3-(3-(ethoxymethyl)-3-(2-fluoro-phenethyl)pyrrolidin-1-yl)methyl)pyridine | 343 | ¹H NMR (300 MHz, MeOD): δ 8.51 (s, 1H), 8.45-8.43 (m, 1H), 7.84 (d, J = 8.1 Hz, 1H), 7.43-7.41 (m, 1H), 7.23-7.14 (m, 2H), 7.08-6.95 (m, 2H), 3.66 (s, 2H), 3.49 (q, J = 6.9 Hz, 2H), 3.35-3.30 (m, 2H), 2.73-2.51 (m, 5H), 2.35 (d, J = 9.6 Hz, 1H), 1.84-1.62 (m, 4H), 1.18 (t, J = 6.9 Hz, 3H). |

TABLE III-continued

| Compound. | Structure | Name | MS (ESI+): [M + H]+ | H-NMR |
|---|---|---|---|---|
| 441 | 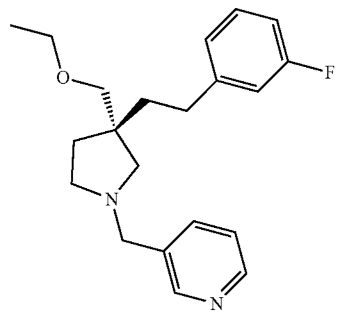 [SMILES: CCOC[C@@]1(CCc2cccc(F)c2)CCN(Cc2cccnc2)C1] | (S)-3-((3-(ethoxymethyl)-3-(3-fluoro-phenethyl)pyrrolidin-1-yl)methyl)pyridine | 343 | $^1$H NMR (300 MHz, MeOD): δ 8.51 (s, 1H), 8.45-8.43 (m, 1H), 7.84 (d, J = 7.7 Hz, 1H), 7.42 (d, J = 7.8, 4.2 Hz, 1H), 7.25-7.21 (m, 1H), 6.98 (d, J = 7.5 Hz, 1H), 6.92-6.86 (m, 2H), 3.66 (s, 2H), 3.49 (q, J = 6.9 Hz, 2H), 3.35-3.30 (m, 2H), 2.73-2.50 (m, 5H), 2.34 (d, J = 9.6 Hz, 1H), 1.79-1.66 (m, 4H), 1.18 (t, J = 6.9 Hz, 3H). |
| 442 | 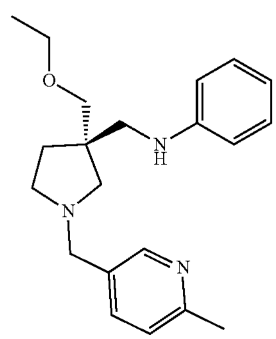 | (R)-N-((3-(ethoxymethyl)-1-((6-methylpyridin-3-yl)methyl)pyrrolidin-3-yl)methyl)aniline HCl | 340 | $^1$H NMR (300 MHz, MeOD): δ 9.08 (s, 1H), 8.76 (d, J = 8.1 Hz, 1H), 8.02 (d, J = 8.1 Hz, 1H), 7.43-7.38 (m, 2H), 7.28-7.18 (m, 3H), 4.72 (s, 2H), 3.80-3.35 (m, 8H), 2.84 (s, 3H), 2.30-2.02 (m, 2H), 1.40-1.15 (m, 5H). |
| 443 | 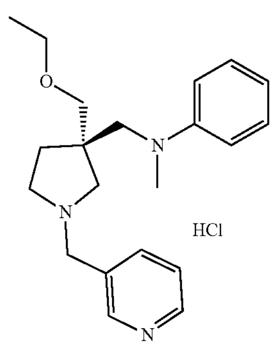 [SMILES: CCOC[C@@]1(CN(C)c2ccccc2)CCN(Cc2cccnc2)C1 ; Cl] | (S)-N-((3-(ethoxymethyl)-1-(pyridin-3-ylmethyl)pyrrolidin-3-yl)methyl)-N-methylaniline HCl | 340 | $^1$H NMR (300 MHz, MeOD): δ 9.12 (s, 1H), 8.94 (d, J = 5.4 Hz, 1H), 8.82-8.73 (m, 1H), 8.10 (t, J = 5.4 Hz, 1H), 7.35-7.25 (m, 2H), 7.18-7.05 (m, 2H), 6.98-6.92 (m, 1H), 4.67 (s, 2H), 3.80-3.42 (m, 10H), 3.13 (s, 3H), 2.30-2.00 (m, 2H), 1.13 (t, J = 7.2 Hz, 3H). |
| 444 | 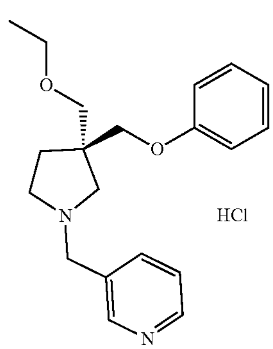 [SMILES: CCOC[C@@]1(COc2ccccc2)CCN(Cc2cccnc2)C1 ; Cl] | (R)-3-((3-(ethoxymethyl)-3-(phenoxy-methyl)pyrrolidin-1-yl)methyl)pyridine HCl | 327 | $^1$H NMR (300 MHz, MeOD): δ 9.24 (s, 1H), 8.97 (d, J = 5.7 Hz, 1H), 8.92 (d, J = 8.1 Hz, 1H), 8.19 (dd, J = 7.8, 6.0 Hz, 1H ), 7.35-7.20 (m, 2H), 7.03-6.96 (m, 3H), 4.76 (s, 2H), 4.05 (s, 2H), 3.85-3.35 (m, 8H), 2.30-2.05 (m, 2H), 1.45-1.15 (m, 3H). |

TABLE III-continued

| Compound. | Structure | Name | MS (ESI+): [M + H]+ | H-NMR |
|---|---|---|---|---|
| 445 | 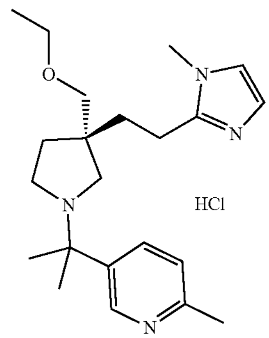 [SMILES: CCOC[C@@]1(CCc2nccn2C)CCN(C(C)(C)c2ccc(C)nc2)C1 ; Cl] | (S)-5-(2-(3-(ethoxymethyl)-3-(2-(1-methyl-1H-imidazol-2-yl)ethyl)pyrrolidin-1-yl)propan-2-yl)-2-methylpyridine HCl | 371 | $^1$H NMR (300 MHz, MeOD): δ 9.19 (d, J = 1.8 Hz, 1H), 9.01 (d, J = 7.5 Hz, 1H), 8.03 (d, J = 8.7 Hz, 1H), 7.44 (d, J = 6.9 Hz, 2H), 3.86 (s, 3H), 3.61-3.42 (m, 8H), 3.04-3.00 (m, 2H), 2.84 (s, 3H), 2.14-2.04 (m, 4H), 2.00 (s, 6H), 1.29-1.24 (m, 3H). |
| 446 | 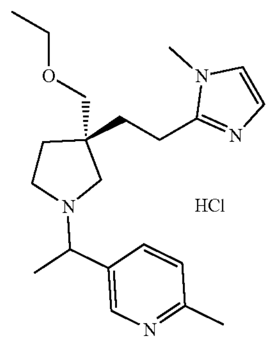 [SMILES: CCOC[C@@]1(CCc2nccn2C)CCN(C(C)c2ccc(C)nc2)C1 ; Cl] | 5-(1-((S)-3-(ethoxymethyl)-3-(2-(1-methyl-1H-imidazol-2-yl)ethyl)pyrrolidin-1-yl)ethyl)-2-methylpyridine HCl | 357 | $^1$H NMR (300 MHz, MeOD): δ 9.18-9.13 (m, 1H), 8.93 (d, J = 7.8 Hz, 1H), 8.03 (d, J = 8.4 Hz, 1H), 7.47-7.42 (m, 2H), 3.96-3.85 (m, 4H), 3.51-3.30 (m, 6H), 3.20-3.10 (m, 2H), 3.06-2.85 (m, 2H), 2.84 (s, 3H), 2.25-2.06 (m, 4H), 1.97 (s, 3H), 1.27-1.24 (m, 3H). |
| 447 | 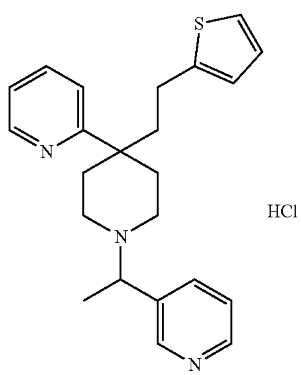 [SMILES: CC(c1cccnc1)N1CCC(CCc2cccs2)(c2ccccn2)CC1 ; Cl] | 2-(1-(1-(pyridin-3-yl)ethyl)-4-(2-(thiophen-2-yl)ethyl)piperidin-4-yl)pyridine HCl | 378 | $^1$H NMR (300 MHz, MeOD): δ 9.22 (s, 1H), 8.97 (d, J = 5.4 Hz, 2H), 8.75 (d, J = 4.8 Hz, 1H), 8.46-8.41 (m, 1H), 8.19 (t, J = 4.8 Hz, 1H), 8.03 (d, J = 8.1 Hz, 1H), 7.91-7.82 (m, 1H), 7.10 (dd, J = 5.1, 1.2 Hz, 1H), 6.79 (dd, J = 8.1, 3.3 Hz, 1H), 6.68 (s, 1H), 2.65-2.10 (m, 8H), 1.86 (s, 3H), 1.40-1.25 (m, 5H). |
| 448 | 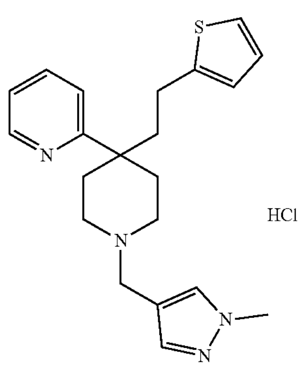 [SMILES: Cn1cc(CN2CCC(CCc3cccs3)(c3ccccn3)CC2)cn1 ; Cl] | 2-(1-((1-methyl-1H-pyrazol-4-yl)methyl)-4-(2-(thiophen-2-yl)ethylpiperidin-4-yl)pyridine HCl | 367 | $^1$H NMR (300 MHz, MeOD): δ 8.82-8.73 (m, 1H ), 8.56-8.54 (m, 1H), 8.10 (dd, J = 8.1, 2.4 Hz, 1H), 7.96-7.88 (m, 1H), 7.82 (s, 1H), 7.69-7.60 (m, 1H), 7.12-7.09 (m, 1H), 6.81-6.78 (m, 1H), 6.71-6.66 (m, 1H), 4.35 (s, 1H), 4.16 (s, 1H), 3.92 (d, J = 4.6 Hz, 3H), 3.62-3.50 (m, 2H), 3.35-3.30 (m, 1H), 2.96-2.80 (m, 2H), 2.70-2.50 (m, 4H), 2.35-2.19 (m, 3H). |

TABLE III-continued

| Compound. | Structure | Name | MS (ESI+): [M + H]+ | H-NMR |
|---|---|---|---|---|
| 449 | 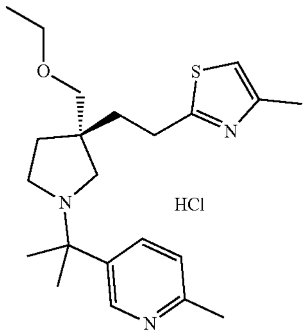 [SMILES: CCOC[C@@]1(CCc2nc(C)cs2)CCN(C(C)(C)c2ccc(C)nc2)C1 ; Cl] | (S)-2-(2-(3-(ethoxymethyl)-1-(2-(6-methylpyridin-3-yl)propan-2-yl)pyrrolidin-3-yl)ethyl)-4-methylthiazole HCl | 388 | ¹H NMR (300 MHz, MeOD): δ 9.11 (s, 1H), 9.01-8.95 (m, 1H), 7.97 (d, J = 8.7 Hz, 1H), 7.53 (s, 1H), 3.51-3.15 (m, 10H), 2.77 (s, 3H), 2.48-2.43 (m, 3H), 2.11-1.89 (m, 10H), 1.11 (t, J = 6.9 Hz, 3H). |
| 450 | 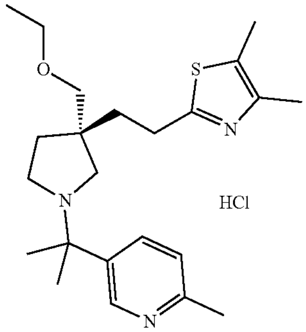 [SMILES: CCOC[C@@]1(CCc2nc(C)c(C)s2)CCN(C(C)(C)c2ccc(C)nc2)C1 ; Cl] | (S)-2-(2-(3-(ethoxymethyl)-1-(2-(6-methylpyridin-3-yl)propan-2-yl)pyrrolidin-3-yl)ethyl)-4,5-dimethylthiazole HCl | 402 | ¹H NMR (300 MHz, MeOD): δ 9.22 (d, J = 2.1 Hz, 1H), 9.04 (dd, J = 8.7, 2.1 Hz, 1H), 8.07 (d, J = 8.4 Hz, 1H), 3.59-3.40 (m, 8H), 3.29-3.22 (m, 2H), 2.86 (s, 3H), 2.46 (s, 3H), 2.44 (s, 3H), 2.18-2.09 (m, 4H), 2.01 (s, 6H), 1.22 (t, J = 6.6 Hz, 3H). |
| 451 | 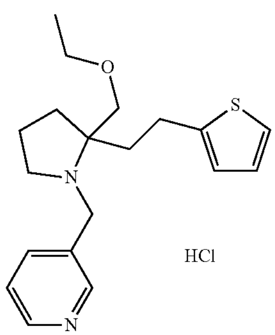 [SMILES: CCOCC1(CCc2cccs2)CCCN1Cc1cccnc1 ; Cl] | 3-((2-(ethoxymethyl)-2-(2-(thiophen-2-yl)ethyl)pyrrolidin-1-yl)methyl)pyridine HCl | 331 | ¹H NMR (300 MHz, MeOD): δ 9.28-9.16 (m, 1H), 9.00-8.86 (m, 2H), 8.25-8.17 (m, 1H), 7.25 (s, 1H), 7.04-6.93 (m, 2H), 5.10-5.00 (m, 1H), 4.64-4.53 (m, 1H), 4.07-3.96 (m, 1H), 3.89-3.39 (m, 5H), 3.08-2.95 (m, 2H), 2.81-2.46 (m, 1H), 2.37-1.99 (m, 5H), 1.39-1.29 (m, 3H). |
| 452 | 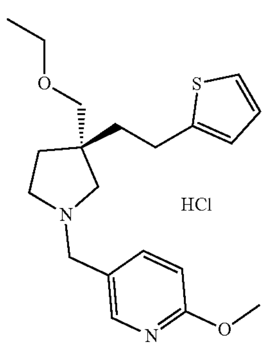 [SMILES: CCOC[C@@]1(CCc2cccs2)CCN(Cc2ccc(OC)nc2)C1 ; Cl] | (S)-5-((3-(ethoxymethyl)-3-(2-(thiophen-2-yl)ethyl)pyrrolidin-1-yl)methyl)-2-methoxypyridine HCl | 361 | ¹H NMR (300 MHz, MeOD): δ 8.45 (s, 1H), 8.32-8.26 (m, 1H), 7.28 (dd, J = 9.0, 3.6 Hz, 1H), 7.07 (dd, J = 9.9, 5.1 Hz, 1H), 6.82-6.73 (m, 2H), 4.45-4.32 (m, 2H), 4.05 (s, 3H), 3.51-3.26 (m, 7H), 3.18-2.94 (m, 1H), 2.81-2.72 (m, 2H), 2.12-1.83 (m, 4H), 1.18-1.06 (m, 3H). |

TABLE III-continued

| Compound. | Structure | Name | MS (ESI+): [M + H]+ | H-NMR |
|---|---|---|---|---|
| 453 | 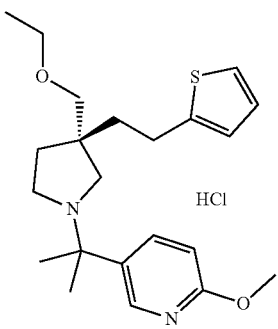 [SMILES: CCOC[C@@]1(CCc2cccs2)CCN(C(C)(C)c2ccc(OC)nc2)C1 ; Cl] HCl | (S)-5-(2-(3-(ethoxymethyl)-3-(2-(thiophen-2-yl)ethyl)pyrrolidin-1-yl)propan-2-yl)-2-methoxypyridine HCl | 389 | ¹H NMR (300 MHz, MeOD): δ 8.67-8.62 (m, 1H), 8.58-8.52 (m, 1H), 7.37-7.30 (m, 1H), 7.20-7.15 (m, 1H), 6.91-6.80 (m, 2 H), 4.17-4.11 (m, 3H), 3.56-3.34 (m, 7H), 3.11-2.96 (m, 1H), 2.86-2.77 (m, 2H), 2.11-1.97 (m, 3H), 1.92 (s, 6H), 1.87-1.70 (m, 1H), 1.23-1.13 (m, 3H). |
| 454 | 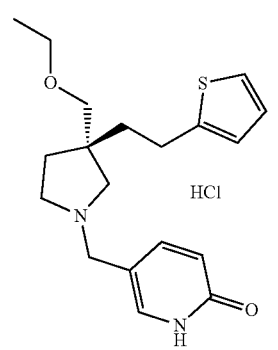 [SMILES: CCOC[C@@]1(CCc2cccs2)CCN(Cc2ccc(=O)[nH]c2)C1 ; Cl] HCl | (S)-5-((3-(ethoxymethyl)-3-(2-(thiophen-2-yl)ethyl)pyrrolidin-1-yl)methyl)pyridin-2(1H)-one HCl | 347 | ¹H NMR (300 MHz, MeOD): δ 8.20-8.11 (m, 2H), 7.10-7.04 (m, 1H), 6.94 (dd, J = 9.0, 1.5 Hz, 1H), 6.82-6.74 (m, 2H), 4.37-4.25 (m, 2H), 3.56-3.26 (m, 7H), 3.15-2.93 (m, 1H), 2.81-2.70 (m, 2H), 2.10-1.82 (m, 4H), 1.17-1.06 (m, 3H). |
| 455 | 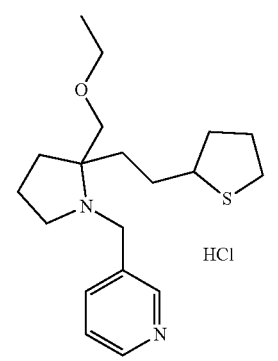 [SMILES: CCOCC1(CCC2CCCS2)CCCN1Cc1cccnc1 ; Cl] HCl | 3-((2-(ethoxymethyl)-2-(2-(tetrahydrothiophen-2-yl)ethyl)pyrrolidin-1-yl)methyl)pyridine HCl | 335 | ¹H NMR (300 MHz, MeOD): δ 9.30-9.14 (m, 1H), 9.01-8.84 (m, 2H), 8.23 (t, J = 6.3 Hz, 1H), 5.08-4.98 (m, 1H), 4.61-4.50 (m, 1H), 3.99-3.84 (m, 1H), 3.80-3.55 (m, 4H), 3.50-3.37 (m, 2H), 2.95-2.79 (m, 2H), 2.40-1.52 (m, 12H), 1.38-1.19 (m, 3H). |
| 456 | 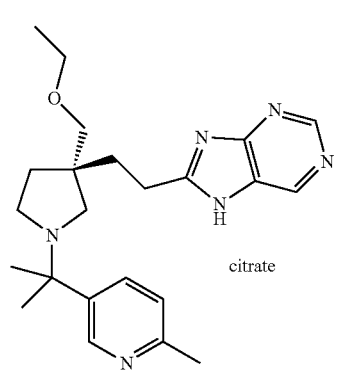 [SMILES: CCOC[C@@]1(CCc2nc3ncncc3[nH]2)CCN(C(C)(C)c2ccc(C)nc2)C1] citrate | (S)-8-(2-(3-(ethoxymethyl)-1-(2-(6-methylpyridin-3-yl)propan-2-yl)pyrrolidin-3-yl)ethyl)-7H-purine citrate | 409 | ¹H NMR (300 MHz, MeOD): δ 8.94 (s, 1H), 8.85 (s, 1H), 8.77 (s, 1H), 8.17 (d, J = 6.9 Hz, 1H), 7.44 (d, J = 8.1 Hz, 1H), 3.47-3.35 (m, 6H), 3.27-3.15 (m, 2H), 3.01-2.94 (m, 2H), 2.93-2.75 (m, 6H), 2.56 (s, 3H), 2.14-1.98 (m, 4H), 1.90 (s, 6H), 1.09 (t, J = 6.9 Hz, 3H). |

TABLE III-continued

| Compound. | Structure | Name | MS (ESI+): [M + H]+ | H-NMR |
|---|---|---|---|---|
| 457 | 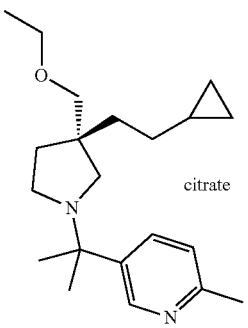 citrate | (S)-5-(2-(3-(2-cyclopropylethyl)-3-(ethoxymethyl)pyrrolidin-1-yl)propan-2-yl)-2-methylpyridine citrate | 331 | $^1$H NMR (300 MHz, MeOD): δ 8.76 (s, 1H), 8.13 (d, J = 8.1 Hz, 1H), 7.47 (d, J = 8.4 Hz, 1H), 3.43-3.35 (m, 4H), 3.26-3.21 (m, 3H), 3.05-2.98 (m, 1H), 2.93-2.75 (m, 6H), 2.59 (s, 3H), 2.03-1.94 (m, 1H), 1.90 (s, 6H), 1.86-1.77 (m, 1H), 1.66-1.50 (m, 2H), 1.14-1.04 (m, 5H), 0.65-0.54 (m, 1H), 0.44-0.36 (m, 2H), 0.03-0.00 (m, 2H). |
| 458 | 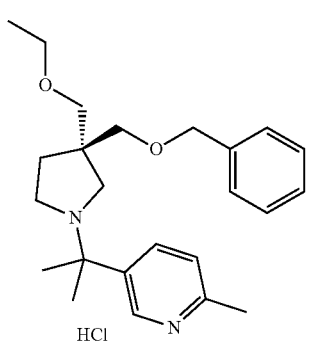 [SMILES: CCOC[C@@]1(COCc2ccccc2)CCN(C(C)(C)c2ccc(C)nc2)C1 ; Cl] HCl | (R)-5-(2-(3-((benzyloxy)methyl)-3-(ethoxymethyl)pyrrolidin-1-yl)propan-2-yl)-2-methylpyridine HCl | 383 | $^1$H NMR (300 MHz, MeOD): δ 9.15 (d, J = 11.1 Hz, 1H), 8.97 (t, J = 9.0 Hz, 1H), 8.07-7.96 (m, 1H), 7.37-7.25 (m, 5H), 4.54-4.43 (m, 2H), 3.55-3.36 (m, 8H), 3.32-3.24 (m, 2H), 2.86-2.78 (m, 3H), 2.07-1.89 (m, 8H), 1.18-1.09 (m, 3H). |
| 459 | 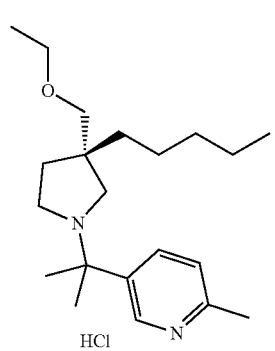 [SMILES: CCCCC[C@]1(COCC)CCN(C(C)(C)c2ccc(C)nc2)C1 ; Cl] HCl | (S)-5-(2-(3-(ethoxymethyl)-3-pentylpyrrolidin-1-yl)propan-2-yl)-2-methylpyridine HCl | 333 | $^1$H NMR (300 MHz, MeOD): δ 9.21-9.15 (m, 1H), 9.03-8.96 (m, 1H), 8.06 (d, J = 8.4 Hz, 1H), 3.53-3.42 (m, 3H), 3.39-3.30 (m, 4H), 3.08-2.95 (m, 1H), 2.85 (s, 3H), 2.08-1.91 (m, 8H), 1.60-1.51 (m, 2H), 1.37-1.18 (m, 9H), 0.93-0.86 (m, 3H). |
| 460 | 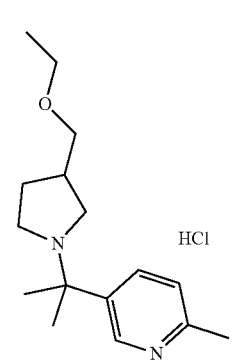 [SMILES: CCOCC1CCN(C(C)(C)c2ccc(C)nc2)C1 ; Cl] HCl | 5-(2-(3-(ethoxymethyl)pyrrolidin-1-yl)propan-2-yl)-2-methylpyridine HCl | 263 | $^1$H NMR (300 MHz, MeOD): δ 9.16 (d, J = 2.1 Hz, 1H), 9.00 (dd, J = 8.7, 2.1 Hz, 1H), 8.06 (d, J = 8.7 Hz, 1H), 3.51-3.29 (m, 7H), 3.16-3.04 (m, 1H), 2.86 (s, 3H), 2.73-2.62 (m, 1H), 2.24-2.13 (m, 1H), 1.97 (s, 6H), 1.91-1.82 (m, 1H), 1.19-1.10 (m, 3H). |

TABLE III-continued

| Compound. | Structure | Name | MS (ESI+): [M + H]+ | H-NMR |
|---|---|---|---|---|
| 461 | 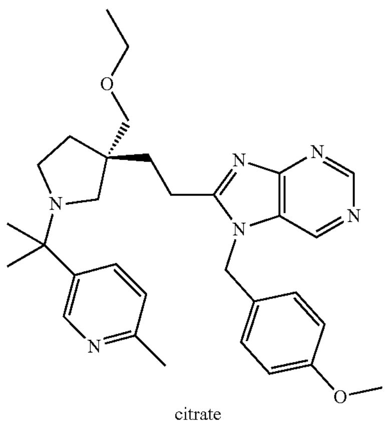 [SMILES: CCOC[C@@]1(CCc2nc3ncncc3n2Cc2ccc(OC)cc2)CCN(C(C)(C)c2ccc(C)nc2)C1] | (S)-8-(2-(3-(ethoxymethyl)-1-(2-(6-methylpyridin-3-yl)propan-2-yl)pyrrolidin-3-yl)ethyl)-7-(4-methoxybenzyl)-7H-purine citrate | 529 | $^1$H NMR (300 MHz, MeOD): δ 8.99 (s, 1H), 8.92 (s, 1H), 8.74 (s, 1H), 8.11 (d, J = 8.1 Hz, 1H), 7.44 (d, J = 7.5 Hz, 1H), 7.16 (d, J = 8.7 Hz, 2H), 6.88 (d, J = 8.4 Hz, 2H), 5.50 (s, 2H), 3.75 (s, 3H), 3.40-3.35 (m, 2H), 3.26-3.17 (m, 3H), 3.10-3.00 (m, 1H), 2.92-2.74 (m, 10H), 2.56 (s, 3H), 2.05-1.91 (m, 4H), 1.87 (s, 6H), 1.06 (t, J = 6.9 Hz, 3H). |
| 462 | 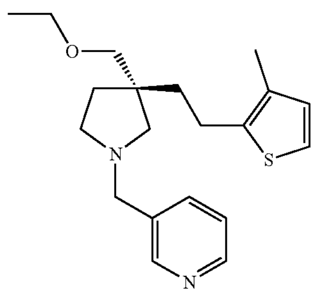 [SMILES: CCOC[C@@]1(CCc2sccc2C)CCN(Cc2cccnc2)C1] | (S)-3-((3-(ethoxymethyl)-3-(2-(3-methylthiophen-2-yl)ethyl)pyrrolidin-1-yl)methyl)pyridine | 345 | $^1$H NMR (300 MHz, MeOD): δ 8.51 (s, 1H), 8.43 (d, J =4.2 Hz, 1H), 7.84 (d, J = 7.8 Hz, 1H), 7.41 (dd, J = 7.8, 5.1 Hz, 1H), 7.00 (d, J = 5.1 Hz, 1H), 6.73 (d, J = 5.1 Hz, 1H), 3.65 (s, 2H), 3.50 (q, J = 6.9 Hz, 2H), 3.46-3.35 (m, 2H), 2.71-2.60 (m, 4H), 2.57-2.53 (m, 1H), 2.35-2.30 (m, 1H), 2.16 (s, 3H), 1.83-1.72 (m, 2H), 1.71-1.67 (m, 2H), 1.18 (t, J = 6.9 Hz, 3H) |
| 463 | 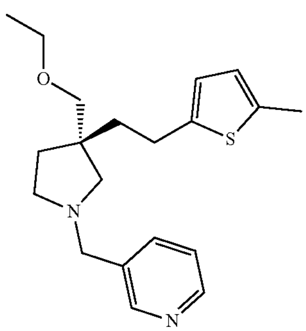 [SMILES: CCOC[C@@]1(CCc2ccc(C)s2)CCN(Cc2cccnc2)C1] | (S)-3-((3-(ethoxymethyl)-3-(2-(5-methylthiophen-2-yl)ethyl)pyrrolidin-1-yl)methyl)pyridine | 345 | $^1$H NMR (300 MHz, CDCl$_3$): δ 8.54 (s, 1H), 8.49-8.47 (m, 1H), 7.67 (d, J = 7.8 Hz, 1H), 7.26-7.22 (m, 1H), 6.54-6.53 (m, 2H), 3.58 (s, 2H), 3.46 (q, J = 6.9 Hz, 2H), 3.31-3.23 (m, 2H), 2.74-2.71 (m, 2H), 2.67-2.53 (m, 3H), 2.49 (s, 3H), 2.30-2.25 (m, 1H), 1.89-1.86 (m, 2H), 1.68-1.64 (m, 2H), 1.18 (t, J = 6.9 Hz, 3H). |
| 464 | 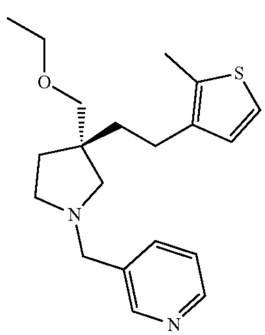 [SMILES: CCOC[C@@]1(CCc2ccsc2C)CCN(Cc2cccnc2)C1] | (S)-3-((3-(ethoxymethyl)-3-(2-(2-methylthiophen-3-yl)ethyl)pyrrolidin-1-yl)methyl)pyridine | 345 | $^1$H NMR (300 MHz, MeOD): δ 8.52 (d, J = 1.5 Hz, 1H), 8.45 (dd, J = 4.8, 1.2 Hz, 1H), 7.85 (d, J = 7.9 Hz, 1H), 7.42 (dd, J = 7.5, 4.8 Hz, 1H), 7.00 (d, J = 5.2 Hz, 1H), 6.77 (d, J = 5.2 Hz, 1H), 3.69 (s, 2H), 3.49 (q, J = 7.0 Hz, 2H), 3.36-3.30 (m, 2H), 2.74-2.61 (m, 2H), 2.58 (d, J = 9.6 Hz, 1H), 2.54-2.40 (m, 2H), 2.36 (d, J = 9.6 Hz, 1H), 2.32 (s, 3H), 1.71-1.56 (m, 4H), 1.18 (t, J = 6.9 Hz, 3H). |

TABLE III-continued

| Compound. | Structure | Name | MS (ESI+): [M + H]+ | H-NMR |
|---|---|---|---|---|
| 465 | 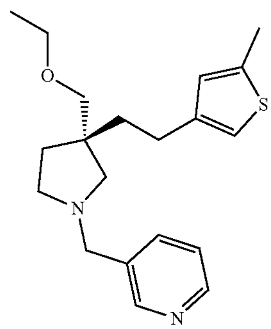 [SMILES: CCOC[C@@]1(CCc2csc(C)c2)CCN(Cc2cccnc2)C1] | (S)-3-((3-(ethoxymethyl)-3-(2-(5-methylthiophen-3-yl)ethyl)pyrrolidin-1-yl)methyl)pyridine | 345 | ¹H NMR (300 MHz, MeOD): δ 8.38 (s, 1H), 8.32 (d, J = 4.2 Hz, 1H), 7.71 (d, J = 7.8 Hz, 1H), 7.31-7.27 (m, 1H), 6.56 (s, 1H), 6.46 (s, 1H), 3.56 (s, 2H), 3.34 (q, J = 6.9 Hz, 2H), 3.22-3.18 (m, 2H), 2.60-2.34 (m, 5H), 2.28 (s, 3H), 2.23 (d, J =9.9 Hz, 1H), 1.71-1.52 (m, 4H), 1.04 (t, J = 7.0 Hz, 3H). |
| 466 | 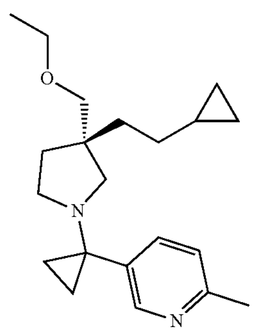 [SMILES: CCOC[C@@]1(CCC2CC2)CCN(C2(c3ccc(C)nc3)CC2)C1] | (S)-5-(1-(3-(2-cyclopropylethyl)-3-(ethoxy-methyl)pyrrolidin-1-yl)cyclopropyl)-2-methylpyridine | 329 | ¹H NMR (300 MHz, MeOD): δ 8.66 (s, 1H), 8.01 (d, J = 7.8 Hz, 1H), 7.47 (d, J = 8.1 Hz, 1H), 3.41-3.37 (m, 2H), 3.32-3.25 (m, 3H), 3.20-3.15 (m, 3H), 2.95-2.79 (m, 4H), 2.62 (s, 3H), 1.90-1.75 (m, 2H), 1.70-1.50 (m, 4H), 1.25-1.20 (m, 2H), 1.19-1.02 (m, 2H), 0.97 (t, J = 6.9 Hz, 3H), 0.69-0.58 (m, 1H), 0.47-0.40 (m, 2H), 0.08-0.00 (m, 2H). |
| 467 | 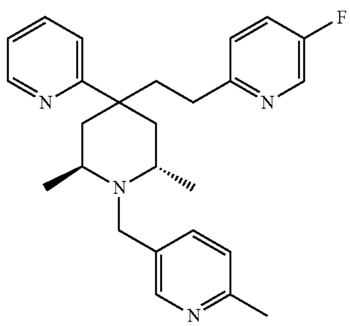 [SMILES: Cc1ccc(CN2[C@@H](C)CC(CCc3ccc(F)cn3)(c3ccccn3)C[C@@H]2C)cn1] | 2-(2-((2S,6S)-2,6-dimethyl-1-((6-methylpyridin-3-yl)methyl)-4-(pyridin-2-yl)piperidin-4-yl)ethyl)-5-fluoropyridine | | 1H NMR (300 MHz, MeOD): δ 8.58 (d, J = 3.6 Hz, 1H), 8.52 (s, 1H), 8.26 (d, J = 2.7 Hz, 1H), 7.95 (d, J = 7.8 Hz, 1H), 7.81 (t, J = 6.0 Hz, 1H), 7.60 (d, J = 8.4 Hz, 1H), 7.52-7.35 (m, 2H), 7.32-7.29 (m, 1H), 7.19-7.10 (m, 1H), 4.65-4.61 (m, 1H), 4.18-4.15 (m, 1H), 3.99-3.83 (m, 1H), 3.45-3.32 (m, 2H), 3.12-3.05 (m, 1H), 2.89-2.72 (m, 4H), 2.70-2.59 (m, 1H), 2.59 (s, 3H), 2.35-1.89 (m, 5H), 1.61 (d, J = 6.3 Hz, 3H), 0.60(d, J = 6.9 Hz, 3H). |
| 468 | 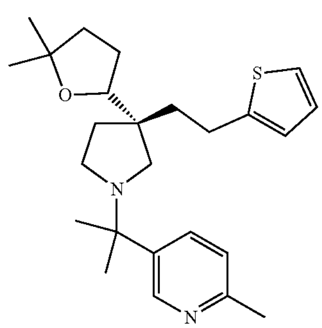 [SMILES: Cc1ccc(C(C)(C)N2CC[C@](CCc3cccs3)(C3CCC(C)(C)O3)C2)cn1] | 5-(2-((S)-3-((S)-5,5-dimethyltetrahydro-furan-2-yl)-3-(2-(thiophen-2-yl)ethyl)pyrrolidin-1-yl)propan-2-yl)-2-methylpyridine | 413 | 1H NMR (300 MHz, MeOD): δ 8.74-8.72 (m, 1H), 8.08 (t, J = 6.0 Hz, 1H), 7.46 (d, J = 8.4 Hz, 1H), 7.18 (d, J = 5.4 Hz, 1H), 6.90-6.89 (m, 1H), 6.82-6.78 (m, 1H), 4.10-4.01 (m, 1H), 3.21-3.15 (m, 2H), 2.81-2.75 (m, 8H), 2.57 (s, 3H), 2.25-2.02 (m, 2H), 1.99-1.72 (m, 12H), 1.29-0.99 (m, 6H) |

TABLE III-continued

| Compound. | Structure | Name | MS (ESI+): [M + H]+ | H-NMR |
|---|---|---|---|---|
| 469 | 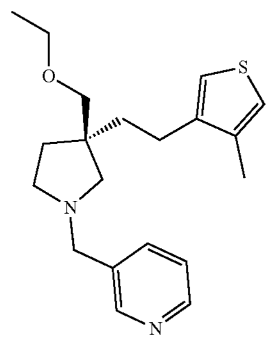 [SMILES: CCOC[C@]1(CCc2cscc2C)CCN(Cc2cccnc2)C1] | (R)-3-((3-(ethoxymethyl)-3-(2-(4-methylthiophen-3-yl)ethyl)pyrrolidin-1-yl)methyl)pyridine | | |
| 470 | 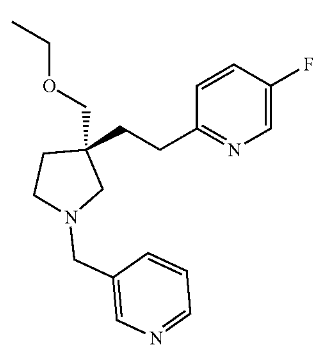 [SMILES: CCOC[C@@]1(CCc2ccc(F)cn2)CCN(Cc2cccnc2)C1] | (S)-2-(2-(3-(ethoxymethyl)-1-(pyridin-3-ylmethyl)pyrrolidin-3-yl)ethyl)-5-fluoropyridine | | |
| 471 | 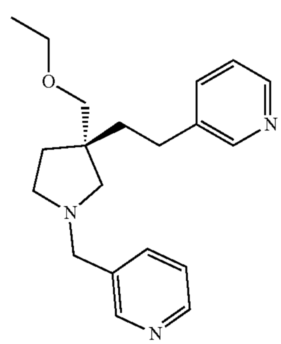 [SMILES: CCOC[C@@]1(CCc2cccnc2)CCN(Cc2cccnc2)C1] | (S)-3-(2-(3-(ethoxymethyl)-1-(pyridin-3-ylmethyl)pyrrolidin-3-yl)ethyl)pyridine | | |
| 472 | 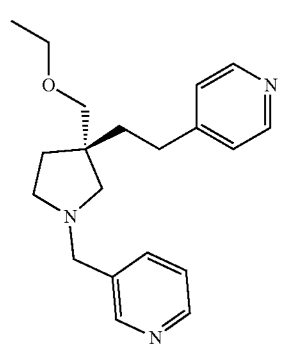 [SMILES: CCOC[C@@]1(CCc2ccncc2)CCN(Cc2cccnc2)C1] | (S)-3-((3-(ethoxymethyl)-3-(2-(pyridin-4-yl)ethyl)pyrrolidin-1-yl)methyl)pyridine | | |

TABLE III-continued

| Compound. | Structure | Name | MS (ESI+): [M + H]+ | H-NMR |
|---|---|---|---|---|
| 473 | 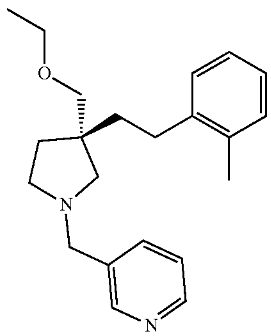 [SMILES: CCOC[C@@]1(CCc2ccccc2C)CCN(Cc2cccnc2)C1] | (S)-3-((3-(ethoxymethyl)-3-(2-methyl-phenethyl)pyrrolidin-1-yl)methyl)pyridine | | |
| 474 | 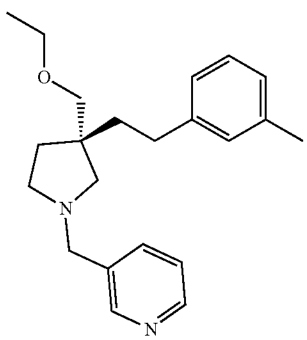 [SMILES: CCOC[C@@]1(CCc2cccc(C)c2)CCN(Cc2cccnc2)C1] | (S)-3-((3-(ethoxymethyl)-3-(3-methyl-phenethyl)pyrrolidin-1-yl)methyl)pyridine | | |
| 475 | 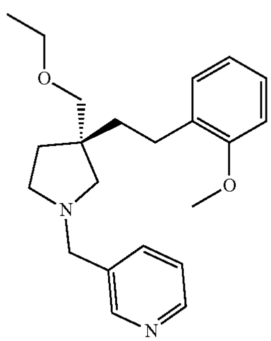 [SMILES: CCOC[C@@]1(CCc2ccccc2OC)CCN(Cc2cccnc2)C1] | (S)-3-((3-(ethoxymethyl)-3-(2-methoxypheneth-yl)pyrrolidin-1-yl)methyl)pyridine | | |
| 476 | 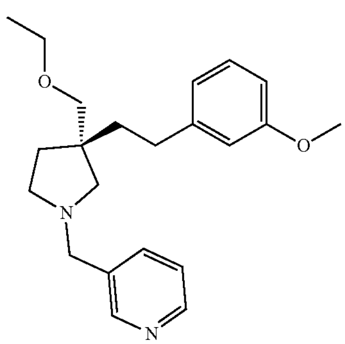 [SMILES: CCOC[C@@]1(CCc2cccc(OC)c2)CCN(Cc2cccnc2)C1] | (S)-3-((3-(ethoxymethyl)-3-(3-methoxy-phenethyl)pyrrolidin-1-yl)methyl)pyridine | | |

TABLE III-continued

| Compound. | Structure | Name | MS (ESI+): [M + H]+ | H-NMR |
|---|---|---|---|---|
| 477 | 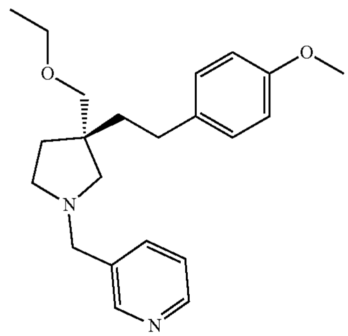 [SMILES: CCOC[C@@]1(CCc2ccc(OC)cc2)CCN(Cc2cccnc2)C1] | (S)-3-((3-(ethoxymethyl)-3-(4-methoxyphenethyl)pyrrolidin-1-yl)methyl)pyridine | | |
| 478 | 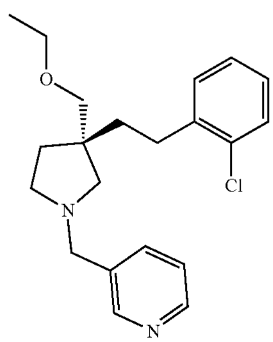 [SMILES: CCOC[C@@]1(CCc2ccccc2Cl)CCN(Cc2cccnc2)C1] | (S)-3-((3-(2-chlorophenethyl)-3-(ethoxymethyl)pyrrolidin-1-yl)methyl)pyridine | | |
| 479 | 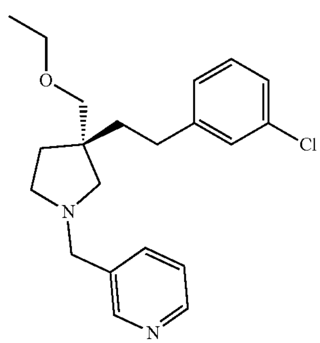 [SMILES: CCOC[C@@]1(CCc2cccc(Cl)c2)CCN(Cc2cccnc2)C1] | (S)-3-((3-(3-chlorophenethyl)-3-(ethoxymethyl)pyrrolidin-1-yl)methyl)pyridine | | |
| 480 | 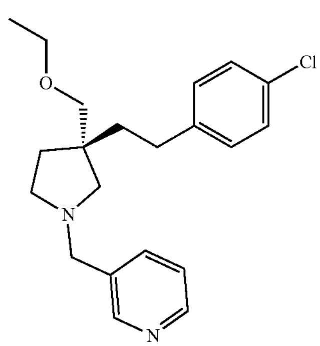 [SMILES: CCOC[C@@]1(CCc2ccc(Cl)cc2)CCN(Cc2cccnc2)C1] | (S)-3-((3-(4-chlorophenethyl)-3-(ethoxymethyl)pyrrolidin-1-yl)methyl)pyridine | | |

TABLE III-continued

| Compound. | Structure | Name | MS (ESI+): [M + H]+ | H-NMR |
|---|---|---|---|---|
| 481 | 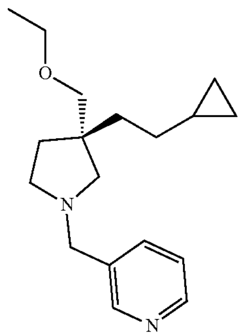 [SMILES: CCOC[C@@]1(CCC2CC2)CCN(Cc2cccnc2)C1] | (S)-3-((3-(2-cyclopropylethyl)-3-(ethoxymethyl)pyrrolidin-1-yl)methyl)pyridine | | |
| 482 | 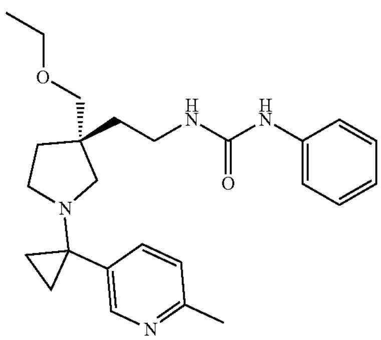 [SMILES: CCOC[C@@]1(CCNC(=O)Nc2ccccc2)CCN(C2(c3ccc(C)nc3)CC2)C1] | (S)-1-(2-(3-(ethoxymethyl)-1-(1-(6-methylpyridin-3-yl)cyclopropyl)pyrrolidin-3-yl)ethyl)-3-phenylurea | | |
| 483 | 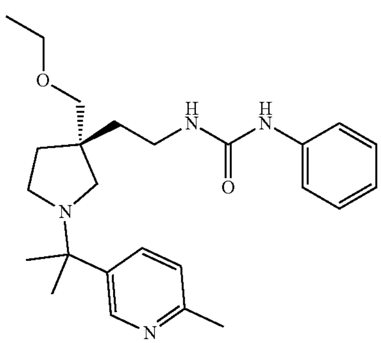 [SMILES: CCOC[C@@]1(CCNC(=O)Nc2ccccc2)CCN(C(C)(C)c2ccc(C)nc2)C1] | (S)-1-(2-(3-(ethoxymethyl)-1-(2-(6-methylpyridin-3-yl)propan-2-yl)pyrrolidin-3-yl)ethyl)-3-phenylurea | | |
| 484 | 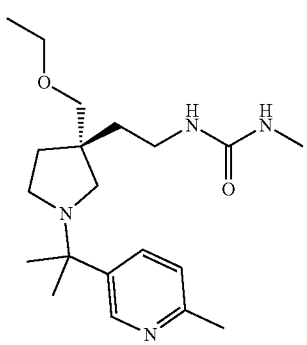 [SMILES: CCOC[C@@]1(CCNC(=O)NC)CCN(C(C)(C)c2ccc(C)nc2)C1] | (S)-1-(2-(3-(ethoxymethyl)-1-(2-(6-methylpyridin-3-yl)propan-2-yl)pyrrolidin-3-yl)ethyl)-3-methylurea | | |

TABLE III-continued

| Compound. | Structure | Name | MS (ESI+): [M + H]+ | H-NMR |
|---|---|---|---|---|
| 485 | 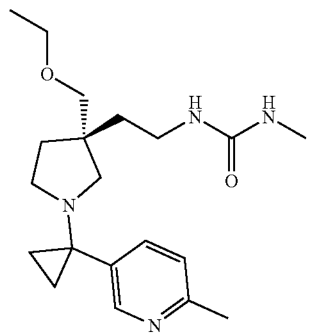 [SMILES: CCOC[C@@]1(CCNC(=O)NC)CCN(C2(c3ccc(C)nc3)CC2)C1] | (S)-1-(2-(3-(ethoxymethyl)-1-(1-(6-methylpyridin-3-yl)cyclopropyl)pyrrolidin-3-yl)ethyl)-3-methylurea | | |
| 486 | 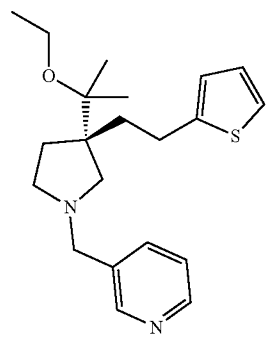 [SMILES: CCOC(C)(C)[C@@]1(CCc2cccs2)CCN(Cc2cccnc2)C1] | (S)-3-((3-(2-ethoxypropan-2-yl)-3-(2-(thiophen-2-yl)ethyl)pyrrolidin-1-yl)methyl)pyridine | | |
| 487 | 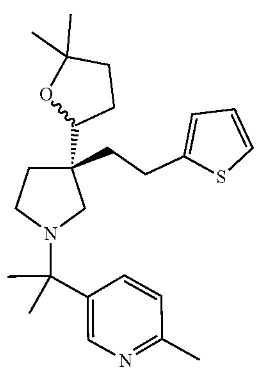 [SMILES: Cc1ccc(C(C)(C)N2CC[C@](CCc3cccs3)(C3CCC(C)(C)O3)C2)cn1] | (S)-5-(2-(3-(5,5-dimethyltetrahydrofuran-2-yl)-3-(2-(thiophen-2-yl)ethyl)pyrrolidin-1-yl)propan-2-yl)-2-methylpyridine | | |
| 488 | 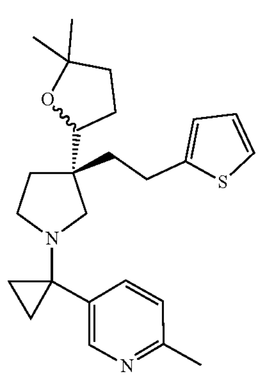 [SMILES: Cc1ccc(C2(N3CC[C@](CCc4cccs4)(C4CCC(C)(C)O4)C3)CC2)cn1] | (S)-5-(1-(3-(5,5-dimethyltetrahydrofuran-2-yl)-3-(2-(thiophen-2-yl)ethyl)pyrrolidin-1-yl)cyclopropyl)-2-methylpyridine | | |

TABLE III-continued

| Compound. | Structure | Name | MS (ESI+): [M + H]+ | H-NMR |
|---|---|---|---|---|
| 489 | 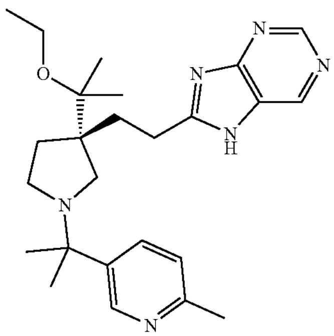 [SMILES: CCOC(C)(C)[C@@]1(CCc2nc3ncncc3[nH]2)CCN(C(C)(C)c2ccc(C)nc2)C1] | (S)-8-(2-(3-(2-ethoxypropan-2-yl)-1-(2-(6-methylpyridin-3-yl)propan-2-yl)pyrrolidin-3-yl)ethyl)-7H-purine | | |
| 490 | 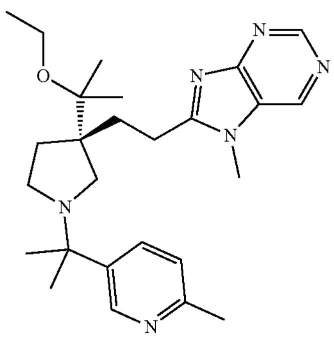 [SMILES: CCOC(C)(C)[C@@]1(CCc2nc3ncncc3n2C)CCN(C(C)(C)c2ccc(C)nc2)C1] | (S)-8-(2-(3-(2-ethoxypropan-2-yl)-1-(2-(6-methylpyridin-3-yl)propan-2-yl)pyrrolidin-3-yl)ethyl)-7-methyl-7H-purine | | |
| 491 | 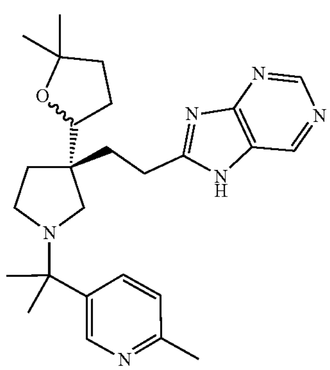 [SMILES: Cc1ccc(C(C)(C)N2CC[C@](CCc3nc4ncncc4[nH]3)(C3CCC(C)(C)O3)C2)cn1] | (S)-8-(2-(3-(5,5-dimethyltetrahydrofuran-2-yl)-1-(2-(6-methylpyridin-3-yl)propan-2-yl)pyrrolidin-3-yl)ethyl)-7H-purine | | |
| 492 | 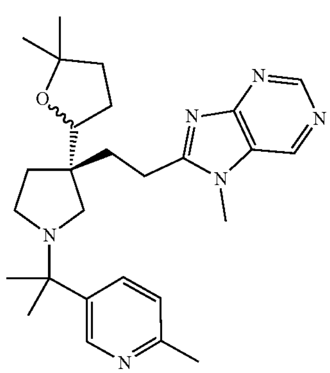 [SMILES: Cc1ccc(C(C)(C)N2CC[C@](CCc3nc4ncncc4n3C)(C3CCC(C)(C)O3)C2)cn1] | (S)-8-(2-(3-(5,5-dimethyltetrahydrofuran-2-yl)-1-(2-(6-methylpyridin-3-yl)propan-2-yl)pyrrolidin-3-yl)ethyl)-7-methyl-7H-purine | | |

TABLE III-continued

| Compound. | Structure | Name | MS (ESI+): [M + H]⁺ | H-NMR |
|---|---|---|---|---|
| 493 | 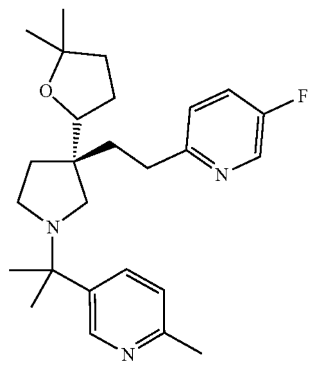 [SMILES: Cc1ccc(C(C)(C)N2CC[C@](CCc3ccc(F)cn3)(C3CCC(C)(C)O3)C2)cn1] | 2-(2-((S)-3-((S)-5,5-dimethyltetrahydrofuran-2-yl)-1-(2-(6-methylpyridin-3-yl)propan-2-yl)pyrrolidin-3-yl)ethyl)-5-fluoropyridine | | |
| 494 | 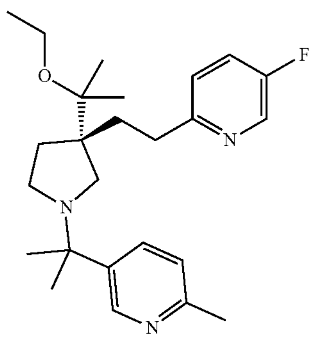 [SMILES: CCOC(C)(C)[C@@]1(CCc2ccc(F)cn2)CCN(C(C)(C)c2ccc(C)nc2)C1] | (S)-2-(2-(3-(2-ethoxypropan-2-yl)-1-(2-(6-methylpyridin-3-yl)propan-2-yl)pyrrolidin-3-yl)ethyl)-5-fluoropyridine | | |
| 495 | 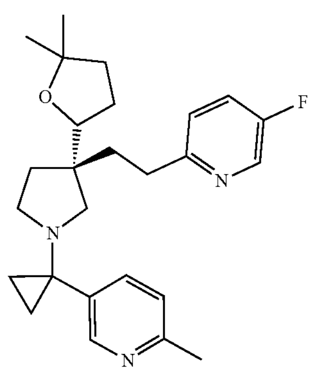 [SMILES: Cc1ccc(C2(N3CC[C@](CCc4ccc(F)cn4)(C4CCC(C)(C)O4)C3)CC2)cn1] | 2-(2-((S)-3-((S)-5,5-dimethyltetrahydrofuran-2-yl)-1-(1-(6-methylpyridin-3-yl)cyclopropyl)pyrrolidin-3-yl)ethyl)-5-fluoropyridine | | |
| 496 | 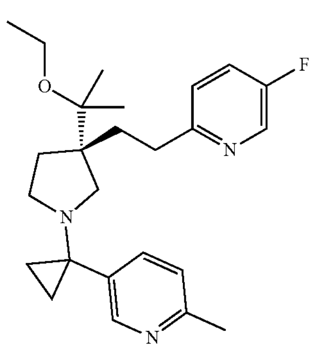 [SMILES: CCOC(C)(C)[C@@]1(CCc2ccc(F)cn2)CCN(C2(c3ccc(C)nc3)CC2)C1] | (S)-2-(2-(3-(2-ethoxypropan-2-yl)-1-(1-(6-methylpyridin-3-yl)cyclopropyl)pyrrolidin-3-yl)ethyl)-5-fluoropyridine | | |

TABLE III-continued

| Compound. | Structure | Name | MS (ESI+): [M + H]+ | H-NMR |
|---|---|---|---|---|
| 497 | 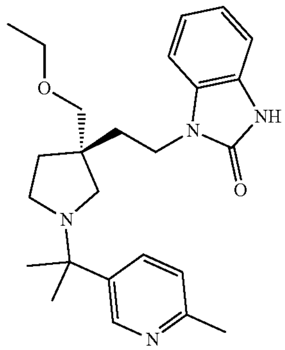 [SMILES: CCOC[C@@]1(CCn2c(=O)[nH]c3ccccc32)CCN(C(C)(C)c2ccc(C)nc2)C1] | (R)-1-(2-(3-(ethoxymethyl)-1-(2-(6-methylpyridin-3-yl)propan-2-yl)pyrrolidin-3-yl)ethyl)-1,3-dihydro-2H-benzo[d]imidazol-2-one | | |
| 498 | 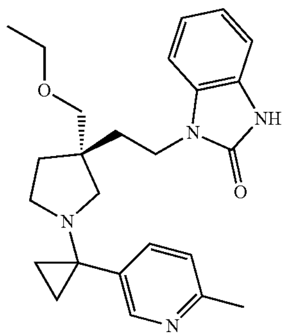 [SMILES: CCOC[C@@]1(CCn2c(=O)[nH]c3ccccc32)CCN(C2(c3ccc(C)nc3)CC2)C1] | (R)-1-(2-(3-(ethoxymethyl)-1-(1-(6-methylpyridin-3-yl)cyclopropyl)pyrrolidin-3-yl)ethyl)-1,3-dihydro-2H-benzo[d]imidazol-2-one | | |
| 499 | 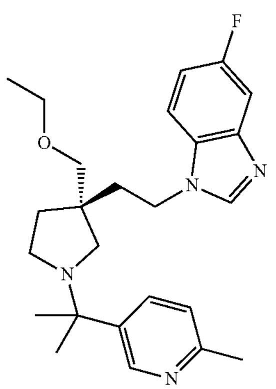 [SMILES: CCOC[C@@]1(CCn2cnc3cc(F)ccc32)CCN(C(C)(C)c2ccc(C)nc2)C1] | (R)-1-(2-(3-(ethoxymethyl)-1-(2-(6-methylpyridin-3-yl)propan-2-yl)pyrrolidin-3-yl)ethyl)-5-fluoro-1H-benzo[d]imidazole | | |
| 500 | 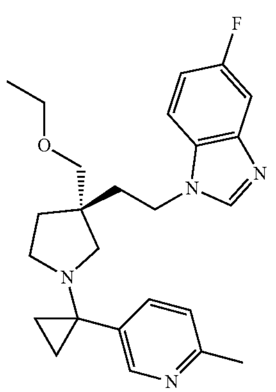 [SMILES: CCOC[C@@]1(CCn2cnc3cc(F)ccc32)CCN(C2(c3ccc(C)nc3)CC2)C1] | (R)-1-(2-(3-(ethoxymethyl)-1-(1-(6-methylpyridin-3-yl)cyclopropyl)pyrrolidin-3-yl)ethyl)-5-fluoro-1H-benzo[d]imidazole | | |

TABLE III-continued

| Compound. | Structure | Name | MS (ESI+): [M + H]+ | H-NMR |
|---|---|---|---|---|
| 501 | 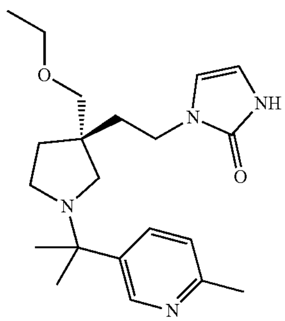 [SMILES: CCOC[C@@]1(CCn2cc[nH]c2=O)CCN(C(C)(C)c2ccc(C)nc2)C1] | (R)-1-(2-(3-(ethoxymethyl)-1-(2-(6-methylpyridin-3-yl)propan-2-yl)pyrrolidin-3-yl)ethyl)-1,3-dihydro-2H-imidazol-2-one | | |
| 502 | 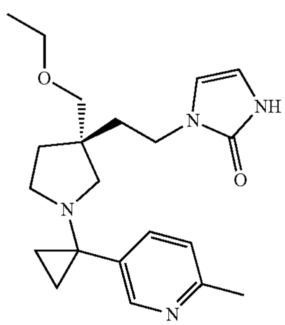 [SMILES: CCOC[C@@]1(CCn2cc[nH]c2=O)CCN(C2(c3ccc(C)nc3)CC2)C1] | (R)-1-(2-(3-(ethoxymethyl)-1-(1-(6-methylpyridin-3-yl)cyclopropyl)pyrrolidin-3-yl)ethyl)-1,3-dihydro-2H-imidazol-2-one | | |
| 503 | 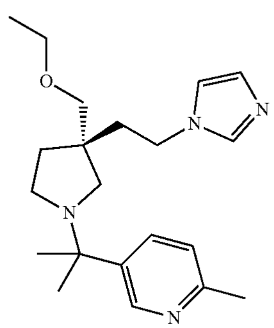 [SMILES: CCOC[C@@]1(CCn2ccnc2)CCN(C(C)(C)c2ccc(C)nc2)C1] | (R)-5-(2-(3-(2-(1H-imidazol-1-yl)ethyl)-3-(ethoxymethyl)pyrrolidin-1-yl)propan-2-yl)-2-methylpyridine | | |
| 504 | 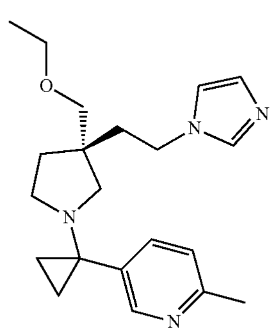 [SMILES: CCOC[C@@]1(CCn2ccnc2)CCN(C2(c3ccc(C)nc3)CC2)C1] | (R)-5-(1-(3-(2-(1H-imidazol-1-yl)ethyl)-3-(ethoxymethyl)pyrrolidin-1-yl)cyclopropyl)-2-methylpyridine | | |

TABLE III-continued

| Compound. | Structure | Name | MS (ESI+): [M + H]+ | H-NMR |
|---|---|---|---|---|
| 505 | 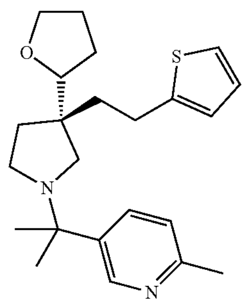 [SMILES: Cc1ccc(C(C)(C)N2CC[C@](CCc3cccs3)(C3CCCO3)C2)cn1] | 2-methyl-5-(2-((S)-3-((S)-tetrahydrofuran-2-yl)-3-(2-(thiophen-2-yl)ethyl)pyrrolidin-1-yl)propan-2-yl)pyridine | | |
| 506 | 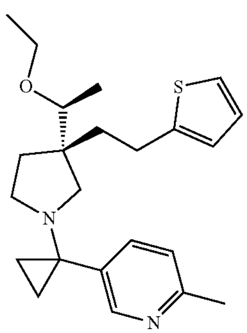 [SMILES: CCO[C@@H](C)[C@@]1(CCc2cccs2)CCN(C2(c3ccc(C)nc3)CC2)C1] | 5-(1-((S)-3-((S)-1-ethoxyethyl)-3-(2-(thiophen-2-yl)ethyl)pyrrolidin-1-yl)cyclopropyl)-2-methylpyridine | | |
| 507 | 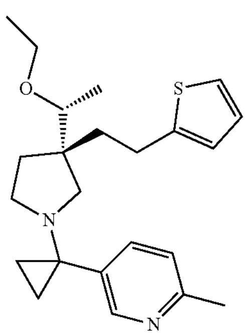 [SMILES: CCO[C@H](C)[C@@]1(CCc2cccs2)CCN(C2(c3ccc(C)nc3)CC2)C1] | 5-(1-((S)-3-((R)-1-ethoxyethyl)-3-(2-(thiophen-2-yl)ethyl)pyrrolidin-1-yl)cyclopropyl)-2-methylpyridine | | |
| 508 | 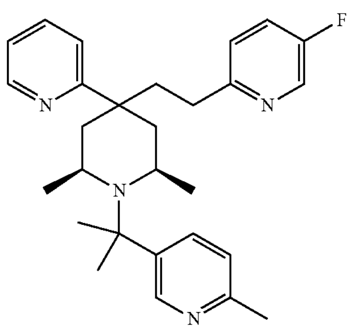 [SMILES: Cc1ccc(C(C)(C)N2[C@H](C)CC(CCc3ccc(F)cn3)(c3ccccn3)C[C@@H]2C)cn1] | 2-(2-((2S,6R)-2,6-dimethyl-1-(2-(6-methylpyridin-3-yl)propan-2-yl)-4-(pyridin-2-yl)piperidin-4-yl)ethyl)-5-fluoropyridine | | |

TABLE III-continued

| Compound. | Structure | Name | MS (ESI+): [M + H]+ | H-NMR |
|---|---|---|---|---|
| 509 | 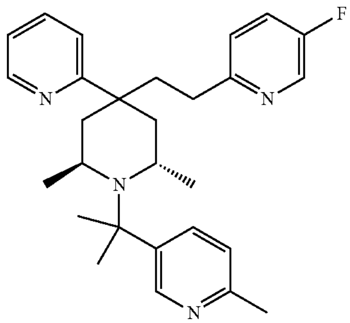 [SMILES: Cc1ccc(C(C)(C)N2[C@@H](C)CC(CCc3ccc(F)cn3)(c3ccccn3)C[C@@H]2C)cn1] | 2-(2-((2S,6S)-2,6-dimethyl-1-(2-(6-methylpyridin-3-yl)propan-2-yl)-4-(pyridin-2-yl)piperidin-4-yl)ethyl)-5-fluoropyridine | | |
| 510 | 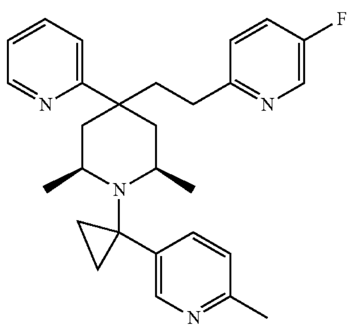 [SMILES: Cc1ccc(C2(N3[C@H](C)CC(CCc4ccc(F)cn4)(c4ccccn4)C[C@@H]3C)CC2)cn1] | 2-(2-((2S,6R)-2,6-dimethyl-1-(1-(6-methylpyridin-3-yl)cyclopropyl)-4-(pyridin-2-yl)piperidin-4-yl)ethyl)-5-fluoropyridine | | |
| 511 | 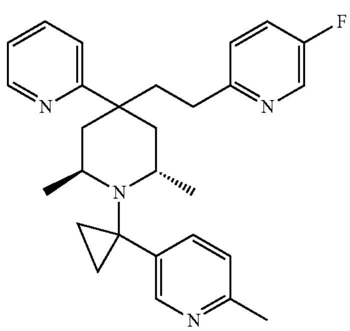 [SMILES: Cc1ccc(C2(N3[C@@H](C)CC(CCc4ccc(F)cn4)(c4ccccn4)C[C@@H]3C)CC2)cn1] | 2-(2-((2S,6S)-2,6-dimethyl-1-(1-(6-methylpyridin-3-yl)cyclopropyl)-4-(pyridin-2-yl)piperidin-4-yl)ethyl)-5-fluoropyridine | | |
| 512 | 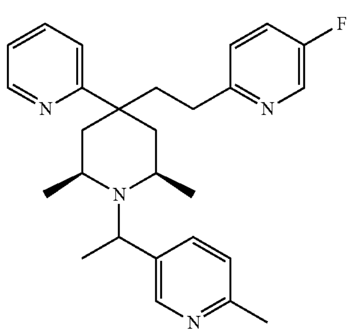 [SMILES: Cc1ccc(C(C)N2[C@H](C)CC(CCc3ccc(F)cn3)(c3ccccn3)C[C@@H]2C)cn1] | 2-(2-((2S,6R)-2,6-dimethyl-1-(1-(6-methylpyridin-3-yl)ethyl)-4-(pyridin-2-yl)piperidin-4-yl)ethyl)-5-fluoropyridine | | |

TABLE III-continued

| Compound. | Structure | Name | MS (ESI+): [M + H]+ | H-NMR |
|---|---|---|---|---|
| 513 | 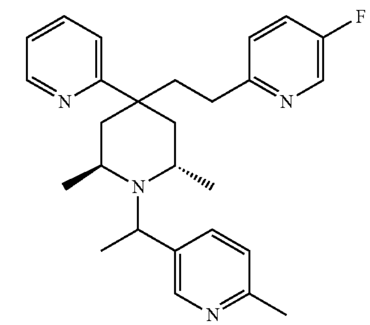 [SMILES: Cc1ccc(C(C)N2[C@@H](C)CC(CCc3ccc(F)cn3)(c3ccccn3)C[C@@H]2C)cn1] | 2-(2-((2S,6S)-2,6-dimethyl-1-(1-(6-methylpyridin-3-yl)ethyl)-4-(pyridin-2-yl)piperidin-4-yl)ethyl)-5-fluoropyridine | | |
| 514 | 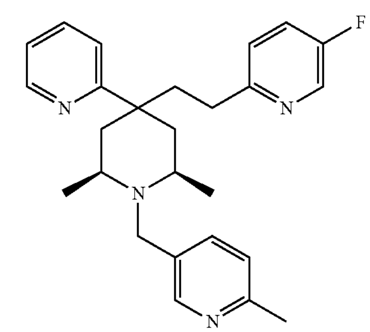 [SMILES: Cc1ccc(CN2[C@H](C)CC(CCc3ccc(F)cn3)(c3ccccn3)C[C@@H]2C)cn1] | 2-(2-((2S,6R)-2,6-dimethyl-1-((6-methylpyridin-3-yl)methyl)-4-(pyridin-2-yl)piperidin-4-yl)ethyl)-5-fluoropyridine | | |
| 515 | 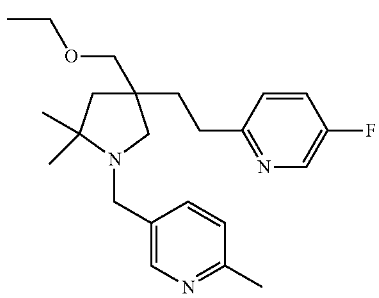 [SMILES: CCOCC1(CCc2ccc(F)cn2)CN(Cc2ccc(C)nc2)C(C)(C)C1] | 5-((4-(ethoxymethyl)-4-(2-(5-fluoropyridin-2-yl)ethyl)-2,2-dimethylpyrrolidin-1-yl)methyl)-2-methylpyridine | | |
| 516 | 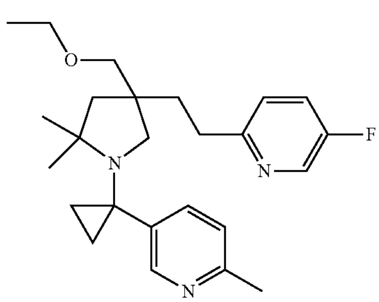 [SMILES: CCOCC1(CCc2ccc(F)cn2)CN(C2(c3ccc(C)nc3)CC2)C(C)(C)C1] | 5-(1-(4-(ethoxymethyl)-4-(2-(5-fluoropyridin-2-yl)ethyl)-2,2-dimethylpyrrolidin-1-yl)cyclopropyl)-2-methylpyridine | | |

TABLE III-continued

| Compound. | Structure | Name | MS (ESI+): [M + H]+ | H-NMR |
|---|---|---|---|---|
| 517 | 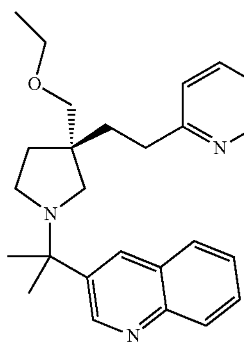 | (S)-3-(2-(3-(ethoxymethyl)-3-(2-(5-fluoropyridin-2-yl)ethyl)pyrrolidin-1-yl)propan-2-yl)quinoline | | |
| 518 | 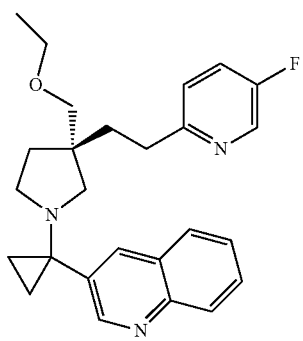 [SMILES: CCOC[C@@]1(CCc2ccc(F)cn2)CCN(C2(c3cnc4ccccc4c3)CC2)C1] | (S)-3-(1-(3-(ethoxymethyl)-3-(2-(5-fluoropyridin-2-yl)ethyl)pyrrolidin-1-yl)cyclopropyl)quinoline | | |
| 519 | 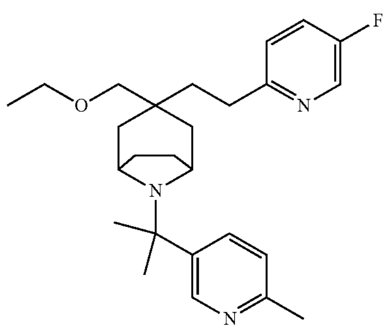 [SMILES: CCOCC1(CCc2ccc(F)cn2)CC2CCC(C1)N2C(C)(C)c1ccc(C)nc1] | (1R,5S)-3-(ethoxymethyl)-3-(2-(5-fluoropyridin-2-yl)ethyl)-8-(2-(6-methylpyridin-3-yl)propan-2-yl)-8-azabicyclo[3.2.1]octane | | |
| 520 | 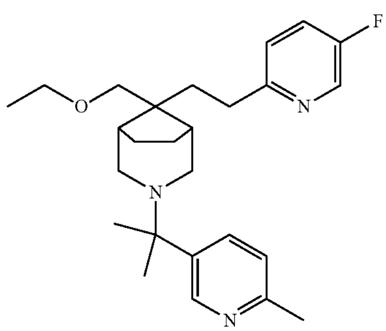 | (1R,5S,8r)-8-(ethoxymethyl)-8-(2-(5-fluoropyridin-2-yl)ethyl)-3-(2-(6-methylpyridin-3-yl)propan-2-yl)-3-azabicyclo[3.2.1]octane | | |

TABLE III-continued

| Compound. | Structure | Name | MS (ESI+): [M + H]+ | H-NMR |
|---|---|---|---|---|
| 521 | 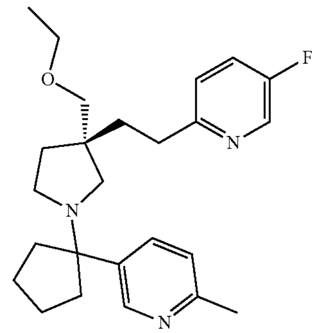 [SMILES: CCOC[C@@]1(CCc2ccc(F)cn2)CCN(C2(c3ccc(C)nc3)CCCC2)C1] | (S)-2-(2-(3-(ethoxymethyl)-1-(1-(6-methylpyridin-3-yl)cyclopentyl)pyrrolidin-3-yl)ethyl)-5-fluoropyridine | | |
| 522 | 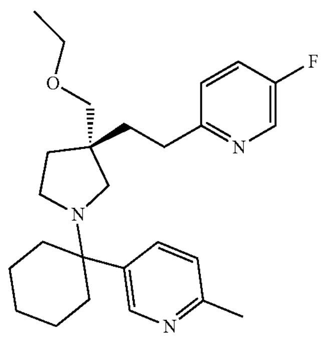 [SMILES: CCOC[C@@]1(CCc2ccc(F)cn2)CCN(C2(c3ccc(C)nc3)CCCCC2)C1] | (S)-2-(2-(3-(ethoxymethyl)-1-(1-(6-methylpyridin-3-yl)cyclohexyl)pyrrolidin-3-yl)ethyl)-5-fluoropyridine | | |
| 523 | 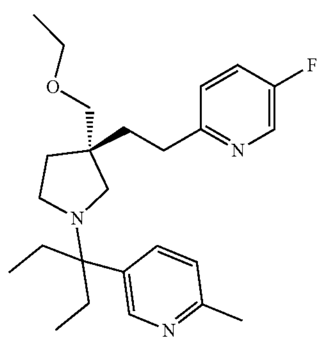 [SMILES: CCOC[C@@]1(CCc2ccc(F)cn2)CCN(C(CC)(CC)c2ccc(C)nc2)C1] | (S)-2-(2-(3-(ethoxymethyl)-1-(3-(6-methylpyridin-3-yl)pentan-3-yl)pyrrolidin-3-yl)ethyl)-5-fluoropyridine | | |
| 524 | 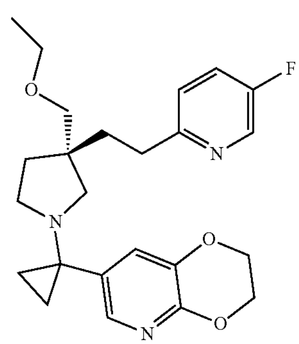 [SMILES: CCOC[C@@]1(CCc2ccc(F)cn2)CCN(C2(c3cnc4c(c3)OCCO4)CC2)C1] | (S)-7-(1-(3-(ethoxymethyl)-3-(2-(5-fluoropyridin-2-yl)ethyl)pyrrolidin-1-yl)cyclopropyl)-2,3-dihydro-[1,4]dioxino[2,3-b]pyridine | | |

TABLE III-continued

| Compound. | Structure | Name | MS (ESI+): [M + H]+ | H-NMR |
|---|---|---|---|---|
| 525 | 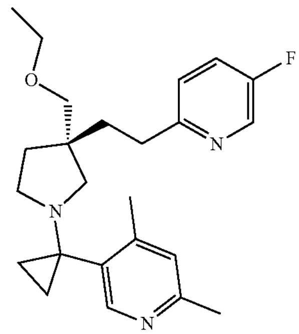 [SMILES: CCOC[C@@]1(CCc2ccc(F)cn2)CCN(C2(c3cnc(C)cc3C)CC2)C1] | (S)-5-(1-(3-(ethoxymethyl)-3-(2-(5-fluoropyridin-2-yl)ethyl)pyrrolidin-1-yl)cyclopropyl)-2,4-dimethylpyridine | | |
| 526 | 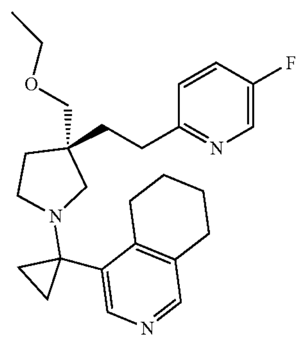 [SMILES: CCOC[C@@]1(CCc2ccc(F)cn2)CCN(C2(c3cncc4c3CCCC4)CC2)C1] | (S)-4-(1-(3-(ethoxymethyl)-3-(2-(5-fluoropyridin-2-yl)ethyl)pyrrolidin-1-yl)cyclopropyl)-5,6,7,8-tetrahydroisoquinoline | | |
| 527 | 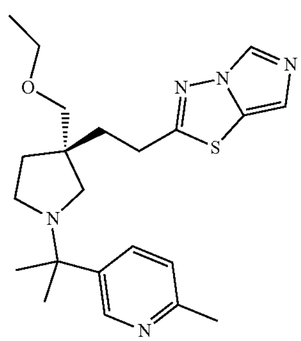 [SMILES: CCOC[C@@]1(CCc2nn3cncc3s2)CCN(C(C)(C)c2ccc(C)nc2)C1] | (S)-2-(2-(3-(ethoxymethyl)-1-(2-(6-methylpyridin-3-yl)propan-2-yl)pyrrolidin-3-yl)ethyl)imidazo[5,1-b][1,3,4]thiadiazole | | |
| 528 | 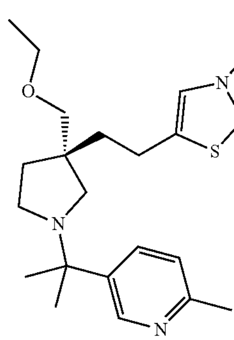 | (S)-2-(2-(3-(ethoxymethyl)-1-(2-(6-methylpyridin-3-yl)propan-2-yl)pyrrolidin-3-yl)ethyl)imidazo[2,1-b]thiazole | | |

TABLE III-continued

| Compound. | Structure | Name | MS (ESI+): [M + H]+ | H-NMR |
|---|---|---|---|---|
| 529 | 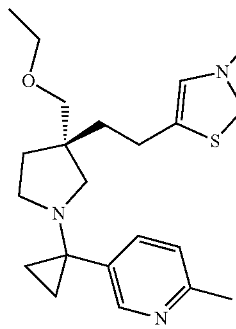 | (S)-2-(2-(3-(ethoxymethyl)-1-(1-(6-methylpyridin-3-yl)cyclopropyl)pyrrolidin-3-yl)ethyl)imidazo[2,1-b]thiazole | | |
| 530 | 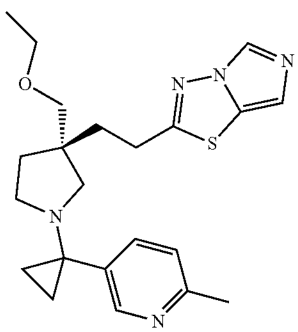 [SMILES: CCOC[C@@]1(CCc2nn3cncc3s2)CCN(C2(c3ccc(C)nc3)CC2)C1] | (S)-2-(2-(3-(ethoxymethyl)-1-(1-(6-methylpyridin-3-yl)cyclopropyl)pyrrolidin-3-yl)ethylimidazo[5,1-b][1,3,4]thiadiazole | | |
| 531 | 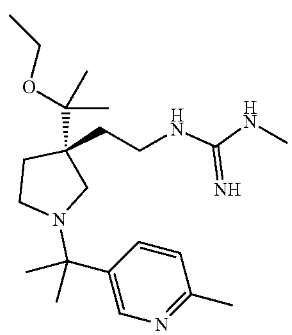 [SMILES: CCOC(C)(C)[C@@]1(CCNC(=N)NC)CCN(C(C)(C)c2ccc(C)nc2)C1] | (S)-1-(2-(3-(2-ethoxypropan-2-yl)-1-(2-(6-methylpyridin-3-yl)propan-2-yl)pyrrolidin-3-yl)ethyl)-3-methylguanidine | | |
| 532 | 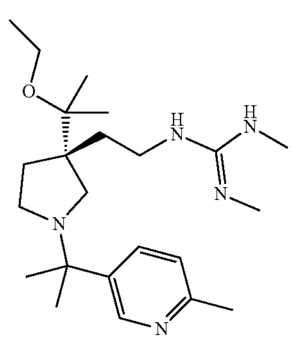 [SMILES: CCOC(C)(C)[C@@]1(CCN/C(=N/C)NC)CCN(C(C)(C)c2ccc(C)nc2)C1] | (S,E)-1-(2-(3-(2-ethoxypropan-2-yl)-1-(2-(6-methylpyridin-3-yl)propan-2-yl)pyrrolidin-3-yl)ethyl)-2,3-dimethylguanidine | | |

TABLE III-continued

| Compound. | Structure | Name | MS (ESI+): [M + H]+ | H-NMR |
|---|---|---|---|---|
| 533 | 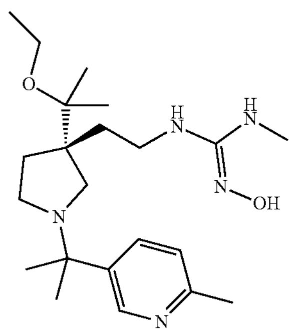 [SMILES: CCOC(C)(C)[C@@]1(CCN/C(=N/O)NC)CCN(C(C)(C)c2ccc(C)nc2)C1] | (S,E)-1-(2-(3-(2-ethoxypropan-2-yl)-1-(2-(6-methylpyridin-3-yl)propan-2-yl)pyrrolidin-3-yl)ethyl)-2-hydroxy-3-methylguanidine | | |
| 534 | 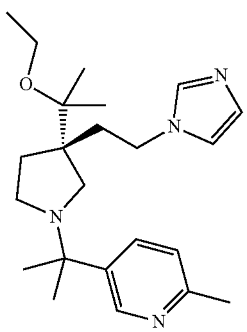 [SMILES: CCOC(C)(C)[C@@]1(CCn2ccnc2)CCN(C(C)(C)c2ccc(C)nc2)C1] | (R)-5-(2-(3-(2-(1H-imidazol-1-yl)ethyl)-3-(2-ethoxypropan-2-yl)pyrrolidin-1-yl)propan-2-yl)-2-methylpyridine | | |
| 535 | 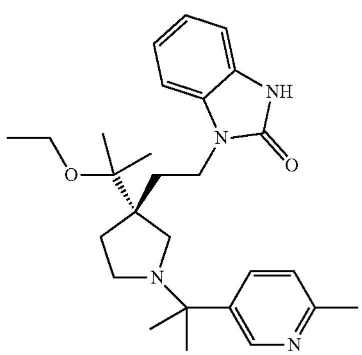 [SMILES: CCOC(C)(C)[C@@]1(CCn2c(=O)[nH]c3ccccc32)CCN(C(C)(C)c2ccc(C)nc2)C1] | (R)-1-(2-(3-(2-ethoxypropan-2-yl)-1-(2-(6-methylpyridin-3-yl)propan-2-yl)pyrrolidin-3-yl)ethyl-1,3-dihydro-2H-benzo[d]imidazol-2-one | | |
| 536 | 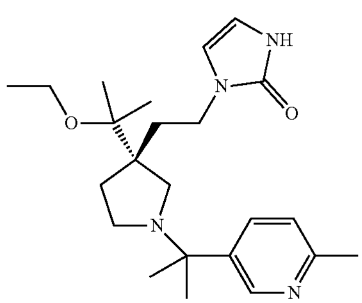 [SMILES: CCOC(C)(C)[C@@]1(CCn2cc[nH]c2=O)CCN(C(C)(C)c2ccc(C)nc2)C1] | (R)-1-(2-(3-(2-ethoxypropan-2-yl)-1-(2-(6-methylpyridin-3-yl)propan-2-yl)pyrrolidin-3-yl)ethyl)-1,3-dihydro-2H-imidazol-2-one | | |

| Compound. | Structure | Name | MS (ESI+): [M + H]+ | H-NMR |
|---|---|---|---|---|
| 537 | 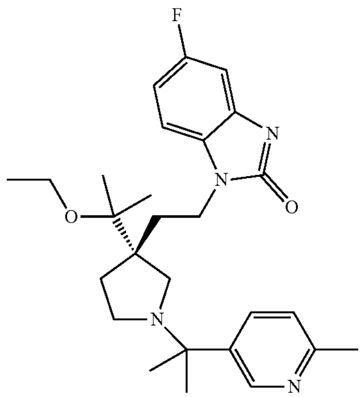 | (R)-1-(2-(3-(2-ethoxypropan-2-yl)-1-(2-(6-methylpyridin-3-yl)propan-2-yl)pyrrolidin-3-yl)ethyl)-5-fluoro-1H-benzo[d]imidazole | | |
| 538 | 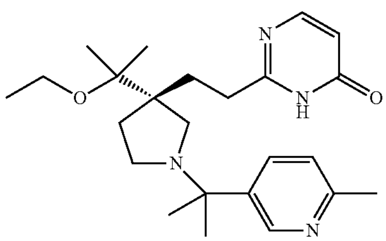 [SMILES: CCOC(C)(C)[C@@]1(CCc2nccc(=O)[nH]2)CCN(C(C)(C)c2ccc(C)nc2)C1] | (S)-2-(2-(3-(2-ethoxypropan-2-yl)-1-(2-(6-methylpyridin-3-yl)propan-2-yl)pyrrolidin-3-yl)ethyl)pyrimidin-4(3H)-one | | |
| 539 | 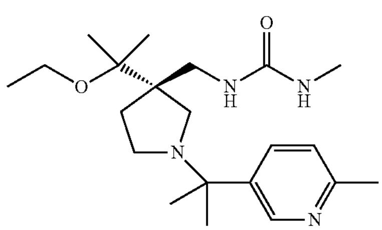 [SMILES: CCOC(C)(C)[C@@]1(CNC(=O)NC)CCN(C(C)(C)c2ccc(C)nc2)C1] | (R)-1-((3-(2-ethoxypropan-2-yl)-1-(2-(6-methylpyridin-3-yl)propan-2-yl)pyrrolidin-3-yl)methyl)-3-methylurea | | |
| 540 | 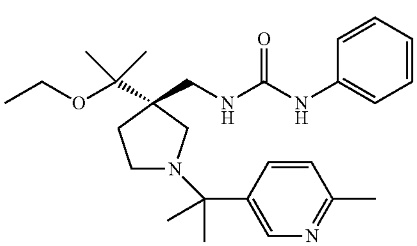 [SMILES: CCOC(C)(C)[C@@]1(CNC(=O)Nc2ccccc2)CCN(C(C)(C)c2ccc(C)nc2)C1] | (R)-1-((3-(2-ethoxypropan-2-yl)-1-(2-(6-methylpyridin-3-yl)propan-2-yl)pyrrolidin-3-yl)methyl)-3-phenylurea | | |
| 541 | 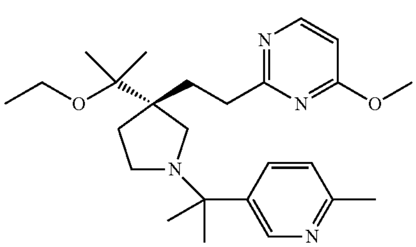 [SMILES: CCOC(C)(C)[C@@]1(CCc2nccc(OC)n2)CCN(C(C)(C)c2ccc(C)nc2)C1] | (S)-2-(2-(3-(2-ethoxypropan-2-yl)-1-(2-(6-methylpyridin-3-yl)propan-2-yl)pyrrolidin-3-yl)ethyl)-4-methoxypyrimidine | | |

TABLE III-continued

| Compound. | Structure | Name | MS (ESI+): [M + H]+ | H-NMR |
|---|---|---|---|---|
| 542 | 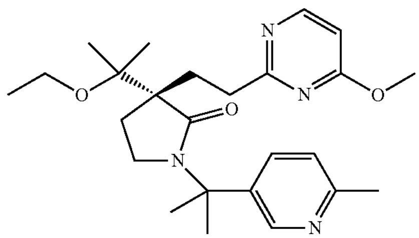 [SMILES: CCOC(C)(C)[C@@]1(CCc2nccc(OC)n2)CCN(C(C)(C)c2ccc(C)nc2)C1=O] | (R)-3-(2-ethoxypropan-2-yl)-3-(2-(4-methoxypyrimidin-2-yl)ethyl)-1-(2-(6-methylpyridin-3-yl)propan-2-yl)pyrrolidin-2-one | | |
| 543 | 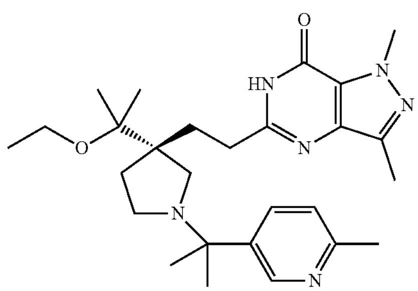 [SMILES: CCOC(C)(C)[C@@]1(CCc2nc3c(C)nn(C)c3c(=O)[nH]2)CCN(C(C)(C)c2ccc(C)nc2)C1] | (S)-5-(2-(3-(2-ethoxypropan-2-yl)-1-(2-(6-methylpyridin-3-yl)propan-2-yl)pyrrolidin-3-yl)ethyl)-1,3-dimethyl-1,6-dihydro-7H-pyrazolo[4,3-d]pyrimidin-7-one | | |
| 544 | 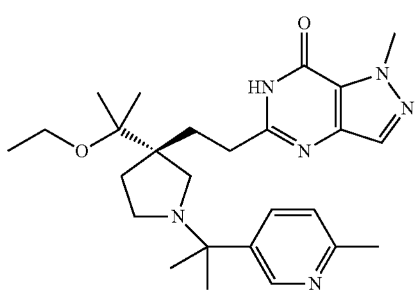 [SMILES: CCOC(C)(C)[C@@]1(CCc2nc3cnn(C)c3c(=O)[nH]2)CCN(C(C)(C)c2ccc(C)nc2)C1] | (S)-5-(2-(3-(2-ethoxypropan-2-yl)-1-(2-(6-methylpyridin-3-yl)propan-2-yl)pyrrolidin-3-yl)ethyl)-1-methyl-1,6-dihydro-7H-pyrazolo[4,3-d]pyrimidin-7-one | | |
| 545 | 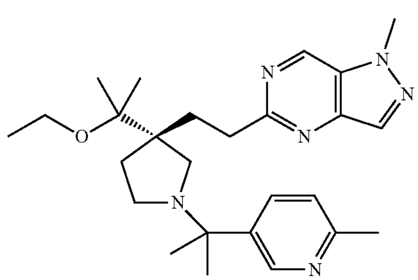 [SMILES: CCOC(C)(C)[C@@]1(CCc2ncc3c(cnn3C)n2)CCN(C(C)(C)c2ccc(C)nc2)C1] | (S)-5-(2-(3-(2-ethoxypropan-2-yl)-1-(2-(6-methylpyridin-3-yl)propan-2-yl)pyrrolidin-3-yl)ethyl)-1-methyl-1H-pyrazolo[4,3-d]pyrimidine | | |
| 546 | 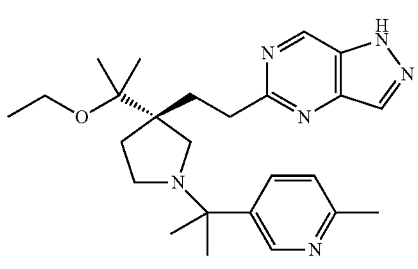 [SMILES: CCOC(C)(C)[C@@]1(CCc2ncc3[nH]ncc3n2)CCN(C(C)(C)c2ccc(C)nc2)C1] | (S)-5-(2-(3-(2-ethoxypropan-2-yl)-1-(2-(6-methylpyridin-3-yl)propan-2-yl)pyrrolidin-3-yl)ethyl)-1H-pyrazolo[4,3-d]pyrimidine | | |

TABLE III-continued

| Compound. | Structure | Name | MS (ESI+): [M + H]+ | H-NMR |
|---|---|---|---|---|
| 547 | 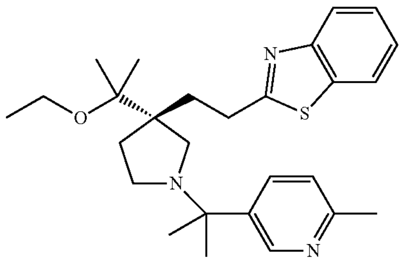 [SMILES: CCOC(C)(C)[C@@]1(CCc2nc3ccccc3s2)CCN(C(C)(C)c2ccc(C)nc2)C1] | (S)-2-(2-(3-(2-ethoxypropan-2-yl)-1-(2-(6-methylpyridin-3-yl)propan-2-yl)pyrrolidin-3-yl)ethyl)benzo[d]thiazole | | |
| 548 | 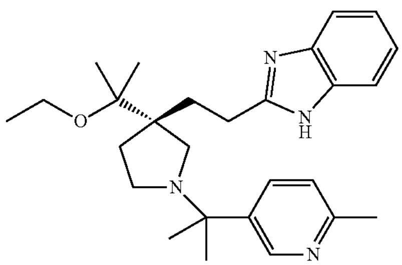 [SMILES: CCOC(C)(C)[C@@]1(CCc2nc3ccccc3[nH]2)CCN(C(C)(C)c2ccc(C)nc2)C1] | (S)-2-(2-(3-(2-ethoxypropan-2-yl)-1-(2-(6-methylpyridin-3-yl)propan-2-yl)pyrrolidin-3-yl)ethyl)-1H-benzo[d]imidazole | | |
| 549 | 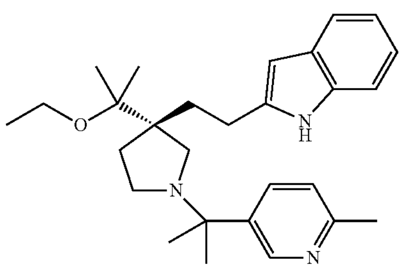 [SMILES: CCOC(C)(C)[C@@]1(CCc2cc3ccccc3[nH]2)CCN(C(C)(C)c2ccc(C)nc2)C1] | (S)-2-(2-(3-(2-ethoxypropan-2-yl)-1-(2-(6-methylpyridin-3-yl)propan-2-yl)pyrrolidin-3-yl)ethyl)-1H-indole | | |
| 550 | 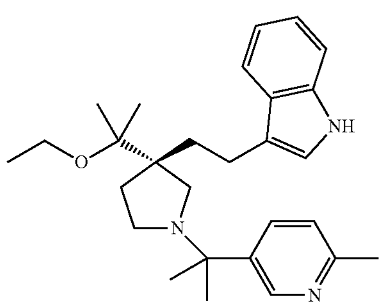 | (S)-3-(2-(3-(2-ethoxypropan-2-yl)-1-(2-(6-methylpyridin-3-yl)propan-2-yl)pyrrolidin-3-yl)ethyl)-1H-indole | | |
| 551 | 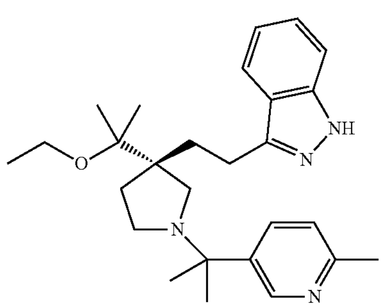 [SMILES: CCOC(C)(C)[C@@]1(CCc2c[nH]c3ccccc23)CCN(C(C)(C)c2ccc(C)nc2)C1] | (S)-3-(2-(3-(2-ethoxypropan-2-yl)-1-(2-(6-methylpyridin-3-yl)propan-2-yl)pyrrolidin-3-yl)ethyl)-1H-indazole | | |

TABLE III-continued

| Compound. | Structure | Name | MS (ESI+): [M + H]+ | H-NMR |
|---|---|---|---|---|
| 552 | 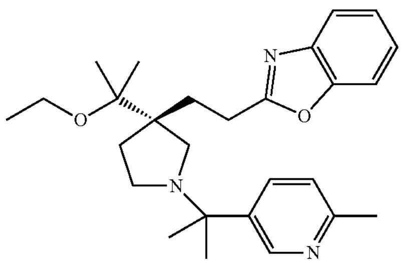 [SMILES: CCOC(C)(C)[C@@]1(CCc2nc3ccccc3o2)CCN(C(C)(C)c2ccc(C)nc2)C1] | (S)-2-(2-(3-(2-ethoxypropan-2-yl)-1-(2-(6-methylpyridin-3-yl)propan-2-yl)pyrrolidin-3-yl)ethyl)benzo[d]oxazole | | |
| 553 | 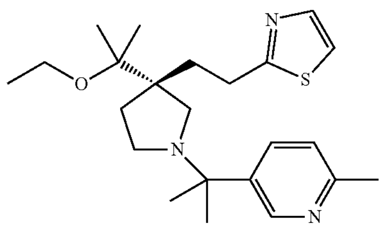 [SMILES: CCOC(C)(C)[C@@]1(CCc2nccs2)CCN(C(C)(C)c2ccc(C)nc2)C1] | (S)-2-(2-(3-(2-ethoxypropan-2-yl)-1-(2-(6-methylpyridin-3-yl)propan-2-yl)pyrrolidin-3-yl)ethyl)thiazole | | |
| 554 | 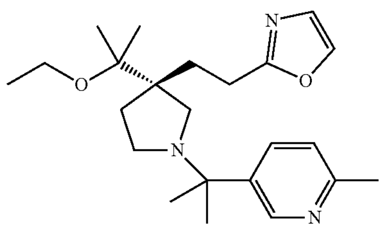 | (S)-2-(2-(3-(2-ethoxypropan-2-yl)-1-(2-(6-methylpyridin-3-yl)propan-2-yl)pyrrolidin-3-yl)ethyl)oxazole | | |
| 555 | 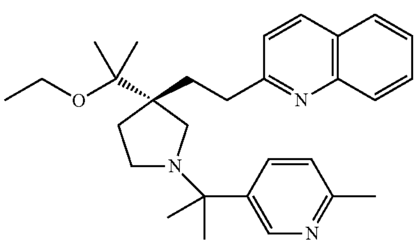 [SMILES: CCOC(C)(C)[C@@]1(CCc2ccc3ccccc3n2)CCN(C(C)(C)c2ccc(C)nc2)C1] | (S)-2-(2-(3-(2-ethoxypropan-2-yl)-1-(2-(6-methylpyridin-3-yl)propan-2-yl)pyrrolidin-3-yl)ethyl)quinoline | | |
| 556 | 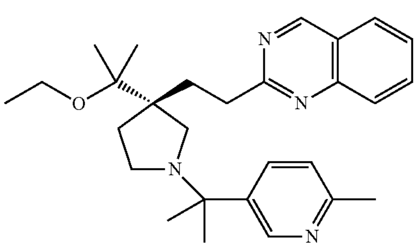 [SMILES: CCOC(C)(C)[C@@]1(CCc2ncc3ccccc3n2)CCN(C(C)(C)c2ccc(C)nc2)C1] | (S)-2-(2-(3-(2-ethoxypropan-2-yl)-1-(2-(6-methylpyridin-3-yl)propan-2-yl)pyrrolidin-3-yl)ethyl)quinazoline | | |
| 557 | 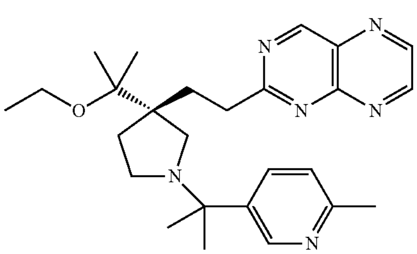 [SMILES: CCOC(C)(C)[C@@]1(CCc2ncc3nccnc3n2)CCN(C(C)(C)c2ccc(C)nc2)C1] | (S)-2-(2-(3-(2-ethoxypropan-2-yl)-1-(2-(6-methylpyridin-3-yl)propan-2-yl)pyrrolidin-3-yl)ethyl)pteridine | | |

The activity of certain compounds of the present invention is set forth in Table IV, below.

TABLE IV

| Compound | ED50 (mg/kg) at 30 min on C57BL/6 mice in Warm-water Tail-flick Test |
|---|---|
| 1 | + |
| 2 | + |
| 3 | + |
| 4 | + |
| 5 | ++ |
| 6 | + |
| 7 | + |
| 8 | + |
| 9 | + |
| 10 | + |
| 11 | + |
| 12 | + |
| 13 | + |
| 14 | + |
| 15 | + |
| 16 | + |
| 17 | + |
| 18 | + |
| 19 | + |
| 20 | + |
| 21 | + |
| 22 | + |
| 23 | + |
| 24 | + |
| 25 | + |
| 26 | + |
| 27 | + |
| 28 | ++ |
| 29 | + |
| 30 | + |
| 31 | + |
| 32 | + |
| 33 | + |
| 34 | + |
| 35 | + |
| 36 | + |
| 37 | + |
| 38 | + |
| 39 | + |
| 40 | + |
| 41 | + |
| 42 | + |
| 43 | + |
| 44 | + |
| 45 | + |
| 46 | + |
| 47 | + |
| 48 | + |
| 49 | + |
| 50 | + |
| 51 | + |
| 52 | + |
| 53 | + |
| 54 | + |
| 55 | + |
| 56 | + |
| 57 | + |
| 58 | + |
| 59 | ++ |
| 60 | + |
| 61 | + |
| 62 | + |
| 63 | + |
| 64 | + |
| 65 | + |
| 66 | + |
| 67 | + |
| 68 | + |
| 69 | ++ |
| 70 | + |
| 71 | + |
| 72 | + |
| 73 | + |
| 74 | ++ |
| 75 | + |
| 76 | + |
| 77 | + |
| 78 | + |
| 79 | + |
| 80 | + |
| 81 | + |
| 82 | + |
| 83 | + |
| 84 | + |
| 85 | + |
| 86 | + |
| 87 | + |
| 88 | + |
| 89 | + |
| 90 | + |
| 91 | ++ |
| 92 | + |
| 93 | + |
| 94 | + |
| 95 | + |
| 96 | ++ |
| 97 | + |
| 98 | + |
| 99 | + |
| 100 | + |
| 101 | + |
| 102 | ++ |
| 103 | + |
| 104 | + |
| 105 | + |
| 106 | + |
| 107 | + |
| 108 | + |
| 109 | + |
| 110 | + |
| 111 | + |
| 112 | + |
| 113 | + |
| 114 | + |
| 115 | + |
| 116 | + |
| 117 | + |
| 118 | + |
| 119 | + |
| 120 | ++ |
| 121 | + |
| 122 | + |
| 123 | + |
| 124 | + |
| 125 | + |
| 126 | + |
| 127 | + |
| 128 | + |
| 129 | + |
| 130 | + |
| 131 | + |
| 132 | + |
| 133 | + |
| 134 | + |
| 135 | + |
| 136 | + |
| 137 | + |
| 138 | + |
| 139 | + |
| 140 | + |
| 141 | + |
| 142 | + |
| 143 | + |
| 144 | + |
| 145 | + |
| 146 | + |
| 147 | ++ |
| 148 | + |

TABLE IV-continued

| Compound | ED50 (mg/kg) at 30 min on C57BL/6 mice in Warm-water Tail-flick Test |
|---|---|
| 149 | + |
| 150 | + |
| 151 | + |
| 152 | + |
| 153 | + |
| 154 | + |
| 155 | + |
| 156 | + |
| 157 | + |
| 158 | + |
| 159 | + |
| 160 | ++ |
| 161 | + |
| 162 | + |
| 163 | + |
| 164 | + |
| 165 | ++ |
| 166 | + |
| 167 | + |
| 168 | + |
| 169 | + |
| 170 | + |
| 171 | ++ |
| 172 | ++ |
| 173 | + |
| 174 | + |
| 175 | ++ |
| 176 | + |
| 177 | ++ |
| 178 | ++ |
| 179 | +++ |
| 180 | + |
| 181 | + |
| 182 | + |
| 183 | + |
| 184 | + |
| 185 | ++ |
| 186 | + |
| 187 | + |
| 188 | + |
| 189 | + |
| 190 | + |
| 191 | ++ |
| 192 | + |
| 193 | + |
| 194 | + |
| 195 | + |
| 196 | + |
| 197 | + |
| 198 | ++ |
| 199 | + |
| 200 | ++ |
| 201 | ++ |
| 202 | ++ |
| 203 | + |
| 204 | + |
| 205 | ++ |
| 206 | + |
| 207 | + |
| 208 | ++ |
| 209 | + |
| 210 | + |
| 211 | + |
| 212 | + |
| 213 | + |
| 214 | + |
| 215 | ++ |
| 216 | ++ |
| 217 | ++ |
| 218 | + |
| 219 | + |
| 220 | + |
| 221 | + |
| 222 | + |
| 223 | + |
| 224 | + |
| 225 | + |
| 226 | ++ |
| 227 | + |
| 228 | + |
| 229 | + |
| 230 | + |
| 231 | ++ |
| 232 | ++ |
| 233 | ++ |
| 234 | + |
| 235 | ++ |
| 236 | + |
| 237 | + |
| 238 | + |
| 239 | + |
| 240 | + |
| 241 | + |
| 242 | + |
| 243 | + |
| 244 | ++ |
| 245 | ++ |
| 246 | + |
| 247 | ++ |
| 248 | + |
| 249 | ++ |
| 250 | ++ |
| 251 | ++ |
| 252 | ++ |
| 253 | + |
| 254 | + |
| 255 | + |
| 256 | ++ |
| 257 | ++ |
| 258 | ++ |
| 259 | ++ |
| 260 | + |
| 261 | + |
| 262 | + |
| 263 | ++ |
| 264 | ++ |
| 265 | + |
| 266 | + |
| 267 | ++ |
| 268 | ++ |
| 269 | ++ |
| 270 | + |
| 271 | + |
| 272 | ++ |
| 273 | ++ |
| 274 | + |
| 275 | ++ |
| 276 | ++ |
| 277 | ++ |
| 278 | ++ |
| 279 | + |
| 280 | ++ |
| 281 | + |
| 282 | + |
| 283 | ++ |
| 284 | ++ |
| 285 | + |
| 286 | ++ |
| 287 | ++ |
| 288 | ++ |
| 289 | + |
| 290 | ++ |
| 291 | + |
| 292 | + |
| 293 | + |
| 294 | ++ |
| 295 | ++ |
| 296 | ++ |
| 297 | ++ |
| 298 | ++ |
| 299 | ++ |
| 300 | ++ |

TABLE IV-continued

| Compound | ED50 (mg/kg) at 30 min on C57BL/6 mice in Warm-water Tail-flick Test |
|---|---|
| 301 | + |
| 302 | ++ |
| 303 | ++ |
| 304 | ++ |
| 305 | ++ |
| 306 | ++ |
| 307 | ++ |
| 308 | + |
| 309 | + |
| 310 | ++ |
| 311 | ++ |
| 312 | ++ |
| 313 | + |
| 314 | + |
| 315 | + |
| 316 | + |
| 317 | + |
| 318 | ++ |
| 319 | ++ |
| 320 | ++ |
| 321 | ++ |
| 322 | ++ |
| 323 | ++ |
| 324 | ++ |
| 325 | ++ |
| 326 | ++ |
| 327 | ++ |
| 328 | ++ |
| 329 | ++ |
| 330 | ++ |
| 331 | ++ |
| 332 | ++ |
| 333 | ++ |
| 334 | ++ |
| 335 | ++ |
| 336 | ++ |
| 337 | ++ |
| 338 | + |
| 339 | + |
| 340 | + |
| 341 | ++ |
| 342 | ++ |
| 343 | ++ |
| 344 | ++ |
| 345 | ++ |
| 346 | ++ |
| 347 | + |
| 348 | ++ |
| 349 | ++ |
| 350 | ++ |
| 351 | ++ |
| 352 | ++ |
| 353 | ++ |
| 354 | ++ |
| 355 | ++ |
| 356 | ++ |
| 357 | ++ |
| 358 | + |
| 359 | ++ |
| 360 | ++ |
| 361 | ++ |
| 362 | ++ |
| 363 | ++ |
| 364 | ++ |
| 365 | ++ |
| 366 | ++ |
| 367 | ++ |
| 368 | ++ |
| 369 | ++ |
| 370 | ++ |
| 371 | ++ |
| 372 | ++ |
| 373 | ++ |
| 374 | ++ |
| 375 | ++ |
| 376 | ++ |
| 377 | ++ |
| 378 | ++ |
| 379 | ++ |
| 380 | + |
| 381 | + |
| 382 | + |
| 383 | ++ |
| 384 | ++ |
| 385 | ++ |
| 386 | ++ |
| 387 | ++ |
| 388 | ++ |
| 389 | ++ |
| 390 | + |
| 391 | ++ |
| 392 | ++ |
| 393 | + |
| 394 | + |
| 395 | ++ |
| 396 | ++ |
| 397 | + |
| 398 | ++ |
| 399 | + |
| 400 | ++ |
| 401 | ++ |
| 402 | ++ |
| 403 | ++ |
| 404 | ++ |
| 405 | + |
| 406 | + |
| 407 | ++ |
| 408 | ++ |
| 409 | ++ |
| 410 | ++ |
| 411 | ++ |
| 412 | ++ |
| 413 | ++ |
| 414 | ++ |
| 415 | ++ |
| 416 | ++ |
| 417 | ++ |
| 418 | + |
| 419 | ++ |
| 420 | ++ |
| 421 | ++ |
| 422 | ++ |
| 423 | ++ |
| 424 | ++ |
| 425 | ++ |
| 426 | ++ |
| 427 | ++ |
| 428 | ++ |
| 429 | ++ |
| 430 | ++ |
| 431 | ++ |
| 432 | ++ |
| 433 | ++ |
| 434 | ++ |
| 435 | ++ |
| 436 | ++ |
| 437 | ++ |
| 438 | + |
| 439 | ++ |
| 440 | ++ |
| 441 | ++ |
| 442 | ++ |
| 443 | ++ |
| 444 | ++ |
| 445 | ++ |
| 446 | ++ |
| 447 | ++ |
| 448 | ++ |
| 449 | ++ |
| 450 | ++ |
| 451 | ++ |
| 452 | ++ |

TABLE IV-continued

| Compound | ED50 (mg/kg) at 30 min on C57BL/6 mice in Warm-water Tail-flick Test |
|---|---|
| 453 | ++ |
| 454 | + |
| 455 | + |
| 456 | ++ |
| 457 | ++ |
| 458 | ++ |
| 459 | ++ |
| 460 | ++ |
| 461 | ++ |
| 462 | ++ |
| 463 | ++ |
| 464 | ++ |
| 465 | ++ |
| 466 | ++ |
| 467 | + |
| 468 | ++ |

Key:
+ indicates ED 50 > 10 mg/kg;
++ indicates ED 50 </= 10 mg/kg

Based on the results in Table IV, and the characteristics of the compounds tested in Table IV which are likely to be safest and most efficacious in human clinical trials, 23 lead compounds were identified. These 23 are Compound Nos. 234, 269, 275, 321, 322, 326, 329, 330, 333, 335, 336, 345, 352, 379, 385, 389, 409, 413, 426, 434, 462, 463 and 465 from Table III.

The specific methods, processes, compounds and compositions described herein are representative of preferred and other embodiments, and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that various substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", "having" etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A compound having a structure according to Formula I, or a pharmaceutically acceptable salt thereof:

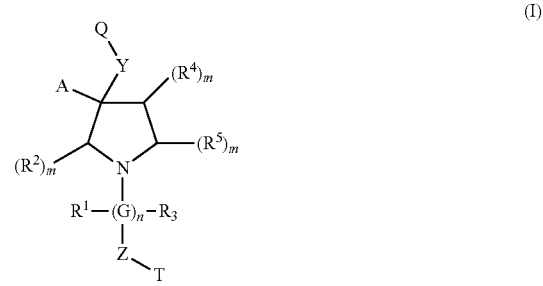

(I)

wherein:

A is $CH_2$—O—$CH_2$-Me;

Y is substituted heteroalkyl or substituted $C_1$ or $C_2$ alkyl or substituted or unsubstituted: $C_3$ to $C_{10}$ alkyl, or substituted or unsubstituted cycloalkyl or heterocycloalkyl;

Q is substituted or unsubstituted: aryl, heteroaryl, or null;

G is methylene and n is an integer that is 2;

Z is a substituted or unsubstituted six membered ring which is not a pyridine ring optionally substituted by T, where T is $NH_2$ or H;

$R^1$ is selected from H and substituted or unsubstituted: alkyl, heteroalkyl, 3- to 7-membered cycloalkyl, 3- to 7-membered heterocycloalkyl, aryl, and heteroaryl;

$R^3$ can be hydrogen or null;

m is an integer and can independently either be 0 or 1 for $R^2$, and $R^5$, and where m is 1 for any of $R^2$, and $R^5$ then said $R^2$, and $R^5$ is hydrogen; and m is an integer from 0-8 for $R^4$ which can be H and substituted or unsubstituted: alkyl, heteroalkyl, 3- to 7-membered cycloalkyl, or 3- to 7-membered heterocycloalkyl.

2. The pharmaceutically acceptable salt of claim 1 which is an HCl salt.

3. A pharmaceutical composition comprising a compound or salt according to claim 1 and a pharmaceutically acceptable carrier.

4. A compound having a formula:
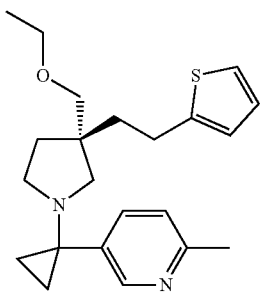 [SMILES: CCOC[C@@]1(CCc2cccs2)CCN(C2(c3ccc(C)nc3)CC2)C1]
or a pharmaceutically acceptable salt thereof.
5. A compound having a formula:
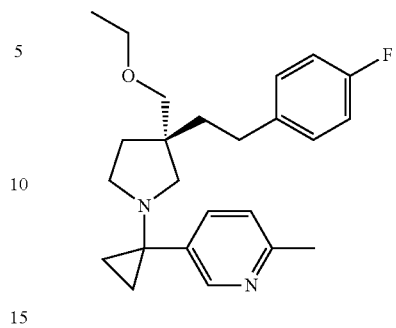
or a pharmaceutically acceptable salt thereof.
* * * * *